United States Patent [19]
Yanagisawa et al.

[11] Patent Number: 6,103,907
[45] Date of Patent: Aug. 15, 2000

[54] PHENYLALKYLCARBOXYLIC ACID COMPOUNDS AND COMPOSITIONS FOR TREATING HYPERGLYCEMIA

[75] Inventors: Hiroaki Yanagisawa, Tokyo; Makoto Takamura, Kawasaki; Takashi Fujita, Kashiwa; Toshihiko Fujiwara, Ebina, all of Japan

[73] Assignee: Sankyo Company, Limited, Tokyo, Japan

[21] Appl. No.: 09/168,973

[22] Filed: Oct. 5, 1998

Related U.S. Application Data

[63] Continuation of application No. PCT/JP97/01122, Apr. 1, 1997.

[30] Foreign Application Priority Data

Apr. 4, 1996 [JP] Japan .................................. 8-082803

[51] Int. Cl.$^7$ ...................... C07D 211/70; C07D 211/82; A61K 31/435; A61K 31/195; C07C 321/00; C07C 249/00
[52] U.S. Cl. .......................... 546/329; 514/277; 514/357; 514/562; 514/567; 544/283; 544/301; 546/162; 548/198; 548/215; 548/336.1; 548/370.1; 548/571; 549/74; 549/491; 562/426; 562/440
[58] Field of Search ..................... 544/283, 301; 546/162, 329; 548/198, 215, 336.1, 370.1, 561; 549/74, 491; 562/426, 440; 514/277, 357, 562, 567

[56] References Cited

U.S. PATENT DOCUMENTS

| 3,872,113 | 3/1975 | Fliedner ............................... 562/440 X |
| 4,703,052 | 10/1987 | Eggler et al. ............................ 514/337 |
| 5,530,156 | 6/1996 | Benori et al. ............................ 562/440 |
| 5,863,946 | 1/1999 | Brooks et al. ........................... 514/564 |

FOREIGN PATENT DOCUMENTS

| 0008203 | 2/1980 | European Pat. Off. . |
| 0139421 | 5/1985 | European Pat. Off. . |
| 0306228 | 3/1989 | European Pat. Off. . |
| 0708098 | 4/1996 | European Pat. Off. . |
| WO 91/19702 | 12/1991 | WIPO . |
| WO 94/29285 | 12/1994 | WIPO . |
| WO 94/29302 | 12/1994 | WIPO . |
| WO 95/03288 | 2/1995 | WIPO . |
| WO 96/04260 | 2/1996 | WIPO . |
| WO 96/38427 | 12/1996 | WIPO . |

OTHER PUBLICATIONS

Fujita et al, "Reduction of Insulin Resistance in Obese and/or Diabetic Animals by 5-[4-(1-Methylcyclohexyl-methoxy)benzyl]-thiazolidine-2,4-dione (ADD-3878, U-63,287, Ciglitazone, a New Antidiabetic Agent", *Diabetes*, vol. 32 (9), pp. 804–810 (Sep. 1983).

Fujiwara et al, "Characterization of New Oral Antidiabetic Agent CS-045", *Diabetes*, vol. 37 (11), pp. 1549–1558 (Nov. 1988).

Chang et al, "The Hypoglycemic Effect of Ciglitazone in Obese, Hyperglycemic Animal Models", *Prog. Clin. Biol. Res.*, 265, pp. 177–192 (1988).

Colca et al, "Ciglitazone, A Hypoglycemic Agents: Early Effects on the Pancreatic Islets of Ob/Ob Mice", *Metabolism*, vol. 37, No. 3, pp. 276–280 (Mar. 1988).

Sohda et al, "Studies on Antidiabetic Agents", *Arzneim–Forsch.*, vol. 40 (1), pp. 37–42 (1990).

Ikeda et al, "Effects of Pioglitazone on Glucose and Lipid Metabolism in Normal and Insulin Resistant Animals", *Arzneim–Forsch.*, vol. 40 (2), pp. 156–162 (1990)

Sugiyama et al, "Effects of Pioglitazone on Glucose and Lipid Metabolism in Wistar Fatty Rats", *Arzneim–Forsch*, vol. 40 (3), pp. 263–267 (1990).

Colca et al, "Pioglitazone Hydrochloride Inhibits Cholesterol Absorption and Lowers Plasma Cholesterol Concentrations in Cholesterol–Fed Rats", *Diabetes*, vol. 40 (12), pp. 1669–1674 (Dec. 1991).

Saha et al, "Lipid abnormalities in tissues of the KKA$^y$ mouse: effects of pioglitazone on malonyl–CoA and diacylglycerol", *Am. J. Physiol.*, 267 (1, Pt. 1), pp. E95–E101 (1994).

Oakes et al, "A New Antidiabetic Agent, BRL 49653, Reduces Lipid Availability and Improves Insulin Action and Glucoregulation in the Rat", *Diabetes*, vol. 43 (10), pp. 1203–1210 (Oct. 1994).

Bowen et al, "The Effect of CP 68,772, a Thiozolidinedione Derivative, on Insulin Sensitivity in Lean and Obese Zucker Rats", *Metabolism*, vol. 40 (10), pp. 1025–1030 (Oct. 1991).

(List continued on next page.)

*Primary Examiner*—Floyd D. Higel
*Attorney, Agent, or Firm*—Frishauf, Holtz, Goodman, Langer & Chick, P.C.

[57] ABSTRACT

Phenylalkylcarboxylic acid compounds of the formula:

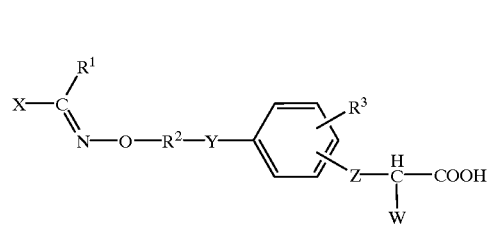

(I)

wherein $R^1$ represents an alkyl group and the like, $R^2$ represents an alkylene group, $R^3$ represents a hydrogen atom and the like, X represents a substituted or unsubstituted aryl group and the like, Y represents an oxygen atom and the like, Z represents an alkylene group and the like, and W represents an alkyl group and the like), the pharmacologically acceptable salts thereof or the pharmacologically acceptable esters thereof are useful as therapeutic or preventive agents for hyperglycemia and the like.

40 Claims, No Drawings

OTHER PUBLICATIONS

Kemnitz et al, "Pioglitazone Increases Insulin Sensitivity, Reduces Blood Glucose, Insulin, and Lipid Levels, and Lowers Blood Pressure in Obese, Insulin–Resistant Rhesus Monkeys", *Diabetes*, vol. 43 (2), pp. 204–211 (Feb. 1994).

Keen, "Insulin Resistance and the Prevention of Diabetes Mellitus", *The New Eng. Journal of Med.*, vol. 331 (18), pp. 1226–1227 (Nov. 1994).

Yoshioka et al, "Antihypertensive Effects of CS–045 Treatment in Obese Zucker Rats", *Metabolism*, vol. 42, No. 1, pp. 75–80 (Jan. 1993).

Dubey et al, "Pioglitazone attenuates hypertension and inhibits growth of renal arteriolar smooth muscle in rats", *Am. J. Physiol.*, vol. 265 (4, Pt. 2), pp. R726–R732 (1993).

Ohsumi et al, "Troglitazone Prevents the Inhibitory Effects of Inflammatory Cytokines on Insulin–Induced Adipocyte Differentiation in 3T3–L1 Cells", *Endocrinology*, vol. 135. No. 5, pp. 2279–2282 (1994).

Szalkowski et al, "Antidiabetic Thiazolidinediones Block the Inhibitory Effect of Tumor Necrosis Factor–$\alpha$ on Differentiation, Insulin–Stimulated Glucose Uptake, and Gene Expression in 3T3–L1 Cells", *Endocrinology*, vol. 136, No. 4, pp. 1474–1481 (1995).

Shikazumi et al, "Efficacy of Pioglitazone on Renal Glomerular Lesions in Wistar Fatty Rats", *Diabetes*, vol. 38 (Special Edition) (38th Annual Technical Meeting of the Japan Diabetes Society, Program Proceedings, 38th Meeting of the Japan Diabetes Society), Program No. 2695 (with an English language translation) (1995).

PHENYLALKYLCARBOXYLIC ACID COMPOUNDS AND COMPOSITIONS FOR TREATING HYPERGLYCEMIA

This application is a continuation application of International Application PCT/JP97/01122, filed Apr. 1, 1997.

TECHNICAL FIELD

The present invention relates to novel phenylalkylcarboxylic acid derivatives having an excellent lowering activity for blood sugar, and its pharmacologically acceptable salts or pharmacologically acceptable esters; a composition comprising the said compound as an active ingredient for treatment or prophylaxis of hyperglycemia; their use for manufacturing a medicament for treatment or prophylaxis of hyperglycemia; or a therapeutic or preventive method for hyperglycemia in which a pharmacologically effective amount of the said compound is administered to warm-blood animals.

BACKGROUND ART

Insulin and sulfonylurea compounds such as tributamide and Glipizide have been used as therapeutic agents for diabetes and hyperglycemia, the use of phenylalkylcarboxylic acid derivatives for treatment of non-insulin-dependent diabetes was recently reported. These compounds include, for example.

(1-1) 3-[4-[2-(5-methyl-2-phenyl-4-oxazolyl)ethoxy]phenyl]-2-(acetylthio)propionic acid and its esters, 2-methoxy-3-[4-[2-(5-methyl-2-phenyl-4-oxazolyl)ethoxy]phenyl]propionic acid, 3-[[4-(4-benzyloxyphenyl)ethoxy]phenyl]-2-methoxypropionic acid, 2-phenoxy-3-[4-(2-phenyl)ethoxyphenyl]propionic acid and the like are disclosed in PCT Publication No. WO91/19702 (Japanese PCT Application (Kokai) No. Hei 5-507920).

(1-2) 3-[4-[2-[N-(2-benzoxazolyl)-N-methylamino]ethoxy]phenyl]-2-((N-ethyl-N-phenyl)amino)propionic acid and its esters and the like are disclosed in PCT Publication No. WO94/29285.

(1-3) 3-[4-[2-[N-(2-benzoxazolyl)-N-methylamino]ethoxy]phenyl]-2-pyrrolepropionic acid and its esters and the like are disclosed in PCT Publication No. WO94/29302.

(1-4) 3-[4-[2-[N-(2-benzoxazolyl)-N-methylamino]ethoxy]phenyl]-2-(propyl)propionic acid and its esters, 3-[4-[2-[N-(2-benzoxazolyl)-N-methylamino]ethoxy]phenyl]-2-(3-phenylpropyl)propionic acid and its esters, 3-[4-[2-[N-(2-benzoxazolyl)-N-methylamino]ethoxy]phenyl]-2-(3-methylbutyl)propionic acid and its esters and the like are disclosed in PCT Publication No. WO95/03288.

(1-5) 3-[4-[2-[N-(2-benzoxazolyl)-N-methylamino]ethoxy]phenyl]-2-(2,2,2-trifluoroethoxy)propionic acid and its esters and the like are disclosed in PCT Publication No. WO96/04260.

Moreover, the use of a large number of thiazolidine derivatives has recently been reported as therapeutic agents for the treatment of non-insulin-dependent diabetes. These compounds include, for example, (2-1) 5-[4-[(6-hydroxy-2,5,7,8-tetramethylchroman-2-yl)methoxy]benzyl]-2,4-thiazolidinedione (International Nonproprietary Name (INN): Troglitazone) is disclosed in U.S. Pat. No. 4,572,912, EP 139421A and Japanese Patent Publication (Kokoku) No. 2-31079.

(2-2) 5-[[4-[2-(5-ethyl-pyridin-2-yl)ethoxy]phenyl]methyl]-2,4-thiazolidinedione (INN: Pioglitazone) is disclosed in EP 8203A, U.S. Pat. No. 4,287,200, U.S. Pat. No. 4,340,605, U.S. Pat. No. 4,438,141, U.S. Pat. No. 4,444,779, U.S. Pat. No. 4,725,610, Japanese Patent Publication (Kokoku) No. Sho 62-42903 and Japanese Patent Publication (Kokoku) No. Hei 5-66956.

(2-3) 5-[[3,4-dihydro-2-(phenylmethyl)-2H-benzopyran-6-yl]methyl]-2,4-thiazolidinedione (INN: Englitazone) is disclosed in U.S. Pat. No. 4,703,052 and Japanese Patent Publication (Kokoku) No. Hei 5-86953.

(2-4) 5-[[4-[2-[N-methyl-N-(pyridin-2-yl)amino]ethoxy]phenyl]methyl]-2,4-thiazolidinedione (Code Designation: BRL-49653) is disclosed in EP 306228A, U.S. Pat. No. 5,002,953, U.S. Pat. No. 5,194,443, U.S. Pat. No. 5,232,925, U.S. Pat. No. 5,260,445 and Japanese Patent Application (Kokai) No. Hei 1-131169.

The relationships between these compounds and various diseases are described in the following references with respect to, for example, thiazolidine derivatives.

The effects of thiazolidine derivatives on hyperglycemia are described in (1) Diabetes., 32(9), 804–810 (1983); (2) Diabetes., 37(11), 1549–1558 (1988); (3) Prog. Clin. Biol. Res., 265, 177–192 (1988); (4) Metabolism., 37(3), 276–280 (1988); (5) Arzneim.-Forsch., 40(1), 37–42 (1990); (6) Arzneim.-Forsch., 40(2, Pt. 1), 156–162 (1990); and, (7) Arzneim.-Forsch., 40(3), 263–267 (1990).

The effects of thiazolidine derivatives on hyperlipemia are reported in (1) Diabetes., 40(12), 1669–1674 (1991); (2) Am. J. Physiol., 267(1, Pt. 1), E95–E101 (1994); and (3) Diabetes., 43(10), 1203–1210 (1994).

The effects of thiazolidine derivatives on impaired glucose tolerance and insulin resistance are reported in (1) Arzneim.-Forsch., 40(2, Pt. 1), 156–162 (1990); (2) Metabolism., 40(10), 1025–1030(1991); (3) Diabetes., 43(2), 204–211 (1994); and, (4) N. Engl. J. Med., 331(18), 1226–1227 (1994).

The effects of thiazolidine derivatives on hypertension are reported in (1) Metabolism., 42(1), 75–80 (1993); (2) Am. J. Physiol., 265(4, Pt. 2), R726–R732 (1993); and, (3) Diabetes., 43(2), 204–211 (1994).

The effects of thiazolidine derivatives on cachexia are reported in (1) Endocrinology., 135(5), 2279–2282 (1994); and, (2) Endocrinology., 136(4), 1474–1481 (1995).

The effects of thiazolidine derivatives on nephropathy are reported in (1) Diabetes., 38 (Special Edition), (1995) (38th Annual Technical Meeting of the Japan Diabetes Society, Program Proceedings, 38th Meeting of the Japan Diabetes Society, 1995).

The effects of thiazolidine derivatives on coronary artery disease are reported in (1) Am. J. Physiol., 265(4, Pt. 2), R726–R732 (1993); and, (2) Hypertension., 24(2), 170–175 (1994).

The effects of thiazolidine derivatives on arteriosclerosis are reported in (1) Am. J. Physiol., 265(4, Pt. 2), R726–R732 (1993).

Moreover, it has recently been reported in (1) N. Engl. J. Med., 331(18), 1226–1227 (1994) that normal individuals having insulin resistance unaccompanied with glucose intolerance have a high risk for the onset of diabetes (referred to as "insulin-resistant non-IGT: NGT"). It is suggested that medicaments which can improve insulin resistance would be useful as preventive drugs against the onset of diabetes in normal individuals like those described above.

However, the compounds mentioned above are different from the compounds of the present invention in that they do not have an oxime bond in their side chain, while the compounds of the present invention have the oxime bond in their side chain.

Incidentally, compounds which have an oxime bond in their side chain and are non-insulin-dependent agents for the treatment of diabetes that have effects similar to those described above, have been disclosed after the date of claiming the priority of the present application. These compounds include, for example, aromatic oximino derivatives such as (4-1) 5-[4-[2-[(4-hydroxyindan-1-yl)iminoxy] ethoxy]benzyl]-2,4-thiazolidinedione, 5-[4-[2-[(2,3-dihydro-6-phenylbenzofuran-3-yl)iminoxy]ethoxy]benzyl]-2,4-thiazolidinedione, 5-[4-[2-[(5-chloroindan-1-yl) iminoxy]ethoxy]benzyl]-2,4-thiazolidinedione, 5-[4-[2-[(5-methylindan-1-yl)iminoxy]ethoxy]benzyl]-2,4-thiazolidinedione, 5-[4-[2-[(5,6-methylenedioxyindan-1-yl) iminoxy]ethoxy]benzyl]-2,4-thiazolidinedione, 5-[4-[2-[(5-phenylindan-1-yl)iminoxy]ethoxy]benzyl]-2,4-thiazolidinedione and they are disclosed in PCT Publication No. WO96/38427 (publication date: Dec. 5, 1996) and Japanese Patent Application (Kokai) No. Hei 9-48770 (publication date: Feb. 18, 1997); oxime derivatives such as (4-2) 5-[4-[2-[[[1-(4-biphenylyl)ethylidene]amino]oxy] ethoxy]benzyl]thiazolidine-2,4-dione, 5-[4-[2-[[[1-[4-(2-pyridyl)phenyl]ethylidene]amino]oxy]ethoxy]benzyl] thiazolidine-2,4-dione, 5-[4-[2-[[[1-(2-phenyl-5-pyridyl) ethylidene]amino]oxy]ethoxy]benzyl]thiazolidine-2,4-dione, 5-[4-[2-[[[1-(2-methoxy-5-pyridyl)ethylidene] amino]oxy]ethoxy]benzyl]thiazolidine-2,4-dione are disclosed in EP 708098A (publication date: Apr. 24, 1996) and Japanese Patent Application (Kokai) No. Hei 9-48779 (publication date: Feb. 18, 1997).

DISCLOSURE OF THE INVENTION

The inventors of the present invention conducted research on phenylalkylcarboxylic acid derivatives having extremely potent activity and extremely high safety and found that these derivatives improve hyperglycemia and the like, and also have an inhibitory effect on aldose reductase.

Namely, the present invention relates to novel phenylalkylcarboxylic acid derivatives of formula (I) having an excellent activity lowering of blood sugar, and its pharmacologically acceptable salts or pharmacologically acceptable esters; a composition comprising the compound of formula (I) as an active ingredient for treatment or prophylaxis of hyperglycemia; their use for manufacturing a medicament for treatment or prophylaxis of hyperglycemia, or a therapeutic or preventive method for hyperglycemia in which a pharmacologically effective amount of the compound of formula (I) is administered to warm-blood animals.

The phenylalkylcarboxylic acid derivatives of the present invention have formula (I):

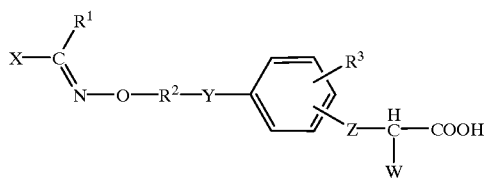

(I)

wherein, $R^1$ represents a hydrogen atom or a straight- or branched-chain alkyl group having from 1 to 6 carbon atoms, $R^2$ represents a straight- or branched-chain alkylene group having from 2 to 6 carbon atoms, $R^3$ represents (i) a hydrogen atom, (ii) a straight- or branched-chain alkyl group having from 1 to 6 carbon atoms, (iii) a straight- or branched-chain alkoxy group having from 1 to 4 carbon atoms, (iv) a straight- or branched-chain alkylthio group having from 1 to 4 carbon atoms, (v) a halogen atom, (vi) a nitro group, (vii) a straight- or branched-chain dialkylamino group in which the alkyl groups are the same as or different from each other and each has from 1 to 4 carbon atoms, (viii) an aryl group having from 6 to 10 carbon atoms which may have from 1 to 3 substituents α mentioned below, or (ix) an aralkyl group having from 7 to 12 carbon atoms which may have 1 to 3 substituents α mentioned below in the aryl moiety, Z represents a single bond or a straight- or branched-chain alkylene group having from 1 to 6 carbon atoms, W represents (i) a straight- or branched-chain alkyl group having from 1 to 6 carbon atoms, (ii) a hydroxyl group, (iii) a straight- or branched-chain alkoxy group having from 1 to 4 carbon atoms, (iv) a straight- or branched-chain alkylthio group having from 1 to 4 carbon atoms, (v) an amino group, (vi) a straight- or branched-chain monoalkylamino group having from 1 to 4 carbon atoms, (vii) a straight- or branched-chain dialkylamino group in which the alkyl groups are the same as or different from each other and each has from 1 to 4 carbon atoms, (viii) an N-alkyl-N-arylamino group having a straight- or branched-chain alkyl having from 1 to 4 carbon atoms and aryl moiety having from 6 to 10 carbon atoms which may have from 1 to 3 substituents α mentioned below, (ix) an aryl group having from 6 to 10 carbon atoms which may have from 1 to 3 substituents α mentioned below, (x) an aryloxy group having from 6 to 10 carbon atoms which may have from 1 to 3 substituents α mentioned below in the aryl moiety, (xi) an arylthio group having from 6 to 10 carbon atoms which may have from 1 to 3 substituents α mentioned below in the aryl moiety, (xii) an arylamino group having from 6 to 10 carbon atoms which may have from 1 to 3 substituents α mentioned below in the aryl moiety, (xiii) an aralkyl group having from 7 to 12 carbon atoms which may have from 1 to 3 substituents α mentioned below in the aryl moiety, (xiv) an aralkyloxy group having from 7 to 12 carbon atoms which may have from 1 to 3 substituents α mentioned below in the aryl moiety, (xv) an aralkylthio group having from 7 to 12 carbon atoms which may have from 1 to 3 substituents α mentioned below in the aryl moiety, (xvi) an aralkylamino group having from 7 to 12 carbon atoms which may have from 1 to 3 substituents α mentioned below in the aryl moiety, (xvii) a 1-pyrrolyl group, (xviii) a 1-pyrrolidinyl group, (xix) a 1-imidazolyl group, (xx) a piperidino group or (xxi) a moipholino group, X represents an aryl group having from 6 to 10 carbon atoms which may have from 1 to 3 substituents α mentioned below, or a 5- to 10-membered monocyclic or bicyclic hetero- aromatic group which may have from 1 to 3 substituents α mentioned below containing from 1 to 4 hetero atoms selected from the group consisting of oxygen, nitrogen and sulfur atoms, The substituent α represents (i) a straight- or branched-chain alkyl group having from 1 to 6 carbon atoms, (ii) a straight- or branched-chain halogenated alkyl group having from 1 to 4 carbon atoms, (iii) a hydroxyl group, (iv) a straight- or branched-chain aliphatic acyloxy group having from 1 to 4 carbon atoms, (v) a straight- or branched-chain alkoxy group having from 1 to 4 carbon atoms, (vi) a straight- or branched-chain alkenedioxy group having from 1 to 4 carbon atoms, (vii) an aralkyloxy group having from 7 to 12 carbon atoms, (viii) a straight- or branched-chain alkylthio group having from 1 to 4 carbon atoms, (ix) a straight- or branched-chain alkylsulfonyl group having from 1 to 4 carbon atoms, (x) a halogen atom, (xi) a nitro group, (xii) a straight- or branched-chain dialkylamino group in which the alkyl groups are the same as or different from each other and each has from 1 to 4 carbon atoms, (xiii) an aralkyl group having from 7 to 12 carbon atoms, (xiv) an aryl group having from 6 to 10 carbon atoms (the aryl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xv) an aryloxy group having from 6 to 10 carbon atoms (the aryl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xvi) an arylthio group having from 6 to 10 carbon atoms (the aryl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xvii) an arylsulfonyl group having from 6 to 10 carbon atoms (the aryl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xviii) an arylsulfonylamino group having from 6 to 10 carbon atoms (the aryl moiety may be substituted by straight- or branched-chain alkyl having form 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms, and the nitrogen atom of the amino moiety may be substituted by straight- or branched-chain alkyl having from 1 to 6 carbon atoms), (xix) a 5- to 10-membered monocyclic or bicyclic hetero aromatic group containing from 1 to 4 hetero atoms selected from the group consisting of oxygen, nitrogen and sulfur atoms, (xx) a 5- to 10-membered monocyclic or bicyclic hetero aromatic oxy group containing from 1 to 4 hetero atoms selected from the group consisting of oxygen, nitrogen and sulfur atoms, (xxi) a 5- to 10-membered monocyclic or bicyclic hetero aromatic thio group containing from 1 to 4 hetero atoms selected from the group consisting of oxygen, nitrogen and sulfur atoms, (xxii) a 5- to 10-membered monocyclic or bicyclic hetero-aromatic sulfonyl group containing from 1 to 4 hetero atoms selected from the group consisting of oxygen, nitrogen and sulfur atoms, or (xxiii) a 5- to 10-membered monocyclic or bicyclic hetero aromatic sulfonylamino group containing from 1 to 4 hetero atoms selected from the group consisting of oxygen, nitrogen and sulfur atoms (the nitrogen atom of the amino moiety may be substituted by straight- or branched-chain alkyl having from 1 to 6 carbon atoms), and Y represents an oxygen atom, a sulfur atom or a group of formula: >N—$R^4$ (wherein $R^4$ represents a hydrogen atom, a straight- or branched-chain alkyl group having from 1 to 6 carbon atoms or a straight- or branched-chain aliphatic acyl group or aromatic acyl group having from 1 to 8 carbon atoms).

In the case where $R^1$, $R^3$, W and $R^4$ represent a straight or branched-chain alkyl group having from 1 to 6 carbon atoms, the alkyl group includes, for example, the methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl group, preferably a straight- or branched-chain alkyl group having from 1 to 4 carbon atoms, more preferably the methyl, ethyl, propyl, isopropyl, butyl or isobutyl group. $R^1$, $R^3$ and $R^4$ are still more preferably a straight- or branched-chain alkyl having from 1 to 3 carbon atoms, most preferably an alkyl having one or two carbon atoms. W is still more preferably the propyl or butyl group, most preferably the butyl group.

In the case where $R^2$ represents a straight- or branched-chain alkylene group having from 2 to 6 carbon atoms, the alkylene group includes, for example, the ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group, preferably a straight- or branched-chain alkylene group having from 2 to 5 carbon atoms, more preferably a straight- or branched-chain alkylene group having from 2 to 4 carbon atoms, still more preferably the ethylene, methylethylene or trimethylene group, most preferably the ethylene group.

In the case where Z represents a straight- or branched-chain alkylene group having from 1 to 6 carbon atoms, the alkylene group includes, for example, the methylene, ethylene, methylethylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene or hexamethylene group, preferably a straight- or branched-chain alkylene group having from 1 to 4 carbon atoms (for example, the methylene, ethylene, methylethylene, ethylethylene, trimethylene, 1-methyltrimethylene or 2-methyltrimethylene group), more preferably an alkylene group having one or two carbon atoms, most preferably the methylene group.

In the case where $R^3$ and W represent a straight- or branched-chain alkoxy group having from 1 to 4 carbon atoms, the alkoxy group includes, for example, the methoxy, ethoxy, propoxy, isopropoxy, butoxy, s-butoxy, t-butoxy or isobutoxy group. $R^3$ is preferably an alkoxy group having one or two carbon atoms, most preferably the methoxy group, and W is preferably an alkoxy group having from 1 to 3 carbon atoms, most preferably the ethoxy group.

In the case where $R^3$ and W represent a straight- or branched-chain alkylthio group having from 1 to 4 carbon atoms, the alkylthio group includes, for example, the methylthio, ethylthio, propylthio, isopropylthio, butylthio, s-butylthio, t-butylthio or isobutylthio group. $R^3$ is preferably an alkylthio group having one or two carbon atoms, most preferably the methylthio group, and W is preferably an alkylthio group having from 1 to 3 carbon atoms, most preferably the methylthio group.

In the case where $R^3$ represents a halogen atom, the halogen atom includes the fluorine, chlorine, bromine or iodine atom, preferably the fluorine, chlorine or bromine atom, more preferably the fluorine or chlorine atom.

In the case where W represents a straight- or branched-chain monoalkylamino group having from 1 to 4 carbon atoms, the monoalkylamino group includes, for example, the methylamino, ethylamino, propylamino, isopropylamino, butylamino, s-butylaamino, t-butylamino or isobutylamino group, preferably a straight- or branched-chain monoalkylamino group having from 1 to 3 carbon atoms, most preferably the ethylamino group.

In the case where $R^3$ and W represent a straight- or branched-chain dialkylamino group in which the alkyl groups are the same as or different from each other and each has from 1 to 4 carbon atoms, the dialkylamino group includes, for example, the dimethylamino, diethylamino, dipropylamino, diisopropylamino, dibutylamino, N-methyl-N-ethyl amino or N-ethyl-N-isopropyl amino group, preferably the dimethylamino or diethylamino group, most preferably the diethylamino group.

In the case where $R^3$ and W represent an aryl group having from 6 to 10 carbon atoms which may have from 1 to 3 substituents α mentioned below, the unsubstituted aryl group includes, for example, the phenyl and naphthyl groups, preferably the phenyl group. The substituted aryl group includes, for example, the 2-methylphenyl, 3-methylphenyl, 4-methylphenyl, 4-ethylphenyl, 4-propylphenyl, 4-isopropylphenyl, 4-trifluorobutylphenyl, 4-hydroxyphenyl, 4-acetoxyphenyl, 4-methoxyphenyl, 3,4-methylenedioxyphenyl, 4-benzyloxyphenyl, 4-methylthiophenyl, 4-methylsulfonylphenyl, 4-fluorophenyl, 4-chlorophenyl, 4-nitrophenyl, 4-dimethylaminophenyl, 4-benzylphenyl, 4-biphenylyl, 4-phenoxyphenyl, 4-phenylthiophenyl, 4-phenylsulfonylphenyl, 4-phenylsulfonylaminophenyl, 4-(2-pyridyl)phenyl, 4-(2-pyridyloxy)phenyl, 4-(2-pyridylthio)phenyl or 4-(2-pyridylsulfonylamino)phenyl group, preferably the 4-methylphenyl, 4-ethylphenyl, 4-isopropylphenyl, 4-methoxyphenyl, 4-methylthiophenyl or 4-chlorophenyl group.

In the case where $R^3$ and W represent an aralkyl group having from 7 to 12 carbon atoms which may have from 1 to 3 substituents α mentioned below, the unsubstituted aralkyl group is a group in which the straight- or branched-chain alkyl group having from 1 to 4 carbon atoms is substituted by the above-mentioned aryl group and includes, for example, the benzyl, phenethyl, 3-phenylpropyl, 4-phenylbutyl, 1-naphthylmethyl or 2-naphthylmethyl group. $R^3$ is preferably the benzyl or phenethyl group, most preferably the benzyl group, and W is preferably the benzyl, phenethyl, 3-phenylpropyl or 4-phenylbutyl group, most preferably the phenethyl or 3-phenylpropyl group. The substituted aralkyl group includes, for example, 4-methylbenzyl, 4-trifluoromethylbenzyl, 4-methoxybenzyl, 3,4-methylenedioxybenzyl, 4-methylthiobenzyl, 4-methylsulfonylbenzyl, 4-fluorobenzyl, 4-chlorobenzyl, 2-(4-methylphenyl)ethyl, 2-(4-methoxyphenyl)ethyl, 3-(4-methylphenyl)propyl, 3-(4-methoxyphenyl)propyl, 4-(4-methylphenyl)butyl or 4-(4-methoxyphenyl)butyl group, preferably the 4-methylbenzyl or 2-(4-methylphenyl)ethyl group.

In the case where W represents an N-alkyl-N-arylamino group having a straight- or branched-chain alkyl having from 1 to 4 carbon atoms and an aryl having from 6 to 10 carbon atoms which may have from 1 to 3 substituents α mentioned below in the aryl moiety, the alkyl moiety of the unsubstituted N-alkyl-N-arylamino group includes, for example, methyl, ethyl, propyl, isopropyl, butyl, isobutyl, s-butyl or t-butyl group, preferably the methyl, ethyl, propyl, isopropyl, butyl or isobutyl group, most preferably the methyl or ethyl group. The aryl moiety includes, for example, the phenyl or naphthyl group, preferably the phenyl group. The example of the unsubstituted N-alkyl-N-arylamino group includes, for example, N-methyl-N-phenylamino, N-ethyl-N-phenylamino, N-propyl-N-phenylamino, N-isopropyl-N-phenylamino, N-butyl-N-phenylamino, N-isobutyl-N-phenylamino or N-methyl-N-naphthylamino group, preferably the N-methyl-N-phenylamino or N-ethyl-N-phenylamino group, most preferably the N-ethyl-N-phenylamino group. The substituted N-alkyl-N-arylamino group includes, for example, N-methyl-N-(4-methylphenyl)amino, N-ethyl-N-(4-methylphenyl)amino, N-methyl-N-(4-methoxyphenyl)amino or N-ethyl-N-(4-methoxyphenyl)amino group, preferably the N-methyl-N-(4-methylphenyl)amino or N-ethyl-N-(4-methylphenyl)amino group.

In the case where W represents an aryloxy group having from 6 to 10 carbon atoms which may have 1 to 3 substituents α mentioned below in the aryl moiety, the unsubstituted aryloxy group includes, for example, the phenoxy or naphthyloxy group, preferably the phenoxy group. The substituted aryloxy group includes, for example, the 4-methylphenoxy, 4-ethylphenoxy, 4-propylphenoxy, 4-isopropylphenoxy, 4-methoxyphenoxy, 4-ethoxyphenoxy, 4-methylthiophenoxy, 4-ethylthiophenoxy, 4-biphenylyloxy or 4-methylsulfonylphenoxy group, preferably the 4-methylphenoxy, 4-ethylphenoxy or 4-isopropylphenoxy group.

In the case where W represents an arylthio group having from 6 to 10 carbon atoms which may have from 1 to 3 substituents α mentioned below in the aryl moiety, the unsubstituted arylthio group includes, for example, the phenylthio or naphthylthio group, preferably the phenylthio group. The substituted arylthio group includes, for example, the 4-methylphenylthio, 4-ethylphenythio, 4-propylphenylthio, 4-isopropylphenylthio, 4-methoxyphenylthio, 4-ethoxyphenylthio, 4-methylthiophenylthio, 4-ethylthiophenylthio, 4-biphenylylthio or 4-methylsulfonylphenylthio group, preferably the 4-methylphenylthio, 4-ethylphenylthio or 4-isopropylphenylthio group.

In the case where W represents an arylamino group having from 6 to 10 carbon atoms which may have 1 to 3 substituents α mentioned below in the aryl moiety, the unsubstituted arylamino group includes, for example, the phenylamino or naphthylamino group, preferably the phenylamino group. The substituted arylamino group includes, for example, the 4-methylphenylamino, 4-ethylphenylamino, 4-propylphenylamino, 4-isopropylphenylamino, 4-methoxyphenylamino, 4-ethoxyphenylamino, 4-methylthiophenylamino, 4-ethylthiophenylamino, 4-biphenylylamino or 4-methylsulfonylphenylamino group, preferably the 4-methylphenylamino, 4-ethylphenylamino or 4-isopropylphenylamino group.

In the case where W represents an aralkyloxy group having from 7 to 12 carbon atoms which may have 1 to 3 substituents α mentioned below in the aryl moiety, the unsubstituted aralkyloxy group is a group in which a straight- or branched-chain alkyloxy group having from 1 to 4 carbon atoms is substituted by the above-mentioned aryl group and includes, for example, the benzyloxy, phenethyloxy, 3-phenylpropyloxy, 4-phenylbutyloxy, 1-naphthylmethyloxy or 2-naphthylmethyloxy group, preferably the benzyloxy or phenethyloxy group, most preferably the benzyloxy group. The substituted aralkyloxy group includes, for example, the 4-methylbenzyloxy, 4-methoxybenzyloxy, 2-(4-methylphenyl)ethoxy, 2-(4-methoxyphenyl)ethoxy, 3-(4-methylphenyl)propoxy, 3-(4- methoxyphenyl)propoxy, 4-(4-methylphenyl)butoxy or 4-(4-methoxyphenyl)butoxy group, preferably the 4-methylbenzyloxy or 2-(4-methylphenyl)ethoxy group.

In the case where W represents an aralkylthio group having from 7 to 12 carbon atoms which may have 1 to 3 substituents α mentioned below in the aryl moiety, the unsubstituted aralkylthio group is a group in which a straight- or branched-chain alkylthio group having from 1 to 4 carbon atoms is substituted by the above-mentioned aryl group and includes, for example, the benzylthio, phenethylthio, 3-phenylpropylthio, 4-phenylbutylthio, 1-naphthylmethylthio or 2-naphthylmethylthio group, preferably the benzylthio or phenethylthio group, most preferably the benzylthio group. The substituted aralkylthio group includes, for example, the 4-methylbenzylthio, 4-methoxybenzylthio, 2-(4-methylphenyl)ethylthio, 2-(4-methoxyphenyl)ethylthio, 3-(4-methylphenyl)propylthio, 3-(4-methoxyphenyl)propylthio, 4-(4-methylphenyl)butylthio or 4-(4-methoxyphenyl)butylthio group, preferably the 4-methylbenzylthio or 2-(4-methylphenyl)ethylthio group.

In the case where W represents an aralkylamino group having from 7 to 12 carbon atoms which may have 1 to 3 substituents α mentioned below in the aryl moiety, the unsubstituted aralkylamino group is a group in which a straight- or branched-chain alkylamino group having from 1 to 4 carbon atoms is substituted by the above-mentioned aryl group and includes, for example, the benzylamino, phenethylamino, 3-phenylpropylamino, 4-phenylbutylamino, 1-naphthylmethylamino or 2-naphthylmethylamino group, preferably the benzylamino or phenethylamino group, most preferably the benzylamino group. The substituted aralkylamino group includes, for example, 4-methylbenzylamino, 4-methoxybenzylamino, 2-(4-methylphenyl)ethylamino, 2-(4-methoxyphenyl) ethylamino, 3-(4-methylphenyl)propylamino, 3-(4-methoxyphenyl)propylamino, 4-(4-methylphenyl) butylamino or 4-(4-methoxyphenyl)butylamino group, preferably the 4-methylbenzylamino or 2-(4-methylphenyl) ethylamino group.

In the case where $R^4$ represents a straight- or branched-chain aliphatic acyl group having from 1 to 8 carbon atoms or an aromatic acyl group, the acyl group includes, for example, the formyl, acetyl, propionyl, butyryl, pentanoyl, hexanoyl, heptanoyl or octanoyl group, or the benzoyl or p-toluoyl group, preferably a straight- or branched-chain alkanoyl group having from 1 to 8 carbon atoms, more preferably a straight- or branched-chain alkanoyl group having from 2 to 5 carbon atoms, most preferably the acetyl group.

In the case where X represents an aryl group having from 6 to 10 carbon atoms which may have 1 to 3 substituents α mentioned below, the unsubstituted aryl group includes, for example, the phenyl or naphthyl group, preferably the phenyl group. In the case where X represents the aryl group which is substituted by from 1 to 3 substituents α mentioned below, the number of the substituents is preferably one or two, more preferably one.

In the case where X represents a 5- to 10-membered monocyclic or bicyclic hetero-aromatic group containing from 1 to 4 hetero atoms selected from the group consisting of oxygen, nitrogen and sulfur atoms which may have from 1 to 3 substituents α mentioned below, the unsubstituted hetero-aromatic group comprises monocyclic ring or bicyclic ring system. In the case where the group is of a bicyclic ring system, one of them at least is a heterocyclic ring. In the case of a bicyclic ring system, the group is a condensed ring, and there is a case where one ring is a heterocyclic ring and the other is a carbocyclic ring or a case where both of the rings are heterocyclic rings. The heterocyclic ring is a 5- or 6-membered ring and contains from 1 to 4 hetero atoms selected from the group consisting of nitrogen, oxygen and sulfur atoms. The carbocyclic ring is an aryl group having from 6 to 10 carbon atoms. The monocyclic ring system and the bicyclic ring system are referred to as monocyclic hetero aromatic group and condensed hetero aromatic ring group, respectively. In the case of a ring having four hetero atoms, it is preferred that four hetero atoms are all nitrogen atoms with no hetero atom to be selected from the group consisting of oxygen and sulfur atoms. In the case of a ring having three hetero atoms, it is preferred that three, two or one of them is a nitrogen atom and one or two hetero atoms are selected from the group consisting of oxygen and sulfur atoms. In the case of a ring having two hetero atoms, it is preferred that two, one or none of them is a nitrogen atom and none, one or two of the hetero atoms are selected from the group consisting of oxygen and sulfur atoms. In the case where X represents the hetero aromatic group which is substituted by from 1 to 3 substituents α mentioned below, the number of the substituents is preferably one or two, more preferably one.

The unsubstituted monocyclic hetero aromatic group includes, for example, a pyrrolyl group such as 2-pyrrolyl and 3-pyrrolyl; a furyl group such as 2-furyl and 3-furyl; a thienyl group such as 2-thienyl and 3-thienyl; a pyridyl group such as 2-pyridyl, 3-pyridyl and 4-pyridyl; an imidazolyl group such as 2-imidazolyl and 4-imidazolyl; a pyrazolyl group such as 3-pyrazolyl and 4-pyrazolyl; an oxazolyl group such as 2-oxazolyl, 4-oxazolyl and 5-oxazolyl; an isoxazolyl group such as 3-isoxazolyl, 4-isoxazolyl and 5-isoxazolyl; a thiazolyl group such as 2-thiazolyl, 4-thiazolyl and 5-thiazolyl; an isothiazolyl group such as 3-isothiazolyl, 4-isothiazolyl and 5-isothiazolyl; a triazolyl group such as 1,2,3-triazol-4-yl and 1,2,4-triazol-3-yl; a thiadiazolyl group such as 1,3,4-thiadiazol-2-yl; an oxadiazolyl group such as 1,3,4-oxadiazol-2-yl; a tetrazolyl group such as 5-tetrazolyl; a pyridazinyl group such as 3-pyridazinyl and 4-pyridazinyl; a pyrimidinyl group such as 2-pyrimidinyl, 4-pyrimidinyl and 5-pyrimidinyl; a pyrazinyl group; an oxazinyl group such as 1,4-oxazin-2-yl and 1,4-oxazin-3-yl; a thiazinyl group such as 1,4-thiazin-2-yl and 1,4-thiazin-3-yl.

The unsubstituted condensed aromatic heterocyclic ring group includes, for example, an indolyl group such as indol-2-yl, indol-3-yl, indol-4-yl, indol-5-yl, indol-6-yl and indol-7-yl; an indazolyl group such as indazol-2-yl, indazol-3-yl, indazol-4-yl, indazol-5-yl, indazol-6-yl and indazol-7-yl; a benzofuranyl group such as benzofuran-2-yl, benzofuran-3-yl, benzofuran-4-yl, benzofuran-5-yl, benzofuran-6-yl and benzofuran-7-yl; a benzothiophenyl group such as benizothiophen-2-yl, benzothiophen-3-yl, benzothiophen-4-yl, benzothiophen-5-yl, benzothiophen-6-yl and benzothiophen-7-yl; a benzimidazolyl group such as benzimidazol-2-yl, benzimidazol-4-yl, benzimidazol-5-yl, benzimidazol-6-yl and benzimidazol-7-yl; a benzoxazolyl group such as benzoxazol-2-yl, benzoxazol-4-yl, benzoxazol-5-yl, benzoxazol-6-yl and benzoxazol-7-yl; a benzothiazolyl group such as benzothiazol-2-yl, benzothiazol-4-yl, benzothiazol-5-yl, benzothiazol-6-yl and benzothiazol-7-yl; a quinolyl group such as 2-quinolyl, 3-quinolyl, 4-quinolyl, 5-quinolyl, 6-quinolyl, 7-quinolyl and 8-quinolyl; an isoquinolyl group such as 1-isoquinolyl, 3-isoquinolyl, 4-isoquinolyl and 8-isoquinolyl; a benzoxazinyl group such as 1,4-benzoxazin-2-yl and 1,4-benzoxazin- 3-yl; a benzothiazinyl group such as 1,4-benzothiazin-2-yl and 1,4-benzothiazin-3-yl; a pyrrolo[2,3-b]pyridyl group such as pyrrolo[2,3-b]pyrid-2-yl and pyrrolo[2,3-b]pyrid-3-yl; a furo[2,3-b]pyridyl group such as furo[2,3-b]pyrid-2-yl and furo[2,3-b]pyrid-3-yl; a thieno[2,3-b]pyridyl group such as thieno[2,3-b]pyrid-2-yl and thieno[2,3-b]pyrid-3-yl; a naphthyridinyl group such as 1,8-naphthyridin-2-yl, 1,8-naphthyridin-3-yl, 1,5-naphthyridin-2-yl, 1,5-naphthyridin-3-yl; an imidazopyridyl group such as imidazo[4,5-b]pyrid-2-yl and imidazo[4,5-b]pyrid-5-yl; an oxazolopyridyl group such as oxazolo[4,5-b]pyrid-2-yl and oxazolo[5,4-b]pyrid-2-yl; and a thiazolopyridyl group such as thiazolo[4,5-b]pyrid-2-yl and thiazolo[4,5-c]pyrid-2-yl.

The monocyclic hetero aromatic group is preferably a 5- or 6-membered ring group having from 1 to 3 hetero atoms selected from the group consisting of nitrogen, oxygen and sulfur atoms, and includes the pyrrolyl, furyl, thienyl, pyridyl, imidazolyl, pyrazolyl, oxazolyl, isoxazolyl, thiazolyl, triazolyl, thiadiazolyl, oxadiazolyl, pyridazinyl, pyrimidinyl and pyrazinyl groups as exemplified above. The condensed hetero aromatic group is preferably the condensed-ring group of a benzene ring with the 5- or 6-membered hetero aromatic group having from 1 to 3 hetero atoms selected from the group consisting of nitrogen, oxygen and sulfur atoms mentioned above, and includes the indolyl, benzofuranyl, benzothiophenyl, benzoimidazolyl, benzoxazolyl, benzothiazolyl, quinolyl aid isoquinolyl groups as exemplified above.

Preferable hetero aromatic groups include the imidazolyl, oxazolyl, pyridyl, indolyl, quinolyl or isoquinolyl group, the pyridyl, indolyl, quinolyl or isoquinolyl group is more preferable, the pyridyl, quinolyl or isoquinolyl group is still more preferable, most preferable group is the pyridyl group.

In the case where the above-mentioned X represents an aryl group having from 6 to 10 carbon atoms or a 5- to 10-membered monocyclic or bicyclic hetero aromatic group containing from 1 to 4 hetero atoms selected from the group consisting of oxygen, nitrogen and sulfur atoms, the aryl group and the hetero aromatic group may have from 1 to 3 substituents α mentioned above.

In the case where the substituent α represents the straight- or branched-chain alkyl group having from 1 to 6 carbon atoms, the straight- or branched-chain alkoxy group having from 1 to 4 carbon atoms, the straight- or branched-chain alkylthio group having from 1 to 4 carbon atoms, the halogen atom or the straight- or branched-chain dialkylamino group in which the alkyl groups are the same as or different from each other and each has from 1 to 4 carbon atoms, these groups include the same groups as exemplified in the above-mentioned $R^3$.

In the case where the substituent α represents the straight- or branched-chain halogenated alkyl group having from 1 to 4 carbon atoms, the halogenated alkyl group includes, for example, the chloromethyl, bromomethyl, fluoromethyl, iodomethyl, difluoromethyl, trifluoromethyl, pentafluoroethyl, 2,2,2-trifluoroethyl, 2,2,2-trichloroethyl or trichloromethyl group, preferably a methyl group having from 1 to 3 fluorine atoms, most preferably the trifluoromethyl group.

In the case where the substituent α represents a straight- or branched-chain aliphatic acyloxy group having from 1 to 4 carbon atoms, the acyloxy group includes, for example, the formyloxy, acetoxy, propionyloxy, butyryloxy, acroyloxy, methacryloyloxy or crotonoyloxy group, preferably the alkanoyloxy groups, more preferably an alkanoyloxy groups having one or two carbon atoms, most preferably the acetoxy group.

In the case where the substituent α represents a straight- or branched-chain alkylenedioxy group having from 1 to 4 carbon atoms, the alkylenedioxy group includes, for example, the methylenedioxy, ethylenedioxy, trimethylenedioxy, tetramethylenedioxy or propylenedioxy group, preferably the methylenedioxy or ethylenedioxy group, most preferably the methylenedioxy group.

In the case where the substituent α represents an aralkyloxy group having from 7 to 12 carbon atoms, the aralkyloxy group is an aralkyloxy group in which the aralkyl moiety is the same aralkyl as mentioned in $R^3$ and includes, for example, the benzyloxy, phenethyloxy, 3-phenylpropoxy, 4-phenylbutoxy, 1-naphthylmethoxy or 2-naphthylmethoxy group, preferably the benzyloxy, phenethyloxy, 1-naphthylmethoxy or 2-naphthylmethoxy group, most preferably the benzyloxy group.

In the case where the substituent α represents a straight- or branched-chain alkylsulfonyl group having from 1 to 4 carbon atoms, the alkylsulfonyl group includes, for example, the methylsulfonyl, ethylsulfonyl, propylsulfonyl, isopropylsulfonyl, butylsulfonyl, isobutylsulfonyl, sec-butylsulfonyl or t-butylsulfonyl group, preferably the methylsulfonyl, ethylsulfonyl or isopropylsulfonyl group, more preferably an alkylsulfonyl group having one or two carbon atoms.

In the case where the substituent α represents an aralkyl group having from 7 to 12 carbon atoms, the aralkyl group is that having the same meaning as defined in $R^3$ and includes, for example, the benzyl, phenethyl, 3-phenylpropyl, 4-phenylbutyl, 1-naphthylmethyl or 2-naphthylmethyl group, preferably the benzyl, phenethyl, 1-naphthylmethyl or 2-naphthylmethyl group, most preferably the benzyl group.

In the case where the substituent α represents an aryl group having from 6 to 10 carbon atoms (the aryl group may be substituted by a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy of the substituent of the aryl group have the same meanings as defined above in the substituent of $R^3$ and X.

The aryl group includes, for example, the phenyl, 1-naphthyl, 2-naphthyl, 4-methylphenyl, 4-trifluoromethylphenyl, 4-methoxyphenyl, 3-ethoxyphenyl, 4-fluorophenyl, 4-chlorophenyl, 3-bromophenyl or 3,4-methylenedioxyphenyl group, preferably the phenyl, 4-methoxyphenyl or 3,4-methylenedioxyphenyl group.

In the case where the substituent α represents an aryloxy group having from 6 to 10 carbon atoms (the aryl moiety may be substituted by a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The aryloxy group includes, for example, the phenoxy, 1-naphthoxy, 2-naphthoxy, 4-methylphenoxy, 4-trifluoromethylphenoxy, 4-methoxyphenoxy 3-ethoxyphenoxy, 4-chlorophenoxy, 3-bromophenoxy or 3,4-methylenedioxyphenoxy group, preferably the phenoxy group.

In the case where the substituent α represents an arylthio group having from 6 to 10 carbon atoms (the aryl moiety may be substituted by a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The arylthio group includes, for example, the phenylthio, 4-methylphenylthio, 4-trifluoromethylphenylthio, 4-methoxyphenylthio, 3-ethoxyphenylthio, 4-chlorophenylthio, 3-bromophenylthio, 3,4-methylenedioxyphenylthio, 1-naphthylthio or 2-naphthylthio group, preferably the phenylthio group.

In the case where the substituent α represents an arylsulfonyl group having from 6 to 10 carbon atoms (the aryl moiety may be substituted by a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms), the alkyl, halogenated alkyl, alkoxy, halogen and alkylenedioxy have the same meanings as defined above.

The arylsulfonyl group includes, for example, the phenylsulfonyl, 4-methylphenylsulfonyl, 4-trifluoromethylphenylsulfonyl, 4-methoxyphenylsulfonyl, 3-ethoxyphenylsulfonyl, 4-chlorophenylsulfonyl, 3-bromophenylsulfonyl, 3,4-methylenedioxyphenylsulfonyl, 1-naphthylsulfonyl or 2-naphthylsulfonyl group, preferably the phenylsulfonyl group.

In the case where the substituent α represents an arylsulfonylamino group having from 6 to 10 carbon atoms (the aryl moiety may be substituted by a straight- or branched-chain alkyl having from 1 to 6 carbon atoms, a straight- or branched-chain halogenated alkyl having from 1 to 4 carbon atoms, a straight- or branched-chain alkoxy having from 1 to 4 carbon atoms, a halogen or a straight- or branched-chain alkylenedioxy having from 1 to 4 carbon atoms and the nitrogen atom of the amino moiety may be substituted by a straight- or branched-chain alkyl having from 1 to 6 carbon atoms), the alkyl, halogenated alkyl, alkoxy, halogen and alkylenedioxy have the same meanings as defined above.

The arylsulfonylamino group includes, for example, the phenylsulfonylamino, 4-methylphenylsulfonylamino, 4-trifluoromethylphenylsulfonylamino, 4-methoxyphenylsulfonylamino, 3-ethoxyphenylsulfonylamino, 4-chlorophenylsulfonylamino, 3-bromophenylsulfonylamino, 3,4-methylenedioxyphenylsulfonylamino, N-methylphenylsulfonylamino, 1-naphthylsulfonylamino, 2-naphthylsulfonylamino or N-methylnaphthylsulfonylamino group, preferably the phenylsulfonylamino or N-methylphenylsulfonylamino group.

In the case where the substituent α represents a 5- to 10-membered monocyclic or bicyclic hetero aromatic group containing from 1 to 4 hetero atoms selected from the group consisting of oxygen, nitrogen and sulfur atoms, the group can be, for example, the furyl, thienyl, oxazolyl, isoxazolyl, thiazolyl, imidazolyl, quinolyl, isoquinolyl, indolyl or pyridyl group, preferably the imidazolyl, quinolyl or pyridyl group, most preferably the pyridyl group.

In the case where the substituent α represents a 5- to 10-membered monocyclic or bicyclic hetero aromatic oxy group containing from 1 to 4 hetero atoms selected from the group consisting of oxygen, nitrogen and sulfur atoms, the hetero aromatic oxy group includes, for example, the furyloxy, thienyloxy, oxazolyloxy, isoxazolyloxy, thiazolyloxy, imidazolyloxy, quinolyloxy, isoquinolyloxy, indolyloxy or pyridyloxy group, preferably the isoxazolyloxy or pyridyloxy group, most preferably the pyridyloxy group.

In the case where the substituent α represents a 5- to 10-membered monocyclic or bicyclic hetero aromatic thio group containing from 1 to 4 hetero atoms selected from the group consisting of oxygen, nitrogen and sulfur atoms, the hetero aromatic thio group includes, for example, the furylthio, thienylthio, oxazolylthio, isoxazolylthio, thiazolylthio, imidazolylthio, quinolylthio, isoquinolylthio, indolylthio or pyridylthio group, preferably the isoxazolylthio or pyridylthio group, most preferably the pyridylthio group.

In the case where the substituent α represents a 5- to 10-membered monocyclic or bicyclic hetero aromatic sulfonyl group containing from 1 to 4 hetero atoms selected from the group consisting of oxygen, nitrogen and sulfur atoms, the hetero aromatic sulfonyl group includes, for example, the furylsulfonyl, thienylsulfonyl, oxazolylsulfonyl, isoxazolylsulfonyl, thiazolylsulfonyl, imidazolylsulfonyl, quinolylsulfonyl, isoquinolylsulfonyl, indolylsulfonyl or pyridylsulfonyl group, preferably the imidazolylsulfonyl, isoxazolylsulfonyl or pyridylsulfonyl group, most preferably the pyridylsulfonyl group.

In the case where the substituent α represents a 5- to 10-membered monocyclic or bicyclic hetero aromatic sulfonylamino group containing from 1 to 4 hetero atoms selected from the group consisting of oxygen, nitrogen and sulfur atoms (the nitrogen atom of the amino moiety may be substituted by straight- or branched-chain alkyl having from 1 to 6 carbon atoms), the hetero aromatic sulfonylamino group includes, for example, the furylsulfonylamino, thienylsulfonylamino, oxazolylsulfonylamino, isoxazolylsulfonylamino, thiazolylsulfonylamino, imidazolylsulfonylamino, N-methylimidazolylsulfonylamino, quinolylsulfonylamino, isoquinolylsulfonylamino, indolylsulfonylamino, pyridylsulfonylamino or N-methylpyridlylsulfonylamino group, preferably the imidazolylsulfonylamino, N-methylimidazolylsulfonylamino, pyridylsulfonylamino or N-methylpyridylsulfonylamino group, more preferably the pyridylsulfonylamino or N-methylpyridylsulfonylamino group.

Therefore, in the case where X represents a substituted or unsubstituted aryl group having from 6 to 10 carbon atoms or a substituted or unsubstituted 5- to 10-membered monocyclic or bicyclic hetero aromatic group containing from 1 to 4 hetero atoms selected from the group consisting of oxygen, nitrogen and sulfur atoms, preferable examples include the phenyl, 1-naphthyl, 2-naphthyl, m-tolyl, p-tolyl, 3-ethylphenyl, 4-ethylphenyl, 3-isopropylphenyl, 4-isopropylphenyl, 3-t-butylphenyl, 4-t-butylphenyl, 4-chloromethylphenyl, 4-bromomethylphenyl, 4-fluoromethylphenyl, 4-iodomethylphenyl, 3-difluoromethylphenyl, 4-trifluoromethylphenyl, 4-pentafluoroethylphenyl, 4-trichloromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, phenethyloxyphenyl, 1-naphthylmethoxyphenyl, 3-methylthiophenyl, 4-methylthiophenyl, 3-ethylthiophenyl, 4-ethylthiophenyl, 3-isopropylthiophenyl, 4-isopropylthiophenyl, 3-methylsulfonylphenyl, 4-methylsulfonylphenyl, 3-ethylsulfonylphenyl, 4-ethylsulfonylphenyl, 3-isopropylsulfonylphenyl, 4-isopropylsulfonylphenyl, 3-chlorophenyl, 4-chlorophenyl, 3-bromophenyl, 4-bromophenyl, 4-nitrophenyl, 4-aminophenyl, 3-methylaminophenyl, 4-ethylaminophenyl, 3-propylaminophenyl, 4-butylaminophenyl, 3-dimethylaminophenyl, 4-diethylaminophenyl, 3-dipropylaminophenyl, 4-dibutylaminophenyl, 3-benzylphenyl, 4-benzylphenyl, 3-phenethylphenyl, 4-(1-naphthylmethyl)phenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 3-(4-methoxyphenyl) phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl) phenyl, 4-(3-chlorophenyl)phenyl, 4-(4-chlorophenyl) phenyl, 4-(3-bromophenyl)phenyl, 4-(4-bromophenyl) phenyl, 3-(3,4-methylenedioxyphenyl)phenyl, 4-(3,4-methylenedioxyphenyl)phenyl, 3-benzylphenyl, 4-benzylphenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino) phenyl, 3-(N-methylphenylsulfonylamino)phenyl, 4-(N-methylphenylsulfonylamino)phenyl, 3-(imidazol-1-yl) phenyl, 4-(imidazol-1-yl)phenyl, 3-(1-methylimidazol-4-yl) phenyl, 4-(1-methylimidazol-4-yl)phenyl, 3-(2-furyl) phenyl, 4-(2-furyl)phenyl, 3-(2-thienyl)phenyl, 4-(2-thienyl)phenyl, 3-(3-thienyl)phenyl, 4-(3-thienyl)phenyl, 3-(2-pyridyl)phenyl, 4-(2-pyridyl)phenyl, 3-(3-pyridyl) phenyl, 4-(3-pyridyl)phenyl, 3-(4-pyridyl)phenyl, 4-(4-pyridyl)phenyl, 4-(imidazol-1-ylthio)phenyl, 4-(2-furylthio) phenyl, 4-(2-thienylthio)phenyl, 4-(2-pyridylthio)phenyl, 4-(4-pyridylthio)phenyl, 3-(2-pyridylsulfonyl)phenyl, 4-(2 -pyridylsulfonyl)phenyl, 3-(3-pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino) phenyl, 3-(N-methyl-3-pyridylsulfonylamino)phenyl, 4-(3-pyridylsulfonylamino)phenyl, 4-(N-methyl-3-pyridylsulfonylamino)phenyl, 3-(oxazol-2-yl)phenyl, 4-(oxazol-2-yl)phenyl, 3-(oxazol-4-yl)phenyl, 4-(oxazol-4-yl)phenyl, 3-(oxazol-5-yl)phenyl, 4-(oxazol-5-yl)phenyl, 3-(thiazol-2-yl)phenyl, 4-(thiazol-2-yl)phenyl, 3-(thiazol-4-yl)phenyl, 4-(thiazol-4-yl)phenyl, 3-(thiazol-5-yl)phenyl, 4-(thiazol-5-yl)phenyl, 1-methyl-2-pyrrolyl, 1-phenyl-2-pyrrolyl, 1-benzyl-2-pyrrolyl, 5-methyl-2-furyl, 5-phenyl-2-furyl, 5-methyl-2-thienyl, 5-phenyl-2-thienyl, 5-methyl-3-thienyl, 5-phenyl-3-thienyl, 1-methyl-3-pyrazolyl, 1-phenyl-3-pyrazolyl, 1-methyl-2-imidazolyl, 1-phenyl-2-imidazolyl, 1-methyl-4-imidazolyl, 1-phenyl-4-imidazolyl, 1-methyl-2-phenyl-4-imidazolyl, 1,5-dimethyl-2-phenyl-4-imidazolyl, 1,4-dimethyl-2-phenyl-5-imidazolyl, 4-oxazolyl, 5-oxazolyl, 2-methyl-4-oxazolyl, 2-phenyl-4-oxazolyl, 2-methyl-5-oxazolyl, 2-phenyl-5-oxazolyl, 4-methyl-2-phenyl-5-oxazolyl, 5-methyl-2-phenyl-4-oxazolyl, 4-thiazolyl, 5-thiazolyl, 2-methyl-4-thiazolyl, 2-phenyl-4-thiazolyl, 2-methyl-5-thiazolyl, 2-phenyl-5-thiazolyl, 4-methyl-2-phenyl-5-thiazolyl, 5-methyl-2-phenyl-4-thiazolyl, 1-methyl-3-pyrazolyl, 1-phenyl-3-pyrazolyl, 3-methyl-5-isoxazolyl, 3-phenyl-5-isoxazolyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-isopropylthio-5-pyridyl, 2-methylsulfonyl-5-pyridyl, 2-ethylsulfonyl-5-pyridyl, 2-isopropylsulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-methyl-4-pyrimidinyl, 2-phenyl-4-pyrimidinyl, 2-methoxy-4-pyrimidinyl, 2-ethoxy-4-pyrimidinyl, 2-isopropoxy-4-pyrimidinyl, 2-methylthio-4-pyrimidinyl, 2-ethylthio-4-pyrimidinyl, 2-isopropylthio-4-pyrimidinyl, 2-phenylthio-4-pyrimidinyl, 2-methylsulfonyl-4-pyrimidinyl, 2-ethylsulfonyl-4-pyrimidinyl, 2-isopropylsulfonyl-4-pyrimidinyl, 2-phenylsulfonyl-4-pyrimidinyl, 2-methyl-5-pyrimidinyl, 2-phenyl-5 -pyrimidinyl, 2-methoxy-5-pyrimidinyl, 2-ethoxy-5-pyrimidinyl, 2-isopropoxy-5-pyrimidinyl, 2-methylthio-5-pyrimidinyl, 2-ethylthio-5-pyrimidinyl, 2-isopropylthio-5-pyrimidinyl, 2-phenylthio-5-pyrimidinyl, 2-methylsulfonyl-5-pyrimidinyl, 2-ethylsulfonyl-5-pyrimidinyl, 2-isopropylsulfonyl-5-pyrimidinyl, 2-phenylsulfonyl-5-pyrimidinyl, 2-indolyl, 3-indolyl, 1-methyl-2-indolyl, 1-methyl-3-indolyl, 2-benzimidazolyl, 1-methyl-2-benzimidazolyl, 2-benzoxazolyl, 2-benzothiazolyl, 2-quinolyl, 3-quinolyl, 4-quinolyl, 1-isoquinolyl, 3-isoquinolyl, 4-isoquinolyl and 8-isoquinolyl groups, more preferably the phenyl, 1-naphthyl, 2-naphthyl, m-tolyl, p-tolyl, 3-ethylphenyl, 4-ethylphenyl, 3-isopropylphenyl, 4-isopropylphenyl, 4-trifluoromethylphenyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-methoxyphenyl, 4-methoxyphenyl, 3-ethoxyphenyl, 4-ethoxyphenyl, 3-isopropoxyphenyl, 4-isopropoxyphenyl, 3,4-methylenedioxyphenyl, benzyloxyphenyl, 3-methylthiophenyl, 4-methylthiophenyl, 3-ethylthiophenyl, 4-ethylthiophenyl, 3-methylsulfonylphenyl, 4-methylsulfonylphenyl, 3-ethylsulfonylphenyl, 4-ethylsulfonylphenyl, 3-chlorophenyl, 4-chlorophenyl, 3-benzylphenyl, 4-benzylphenyl, 3-biphenylyl, 4-biphenylyl, 3-(4-methylphenyl)phenyl, 4-(4-methylphenyl)phenyl, 3-(4-ethylphenyl)phenyl, 3-(4-trifluoromethylphenyl)phenyl, 4-(4-trifluoromethylphenyl)phenyl, 3-(4-methoxyphenyl) phenyl, 4-(4-methoxyphenyl)phenyl, 3-(2,4-dimethoxyphenyl)phenyl, 4-(2,4-dimethoxyphenyl)phenyl, 3-(2,5-dimethoxyphenyl)phenyl, 4-(2,5-dimethoxyphenyl) phenyl, 4-(3-chlorophenyl)pnenyl, 4-(4-chlorophenyl) phenyl, 3-(3,4-methylenedioxyphenyl)phenyl, 4-(3,4-methylenedioxyphenyl)phenyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino) phenyl, 3-(N-methylphenylsulfonylamino)phenyl, 4-(N-methylphenylsulfonylamino)phenyl, 3-(2-pyridyl)phenyl, 4-(2-pyridyl)phenyl, 3-(3-pyridyl)phenyl, 4-(3-pyridyl) phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3- pyridylsulfonyl)phenyl, 4-(3-pyridylsulfonyl)phenyl, 3-(2-pyridylsulfonylamino)phenyl, 3-(N-methyl-2-pyridylsulfonylamino)phenyl, 4-(2-pyridylsulfonylamino)phenyl, 4-(N-methyl-2-pyridylsulfonylamino)phenyl, 3-(3-pyridylsulfonylamino)phenyl, 3-(N-methyl-3-pyridylsulfonylamino)phenyl, 4-(3-pyridylsulfonylamino)phenyl, 4-(N-methyl-3-pyridylsulfonylamino)phenyl, 2-pyridyl, 3-pyridyl, 4-pyridyl, 3-methyl-5-pyridyl, 3-ethyl-5-pyridyl, 3-phenyl-5-pyridyl, 2-methyl-5-pyridyl, 2-ethyl-5-pyridyl, 2-phenyl-5-pyridyl, 2-hydroxy-5-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-isopropylthio-5-pyridyl, 2-methylsulfonyl-5-pyridyl, 2-ethylsulfonyl-5-pyridyl, 2-isopropylsulfonyl-5-pyridyl, 2-benzyl-5-pyridyl, 2-phenoxy-5-pyridyl, 2-phenylthio-5-pyridyl, 2-phenylsulfonyl-5-pyridyl, 2-phenylsulfonylamino-5-pyridyl, 2-(N-methylphenylsulfonylamino)-5-pyridyl, 3-methyl-6-pyridyl, 3-phenyl-6-pyridyl, 2-methyl-6-pyridyl, 2-phenyl-6-pyridyl, 2-quinolyl, 3-quinolyl, 4-quinolyl, 1-isoquinolyl, 3-isoquinolyl, 4-isoquinolyl and 8-isoquinolyl groups, most preferably the phenyl, m-tolyl, p-tolyl, 3-hydroxyphenyl, 4-hydroxyphenyl, 4-hydroxy-3,5-dimethylphenyl, 3-acetoxyphenyl, 4-acetoxyphenyl, 5-acetoxy-2-hydroxy-3,4,6-trimethylphenyl, 3-chlorophenyl, 4-chlorophenyl, 3-benzylphenyl, 4-benzylphenyl, 3-biphenylyl, 4-biphenylyl, 3-phenoxyphenyl, 4-phenoxyphenyl, 3-phenylthiophenyl, 4-phenylthiophenyl, 3-phenylsulfonylphenyl, 4-phenylsulfonylphenyl, 3-(phenylsulfonylamino)phenyl, 4-(phenylsulfonylamino)phenyl, 3-(N-methylphenylsulfonylamino)phenyl, 4-(N-methylphenylsulfonylamino)phenyl, 3-(2-pyridyl)phenyl, 4-(2-pyridyl)phenyl, 3-(3-pyridyl)phenyl, 4-(3-pyridyl)phenyl, 3-(4-pyridyl)phenyl, 4-(4-pyridyl)phenyl, 4-(2-pyridyloxy)phenyl, 4-(4-pyridyloxy)phenyl, 4-(2-pyridylthio)phenyl, 4-(4-pyridylthio)phenyl, 3-(2-pyridylsulfonyl)phenyl, 4-(2-pyridylsulfonyl)phenyl, 3-(3-pyridylsulfonyl)phenyl, 4-(3-pyridylsulfonyl)phenyl, 3-(2-pyridylsulfonylamino)phenyl, 2-pyridyl, 3-pyridyl, 4-pyridyl, 2-methoxy-5-pyridyl, 2-ethoxy-5-pyridyl, 2-isopropoxy-5-pyridyl, 2-benzyloxy-5-pyridyl, 2-methylthio-5-pyridyl, 2-ethylthio-5-pyridyl, 2-methylsulfonyl-5-pyridyl, 2-ethylsulfonyl-5-pyridyl, 2-benzyl-5-pyridyl, 2-phenyl-5-pyridyl, 3-phenyl-5-pyridyl, 2-phenyl-6-pyridyl, 3-phenyl-6-pyridyl, 2-phenoxy-5-pyridyl, 2-phenylthio-5-pyridyl, 2-phenylsulfonyl-5-pyridyl, 2-phenylsulfonylamino-5-pyridyl and 2-(N-methylphenylsulfonylamino)-5-pyridyl groups.

In the case where Y represents a group of formula >N—$R^4$ (wherein $R^4$ represents a hydrogen atom, a straight- or branched-chain alkyl group having from 1 to 6 carbon atoms (which has the same meaning as defined above in $R^3$) or a straight- or branched-chain aliphatic acyl group having from 1 to 8 carbon atoms (which includes alkanoyl groups having from 1 to 8 carbon atoms and alkenoyl groups having from 3 to 8 carbon atoms) or the aromatic acyl group), the group of formula >N—$R^4$ includes, for example, the imino, methylimino, ethylimino, propylimino, isopropylimino, butylimino, isobutylimino, s-butylimino, t-butylimino, pentylimino, 1-methylbutylimino, 2-methylbutylimino, 3-methylbutylimino, 1,1-dimethylpropylimino, 1,2-dimethylpropylimino, 2,2-dimethylpropylimino, 1-ethylpropylimino, hexylimino, 1-methylpentylimino, 2-methylpentylimino, 3-methylpentylimino, 4-methylpentylimino, 1,1-dimethylbutylimino, 1,2-dimethylbutylimino, 1,3-dimethylbutylimino, 2,2-dimethylbutylimino, 2,3-dimethylbutylimino, 3,3-dimethylbutylimino, 1-ethylbutylimino, 1,1,2-trimethylpropylimino, 1,2,2-trimethylpropylimino, acetylimino, propionylimino, butyrylimino, pentanoylimino, hexanoylimino, heptanoylimino, octanoylimino, benzoylimino or p-toluoylimino group, preferably the imino, straight- or branched-chain alkylimino having from 1 to 4 carbon atoms or acetylimino group, more preferably the imino, methylimino, ethylimino or acetylimino group.

The phenylalkylcarboxylic acid derivatives of formula (I) can be converted to an acid addition salt according to conventional methods when they have a basic group. Such a salt includes, for example, salts of hydrohalogenic acid such as hydrofluoric acid, hydrochloric acid, hydrobromic acid and hydroiodic acid; inorganic acid salts such as nitrate, perchlorate, sulfate and phosphate; salts of lower alkanesulfonic acid such as methanesulfonic acid, trifluoromethanesulfonic acid and ethanesulfonic acid; salts of arylsulfonic acid such as benzenesulfonic acid and p-toluenesulfonic acid; salts of amino acid such as glutamic acid and aspartic acid; and salts of carboxylic acid such as acetic acid, fumaric acid, tartaric acid, oxalic acid, maleic acid, malic acid, succinic acid, benzoic acid, mandelic acid, ascorbic acid, lactic acid, gluconic acid and citric acid, preferably the salts of hydrohalogenic acid.

Further, the compounds of formula (I) can be converted to a metal salt according to conventional methods when they have a carboxyl group. Such a salt includes, for example, salts of alkali metal such as lithium, sodium and potassium; salts of alkaline earth metal such as calcium, barium and magnesium; aluminum salts; and the like, preferably the salts of alkali metal.

The phenylalkylcarboxylic acid derivatives of formula (I) can be converted to a pharmacologically acceptable ester according to conventional methods. The pharmacologically acceptable esters of the phenylalkylcarboxylic acid derivatives of formula (I) are medically used as compared with the phenylalkylcarboxylic acid of formula (I) and are not particularly limited so long as it can be pharmacologically accepted.

The ester of the phenylalkylcarboxylic acid of formula (I) of the present invention includes, for example, the straight- or branched-chain alkyl group having from 1 to 6 carbon atoms, the aralkyl group having from 7 to 19 carbon atoms, the straight- or branched-chain alkyl group having from 1 to 5 carbon atoms which is substituted by straight- or branched-chain alkanoyloxy having from 1 to 6 carbon atoms, the straight- or branched-chain alkyl group having from 1 to 5 carbon atoms which is substituted by straight- or branched-chain alkyloxycarbonyloxy having from 1 to 6 carbon atoms, the straight- or branched-chain alkyl group having from 1 to 5 carbon atoms which is substituted by cycloalkylcarbonyloxy having from 5 to 7 carbon atoms, the straight- or branched-chain alkyl group having from 1 to 5 carbon atoms which is substituted by cycloalkyloxycarbonyloxy having from 5 to 7 carbon atoms, the straight- or branched-chain alkyl group having from 1 to 5 carbon atoms which is substituted by arylcarbonyloxy having from 6 to 10 carbon atoms, the straight- or branched-chain alkyl group having from 1 to 5 carbon atoms which is substituted by aryloxycarbonyloxy having from 6 to 10 carbon atoms and the 2-oxo-1,3-dioxolen-4-yl group having straight- or branched-chain alkyl having from 1 to 6 carbon atoms as a substituent at the 5-position.

Here, the straight- or branched-chain alkyl group having from 1 to 4 carbon atoms and the straight- or branched-chain alkyl group having from 1 to 6 carbon atoms include, for example, methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl or 1,2,2-trimethylpropyl groups, preferably the straight- or branched-chain alkyl group having from 1 to 4 carbon atoms, more preferably methyl, ethyl, propyl, isopropyl, butyl and isobutyl, most preferably methyl and ethyl.

The aralkyl group having from 7 to 19 carbon atoms includes, for example, the benzyl, phenethyl, 3-phenylpropyl, 4-phenylbutyl, 1-naphthylmethyl, 2-naphthylmethyl or diphenylmethyl group, preferably the benzyl group.

The cycloalkyl group having from 5 to 7 carbon atoms includes, for example, cyclopentyl, cyclohexyl and cycloheptyl, preferably the cyclohexyl.

The aryl group having from 6 to 10 carbon atoms includes, for example, phenyl or naphthyl, preferably phenyl.

Examples of preferable ester residual groups include, for example, the methyl, ethyl, propyl, isopropyl, butyl, isobutyl, t-butyl, benzyl, acetoxymethyl, 1-(acetoxy)ethyl, propionyloxymethyl, 1-(propionyloxy)ethyl, butyryloxymethyl, 1-(butyryloxy)ethyl, isobutyryloxymethyl, 1-(isobutyryloxy)ethyl, valeryloxymethyl, 1-(valeryloxy)ethyl, isovaleryloxymethyl, 1-(isovaleryloxy)ethyl, pivaloyloxymethyl, 1-(pivaloyloxy)ethyl, methoxycarbonyloxymethyl, 1-(methoxycarbonyloxy)ethyl, ethoxycarbonyloxymethyl, 1-(ethoxycarbonyloxy)ethyl, propoxycarbonyloxymethyl, 1-(propoxycarbonyloxy)ethyl, isopropoxycarbonyloxymethyl, 1-(isopropoxycarbonyloxy)ethyl, butoxycarbonyloxymethyl, 1-(butoxycarbonyloxy)ethyl, isobutoxycarbonyloxymethyl, 1-(isobutoxycarbonyloxy)ethyl, t-butoxycarbonyloxymethyl, 1-(t-butoxycarbonyloxy)ethyl, cyclopentanecarbonyloxymethyl, 1-(cyclopentanecarbonyloxy)ethyl, cyclohexanecarbonyloxymethyl, 1-(cyclohexanecarbonyloxy)ethyl, cyclopentyloxycarbonyloxymethyl, 1-(cyclopentyloxycarbonyloxy)ethyl, cyclohexyloxycarbonyloxymethyl, 1-(cyclohexyloxycarbonyloxy)ethyl, benzoyloxymethyl, 1-(benzoyloxy)ethyl, phenoxycarbonyloxymethyl, 1-(phenoxycarbonyloxy)ethyl and 5-methyl-2-oxo-1,3-dioxolen-4-yl groups.

Incidentally, the compound of formula (I) has various isomers. For example, there are optical isomers derived from the asymmetry of the carbon at the α-position of carboxylic group. In the formula (I), stereoisomers based on the asymmetric carbon atom and equivalent and non-equivalent weight mixtures of these stereoisomers all are represented by the single formula. Therefore, the present invention includes all these isomers and the mixture of these isomers.

Further, in the phenylalkylcarboxylic acid derivatives of formula (I), cis-isomers and trans-isomers based on geometrical isomerism can exist in the oxime moiety. In the formula (I), both isomers based on the geometrical isomerism and the equivalent and non-equivalent weight mixture of these isomers are all represented by the single formula. Therefore, the present invention includes all these isomers and the mixture of these isomers.

Further, in the case where the phenylalkylcarboxylic acid of formula (I) or the salt thereof forms solvates (for example, hydrates), the present invention includes all these compounds.

Further, the present invention includes all compounds which are metabolized in vivo to be converted to the phenylalkylcarboxylic acid derivatives of formula (I) or the salts thereof, for example, the amide derivatives, i.e. prodrugs.

The phenylalkylcarboxylic acid derivatives of formula (I) include preferably (1) a compound in which $R^1$ is a hydrogen atom or a straight- or branched-chain alkyl group having from 1 to 4 carbon atoms, (2) a compound in which $R^1$ is a hydrogen atom or a straight- or branched-chain alkyl group having from 1 to 3 carbon atoms, (3) a compound in which $R^1$ is a hydrogen atom or a alkyl group having one or two carbon atoms, (4) a compound in which $R^1$ is an alkyl group having one or two carbon atoms, (5) a compound in which $R^2$ is a straight- or branched-chain alkylene group having from 2 to 5 carbon atoms, (6) a compound in which $R^2$ is a straight- or branched-chain alkylene group having from 2 to 4 carbon atoms, (7) a compound in which $R^2$ is an ethylene, trimethylene or methylethylene group, (8) a compound in which $R^2$ is the ethylene group, (9) a compound in which $R^3$ is a hydrogen atom, a straight- or branched-chain alkyl group having from 1 to 4 carbon atoms, an alkoxy group having one or two carbon atoms, an alkylthio group having one or two carbon atoms or a halogen atom,

(10) a compound in which $R^3$ is a hydrogen atom,

(11) a compound in which X is an aryl group having from 6 to 10 carbon atoms which may have from 1 to 3 substituents α mentioned below or a 5- to 10-membered hetero aromatic group (comprising monocyclic or bicyclic) containing from 1 to 4 hetero atoms selected from the group consisting of oxygen, nitrogen and sulfur atoms which may have from 1 to 3 substituents α mentioned below, the substituent α is selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) the fluorine atom, (xi) the chlorine atom, (xii) the bromine atom, (xiii) aralkyl having from 7 to 12 carbon atoms, (xiv) phenyl (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xv) phenoxy (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) phenylthio (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) phenylsulfonylamino (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms, and the nitrogen atom of the amino moiety may be substituted by straight- or branched-chain alkyl having from 1 to 6 carbon atoms), (xix) furyl, (xx) thienyl, (xxi) oxazolyl, (xxii) isoxazolyl, (xxiii) thiazolyl (xxiv) pyridyl, (xxv) pyridyloxy, (xxvi) pyridylthio, (xxvii) pyridylsulfonyl, (xxviii) imidazolyl (the nitrogen atom of the ring may be substituted by straight- or branched-chain alkyl having from 1 to 6 carbon atoms) and (xxix) pyridylsulfonylamino (the nitrogen atom of the amino moiety may be substituted by straight- or branched-chain alkyl having from 1 to 6 carbon atoms),

(12) a compound in which X is the phenyl, naphthyl, imidazolyl, oxazolyl, pyridyl, indolyl, quinolyl or isoquinolyl group, and these groups may have from 1 to 3 substituents α mentioned below, the substituent α is selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) methylenedioxy, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) the fluorine atom, (xi) the chlorine atom, (xii) the bromine atom, (xiii) aralkyl having from 7 to 12 carbon atoms, (xiv) phenyl (the phenyl moiety may be substituted by methyl, trifluoromethyl, methoxy, fluoro or methylenedioxy), (xv) phenoxy (the phenyl moiety may be substituted by methyl, trifluoromethyl, methoxy, fluoro or methylenedioxy), (xvi) phenylthio (the phenyl moiety may be substituted by methyl, trifluoromethyl, methoxy, fluoro or methylenedioxy), (xvii) phenylsulfonyl (the phenyl moiety may be substituted by methyl, trifluoromethyl, methoxy, fluoro or methylenedioxy), (xviii) phenylsulfonylamino (the phenyl moiety may be substituted by methyl, trifluoromethyl, methoxy, fluoro or methylenedioxy, and the nitrogen atom of the amino moiety may be substituted by straight- or branched-chain alkyl having from 1 to 6 carbon atoms), (xix) furyl, (xx) thienyl, (xxi) oxazolyl, (xxii) isoxazolyl, (xxiii) thiazolyl, (xxiv) pyridyl, (xxv) pyridyloxy, (xxvi) pyridylthio, (xxvii) pyridylsulfonyl, (xxviii) imidazolyl (the nitrogen atom of the ring may be substituted by straight- or branched-chain alkyl having from 1 to 6 carbon atoms) and (xxix) pyridylsulfonylamino (the nitrogen atom of the amino moiety may be substituted by straight- or branched-chain alkyl having from 1 to 6 carbon atoms),

(13) a compound in which X is the phenyl, naphthyl, imidazolyl, oxazolyl, pyridyl, indolyl, quinolyl or isoquinolyl group, and these groups may have from 1 to 3 substituents α mentioned below the substituent α is selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) methylenedioxy, (vii) benzyloxy, (viii) phenethyloxy, (ix) naphthylmethoxy, (x) straight- or branched-chain alkylthio having from 1 to 4 carbon atoms, (xi) straight- or branched-chain alkylsulfonyl having from 1 to 4 carbon atoms, (xii) fluorine atom, (xiii) chlorine atom, (xiv) bromine atom, (xv) benzyl, (xvi) phenyl (the phenyl moiety may be substituted by methyl, trifluoromethyl, methoxy, fluoro or methylenedioxy), (xvii) phenoxy (the phenyl moiety may be substituted by methyl, trifluoromethyl, methoxy, fluoro or methylenedioxy), (xviii) phenylthio, (xix) phenylsulfonyl, (xx) phenylsulfonylamino, (xxi) N-methylphenylsulfonylamino, (xxii) furyl, (xxiii) thienyl, (xxiv) oxazolyl, (xxv) isoxazolyl, (xxvi) thiazolyl, (xxvii) pyridyl, (xxviii) pyridyloxy, (xxix) pyridylthio, (xxx) pyridylsulfonyl, (xxxi) pyridylsulfonylamino, (xxxii) N-methylpyridylsulfonylamino and (xxxiii) imidazolyl (the nitrogen atom of the ring may be substituted by straight- or branched-chain alkyl having from 1 to 6 carbon atoms),

(14) a compound in which X is the phenyl, naphthyl, pyridyl, indolyl, quinolyl or isoquinolyl group, and these groups may have one or two substituents α mentioned below the substituent α is selected from the group consisting of straight- or branched-chain alkyl having from 1 to 3 carbon atoms, methyl having from 1 to 3 fluorine atoms, hydroxy, alkanoyloxy having one or two carbon atoms, straight- or branched-chain alkoxy having from 1 to 3 carbon atoms, methylenedioxy, benzyloxy, alkylthio having one or two carbon atoms, alkylsulfonyl having one or two carbon atoms, fluorine atom, chlorine atom, bromine atom, benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and N-methylpyridylsulfonylamino groups,

(15) a compound in which X is the phenyl, naphthyl, pyridyl, quinolyl or isoquinolyl group, and these groups may have one substituent α mentioned below the substituent α is selected from the methyl, ethyl, isopropyl, trifluoromethyl, hydroxy, acetoxy, methoxy, ethoxy, isopropoxy, methylenedioxy, benzyloxy, alkylthio having one or two carbon atoms, alkylsulfonyl having one or two carbon atoms, the chlorine atom, the benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and N-methylpyridylsulfonylamino groups,

(16) a compound in which X is the phenyl group which may have one substituent α mentioned below, the substituent α is selected from the group consisting of the methyl, hydroxy and acetoxy, chlorine atom, benzyl, phenyl, phenoxy, phenylthio, phenylsulfonyl, phenylsulfonylamino, N-methylphenylsulfonylamino, pyridyl, pyridyloxy, pyridylthio and pyridylsulfonyl groups, or X is the pyridyl group which may have one substituent α mentioned below, here, the substituent α is selected from the group consisting of the methoxy, ethoxy, isopropoxy and benzyloxy groups, alkylthio having one or two carbon atoms, alkylsulfonyl having one or two carbon atoms, benzyl, phenyl, phenoxy, phenylthio, phenylsulfonyl, phenylsulfonylamino and N-methylphenylsulfonylamino groups,

(17) a compound in which X is a phenyl group which may have one substituent α mentioned below, the substituent α is selected from the group consisting of the hydroxy, chlorine atom, benzyl, phenyl, phenoxy, phenylthio, pyridyl, pyridyloxy and pyridylthio groups,

(18) a compound in which Y is an oxygen or sulfur atom or a group of formula >N—$R^4$ (wherein $R^4$ represents a hydrogen atom, a straight- or branched-chain alkyl group having from 1 to 3 carbon atoms or a straight- or branched-chain alkanoyl group having from 2 to 5 carbon atoms),

(19) a compound in which Y is an oxygen atom,

(20) a compound in which Z is a single bond or a straight- or branched-chain alkylene group having from 1 to 4 carbon atoms,

(21) a compound in which Z is a straight- or branched-chain alkylene group having from 1 to 4 carbon atoms,

(22) a compound in which Z is a straight- or branched-chain alkylene group having one or two carbon atoms,

(23) a compound in which Z is a methylene group,

(24) a compound in which W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group in which the alkyl moiety has a straight- or branched-chain alkyl having from 1 to 4 carbon atoms and the aryl moiety has from 6 to 10 carbon atoms which may have from 1 to 3 substituents α mentioned below in the aryl moiety, (vii) an aryloxy group having from 6 to 10 carbon atoms which may have from 1 to 3 substituents α mentioned below in the aryl moiety, (viii) an arylthio group having from 6 to 10 carbon atoms which may have from 1 to 3 substituents α mentioned below in the aryl moiety, (ix) an arylamino group having from 6 to 10 carbon atoms which may have from 1 to 3 substituents α mentioned below in the aryl moiety, (x) an aralkyl group having from 7 to 12 carbon atoms which may have from 1 to 3 substituents α mentioned below in the aryl moiety, (xi) a 1-pyrrolyl group, (xii) a 1-pyrrolidinyl group, (xiii) a 1-imidazolyl group, (xiv) a piperidino group or (xv) a morpholino group, here, the substituent α is selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl having from 7 to 12 carbon atoms, (xiv) phenyl (the phenyl may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) phenoxy (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) phenylthio (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) phenylsulfonylamino (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms, and the nitrogen atom of the amino moiety may be substituted by straight- or branched-chain alkyl having from 1 to 6 carbon atoms), (xix) furyl, (xx) thienyl, (xxi) oxazolyl, (xxii) isoxazolyl, (xxiii) thiazolyl (xxiv) pyridyl, (xxv) pyridyloxy, (xxvi) pyridylthio, (xxvii) pyridylsulfonyl, (xxviii) imidazolyl (the nitrogen atom of the ring may be substituted by straight- or branched-chain alkyl having from 1 to 6 carbon atoms) and (xxix) pyridylsulfonylamino (the nitrogen atom of the amino moiety may be substituted by straight- or branched-chain alkyl having from 1 to 6 carbon atoms),

(25) a compound in which W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group in which the alkyl moiety has a straight- or branched-chain alkyl having from 1 to 4 carbon atoms and the aryl moiety has from 6 to 10 carbon atoms which may have from 1 to 3 substituents α mentioned below in the aryl moiety, (vii) an aryloxy group having from 6 to 10 carbon atoms which may have from 1 to 3 substituents α mentioned below in the aryl moiety, (viii) an arylthio group having from 6 to 10 carbon atoms which may have from 1 to 3 substituents α mentioned below in the aryl moiety, (ix) an arylamino group having from 6 to 10 carbon atoms which may have from 1 to 3 substituents α mentioned below in the aryl moiety, (x) an aralkyl group having from 7 to 12 carbon atoms which may have from 1 to 3 substituents α mentioned below in the aryl moiety, or (xi) a 1-pyrrolyl group, the substituent α is selected from the hydroxy, chlorine atom, benzyl, phenyl, phenoxy, phenylthio, pyridyl, pyridyloxy and pyridylthio groups,

(26) a compound in which W is (i) a straight- or branched-chain alkyl group having from 1 to 4 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group in which the alkyl moiety has the straight- or branched-chain alkyl having from 1 to 4 carbon atoms and the aryl moiety has from 6 to 10 carbon atoms, (vii) a phenoxy group, (viii) a phenylthio group, (ix) a phenylamino group, (x) an aralkyl group having from 7 to 10 carbon atoms, (xi) a 1-pyrrolyl group, (xii) a 1-pyrrolidinyl group or (xiii) a 1-imidazolyl group,

(27) a compound in which W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group,

(28) a compound in which W is a butyl, ethoxy, methylthio, ethylamino, diethylamino, N-phenyl-N-ethylamino, phenoxy, phenylthio, phenylamino, 3-phenylpropyl or 1-pyrrolyl group,

(29) a compound in which W is a butyl, ethoxy, methylthio, ethlyamino, phenoxy, phenylthio, phenylamino or 3-phenylpropyl group.

Further, $R^1$ is selected from (1) to (4), $R^2$ is selected from (5) to (8), $R^3$ is selected from (9) and (10), X is selected from (11) to (17), Y is selected from (18) and (19), Z is selected from (20) to (23) and W is selected from (24) to (29), and the compounds obtained by combining them are also preferable.

The phenylalkylcarboxylic acid derivatives of formula (I) include, for example,

(30) a compound in which $R^1$ is a hydrogen atom or a straight- or branched-chain alkyl group having from 1 to 4 carbon atoms;

$R^2$ is a straight- or branched-chain alkylene group having from 2 to 5 carbon atoms;

$R^3$ is a hydrogen atom, a straight- or branched-chain alkyl group having from 1 to 4 carbon atoms, an alkoxy group having one or two carbon atoms, an alkylthio group having one or two carbon atoms or a halogen atom;

Z is a single bond or a straight- or branched-chain alkylene group having from 1 to 4 carbon atoms;

W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group in which the alkyl moiety has the straight- or branched-chain alkyl having from 1 to 4 carbon atoms and the aryl moiety has from 6 to 10 carbon atoms which may have from 1 to 3 substituents α mentioned below in the aryl moiety, (vii) an aryloxy group having from 6 to 10 carbon atoms which may have from 1 to 3 substituents α mentioned below in the aryl moiety, (viii) an arylthio group having from 6 to 10 carbon atoms which may have from 1 to 3 substituents α mentioned below in the aryl moiety, (ix) an arylamino group having from 6 to 10 carbon atoms which may have from 1 to 3 substituents α mentioned below in the aryl moiety, (x) an aralkyl group having from 7 to 12 carbon atoms which may have from 1 to 3 substituents α mentioned below in the aryl moiety, (xi) a 1-pyrrolyl group, (xii) a 1-pyrrolidinyl group, (xiii) a 1-imidazolyl group, (xiv) a piperidino group or (xv) a morpholino group;

X is an aryl group having from 6 to 10 carbon atoms which may have from 1 to 3 substituents α mentioned below or a 5- to 10-membered hetero aromatic group (comprising monocyclic or bicyclic) having from 1 to 4 hetero atoms selected from the group consisting of oxygen, nitrogen and sulfur atoms which may have from 1 to 3 substituents α mentioned below;

here, the substituent α mentioned below is selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl having from 7 to 12 carbon atoms, (xiv) phenyl (the phenyl may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) phenoxy (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) phenylthio (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xviii) phenylsulfonylamino (the phenyl moiety may be substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms, and the nitrogen atom of the amino moiety may be substituted by straight- or branched-chain alkyl having from 1 to 6 carbon atoms), (xix) furyl, (xx) thienyl, (xxi) oxazolyl, (xxii) isoxazolyl, (xxiii) thiazolyl, (xxiv) pyridyl, (xxv) pyridyloxy, (xxvi) pyridylthio, (xxvii) pyridylsulfonyl, (xxviii) imidazolyl (the nitrogen atom of the ring may be substituted by straight- or branched-chain alkyl having from 1 to 6 carbon atoms) and (xxix) pyridylsulfonylamino (the nitrogen atom of the amino moiety may be substituted by straight- or branched-chain alkyl having from 1 to 6 carbon atoms); and Y is an oxygen or sulfur atom or a group of formula >N—$R^4$ (wherein $R^4$ represents a hydrogen atom, a straight- or branched-chain alkyl group having from 1 to 3 carbon atoms or a straight- or branched-chain alkanoyl group having from 2 to 5 carbon atoms);

(31) a compound in which $R^1$ is a straight- or branched-chain alkyl group having from 1 to 4 carbon atoms;

$R^2$ is a straight- or branched-chain alkylene group having from 2 to 5 carbon atoms;

$R^3$ is a hydrogen atom;

Z is a straight- or branched-chain alkylene group having from 1 to 4 carbon atoms;

W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group in which the alkyl moiety has a straight- or branched-chain alkyl having from 1 to 4 carbon atoms and the aryl moiety has from 6 to 10 carbon atoms which may have from 1 to 3 substituents α mentioned below in the aryl moiety, (vii) an aryloxy group having from 6 to 10 carbon atoms which may have from 1 to 3 substituents α mentioned below in the aryl moiety, (viii) an arylthio group having from 6 to 10 carbon atoms which may have from 1 to 3 substituents α mentioned below in the aryl moiety, (ix) an arylamino group having from 6 to 10 carbon atoms which may have from 1 to 3 substituents α mentioned below in the aryl moiety, (x) an aralkyl group having from 7 to 12 carbon atoms which may have from 1 to 3 substituents α mentioned below in the aryl moiety, (xi) a 1-pyrrolyl group;

X is a phenyl group which may have one substituent α mentioned below;

here, the substituent α is selected from the group consisting of hydroxy, chlorine atom, benzyl, phenyl, phenoxy, phenylthio, pyridyl, pyridyloxy and pyridylthio groups; and Y is an oxygen atom;

(32) a compound in which $R^1$ is an alkyl group having one or two carbon atoms;

$R^2$ is an ethylene group;

$R^3$ is a hydrogen atom;

Z is a methylene group;

W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group;

X is a phenyl group which may have one substituent α mentioned below;

here, the substituent α is selected from the group consisting of methyl, hydroxy, acetoxy, chlorine atom, benzyl, phenyl, phenoxy, phenylthio, phenylsulfonyl, phenylsulfonylamino, N-methylphenylsulfonylamino, pyridyl, pyridyloxy, pyridylthio and pyridylsulfonyl; or X is a pyridyl group which may have one substituent α mentioned below;

here, the substituent α is selected from the group consisting of methoxy, ethoxy, isopropoxy, benzyloxy, alkylthio having one or two carbon atoms, alkylsulfonyl having one or two carbon atoms, benzyl, phenyl, phenoxy, phenylthio, phenylsulfonyl, phenylsulfonylamino and N-methylphenylsulfonylamino groups; and Y is an oxygen atom;

(33) a compound in which $R^1$ is an alkyl group having one or two carbon atoms;

$R^2$ is an ethylene group;

$R^3$ is a hydrogen atom;

Z is a methylene group;

W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group;

X is a phenyl group which may have one substituent α mentioned below;

here, the substituent α is selected from the group consisting of hydroxy, chlorine atom, benzyl, phenyl, phenoxy, phenylthio, pyridyl, pyridyloxy and pyridylthio groups; and Y is an oxygen atom;

(34) a compound in which $R^1$ is an alkyl group having one or two carbon atoms;

$R^2$ is an ethylene group;

$R^3$ is a hydrogen atom;

Z is a methylene group;

W is a butyl, ethoxy, methylthio, ethylamino, diethylamino, N-phenyl-N-ethylamino, phenoxy, phenylthio, phenylamino, 3-phenylpropyl or 1-pyrrolyl group;

X is a phenyl group which may have one substituent α mentioned below;

the substituent α is selected from the group consisting of hydroxy, chlorine atom, benzyl, phenyl, phenoxy, phenylthio, pyridyl, pyridyloxy and pyridylthio groups; and Y is an oxygen atom; and

(35) a compound in which $R^1$ is an alkyl group having one or two carbon atoms;

$R^2$ is an ethylene group;

$R^3$ is a hydrogen atom;

Z is a methylene group;

W is a butyl, ethoxy, methylthio, ethylamino, phenoxy, phenylthio, phenylamino or 3-phenylpropyl group;

X is a phenyl group which may have one substituent α mentioned below;

here, the substituent α is selected from the group consisting of hydroxy, chlorine atom, benzyl, phenyl, phenoxy, phenylthio, pyridyl, pyridyloxy and pyridylthio groups; and Y is an oxygen atom.

Examples of the phenylalkylcarboxylic acid derivatives of formula (I), the pharmacologically acceptable salt thereof or the pharmacologically acceptable ester thereof include the compounds exemplified in the following.

In Table 1 to Table 68, the following abbreviations are used.

Ac: acetyl, Bu: butyl, tBu: t-butyl, Bimid: benzimidazolyl, Boxa: benzoxazolyl, Bthiz: benzothiazolyl, Bz: benzyl, Et: ethyl, Fur: furyl, Hex: hexyl, Imid: imidazolyl, Ind: indolyl, Isox: isoxazolyl, MdO: methylenedioxy, Me: methyl, Mor: morpholino, Np: naphthyl, Oxa: oxazolyl, Pen: pentyl, Ph: phenyl, Pip: piperidyl, Pr: propyl, iPr: isopropyl, Pym: pyrimidinyl, Pyr: pyridyl, Pyrd: pyrrolidinyl, Pyrr: pyrrolyl, Pyza: pyrazolyl, Quin: quinolyl, iQuin: isoquinolyl, Thi: thienyl, Thiz: thiazolyl.

The compounds in Tables 1 to 55 and Tables 66 to 68 have the following formula (Ia), and the compounds in Tables 56 to 65 have the following formula (Ib).

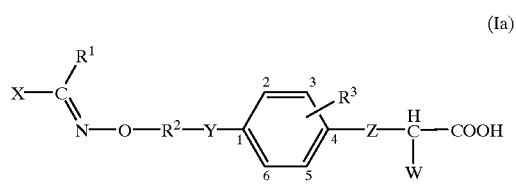

(Ia)

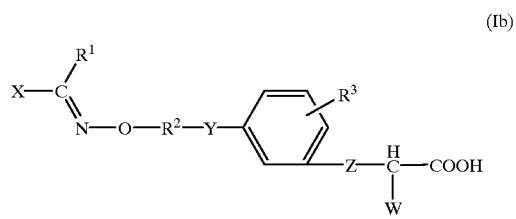

(Ib)

TABLE 1

| Exemplification No. compound. | $R^1$ | $R^2$ | $R^3$ | Z | W | X | Y |
|---|---|---|---|---|---|---|---|
| 1-1 | H | $(CH_2)_2$ | H | $CH_2$ | OEt | Ph | O |
| 1-2 | H | $(CH_2)_2$ | H | $CH_2$ | OEt | 1-Np | O |
| 1-3 | H | $(CH_2)_2$ | H | $CH_2$ | OEt | 2-Np | O |
| 1-4 | H | $(CH_2)_2$ | H | $CH_2$ | OEt | 4-Me—Ph | O |
| 1-5 | H | $(CH_2)_2$ | H | $CH_2$ | OEt | 4-Et—Ph | O |
| 1-6 | H | $(CH_2)_2$ | H | $CH_2$ | OEt | 3-iPr—Ph | O |
| 1-7 | H | $(CH_2)_2$ | H | $CH_2$ | OEt | 4-iPr—Ph | O |
| 1-8 | H | $(CH_2)_2$ | H | $CH_2$ | OEt | 3-tBu—Ph | O |
| 1-9 | H | $(CH_2)_2$ | H | $CH_2$ | OEt | 4-tBu—Ph | O |
| 1-10 | H | $(CH_2)_2$ | H | $CH_2$ | OEt | 3-Cl—Ph | O |
| 1-11 | H | $(CH_2)_2$ | H | $CH_2$ | OEt | 4-Cl—Ph | O |
| 1-12 | H | $(CH_2)_2$ | H | $CH_2$ | OEt | 3-Br—Ph | O |
| 1-13 | H | $(CH_2)_2$ | H | $CH_2$ | OEt | 4-Br—Ph | O |
| 1-14 | H | $(CH_2)_2$ | H | $CH_2$ | OEt | 3-Ph—Ph | O |
| 1-15 | H | $(CH_2)_2$ | H | $CH_2$ | OEt | 4-Ph—Ph | O |
| 1-16 | H | $(CH_2)_2$ | H | $CH_2$ | OEt | 3-Bz—Ph | O |
| 1-17 | H | $(CH_2)_2$ | H | $CH_2$ | OEt | 4-Bz—Ph | O |
| 1-18 | H | $(CH_2)_2$ | H | $CH_2$ | OEt | 3-PhO—Ph | O |
| 1-19 | H | $(CH_2)_2$ | H | $CH_2$ | OEt | 4-PhO—Ph | O |
| 1-20 | H | $(CH_2)_2$ | H | $CH_2$ | OEt | 3-PhS—Ph | O |
| 1-21 | H | $(CH_2)_2$ | H | $CH_2$ | OEt | 4-PhS—Ph | O |
| 1-22 | H | $(CH_2)_2$ | H | $CH_2$ | OEt | 3-$PhSO_2$—Ph | O |
| 1-23 | H | $(CH_2)_2$ | H | $CH_2$ | OEt | 4-$PhSO_2$—Ph | O |
| 1-24 | H | $(CH_2)_2$ | H | $CH_2$ | OEt | 3-(Imid-1)—Ph | O |
| 1-25 | H | $(CH_2)_2$ | H | $CH_2$ | OEt | 4-(Imid-1)—Ph | O |
| 1-26 | H | $(CH_2)_2$ | H | $CH_2$ | OEt | 3-(Imid-4)—Ph | O |
| 1-27 | H | $(CH_2)_2$ | H | $CH_2$ | OEt | 4-(Imid-4)—Ph | O |
| 1-28 | H | $(CH_2)_2$ | H | $CH_2$ | OEt | 3-(Fur-2)—Ph | O |
| 1-29 | H | $(CH_2)_2$ | H | CH | OEt | 4-(Fur-2)—Ph | O |
| 1-30 | H | $(CH_2)_2$ | H | $CH_2$ | OEt | 3-(Thi-2)—Ph | O |
| 1-31 | H | $(CH_2)_2$ | H | $CH_2$ | OEt | 4-(Thi-2)—Ph | O |
| 1-32 | H | $(CH_2)_2$ | H | $CH_2$ | OEt | 3-(Thi-3)—Ph | O |
| 1-33 | H | $(CH_2)_2$ | H | $CH_2$ | OEt | 4-(Thi-3)—Ph | O |
| 1-34 | H | $(CH_2)_2$ | H | $CH_2$ | OEt | 3-(Pyr-2)—Ph | O |
| 1-35 | H | $(CH_2)_2$ | H | $CH_2$ | OEt | 4-(Pyr-2)—Ph | O |
| 1-36 | H | $(CH_2)_2$ | H | $CH_2$ | OEt | 3-(Pyr-3)—Ph | O |
| 1-37 | H | $(CH_2)_2$ | H | $CH_2$ | OEt | 4-(Pyr-3)—Ph | O |
| 1-38 | H | $(CH_2)_2$ | H | $CH_2$ | OEt | 3-(Pyr-4)—Ph | O |
| 1-39 | H | $(CH_2)_2$ | H | $CH_2$ | OEt | 4-(Pyr-4)—Ph | O |
| 1-40 | H | $(CH_2)_2$ | H | $CH_2$ | OEt | 3-(Oxa-2)—Ph | O |
| 1-41 | H | $(CH_2)_2$ | H | $CH_2$ | OEt | 4-(Oxa-2)—Ph | O |
| 1-42 | H | $(CH_2)_2$ | H | $CH_2$ | OEt | 3-(Oxa-4)—Ph | O |
| 1-43 | H | $(CH_2)_2$ | H | $CH_2$ | OEt | 4-(Oxa-4)—Ph | O |
| 1-44 | H | $(CH_2)_2$ | H | $CH_2$ | OEt | 3-(Oxa-5)—Ph | O |
| 1-45 | H | $(CH_2)_2$ | H | $CH_2$ | OEt | 4-(Oxa-5)—Ph | O |
| 1-46 | H | $(CH_2)_2$ | H | $CH_2$ | OEt | 3-(Thiz-2)—Ph | O |
| 1-47 | H | $(CH_2)_2$ | H | $CH_2$ | OEt | 4-(Thiz-2)—Ph | O |
| 1-48 | H | $(CH_2)_2$ | H | $CH_2$ | OEt | 3-(Thiz-4)—Ph | O |
| 1-49 | H | $(CH_2)_2$ | H | $CH_2$ | OEt | 4-(Thiz-4)—Ph | O |
| 1-50 | H | $(CH_2)_2$ | H | $CH_2$ | OEt | 3-(Thiz-5)—Ph | O |
| 1-51 | H | $(CH_2)_2$ | H | $CH_2$ | OEt | 4-(Thiz-5)—Ph | O |

TABLE 1-continued

| Exemplification No. compound. | R¹ | R² | R³ | Z | W | X | Y |
|---|---|---|---|---|---|---|---|
| 1-52 | H | (CH₂)₂ | H | CH₂ | OEt | 1-Me-2-Pyrr | O |
| 1-53 | H | (CH₂)₂ | H | CH₂ | OEt | 1-Ph-2-Pyrr | O |
| 1-54 | H | (CH₂)₂ | H | CH₂ | OEt | 1-Bz-2-Pyrr | O |
| 1-55 | H | (CH₂)₂ | H | CH₂ | OEt | 5-Me-2-Fur | O |
| 1-56 | H | (CH₂)₂ | H | CH₂ | OEt | 5-Ph-2-Fur | O |
| 1-57 | H | (CH₂)₂ | H | CH₂ | OEt | 5-Me-2-Thi | O |
| 1-58 | H | (CH₂)₂ | H | CH₂ | OEt | 5-Ph-2-Thi | O |
| 1-59 | H | (CH₂)₂ | H | CH₂ | OEt | 5-Me-3-Thi | O |
| 1-60 | H | (CH₂)₂ | H | CH₂ | OEt | 5-Ph-3-Thi | O |
| 1-61 | H | (CH₂)₂ | H | CH₂ | OEt | 1-Me-3-Pyza | O |
| 1-62 | H | (CH₂)₂ | H | CH₂ | OEt | 1-Ph-3-Pyza | O |
| 1-63 | H | (CH₂)₂ | H | CH₂ | OEt | 1-Me-2-Imid | O |
| 1-64 | H | (CH₂)₂ | H | CH₂ | OEt | 1-Ph-2-Imid | O |
| 1-65 | H | (CH₂)₂ | H | CH₂ | OEt | 1-Me-4-Imid | O |
| 1-66 | H | (CH₂)₂ | H | CH₂ | OEt | 1-Ph-4-Imid | O |
| 1-67 | H | (CH₂)₂ | H | CH₂ | OEt | 4-Oxa | O |
| 1-68 | H | (CH₂)₂ | H | CH₂ | OEt | 5-Oxa | O |
| 1-69 | H | (CH₂)₂ | H | CH₂ | OEt | 2-Me-4-Oxa | O |
| 1-70 | H | (CH₂)₂ | H | CH₂ | OEt | 2-Ph-4-Oxa | O |
| 1-71 | H | (CH₂)₂ | H | CH₂ | OEt | 2-Me-5-Oxa | O |
| 1-72 | H | (CH₂)₂ | H | CH₂ | OEt | 2-Ph-5-Oxa | O |
| 1-73 | H | (CH₂)₂ | H | CH₂ | OEt | 4-Me-2-Ph-5-Oxa | O |
| 1-74 | H | (CH₂)₂ | H | CH₂ | OEt | 5-Me-2-Ph-4-Oxa | O |
| 1-75 | H | (CH₂)₂ | H | CH₂ | OEt | 4-Thiz | O |
| 1-76 | H | (CH₂)₂ | H | CH₂ | OEt | 5-Thiz | O |
| 1-77 | H | (CH₂)₂ | H | CH₂ | OEt | 2-Me-4-Thiz | O |
| 1-78 | H | (CH₂)₂ | H | CH₂ | OEt | 2-Ph-4-Thiz | O |
| 1-79 | H | (CH₂)₂ | H | CH₂ | OEt | 2-Me-5-Thiz | O |
| 1-80 | H | (CH₂)₂ | H | CH₂ | OEt | 2-Ph-5-Thiz | O |
| 1-81 | H | (CH₂)₂ | H | CH₂ | OEt | 4-Me-2-Ph-5-Thiz | O |
| 1-82 | H | (CH₂)₂ | H | CH₂ | OEt | 5-Me-2-Ph-4-Thiz | O |
| 1-83 | H | (CH₂)₂ | H | CH₂ | OEt | 1-Me-4-Pyza | O |
| 1-84 | H | (CH₂)₂ | H | CH₂ | OEt | 1-Ph-4-Pyza | O |
| 1-85 | H | (CH₂)₂ | H | CH₂ | OEt | 2-Me-4-Isox | O |
| 1-86 | H | (CH₂)₂ | H | CH₂ | OEt | 2-Ph-4-Isox | O |
| 1-87 | H | (CH₂)₂ | H | CH₂ | OEt | 2-Pyr | O |
| 1-88 | H | (CH₂)₂ | H | CH₂ | OEt | 3-Pyr | O |
| 1-89 | H | (CH₂)₂ | H | CH₂ | OEt | 4-Pyr | O |
| 1-90 | H | (CH₂)₂ | H | CH₂ | OEt | 3-Me-5-Pyr | O |
| 1-91 | H | (CH₂)₂ | H | CH₂ | OEt | 3-Et-5-Pyr | O |
| 1-92 | H | (CH₂)₂ | H | CH₂ | OEt | 3-Ph-5-Pyr | O |
| 1-93 | H | (CH₂)₂ | H | CH₂ | OEt | 2-Me-5-Pyr | O |
| 1-94 | H | (CH₂)₂ | H | CH₂ | OEt | 2-Et-5-Pyr | O |
| 1-95 | H | (CH₂)₂ | H | CH₂ | OEt | 2-Ph-5-Pyr | O |
| 1-96 | H | (CH₂)₂ | H | CH₂ | OEt | 2-MeO-5-Pyr | O |
| 1-97 | H | (CH₂)₂ | H | CH₂ | OEt | 2-EtO-5-Pyr | O |
| 1-98 | H | (CH₂)₂ | H | CH₂ | OEt | 2-iPrO-5-Pyr | O |
| 1-99 | H | (CH₂)₂ | H | CH₂ | OEt | 2-MeS-5-Pyr | O |
| 1-100 | H | (CH₂)₂ | H | CH₂ | OEt | 2-EtS-5-Pyr | O |
| 1-101 | H | (CH₂)₂ | H | CH₂ | OEt | 2-iPrS-5-Pyr | O |
| 1-102 | H | (CH₂)₂ | H | CH₂ | OEt | 2-MeSO₂-5-Pyr | O |
| 1-103 | H | (CH₂)₂ | H | CH₂ | OEt | 2-EtSO₂-5-Pyr | O |
| 1-104 | H | (CH₂)₂ | H | CH₂ | OEt | 2-iPrSO₂-5-Pyr | O |
| 1-105 | H | (CH₂)₂ | H | CH₂ | OEt | 2-Bz-5-Pyr | O |
| 1-106 | H | (CH₂)₂ | H | CH₂ | OEt | 2-PhO-5-Pyr | O |
| 1-107 | H | (CH₂)₂ | H | CH₂ | OEt | 2-PhS-5-Pyr | O |
| 1-108 | H | (CH₂)₂ | H | CH₂ | OEt | 2-PhSO₂-5-Pyr | O |
| 1-109 | H | (CH₂)₂ | H | CH₂ | OEt | 3-Me-6-Pyr | O |
| 1-110 | H | (CH₂)₂ | H | CH₂ | OEt | 3-Ph-6-Pyr | O |
| 1-111 | H | (CH₂)₂ | H | CH₂ | OEt | 2-Me-6-Pyr | O |
| 1-112 | H | (CH₂)₂ | H | CH₂ | OEt | 2-Ph-6-Pyr | O |
| 1-113 | H | (CH₂)₂ | H | CH₂ | OEt | 2-Me-4-Pym | O |
| 1-114 | H | (CH₂)₂ | H | CH₂ | OEt | 2-Ph-4-Pym | O |
| 1-115 | H | (CH₂)₂ | H | CH₂ | OEt | 2-MeO-4-Pym | O |
| 1-116 | H | (CH₂)₂ | H | CH₂ | OEt | 2-EtO-4-Pym | O |
| 1-117 | H | (CH₂)₂ | H | CH₂ | OEt | 2-iPrO-4-Pym | O |
| 1-118 | H | (CH₂)₂ | H | CH₂ | OEt | 2-MeS-4-Pym | O |
| 1-119 | H | (CH₂)₂ | H | CH₂ | OEt | 2-EtS-4-Pym | O |
| 1-120 | H | (CH₂)₂ | H | CH₂ | OEt | 2-iPrS-4-Pym | O |
| 1-121 | H | (CH₂)₂ | H | CH₂ | OEt | 6-MeS-4-Pym | O |
| 1-122 | H | (CH₂)₂ | H | CH₂ | OEt | 6-EtS-4-Pym | O |
| 1-123 | H | (CH₂)₂ | H | CH₂ | OEt | 6-iPrS-4-Pym | O |
| 1-124 | H | (CH₂)₂ | H | CH₂ | OEt | 2-PhS-4-Pym | O |
| 1-125 | H | (CH₂)₂ | H | CH₂ | OEt | 2-MeSO₂-4-Pym | O |
| 1-126 | H | (CH₂)₂ | H | CH₂ | OEt | 2-EtSO₂-4-Pym | O |
| 1-127 | H | (CH₂)₂ | H | CH₂ | OEt | 2-iPrSO₂-4-Pym | O |

TABLE 1-continued

| Exemplification No. compound. | R¹ | R² | R³ | Z | W | X | Y |
|---|---|---|---|---|---|---|---|
| 1-128 | H | (CH₂)₂ | H | CH₂ | OEt | 2-PhSO₂-4-Pym | O |
| 1-129 | H | (CH₂)₂ | H | CH₂ | OEt | 2-Me-5-Pym | O |
| 1-130 | H | (CH₂)₂ | H | CH₂ | OEt | 2-Ph-5-Pym | O |
| 1-131 | H | (CH₂)₂ | H | CH₂ | OEt | 2-MeO-5-Pym | O |
| 1-132 | H | (CH₂)₂ | H | CH₂ | OEt | 2-EtO-5-Pym | O |
| 1-133 | H | (CH₂)₂ | H | CH₂ | OEt | 2-iPrO-5-Pym | O |
| 1-134 | H | (CH₂)₂ | H | CH₂ | OEt | 2-MeS-5-Pym | O |
| 1-135 | H | (CH₂)₂ | H | CH₂ | OEt | 2-EtS-5-Pym | O |
| 1-136 | H | (CH₂)₂ | H | CH₂ | OEt | 2-iPrS-5-Pym | O |
| 1-137 | H | (CH₂)₂ | H | CH₂ | OEt | 2-PhS-5-Pym | O |
| 1-138 | H | (CH₂)₂ | H | CH₂ | OEt | 2-MeSO₂-5-Pym | O |
| 1-139 | H | (CH₂)₂ | H | CH₂ | OEt | 2-EtSO₂-5-Pym | O |
| 1-140 | H | (CH₂)₂ | H | CH₂ | OEt | 2-iPrSO₂-5-Pym | O |
| 1-141 | H | (CH₂)₂ | H | CH₂ | OEt | 2-PhSO₂-5-Pym | O |
| 1-142 | H | (CH₂)₂ | H | CH₂ | OEt | 2-Ind | O |
| 1-143 | H | (CH₂)₂ | H | CH₂ | OEt | 3-Ind | O |
| 1-144 | H | (CH₂)₂ | H | CH₂ | OEt | 1-Me-2-Ind | O |
| 1-145 | H | (CH₂)₂ | H | CH₂ | OEt | 1-Me-3-Ind | O |
| 1-146 | H | (CH₂)₂ | H | CH₂ | OEt | 2-Bimid | O |
| 1-147 | H | (CH₂)₂ | H | CH₂ | OEt | 2-Boxa | O |
| 1-148 | H | (CH₂)₂ | H | CH₂ | OEt | 2-Bthiz | O |
| 1-149 | H | (CH₂)₂ | H | CH₂ | OEt | 2-Quin | O |
| 1-150 | H | (CH₂)₂ | H | CH₂ | OEt | 3-Quin | O |
| 1-151 | H | (CH₂)₂ | H | CH₂ | OEt | 4-Quin | O |
| 1-152 | H | (CH₂)₂ | H | CH₂ | OEt | 1-iQuin | O |
| 1-153 | H | (CH₂)₂ | H | CH₂ | OEt | 3-iQuin | O |
| 1-154 | H | (CH₂)₂ | H | CH₂ | OEt | 4-iQuin | O |
| 1-155 | H | (CH₂)₂ | H | CH₂ | OEt | 3-MeO—Ph | O |
| 1-156 | H | (CH₂)₂ | H | CH₂ | OEt | 4-MeO—Ph | O |
| 1-157 | H | (CH₂)₂ | H | CH₂ | OEt | 3-EtO—Ph | O |
| 1-158 | H | (CH₂)₂ | H | CH₂ | OEt | 4-EtO—Ph | O |
| 1-159 | H | (CH₂)₂ | H | CH₂ | OEt | 3-iPrO—Ph | O |
| 1-160 | H | (CH₂)₂ | H | CH₂ | OEt | 4-iPrO—Ph | O |
| 1-161 | H | (CH₂)₂ | H | CH₂ | OEt | 3-MeS—Ph | O |
| 1-162 | H | (CH₂)₂ | H | CH₂ | OEt | 4-MeS—Ph | O |
| 1-163 | H | (CH₂)₂ | H | CH₂ | OEt | 3-EtS—Ph | O |
| 1-164 | H | (CH₂)₂ | H | CH₂ | OEt | 4-EtS—Ph | O |
| 1-165 | H | (CH₂)₂ | H | CH₂ | OEt | 3-iPrS—Ph | O |
| 1-166 | H | (CH₂)₂ | H | CH₂ | OEt | 4-iPrS—Ph | O |
| 1-167 | H | (CH₂)₂ | H | CH₂ | OEt | 3-MeSO₂—Ph | O |
| 1-169 | H | (CH₂)₂ | H | CH₂ | OEt | 4-MeSO₂—Ph | O |
| 1-169 | H | (CH₂)₂ | H | CH₂ | OEt | 3-EtSO₂—Ph | O |
| 1-170 | H | (CH₂)₂ | H | CH₂ | OEt | 4-EtSO₂—Ph | O |
| 1-171 | H | (CH₂)₂ | H | CH₂ | OEt | 3-iPrSO₂—Ph | O |
| 1-172 | H | (CH₂)₂ | H | CH₂ | OEt | 4-iPrSO₂—Ph | O |
| 1-173 | H | (CH₂)₂ | H | CH₂ | OEt | 3-(1-Me-Imid-4)—Ph | O |
| 1-174 | H | (CH₂)₂ | H | CH₂ | OEt | 4-(1-Me-Imid-4)—Ph | O |
| 1-175 | H | (CH₂)₂ | H | CH₂ | OEt | 1-Me-2-Ph-4-Imid | O |
| 1-176 | H | (CH₂)₂ | H | CH₂ | OEt | 1,4-di-Me-2-Ph-5-Imid | O |
| 1-177 | H | (CH₂)₂ | H | CH₂ | OEt | 1,5-di-Me-2-Ph-4-Imid | O |
| 1-178 | H | (CH₂)₂ | H | CH₂ | OEt | 3,4-MdO—Ph | O |
| 1-179 | H | (CH₂)₂ | H | CH₂ | OEt | 4-(4-MeO—Ph)—Ph | O |
| 1-180 | H | (CH₂)₂ | H | CH₂ | OEt | 4-(3,4-MdO—Ph)—Ph | O |
| 1-181 | H | (CH₂)₂ | H | CH₂ | OEt | 4-[PhSO₂N(Me)]—Ph | O |
| 1-182 | H | (CH₂)₂ | H | CH₂ | OEt | 4-[(Pyr-3)SO₂N(Me)]—Ph | O |
| 1-183 | H | (CH₂)₂ | H | CH₂ | OEt | 4-(PhSO₂NH)—Ph | O |
| 1-184 | H | (CH₂)₂ | H | CH₂ | OEt | 4-[(Pyr-3)SO₂NH]—Ph | O |
| 1-185 | H | (CH₂)₂ | H | CH₂ | OEt | 4-[(Pyr-2)SO₂]—Ph | O |
| 1-186 | H | (CH₂)₂ | H | CH₂ | OEt | 4-[(Pyr-3)SO₂]—Ph | O |
| 1-187 | H | (CH₂)₂ | H | CH₂ | OEt | 4-[(Pyr-2)SO₂N(Me)]—Ph | O |
| 1-188 | H | (CH₂)₂ | H | CH₂ | OEt | 4-[(Pyr-2)SO₂NH]—Ph | O |
| 1-189 | H | (CH₂)₂ | H | CH₂ | OEt | 4-(4-Me—Ph)—Ph | O |
| 1-190 | H | (CH₂)₂ | H | CH₂ | OEt | 4-(4-F—Ph)—Ph | O |
| 1-191 | H | (CH₂)₂ | H | CH₂ | OEt | 4-(4-CF₃—Ph)—Ph | O |
| 1-192 | H | (CH₂)₂ | H | CH₂ | OEt | 2-[4-Me—PhSO₂N(Me)]-5-Pyr | O |
| 1-193 | H | (CH₂)₂ | H | CH₂ | OEt | 2-HO-5-Pyr | O |
| 1-194 | H | (CH₂)₂ | H | CH₂ | OEt | 2-BzO-5-Pyr | O |
| 1-195 | H | (CH₂)₂ | H | CH₂ | OEt | 4-[(Pyr-4)SO₂]—Ph | O |
| 1-196 | H | (CH₂)₂ | H | CH₂ | OEt | 4-(2,4-di-MeO—Ph)—Ph | O |
| 1-197 | H | (CH₂)₂ | H | CH₂ | OEt | 4-(2,5-di-MeO—Ph)—Ph | O |
| 1-198 | H | (CH₂)₂ | H | CH₂ | OEt | 3-HO—Ph | O |
| 1-199 | H | (CH₂)₂ | H | CH₂ | OEt | 4-HO—Ph | O |
| 1-200 | H | (CH₂)₂ | H | CH₂ | OEt | 5-AcO-2-HO-3,4,6-tri-Me—Ph | O |
| 1-201 | H | (CH₂)₂ | H | CH₂ | OEt | 4-HO-3,5-di-Me—Ph | O |

TABLE 1-continued

| Exemplification No. compound. | R¹ | R² | R³ | Z | W | X | Y |
|---|---|---|---|---|---|---|---|
| 1-202 | H | (CH₂)₂ | H | CH₂ | OEt | 3-AcO—Ph | O |
| 1-203 | H | (CH₂)₂ | H | CH₂ | OEt | 4-AcO—Ph | O |

TABLE 2

| Exemplification No. compound. | R¹ | R² | R³ | Z | W | X | Y |
|---|---|---|---|---|---|---|---|
| 2-1 | Me | (CH₂)₂ | H | CH₂ | OEt | Ph | O |
| 2-2 | Me | (CH₂)₂ | H | CH₂ | OEt | 1-Np | O |
| 2-3 | Me | (CH₂)₂ | H | CH₂ | OEt | 2-Np | O |
| 2-4 | Me | (CH₂)₂ | H | CH₂ | OEt | 4-Me—Ph | O |
| 2-5 | Me | (CH₂)₂ | H | CH₂ | OEt | 4-Et—Ph | O |
| 2-6 | Me | (CH₂)₂ | H | CH₂ | OEt | 3-iPr—Ph | O |
| 2-7 | Me | (CH₂)₂ | H | CH₂ | OEt | 4-iPr—Ph | O |
| 2-8 | Me | (CH₂)₂ | H | CH₂ | OEt | 3-tBu—Ph | O |
| 2-9 | Me | (CH₂)₂ | H | CH₂ | OEt | 4-tBu—Ph | O |
| 2-10 | Me | (CH₂)₂ | H | CH₂ | OEt | 3-Cl—Ph | O |
| 2-11 | Me | (CH₂)₂ | H | CH₂ | OEt | 4-Cl—Ph | O |
| 2-12 | Me | (CH₂)₂ | H | CH₂ | OEt | 3-Br—Ph | O |
| 2-13 | Me | (CH₂)₂ | H | CH₂ | OEt | 4-Br—Ph | O |
| 2-14 | Me | (CH₂)₂ | H | CH₂ | OEt | 3-Ph—Ph | O |
| 2-15 | Me | (CH₂)₂ | H | CH₂ | OEt | 4-Ph—Ph | O |
| 2-16 | Me | (CH₂)₂ | H | CH₂ | OEt | 3-Bz—Ph | O |
| 2-17 | Me | (CH₂)₂ | H | CH₂ | OEt | 4-Bz—Ph | O |
| 2-18 | Me | (CH₂)₂ | H | CH₂ | OEt | 3-PhO—Ph | O |
| 2-19 | Me | (CH₂)₂ | H | CH₂ | OEt | 4-PhO—Ph | O |
| 2-20 | Me | (CH₂)₂ | H | CH₂ | OEt | 3-PhS—Ph | O |
| 2-21 | Me | (CH₂)₂ | H | CH₂ | OEt | 4-PhS—Ph | O |
| 2-22 | Me | (CH₂)₂ | H | CH₂ | OEt | 3-PhSO₂—Ph | O |
| 2-23 | Me | (CH₂)₂ | H | CH₂ | OEt | 4-PhSO₂—Ph | O |
| 2-24 | Me | (CH₂)₂ | H | CH₂ | OEt | 3-(Imid-1)—Ph | O |
| 2-25 | Me | (CH₂)₂ | H | CH₂ | OEt | 4-(Imid-1)—Ph | O |
| 2-26 | Me | (CH₂)₂ | H | CH₂ | OEt | 3-(Imid-4)—Ph | O |
| 2-27 | Me | (CH₂)₂ | H | CH₂ | OEt | 4-(Imid-4)—Ph | O |
| 2-28 | Me | (CH₂)₂ | H | CH₂ | OEt | 3-(Fur-2)—Ph | O |
| 2-29 | Me | (CH₂)₂ | H | CH₂ | OEt | 4-(Fur-2)—Ph | O |
| 2-30 | Me | (CH₂)₂ | H | CH₂ | OEt | 3-(Thi-2)—Ph | O |
| 2-31 | Me | (CH₂)₂ | H | CH₂ | OEt | 4-(Thi-2)—Ph | O |
| 2-32 | Me | (CH₂)₂ | H | CH₂ | OEt | 3-(Thi-3)—Ph | O |
| 2-33 | Me | (CH₂)₂ | H | CH₂ | OEt | 4-(Thi-3)—Ph | O |
| 2-34 | Me | (CH₂)₂ | H | CH₂ | OEt | 3-(Pyr-2)—Ph | O |
| 2-35 | Me | (CH₂)₂ | H | CH₂ | OEt | 4-(Pyr-2)—Ph | O |
| 2-36 | Me | (CH₂)₂ | H | CH₂ | OEt | 3-(Pyr-3)—Ph | O |
| 2-37 | Me | (CH₂)₂ | H | CH₂ | OEt | 4-(Pyr-3)—Ph | O |
| 2-38 | Me | (CH₂)₂ | H | CH₂ | OEt | 3-(Pyr-4)—Ph | O |
| 2-39 | Me | (CH₂)₂ | H | CH₂ | OEt | 4-(Pyr-4)—Ph | O |
| 2-40 | Me | (CH₂)₂ | H | CH₂ | OEt | 3-(Oxa-2)—Ph | O |
| 2-41 | Me | (CH₂)₂ | H | CH₂ | OEt | 4-(Oxa-2)—Ph | O |
| 2-42 | Me | (CH₂)₂ | H | CH₂ | OEt | 3-(Oxa-4)—Ph | O |
| 2-43 | Me | (CH₂)₂ | H | CH₂ | OEt | 4-(Oxa-4)—Ph | O |
| 2-44 | Me | (CH₂)₂ | H | CH₂ | OEt | 3-(Oxa-5)—Ph | O |
| 2-45 | Me | (CH₂)₂ | H | CH₂ | OEt | 4-(Oxa-5)—Ph | O |
| 2-46 | Me | (CH₂)₂ | H | CH₂ | OEt | 3-(Thiz-2)—Ph | O |
| 2-47 | Me | (CH₂)₂ | H | CH₂ | OEt | 4-(Thiz-2)—Ph | O |
| 2-48 | Me | (CH₂)₂ | H | CH₂ | OEt | 3-(Thiz-4)—Ph | O |
| 2-49 | Me | (CH₂)₂ | H | CH₂ | OEt | 4-(Thiz-4)—Ph | O |
| 2-50 | Me | (CH₂)₂ | H | CH₂ | OEt | 3-(Thiz-5)—Ph | O |
| 2-51 | Me | (CH₂)₂ | H | CH₂ | OEt | 4-(Thiz-5)—Ph | O |
| 2-52 | Me | (CH₂)₂ | H | CH₂ | OEt | 1-Me-2-Pyrr | O |
| 2-53 | Me | (CH₂)₂ | H | CH₂ | OEt | 1-Ph-2-Pyrr | O |
| 2-54 | Me | (CH₂)₂ | H | CH₂ | OEt | 1-Bz-2-Pyrr | O |
| 2-55 | Me | (CH₂)₂ | H | CH₂ | OEt | 5-Me-2-Fur | O |
| 2-56 | Me | (CH₂)₂ | H | CH₂ | OEt | 5-Ph-2-Fur | O |
| 2-57 | Me | (CH₂)₂ | H | CH₂ | OEt | 5-Me-2-Thi | O |
| 2-58 | Me | (CH₂)₂ | H | CH₂ | OEt | 5-Ph-2-Thi | O |
| 2-59 | Me | (CH₂)₂ | H | CH₂ | OEt | 5-Me-3-Thi | O |
| 2-60 | Me | (CH₂)₂ | H | CH₂ | OEt | 5-Ph-3-Thi | O |
| 2-61 | Me | (CH₂)₂ | H | CH₂ | OEt | 1-Me-3-Pyza | O |
| 2-62 | Me | (CH₂)₂ | H | CH₂ | OEt | 1-Ph-3-Pyza | O |
| 2-63 | Me | (CH₂)₂ | H | CH₂ | OEt | 1-Me-2-Imid | O |
| 2-64 | Me | (CH₂₂ | H | CH₂ | OEt | 1-Ph-2-Imid | O |
| 2-65 | Me | (CH₂)₂ | H | CH₂ | OEt | 1-Me-4-Imid | O |

TABLE 2-continued

| Exemplification No. compound. | R¹ | R² | R³ | Z | W | X | Y |
|---|---|---|---|---|---|---|---|
| 2-66 | Me | (CH$_2$)$_2$ | H | CH$_2$ | OEt | 1-Ph-4-Imid | O |
| 2-67 | Me | (CH$_2$)$_2$ | H | CH$_2$ | OEt | 4-Oxa | O |
| 2-68 | Me | (CH$_2$)$_2$ | H | CH$_2$ | OEt | 5-Oxa | O |
| 2-69 | Me | (CH$_2$)$_2$ | H | CH$_2$ | OEt | 2-Me-4-Oxa | O |
| 2-70 | Me | (CH$_2$)$_2$ | H | CH$_2$ | OEt | 2-Ph-4-Oxa | O |
| 2-71 | Me | (CH$_2$)$_2$ | H | CH$_2$ | OEt | 2-Me-5-Oxa | O |
| 2-72 | Me | (CH$_2$)$_2$ | H | CH$_2$ | OEt | 2-Ph-5-Oxa | O |
| 2-73 | Me | (CH$_2$)$_2$ | H | CH$_2$ | OEt | 4-Me-2-Ph-5-Oxa | O |
| 2-74 | Me | (CH$_2$)$_2$ | H | CH$_2$ | OEt | 5-Me-2-Ph-4-Oxa | O |
| 2-75 | Me | (CH$_2$)$_2$ | H | CH$_2$ | OEt | 4-Thiz | O |
| 2-76 | Me | (CH$_2$)$_2$ | H | CH$_2$ | OEt | 5-Thiz | O |
| 2-77 | Me | (CH$_2$)$_2$ | H | CH$_2$ | OEt | 2-Me-4-Thiz | O |
| 2-78 | Me | (CH$_2$)$_2$ | H | CH$_2$ | OEt | 2-Ph-4-Thiz | O |
| 2-79 | Me | (CH$_2$)$_2$ | H | CH$_2$ | OEt | 2-Me-5-Thiz | O |
| 2-80 | Me | (CH$_2$)$_2$ | H | CH$_2$ | OEt | 2-Ph-5-Thiz | O |
| 2-81 | Me | (CH$_2$)$_2$ | H | CH$_2$ | OEt | 4-Me-2-Ph-5-Thiz | O |
| 2-82 | Me | (CH$_2$)$_2$ | H | CH$_2$ | OEt | 5-Me-2-Ph-4-Thiz | O |
| 2-83 | Me | (CH$_2$)$_2$ | H | CH$_2$ | OEt | 1-Me-4-Pyza | O |
| 2-84 | Me | (CH$_2$)$_2$ | H | CH$_2$ | OEt | 1-Ph-4-Pyza | O |
| 2-85 | Me | (CH$_2$)$_2$ | H | CH$_2$ | OEt | 2-Me-4-Isox | O |
| 2-86 | Me | (CH$_2$)$_2$ | H | CH$_2$ | OEt | 2-Ph-4-Isox | O |
| 2-87 | Me | (CH$_2$)$_2$ | H | CH$_2$ | OEt | 2-Pyr | O |
| 2-88 | Me | (CH$_2$)$_2$ | H | CH$_2$ | OEt | 3-Pyr | O |
| 2-89 | Me | (CH$_2$)$_2$ | H | CH$_2$ | OEt | 4-Pyr | O |
| 2-90 | Me | (CH$_2$)$_2$ | H | CH$_2$ | OEt | 3-Me-5-Pyr | O |
| 2-91 | Me | (CH$_2$)$_2$ | H | CH$_2$ | OEt | 3-Et-5-Pyr | O |
| 2-92 | Me | (CH$_2$)$_2$ | H | CH$_2$ | OEt | 3-Ph-5-Pyr | O |
| 2-93 | Me | (CH$_2$)$_2$ | H | CH$_2$ | OEt | 2-Me-5-Pyr | O |
| 2-94 | Me | (CH$_2$)$_2$ | H | CH$_2$ | OEt | 2-Et-5-Pyr | O |
| 2-95 | Me | (CH$_2$)$_2$ | H | CH$_2$ | OEt | 2-Ph-5-Pyr | O |
| 2-96 | Me | (CH$_2$)$_2$ | H | CH$_2$ | OEt | 2-MeO-5-Pyr | O |
| 2-97 | Me | (CH$_2$)$_2$ | H | CH$_2$ | OEt | 2-EtO-5-Pyr | O |
| 2-98 | Me | (CH$_2$)$_2$ | H | CH$_2$ | OEt | 2-iPrO-5-Pyr | O |
| 2-99 | Me | (CH$_2$)$_2$ | H | CH$_2$ | OEt | 2-MeS-5-Pyr | O |
| 2-100 | Me | (CH$_2$)$_2$ | H | CH$_2$ | OEt | 2-EtS-5-Pyr | O |
| 2-101 | Me | (CH$_2$)$_2$ | H | CH$_2$ | OEt | 2-iPrS-5-Pyr | O |
| 2-102 | Me | (CH$_2$)$_2$ | H | CH$_2$ | OEt | 2-MeSO$_2$-5-Pyr | O |
| 2-103 | Me | (CH$_2$)$_2$ | H | CH$_2$ | OEt | 2-EtSO$_2$-5-Pyr | O |
| 2-104 | Me | (CH$_2$)$_2$ | H | CH$_2$ | OEt | 2-iPrSO$_2$-5 -Pyr | O |
| 2-105 | Me | (CH$_2$)$_2$ | H | CH$_2$ | OEt | 2-Bz-5-Pyr | O |
| 2-106 | Me | (CH$_2$)$_2$ | H | CH$_2$ | OEt | 2-PhO-5-Pyr | O |
| 2-107 | Me | (CH$_2$)$_2$ | H | CH$_2$ | OEt | 2-PhS-5-Pyr | O |
| 2-108 | Me | (CH$_2$)$_2$ | H | CH$_2$ | OEt | 2-PhSO$_2$-5-Pyr | O |
| 2-109 | Me | (CH$_2$)$_2$ | H | CH$_2$ | OEt | 3-Me-6-Pyr | O |
| 2-110 | Me | (CH$_2$)$_2$ | H | CH$_2$ | OEt | 3-Ph-6-Pyr | O |
| 2-111 | Me | (CH$_2$)$_2$ | H | CH$_2$ | OEt | 2-Me-6-Pyr | O |
| 2-112 | Me | (CH$_2$)$_2$ | H | CH$_2$ | OEt | 2-Ph-6-Pyr | O |
| 2-113 | Me | (CH$_2$)$_2$ | H | CH$_2$ | OEt | 2-Me-4-Pym | O |
| 2-114 | Me | (CH$_2$)$_2$ | H | CH$_2$ | OEt | 2-Ph-4-Pym | O |
| 2-115 | Me | (CH$_2$)$_2$ | H | CH$_2$ | OEt | 2-MeO-4-Pym | O |
| 2-116 | Me | (CH$_2$)$_2$ | H | CH$_2$ | OEt | 2-EtO-4-Pym | O |
| 2-117 | Me | (CH$_2$)$_2$ | H | CH$_2$ | OEt | 2-iPrO-4-Pym | O |
| 2-118 | Me | (CH$_2$)$_2$ | H | CH$_2$ | OEt | 2-MeS-4-Pym | O |
| 2-119 | Me | (CH$_2$)$_2$ | H | CH$_2$ | OEt | 2-EtS-4-Pym | O |
| 2-120 | Me | (CH$_2$)$_2$ | H | CH$_2$ | OEt | 2-iPrS-4-Pym | O |
| 2-121 | Me | (CH$_2$)$_2$ | H | CH$_2$ | OEt | 6-MeS-4-Pym | O |
| 2-122 | Me | (CH$_2$)$_2$ | H | CH$_2$ | OEt | 6-EtS-4-Pym | O |
| 2-123 | Me | (CH$_2$)$_2$ | H | CH$_2$ | OEt | 6-iPrS-4-Pym | O |
| 2-124 | Me | (CH$_2$)$_2$ | H | CH$_2$ | OEt | 2-PhS-4-Pym | O |
| 2-125 | Me | (CH$_2$)$_2$ | H | CH$_2$ | OEt | 2-MeSO$_2$-4-Pym | O |
| 2-126 | Me | (CH$_2$)$_2$ | H | CH$_2$ | OEt | 2-EtSO$_2$-4-Pym | O |
| 2-127 | Me | (CH$_2$)$_2$ | H | CH$_2$ | OEt | 2-iPrSO$_2$-4-Pym | O |
| 2-128 | Me | (CH$_2$)$_2$ | H | CH$_2$ | OEt | 2-PhSO$_2$-4-Pym | O |
| 2-129 | Me | (CH$_2$)$_2$ | H | CH$_2$ | OEt | 2-Me-5-Pym | O |
| 2-130 | Me | (CH$_2$)$_2$ | H | CH$_2$ | OEt | 2-Ph-5-Pym | O |
| 2-131 | Me | (CH$_2$)$_2$ | H | CH$_2$ | OEt | 2-MeO-5-Pym | O |
| 2-132 | Me | (CH$_2$)$_2$ | H | CH$_2$ | OEt | 2-EtO-5-Pym | O |
| 2-133 | Me | (CH$_2$)$_2$ | H | CH$_2$ | OEt | 2-iPrO-5-Pym | O |
| 2-134 | Me | (CH$_2$)$_2$ | H | CH$_2$ | OEt | 2-MeS-5-Pym | O |
| 2-135 | Me | (CH$_2$)$_2$ | H | CH$_2$ | OEt | 2-EtS-5-Pym | O |
| 2-136 | Me | (CH$_2$)$_2$ | H | CH$_2$ | OEt | 2-iPrS-5-Pym | O |
| 2-137 | Me | (CH$_2$)$_2$ | H | CH$_2$ | OEt | 2-PhS-5-Pym | O |
| 2-138 | Me | (CH$_2$)$_2$ | H | CH$_2$ | OEt | 2-MeSO$_2$-5-Pym | O |
| 2-139 | Me | (CH$_2$)$_2$ | H | CH$_2$ | OEt | 2-EtSO$_2$-5-Pym | O |
| 2-140 | Me | (CH$_2$)$_2$ | H | CH$_2$ | OEt | 2-iPrSO$_2$-5-Pym | O |
| 2-141 | Me | (CH$_2$)$_2$ | H | CH$_2$ | OEt | 2-PhSO$_2$-5-Pym | O |

TABLE 2-continued

| Exemplification No. compound. | R¹ | R² | R³ | Z | W | X | Y |
|---|---|---|---|---|---|---|---|
| 2-142 | Me | (CH₂)₂ | H | CH₂ | OEt | 2-Ind | O |
| 2-143 | Me | (CH₂)₂ | H | CH₂ | OEt | 3-Ind | O |
| 2-144 | Me | (CH₂)₂ | H | CH₂ | OEt | 1-Me-2-Ind | O |
| 2-145 | Me | (CH₂)₂ | H | CH₂ | OEt | 1-Me-3-Ind | O |
| 2-146 | Me | (CH₂)₂ | H | CH₂ | OEt | 2-Bimid | O |
| 2-147 | Me | (CH₂)₂ | H | CH₂ | OEt | 2-Boxa | O |
| 2-148 | Me | (CH₂)₂ | H | CH₂ | OEt | 2-Bthiz | O |
| 2-149 | Me | (CH₂)₂ | H | CH₂ | OEt | 2-Quin | O |
| 2-150 | Me | (CH₂)₂ | H | CH₂ | OEt | 3-Quin | O |
| 2-151 | Me | (CH₂)₂ | H | CH₂ | OEt | 4-Quin | O |
| 2-152 | Me | (CH₂)₂ | H | CH₂ | OEt | 1-iQuin | O |
| 2-153 | Me | (CH₂)₂ | H | CH₂ | OEt | 3-iQuin | O |
| 2-154 | Me | (CH₂)₂ | H | CH₂ | OEt | 4-iQuin | O |
| 2-155 | Me | (CH₂)₂ | H | CH₂ | OEt | 3-MeO—Ph | O |
| 2-156 | Me | (CH₂)₂ | H | CH₂ | OEt | 4-MeO—Ph | O |
| 2-157 | Me | (CH₂)₂ | H | CH₂ | OEt | 3-EtO—Ph | O |
| 2-158 | Me | (CH₂)₂ | H | CH₂ | OEt | 4-EtO—Ph | O |
| 2-159 | Me | (CH₂)₂ | H | CH₂ | OEt | 3-iPrO—Ph | O |
| 2-160 | Me | (CH₂)₂ | H | CH₂ | OEt | 4-iPrO—Ph | O |
| 2-161 | Me | (CH₂)₂ | H | CH₂ | OEt | 3-MeS—Ph | O |
| 2-162 | Me | (CH₂)₂ | H | CH₂ | OEt | 4-MeS—Ph | O |
| 2-163 | Me | (CH₂)₂ | H | CH₂ | OEt | 3-EtS—Ph | O |
| 2-164 | Me | (CH₂)₂ | H | CH₂ | OEt | 4-EtS—Ph | O |
| 2-165 | Me | (CH₂)₂ | H | CH₂ | OEt | 3-iPrS—Ph | O |
| 2-166 | Me | (CH₂)₂ | H | CH₂ | OEt | 4-iPrS—Ph | O |
| 2-167 | Me | (CH₂)₂ | H | CH₂ | OEt | 3-MeSO₂—Ph | O |
| 2-168 | Me | (CH₂)₂ | H | CH₂ | OEt | 4-MeSO₂—Ph | O |
| 2-169 | Me | (CH₂)₂ | H | CH₂ | OEt | 3-EtSO₂—Ph | O |
| 2-170 | Me | (CH₂)₂ | H | CH₂ | OEt | 4-EtSO₂—Ph | O |
| 2-171 | Me | (CH₂)₂ | H | CH₂ | OEt | 3-iPrSO₂—Ph | O |
| 2-172 | Me | (CH₂)₂ | H | CH₂ | OEt | 4-iPrSO₂—Ph | O |
| 2-173 | Me | (CH₂)₂ | H | CH₂ | OEt | 3-(1-Me-Imid-4)—Ph | O |
| 2-174 | Me | (CH₂)₂ | H | CH₂ | OEt | 4-(1-Me-Imid-4)—Ph | O |
| 2-175 | Me | (CH₂)₂ | H | CH₂ | OEt | 1-Me-2-Ph-4-Imid | O |
| 2-176 | Me | (CH₂)₂ | H | CH₂ | OEt | 1,4-di-Me-2-Ph-5-Imid | O |
| 2-177 | Me | (CH₂)₂ | H | CH₂ | OEt | 1,5-di-Me-2-Ph-4-Imid | O |
| 2-178 | Me | (CH₂)₂ | H | CH₂ | OEt | 3,4-MdO—Ph | O |
| 2-179 | Me | (CH₂)₂ | H | CH₂ | OEt | 4-(4-MeO—Ph)—Ph | O |
| 2-180 | Me | (CH₂)₂ | H | CH₂ | OEt | 4-(3,4-MdO—Ph)—Ph | O |
| 2-181 | Me | (CH₂)₂ | H | CH₂ | OEt | 4-[PhSO₂N(Me)]—Ph | O |
| 2-182 | Me | (CH₂)₂ | H | CH₂ | OEt | 4-[(Pyr-3)SO₂N(Me)]—Ph | O |
| 2-183 | Me | (CH₂)₂ | H | CH₂ | OEt | 4-(PhSO₂NH)—Ph | O |
| 2-184 | Me | (CH₂)₂ | H | CH₂ | OEt | 4-[(Pyr-3)SO₂NH]—Ph | O |
| 2-185 | Me | (CH₂)₂ | H | CH₂ | OEt | 4-[(Pyr-2)SO₂]—Ph | O |
| 2-186 | Me | (CH₂)₂ | H | CH₂ | OEt | 4-[(Pyr-3)SO₂]—Ph | O |
| 2-187 | Me | (CH₂)₂ | H | CH₂ | OEt | 4-[(Pyr-2)SO₂N(Me)]—Ph | O |
| 2-188 | Me | (CH₂)₂ | H | CH₂ | OEt | 4-[(Pyr-2)SO₂NH]—Ph | O |
| 2-189 | Me | (CH₂)₂ | H | CH₂ | OEt | 4-(4-Me—Ph)—Ph | O |
| 2-190 | Me | (CH₂)₂ | H | CH₂ | OEt | 4-(4-F—Ph)—Ph | O |
| 2-191 | Me | (CH₂)₂ | H | CH₂ | OEt | 4-(4-CF₃—Ph)—Ph | O |
| 2-192 | Me | (CH₂)₂ | H | CH₂ | OEt | 2-[4-Me—PhSO₂N(Me)]-5-Pyr | O |
| 2-193 | Me | (CH₂)₂ | H | CH₂ | OEt | 2-HO-5-Pyr | O |
| 2-194 | Me | (CH₂)₂ | H | CH₂ | OEt | 2-BzO-5-Pyr | O |
| 2-195 | Me | (CH₂)₂ | H | CH₂ | OEt | 4-[(Pyr-4)SO₂]—Ph | O |
| 2-196 | Me | (CH₂)₂ | H | CH₂ | OEt | 4-(2,4-di-MeO—Ph)—Ph | O |
| 2-197 | Me | (CH₂)₂ | H | CH₂ | OEt | 4-(2,5-di-MeO—Ph)—Ph | O |
| 2-198 | Me | (CH₂)₂ | H | CH₂ | OEt | 3-HO—Ph | O |
| 2-199 | Me | (CH₂)₂ | H | CH₂ | OEt | 4-HO—Ph | O |
| 2-200 | Me | (CH₂)₂ | H | CH₂ | OEt | 5-AcO-2-HO-3,4,6-tri-Me—Ph | O |
| 2-201 | Me | (CH₂)₂ | H | CH₂ | OEt | 4-HO-3,5-di-Me—Ph | O |
| 2-202 | Me | (CH₂)₂ | H | CH₂ | OEt | 3-AcO—Ph | O |
| 2-203 | Me | (CH₂)₂ | H | CH₂ | OEt | 4-AcO—Ph | O |

TABLE 3

| Exemplification No. compound. | R¹ | R² | R³ | Z | W | X | Y |
|---|---|---|---|---|---|---|---|
| 3-1 | Et | (CH₂)₂ | H | CH₂ | OEt | Ph | O |
| 3-2 | Et | (CH₂)₂ | H | CH₂ | OEt | 1-Np | O |
| 3-3 | Et | (CH₂)₂ | H | CH₂ | OEt | 2-Np | O |
| 3-4 | Et | (CH₂)₂ | H | CH₂ | OEt | 4-Me—Ph | O |
| 3-5 | Et | (CH₂)₂ | H | CH₂ | OEt | 4-Et—Ph | O |

TABLE 3-continued

| Exemplification No. compound. | R¹ | R² | R³ | Z | W | X | Y |
|---|---|---|---|---|---|---|---|
| 3-6 | Et | (CH₂)₂ | H | CH₂ | OEt | 3-iPr—Ph | O |
| 3-7 | Et | (CH₂)₂ | H | CH₂ | OEt | 4-iPr—Ph | O |
| 3-8 | Et | (CH₂)₂ | H | CH₂ | OEt | 3-tBu—Ph | O |
| 3-9 | Et | (CH₂)₂ | H | CH₂ | OEt | 4-tBu—Ph | O |
| 3-10 | Et | (CH₂)₂ | H | CH₂ | OEt | 3-Cl—Ph | O |
| 3-11 | Et | (CH₂)₂ | H | CH₂ | OEt | 4-Cl—Ph | O |
| 3-12 | Et | (CH₂)₂ | H | CH₂ | OEt | 3-Br—Ph | O |
| 3-13 | Et | (CH₂)₂ | H | CH₂ | OEt | 4-Br—Ph | O |
| 3-14 | Et | (CH₂)₂ | H | CH₂ | OEt | 3-Ph—Ph | O |
| 3-15 | Et | (CH₂)₂ | H | CH₂ | OEt | 4-Ph—Ph | O |
| 3-16 | Et | (CH₂)₂ | H | CH₂ | OEt | 3-Bz—Ph | O |
| 3-17 | Et | (CH₂)₂ | H | CH₂ | OEt | 4-Bz—Ph | O |
| 3-18 | Et | (CH₂)₂ | H | CH₂ | OEt | 3-PhO—Ph | O |
| 3-19 | Et | (CH₂)₂ | H | CH₂ | OEt | 4-PhO—Ph | O |
| 3-20 | Et | (CH₂)₂ | H | CH₂ | OEt | 3-PhS—Ph | O |
| 3-21 | Et | (CH₂)₂ | H | CH₂ | OEt | 4-PhS—Ph | O |
| 3-22 | Et | (CH₂)₂ | H | CH₂ | OEt | 3-PhSO₂—Ph | O |
| 3-23 | Et | (CH₂)₂ | H | CH₂ | OEt | 4-PhSO₂—Ph | O |
| 3-24 | Et | (CH₂)₂ | H | CH₂ | OEt | 3-(Imid-1)—Ph | O |
| 3-25 | Et | (CH₂)₂ | H | CH₂ | OEt | 4-(Imid-1)—Ph | O |
| 3-26 | Et | (CH₂)₂ | H | CH₂ | OEt | 3-(Imid-4)—Ph | O |
| 3-27 | Et | (CH₂)₂ | H | CH₂ | OEt | 4-(Imid-4)—Ph | O |
| 3-28 | Et | (CH₂)₂ | H | CH₂ | OEt | 3-(Fur-2)—Ph | O |
| 3-29 | Et | (CH₂)₂ | H | CH₂ | OEt | 4-(Fur-2)—Ph | O |
| 3-30 | Et | (CH₂)₂ | H | CH₂ | OEt | 3-(Thi-2)—Ph | O |
| 3-31 | Et | (CH₂)₂ | H | CH₂ | OEt | 4-(Thi-2)—Ph | O |
| 3-32 | Et | (CH₂)₂ | H | CH₂ | OEt | 3-(Thi-3)—Ph | O |
| 3-33 | Et | (9H₂)₂ | H | CH₂ | OEt | 4-(Thi-3)—Ph | O |
| 3-34 | Et | (CH₂)₂ | H | CH₂ | OEt | 3-(Pyr-2)—Ph | O |
| 3-35 | Et | (CH₂)₂ | H | CH₂ | OEt | 4-(Pyr-2)—Ph | O |
| 3-36 | Et | (CH₂)₂ | H | CH₂ | OEt | 3-(Pyr-3)—Ph | O |
| 3-37 | Et | (CH₂)₂ | H | CH₂ | OEt | 4-(Pyr-3)—Ph | O |
| 3-38 | Et | (CH₂)₂ | H | CH₂ | OEt | 3-(Pyr-4)—Ph | O |
| 3-39 | Et | (CH₂)₂ | H | CH₂ | OEt | 4-(Pyr-4)—Ph | O |
| 3-40 | Et | (CH₂)₂ | H | CH₂ | OEt | 3-(Oxa-2)—Ph | O |
| 3-41 | Et | (CH₂)₂ | H | CH₂ | OEt | 4-(Oxa-2)—Ph | O |
| 3-42 | Et | (CH₂)₂ | H | CH₂ | OEt | 3-(Oxa-4)—Ph | O |
| 3-43 | Et | (CH₂)₂ | H | CH₂ | OEt | 4-(Oxa-4)—Ph | O |
| 3-44 | Et | (CH₂)₂ | H | CH₂ | OEt | 3-(Oxa-5)—Ph | O |
| 3-45 | Et | (CH₂)₂ | H | CH₂ | OEt | 4-(Oxa-5)—Ph | O |
| 3-46 | Et | (CH₂)₂ | H | CH₂ | OEt | 3-(Thiz-2)—Ph | O |
| 3-47 | Et | (CH₂)₂ | H | CH₂ | OEt | 4-(Thiz-2)—Ph | O |
| 3-48 | Et | (CH₂)₂ | H | CH₂ | OEt | 3-(Thiz-4)—Ph | O |
| 3-49 | Et | (CH₂)₂ | H | CH₂ | OEt | 4-(Thiz-4)—Ph | O |
| 3-50 | Et | (CH₂)₂ | H | CH₂ | OEt | 3-(Thiz-5)—Ph | O |
| 3-51 | Et | (CH₂)₂ | H | CH₂ | OEt | 4-(Thiz-5)—Ph | O |
| 3-52 | Et | (CH₂)₂ | H | CH₂ | OEt | 1-Me-2-Pyrr | O |
| 3-53 | Et | (CH₂)₂ | H | CH₂ | OEt | 1-Ph-2-Pyrr | O |
| 3-54 | Et | (CH₂)₂ | H | CH₂ | OEt | 1-Bz-2-Pyrr | O |
| 3-55 | Et | (CH₂)₂ | H | CH₂ | OEt | 5-Me-2-Fur | O |
| 3-56 | Et | (CH₂)₂ | H | CH₂ | OEt | 5-Ph-2-Fur | O |
| 3-57 | Et | (CH₂)₂ | H | CH₂ | OEt | 5-Me-2-Thi | O |
| 3-58 | Et | (CH₂)₂ | H | CH₂ | OEt | 5-Ph-2-Thi | O |
| 3-59 | Et | (CH₂)₂ | H | CH₂ | OEt | 5-Me-3-Thi | O |
| 3-60 | Et | (CH₂)₂ | H | CH₂ | OEt | 5-Ph-3-Thi | O |
| 3-61 | Et | (CH₂)₂ | H | CH₂ | OEt | 1-Me-3-Pyza | O |
| 3-62 | Et | (CH₂)₂ | H | CH₂ | OEt | 1-Ph-3-Pyza | O |
| 3-63 | Et | (CH₂)₂ | H | CH₂ | OEt | I-Me-2-Imid | O |
| 3-64 | Et | (CH₂)₂ | H | CH₂ | OEt | 1-Ph-2-Imid | O |
| 3-65 | Et | (CH₂)₂ | H | CH₂ | OEt | 1-Me-4-Imid | O |
| 3-66 | Et | (CH₂)₂ | H | CH₂ | OEt | 1-Ph-4-Imid | O |
| 3-67 | Et | (CH₂)₂ | H | CH₂ | OEt | 4-Oxa | O |
| 3-68 | Et | (CH₂)₂ | H | CH₂ | OEt | 5-Oxa | O |
| 3-69 | Et | (CH₂)₂ | H | CH₂ | OEt | 2-Me-4-Oxa | O |
| 3-70 | Et | (CH₂)₂ | H | CH₂ | OEt | 2-Ph-4-Oxa | O |
| 3-71 | Et | (CH₂)₂ | H | CH₂ | OEt | 2-Me-5-Oxa | O |
| 3-72 | Et | (CH₂)₂ | H | CH₂ | OEt | 2-Ph-5-Oxa | O |
| 3-73 | Et | (CH₂)₂ | H | CH₂ | OEt | 4-Me-2-Ph-5-Oxa | O |
| 3-74 | Et | (CH₂)₂ | H | CH₂ | OEt | 5-Me-2-Ph-4-Oxa | O |
| 3-75 | Et | (CH₂)₂ | H | CH₂ | OEt | 4-Thiz | O |
| 3-76 | Et | (CH₂)₂ | H | CH₂ | OEt | 5-Thiz | O |
| 3-77 | Et | (CH₂)₂ | H | CH₂ | OEt | 2-Me-4-Thiz | O |
| 3-78 | Et | (CH₂)₂ | H | CH₂ | OEt | 2-Ph-4-Thiz | O |
| 3-79 | Et | (CH₂)₂ | H | CH₂ | OEt | 2-Me-5-Thiz | O |
| 3-80 | Et | (CH₂)₂ | H | CH₂ | OEt | 2-Ph-5-Thiz | O |
| 3-81 | Et | (CH₂)₂ | H | CH₂ | OEt | 4-Me-2-Ph-5-Thiz | O |

TABLE 3-continued

| Exemplification No. compound. | R¹ | R² | R³ | Z | W | X | Y |
|---|---|---|---|---|---|---|---|
| 3-82 | Et | (CH₂)₂ | H | CH₂ | OEt | 5-Me-2-Ph-4-Thiz | O |
| 3-83 | Et | (CH₂)₂ | H | CH₂ | OEt | 1-Me-4-Pyza | O |
| 3-84 | Et | (CH₂)₂ | H | CH₂ | OEt | 1-Ph-4-Pyza | O |
| 3-85 | Et | (CH₂)₂ | H | CH₂ | OEt | 2-Me-4-Isox | O |
| 3-86 | Et | (CH₂)₂ | H | CH₂ | OEt | 2-Ph-4-Isox | O |
| 3-87 | Et | (CH₂)₂ | H | CH₂ | OEt | 2-Pyr | O |
| 3-88 | Et | (CH₂)₂ | H | CH₂ | OEt | 3-Pyr | O |
| 3-89 | Et | (CH₂)₂ | H | CH₂ | OEt | 4-Pyr | O |
| 3-90 | Et | (CH₂)₂ | H | CH₂ | OEt | 3-Me-5-Pyr | O |
| 3-91 | Et | (CH₂)₂ | H | CH₂ | OEt | 3-Et-5-Pyr | O |
| 3-92 | Et | (CH₂)₂ | H | CH₂ | OEt | 3-Ph-5-Pyr | O |
| 3-93 | Et | (CH₂)₂ | H | CH₂ | OEt | 2-Me-5-Pyr | O |
| 3-94 | Et | (CH₂)₂ | H | CH₂ | OEt | 2-Et-5-Pyr | O |
| 3-95 | Et | (CH₂)₂ | H | CH₂ | OEt | 2-Ph-5-Pyr | O |
| 3-96 | Et | (CH₂)₂ | H | CH₂ | OEt | 2-MeO-5-Pyr | O |
| 3-97 | Et | (CH₂)₂ | H | CH₂ | OEt | 2-EtO-5-Pyr | O |
| 3-98 | Et | (CH₂)₂ | H | CH₂ | OEt | 2-iPrO-5-Pyr | O |
| 3-99 | Et | (CH₂)₂ | H | CH₂ | OEt | 2-MeS-5-Pyr | O |
| 3-100 | Et | (CH₂)₂ | H | CH₂ | OEt | 2-EtS-5-Pyr | O |
| 3-101 | Et | (CH₂)₂ | H | CH₂ | OEt | 2-iPrS-5-Pyr | O |
| 3-102 | Et | (CH₂)₂ | H | CH₂ | OEt | 2-MeSO₂-5-Pyr | O |
| 3-103 | Et | (CH₂)₂ | H | CH₂ | OEt | 2-EtSO₂-5-Pyr | O |
| 3-104 | Et | (CH₂)₂ | H | CH₂ | OEt | 2-iPrSO₂-5-Pyr | O |
| 3-105 | Et | (CH₂)₂ | H | CH₂ | OEt | 2-Bz-5-Pyr | O |
| 3-106 | Et | (CH₂)₂ | H | CH₂ | OEt | 2-PhO-5-Pyr | O |
| 3-107 | Et | (CH₂)₂ | H | CH₂ | OEt | 2-PhS-5-Pyr | O |
| 3-108 | Et | (CH₂)₂ | H | CH₂ | OEt | 2-PhSO₂-5-Pyr | O |
| 3-109 | Et | (CH₂)₂ | H | CH₂ | OEt | 3-Me-6-Pyr | O |
| 3-110 | Et | (CH₂)₂ | H | CH₂ | OEt | 3-Ph-6-Pyr | O |
| 3-111 | Et | (CH₂)₂ | H | CH₂ | OEt | 2-Me-6-Pyr | O |
| 3-112 | Et | (CH₂)₂ | H | CH₂ | OEt | 2-Ph-6-Pyr | O |
| 3-113 | Et | (CH₂)₂ | H | CH₂ | OEt | 2-Me-4-Pym | O |
| 3-114 | Et | (CH₂)₂ | H | CH₂ | OEt | 2-Ph-4-Pym | O |
| 3-115 | Et | (CH₂)₂ | H | CH₂ | OEt | 2-MeO-4-Pym | O |
| 3-116 | Et | (CH₂)₂ | H | CH₂ | OEt | 2-EtO-4-Pym | O |
| 3-117 | Et | (CH₂)₂ | H | CH₂ | OEt | 2-iPrO-4-Pym | O |
| 3-118 | Et | (CH₂)₂ | H | CH₂ | OEt | 2-MeS-4-Pym | O |
| 3-119 | Et | (CH₂)₂ | H | CH₂ | OEt | 2-EtS-4-Pym | O |
| 3-120 | Et | (CH₂)₂ | H | CH₂ | OEt | 2-iPrS-4-Pym | O |
| 3-121 | Et | (CH₂)₂ | H | CH₂ | OEt | 6-MeS-4-Pym | O |
| 3-122 | Et | (CH₂)₂ | H | CH₂ | OEt | 6-EtS-4-Pym | O |
| 3-123 | Et | (CH₂)₂ | H | CH₂ | OEt | 6-iPrS-4-Pym | O |
| 3-124 | Et | (CH₂)₂ | H | CH₂ | OEt | 2-PhS-4-Pym | O |
| 3-125 | Et | (CH₂)₂ | H | CH₂ | OEt | 2-MeSO₂-4-Pym | O |
| 3-126 | Et | (CH₂)₂ | H | CH₂ | OEt | 2-EtSO₂-4-Pym | O |
| 3-127 | Et | (CH₂)₂ | H | CH₂ | OEt | 2-iPrSO₂-4-Pym | O |
| 3-128 | Et | (CH₂)₂ | H | CH₂ | OEt | 2-PhSO₂-4-Pym | O |
| 3-129 | Et | (CH₂)₂ | H | CH₂ | OEt | 2-Me-5-Pym | O |
| 3-130 | Et | (CH₂)₂ | H | CH₂ | OEt | 2-Ph-5-Pym | O |
| 3-131 | Et | (CH₂)₂ | H | CH₂ | OEt | 2-MeO-5-Pym | O |
| 3-132 | Et | (CH₂)₂ | H | CH₂ | OEt | 2-EtO-5-Pym | O |
| 3-133 | Et | (CH₂)₂ | H | CH₂ | OEt | 2-iPrO-5-Pym | O |
| 3-134 | Et | (CH₂)₂ | H | CH₂ | OEt | 2-MeS-5-Pym | O |
| 3-135 | Et | (CH₂)₂ | H | CH₂ | OEt | 2-EtS-5-Pym | O |
| 3-136 | Et | (CH₂)₂ | H | CH₂ | OEt | 2-iPrS-5-Pym | O |
| 3-137 | Et | (CH₂)₂ | H | CH₂ | OEt | 2-PhS-5-Pym | O |
| 3-138 | Et | (CH₂)₂ | H | CH₂ | OEt | 2-MeSO₂-5-Pym | O |
| 3-139 | Et | (CH₂)₂ | H | CH₂ | OEt | 2-EtSO₂-5-Pym | O |
| 3-140 | Et | (CH₂)₂ | H | CH₂ | OEt | 2-iPrSO₂-5-Pym | O |
| 3-141 | Et | (CH₂)₂ | H | CH₂ | OEt | 2-PhSO₂-5-Pym | O |
| 3-142 | Et | (CH₂)₂ | H | CH₂ | OEt | 2-Ind | O |
| 3-143 | Et | (CH₂)₂ | H | CH₂ | OEt | 3-Ind | O |
| 3-144 | Et | (CH₂)₂ | H | CH₂ | OEt | 1-Me-2-Ind | O |
| 3-145 | Et | (CH₂)₂ | H | CH₂ | OEt | 1-Me-3-Ind | O |
| 3-146 | Et | (CH₂)₂ | H | CH₂ | OEt | 2-Bimid | O |
| 3-147 | Et | (CH₂)₂ | H | CH₂ | OEt | 2-Boxa | O |
| 3-148 | Et | (CH₂)₂ | H | CH₂ | OEt | 2-Bthiz | O |
| 3-149 | Et | (CH₂)₂ | H | CH₂ | OEt | 2-Quin | O |
| 3-150 | Et | (CH₂)₂ | H | CH₂ | OEt | 3-Quin | O |
| 3-151 | Et | (CH₂)₂ | H | CH₂ | OEt | 4-Quin | O |
| 3-152 | Et | (CH₂)₂ | H | CH₂ | OEt | 1-iQuin | O |
| 3-153 | Et | (CH₂)₂ | H | CH₂ | OEt | 3-iQuin | O |
| 3-154 | Et | (CH₂)₂ | H | CH₂ | OEt | 4-iQuin | O |
| 3-155 | Et | (CH₂)₂ | H | CH₂ | OEt | 3-MeO—Ph | O |
| 3-156 | Et | (CH₂)₂ | H | CH₂ | OEt | 4-MeO—Ph | O |
| 3-157 | Et | (CH₂)₂ | H | CH₂ | OEt | 3-EtO—Ph | O |

TABLE 3-continued

| Exemplification No. compound. | R¹ | R² | R³ | Z | W | X | Y |
|---|---|---|---|---|---|---|---|
| 3-158 | Et | (CH₂)₂ | H | CH₂ | OEt | 4-EtO—Ph | O |
| 3-159 | Et | (CH₂)₂ | H | CH₂ | OEt | 3-iPrO—Ph | O |
| 3-160 | Et | (CH₂)₂ | H | CH₂ | OEt | 4-iPrO—Ph | O |
| 3-161 | Et | (CH₂)₂ | H | CH₂ | OEt | 3-MeS—Ph | O |
| 3-162 | Et | (CH₂)₂ | H | CH₂ | OEt | 4-MeS—Ph | O |
| 3-163 | Et | (CH₂)₂ | H | CH₂ | OEt | 3-EtS—Ph | O |
| 3-164 | Et | (CH₂)₂ | H | CH₂ | OEt | 4-EtS—Ph | O |
| 3-165 | Et | (CH₂)₂ | H | CH₂ | OEt | 3-iPrS—Ph | O |
| 3-166 | Et | (CH₂)₂ | H | CH₂ | OEt | 4-iPrS—Ph | O |
| 3-167 | Et | (CH₂)₂ | H | CH₂ | OEt | 3-MeSO₂—Ph | O |
| 3-168 | Et | (CH₂)₂ | H | CH₂ | OEt | 4-MeSO₂—Ph | O |
| 3-169 | Et | (CH₂)₂ | H | CH₂ | OEt | 3-EtSO₂—Ph | O |
| 3-170 | Et | (CH₂)₂ | H | CH₂ | OEt | 4-EtSO₂—Ph | O |
| 3-171 | Et | (CH₂)₂ | H | CH₂ | OEt | 3-iPrSO₂—Ph | O |
| 3-172 | Et | (CH₂)₂ | H | CH₂ | OEt | 4-iPrSO₂—Ph | O |
| 3-173 | Et | (CH₂)₂ | H | CH₂ | OEt | 3-(1-Me-Imid-4)—Ph | O |
| 3-174 | Et | (CH₂)₂ | H | CH₂ | OEt | 4-(1-Me-Imid-4)—Ph | O |
| 3-175 | Et | (CH₂)₂ | H | CH₂ | OEt | 1-Me-2-Ph-4-Imid | O |
| 3-176 | Et | (CH₂)₂ | H | CH₂ | OEt | 1,4-di-Me-2-Ph-5-Imid | O |
| 3-177 | Et | (CH₂)₂ | H | CH₂ | OEt | 1,5-di-Me-2-Ph-4-Imid | O |
| 3-178 | Et | (CH₂)₂ | H | CH₂ | OEt | 3,4-MdO—Ph | O |
| 3-179 | Et | (CH₂)₂ | H | CH₂ | OEt | 4-(4-MeO—Ph)—Ph | O |
| 3-180 | Et | (CH₂)₂ | H | CH₂ | OEt | 4-(3,4-MdO—Ph)—Ph | O |
| 3-181 | Et | (CH₂)₂ | H | CH₂ | OEt | 4-[PhSO₂N(Me)]—Ph | O |
| 3-182 | Et | (CH₂)₂ | H | CH₂ | OEt | 4-[(Pyr-3)SO₂N(Me)]—Ph | O |
| 3-183 | Et | (CH₂)₂ | H | CH₂ | OEt | 4-(PhSO₂NH)—Ph | O |
| 3-184 | Et | (CH₂)₂ | H | CH₂ | OEt | 4-[(Pyr-3)SO₂NH]—Ph | O |
| 3-185 | Et | (CH₂)₂ | H | CH₂ | OEt | 4-[(Pyr-2)SO₂]—Ph | O |
| 3-186 | Et | (CH₂)₂ | H | CH₂ | OEt | 4-[(Pyr-3)SO₂]—Ph | O |
| 3-187 | Et | (CH₂)₂ | H | CH₂ | OEt | 4-[(Pyr-2)SO₂N(Me)]—Ph | O |
| 3-188 | Et | (CH₂)₂ | H | CH₂ | OEt | 4-[(Pyr-2)SO₂NH]—Ph | O |
| 3-189 | Et | (CH₂)₂ | H | CH₂ | OEt | 4-(4-Me—Ph)—Ph | O |
| 3-190 | Et | (CH₂)₂ | H | CH₂ | OEt | 4-(4-F—Ph)—Ph | O |
| 3-191 | Et | (CH₂)₂ | H | CH₂ | OEt | 4-(4-CF₃—Ph)—Ph | O |
| 3-192 | Et | (CH₂)₂ | H | CH₂ | OEt | 2-[4-Me-PhSO₂N(Me)]-5-Pyr | O |
| 3-193 | Et | (CH₂)₂ | H | CH₂ | OEt | 2-HO-5-Pyr | O |
| 3-194 | Et | (CH₂)₂ | H | CH₂ | OEt | 2-BzO-5-Pyr | O |
| 3-195 | Et | (CH₂)₂ | H | CH₂ | OEt | 4-[(Pyr-4)SO₂]—Ph | O |
| 3-196 | Et | (CH₂)₂ | H | CH₂ | OEt | 4-(2,4-di-MeO—Ph)—Ph | O |
| 3-197 | Et | (CH₂)₂ | H | CH₂ | OEt | 4-(2,5-di-MeO—Ph)—Ph | O |
| 3-198 | Et | (CH₂)₂ | H | CH₂ | OEt | 3-HO—Ph | O |
| 3-199 | Et | (CH₂)₂ | H | CH₂ | OEt | 4-HO—Ph | O |
| 3-200 | Et | (CH₂)₂ | H | CH₂ | OEt | 5-AcO-2-HO-3,4,6-tri-Me—Ph | O |
| 3-201 | Et | (CH₂)₂ | H | CH₂ | OEt | 4-HO-3,5-di-Me—Ph | O |
| 3-202 | Et | (CH₂)₂ | H | CH₂ | OEt | 3-AcO—Ph | O |
| 3-203 | Et | (CH₂)₂ | H | CH₂ | OEt | 4-AcO—Ph | O |

TABLE 4

| Exemplification No. compound. | R¹ | R² | R³ | Z | W | X | Y |
|---|---|---|---|---|---|---|---|
| 4-1 | iPr | (CH₂)₂ | H | CH₂ | OEt | Ph | O |
| 4-2 | iPr | (CH₂)₂ | H | CH₂ | OEt | 1-Np | O |
| 4-3 | iPr | (CH₂)₂ | H | CH₂ | OEt | 2-Np | O |
| 4-4 | iPr | (CH₂)₂ | H | CH₂ | OEt | 4-Me—Ph | O |
| 4-5 | iPr | (CH₂)₂ | H | CH₂ | OEt | 4-Et—Ph | O |
| 4-6 | iPr | (CH₂)₂ | H | CH₂ | OEt | 3-iPr—Ph | O |
| 4-7 | iPr | (CH₂)₂ | H | CH₂ | OEt | 4-iPr-Ph | O |
| 4-8 | iPr | (CH₂)₂ | H | CH₂ | OEt | 3-tBu—Ph | O |
| 4-9 | iPr | (CH₂)₂ | H | CH₂ | OEt | 4-tBu—Ph | O |
| 4-10 | iPr | (CH₂)₂ | H | CH₂ | OEt | 3-Cl—Ph | O |
| 4-11 | iPr | (CH₂)₂ | H | CH₂ | OEt | 4-Cl—Ph | O |
| 4-12 | iPr | (CH₂)₂ | H | CH₂ | OEt | 3-Br—Ph | O |
| 4-13 | iPr | (CH₂)₂ | H | CH₂ | OEt | 4-Br—Ph | O |
| 4-14 | iPr | (CH₂)₂ | H | CH₂ | OEt | 3-Ph—Ph | O |
| 4-15 | iPr | (CH₂)₂ | H | CH₂ | OEt | 4-Ph—Ph | O |
| 4-16 | iPr | (CH₂)₂ | H | CH₂ | OEt | 3-Bz—Ph | O |
| 4-17 | iPr | (CH₂)₂ | H | CH₂ | OEt | 4-Bz—Ph | O |
| 4-18 | iPr | (CH₂)₂ | H | CH₂ | OEt | 3-PhO—Ph | O |
| 4-19 | iPr | (CH₂)₂ | H | CH₂ | OEt | 4-PhO—Ph | O |
| 4-20 | iPr | (CH₂)₂ | H | CH₂ | OEt | 3-PhS—Ph | O |
| 4-21 | iPr | (CH₂)₂ | H | CH₂ | OEt | 4-PhS—Ph | O |

TABLE 4-continued

| Exemplification No. compound. | R¹ | R² | R³ | Z | W | X | Y |
|---|---|---|---|---|---|---|---|
| 4-22 | iPr | (CH$_2$)$_2$ | H | CH$_2$ | OEt | 3-PhSO$_2$—Ph | O |
| 4-23 | iPr | (CH$_2$)$_2$ | H | CH$_2$ | OEt | 4-PhSO$_2$—Ph | O |
| 4-24 | iPr | (CH$_2$)$_2$ | H | CH$_2$ | OEt | 3-(Imid-1)—Ph | O |
| 4-25 | iPr | (CH$_2$)$_2$ | H | CH$_2$ | OEt | 4-(Imid-1)—Ph | O |
| 4-26 | iPr | (CH$_2$)$_2$ | H | CH$_2$ | OEt | 3-(Imid-4)—Ph | O |
| 4-27 | iPr | (CH$_2$)$_2$ | H | CH$_2$ | OEt | 4-(Imid-4)—Ph | O |
| 4-28 | iPr | (CH$_2$)$_2$ | H | CH$_2$ | OEt | 3-(Fur-2)—Ph | O |
| 4-29 | iPr | (CH$_2$)$_2$ | H | CH$_2$ | OEt | 4-(Fur-2)—Ph | O |
| 4-30 | iPr | (CH$_2$)$_2$ | H | CH$_2$ | OEt | 3-(Thi-2)—Ph | O |
| 4-31 | iPr | (CH$_2$)$_2$ | H | CH$_2$ | OEt | 4-(Thi-2)—Ph | O |
| 4-32 | iPr | (CH$_2$)$_2$ | H | CH$_2$ | OEt | 3-(Thi-3)—Ph | O |
| 4-33 | iPr | (CH$_2$)$_2$ | H | CH$_2$ | OEt | 4-(Thi-3)—Ph | O |
| 4-34 | iPr | (CH$_2$)$_2$ | H | CH$_2$ | OEt | 3-(Pyr-2)—Ph | O |
| 4-35 | iPr | (CH$_2$)$_2$ | H | CH$_2$ | OEt | 4-(Pyr-2)—Ph | O |
| 4-36 | iPr | (CH$_2$)$_2$ | H | CH$_2$ | OEt | 3-(Pyr-3)—Ph | O |
| 4-37 | iPr | (CH$_2$)$_2$ | H | CH$_2$ | OEt | 4-(Pyr-3)—Ph | O |
| 4-38 | iPr | (CH$_2$)$_2$ | H | CH$_2$ | OEt | 3-(Pyr-4)—Ph | O |
| 4-39 | iPr | (CH$_2$)$_2$ | H | CH$_2$ | OEt | 4-(Pyr-4)—Ph | O |
| 4-40 | iPr | (CH$_2$)$_2$ | H | CH$_2$ | OEt | 3-(Oxa-2)—Ph | O |
| 4-41 | iPr | (CH$_2$)$_2$ | H | CH$_2$ | OEt | 4-(Oxa-2)—Ph | O |
| 4-42 | iPr | (CH$_2$)$_2$ | H | CH$_2$ | OEt | 3-(Oxa-4)—Ph | O |
| 4-43 | iPr | (CH$_2$)$_2$ | H | CH$_2$ | OEt | 4-(Oxa-4)—Ph | O |
| 4-44 | iPr | (CH$_2$)$_2$ | H | CH$_2$ | OEt | 3-(Oxa-5)—Ph | O |
| 4-45 | iPr | (CH$_2$)$_2$ | H | CH$_2$ | OEt | 4-(Oxa-5)—Ph | O |
| 4-46 | iPr | (CH$_2$)$_2$ | H | CH$_2$ | OEt | 3-(Thiz-2)—Ph | O |
| 4-47 | iPr | (CH$_2$)$_2$ | H | CH$_2$ | OEt | 4-(Thiz-2)—Ph | O |
| 4-48 | iPr | (CH$_2$)$_2$ | H | CH$_2$ | OEt | 3-(Thiz-4)—Ph | O |
| 4-49 | iPr | (CH$_2$)$_2$ | H | CH$_2$ | OEt | 4-(Thiz-4)—Ph | O |
| 4-50 | iPr | (CH$_2$)$_2$ | H | CH$_2$ | OEt | 3-(Thiz-5)—Ph | O |
| 4-51 | iPr | (CH$_2$)$_2$ | H | CH$_2$ | OEt | 4-(Thiz-5)—Ph | O |
| 4-52 | iPr | (CH$_2$)$_2$ | H | CH$_2$ | OEt | 1-Me-2-Pyrr | O |
| 4-53 | iPr | (CH$_2$)$_2$ | H | CH$_2$ | OEt | 1-Ph-2-Pyrr | O |
| 4-54 | iPr | (CH$_2$)$_2$ | H | CH$_2$ | OEt | 1-Bz-2-Pyrr | O |
| 4-55 | iPr | (CH$_2$)$_2$ | H | CH$_2$ | OEt | 5-Me-2-Fur | O |
| 4-56 | iPr | (CH$_2$)$_2$ | H | CH$_2$ | OEt | 5-Ph-2-Fur | O |
| 4-57 | iPr | (CH$_2$)$_2$ | H | CH$_2$ | OEt | 5-Me-2-Thi | O |
| 4-58 | iPr | (CH$_2$)$_2$ | H | CH$_2$ | OEt | 5-Ph-2-Thi | O |
| 4-59 | iPr | (CH$_2$)$_2$ | H | CH$_2$ | OEt | 5-Me-3-Thi | O |
| 4-60 | iPr | (CH$_2$)$_2$ | H | CH$_2$ | OEt | 5-Ph-3-Thi | O |
| 4-61 | iPr | (CH$_2$)$_2$ | H | CH$_2$ | OEt | 1-Me-3-Pyza | O |
| 4-62 | iPr | (CH$_2$)$_2$ | H | CH$_2$ | OEt | 1-Ph-3-Pyza | O |
| 4-63 | iPr | (CH$_2$)$_2$ | H | CH$_2$ | OEt | 1-Me-2-Imid | O |
| 4-64 | iPr | (CH$_2$)$_2$ | H | CH$_2$ | OEt | 1-Ph-2-Imid | O |
| 4-65 | iPr | (CH$_2$)$_2$ | H | CH$_2$ | OEt | 1-Me-4-Imid | O |
| 4-66 | iPr | (CH$_2$)$_2$ | H | CH$_2$ | OEt | 1-Ph-4-Imid | O |
| 4-67 | iPr | (CH$_2$)$_2$ | H | CH$_2$ | OEt | 4-Oxa | O |
| 4-68 | iPr | (CH$_2$)$_2$ | H | CH$_2$ | OEt | 5-Oxa | O |
| 4-69 | iPr | (CH$_2$)$_2$ | H | CH$_2$ | OEt | 2-Me-4-Oxa | O |
| 4-70 | iPr | (CH$_2$)$_2$ | H | CH$_2$ | OEt | 2-Ph-4-Oxa | O |
| 4-71 | iPr | (CH$_2$)$_2$ | H | CH$_2$ | OEt | 2-Me-5-Oxa | O |
| 4-72 | iPr | (CH$_2$)$_2$ | H | CH$_2$ | OEt | 2-Ph-5-Oxa | O |
| 4-73 | iPr | (CH$_2$)$_2$ | H | CH$_2$ | OEt | 4-Me-2-Ph-5-Oxa | O |
| 4-74 | iPr | (CH$_2$)$_2$ | H | CH$_2$ | OEt | 5-Me-2-Ph-4-Oxa | O |
| 4-75 | iPr | (CH$_2$)$_2$ | H | CH$_2$ | OEt | 4-Thiz | O |
| 4-76 | iPr | (CH$_2$)$_2$ | H | CH$_2$ | OEt | 5-Thiz | O |
| 4-77 | iPr | (CH$_2$)$_2$ | H | CH$_2$ | OEt | 2-Me-4-Thiz | O |
| 4-78 | iPr | (CH$_2$)$_2$ | H | CH$_2$ | OEt | 2-Ph-4-Thiz | O |
| 4-79 | iPr | (CH$_2$)$_2$ | H | CH$_2$ | OEt | 2-Me-5-Thiz | O |
| 4-80 | iPr | (CH$_2$)$_2$ | H | CH$_2$ | OEt | 2-Ph-5-Thiz | O |
| 4-81 | iPr | (CH$_2$)$_2$ | H | CH$_2$ | OEt | 4-Me-2-Ph-5-Thiz | O |
| 4-82 | iPr | (CH$_2$)$_2$ | H | CH$_2$ | OEt | 5-Me-2-Ph-4-Thiz | O |
| 4-83 | iPr | (CH$_2$)$_2$ | H | CH$_2$ | OEt | 1-Me-4-Pyza | O |
| 4-84 | iPr | (CH$_2$)$_2$ | H | CH$_2$ | OEt | 1-Ph-4-Pyza | O |
| 4-85 | iPr | (CH$_2$)$_2$ | H | CH$_2$ | OEt | 2-Me-4-Isox | O |
| 4-86 | iPr | (CH$_2$)$_2$ | H | CH$_2$ | OEt | 2-Ph-4-Isox | O |
| 4-87 | iPr | (CH$_2$)$_2$ | H | CH$_2$ | OEt | 2-Pyr | O |
| 4-88 | iPr | (CH$_2$)$_2$ | H | CH$_2$ | OEt | 3-Pyr | O |
| 4-89 | iPr | (CH$_2$)$_2$ | H | CH$_2$ | OEt | 4-Pyr | O |
| 4-90 | iPr | (CH$_2$)$_2$ | H | CH$_2$ | OEt | 3-Me-5-Pyr | O |
| 4-91 | iPr | (CH$_2$)$_2$ | H | CH$_2$ | OEt | 3-Et-5-Pyr | O |
| 4-92 | iPr | (CH$_2$)$_2$ | H | CH$_2$ | OEt | 3-Ph-5-Pyr | O |
| 4-93 | iPr | (CH$_2$)$_2$ | H | CH$_2$ | OEt | 2-Me-5-Pyr | O |
| 4-94 | iPr | (CH$_2$)$_2$ | H | CH$_2$ | OEt | 2-Et-5-Pyr | O |
| 4-95 | iPr | (CH$_2$)$_2$ | H | CH$_2$ | OEt | 2-Ph-5-Pyr | O |
| 4-96 | iPr | (CH$_2$)$_2$ | H | CH$_2$ | OEt | 2-MeO-5-Pyr | O |
| 4-97 | iPr | (CH$_2$)$_2$ | H | CH$_2$ | OEt | 2-EtO-5-Pyr | O |

TABLE 4-continued

| Exemplification No. compound. | R¹ | R² | R³ | Z | W | X | Y |
|---|---|---|---|---|---|---|---|
| 4-98 | iPr | (CH₂)₂ | H | CH₂ | OEt | 2-iPrO-5-Pyr | O |
| 4-99 | iPr | (CH₂)₂ | H | CH₂ | OEt | 2-MeS-5-Pyr | O |
| 4-100 | iPr | (CH₂)₂ | H | CH₂ | OEt | 2-EtS-5-Pyr | O |
| 4-101 | iPr | (CH₂)₂ | H | CH₂ | OEt | 2-iPrS-5-Pyr | O |
| 4-102 | iPr | (CH₂)₂ | H | CH₂ | OEt | 2-MeSO₂-5-Pyr | O |
| 4-103 | iPr | (CH₂)₂ | H | CH₂ | OEt | 2-EtSO₂-5-Pyr | O |
| 4-104 | iPr | (CH₂)₂ | H | CH₂ | OEt | 2-iPrSO₂-5-Pyr | O |
| 4-105 | iPr | (CH₂)₂ | H | CH₂ | OEt | 2-Bz-5-Pyr | O |
| 4-106 | iPr | (CH₂)₂ | H | CH₂ | OEt | 2-PhO-5-Pyr | O |
| 4-107 | iPr | (CH₂)₂ | H | CH₂ | OEt | 2-PhS-5-Pyr | O |
| 4-108 | iPr | (CH₂)₂ | H | CH₂ | OEt | 2-PhSO₂-5-Pyr | O |
| 4-109 | iPr | (CH₂)₂ | H | CH₂ | OEt | 3-Me-6-Pyr | O |
| 4-110 | iPr | (CH₂)₂ | H | CH₂ | OEt | 3-Ph-6-Pyr | O |
| 4-111 | iPr | (CH₂)₂ | H | CH₂ | OEt | 2-Me-6-Pyr | O |
| 4-112 | iPr | (CH₂)₂ | H | CH₂ | OEt | 2-Ph-6-Pyr | O |
| 4-113 | iPr | (CH₂)₂ | H | CH₂ | OEt | 2-Me-4-Pym | O |
| 4-114 | iPr | (CH₂)₂ | H | CH₂ | OEt | 2-Ph-4-Pym | O |
| 4-115 | iPr | (CH₂)₂ | H | CH₂ | OEt | 2-MeO-4-Pym | O |
| 4-116 | iPr | (CH₂)₂ | H | CH₂ | OEt | 2-EtO-4-Pym | O |
| 4-117 | iPr | (CH₂)₂ | H | CH₂ | OEt | 2-iPrO-4-Pym | O |
| 4-118 | iPr | (CH₂)₂ | H | CH₂ | OEt | 2-MeS-4-Pym | O |
| 4-119 | iPr | (CH₂)₂ | H | CH₂ | OEt | 2-EtS-4-Pym | O |
| 4-120 | iPr | (CH₂)₂ | H | CH₂ | OEt | 2-iPrS-4-Pym | O |
| 4-121 | iPr | (CH₂)₂ | H | CH₂ | OEt | 6-MeS-4-Pym | O |
| 4-122 | iPr | (CH₂)₂ | H | CH₂ | OEt | 6-EtS-4-Pym | O |
| 4-123 | iPr | (CH₂)₂ | H | CH₂ | OEt | 6-iPrS-4-Pym | O |
| 4-124 | iPr | (CH₂)₂ | H | CH₂ | OEt | 2-PhS-4-Pym | O |
| 4-125 | iPr | (CH₂)₂ | H | CH₂ | OEt | 2-MeSO₂-4-Pym | O |
| 4-126 | iPr | (CH₂)₂ | H | CH₂ | OEt | 2-EtSO₂-4-Pym | O |
| 4-127 | iPr | (CH₂)₂ | H | CH₂ | OEt | 2-iPrSO₂-4-Pym | O |
| 4-128 | iPr | (CH₂)₂ | H | CH₂ | OEt | 2-PhSO₂-4-Pym | O |
| 4-129 | iPr | (CH₂)₂ | H | CH₂ | OEt | 2-Me-5-Pym | O |
| 4-130 | iPr | (CH₂)₂ | H | CH₂ | OEt | 2-Ph-5-Pym | O |
| 4-131 | iPr | (CH₂)₂ | H | CH₂ | OEt | 2-MeO-5-Pym | O |
| 4-132 | iPr | (CH₂)₂ | H | CH₂ | OEt | 2-EtO-5-Pym | O |
| 4-133 | iPr | (CH₂)₂ | H | CH₂ | OEt | 2-iPrO-5-Pym | O |
| 4-134 | iPr | (CH₂)₂ | H | CH₂ | OEt | 2-MeS-5-Pym | O |
| 4-135 | iPr | (CH₂)₂ | H | CH₂ | OEt | 2-EtS-5-Pym | O |
| 4-136 | iPr | (CH₂)₂ | H | CH₂ | OEt | 2-iPrS-5-Pym | O |
| 4-137 | iPr | (CH₂)₂ | H | CH₂ | OEt | 2-PhS-5-Pym | O |
| 4-138 | iPr | (CH₂)₂ | H | CH₂ | OEt | 2-MeSO₂-5-Pym | O |
| 4-139 | iPr | (CH₂)₂ | H | CH₂ | OEt | 2-EtSO₂-5-Pym | O |
| 4-140 | iPr | (CH₂)₂ | H | CH₂ | OEt | 2-iPrSO₂-5-Pym | O |
| 4-141 | iPr | (CH₂)₂ | H | CH₂ | OEt | 2-PhSO₂-5-Pym | O |
| 4-142 | iPr | (CH₂)₂ | H | CH₂ | OEt | 2-Ind | O |
| 4-143 | iPr | (CH₂)₂ | H | CH₂ | OEt | 3-Ind | O |
| 4-144 | iPr | (CH₂)₂ | H | CH₂ | OEt | 1-Me-2-Ind | O |
| 4-145 | iPr | (CH₂)₂ | H | CH₂ | OEt | 1-Me-3-Ind | O |
| 4-146 | iPr | (CH₂)₂ | H | CH₂ | OEt | 2-Bimid | O |
| 4-147 | iPr | (CH₂)₂ | H | CH₂ | OEt | 2-Boxa | O |
| 4-148 | iPr | (CH₂)₂ | H | CH₂ | OEt | 2-Bthiz | O |
| 4-149 | iPr | (CH₂)₂ | H | CH₂ | OEt | 2-Quin | O |
| 4-150 | iPr | (CH₂)₂ | H | CH₂ | OEt | 3-Quin | O |
| 4-151 | iPr | (CH₂)₂ | H | CH₂ | OEt | 4-Quin | O |
| 4-152 | iPr | (CH₂)₂ | H | CH₂ | OEt | 1-iQuin | O |
| 4-153 | iPr | (CH₂)₂ | H | CH₂ | OEt | 3-iQuin | O |
| 4-154 | iPr | (CH₂)₂ | H | CH₂ | OEt | 4-iQuin | O |
| 4-155 | iPr | (CH₂)₂ | H | CH₂ | OEt | 3-MeO—Ph | O |
| 4-156 | iPr | (CH₂)₂ | H | CH₂ | OEt | 4-MeO—Ph | O |
| 4-157 | iPr | (CH₂)₂ | H | CH₂ | OEt | 3-EtO—Ph | O |
| 4-158 | iPr | (CH₂)₂ | H | CH₂ | OEt | 4-EtO—Ph | O |
| 4-159 | iPr | (CH₂)₂ | H | CH₂ | OEt | 3-iPrO—Ph | O |
| 4-160 | iPr | (CH₂)₂ | H | CH₂ | OEt | 4-iPrO—Ph | O |
| 4-161 | iPr | (CH₂)₂ | H | CH₂ | OEt | 3-MeS—Ph | O |
| 4-162 | iPr | (CH₂)₂ | H | CH₂ | OEt | 4-MeS—Ph | O |
| 4-163 | iPr | (CH₂)₂ | H | CH₂ | OEt | 3-EtS—Ph | O |
| 4-164 | iPr | (CH₂)₂ | H | CH₂ | OEt | 4-EtS—Ph | O |
| 4-165 | iPr | (CH₂)₂ | H | CH₂ | OEt | 3-iPrS—Ph | O |
| 4-166 | iPr | (CH₂)₂ | H | CH₂ | OEt | 4-iPrS—Ph | O |
| 4-167 | iPr | (CH₂)₂ | H | CH₂ | OEt | 3-MeSO₂—Ph | O |
| 4-168 | iPr | (CH₂)₂ | H | CH₂ | OEt | 4-MeSO₂—Ph | O |
| 4-169 | iPr | (CH₂)₂ | H | CH₂ | OEt | 3-EtSO₂—Ph | O |
| 4-170 | iPr | (CH₂)₂ | H | CH₂ | OEt | 4-EtSO₂—Ph | O |
| 4-171 | iPr | (CH₂)₂ | H | CH₂ | OEt | 3-iPrSO₂—Ph | O |
| 4-172 | iPr | (CH₂)₂ | H | CH₂ | OEt | 4-iPrSO₂—Ph | O |
| 4-173 | iPr | (CH₂)₂ | H | CH₂ | OEt | 3-(1-Me-Imid-4)—Ph | O |

TABLE 4-continued

| Exemplification No. compound. | R¹ | R² | R³ | Z | W | X | Y |
|---|---|---|---|---|---|---|---|
| 4-174 | iPr | (CH₂)₂ | H | CH₂ | OEt | 4-(1-Me-Imid-4)—Ph | O |
| 4-175 | iPr | (CH₂)₂ | H | CH₂ | OEt | 1-Me-2-Ph-4-Imid | O |
| 4-176 | iPr | (CH₂)₂ | H | CH₂ | OEt | 1,4-di-Me-2-Ph-5-Imid | O |
| 4-177 | iPr | (CH₂)₂ | H | CH₂ | OEt | 1,5-di-Me-2-Ph-4-Imid | O |
| 4-178 | iPr | (CH₂)₂ | H | CH₂ | OEt | 3,4-MdO—Ph | O |
| 4-179 | iPr | (CH₂)₂ | H | CH₂ | OEt | 4-(4-MeO—Ph)—Ph | O |
| 4-180 | iPr | (CH₂)₂ | H | CH₂ | OEt | 4-(3,4-MdO—Ph)—Ph | O |
| 4-181 | iPr | (CH₂)₂ | H | CH₂ | OEt | 4-[PhSO₂N(Me)]—Ph | O |
| 4-182 | iPr | (CH₂)₂ | H | CH₂ | OEt | 4-[(Pyr-3)SO₂N(Me)]—Ph | O |
| 4-183 | iPr | (CH₂)₂ | H | CH₂ | OEt | 4-(PhSO₂NH)—Ph | O |
| 4-184 | iPr | (CH₂)₂ | H | CH₂ | OEt | 4-[(Pyr-3)SO₂NH]—Ph | O |
| 4-185 | iPr | (CH₂)₂ | H | CH₂ | OEt | 4-[(Pyr-2)SO₂]—Ph | O |
| 4-186 | iPr | (CH₂)₂ | H | CH₂ | OEt | 4-[(Pyr-3)SO₂]—Ph | O |
| 4-187 | iPr | (CH₂)₂ | H | CH₂ | OEt | 4-[(Pyr-2)SO₂N(Me)]—Ph | O |
| 4-188 | iPr | (CH₂)₂ | H | CH₂ | OEt | 4-[(Pyr-2)SO₂NH]—Ph | O |
| 4-189 | iPr | (CH₂)₂ | H | CH₂ | OEt | 4-(4-Me—Ph)—Ph | O |
| 4-190 | iPr | (CH₂)₂ | H | CH₂ | OEt | 4-(4-F—Ph)—Ph | O |
| 4-191 | iPr | (CH₂)₂ | H | CH₂ | OEt | 4-(4-CF₃—Ph)—Ph | O |
| 4-192 | iPr | (CH₂)₂ | H | CH₂ | OEt | 2-[4-Me—PhSO₂N(Me)]-5-Pyr | O |
| 4-193 | iPr | (CH₂)₂ | H | CH₂ | OEt | 2-HO-5-Pyr | O |
| 4-194 | iPr | (CH₂)₂ | H | CH₂ | OEt | 2-BzO-5-Pyr | O |
| 4-195 | iPr | (CH₂)₂ | H | CH₂ | OEt | 4-[(Pyr-4)SO₂]—Ph | O |
| 4-196 | iPr | (CH₂)₂ | H | CH₂ | OEt | 4-(2,4-di-MeO—Ph)—Ph | O |
| 4-197 | iPr | (CH₂)₂ | H | CH₂ | OEt | 4-(2,5-di-MeO—Ph)—Ph | O |
| 4-198 | iPr | (CH₂)₂ | H | CH₂ | OEt | 3-HO—Ph | O |
| 4-199 | iPr | (CH₂)₂ | H | CH₂ | OEt | 4-HO—Ph | O |
| 4-200 | iPr | (CH₂)₂ | H | CH₂ | OEt | 5-AcO-2-HO-3,4,6-tri-Me—Ph | O |
| 4-201 | iPr | (CH₂)₂ | H | CH₂ | OEt | 4-HO-3,5-di-Me—Ph | O |
| 4-202 | iPr | (CH₂)₂ | H | CH₂ | OEt | 3-AcO—Ph | O |
| 4-203 | iPr | (CH₂)₂ | H | CH₂ | OEt | 4-AcO—Ph | O |

TABLE 5

| Exemplification No. compound. | R¹ | R² | R³ | Z | W | X | Y |
|---|---|---|---|---|---|---|---|
| 5-1 | H | (CH₂)₂ | H | CH₂ | OMe | Ph | O |
| 5-2 | H | (CH₂)₂ | H | CH₂ | OMe | 1-Np | O |
| 5-3 | H | (CH₂)₂ | H | CH₂ | OMe | 2-Np | O |
| 5-4 | H | (CH₂)₂ | H | CH₂ | OMe | 4-Me—Ph | O |
| 5-5 | H | (CH₂)₂ | H | CH₂ | OMe | 4-Et—Ph | O |
| 5-6 | H | (CH₂)₂ | H | CH₂ | OMe | 3-iPr—Ph | O |
| 5-7 | H | (CH₂)₂ | H | CH₂ | OMe | 4-iPr—Ph | O |
| 5-8 | H | (CH₂)₂ | H | CH₂ | OMe | 3-tBu—Ph | O |
| 5-9 | H | (CH₂)₂ | H | CH₂ | OMe | 4-tBu—Ph | O |
| 5-10 | H | (CH₂)₂ | H | CH₂ | OMe | 3-Cl—Ph | O |
| 5-11 | H | (CH₂)₂ | H | CH₂ | OMe | 4-Cl—Ph | O |
| 5-12 | H | (CH₂)₂ | H | CH₂ | OMe | 3-Br—Ph | O |
| 5-13 | H | (CH₂)₂ | H | CH₂ | OMe | 4-Br—Ph | O |
| 5-14 | H | (CH₂)₂ | H | CH₂ | OMe | 3-Ph—Ph | O |
| 5-15 | H | (CH₂)₂ | H | CH₂ | OMe | 4-Ph—Ph | O |
| 5-16 | H | (CH₂)₂ | H | CH₂ | OMe | 3-Bz—Ph | O |
| 5-17 | H | (CH₂)₂ | H | CH₂ | OMe | 4-Bz—Ph | O |
| 5-18 | H | (CH₂)₂ | H | CH₂ | OMe | 3-PhO—Ph | O |
| 5-19 | H | (CH₂)₂ | H | CH₂ | OMe | 4-PhO—Ph | O |
| 5-20 | H | (CH₂)₂ | H | CH₂ | OMe | 3-PhS—Ph | O |
| 5-21 | H | (CH₂)₂ | H | CH₂ | OMe | 4-PhS—Ph | O |
| 5-22 | H | (CH₂)₂ | H | CH₂ | OMe | 3-PhSO₂—Ph | O |
| 5-23 | H | (CH₂)₂ | H | CH₂ | OMe | 4-PhSO₂—Ph | O |
| 5-24 | H | (CH₂)₂ | H | CH₂ | OMe | 3-(Imid-1)-Ph | O |
| 5-25 | H | (CH₂)₂ | H | CH₂ | OMe | 4-(Imid-1)-Ph | O |
| 5-26 | H | (CH₂)₂ | H | CH₂ | OMe | 3-(Imid-4)-Ph | O |
| 5-27 | H | (CH₂)₂ | H | CH₂ | OMe | 4-(Imid-4)-Ph | O |
| 5-28 | H | (CH₂)₂ | H | CH₂ | OMe | 3-(Fur-2)-Ph | O |
| 5-29 | H | (CH₂)₂ | H | CH₂ | OMe | 4-(Fur-2)-Ph | O |
| 5-30 | H | (CH₂)₂ | H | CH₂ | OMe | 3-(Thi-2)-Ph | O |
| 5-31 | H | (CH₂)₂ | H | CH₂ | OMe | 4-(Thi-2)-Ph | O |
| 5-32 | H | (CH₂)₂ | H | CH₂ | OMe | 3-(Thi-3)-Ph | O |
| 5-33 | H | (CH₂)₂ | H | CH₂ | OMe | 4-(Thi-3)-Ph | O |
| 5-34 | H | (CH₂)₂ | H | CH₂ | OMe | 3-(Pyr-2)-Ph | O |
| 5-35 | H | (CH₂)₂ | H | CH₂ | OMe | 4-(Pyr-2)-Ph | O |
| 5-36 | H | (CH₂)₂ | H | CH₂ | OMe | 3-(Pyr-3)-Ph | O |
| 5-37 | H | (CH₂)₂ | H | CH₂ | OMe | 4-(Pyr-3)-Ph | O |
| 5-38 | H | (CH₂)₂ | H | CH₂ | OMe | 3-(Pyr-4)-Ph | O |
| 5-39 | H | (CH₂)₂ | H | CH₂ | OMe | 4-(Pyr-4)-Ph | O |
| 5-40 | H | (CH₂)₂ | H | CH₂ | OMe | 3-(Oxa-2)-Ph | O |
| 5-41 | H | (CH₂)₂ | H | CH₂ | OMe | 4-(Oxa-2)-Ph | O |
| 5-42 | H | (CH₂)₂ | H | CH₂ | OMe | 3-(Oxa-4)-Ph | O |
| 5-43 | H | (CH₂)₂ | H | CH₂ | OMe | 4-(Oxa-4)-Ph | O |
| 5-44 | H | (CH₂)₂ | H | CH₂ | OMe | 3-(Oxa-5)-Ph | O |
| 5-45 | H | (CH₂)₂ | H | CH₂ | OMe | 4-(Oxa-5)-Ph | O |
| 5-46 | H | (CH₂)₂ | H | CH₂ | OMe | 3-(Thiz-2)-Ph | O |
| 5-47 | H | (CH₂)₂ | H | CH₂ | OMe | 4-(Thiz-2)-Ph | O |
| 5-48 | H | (CH₂)₂ | H | CH₂ | OMe | 3-(Thiz-4)-Ph | O |
| 5-49 | H | (CH₂)₂ | H | CH₂ | OMe | 4-(Thiz-4)-Ph | O |
| 5-50 | H | (CH₂)₂ | H | CH₂ | OMe | 3-(Thiz-5)-Ph | O |
| 5-51 | H | (CH₂)₂ | H | CH₂ | OMe | 4-(Thiz-5)-Ph | O |
| 5-52 | H | (CH₂)₂ | H | CH₂ | OMe | 1-Me-2-Pyrr | O |
| 5-53 | H | (CH₂)₂ | H | CH₂ | OMe | 1-Ph-2-Pyrr | O |
| 5-54 | H | (CH₂)₂ | H | CH₂ | OMe | 1-Bz-2-Pyrr | O |
| 5-55 | H | (CH₂)₂ | H | CH₂ | OMe | 5-Me-2-Fur | O |
| 5-56 | H | (CH₂)₂ | H | CH₂ | OMe | 5-Ph-2-Fur | O |
| 5-57 | H | (CH₂)₂ | H | CH₂ | OMe | 5-Me-2-Thi | O |
| 5-58 | H | (CH₂)₂ | H | CH₂ | OMe | 5-Ph-2-Thi | O |
| 5-59 | H | (CH₂)₂ | H | CH₂ | OMe | 5-Me-3-Thi | O |
| 5-60 | H | (CH₂)₂ | H | CH₂ | OMe | 5-Ph-3-Thi | O |
| 5-61 | H | (CH₂)₂ | H | CH₂ | OMe | 1-Me-3-Pyza | O |
| 5-62 | H | (CH₂)₂ | H | CH₂ | OMe | 1-Ph-3-Pyza | O |
| 5-63 | H | (CH₂)₂ | H | CH₂ | OMe | 1-Me-2-Imid | O |
| 5-64 | H | (CH₂)₂ | H | CH₂ | OMe | 1-Ph-2-Imid | O |

TABLE 5-continued

| Exemplification No. compound. | R¹ | R² | R³ | Z | W | X | Y |
|---|---|---|---|---|---|---|---|
| 5-65 | H | (CH₂)₂ | H | CH₂ | OMe | 1-Me-4-Imid | O |
| 5-66 | H | (CH₂)₂ | H | CH₂ | OMe | 1-Ph-4-Imid | O |
| 5-67 | H | (CH₂)₂ | H | CH₂ | OMe | 4-Oxa | O |
| 5-68 | H | (CH₂)₂ | H | CH₂ | OMe | 5-Oxa | O |
| 5-69 | H | (CH₂)₂ | H | CH₂ | OMe | 2-Me-4-Oxa | O |
| 5-70 | H | (CH₂)₂ | H | CH₂ | OMe | 2-Ph-4-Oxa | O |
| 5-71 | H | (CH₂)₂ | H | CH₂ | OMe | 2-Me-5-Oxa | O |
| 5-72 | H | (CH₂)₂ | H | CH₂ | OMe | 2-Ph-5-Oxa | O |
| 5-73 | H | (CH₂)₂ | H | CH₂ | OMe | 4-Me-2-Ph-5-Oxa | O |
| 5-74 | H | (CH₂)₂ | H | CH₂ | OMe | 5-Me-2-Ph-4-Oxa | O |
| 5-75 | H | (CH₂)₂ | H | CH₂ | OMe | 4-Thiz | O |
| 5-76 | H | (CH₂)₂ | H | CH₂ | OMe | 5-Thiz | O |
| 5-77 | H | (CH₂)₂ | H | CH₂ | OMe | 2-Me-4-Thiz | O |
| 5-78 | H | (CH₂)₂ | H | CH₂ | OMe | 2-Ph-4-Thiz | O |
| 5-79 | H | (CH₂)₂ | H | CH₂ | OMe | 2-Me-5-Thiz | O |
| 5-80 | H | (CH₂)₂ | H | CH₂ | OMe | 2-Ph-5-Thiz | O |
| 5-81 | H | (CH₂)₂ | H | CH₂ | OMe | 4-Me-2-Ph-5-Thiz | O |
| 5-82 | H | (CH₂)₂ | H | CH₂ | OMe | 5-Me-2-Ph-4-Thiz | O |
| 5-83 | H | (CH₂)₂ | H | CH₂ | OMe | 1-Me-4-Pyza | O |
| 5-84 | H | (CH₂)₂ | H | CH₂ | OMe | 1-Ph-4-Pyza | O |
| 5-85 | H | (CH₂)₂ | H | CH₂ | OMe | 2-Me-4-Isox | O |
| 5-86 | H | (CH₂)₂ | H | CH₂ | OMe | 2-Ph-4-Isox | O |
| 5-87 | H | (CH₂)₂ | H | CH₂ | OMe | 2-Pyr | O |
| 5-88 | H | (CH₂)₂ | H | CH₂ | OMe | 3-Pyr | O |
| 5-89 | H | (CH₂)₂ | H | CH₂ | OMe | 4-Pyr | O |
| 5-90 | H | (CH₂)₂ | H | CH₂ | OMe | 3-Me-5-Pyr | O |
| 5-91 | H | (CH₂)₂ | H | CH₂ | OMe | 3-Et-5-Pyr | O |
| 5-92 | H | (CH₂)₂ | H | CH₂ | OMe | 3-Ph-5-Pyr | O |
| 5-93 | H | (CH₂)₂ | H | CH₂ | OMe | 2-Me-5-Pyr | O |
| 5-94 | H | (CH₂)₂ | H | CH₂ | OMe | 2-Et-5-Pyr | O |
| 5-95 | H | (CH₂)₂ | H | CH₂ | OMe | 2-Ph-5-Pyr | O |
| 5-96 | H | (CH₂)₂ | H | CH₂ | OMe | 2-MeO-5-Pyr | O |
| 5-97 | H | (CH₂)₂ | H | CH₂ | OMe | 2-EtO-5-Pyr | O |
| 5-98 | H | (CH₂)₂ | H | CH₂ | OMe | 2-iPrO-5-Pyr | O |
| 5-99 | H | (CH₂)₂ | H | CH₂ | OMe | 2-MeS-5-Pyr | O |
| 5-100 | H | (CH₂)₂ | H | CH₂ | OMe | 2-EtS-5-Pyr | O |
| 5-101 | H | (CH₂)₂ | H | CH₂ | OMe | 2-iPrS-5-Pyr | O |
| 5-102 | H | (CH₂)₂ | H | CH₂ | OMe | 2-MeSO₂-5-Pyr | O |
| 5-103 | H | (CH₂)₂ | H | CH₂ | OMe | 2-EtSO₂-5-Pyr | O |
| 5-104 | H | (CH₂)₂ | H | CH₂ | OMe | 2-iPrSO₂-5-Pyr | O |
| 5-105 | H | (CH₂)₂ | H | CH₂ | OMe | 2-Bz-5-Pyr | O |
| 5-106 | H | (CH₂)₂ | H | CH₂ | OMe | 2-PhO-5-Pyr | O |
| 5-107 | H | (CH₂)₂ | H | CH₂ | OMe | 2-PhS-5-Pyr | O |
| 5-108 | H | (CH₂)₂ | H | CH₂ | OMe | 2-PhSO₂-5-Pyr | O |
| 5-109 | H | (CH₂)₂ | H | CH₂ | OMe | 3-Me-6-Pyr | O |
| 5-110 | H | (CH₂)₂ | H | CH₂ | OMe | 3-Ph-6-Pyr | O |
| 5-111 | H | (CH₂)₂ | H | CH₂ | OMe | 2-Me-6-Pyr | O |
| 5-112 | H | (CH₂)₂ | H | CH₂ | OMe | 2-Ph-6-Pyr | O |
| 5-113 | H | (CH₂)₂ | H | CH₂ | OMe | 2-Me-4-Pym | O |
| 5-114 | H | (CH₂)₂ | H | CH₂ | OMe | 2-Ph-4-Pym | O |
| 5-115 | H | (CH₂)₂ | H | CH₂ | OMe | 2-MeO-4-Pym | O |
| 5-116 | H | (CH₂)₂ | H | CH₂ | OMe | 2-EtO-4-Pym | O |
| 5-117 | H | (CH₂)₂ | H | CH₂ | OMe | 2-iPrO-4-Pym | O |
| 5-118 | H | (CH₂)₂ | H | CH₂ | OMe | 2-MeS-4-Pym | O |
| 5-119 | H | (CH₂)₂ | H | CH₂ | OMe | 2-EtS-4-Pym | O |
| 5-120 | H | (CH₂)₂ | H | CH₂ | OMe | 2-iPrS-4-Pym | O |
| 5-121 | H | (CH₂)₂ | H | CH₂ | OMe | 6-MeS-4-Pym | O |
| 5-122 | H | (CH₂)₂ | H | CH₂ | OMe | 6-EtS-4-Pym | O |
| 5-123 | H | (CH₂)₂ | H | CH₂ | OMe | 6-iPrS-4-Pym | O |
| 5-124 | H | (CH₂)₂ | H | CH₂ | OMe | 2-PhS-4-Pym | O |
| 5-125 | H | (CH₂)₂ | H | CH₂ | OMe | 2-MeSO₂-4-Pym | O |
| 5-126 | H | (CH₂)₂ | H | CH₂ | OMe | 2-EtSO₂-4-Pym | O |
| 5-127 | H | (CH₂)₂ | H | CH₂ | OMe | 2-iPrSO₂-4-Pym | O |
| 5-128 | H | (CH₂)₂ | H | CH₂ | OMe | 2-PhSO₂-4-Pym | O |
| 5-129 | H | (CH₂)₂ | H | CH₂ | OMe | 2-Me-5-Pym | O |
| 5-130 | H | (CH₂)₂ | H | CH₂ | OMe | 2-Ph-5-Pym | O |
| 5-131 | H | (CH₂)₂ | H | CH₂ | OMe | 2-MeO-5-Pym | O |
| 5-132 | H | (CH₂)₂ | H | CH₂ | OMe | 2-EtO-5-Pym | O |
| 5-133 | H | (CH₂)₂ | H | CH₂ | OMe | 2-iPrO-5-Pym | O |
| 5-134 | H | (CH₂)₂ | H | CH₂ | OMe | 2-MeS-5-Pym | O |
| 5-135 | H | (CH₂)₂ | H | CH₂ | OMe | 2-EtS-5-Pym | O |
| 5-136 | H | (CH₂)₂ | H | CH₂ | OMe | 2-iPrS-5-Pym | O |
| 5-137 | H | (CH₂)₂ | H | CH₂ | OMe | 2-PhS-5-Pym | O |
| 5-138 | H | (CH₂)₂ | H | CH₂ | OMe | 2-MeSO₂-5-Pym | O |
| 5-139 | H | (CH₂)₂ | H | CH₂ | OMe | 2-EtSO₂-5-Pym | O |
| 5-140 | H | (CH₂)₂ | H | CH₂ | OMe | 2-iPrSO₂-5-Pym | O |
| 5-141 | H | (CH₂)₂ | H | CH₂ | OMe | 2-PhSO₂-5-Pym | O |
| 5-142 | H | (CH₂)₂ | H | CH₂ | OMe | 2-Ind | O |
| 5-143 | H | (CH₂)₂ | H | CH₂ | OMe | 3-Ind | O |
| 5-144 | H | (CH₂)₂ | H | CH₂ | OMe | 1-Me-2-Ind | O |
| 5-145 | H | (CH₂)₂ | H | CH₂ | OMe | 1-Me-3-Ind | O |
| 5-146 | H | (CH₂)₂ | H | CH₂ | OMe | 2-Bimid | O |
| 5-147 | H | (CH₂)₂ | H | CH₂ | OMe | 2-Boxa | O |
| 5-148 | H | (CH₂)₂ | H | CH₂ | OMe | 2-Bthiz | O |
| 5-149 | H | (CH₂)₂ | H | CH₂ | OMe | 2-Quin | O |
| 5-150 | H | (CH₂)₂ | H | CH₂ | OMe | 3-Quin | O |
| 5-151 | H | (CH₂)₂ | H | CH₂ | OMe | 4-Quin | O |
| 5-152 | H | (CH₂)₂ | H | CH₂ | OMe | 1-iQuin | O |
| 5-153 | H | (CH₂)₂ | H | CH₂ | OMe | 3-iQuin | O |
| 5-154 | H | (CH₂)₂ | H | CH₂ | OMe | 4-iQuin | O |
| 5-155 | H | (CH₂)₂ | H | CH₂ | OMe | 3-MeO—Ph | O |
| 5-156 | H | (CH₂)₂ | H | CH₂ | OMe | 4-MeO—Ph | O |
| 5-157 | H | (CH₂)₂ | H | CH₂ | OMe | 3-EtO—Ph | O |
| 5-158 | H | (CH₂)₂ | H | CH₂ | OMe | 4-EtO—Ph | O |
| 5-159 | H | (CH₂)₂ | H | CH₂ | OMe | 3-iPrO—Ph | O |
| 5-160 | H | (CH₂)₂ | H | CH₂ | OMe | 4-iPrO—Ph | O |
| 5-161 | H | (CH₂)₂ | H | CH₂ | OMe | 3-MeS—Ph | O |
| 5-162 | H | (CH₂)₂ | H | CH₂ | OMe | 4-MeS—Ph | O |
| 5-163 | H | (CH₂)₂ | H | CH₂ | OMe | 3-EtS—Ph | O |
| 5-164 | H | (CH₂)₂ | H | CH₂ | OMe | 4-EtS—Ph | O |
| 5-165 | H | (CH₂)₂ | H | CH₂ | OMe | 3-iPrS—Ph | O |
| 5-166 | H | (CH₂)₂ | H | CH₂ | OMe | 4-iPrS—Ph | O |
| 5-167 | H | (CH₂)₂ | H | CH₂ | OMe | 3-MeSO₂—Ph | O |
| 5-168 | H | (CH₂)₂ | H | CH₂ | OMe | 4-MeSO₂—Ph | O |
| 5-169 | H | (CH₂)₂ | H | CH₂ | OMe | 3-EtSO₂—Ph | O |
| 5-170 | H | (CH₂)₂ | H | CH₂ | OMe | 4-EtSO₂—Ph | O |
| 5-171 | H | (CH₂)₂ | H | CH₂ | OMe | 3-iPrSO₂—Ph | O |
| 5-172 | H | (CH₂)₂ | H | CH₂ | OMe | 4-iPrSO₂—Ph | O |
| 5-173 | H | (CH₂)₂ | H | CH₂ | OMe | 3-(1-Me—Imid-4)-Ph | O |
| 5-174 | H | (CH₂)₂ | H | CH₂ | OMe | 4-(1-Me—Imid-4)-Ph | O |
| 5-175 | H | (CH₂)₂ | H | CH₂ | OMe | 1-Me-2-Ph-4-Imid | O |
| 5-176 | H | (CH₂)₂ | H | CH₂ | OMe | 1,4-di-Me-2-Ph-5-Imid | O |
| 5-177 | H | (CH₂)₂ | H | CH₂ | OMe | 1,5-di-Me-2-Ph-4-Imid | O |
| 5-178 | H | (CH₂)₂ | H | CH₂ | OMe | 3,4-MdO—Ph | O |
| 5-179 | H | (CH₂)₂ | H | CH₂ | OMe | 4-(4-MeO—Ph)—Ph | O |
| 5-180 | H | (CH₂)₂ | H | CH₂ | OMe | 4-(3,4-MdO—Ph)—Ph | O |
| 5-181 | H | (CH₂)₂ | H | CH₂ | OMe | 4-[PhSO₂N(Me)]—Ph | O |
| 5-182 | H | (CH₂)₂ | H | CH₂ | OMe | 4-[(Pyr-3)SO₂N(Me)]—Ph | O |
| 5-183 | H | (CH₂)₂ | H | CH₂ | OMe | 4-(PhSO₂NH)—Ph | O |

TABLE 5-continued

| Exemplification No. compound. | R¹ | R² | R³ | Z | W | X | Y |
|---|---|---|---|---|---|---|---|
| 5-184 | H | (CH$_2$)$_2$ | H | CH$_2$ | OMe | 4-[(Pyr-3)SO$_2$NH]—Ph | O |
| 5-185 | H | (CH$_2$)$_2$ | H | CH$_2$ | OMe | 4-[(Pyr-2)SO$_2$]—Ph | O |
| 5-186 | H | (CH$_2$)$_2$ | H | CH$_2$ | OMe | 4-[(Pyr-3)SO$_2$]—Ph | O |
| 5-187 | H | (CH$_2$)$_2$ | H | CH$_2$ | OMe | 4-[(Pyr-2)SO$_2$N(Me)]—Ph | O |
| 5-188 | H | (CH$_2$)$_2$ | H | CH$_2$ | OMe | 4-[(Pyr-2)SO$_2$NH]—Ph | O |
| 5-189 | H | (CH$_2$)$_2$ | H | CH$_2$ | OMe | 4-(4-Me—Ph)—Ph | O |
| 5-190 | H | (CH$_2$)$_2$ | H | CH$_2$ | OMe | 4-(4-F—Ph)—Ph | O |
| 5-191 | H | (CH$_2$)$_2$ | H | CH$_2$ | OMe | 4-(4-CF$_3$—Ph)—Ph | O |
| 5-192 | H | (CH$_2$)$_2$ | H | CH$_2$ | OMe | 2-[4-Me—PhSO$_2$N(Me)]-5-Pyr | O |
| 5-193 | H | (CH$_2$)$_2$ | H | CH$_2$ | OMe | 2-HO-5-Pyr | O |
| 5-194 | H | (CH$_2$)$_2$ | H | CH$_2$ | OMe | 2-BzO-5-Pyr | O |
| 5-195 | H | (CH$_2$)$_2$ | H | CH$_2$ | OMe | 4-[(Pyr-4)SO$_2$]—Ph | O |
| 5-196 | H | (CH$_2$)$_2$ | H | CH$_2$ | OMe | 4-(2,4-di-MeO—Ph)—Ph | O |
| 5-197 | H | (CH$_2$)$_2$ | H | CH$_2$ | OMe | 4-(2,5-di-MeO—Ph)—Ph | O |
| 5-198 | H | (CH$_2$)$_2$ | H | CH$_2$ | OMe | 3-HO—Ph | O |
| 5-199 | H | (CH$_2$)$_2$ | H | CH$_2$ | OMe | 4-HO—Ph | O |
| 5-200 | H | (CH$_2$)$_2$ | H | CH$_2$ | OMe | 5-AcO-2-HO-3,4,6-tri-Me—Ph | O |
| 5-201 | H | (CH$_2$)$_2$ | H | CH$_2$ | OMe | 4-HO-3,5-di-Me—Ph | O |
| 5-202 | H | (CH$_2$)$_2$ | H | CH$_2$ | OMe | 3-AcO—Ph | O |
| 5-203 | H | (CH$_2$)$_2$ | H | CH$_2$ | OMe | 4-AcO—Ph | O |

TABLE 6

| Exemplification No. compound. | R¹ | R² | R³ | Z | W | X | Y |
|---|---|---|---|---|---|---|---|
| 6-1 | Me | (CH$_2$)$_2$ | H | CH$_2$ | OMe | Ph | O |
| 6-2 | Me | (CH$_2$)$_2$ | H | CH$_2$ | OMe | 1-Np | O |
| 6-3 | Me | (CH$_2$)$_2$ | H | CH$_2$ | OMe | 2-Np | O |
| 6-4 | Me | (CH$_2$)$_2$ | H | CH$_2$ | OMe | 4-Me—Ph | O |
| 6-5 | Me | (CH$_2$)$_2$ | H | CH$_2$ | OMe | 4-Et—Ph | O |
| 6-6 | Me | (CH$_2$)$_2$ | H | CH$_2$ | OMe | 3-iPr—Ph | O |
| 6-7 | Me | (CH$_2$)$_2$ | H | CH$_2$ | OMe | 4-iPr—Ph | O |
| 6-8 | Me | (CH$_2$)$_2$ | H | CH$_2$ | OMe | 3-tBu—Ph | O |
| 6-9 | Me | (CH$_2$)$_2$ | H | CH$_2$ | OMe | 4-tBu—Ph | O |
| 6-10 | Me | (CH$_2$)$_2$ | H | CH$_2$ | OMe | 3-Cl—Ph | O |
| 6-11 | Me | (CH$_2$)$_2$ | H | CH$_2$ | OMe | 4-Cl—Ph | O |
| 6-12 | Me | (CH$_2$)$_2$ | H | CH$_2$ | OMe | 3-Br—Ph | O |
| 6-13 | Me | (CH$_2$)$_2$ | H | CH$_2$ | OMe | 4-Br—Ph | O |
| 6-14 | Me | (CH$_2$)$_2$ | H | CH$_2$ | OMe | 3-Ph—Ph | O |
| 6-15 | Me | (CH$_2$)$_2$ | H | CH$_2$ | OMe | 4-Ph—Ph | O |
| 6-16 | Me | (CH$_2$)$_2$ | H | CH$_2$ | OMe | 3-Bz—Ph | O |
| 6-17 | Me | (CH$_2$)$_2$ | H | CH$_2$ | OMe | 4-Bz—Ph | O |
| 6-18 | Me | (CH$_2$)$_2$ | H | CH$_2$ | OMe | 3-PhO—Ph | O |
| 6-19 | Me | (CH$_2$)$_2$ | H | CH$_2$ | OMe | 4-PhO—Ph | O |
| 6-20 | Me | (CH$_2$)$_2$ | H | CH$_2$ | OMe | 3-PhS—Ph | O |
| 6-21 | Me | (CH$_2$)$_2$ | H | CH$_2$ | OMe | 4-PhS—Ph | O |
| 6-22 | Me | (CH$_2$)$_2$ | H | CH$_2$ | OMe | 3-PhSO$_2$—Ph | O |
| 6-23 | Me | (CH$_2$)$_2$ | H | CH$_2$ | OMe | 4-PhSO$_2$—Ph | O |
| 6-24 | Me | (CH$_2$)$_2$ | H | CH$_2$ | OMe | 3-(Imid-1)-Ph | O |
| 6-25 | Me | (CH$_2$)$_2$ | H | CH$_2$ | OMe | 4-(Imid-1)-Ph | O |
| 6-26 | Me | (CH$_2$)$_2$ | H | CH$_2$ | OMe | 3-(Imid-4)-Ph | O |
| 6-27 | Me | (CH$_2$)$_2$ | H | CH$_2$ | OMe | 4-(Imid-4)-Ph | O |
| 6-28 | Me | (CH$_2$)$_2$ | H | CH$_2$ | OMe | 3-(Fur-2)-Ph | O |
| 6-29 | Me | (CH$_2$)$_2$ | H | CH$_2$ | OMe | 4-(Fur-2)-Ph | O |
| 6-30 | Me | (CH$_2$)$_2$ | H | CH$_2$ | OMe | 3-(Thi-2)-Ph | O |
| 6-31 | Me | (CH$_2$)$_2$ | H | CH$_2$ | OMe | 4-(Thi-2)-Ph | O |
| 6-32 | Me | (CH$_2$)$_2$ | H | CH$_2$ | OMe | 3-(Thi-3)-Ph | O |
| 6-33 | Me | (CH$_2$)$_2$ | H | CH$_2$ | OMe | 4-(Thi-3)-Ph | O |
| 6-34 | Me | (CH$_2$)$_2$ | H | CH$_2$ | OMe | 3-(Pyr-2)-Ph | O |
| 6-35 | Me | (CH$_2$)$_2$ | H | CH$_2$ | OMe | 4-(Pyr-2)-Ph | O |
| 6-36 | Me | (CH$_2$)$_2$ | H | CH$_2$ | OMe | 3-(Pyr-3)-Ph | O |
| 6-37 | Me | (CH$_2$)$_2$ | H | CH$_2$ | OMe | 4-(Pyr-3)-Ph | O |
| 6-38 | Me | (CH$_2$)$_2$ | H | CH$_2$ | OMe | 3-(Pyr-4)-Ph | O |
| 6-39 | Me | (CH$_2$)$_2$ | H | CH$_2$ | OMe | 4-(Pyr-4)-Ph | O |
| 6-40 | Me | (CH$_2$)$_2$ | H | CH$_2$ | OMe | 3-(Oxa-2)-Ph | O |
| 6-41 | Me | (CH$_2$)$_2$ | H | CH$_2$ | OMe | 4-(Oxa-2)-Ph | O |
| 6-42 | Me | (CH$_2$)$_2$ | H | CH$_2$ | OMe | 3-(Oxa-4)-Ph | O |
| 6-43 | Me | (CH$_2$)$_2$ | H | CH$_2$ | OMe | 4-(Oxa-4)-Ph | O |
| 6-44 | Me | (CH$_2$)$_2$ | H | CH$_2$ | OMe | 3-(Oxa-5)-Ph | O |
| 6-45 | Me | (CH$_2$)$_2$ | H | CH$_2$ | OMe | 4-(Oxa-5)-Ph | O |
| 6-46 | Me | (CH$_2$)$_2$ | H | CH$_2$ | OMe | 3-(Thiz-2)-Ph | O |
| 6-47 | Me | (CH$_2$)$_2$ | H | CH$_2$ | OMe | 4-(Thiz-2)-Ph | O |
| 6-48 | Me | (CH$_2$)$_2$ | H | CH$_2$ | OMe | 3-(Thiz-4)-Ph | O |
| 6-49 | Me | (CH$_2$)$_2$ | H | CH$_2$ | OMe | 4-(Thiz-4)-Ph | O |
| 6-50 | Me | (CH$_2$)$_2$ | H | CH$_2$ | OMe | 3-(Thiz-5)-Ph | O |
| 6-51 | Me | (CH$_2$)$_2$ | H | CH$_2$ | OMe | 4-(Thiz-5)-Ph | O |
| 6-52 | Me | (CH$_2$)$_2$ | H | CH$_2$ | OMe | 1-Me-2-Pyrr | O |
| 6-53 | Me | (CH$_2$)$_2$ | H | CH$_2$ | OMe | 1-Ph-2-Pyrr | O |
| 6-54 | Me | (CH$_2$)$_2$ | H | CH$_2$ | OMe | 1-Bz-2-Pyrr | O |
| 6-55 | Me | (CH$_2$)$_2$ | H | CH$_2$ | OMe | 5-Me-2-Fur | O |
| 6-56 | Me | (CH$_2$)$_2$ | H | CH$_2$ | OMe | 5-Ph-2-Fur | O |
| 6-57 | Me | (CH$_2$)$_2$ | H | CH$_2$ | OMe | 5-Me-2-Thi | O |
| 6-58 | Me | (CH$_2$)$_2$ | H | CH$_2$ | OMe | 5-Ph-2-Thi | O |
| 6-59 | Me | (CH$_2$)$_2$ | H | CH$_2$ | OMe | 5-Me-3-Thi | O |
| 6-60 | Me | (CH$_2$)$_2$ | H | CH$_2$ | OMe | 5-Ph-3-Thi | O |
| 6-61 | Me | (CH$_2$)$_2$ | H | CH$_2$ | OMe | 1-Me-3-Pyza | O |
| 6-62 | Me | (CH$_2$)$_2$ | H | CH$_2$ | OMe | 1-Ph-3-Pyza | O |
| 6-63 | Me | (CH$_2$)$_2$ | H | CH$_2$ | OMe | 1-Me-2-Imid | O |
| 6-64 | Me | (CH$_2$)$_2$ | H | CH$_2$ | OMe | 1-Ph-2-Imid | O |
| 6-65 | Me | (CH$_2$)$_2$ | H | CH$_2$ | OMe | 1-Me-4-Imid | O |
| 6-66 | Me | (CH$_2$)$_2$ | H | CH$_2$ | OMe | 1-Ph-4-Imid | O |
| 6-67 | Me | (CH$_2$)$_2$ | H | CH$_2$ | OMe | 4-Oxa | O |
| 6-68 | Me | (CH$_2$)$_2$ | H | CH$_2$ | OMe | 5-Oxa | O |
| 6-69 | Me | (CH$_2$)$_2$ | H | CH$_2$ | OMe | 2-Me-4-Oxa | O |
| 6-70 | Me | (CH$_2$)$_2$ | H | CH$_2$ | OMe | 2-Ph-4-Oxa | O |
| 6-71 | Me | (CH$_2$)$_2$ | H | CH$_2$ | OMe | 2-Me-5-Oxa | O |
| 6-72 | Me | (CH$_2$)$_2$ | H | CH$_2$ | OMe | 2-Ph-5-Oxa | O |
| 6-73 | Me | (CH$_2$)$_2$ | H | CH$_2$ | OMe | 4-Me-2-Ph-5-Oxa | O |
| 6-74 | Me | (CH$_2$)$_2$ | H | CH$_2$ | OMe | 5-Me-2-Ph-4-Oxa | O |
| 6-75 | Me | (CH$_2$)$_2$ | H | CH$_2$ | OMe | 4-Thiz | O |
| 6-76 | Me | (CH$_2$)$_2$ | H | CH$_2$ | OMe | 5-Thiz | O |
| 6-77 | Me | (CH$_2$)$_2$ | H | CH$_2$ | OMe | 2-Me-4-Thiz | O |
| 6-78 | Me | (CH$_2$)$_2$ | H | CH$_2$ | OMe | 2-Ph-4-Thiz | O |
| 6-79 | Me | (CH$_2$)$_2$ | H | CH$_2$ | OMe | 2-Me-5-Thiz | O |
| 6-80 | Me | (CH$_2$)$_2$ | H | CH$_2$ | OMe | 2-Ph-5-Thiz | O |
| 6-81 | Me | (CH$_2$)$_2$ | H | CH$_2$ | OMe | 4-Me-2-Ph-5-Thiz | O |
| 6-82 | Me | (CH$_2$)$_2$ | H | CH$_2$ | OMe | 5-Me-2-Ph-4-Thiz | O |
| 6-83 | Me | (CH$_2$)$_2$ | H | CH$_2$ | OMe | 1-Me-4-Pyza | O |
| 6-84 | Me | (CH$_2$)$_2$ | H | CH$_2$ | OMe | 1-Ph-4-Pyza | O |
| 6-85 | Me | (CH$_2$)$_2$ | H | CH$_2$ | OMe | 2-Me-4-Isox | O |
| 6-86 | Me | (CH$_2$)$_2$ | H | CH$_2$ | OMe | 2-Ph-4-Isox | O |
| 6-87 | Me | (CH$_2$)$_2$ | H | CH$_2$ | OMe | 2-Pyr | O |
| 6-88 | Me | (CH$_2$)$_2$ | H | CH$_2$ | OMe | 3-Pyr | O |
| 6-89 | Me | (CH$_2$)$_2$ | H | CH$_2$ | OMe | 4-Pyr | O |
| 6-90 | Me | (CH$_2$)$_2$ | H | CH$_2$ | OMe | 3-Me-5-Pyr | O |
| 6-91 | Me | (CH$_2$)$_2$ | H | CH$_2$ | OMe | 3-Et-5-Pyr | O |
| 6-92 | Me | (CH$_2$)$_2$ | H | CH$_2$ | OMe | 3-Ph-5-Pyr | O |
| 6-93 | Me | (CH$_2$)$_2$ | H | CH$_2$ | OMe | 2-Me-5-Pyr | O |
| 6-94 | Me | (CH$_2$)$_2$ | H | CH$_2$ | OMe | 2-Et-5-Pyr | O |
| 6-95 | Me | (CH$_2$)$_2$ | H | CH$_2$ | OMe | 2-Ph-5-Pyr | O |

TABLE 6-continued

| Exemplification No. compound. | R¹ | R² | R³ | Z | W | X | Y |
|---|---|---|---|---|---|---|---|
| 6-96 | Me | (CH₂)₂ | H | CH₂ | OMe | 2-MeO-5-Pyr | O |
| 6-97 | Me | (CH₂)₂ | H | CH₂ | OMe | 2-EtO-5-Pyr | O |
| 6-98 | Me | (CH₂)₂ | H | CH₂ | OMe | 2-iPrO-5-Pyr | O |
| 6-99 | Me | (CH₂)₂ | H | CH₂ | OMe | 2-MeS-5-Pyr | O |
| 6-100 | Me | (CH₂)₂ | H | CH₂ | OMe | 2-EtS-5-Pyr | O |
| 6-101 | Me | (CH₂)₂ | H | CH₂ | OMe | 2-iPrS-5-Pyr | O |
| 6-102 | Me | (CH₂)₂ | H | CH₂ | OMe | 2-MeSO₂-5-Pyr | O |
| 6-103 | Me | (CH₂)₂ | H | CH₂ | OMe | 2-EtSO₂-5-Pyr | O |
| 6-104 | Me | (CH₂)₂ | H | CH₂ | OMe | 2-iPrSO₂-5-Pyr | O |
| 6-105 | Me | (CH₂)₂ | H | CH₂ | OMe | 2-Bz-5-Pyr | O |
| 6-106 | Me | (CH₂)₂ | H | CH₂ | OMe | 2-PhO-5-Pyr | O |
| 6-107 | Me | (CH₂)₂ | H | CH₂ | OMe | 2-PhS-5-Pyr | O |
| 6-108 | Me | (CH₂)₂ | H | CH₂ | OMe | 2-PhSO₂-5-Pyr | O |
| 6-109 | Me | (CH₂)₂ | H | CH₂ | OMe | 3-Me-6-Pyr | O |
| 6-110 | Me | (CH₂)₂ | H | CH₂ | OMe | 3-Ph-6-Pyr | O |
| 6-111 | Me | (CH₂)₂ | H | CH₂ | OMe | 2-Me-6-Pyr | O |
| 6-112 | Me | (CH₂)₂ | H | CH₂ | OMe | 2-Ph-6-Pyr | O |
| 6-113 | Me | (CH₂)₂ | H | CH₂ | OMe | 2-Me-4-Pym | O |
| 6-114 | Me | (CH₂)₂ | H | CH₂ | OMe | 2-Ph-4-Pym | O |
| 6-115 | Me | (CH₂)₂ | H | CH₂ | OMe | 2-MeO-4-Pym | O |
| 6-116 | Me | (CH₂)₂ | H | CH₂ | OMe | 2-EtO-4-Pym | O |
| 6-117 | Me | (CH₂)₂ | H | CH₂ | OMe | 2-iPrO-4-Pym | O |
| 6-118 | Me | (CH₂)₂ | H | CH₂ | OMe | 2-MeS-4-Pym | O |
| 6-119 | Me | (CH₂)₂ | H | CH₂ | OMe | 2-EtS-4-Pym | O |
| 6-120 | Me | (CH₂)₂ | H | CH₂ | OMe | 2-iPrS-4-Pym | O |
| 6-121 | Me | (CH₂)₂ | H | CH₂ | OMe | 6-MeS-4-Pym | O |
| 6-122 | Me | (CH₂)₂ | H | CH₂ | OMe | 6-EtS-4-Pym | O |
| 6-123 | Me | (CH₂)₂ | H | CH₂ | OMe | 6-iPrS-4-Pym | O |
| 6-124 | Me | (CH₂)₂ | H | CH₂ | OMe | 2-PhS-4-Pym | O |
| 6-125 | Me | (CH₂)₂ | H | CH₂ | OMe | 2-MeSO₂-4-Pym | O |
| 6-126 | Me | (CH₂)₂ | H | CH₂ | OMe | 2-EtSO₂-4-Pym | O |
| 6-127 | Me | (CH₂)₂ | H | CH₂ | OMe | 2-iPrSO₂-4-Pym | O |
| 6-128 | Me | (CH₂)₂ | H | CH₂ | OMe | 2-PhSO₂-4-Pym | O |
| 6-129 | Me | (CH₂)₂ | H | CH₂ | OMe | 2-Me-5-Pym | O |
| 6-130 | Me | (CH₂)₂ | H | CH₂ | OMe | 2-Ph-5-Pym | O |
| 6-131 | Me | (CH₂)₂ | H | CH₂ | OMe | 2-MeO-5-Pym | O |
| 6-132 | Me | (CH₂)₂ | H | CH₂ | OMe | 2-EtO-5-Pym | O |
| 6-133 | Me | (CH₂)₂ | H | CH₂ | OMe | 2-iPrO-5-Pym | O |
| 6-134 | Me | (CH₂)₂ | H | CH₂ | OMe | 2-MeS-5-Pym | O |
| 6-135 | Me | (CH₂)₂ | H | CH₂ | OMe | 2-EtS-5-Pym | O |
| 6-136 | Me | (CH₂)₂ | H | CH₂ | OMe | 2-iPrS-5-Pym | O |
| 6-137 | Me | (CH₂)₂ | H | CH₂ | OMe | 2-PhS-5-Pym | O |
| 6-138 | Me | (CH₂)₂ | H | CH₂ | OMe | 2-MeSO₂-5-Pym | O |
| 6-139 | Me | (CH₂)₂ | H | CH₂ | OMe | 2-EtSO₂-5-Pym | O |
| 6-140 | Me | (CH₂)₂ | H | CH₂ | OMe | 2-iPrSO₂-5-Pym | O |
| 6-141 | Me | (CH₂)₂ | H | CH₂ | OMe | 2-PhSO₂-5-Pym | O |
| 6-142 | Me | (CH₂)₂ | H | CH₂ | OMe | 2-Ind | O |
| 6-143 | Me | (CH₂)₂ | H | CH₂ | OMe | 3-Ind | O |
| 6-144 | Me | (CH₂)₂ | H | CH₂ | OMe | 1-Me-2-Ind | O |
| 6-145 | Me | (CH₂)₂ | H | CH₂ | OMe | 1-Me-3-Ind | O |
| 6-146 | Me | (CH₂)₂ | H | CH₂ | OMe | 2-Bimid | O |
| 6-147 | Me | (CH₂)₂ | H | CH₂ | OMe | 2-Boxa | O |
| 6-148 | Me | (CH₂)₂ | H | CH₂ | OMe | 2-Bthiz | O |
| 6-149 | Me | (CH₂)₂ | H | CH₂ | OMe | 2-Quin | O |
| 6-150 | Me | (CH₂)₂ | H | CH₂ | OMe | 3-Quin | O |
| 6-151 | Me | (CH₂)₂ | H | CH₂ | OMe | 4-Quin | O |
| 6-152 | Me | (CH₂)₂ | H | CH₂ | OMe | 1-iQuin | O |
| 6-153 | Me | (CH₂)₂ | H | CH₂ | OMe | 3-iQuin | O |
| 6-154 | Me | (CH₂)₂ | H | CH₂ | OMe | 4-iQuin | O |
| 6-155 | Me | (CH₂)₂ | H | CH₂ | OMe | 3-MeO—Ph | O |
| 6-156 | Me | (CH₂)₂ | H | CH₂ | OMe | 4-MeO—Ph | O |
| 6-157 | Me | (CH₂)₂ | H | CH₂ | OMe | 3-EtO—Ph | O |
| 6-158 | Me | (CH₂)₂ | H | CH₂ | OMe | 4-EtO—Ph | O |
| 6-159 | Me | (CH₂)₂ | H | CH₂ | OMe | 3-iPrO—Ph | O |
| 6-160 | Me | (CH₂)₂ | H | CH₂ | OMe | 4-iPrO—Ph | O |
| 6-161 | Me | (CH₂)₂ | H | CH₂ | OMe | 3-MeS—Ph | O |
| 6-162 | Me | (CH₂)₂ | H | CH₂ | OMe | 4-MeS—Ph | O |
| 6-163 | Me | (CH₂)₂ | H | CH₂ | OMe | 3-EtS—Ph | O |
| 6-164 | Me | (CH₂)₂ | H | CH₂ | OMe | 4-EtS—Ph | O |
| 6-165 | Me | (CH₂)₂ | H | CH₂ | OMe | 3-iPrS—Ph | O |
| 6-166 | Me | (CH₂)₂ | H | CH₂ | OMe | 4-iPrS—Ph | O |
| 6-167 | Me | (CH₂)₂ | H | CH₂ | OMe | 3-MeSO₂—Ph | O |
| 6-168 | Me | (CH₂)₂ | H | CH₂ | OMe | 4-MeSO₂—Ph | O |
| 6-169 | Me | (CH₂)₂ | H | CH₂ | OMe | 3-EtSO₂—Ph | O |
| 6-170 | Me | (CH₂)₂ | H | CH₂ | OMe | 4-EtSO₂—Ph | O |
| 6-171 | Me | (CH₂)₂ | H | CH₂ | OMe | 3-iPrSO₂—Ph | O |
| 6-172 | Me | (CH₂)₂ | H | CH₂ | OMe | 4-iPrSO₂—Ph | O |
| 6-173 | Me | (CH₂)₂ | H | CH₂ | OMe | 3-(1-Me—Imid-4)-Ph | O |
| 6-174 | Me | (CH₂)₂ | H | CH₂ | OMe | 4-(1-Me—Imid-4)-Ph | O |
| 6-175 | Me | (CH₂)₂ | H | CH₂ | OMe | 1-Me-2-Ph-4-Imid | O |
| 6-176 | Me | (CH₂)₂ | H | CH₂ | OMe | 1,4-di-Me-2-Ph-5-Imid | O |
| 6-177 | Me | (CH₂)₂ | H | CH₂ | OMe | 1,5-di-Me-2-Ph-4-Imid | O |
| 6-178 | Me | (CH₂)₂ | H | CH₂ | OMe | 3,4-MdO—Ph | O |
| 6-179 | Me | (CH₂)₂ | H | CH₂ | OMe | 4-(4-MeO—Ph)—Ph | O |
| 6-180 | Me | (CH₂)₂ | H | CH₂ | OMe | 4-(3,4-MdO—Ph)—Ph | O |
| 6-181 | Me | (CH₂)₂ | H | CH₂ | OMe | 4-[PhSO₂N(Me)]—Ph | O |
| 6-182 | Me | (CH₂)₂ | H | CH₂ | OMe | 4-[(Pyr-3)SO₂N(Me)]—Ph | O |
| 6-183 | Me | (CH₂)₂ | H | CH₂ | OMe | 4-(PhSO₂NH)—Ph | O |
| 6-184 | Me | (CH₂)₂ | H | CH₂ | OMe | 4-[(Pyr-3)SO₂NH]—Ph | O |
| 6-185 | Me | (CH₂)₂ | H | CH₂ | OMe | 4-[(Pyr-2)SO₂]—Ph | O |
| 6-186 | Me | (CH₂)₂ | H | CH₂ | OMe | 4-[(Pyr-3)SO₂]—Ph | O |
| 6-187 | Me | (CH₂)₂ | H | CH₂ | OMe | 4-[(Pyr-2)SO₂N(Me)]—Ph | O |
| 6-188 | Me | (CH₂)₂ | H | CH₂ | OMe | 4-[(Pyr-2)SO₂NH]—Ph | O |
| 6-189 | Me | (CH₂)₂ | H | CH₂ | OMe | 4-(4-Me—Ph)—Ph | O |
| 6-190 | Me | (CH₂)₂ | H | CH₂ | OMe | 4-(4-F—Ph)—Ph | O |
| 6-191 | Me | (CH₂)₂ | H | CH₂ | OMe | 4-(4-CF₃—Ph)—Ph | O |
| 6-192 | Me | (CH₂)₂ | H | CH₂ | OMe | 2-[4-Me—PhSO₂N(Me)]-5-Pyr | O |
| 6-193 | Me | (CH₂)₂ | H | CH₂ | OMe | 2-HO-5-Pyr | O |
| 6-194 | Me | (CH₂)₂ | H | CH₂ | OMe | 2-BzO-5-Pyr | O |
| 6-195 | Me | (CH₂)₂ | H | CH₂ | OMe | 4-[(Pyr-4)SO₂]—Ph | O |
| 6-196 | Me | (CH₂)₂ | H | CH₂ | OMe | 4-(2,4-di-MeO—Ph)—Ph | O |
| 6-197 | Me | (CH₂)₂ | H | CH₂ | OMe | 4-(2,5-di-MeO—Ph)—Ph | O |
| 6-198 | Me | (CH₂)₂ | H | CH₂ | OMe | 3-HO—Ph | O |
| 6-199 | Me | (CH₂)₂ | H | CH₂ | OMe | 4-HO—Ph | O |
| 6-200 | Me | (CH₂)₂ | H | CH₂ | OMe | 5-AcO-2-HO-3,4,6-tri-Me—Ph | O |
| 6-201 | Me | (CH₂)₂ | H | CH₂ | OMe | 4-HO-3,5-di-Me—Ph | O |
| 6-202 | Me | (CH₂)₂ | H | CH₂ | OMe | 3-AcO—Ph | O |
| 6-203 | Me | (CH₂)₂ | H | CH₂ | OMe | 4-AcO—Ph | O |

TABLE 7

| Exemplification No. compound. | R¹ | R² | R³ | Z | W | X | Y |
|---|---|---|---|---|---|---|---|
| 7-1 | H | (CH₂)₃ | H | CH₂ | OEt | Ph | O |
| 7-2 | H | (CH₂)₃ | H | CH₂ | OEt | 1-Np | O |

TABLE 7-continued

| Exemplification No. compound. | R¹ | R² | R³ | Z | W | X | Y |
|---|---|---|---|---|---|---|---|
| 7-3 | H | (CH₂)₃ | H | CH₂ | OEt | 2-Np | O |
| 7-4 | H | (CH₂)₃ | H | CH₂ | OEt | 4-Me—Ph | O |
| 7-5 | H | (CH₂)₃ | H | CH₂ | OEt | 4-Et—Ph | O |
| 7-6 | H | (CH₂)₃ | H | CH₂ | OEt | 3-iPr—Ph | O |
| 7-7 | H | (CH₂)₃ | H | CH₂ | OEt | 4-iPr—Ph | O |
| 7-8 | H | (CH₂)₃ | H | CH₂ | OEt | 3-tBu—Ph | O |
| 7-9 | H | (CH₂)₃ | H | CH₂ | OEt | 4-tBu—Ph | O |
| 7-10 | H | (CH₂)₃ | H | CH₂ | OEt | 3-Cl—Ph | O |
| 7-11 | H | (CH₂)₃ | H | CH₂ | OEt | 4-Cl—Ph | O |
| 7-12 | H | (CH₂)₃ | H | CH₂ | OEt | 3-Br—Ph | O |
| 7-13 | H | (CH₂)₃ | H | CH₂ | OEt | 4-Br—Ph | O |
| 7-14 | H | (CH₂)₃ | H | CH₂ | OEt | 3-Ph—Ph | O |
| 7-15 | H | (CH₂)₃ | H | CH₂ | OEt | 4-Ph—Ph | O |
| 7-16 | H | (CH₂)₃ | H | CH₂ | OEt | 3-Bz—Ph | O |
| 7-17 | H | (CH₂)₃ | H | CH₂ | OEt | 4-Bz—Ph | O |
| 7-18 | H | (CH₂)₃ | H | CH₂ | OEt | 3-PhO—Ph | O |
| 7-19 | H | (CH₂)₃ | H | CH₂ | OEt | 4-PhO—Ph | O |
| 7-20 | H | (CH₂)₃ | H | CH₂ | OEt | 3-PhS—Ph | O |
| 7-21 | H | (CH₂)₃ | H | CH₂ | OEt | 4-PhS—Ph | O |
| 7-22 | H | (CH₂)₃ | H | CH₂ | OEt | 3-PhSO₂—Ph | O |
| 7-23 | H | (CH₂)₃ | H | CH₂ | OEt | 4-PhSO₂—Ph | O |
| 7-24 | H | (CH₂)₃ | H | CH₂ | OEt | 3-(Imid-1)-Ph | O |
| 7-25 | H | (CH₂)₃ | H | CH₂ | OEt | 4-(Imid-1)-Ph | O |
| 7-26 | H | (CH₂)₃ | H | CH₂ | OEt | 3-(Imid-4)-Ph | O |
| 7-27 | H | (CH₂)₃ | H | CH₂ | OEt | 4-(Imid-4)-Ph | O |
| 7-28 | H | (CH₂)₃ | H | CH₂ | OEt | 3-(Fur-2)-Ph | O |
| 7-29 | H | (CH₂)₃ | H | CH₂ | OEt | 4-(Fur-2)-Ph | O |
| 7-30 | H | (CH₂)₃ | H | CH₂ | OEt | 3-(Thi-2)-Ph | O |
| 7-31 | H | (CH₂)₃ | H | CH₂ | OEt | 4-(Thi-2)-Ph | O |
| 7-32 | H | (CH₂)₃ | H | CH₂ | OEt | 3-(Thi-3)-Ph | O |
| 7-33 | H | (CH₂)₃ | H | CH₂ | OEt | 4-(Thi-3)-Ph | O |
| 7-34 | H | (CH₂)₃ | H | CH₂ | OEt | 3-(Pyr-2)-Ph | O |
| 7-35 | H | (CH₂)₃ | H | CH₂ | OEt | 4-(Pyr-2)-Ph | O |
| 7-36 | H | (CH₂)₃ | H | CH₂ | OEt | 3-(Pyr-3)-Ph | O |
| 7-37 | H | (CH₂)₃ | H | CH₂ | OEt | 4-(Pyr-3)-Ph | O |
| 7-38 | H | (CH₂)₃ | H | CH₂ | OEt | 3-(Pyr-4)-Ph | O |
| 7-39 | H | (CH₂)₃ | H | CH₂ | OEt | 4-(Pyr-4)-Ph | O |
| 7-40 | H | (CH₂)₃ | H | CH₂ | OEt | 3-(Oxa-2)-Ph | O |
| 7-41 | H | (CH₂)₃ | H | CH₂ | OEt | 4-(Oxa-2)-Ph | O |
| 7-42 | H | (CH₂)₃ | H | CH₂ | OEt | 3-(Oxa-4)-Ph | O |
| 7-43 | H | (CH₂)₃ | H | CH₂ | OEt | 4-(Oxa-4)-Ph | O |
| 7-44 | H | (CH₂)₃ | H | CH₂ | OEt | 3-(Oxa-5)-Ph | O |
| 7-45 | H | (CH₂)₃ | H | CH₂ | OEt | 4-(Oxa-5)-Ph | O |
| 7-46 | H | (CH₂)₃ | H | CH₂ | OEt | 3-(Thiz-2)-Ph | O |
| 7-47 | H | (CH₂)₃ | H | CH₂ | OEt | 4-(Thiz-2)-Ph | O |
| 7-48 | H | (CH₂)₃ | H | CH₂ | OEt | 3-(Thiz-4)-Ph | O |
| 7-49 | H | (CH₂)₃ | H | CH₂ | OEt | 4-(Thiz-4)-Ph | O |
| 7-50 | H | (CH₂)₃ | H | CH₂ | OEt | 3-(Thiz-5)-Ph | O |
| 7-51 | H | (CH₂)₃ | H | CH₂ | OEt | 4-(Thiz-5)-Ph | O |
| 7-52 | H | (CH₂)₃ | H | CH₂ | OEt | 1-Me-2-Pyrr | O |
| 7-53 | H | (CH₂)₃ | H | CH₂ | OEt | 1-Ph-2-Pyrr | O |
| 7-54 | H | (CH₂)₃ | H | CH₂ | OEt | 1-Bz-2-Pyrr | O |
| 7-55 | H | (CH₂)₃ | H | CH₂ | OEt | 5-Me-2-Fur | O |
| 7-56 | H | (CH₂)₃ | H | CH₂ | OEt | 5-Ph-2-Fur | O |
| 7-57 | H | (CH₂)₃ | H | CH₂ | OEt | 5-Me-2-Thi | O |
| 7-58 | H | (CH₂)₃ | H | CH₂ | OEt | 5-Ph-2-Thi | O |
| 7-59 | H | (CH₂)₃ | H | CH₂ | OEt | 5-Me-3-Thi | O |
| 7-60 | H | (CH₂)₃ | H | CH₂ | OEt | 5-Ph-3-Thi | O |
| 7-61 | H | (CH₂)₃ | H | CH₂ | OEt | 1-Me-3-Pyza | O |
| 7-62 | H | (CH₂)₃ | H | CH₂ | OEt | 1-Ph-3-Pyza | O |
| 7-63 | H | (CH₂)₃ | H | CH₂ | OEt | 1-Me-2-Imid | O |
| 7-64 | H | (CH₂)₃ | H | CH₂ | OEt | 1-Ph-2-Imid | O |
| 7-65 | H | (CH₂)₃ | H | CH₂ | OEt | 1-Me-4-Imid | O |
| 7-66 | H | (CH₂)₃ | H | CH₂ | OEt | 1-Ph-4-Imid | O |
| 7-67 | H | (CH₂)₃ | H | CH₂ | OEt | 4-Oxa | O |
| 7-68 | H | (CH₂)₃ | H | CH₂ | OEt | 5-Oxa | O |
| 7-69 | H | (CH₂)₃ | H | CH₂ | OEt | 2-Me-4-Oxa | O |
| 7-70 | H | (CH₂)₃ | H | CH₂ | OEt | 2-Ph-4-Oxa | O |
| 7-71 | H | (CH₂)₃ | H | CH₂ | OEt | 2-Me-5-Oxa | O |
| 7-72 | H | (CH₂)₃ | H | CH₂ | OEt | 2-Ph-5-Oxa | O |
| 7-73 | H | (CH₂)₃ | H | CH₂ | OEt | 4-Me-2-Ph-5-Oxa | O |
| 7-74 | H | (CH₂)₃ | H | CH₂ | OEt | 5-Me-2-Ph-4-Oxa | O |
| 7-75 | H | (CH₂)₃ | H | CH₂ | OEt | 4-Thiz | O |
| 7-76 | H | (CH₂)₃ | H | CH₂ | OEt | 5-Thiz | O |
| 7-77 | H | (CH₂)₃ | H | CH₂ | OEt | 2-Me-4-Thiz | O |
| 7-78 | H | (CH₂)₃ | H | CH₂ | OEt | 2-Ph-4-Thiz | O |
| 7-79 | H | (CH₂)₃ | H | CH₂ | OEt | 2-Me-5-Thiz | O |
| 7-80 | H | (CH₂)₃ | H | CH₂ | OEt | 2-Ph-5-Thiz | O |
| 7-81 | H | (CH₂)₃ | H | CH₂ | OEt | 4-Me-2-Ph-5-Thiz | O |
| 7-82 | H | (CH₂)₃ | H | CH₂ | OEt | 5-Me-2-Ph-4-Thiz | O |
| 7-83 | H | (CH₂)₃ | H | CH₂ | OEt | 1-Me-4-Pyza | O |
| 7-84 | H | (CH₂)₃ | H | CH₂ | OEt | 1-Ph-4-Pyza | O |
| 7-85 | H | (CH₂)₃ | H | CH₂ | OEt | 2-Me-4-Isox | O |
| 7-86 | H | (CH₂)₃ | H | CH₂ | OEt | 2-Ph-4-Isox | O |
| 7-87 | H | (CH₂)₃ | H | CH₂ | OEt | 2-Pyr | O |
| 7-88 | H | (CH₂)₃ | H | CH₂ | OEt | 3-Pyr | O |
| 7-89 | H | (CH₂)₃ | H | CH₂ | OEt | 4-Pyr | O |
| 7-90 | H | (CH₂)₃ | H | CH₂ | OEt | 3-Me-5-Pyr | O |
| 7-91 | H | (CH₂)₃ | H | CH₂ | OEt | 3-Et-5-Pyr | O |
| 7-92 | H | (CH₂)₃ | H | CH₂ | OEt | 3-Ph-5-Pyr | O |
| 7-93 | H | (CH₂)₃ | H | CH₂ | OEt | 2-Me-5-Pyr | O |
| 7-94 | H | (CH₂)₃ | H | CH₂ | OEt | 2-Et-5-Pyr | O |
| 7-95 | H | (CH₂)₃ | H | CH₂ | OEt | 2-Ph-5-Pyr | O |
| 7-96 | H | (CH₂)₃ | H | CH₂ | OEt | 2-MeO-5-Pyr | O |
| 7-97 | H | (CH₂)₃ | H | CH₂ | OEt | 2-EtO-5-Pyr | O |
| 7-98 | H | (CH₂)₃ | H | CH₂ | OEt | 2-iPrO-5-Pyr | O |
| 7-99 | H | (CH₂)₃ | H | CH₂ | OEt | 2-MeS-5-Pyr | O |
| 7-100 | H | (CH₂)₃ | H | CH₂ | OEt | 2-EtS-5-Pyr | O |
| 7-101 | H | (CH₂)₃ | H | CH₂ | OEt | 2-iPrS-5-Pyr | O |
| 7-102 | H | (CH₂)₃ | H | CH₂ | OEt | 2-MeSO₂-5-Pyr | O |
| 7-103 | H | (CH₂)₃ | H | CH₂ | OEt | 2-EtSO₂-5-Pyr | O |
| 7-104 | H | (CH₂)₃ | H | CH₂ | OEt | 2-iPrSO₂-5-Pyr | O |
| 7-105 | H | (CH₂)₃ | H | CH₂ | OEt | 2-Bz-5-Pyr | O |
| 7-106 | H | (CH₂)₃ | H | CH₂ | OEt | 2-PhO-5-Pyr | O |
| 7-107 | H | (CH₂)₃ | H | CH₂ | OEt | 2-PhS-5-Pyr | O |
| 7-108 | H | (CH₂)₃ | H | CH₂ | OEt | 2-PhSO₂-5-Pyr | O |
| 7-109 | H | (CH₂)₃ | H | CH₂ | OEt | 3-Me-6-Pyr | O |
| 7-110 | H | (CH₂)₃ | H | CH₂ | OEt | 3-Ph-6-Pyr | O |
| 7-111 | H | (CH₂)₃ | H | CH₂ | OEt | 2-Me-6-Pyr | O |
| 7-112 | H | (CH₂)₃ | H | CH₂ | OEt | 2-Ph-6-Pyr | O |
| 7-113 | H | (CH₂)₃ | H | CH₂ | OEt | 2-Me-4-Pym | O |
| 7-114 | H | (CH₂)₃ | H | CH₂ | OEt | 2-Ph-4-Pym | O |
| 7-115 | H | (CH₂)₃ | H | CH₂ | OEt | 2-MeO-4-Pym | O |
| 7-116 | H | (CH₂)₃ | H | CH₂ | OEt | 2-EtO-4-Pym | O |
| 7-117 | H | (CH₂)₃ | H | CH₂ | OEt | 2-iPrO-4-Pym | O |
| 7-118 | H | (CH₂)₃ | H | CH₂ | OEt | 2-MeS-4-Pym | O |
| 7-119 | H | (CH₂)₃ | H | CH₂ | OEt | 2-EtS-4-Pym | O |
| 7-120 | H | (CH₂)₃ | H | CH₂ | OEt | 2-iPrS-4-Pym | O |
| 7-121 | H | (CH₂)₃ | H | CH₂ | OEt | 6-MeS-4-Pym | O |
| 7-122 | H | (CH₂)₃ | H | CH₂ | OEt | 6-EtS-4-Pym | O |
| 7-123 | H | (CH₂)₃ | H | CH₂ | OEt | 6-iPrS-4-Pym | O |
| 7-124 | H | (CH₂)₃ | H | CH₂ | OEt | 2-PhS-4-Pym | O |
| 7-125 | H | (CH₂)₃ | H | CH₂ | OEt | 2-MeSO₂-4-Pym | O |
| 7-126 | H | (CH₂)₃ | H | CH₂ | OEt | 2-EtSO₂-4-Pym | O |
| 7-127 | H | (CH₂)₃ | H | CH₂ | OEt | 2-iPrSO₂-4-Pym | O |
| 7-128 | H | (CH₂)₃ | H | CH₂ | OEt | 2-PhSO₂-4-Pym | O |
| 7-129 | H | (CH₂)₃ | H | CH₂ | OEt | 2-Me-5-Pym | O |
| 7-130 | H | (CH₂)₃ | H | CH₂ | OEt | 2-Ph-5-Pym | O |
| 7-131 | H | (CH₂)₃ | H | CH₂ | OEt | 2-MeO-5-Pym | O |
| 7-132 | H | (CH₂)₃ | H | CH₂ | OEt | 2-EtO-5-Pym | O |
| 7-133 | H | (CH₂)₃ | H | CH₂ | OEt | 2-iPrO-5-Pym | O |
| 7-134 | H | (CH₂)₃ | H | CH₂ | OEt | 2-MeS-5-Pym | O |
| 7-135 | H | (CH₂)₃ | H | CH₂ | OEt | 2-EtS-5-Pym | O |
| 7-136 | H | (CH₂)₃ | H | CH₂ | OEt | 2-iPrS-5-Pym | O |
| 7-137 | H | (CH₂)₃ | H | CH₂ | OEt | 2-PhS-5-Pym | O |
| 7-138 | H | (CH₂)₃ | H | CH₂ | OEt | 2-MeSO₂-5-Pym | O |
| 7-139 | H | (CH₂)₃ | H | CH₂ | OEt | 2-EtSO₂-5-Pym | O |
| 7-140 | H | (CH₂)₃ | H | CH₂ | OEt | 2-iPrSO₂-5-Pym | O |
| 7-141 | H | (CH₂)₃ | H | CH₂ | OEt | 2-PhSO₂-5-Pym | O |
| 7-142 | H | (CH₂)₃ | H | CH₂ | OEt | 2-Ind | O |

TABLE 7-continued

| Exemplification No. compound. | R¹ | R² | R³ | Z | W | X | Y |
|---|---|---|---|---|---|---|---|
| 7-143 | H | (CH₂)₃ | H | CH₂ | OEt | 3-Ind | O |
| 7-144 | H | (CH₂)₃ | H | CH₂ | OEt | 1-Me-2-Ind | O |
| 7-145 | H | (CH₂)₃ | H | CH₂ | OEt | 1-Me-3-Ind | O |
| 7-146 | H | (CH₂)₃ | H | CH₂ | OEt | 2-Bimid | O |
| 7-147 | H | (CH₂)₃ | H | CH₂ | OEt | 2-Boxa | O |
| 7-148 | H | (CH₂)₃ | H | CH₂ | OEt | 2-Bthiz | O |
| 7-149 | H | (CH₂)₃ | H | CH₂ | OEt | 2-Quin | O |
| 7-150 | H | (CH₂)₃ | H | CH₂ | OEt | 3-Quin | O |
| 7-151 | H | (CH₂)₃ | H | CH₂ | OEt | 4-Quin | O |
| 7-152 | H | (CH₂)₃ | H | CH₂ | OEt | 1-iQuin | O |
| 7-153 | H | (CH₂)₃ | H | CH₂ | OEt | 3-iQuin | O |
| 7-154 | H | (CH₂)₃ | H | CH₂ | OEt | 4-iQuin | O |
| 7-155 | H | (CH₂)₃ | H | CH₂ | OEt | 3-MeO—Ph | O |
| 7-156 | H | (CH₂)₃ | H | CH₂ | OEt | 4-MeO—Ph | O |
| 7-157 | H | (CH₂)₃ | H | CH₂ | OEt | 3-EtO—Ph | O |
| 7-158 | H | (CH₂)₃ | H | CH₂ | OEt | 4-EtO—Ph | O |
| 7-159 | H | (CH₂)₃ | H | CH₂ | OEt | 3-iPrO—Ph | O |
| 7-160 | H | (CH₂)₃ | H | CH₂ | OEt | 4-iPrO—Ph | O |
| 7-161 | H | (CH₂)₃ | H | CH₂ | OEt | 3-MeS—Ph | O |
| 7-162 | H | (CH₂)₃ | H | CH₂ | OEt | 4-MeS—Ph | O |
| 7-163 | H | (CH₂)₃ | H | CH₂ | OEt | 3-EtS—Ph | O |
| 7-164 | H | (CH₂)₃ | H | CH₂ | OEt | 4-EtS—Ph | O |
| 7-165 | H | (CH₂)₃ | H | CH₂ | OEt | 3-iPrS—Ph | O |
| 7-166 | H | (CH₂)₃ | H | CH₂ | OEt | 4-iPrS—Ph | O |
| 7-167 | H | (CH₂)₃ | H | CH₂ | OEt | 3-MeSO₂—Ph | O |
| 7-168 | H | (CH₂)₃ | H | CH₂ | OEt | 4-MeSO₂—Ph | O |
| 7-169 | H | (CH₂)₃ | H | CH₂ | OEt | 3-EtSO₂—Ph | O |
| 7-170 | H | (CH₂)₃ | H | CH₂ | OEt | 4-EtSO₂—Ph | O |
| 7-171 | H | (CH₂)₃ | H | CH₂ | OEt | 3-iPrSO₂—Ph | O |
| 7-172 | H | (CH₂)₃ | H | CH₂ | OEt | 4-iPrSO₂—Ph | O |
| 7-173 | H | (CH₂)₃ | H | CH₂ | OEt | 3-(1-Me-Imid-4)-Ph | O |
| 7-174 | H | (CH₂)₃ | H | CH₂ | OEt | 1-Me-Imid-4)-Ph | O |
| 7-175 | H | (CH₂)₃ | H | CH₂ | OEt | 1-Me-2-Ph-4-Imid | O |
| 7-176 | H | (CH₂)₃ | H | CH₂ | OEt | 1,4-di-Me-2-Ph-5-Imid | O |
| 7-177 | H | (CH₂)₃ | H | CH₂ | OEt | 1,5-di-Me-2-Ph-4-Imid | O |
| 7-178 | H | (CH₂)₃ | H | CH₂ | OEt | 3,4-MdO—Ph | O |
| 7-179 | H | (CH₂)₃ | H | CH₂ | OEt | 4-(4-MeO—Ph)—Ph | O |
| 7-180 | H | (CH₂)₃ | H | CH₂ | OEt | 4-(3,4-MdO—Ph)—Ph | O |
| 7-181 | H | (CH₂)₃ | H | CH₂ | OEt | 4-[PhSO₂N(Me)]—Ph | O |
| 7-182 | H | (CH₂)₃ | H | CH₂ | OEt | 4-[(Pyr-3)SO₂N(Me)]—Ph | O |
| 7-183 | H | (CH₂)₃ | H | CH₂ | OEt | 4-(PhSO₂NH)—Ph | O |
| 7-184 | H | (CH₂)₃ | H | CH₂ | OEt | 4-[(Pyr-3)SO₂NH]—Ph | O |
| 7-185 | H | (CH₂)₃ | H | CH₂ | OEt | 4-[(Pyr-2)SO₂]—Ph | O |
| 7-186 | H | (CH₂)₃ | H | CH₂ | OEt | 4-[(Pyr-3)SO₂]—Ph | O |
| 7-187 | H | (CH₂)₃ | H | CH₂ | OEt | 4-[(Pyr-2)SO₂N(Me)]—Ph | O |
| 7-188 | H | (CH₂)₃ | H | CH₂ | OEt | 4-[(Pyr-2)SO₂NH]—Ph | O |
| 7-189 | H | (CH₂)₃ | H | CH₂ | OEt | 4-(4-Me—Ph)—Ph | O |
| 7-190 | H | (CH₂)₃ | H | CH₂ | OEt | 4-(4-F—Ph)—Ph | O |
| 7-191 | H | (CH₂)₃ | H | CH₂ | OEt | 4-(4-CF₃—Ph)—Ph | O |
| 7-192 | H | (CH₂)₃ | H | CH₂ | OEt | 2-[4-Me—PhSO₂(Me)]-5-Pyr | O |
| 7-193 | H | (CH₂)₃ | H | CH₂ | OEt | 2-HO-5-Pyr | O |
| 7-194 | H | (CH₂)₃ | H | CH₂ | OEt | 2-BzO-5-Pyr | O |
| 7-195 | H | (CH₂)₃ | H | CH₂ | OEt | 4-[(Pyr-4)SO₂]—Ph | O |
| 7-196 | H | (CH₂)₃ | H | CH₂ | OEt | 4-(2,4-di-MeO—Ph)—Ph | O |
| 7-197 | H | (CH₂)₃ | H | CH₂ | OEt | 4-(2,5-di-MeO—Ph)—Ph | O |
| 7-198 | H | (CH₂)₃ | H | CH₂ | OEt | 3-HO—Ph | O |
| 7-199 | H | (CH₂)₃ | H | CH₂ | OEt | 4-HO—Ph | O |
| 7-200 | H | (CH₂)₃ | H | CH₂ | OEt | 5-AcO-2-HO-3,4,6-tri-Me—Ph | O |
| 7-201 | H | (CH₂)₃ | H | CH₂ | OEt | 4-HO-3,5-di-Me—Ph | O |
| 7-202 | H | (CH₂)₃ | H | CH₂ | OEt | 3-AcO—Ph | O |
| 7-203 | H | (CH₂)₃ | H | CH₂ | OEt | 4-AcO—Ph | O |

TABLE 8

| Exemplification No. compound. | R¹ | R² | R³ | Z | W | X | Y |
|---|---|---|---|---|---|---|---|
| 8-1 | Me | (CH₂)₃ | H | CH₂ | OEt | Ph | O |
| 8-2 | Me | (CH₂)₃ | H | CH₂ | OEt | 1-Np | O |
| 8-3 | Me | (CH₂)₃ | H | CH₂ | OEt | 2-Np | O |
| 8-4 | Me | (CH₂)₃ | H | CH₂ | OEt | 4-Me—Ph | O |
| 8-5 | Me | (CH₂)₃ | H | CH₂ | OEt | 4-Et—Ph | O |
| 8-6 | Me | (CH₂)₃ | H | CH₂ | OEt | 3-iPr—Ph | O |
| 8-7 | Me | (CH₂)₃ | H | CH₂ | OEt | 4-iPr—Ph | O |
| 8-8 | Me | (CH₂)₃ | H | CH₂ | OEt | 3-tBu—Ph | O |
| 8-9 | Me | (CH₂)₃ | H | CH₂ | OEt | 4-tBu—Ph | O |
| 8-10 | Me | (CH₂)₃ | H | CH₂ | OEt | 3-Cl—Ph | O |
| 8-11 | Me | (CH₂)₃ | H | CH₂ | OEt | 4-Cl—Ph | O |
| 8-12 | Me | (CH₂)₃ | H | CH₂ | OEt | 3-Br—Ph | O |
| 8-13 | Me | (CH₂)₃ | H | CH₂ | OEt | 4-Br—Ph | O |
| 8-14 | Me | (CH₂)₃ | H | CH₂ | OEt | 3-Ph—Ph | O |
| 8-15 | Me | (CH₂)₃ | H | CH₂ | OEt | 4-Ph—Ph | O |
| 8-16 | Me | (CH₂)₃ | H | CH₂ | OEt | 3-Bz—Ph | O |
| 8-17 | Me | (CH₂)₃ | H | CH₂ | OEt | 4-Bz—Ph | O |
| 8-18 | Me | (CH₂)₃ | H | CH₂ | OEt | 3-PhO—Ph | O |
| 8-19 | Me | (CH₂)₃ | H | CH₂ | OEt | 4-PhO—Ph | O |
| 8-20 | Me | (CH₂)₃ | H | CH₂ | OEt | 3-PhS—Ph | O |
| 8-21 | Me | (CH₂)₃ | H | CH₂ | OEt | 4-PhS—Ph | O |
| 8-22 | Me | (CH₂)₃ | H | CH₂ | OEt | 3-PhSO₂—Ph | O |
| 8-23 | Me | (CH₂)₃ | H | CH₂ | OEt | 4-PhSO₂—Ph | O |
| 8-24 | Me | (CH₂)₃ | H | CH₂ | OEt | 3-(Imid-1)-Ph | O |
| 8-25 | Me | (CH₂)₃ | H | CH₂ | OEt | 4-(Imid-1)-Ph | O |
| 8-26 | Me | (CH₂)₃ | H | CH₂ | OEt | 3-(Imid-4)-Ph | O |
| 8-27 | Me | (CH₂)₃ | H | CH₂ | OEt | 4-(Imid-4)-Ph | O |
| 8-28 | Me | (CH₂)₃ | H | CH₂ | OEt | 3-(Fur-2)-Ph | O |
| 8-29 | Me | (CH₂)₃ | H | CH₂ | OEt | 4-(Fur-2)-Ph | O |
| 8-30 | Me | (CH₂)₃ | H | CH₂ | OEt | 3-(Thi-2)-Ph | O |
| 8-31 | Me | (CH₂)₃ | H | CH₂ | OEt | 4-(Thi-2)-Ph | O |
| 8-32 | Me | (CH₂)₃ | H | CH₂ | OEt | 3-(Thi-3)-Ph | O |
| 8-33 | Me | (CH₂)₃ | H | CH₂ | OEt | 4-(Thi-3)-Ph | O |
| 8-34 | Me | (CH₂)₃ | H | CH₂ | OEt | 3-(Pyr-2)-Ph | O |
| 8-35 | Me | (CH₂)₃ | H | CH₂ | OEt | 4-(Pyr-2)-Ph | O |
| 8-36 | Me | (CH₂)₃ | H | CH₂ | OEt | 3-(Pyr-3)-Ph | O |
| 8-37 | Me | (CH₂)₃ | H | CH₂ | OEt | 4-(Pyr-3)-Ph | O |
| 8-38 | Me | (CH₂)₃ | H | CH₂ | OEt | 3-(Pyr-4)-Ph | O |
| 8-39 | Me | (CH₂)₃ | H | CH₂ | OEt | 4-(Pyr-4)-Ph | O |
| 8-40 | Me | (CH₂)₃ | H | CH₂ | OEt | 3-(Oxa-2)-Ph | O |
| 8-41 | Me | (CH₂)₃ | H | CH₂ | OEt | 4-(Oxa-2)-Ph | O |
| 8-42 | Me | (CH₂)₃ | H | CH₂ | OEt | 3-(Oxa-4)-Ph | O |
| 8-43 | Me | (CH₂)₃ | H | CH₂ | OEt | 4-(Oxa-4)-Ph | O |
| 8-44 | Me | (CH₂)₃ | H | CH₂ | OEt | 3-(Oxa-5)-Ph | O |
| 8-45 | Me | (CH₂)₃ | H | CH₂ | OEt | 4-(Oxa-5)-Ph | O |
| 8-46 | Me | (CH₂)₃ | H | CH₂ | OEt | 3-(Thiz-2)-Ph | O |
| 8-47 | Me | (CH₂)₃ | H | CH₂ | OEt | 4-(Thiz-2)-Ph | O |
| 8-48 | Me | (CH₂)₃ | H | CH₂ | OEt | 3-(Thiz-4)-Ph | O |

TABLE 8-continued

| Exemplification No. compound. | R¹ | R² | R³ | Z | W | X | Y |
|---|---|---|---|---|---|---|---|
| 8-49 | Me | (CH₂)₃ | H | CH₂ | OEt | 4-(Thiz-4)-Ph | O |
| 8-50 | Me | (CH₂)₃ | H | CH₂ | OEt | 3-(Thiz-5)-Ph | O |
| 8-51 | Me | (CH₂)₃ | H | CH₂ | OEt | 4-(Thiz-5)-Ph | O |
| 8-52 | Me | (CH₂)₃ | H | CH₂ | OEt | 1-Me-2-Pyrr | O |
| 8-53 | Me | (CH₂)₃ | H | CH₂ | OEt | 1-Ph-2-Pyrr | O |
| 8-54 | Me | (CH₂)₃ | H | CH₂ | OEt | 1-Bz-2-Pyrr | O |
| 8-55 | Me | (CH₂)₃ | H | CH₂ | OEt | 5-Me-2-Fur | O |
| 8-56 | Me | (CH₂)₃ | H | CH₂ | OEt | 5-Ph-2-Fur | O |
| 8-57 | Me | (CH₂)₃ | H | CH₂ | OEt | 5-Me-2-Thi | O |
| 8-58 | Me | (CH₂)₃ | H | CH₂ | OEt | 5-Ph-2-Thi | O |
| 8-59 | Me | (CH₂)₃ | H | CH₂ | OEt | 5-Me-3-Thi | O |
| 8-60 | Me | (CH₂)₃ | H | CH₂ | OEt | 5-Ph-3-Thi | O |
| 8-61 | Me | (CH₂)₃ | H | CH₂ | OEt | 1-Me-3-Pyza | O |
| 8-62 | Me | (CH₂)₃ | H | CH₂ | OEt | 1-Ph-3-Pyza | O |
| 8-63 | Me | (CH₂)₃ | H | CH₂ | OEt | 1-Me-2-Imid | O |
| 8-64 | Me | (CH₂)₃ | H | CH₂ | OEt | 1-Ph-2-Imid | O |
| 8-65 | Me | (CH₂)₃ | H | CH₂ | OEt | 1-Me-4-Imid | O |
| 8-66 | Me | (CH₂)₃ | H | CH₂ | OEt | 1-Ph-4-Imid | O |
| 8-67 | Me | (CH₂)₃ | H | CH₂ | OEt | 4-Oxa | O |
| 8-68 | Me | (CH₂)₃ | H | CH₂ | OEt | 5-Oxa | O |
| 8-69 | Me | (CH₂)₃ | H | CH₂ | OEt | 2-Me-4-Oxa | O |
| 8-70 | Me | (CH₂)₃ | H | CH₂ | OEt | 2-Ph-4-Oxa | O |
| 8-71 | Me | (CH₂)₃ | H | CH₂ | OEt | 2-Me-5-Oxa | O |
| 8-72 | Me | (CH₂)₃ | H | CH₂ | OEt | 2-Ph-5-Oxa | O |
| 8-73 | Me | (CH₂)₃ | H | CH₂ | OEt | 4-Me-2-Ph-5-Oxa | O |
| 8-74 | Me | (CH₂)₃ | H | CH₂ | OEt | 5-Me-2-Ph-4-Oxa | O |
| 8-75 | Me | (CH₂)₃ | H | CH₂ | OEt | 4-Thiz | O |
| 8-76 | Me | (CH₂)₃ | H | CH₂ | OEt | 5-Thiz | O |
| 8-77 | Me | (CH₂)₃ | H | CH₂ | OEt | 2-Me-4-Thiz | O |
| 8-78 | Me | (CH₂)₃ | H | CH₂ | OEt | 2-Ph-4-Thiz | O |
| 8-79 | Me | (CH₂)₃ | H | CH₂ | OEt | 2-Me-5-Thiz | O |
| 8-80 | Me | (CH₂)₃ | H | CH₂ | OEt | 2-Ph-5-Thiz | O |
| 8-81 | Me | (CH₂)₃ | H | CH₂ | OEt | 4-Me-2-Ph-5-Thiz | O |
| 8-82 | Me | (CH₂)₃ | H | CH₂ | OEt | 5-Me-2-Ph-4-Thiz | O |
| 8-83 | Me | (CH₂)₃ | H | CH₂ | OEt | 1-Me-4-Pyza | O |
| 8-84 | Me | (CH₂)₃ | H | CH₂ | OEt | 1-Ph-4-Pyza | O |
| 8-85 | Me | (CH₂)₃ | H | CH₂ | OEt | 2-Me-4-Isox | O |
| 8-86 | Me | (CH₂)₃ | H | CH₂ | OEt | 2-Ph-4-Isox | O |
| 8-87 | Me | (CH₂)₃ | H | CH₂ | OEt | 2-Pyr | O |
| 8-88 | Me | (CH₂)₃ | H | CH₂ | OEt | 3-Pyr | O |
| 8-89 | Me | (CH₂)₃ | H | CH₂ | OEt | 4-Pyr | O |
| 8-90 | Me | (CH₂)₃ | H | CH₂ | OEt | 3-Me-5-Pyr | O |
| 8-91 | Me | (CH₂)₃ | H | CH₂ | OEt | 3-Et-5-Pyr | O |
| 8-92 | Me | (CH₂)₃ | H | CH | OEt | 3-Ph-5-Pyr | O |
| 8-93 | Me | (CH₂)₃ | H | CH₂ | OEt | 2-Me-5-Pyr | O |
| 8-94 | Me | (CH₂)₃ | H | CH₂ | OEt | 2-Et-5-Pyr | O |
| 8-95 | Me | (CH₂)₃ | H | CH₂ | OEt | 2-Ph-5-Pyr | O |
| 8-96 | Me | (CH₂)₃ | H | CH₂ | OEt | 2-MeO-5-Pyr | O |
| 8-97 | Me | (CH₂)₃ | H | CH₂ | OEt | 2-EtO-5-Pyr | O |
| 8-98 | Me | (CH₂)₃ | H | CH₂ | OEt | 2-iPrO-5-Pyr | O |
| 8-99 | Me | (CH₂)₃ | H | CH₂ | OEt | 2-MeS-5-Pyr | O |
| 8-100 | Me | (CH₂)₃ | H | CH₂ | OEt | 2-EtS-5-Pyr | O |
| 8-101 | Me | (CH₂)₃ | H | CH₂ | OEt | 2-iPrS-5-Pyr | O |
| 8-102 | Me | (CH₂)₃ | H | CH₂ | OEt | 2-MeSO₂-5-Pyr | O |
| 8-103 | Me | (CH₂)₃ | H | CH₂ | OEt | 2-EtSO₂-5-Pyr | O |
| 8-104 | Me | (CH₂)₃ | H | CH₂ | OEt | 2-iPrSO₂-5-Pyr | O |
| 8-105 | Me | (CH₂)₃ | H | CH₂ | OEt | 2-Bz-5-Pyr | O |
| 8-106 | Me | (CH₂)₃ | H | CH₂ | OEt | 2-PhO-5-Pyr | O |
| 8-107 | Me | (CH₂)₃ | H | CH₂ | OEt | 2-PhS-5-Pyr | O |
| 8-108 | Me | (CH₂)₃ | H | CH₂ | OEt | 2-PhSO₂-5-Pyr | O |
| 8-109 | Me | (CH₂)₃ | H | CH₂ | OEt | 3-Me-6-Pyr | O |
| 8-110 | Me | (CH₂)₃ | H | CH₂ | OEt | 3-Ph-6-Pyr | O |
| 8-111 | Me | (CH₂)₃ | H | CH₂ | OEt | 2-Me-6-Pyr | O |
| 8-112 | Me | (CH₂)₃ | H | CH₂ | OEt | 2-Ph-6-Pyr | O |
| 8-113 | Me | (CH₂)₃ | H | CH₂ | OEt | 2-Me-4-Pym | O |
| 8-114 | Me | (CH₂)₃ | H | CH₂ | OEt | 2-Ph-4-Pym | O |
| 8-115 | Me | (CH₂)₃ | H | CH₂ | OEt | 2-MeO-4-Pym | O |
| 8-116 | Me | (CH₂)₃ | H | CH₂ | OEt | 2-EtO-4-Pym | O |
| 8-117 | Me | (CH₂)₃ | H | CH₂ | OEt | 2-iPrO-4-Pym | O |
| 8-118 | Me | (CH₂)₃ | H | CH₂ | OEt | 2-MeS-4-Pym | O |
| 8-119 | Me | (CH₂)₃ | H | CH₂ | OEt | 2-EtS-4-Pym | O |
| 8-120 | Me | (CH₂)₃ | H | CH₂ | OEt | 2-iPrS-4-Pym | O |
| 8-121 | Me | (CH₂)₃ | H | CH₂ | OEt | 6-MeS-4-Pym | O |
| 8-122 | Me | (CH₂)₃ | H | CH₂ | OEt | 6-EtS-4-Pym | O |
| 8-123 | Me | (CH₂)₃ | H | CH₂ | OEt | 6-iPrS-4-Pym | O |
| 8-124 | Me | (CH₂)₃ | H | CH₂ | OEt | 2-PhS-4-Pym | O |
| 8-125 | Me | (CH₂)₃ | H | CH₂ | OEt | 2-MeSO₂-4-Pym | O |
| 8-126 | Me | (CH₂)₃ | H | CH₂ | OEt | 2-EtSO₂-4-Pym | O |
| 8-127 | Me | (CH₂)₃ | H | CH₂ | OEt | 2-iPrSO₂-4-Pym | O |
| 8-128 | Me | (CH₂)₃ | H | CH₂ | OEt | 2-PhSO₂-4-Pym | O |
| 8-129 | Me | (CH₂)₃ | H | CH₂ | OEt | 2-Me-5-Pym | O |
| 8-130 | Me | (CH₂)₃ | H | CH₂ | OEt | 2-Ph-5-Pym | O |
| 8-131 | Me | (CH₂)₃ | H | CH₂ | OEt | 2-MeO-5-Pym | O |
| 8-132 | Me | (CH₂)₃ | H | CH₂ | OEt | 2-EtO-5-Pym | O |
| 8-133 | Me | (CH₂)₃ | H | CH₂ | OEt | 2-iPrO-5-Pym | O |
| 8-134 | Me | (CH₂)₃ | H | CH₂ | OEt | 2-MeS-5-Pym | O |
| 8-135 | Me | (CH₂)₃ | H | CH₂ | OEt | 2-EtS-5-Pym | O |
| 8-136 | Me | (CH₂)₃ | H | CH₂ | OEt | 2-iPrS-5-Pym | O |
| 8-137 | Me | (CH₂)₃ | H | CH₂ | OEt | 2-PhS-5-Pym | O |
| 8-138 | Me | (CH₂)₃ | H | CH₂ | OEt | 2-MeSO₂-5-Pym | O |
| 8-139 | Me | (CH₂)₃ | H | CH₂ | OEt | 2-EtSO₂-5-Pym | O |
| 8-140 | Me | (CH₂)₃ | H | CH₂ | OEt | 2-iPrSO₂-5-Pym | O |
| 8-141 | Me | (CH₂)₃ | H | CH₂ | OEt | 2-PhSO₂-5-Pym | O |
| 8-142 | Me | (CH₂)₃ | H | CH₂ | OEt | 2-Ind | O |
| 8-143 | Me | (CH₂)₃ | H | CH₂ | OEt | 3-Ind | O |
| 8-144 | Me | (CH₂)₃ | H | CH₂ | OEt | 1-Me-2-Ind | O |
| 8-145 | Me | (CH₂)₃ | H | CH₂ | OEt | 1-Me-3-Ind | O |
| 8-146 | Me | (CH₂)₃ | H | CH₂ | OEt | 2-Bimid | O |
| 8-147 | Me | (CH₂)₃ | H | CH₂ | OEt | 2-Boxa | O |
| 8-148 | Me | (CH₂)₃ | H | CH₂ | OEt | 2-Bthiz | O |
| 8-149 | Me | (CH₂)₃ | H | CH₂ | OEt | 2-Quin | O |
| 8-150 | Me | (CH₂)₃ | H | CH₂ | OEt | 3-Quin | O |
| 8-151 | Me | (CH₂)₃ | H | CH₂ | OEt | 4-Quin | O |
| 8-152 | Me | (CH₂)₃ | H | CH₂ | OEt | 1-iQuin | O |
| 8-153 | Me | (CH₂)₃ | H | CH₂ | OEt | 3-iQuin | O |
| 8-154 | Me | (CH₂)₃ | H | CH₂ | OEt | 4-iQuin | O |
| 8-155 | Me | (CH₂)₃ | H | CH₂ | OEt | 3-MeO—Ph | O |
| 8-156 | Me | (CH₂)₃ | H | CH₂ | OEt | 4-MeO—Ph | O |
| 8-157 | Me | (CH₂)₃ | H | CH₂ | OEt | 3-EtO—Ph | O |
| 8-158 | Me | (CH₂)₃ | H | CH₂ | OEt | 4-EtO—Ph | O |
| 8-159 | Me | (CH₂)₃ | H | CH₂ | OEt | 3-iPrO—Ph | O |
| 8-160 | Me | (CH₂)₃ | H | CH₂ | OEt | 4-iPrO—Ph | O |
| 8-161 | Me | (CH₂)₃ | H | CH₂ | OEt | 3-MeS—Ph | O |
| 8-162 | Me | (CH₂)₃ | H | CH₂ | OEt | 4-MeS—Ph | O |
| 8-163 | Me | (CH₂)₃ | H | CH₂ | OEt | 3-EtS—Ph | O |
| 8-164 | Me | (CH₂)₃ | H | CH₂ | OEt | 4-EtS—Ph | O |
| 8-165 | Me | (CH₂)₃ | H | CH₂ | OEt | 3-iPrS—Ph | O |
| 8-166 | Me | (CH₂)₃ | H | CH₂ | OEt | 4-iPrS—Ph | O |
| 8-167 | Me | (CH₂)₃ | H | CH₂ | OEt | 3-MeSO₂—Ph | O |
| 8-168 | Me | (CH₂)₃ | H | CH₂ | OEt | 4-MeSO₂—Ph | O |
| 8-169 | Me | (CH₂)₃ | H | CH₂ | OEt | 3-EtSO₂—Ph | O |
| 8-170 | Me | (CH₂)₃ | H | CH₂ | OEt | 4-EtSO₂—Ph | O |
| 8-171 | Me | (CH₂)₃ | H | CH₂ | OEt | 3-iPrSO₂—Ph | O |
| 8-172 | Me | (CH₂)₃ | H | CH₂ | OEt | 4-iPrSO₂—Ph | O |
| 8-173 | Me | (CH₂)₃ | H | CH₂ | OEt | 3-(1-Me—Imid-4)-Ph | O |
| 8-174 | Me | (CH₂)₃ | H | CH₂ | OEt | 4-(1-Me—Imid-4)-Ph | O |
| 8-175 | Me | (CH₂)₃ | H | CH₂ | OEt | 1-Me-2-Ph-4-Imid | O |
| 8-176 | Me | (CH₂)₃ | H | CH₂ | OEt | 1,4-di-Me-2-Ph-5-Imid | O |
| 8-177 | Me | (CH₂)₃ | H | CH₂ | OEt | 1,5-di-Me-2-Ph-4-Imid | O |
| 8-178 | Me | (CH₂)₃ | H | CH₂ | OEt | 3,4-MdO—Ph | O |
| 8-179 | Me | (CH₂)₃ | H | CH₂ | OEt | 4-(4-MeO—Ph)—Ph | O |
| 8-180 | Me | (CH₂)₃ | H | CH₂ | OEt | 4-(3,4-MdO—Ph)—Ph | O |
| 8-181 | Me | (CH₂)₃ | H | CH₂ | OEt | 4- | O |

TABLE 8-continued

| Exemplification No. compound. | R¹ | R² | R³ | Z | W | X | Y |
|---|---|---|---|---|---|---|---|
| 8-182 | Me | $(CH_2)_3$ | H | $CH_2$ | OEt | 4-[PhSO$_2$N(Me)]—Ph | O |
| 8-183 | Me | $(CH_2)_3$ | H | $CH_2$ | OEt | 4-[(Pyr-3)SO$_2$N(Me)]—Ph | O |
| 8-184 | Me | $(CH_2)_3$ | H | $CH_2$ | OEt | 4-(PhSO$_2$NH)—Ph | O |
| 8-185 | Me | $(CH_2)_3$ | H | $CH_2$ | OEt | 4-[(Pyr-3)SO$_2$NH]—Ph | O |
| 8-186 | Me | $(CH_2)_3$ | H | $CH_2$ | OEt | 4-[(Pyr-2)SO$_2$]—Ph | O |
| 8-187 | Me | $(CH_2)_3$ | H | $CH_2$ | OEt | 4-[(Pyr-3)SO$_2$]—Ph | O |
| 8-188 | Me | $(CH_2)_3$ | H | $CH_2$ | OEt | 4-[(Pyr-2)SO$_2$N(Me)]—Ph | O |
| 8-189 | Me | $(CH_2)_3$ | H | $CH_2$ | OEt | 4-[(Pyr-2)SO$_2$NH]—Ph | O |
| 8-190 | Me | $(CH_2)_3$ | H | $CH_2$ | OEt | 4-(4-Me—Ph)—Ph | O |
| 8-191 | Me | $(CH_2)_3$ | H | $CH_2$ | OEt | 4-(4-F—Ph)—Ph | O |
| 8-192 | Me | $(CH_2)_3$ | H | $CH_2$ | OEt | 4-(4-CF$_3$—Ph)—Ph | O |
| 8-193 | Me | $(CH_2)_3$ | H | $CH_2$ | OEt | 2-[4-Me—PhSO$_2$N(Me)]-5-Pyr | O |
| 8-194 | Me | $(CH_2)_3$ | H | $CH_2$ | OEt | 2-HO-5-Pyr | O |
| 8-195 | Me | $(CH_2)_3$ | H | $CH_2$ | OEt | 2-BzO-5-Pyr | O |
| 8-196 | Me | $(CH_2)_3$ | H | $CH_2$ | OEt | 4-[(Pyr-4)SO$_2$]—Ph | O |
| 8-197 | Me | $(CH_2)_3$ | H | $CH_2$ | OEt | 4-(2,4-di-MeO—Ph)—Ph | O |
| 8-198 | Me | $(CH_2)_3$ | H | $CH_2$ | OEt | 4-(2,5-di-MeO—Ph)—Ph | O |
| 8-199 | Me | $(CH_2)_3$ | H | $CH_2$ | OEt | 3-HO—Ph | O |
| 8-200 | Me | $(CH_2)_3$ | H | $CH_2$ | OEt | 4-HO—Ph | O |
| 8-201 | Me | $(CH_2)_3$ | H | $CH_2$ | OEt | 5-AcO-2-HO-3,4,6-tri-Me—Ph | O |
| 8-202 | Me | $(CH_2)_3$ | H | $CH_2$ | OEt | 4-HO-3,5-di-Me—Ph | O |
| 8-203 | Me | $(CH_2)_3$ | H | $CH_2$ | OEt | 3-AcO—Ph | O |
|  | Me | $(CH_2)_3$ | H | $CH_2$ | OEt | 4-AcO—Ph | O |

TABLE 9

| Exemplification No. compound. | R¹ | R² | R³ | Z | W | X | Y |
|---|---|---|---|---|---|---|---|
| 9-1 | H | CH(Me)CH$_2$ | H | $CH_2$ | OEt | Ph | O |
| 9-2 | H | CH(Me)CH$_2$ | H | $CH_2$ | OEt | 1-Np | O |
| 9-3 | H | CH(Me)CH$_2$ | H | $CH_2$ | OEt | 2-Np | O |
| 9-4 | H | CH(Me)CH$_2$ | H | $CH_2$ | OEt | 4-Me—Ph | O |
| 9-5 | H | CH(Me)CH$_2$ | H | $CH_2$ | OEt | 4-Et—Ph | O |
| 9-6 | H | CH(Me)CH$_2$ | H | $CH_2$ | OEt | 3-iPr—Ph | O |
| 9-7 | H | CH(Me)CH$_2$ | H | $CH_2$ | OEt | 4-iPr—Ph | O |
| 9-8 | H | CH(Me)CH$_2$ | H | $CH_2$ | OEt | 3-tBu—Ph | O |
| 9-9 | H | CH(Me)CH$_2$ | H | $CH_2$ | OEt | 4-tBu—Ph | O |
| 9-10 | H | CH(Me)CH$_2$ | H | $CH_2$ | OEt | 3-Cl—Ph | O |
| 9-11 | H | CH(Me)CH$_2$ | H | $CH_2$ | OEt | 4-Cl—Ph | O |
| 9-12 | H | CH(Me)CH$_2$ | H | $CH_2$ | OEt | 3-Br—Ph | O |
| 9-13 | H | CH(Me)CH$_2$ | H | $CH_2$ | OEt | 4-Br—Ph | O |
| 9-14 | H | CH(Me)CH$_2$ | H | $CH_2$ | OEt | 3-Ph—Ph | O |
| 9-15 | H | CH(Me)CH$_2$ | H | $CH_2$ | OEt | 4-Ph—Ph | O |
| 9-16 | H | CH(Me)CH$_2$ | H | $CH_2$ | OEt | 3-Bz—Ph | O |
| 9-17 | H | CH(Me)CH$_2$ | H | $CH_2$ | OEt | 4-Bz—Ph | O |
| 9-18 | H | CH(Me)CH$_2$ | H | $CH_2$ | OEt | 3-PhO—Ph | O |
| 9-19 | H | CH(Me)CH$_2$ | H | $CH_2$ | OEt | 4-PhO—Ph | O |
| 9-20 | H | CH(Me)CH$_2$ | H | $CH_2$ | OEt | 3-PhS—Ph | O |
| 9-21 | H | CH(Me)CH$_2$ | H | $CH_2$ | OEt | 4-PhS—Ph | O |
| 9-22 | H | CH(Me)CH$_2$ | H | $CH_2$ | OEt | 3-PhSO$_2$—Ph | O |
| 9-23 | H | CH(Me)CH$_2$ | H | $CH_2$ | OEt | 4-PhSO$_2$—Ph | O |
| 9-24 | H | CH(Me)CH$_2$ | H | $CH_2$ | OEt | 3-(Imid-1)-Ph | O |
| 9-25 | H | CH(Me)CH$_2$ | H | $CH_2$ | OEt | 4-(Imid-1)-Ph | O |
| 9-26 | H | CH(Me)CH$_2$ | H | $CH_2$ | OEt | 3-(Imid-4)-Ph | O |
| 9-27 | H | CH(Me)CH$_2$ | H | $CH_2$ | OEt | 4-(Imid-4)-Ph | O |
| 9-28 | H | CH(Me)CH$_2$ | H | $CH_2$ | OEt | 3-(Fur-2)-Ph | O |
| 9-29 | H | CH(Me)CH$_2$ | H | $CH_2$ | OEt | 4-(Fur-2)-Ph | O |
| 9-30 | H | CH(Me)CH$_2$ | H | $CH_2$ | OEt | 3-(Thi-2)-Ph | O |
| 9-31 | H | CH(Me)CH$_2$ | H | $CH_2$ | OEt | 4-(Thi-2)-Ph | O |
| 9-32 | H | CH(Me)CH$_2$ | H | $CH_2$ | OEt | 3-(Thi-3)-Ph | O |
| 9-33 | H | CH(Me)CH$_2$ | H | $CH_2$ | OEt | 4-(Thi-3)-Ph | O |
| 9-34 | H | CH(Me)CH$_2$ | H | $CH_2$ | OEt | 3-(Pyr-2)-Ph | O |
| 9-35 | H | CH(Me)CH$_2$ | H | $CH_2$ | OEt | 4-(Pyr-2)-Ph | O |
| 9-36 | H | CH(Me)CH$_2$ | H | $CH_2$ | OEt | 3-(Pyr-3)-Ph | O |
| 9-37 | H | CH(Me)CH$_2$ | H | $CH_2$ | OEt | 4-(Pyr-3)-Ph | O |
| 9-38 | H | CH(Me)CH$_2$ | H | $CH_2$ | OEt | 3-(Pyr-4)-Ph | O |
| 9-39 | H | CH(Me)CH$_2$ | H | $CH_2$ | OEt | 4-(Pyr-4)-Ph | O |
| 9-40 | H | CH(Me)CH$_2$ | H | $CH_2$ | OEt | 3-(Oxa-2)-Ph | O |
| 9-41 | H | CH(Me)CH$_2$ | H | $CH_2$ | OEt | 4-(Oxa-2)-Ph | O |
| 9-42 | H | CH(Me)CH$_2$ | H | $CH_2$ | OEt | 3-(Oxa-4)-Ph | O |
| 9-43 | H | CH(Me)CH$_2$ | H | $CH_2$ | OEt | 4-(Oxa-4)-Ph | O |
| 9-44 | H | CH(Me)CH$_2$ | H | $CH_2$ | OEt | 3-(Oxa-5)-Ph | O |
| 9-45 | H | CH(Me)CH$_2$ | H | $CH_2$ | OEt | 4-(Oxa-5)-Ph | O |
| 9-46 | H | CH(Me)CH$_2$ | H | $CH_2$ | OEt | 3-(Thiz-2)-Ph | O |
| 9-47 | H | CH(Me)CH$_2$ | H | $CH_2$ | OEt | 4-(Thiz-2)-Ph | O |
| 9-48 | H | CH(Me)CH$_2$ | H | $CH_2$ | OEt | 3-(Thiz-4)-Ph | O |
| 9-49 | H | CH(Me)CH$_2$ | H | $CH_2$ | OEt | 4-(Thiz-4)-Ph | O |
| 9-50 | H | CH(Me)CH$_2$ | H | $CH_2$ | OEt | 3-(Thiz-5)-Ph | O |
| 9-51 | H | CH(Me)CH$_2$ | H | $CH_2$ | OEt | 4-(Thiz-5)-Ph | O |
| 9-52 | H | CH(Me)CH$_2$ | H | $CH_2$ | OEt | 1-Me-2-Pyrr | O |
| 9-53 | H | CH(Me)CH$_2$ | H | $CH_2$ | OEt | 1-Ph-2-Pyrr | O |
| 9-54 | H | CH(Me)CH$_2$ | H | $CH_2$ | OEt | 1-Bz-2-Pyrr | O |
| 9-55 | H | CH(Me)CH$_2$ | H | $CH_2$ | OEt | 5-Me-2-Fur | O |
| 9-56 | H | CH(Me)CH$_2$ | H | $CH_2$ | OEt | 5-Ph-2-Fur | O |
| 9-57 | H | CH(Me)CH$_2$ | H | $CH_2$ | OEt | 5-Me-2-Thi | O |
| 9-58 | H | CH(Me)CH$_2$ | H | $CH_2$ | OEt | 5-Ph-2-Thi | O |
| 9-59 | H | CH(Me)CH$_2$ | H | $CH_2$ | OEt | 5-Me-3-Thi | O |
| 9-60 | H | CH(Me)CH$_2$ | H | $CH_2$ | OEt | 5-Ph-3-Thi | O |
| 9-61 | H | CH(Me)CH$_2$ | H | $CH_2$ | OEt | 1-Me-3-Pyza | O |
| 9-62 | H | CH(Me)CH$_2$ | H | $CH_2$ | OEt | 1-Ph-3-Pyza | O |
| 9-63 | H | CH(Me)CH$_2$ | H | $CH_2$ | OEt | 1-Me-2-Imid | O |
| 9-64 | H | CH(Me)CH$_2$ | H | $CH_2$ | OEt | 1-Ph-2-Imid | O |
| 9-65 | H | CH(Me)CH$_2$ | H | $CH_2$ | OEt | 1-Me-4-Imid | O |
| 9-66 | H | CH(Me)CH$_2$ | H | $CH_2$ | OEt | 1-Ph-4-Imid | O |
| 9-67 | H | CH(Me)CH$_2$ | H | $CH_2$ | OEt | 4-Oxa | O |
| 9-68 | H | CH(Me)CH$_2$ | H | $CH_2$ | OEt | 5-Oxa | O |
| 9-69 | H | CH(Me)CH$_2$ | H | $CH_2$ | OEt | 2-Me-4-Oxa | O |
| 9-70 | H | CH(Me)CH$_2$ | H | $CH_2$ | OEt | 2-Ph-4-Oxa | O |
| 9-71 | H | CH(Me)CH$_2$ | H | $CH_2$ | OEt | 2-Me-5-Oxa | O |
| 9-72 | H | CH(Me)CH$_2$ | H | $CH_2$ | OEt | 2-Ph-5-Oxa | O |
| 9-73 | H | CH(Me)CH$_2$ | H | $CH_2$ | OEt | 4-Me-2-Ph-5-Oxa | O |
| 9-74 | H | CH(Me)CH$_2$ | H | $CH_2$ | OEt | 5-Me-2-Ph-4-Oxa | O |
| 9-75 | H | CH(Me)CH$_2$ | H | $CH_2$ | OEt | 4-Thiz | O |
| 9-76 | H | CH(Me)CH$_2$ | H | $CH_2$ | OEt | 5-Thiz | O |
| 9-77 | H | CH(Me)CH$_2$ | H | $CH_2$ | OEt | 2-Me-4-Thiz | O |
| 9-78 | H | CH(Me)CH$_2$ | H | $CH_2$ | OEt | 2-Ph-4-Thiz | O |
| 9-79 | H | CH(Me)CH$_2$ | H | $CH_2$ | OEt | 2-Me-5-Thiz | O |
| 9-80 | H | CH(Me)CH$_2$ | H | $CH_2$ | OEt | 2-Ph-5-Thiz | O |
| 9-81 | H | CH(Me)CH$_2$ | H | $CH_2$ | OEt | 4-Me-2-Ph-5-Thiz | O |
| 9-82 | H | CH(Me)CH$_2$ | H | $CH_2$ | OEt | 5-Me-2-Ph-4-Thiz | O |
| 9-83 | H | CH(Me)CH$_2$ | H | $CH_2$ | OEt | 1-Me-4-Pyza | O |
| 9-84 | H | CH(Me)CH$_2$ | H | $CH_2$ | OEt | 1-Ph-4-Pyza | O |
| 9-85 | H | CH(Me)CH$_2$ | H | $CH_2$ | OEt | 2-Me-3-Isox | O |
| 9-86 | H | CH(Me)CH$_2$ | H | $CH_2$ | OEt | 2-Ph-4-Isox | O |
| 9-87 | H | CH(Me)CH$_2$ | H | $CH_2$ | OEt | 2-Pyr | O |
| 9-88 | H | CH(Me)CH$_2$ | H | $CH_2$ | OEt | 3-Pyr | O |

TABLE 9-continued

| Exemplification No. compound. | R¹ | R² | R³ | Z | W | X | Y |
|---|---|---|---|---|---|---|---|
| 9-89 | H | CH(Me)CH₂ | H | CH₂ | OEt | 4-Pyr | O |
| 9-90 | H | CH(Me)CH₂ | H | CH₂ | OEt | 3-Me-5-Pyr | O |
| 9-91 | H | CH(Me)CH₂ | H | CH₂ | OEt | 3-Et-5-Pyr | O |
| 9-92 | H | CH(Me)CH₂ | H | CH₂ | OEt | 3-Ph-5-Pyr | O |
| 9-93 | H | CH(Me)CH₂ | H | CH₂ | OEt | 2-Me-5-Pyr | O |
| 9-94 | H | CH(Me)CH₂ | H | CH₂ | OEt | 2-Et-5-Pyr | O |
| 9-95 | H | CH(Me)CH₂ | H | CH₂ | OEt | 2-Ph-5-Pyr | O |
| 9-96 | H | CH(Me)CH₂ | H | CH₂ | OEt | 2-MeO-5-Pyr | O |
| 9-97 | H | CH(Me)CH₂ | H | CH₂ | OEt | 2-EtO-5-Pyr | O |
| 9-98 | H | CH(Me)CH₂ | H | CH₂ | OEt | 2-iPrO-5-Pyr | O |
| 9-99 | H | CH(Me)CH₂ | H | CH₂ | OEt | 2-MeS-5-Pyr | O |
| 9-100 | H | CH(Me)CH₂ | H | CH₂ | OEt | 2-EtS-5-Pyr | O |
| 9-101 | H | CH(Me)CH₂ | H | CH₂ | OEt | 2-iPrS-5-Pyr | O |
| 9-102 | H | CH(Me)CH₂ | H | CH₂ | OEt | 2-MeSO₂-5-Pyr | O |
| 9-103 | H | CH(Me)CH₂ | H | CH₂ | OEt | 2-EtSO₂-5-Pyr | O |
| 9-104 | H | CH(Me)CH₂ | H | CH₂ | OEt | 2-iPrSO₂-5-Pyr | O |
| 9-105 | H | CH(Me)CH₂ | H | CH₂ | OEt | 2-Bz-5-Pyr | O |
| 9-106 | H | CH(Me)CH₂ | H | CH₂ | OEt | 2-PhO-5-Pyr | O |
| 9-107 | H | CH(Me)CH₂ | H | CH₂ | OEt | 2-PhS-5-Pyr | O |
| 9-108 | H | CH(Me)CH₂ | H | CH₂ | OEt | 2-PhSO₂-5-Pyr | O |
| 9-109 | H | CH(Me)CH₂ | H | CH₂ | OEt | 3-Me-6-Pyr | O |
| 9-110 | H | CH(Me)CH₂ | H | CH₂ | OEt | 3-Ph-6-Pyr | O |
| 9-111 | H | CH(Me)CH₂ | H | CH₂ | OEt | 2-Me-6-Pyr | O |
| 9-112 | H | CH(Me)CH₂ | H | CH₂ | OEt | 2-Ph-6-Pyr | O |
| 9-113 | H | CH(Me)CH₂ | H | CH₂ | OEt | 2-Me-4-Pym | O |
| 9-114 | H | CH(Me)CH₂ | H | CH₂ | OEt | 2-Ph-4-Pym | O |
| 9-115 | H | CH(Me)CH₂ | H | CH₂ | OEt | 2-MeO-4-Pym | O |
| 9-116 | H | CH(Me)CH₂ | H | CH₂ | OEt | 2-EtO-4-Pym | O |
| 9-117 | H | CH(Me)CH₂ | H | CH₂ | OEt | 2-iPrO-4-Pym | O |
| 9-118 | H | CH(Me)CH₂ | H | CH₂ | OEt | 2-MeS-4-Pym | O |
| 9-119 | H | CH(Me)CH₂ | H | CH₂ | OEt | 2-EtS-4-Pym | O |
| 9-120 | H | CH(Me)CH₂ | H | CH₂ | OEt | 2-iPrS-4-Pym | O |
| 9-121 | H | CH(Me)CH₂ | H | CH₂ | OEt | 6-MeS-4-Pym | O |
| 9-122 | H | CH(Me)CH₂ | H | CH₂ | OEt | 6-EtS-4-Pym | O |
| 9-123 | H | CH(Me)CH₂ | H | CH₂ | OEt | 6-iPrS-4-Pym | O |
| 9-124 | H | CH(Me)CH₂ | H | CH₂ | OEt | 2-PhS-4-Pym | O |
| 9-125 | H | CH(Me)CH₂ | H | CH₂ | OEt | 2-MeSO₂-4-Pym | O |
| 9-126 | H | CH(Me)CH₂ | H | CH₂ | OEt | 2-EtSO₂-4-Pym | O |
| 9-127 | H | CH(Me)CH₂ | H | CH₂ | OEt | 2-iPrSO₂-4-Pym | O |
| 9-128 | H | CH(Me)CH₂ | H | CH₂ | OEt | 2-PhSO₂-4-Pym | O |
| 9-129 | H | CH(Me)CH₂ | H | CH₂ | OEt | 2-Me-5-Pym | O |
| 9-130 | H | CH(Me)CH₂ | H | CH₂ | OEt | 2-Ph-5-Pym | O |
| 9-131 | H | CH(Me)CH₂ | H | CH₂ | OEt | 2-MeO-5-Pym | O |
| 9-132 | H | CH(Me)CH₂ | H | CH₂ | OEt | 2-EtO-5-Pym | O |
| 9-133 | H | CH(Me)CH₂ | H | CH₂ | OEt | 2-iPrO-5-Pym | O |
| 9-134 | H | CH(Me)CH₂ | H | CH₂ | OEt | 2-MeS-5-Pym | O |
| 9-135 | H | CH(Me)CH₂ | H | CH₂ | OEt | 2-EtS-5-Pym | O |
| 9-136 | H | CH(Me)CH₂ | H | CH₂ | OEt | 2-iPrS-5-Pym | O |
| 9-137 | H | CH(Me)CH₂ | H | CH₂ | OEt | 2-PhS-5-Pym | O |
| 9-138 | H | CH(Me)CH₂ | H | CH₂ | OEt | 2-MeSO₂-5-Pym | O |
| 9-139 | H | CH(Me)CH₂ | H | CH₂ | OEt | 2-EtSO₂-5-Pym | O |
| 9-140 | H | CH(Me)CH₂ | H | CH₂ | OEt | 2-iPrSO₂-5-Pym | O |
| 9-141 | H | CH(Me)CH₂ | H | CH₂ | OEt | 2-PhSO₂-5-Pym | O |
| 9-142 | H | CH(Me)CH₂ | H | CH₂ | OEt | 2-Ind | O |
| 9-143 | H | CH(Me)CH₂ | H | CH₂ | OEt | 3-Ind | O |
| 9-144 | H | CH(Me)CH₂ | H | CH₂ | OEt | 1-Me-2-Ind | O |
| 9-145 | H | CH(Me)CH₂ | H | CH₂ | OEt | 1-Me-3-Ind | O |
| 9-146 | H | CH(Me)CH₂ | H | CH₂ | OEt | 2-Bimid | O |
| 9-147 | H | CH(Me)CH₂ | H | CH₂ | OEt | 2-Boxa | O |
| 9-148 | H | CH(Me)CH₂ | H | CH₂ | OEt | 2-Bthiz | O |
| 9-149 | H | CH(Me)CH₂ | H | CH₂ | OEt | 2-Quin | O |
| 9-150 | H | CH(Me)CH₂ | H | CH₂ | OEt | 3-Quin | O |
| 9-151 | H | CH(Me)CH₂ | H | CH₂ | OEt | 4-Quin | O |
| 9-152 | H | CH(Me)CH₂ | H | CH₂ | OEt | 1-iQuin | O |
| 9-153 | H | CH(Me)CH₂ | H | CH₂ | OEt | 3-iQuin | O |
| 9-154 | H | CH(Me)CH₂ | H | CH₂ | OEt | 4-iQuin | O |
| 9-155 | H | CH(Me)CH₂ | H | CH₂ | OEt | 3-MeO—Ph | O |
| 9-156 | H | CH(Me)CH₂ | H | CH₂ | OEt | 4-MeO—Ph | O |
| 9-157 | H | CH(Me)CH₂ | H | CH₂ | OEt | 3-EtO—Ph | O |
| 9-158 | H | CH(Me)CH₂ | H | CH₂ | OEt | 4-EtO—Ph | O |
| 9-159 | H | CH(Me)CH₂ | H | CH₂ | OEt | 3-iPrO—Ph | O |
| 9-160 | H | CH(Me)CH₂ | H | CH₂ | OEt | 4-iPrO—Ph | O |
| 9-161 | H | CH(Me)CH₂ | H | CH₂ | OEt | 3-MeS—Ph | O |
| 9-162 | H | CH(Me)CH₂ | H | CH₂ | OEt | 4-MeS—Ph | O |
| 9-163 | H | CH(Me)CH₂ | H | CH₂ | OEt | 3-EtS—Ph | O |
| 9-164 | H | CH(Me)CH₂ | H | CH₂ | OEt | 4-EtS—Ph | O |
| 9-165 | H | CH(Me)CH₂ | H | CH₂ | OEt | 3-iPrS—Ph | O |
| 9-166 | H | CH(Me)CH₂ | H | CH₂ | OEt | 4-iPrS—Ph | O |
| 9-167 | H | CH(Me)CH₂ | H | CH₂ | OEt | 3-MeSO₂—Ph | O |
| 9-168 | H | CH(Me)CH₂ | H | CH₂ | OEt | 4-MeSO₂—Ph | O |
| 9-169 | H | CH(Me)CH₂ | H | CH₂ | OEt | 3-EtSO₂—Ph | O |
| 9-170 | H | CH(Me)CH₂ | H | CH₂ | OEt | 4-EtSO₂—Ph | O |
| 9-171 | H | CH(Me)CH₂ | H | CH₂ | OEt | 3-iPrSO₂—Ph | O |
| 9-172 | H | CH(Me)CH₂ | H | CH₂ | OEt | 4-iPrSO₂—Ph | O |
| 9-173 | H | CH(Me)CH₂ | H | CH₂ | OEt | 3-(1-Me-Imid-4)-Ph | O |
| 9-174 | H | CH(Me)CH₂ | H | CH₂ | OEt | 4(1-Me—Imid-4)-Ph | O |
| 9-175 | H | CH(Me)CH₂ | H | CH₂ | OEt | 1-Me-2-Ph-4-Imid | O |
| 9-176 | H | CH(Me)CH₂ | H | CH₂ | OEt | 1,4-di-Me-2-Ph-5-Imid | O |
| 9-177 | H | CH(Me)CH₂ | H | CH₂ | OEt | 1,5-di-Me-2-Ph-4-Imid | O |
| 9-178 | H | CH(Me)CH₂ | H | CH₂ | OEt | 3,4-MdO—Ph | O |
| 9-179 | H | CH(Me)CH₂ | H | CH₂ | OEt | 4-(4-MeO—Ph)—Ph | O |
| 9-180 | H | CH(Me)CH₂ | H | CH₂ | OEt | 4-(3,4-MdO—Ph)—Ph | O |
| 9-181 | H | CH(Me)CH₂ | H | CH₂ | OEt | 4-[PhSO₂N(Me)]—Ph | O |
| 9-182 | H | CH(Me)CH₂ | H | CH₂ | OEt | 4-[(Pyr-3)SO₂N(Me)]—Ph | O |
| 9-183 | H | CH(Me)CH₂ | H | CH₂ | OEt | 4-(PhSO₂NH)—Ph | O |
| 9-184 | H | CH(Me)CH₂ | H | CH₂ | OEt | 4-[(Pyr-3)SO₂NH]—Ph | O |
| 9-185 | H | CH(Me)CH₂ | H | CH₂ | OEt | 4-[(Pyr-2)SO₂]—Ph | O |
| 9-186 | H | CH(Me)CH₂ | H | CH₂ | OEt | 4-[(Pyr-3)SO₂]—Ph | O |
| 9-187 | H | CH(Me)CH₂ | H | CH₂ | OEt | 4-[(Pyr-2)SO₂N(Me)]—Ph | O |
| 9-188 | H | CH(Me)CH₂ | H | CH₂ | OEt | 4-[(Pyr-2)SO₂NH]—Ph | O |
| 9-189 | H | CH(Me)CH₂ | H | CH₂ | OEt | 4-(4-Me—Ph)—Ph | O |
| 9-190 | H | CH(Me)CH₂ | H | CH₂ | OEt | 4-(4-F—Ph)—Ph | O |
| 9-191 | H | CH(Me)CH₂ | H | CH₂ | OEt | 4-(4-CF₃—Ph)—Ph | O |
| 9-192 | H | CH(Me)CH₂ | H | CH₂ | OEt | 2-[4-Me—PhSO₂(Me)]-5-Pyr | O |
| 9-193 | H | CH(Me)CH₂ | H | CH₂ | OEt | 2-HO-5-Pyr | O |
| 9-194 | H | CH(Me)CH₂ | H | CH₂ | OEt | 2-BzO-5-Pyr | O |
| 9-195 | H | CH(Me)CH₂ | H | CH₂ | OEt | 4-[(Pyr-4)SO₂]—Ph | O |
| 9-196 | H | CH(Me)CH₂ | H | CH₂ | OEt | 4-(2,4-di-MeO—Ph)—Ph | O |
| 9-197 | H | CH(Me)CH₂ | H | CH₂ | OEt | 4-(2,5-di-MeO—Ph)—Ph | O |

TABLE 9-continued

| Exemplification No. compound. | R¹ | R² | R³ | Z | W | X | Y |
|---|---|---|---|---|---|---|---|
| 9-198 | H | CH(Me)CH₂ | H | CH₂ | OEt | 3-HO—Ph | O |
| 9-199 | H | CH(Me)CH₂ | H | CH₂ | OEt | 4-HO—Ph | O |
| 9-200 | H | CH(Me)CH₂ | H | CH₂ | OEt | 5-AcO-2-HO-3,4,6,-tri-Me—Ph | O |
| 9-201 | H | CH(Me)CH₂ | H | CH₂ | OEt | 4-HO-3,5-di-Me—Ph | O |
| 9-202 | H | CH(Me)CH₂ | H | CH₂ | OEt | 3-AcO—Ph | O |
| 9-203 | H | CH(Me)CH₂ | H | CH₂ | OEt | 4-AcO—Ph | O |

TABLE 10

| Exemplification No. compound. | R¹ | R² | R³ | Z | W | X | Y |
|---|---|---|---|---|---|---|---|
| 10-1 | Me | CH(Me)CH₂ | H | CH₂ | OEt | Ph | O |
| 10-2 | Me | CH(Me)CH₂ | H | CH₂ | OEt | 1-Np | O |
| 10-3 | Me | CH(Me)CH₂ | H | CH₂ | OEt | 2-Np | O |
| 10-4 | Me | CH(Me)CH₂ | H | CH₂ | OEt | 4-Me—Ph | O |
| 10-5 | Me | CH(Me)CH₂ | H | CH₂ | OEt | 4-Et—Ph | O |
| 10-6 | Me | CH(Me)CH₂ | H | CH₂ | OEt | 3-iPr—Ph | O |
| 10-7 | Me | CH(Me)CH₂ | H | CH₂ | OEt | 4-iPr—Ph | O |
| 10-8 | Me | CH(Me)CH₂ | H | CH₂ | OEt | 3-tBu—Ph | O |
| 10-9 | Me | CH(Me)CH₂ | H | CH₂ | OEt | 4-tBu—Ph | O |
| 10-10 | Me | CH(Me)CH₂ | H | CH₂ | OEt | 3-Cl—Ph | O |
| 10-11 | Me | CH(Me)CH₂ | H | CH₂ | OEt | 4-Cl—Ph | O |
| 10-12 | Me | CH(Me)CH₂ | H | CH₂ | OEt | 3-Br—Ph | O |
| 10-13 | Me | CH(Me)CH₂ | H | CH₂ | OEt | 4-Br—Ph | O |
| 10-14 | Me | CH(Me)CH₂ | H | CH₂ | OEt | 3-Ph—Ph | O |
| 10-15 | Me | CH(Me)CH₂ | H | CH₂ | OEt | 4-Ph—Ph | O |
| 10-16 | Me | CH(Me)CH₂ | H | CH₂ | OEt | 3-Bz—Ph | O |
| 10-17 | Me | CH(Me)CH₂ | H | CH₂ | OEt | 4-Bz—Ph | O |
| 10-18 | Me | CH(Me)CH₂ | H | CH₂ | OEt | 3-PhO—Ph | O |
| 10-19 | Me | CH(Me)CH₂ | H | CH₂ | OEt | 4-PhO—Ph | O |
| 10-20 | Me | CH(Me)CH₂ | H | CH₂ | OEt | 3-PhS—Ph | O |
| 10-21 | Me | CH(Me)CH₂ | H | CH₂ | OEt | 4-PhS—Ph | O |
| 10-22 | Me | CH(Me)CH₂ | H | CH₂ | OEt | 3-PhSO₂—Ph | O |
| 10-23 | Me | CH(Me)CH₂ | H | CH₂ | OEt | 4-PhSO₂—Ph | O |
| 10-24 | Me | CH(Me)CH₂ | H | CH₂ | OEt | 3-(Imid-1)-Ph | O |
| 10-25 | Me | CH(Me)CH₂ | H | CH₂ | OEt | 4-(Imid-1)-Ph | O |
| 10-26 | Me | CH(Me)CH₂ | H | CH₂ | OEt | 3-(Imid-4)-Ph | O |
| 10-27 | Me | CH(Me)CH₂ | H | CH₂ | OEt | 4-(Imid-4)-Ph | O |
| 10-28 | Me | CH(Me)CH₂ | H | CH₂ | OEt | 3-(Fur-2)-Ph | O |
| 10-29 | Me | CH(Me)CH₂ | H | CH₂ | OEt | 4-(Fur-2)-Ph | O |
| 10-30 | Me | CH(Me)CH₂ | H | CH₂ | OEt | 3-(Thi-2)-Ph | O |
| 10-31 | Me | CH(Me)CH₂ | H | CH₂ | OEt | 4-(Thi-2)-Ph | O |
| 10-32 | Me | CH(Me)CH₂ | H | CH₂ | OEt | 3-(Thi-3)-Ph | O |
| 10-33 | Me | CH(Me)CH₂ | H | CH₂ | OEt | 4-(Thi-3)-Ph | O |
| 10-34 | Me | CH(Me)CH₂ | H | CH₂ | OEt | 3-(Pyr-2)-Ph | O |
| 10-35 | Me | CH(Me)CH₂ | H | CH₂ | OEt | 4-(Pyr-2)-Ph | O |
| 10-36 | Me | CH(Me)CH₂ | H | CH₂ | OEt | 3-(Pyr-3)-Ph | O |
| 10-37 | Me | CH(Me)CH₂ | H | CH₂ | OEt | 4-(Pyr-3)-Ph | O |
| 10-38 | Me | CH(Me)CH₂ | H | CH₂ | OEt | 3-(Pyr-4)-Ph | O |
| 10-39 | Me | CH(Me)CH₂ | H | CH₂ | OEt | 4-(Pyr-4)-Ph | O |
| 10-40 | Me | CH(Me)CH₂ | H | CH₂ | OEt | 3-(Oxa-2)-Ph | O |
| 10-41 | Me | CH(Me)CH₂ | H | CH₂ | OEt | 4-(Oxa-2)-Ph | O |
| 10-42 | Me | CH(Me)CH₂ | H | CH₂ | OEt | 3-(Oxa-4)-Ph | O |
| 10-43 | Me | CH(Me)CH₂ | H | CH₂ | OEt | 4-(Oxa-4)-Ph | O |
| 10-44 | Me | CH(Me)CH₂ | H | CH₂ | OEt | 3-(Oxa-5)-Ph | O |
| 10-45 | Me | CH(Me)CH₂ | H | CH₂ | OEt | 4-(Oxa-5)-Ph | O |
| 10-46 | Me | CH(Me)CH₂ | H | CH₂ | OEt | 3-(Thiz-2)-Ph | O |
| 10-47 | Me | CH(Me)CH₂ | H | CH₂ | OEt | 4-(Thiz-2)-Ph | O |
| 10-48 | Me | CH(Me)CH₂ | H | CH₂ | OEt | 3-(Thiz-4)-Ph | O |
| 10-49 | Me | CH(Me)CH₂ | H | CH₂ | OEt | 4-(Thiz-4)-Ph | O |
| 10-50 | Me | CH(Me)CH₂ | H | CH₂ | OEt | 3-(Thiz-5)-Ph | O |
| 10-51 | Me | CH(Me)CH₂ | H | CH₂ | OEt | 4-(Thiz-5)-Ph | O |
| 10-52 | Me | CH(Me)CH₂ | H | CH₂ | OEt | 1-Me-2-Pyrr | O |
| 10-53 | Me | CH(Me)CH₂ | H | CH₂ | OEt | 1-Ph-2-Pyrr | O |
| 10-54 | Me | CH(Me)CH₂ | H | CH₂ | OEt | 1-Bz-2-Pyrr | O |
| 10-55 | Me | CH(Me)CH₂ | H | CH₂ | OEt | 5-Me-2-Fur | O |
| 10-56 | Me | CH(Me)CH₂ | H | CH₂ | OEt | 5-Ph-2-Fur | O |
| 10-57 | Me | CH(Me)CH₂ | H | CH₂ | OEt | 5-Me-2-Thi | O |
| 10-58 | Me | CH(Me)CH₂ | H | CH₂ | OEt | 5-Ph-2-Thi | O |
| 10-59 | Me | CH(Me)CH₂ | H | CH₂ | OEt | 5-Me-3-Thi | O |
| 10-60 | Me | CH(Me)CH₂ | H | CH₂ | OEt | 5-Ph-3-Thi | O |
| 10-61 | Me | CH(Me)CH₂ | H | CH₂ | OEt | 1-Me-3-Pyza | O |
| 10-62 | Me | CH(Me)CH₂ | H | CH₂ | OEt | 1-Ph-3-Pyza | O |
| 10-63 | Me | CH(Me)CH₂ | H | CH₂ | OEt | 1-Me-2-Imid | O |
| 10-64 | Me | CH(Me)CH₂ | H | CH₂ | OEt | 1-Ph-2-Imid | O |
| 10-65 | Me | CH(Me)CH₂ | H | CH₂ | OEt | 1-Me-4-Imid | O |
| 10-66 | Me | CH(Me)CH₂ | H | CH₂ | OEt | 1-Ph-4-Imid | O |
| 10-67 | Me | CH(Me)CH₂ | H | CH₂ | OEt | 4-Oxa | O |
| 10-68 | Me | CH(Me)CH₂ | H | CH₂ | OEt | 5-Oxa | O |
| 10-69 | Me | CH(Me)CH₂ | H | CH₂ | OEt | 2-Me-4-Oxa | O |
| 10-70 | Me | CH(Me)CH₂ | H | CH₂ | OEt | 2-Ph-4-Oxa | O |
| 10-71 | Me | CH(Me)CH₂ | H | CH₂ | OEt | 2-Me-5-Oxa | O |
| 10-72 | Me | CH(Me)CH₂ | H | CH₂ | OEt | 2-Ph-5-Oxa | O |
| 10-73 | Me | CH(Me)CH₂ | H | CH₂ | OEt | 4-Me-2-Ph-5-Oxa | O |
| 10-74 | Me | CH(Me)CH₂ | H | CH₂ | OEt | 5-Me-2-Ph-4-Oxa | O |
| 10-75 | Me | CH(Me)CH₂ | H | CH₂ | OEt | 4-Thiz | O |
| 10-76 | Me | CH(Me)CH₂ | H | CH₂ | OEt | 5-Thiz | O |
| 10-77 | Me | CH(Me)CH₂ | H | CH₂ | OEt | 2-Me-4-Thiz | O |
| 10-78 | Me | CH(Me)CH₂ | H | CH₂ | OEt | 2-Ph-4-Thiz | O |
| 10-79 | Me | CH(Me)CH₂ | H | CH₂ | OEt | 2-Me-5-Thiz | O |
| 10-80 | Me | CH(Me)CH₂ | H | CH₂ | OEt | 2-Ph-5-Thiz | O |
| 10-81 | Me | CH(Me)CH₂ | H | CH₂ | OEt | 4-Me-2-Ph-5-Thiz | O |
| 10-82 | Me | CH(Me)CH₂ | H | CH₂ | OEt | 5-Me-2-Ph-4-Thiz | O |
| 10-83 | Me | CH(Me)CH₂ | H | CH₂ | OEt | 1-Me-4-Pyza | O |
| 10-84 | Me | CH(Me)CH₂ | H | CH₂ | OEt | 1-Ph-4-Pyza | O |
| 10-85 | Me | CH(Me)CH₂ | H | CH₂ | OEt | 2-Me-4-Isox | O |
| 10-86 | Me | CH(Me)CH₂ | H | CH₂ | OEt | 2-Ph-4-Isox | O |
| 10-87 | Me | CH(Me)CH₂ | H | CH₂ | OEt | 2-Pyr | O |
| 10-88 | Me | CH(Me)CH₂ | H | CH₂ | OEt | 3-Pyr | O |
| 10-89 | Me | CH(Me)CH₂ | H | CH₂ | OEt | 4-Pyr | O |
| 10-90 | Me | CH(Me)CH₂ | H | CH₂ | OEt | 3-Me-5-Pyr | O |
| 10-91 | Me | CH(Me)CH₂ | H | CH₂ | OEt | 3-Et-5-Pyr | O |
| 10-92 | Me | CH(Me)CH₂ | H | CH₂ | OEt | 3-Ph-5-Pyr | O |
| 10-93 | Me | CH(Me)CH₂ | H | CH₂ | OEt | 2-Me-5-Pyr | O |
| 10-94 | Me | CH(Me)CH₂ | H | CH₂ | OEt | 2-Et-5-Pyr | O |
| 10-95 | Me | CH(Me)CH₂ | H | CH₂ | OEt | 2-Ph-5-Pyr | O |
| 10-96 | Me | CH(Me)CH₂ | H | CH₂ | OEt | 2-MeO-5-Pyr | O |
| 10-97 | Me | CH(Me)CH₂ | H | CH₂ | OEt | 2-EtO-5-Pyr | O |
| 10-98 | Me | CH(Me)CH₂ | H | CH₂ | OEt | 2-iPrO-5-Pyr | O |
| 10-99 | Me | CH(Me)CH₂ | H | CH₂ | OEt | 2-MeS-5-Pyr | O |
| 10-100 | Me | CH(Me)CH₂ | H | CH₂ | OEt | 2-EtS-5-Pyr | O |
| 10-101 | Me | CH(Me)CH₂ | H | CH₂ | OEt | 2-iPrS-5-Pyr | O |
| 10-102 | Me | CH(Me)CH₂ | H | CH₂ | OEt | 2-MeSO₂-5-Pyr | O |
| 10-103 | Me | CH(Me)CH₂ | H | CH₂ | OEt | 2-EtSO₂-5-Pyr | O |
| 10-104 | Me | CH(Me)CH₂ | H | CH₂ | OEt | 2-iPrSO₂-5-Pyr | O |
| 10-105 | Me | CH(Me)CH₂ | H | CH₂ | OEt | 2-Bz-5-Pyr | O |
| 10-106 | Me | CH(Me)CH₂ | H | CH₂ | OEt | 2-PhO-5-Pyr | O |
| 10-107 | Me | CH(Me)CH₂ | H | CH₂ | OEt | 2-PhS-5-Pyr | O |
| 10-108 | Me | CH(Me)CH₂ | H | CH₂ | OEt | 2-PhSO₂-5-Pyr | O |
| 10-109 | Me | CH(Me)CH₂ | H | CH₂ | OEt | 3-Me-6-Pyr | O |
| 10-110 | Me | CH(Me)CH₂ | H | CH₂ | OEt | 3-Ph-6-Pyr | O |
| 10-111 | Me | CH(Me)CH₂ | H | CH₂ | OEt | 2-Me-6-Pyr | O |
| 10-112 | Me | CH(Me)CH₂ | H | CH₂ | OEt | 2-Ph-6-Pyr | O |
| 10-113 | Me | CH(Me)CH₂ | H | CH₂ | OEt | 2-Me-4-Pym | O |
| 10-114 | Me | CH(Me)CH₂ | H | CH₂ | OEt | 2-Ph-4-Pym | O |

TABLE 10-continued

| Exemplification No. compound. | R¹ | R² | R³ | Z | W | X | Y |
|---|---|---|---|---|---|---|---|
| 10-115 | Me | CH(Me)CH₂ | H | CH₂ | OEt | 2-MeO-4-Pym | O |
| 10-116 | Me | CH(Me)CH₂ | H | CH₂ | OEt | 2-EtO-4-Pym | O |
| 10-117 | Me | CH(Me)CH₂ | H | CH₂ | OEt | 2-iPrO-4-Pym | O |
| 10-118 | Me | CH(Me)CH₂ | H | CH₂ | OEt | 2-MeS-4-Pym | O |
| 10-119 | Me | CH(Me)CH₂ | H | CH₂ | OEt | 2-EtS-4-Pym | O |
| 10-120 | Me | CH(Me)CH₂ | H | CH₂ | OEt | 2-iPrS-4-Pym | O |
| 10-121 | Me | CH(Me)CH₂ | H | CH₂ | OEt | 6-MeS-4-Pym | O |
| 10-122 | Me | CH(Me)CH₂ | H | CH₂ | OEt | 6-EtS-4-Pym | O |
| 10-123 | Me | CH(Me)CH₂ | H | CH₂ | OEt | 6-iPrS-4-Pym | O |
| 10-124 | Me | CH(Me)CH₂ | H | CH₂ | OEt | 2-PhS-4-Pym | O |
| 10-125 | Me | CH(Me)CH₂ | H | CH₂ | OEt | 2-MeSO₂-4-Pym | O |
| 10-126 | Me | CH(Me)CH₂ | H | CH₂ | OEt | 2-EtSO₂-4-Pym | O |
| 10-127 | Me | CH(Me)CH₂ | H | CH₂ | OEt | 2-iPrSO₂-4-Pym | O |
| 10-128 | Me | CH(Me)CH₂ | H | CH₂ | OEt | 2-PhSO₂-4-Pym | O |
| 10-129 | Me | CH(Me)CH₂ | H | CH₂ | OEt | 2-Me-5-Pym | O |
| 10-130 | Me | CH(Me)CH₂ | H | CH₂ | OEt | 2-Ph-5-Pym | O |
| 10-131 | Me | CH(Me)CH₂ | H | CH₂ | OEt | 2-MeO-5-Pym | O |
| 10-132 | Me | CH(Me)CH₂ | H | CH₂ | OEt | 2-EtO-5-Pym | O |
| 10-133 | Me | CH(Me)CH₂ | H | CH₂ | OEt | 2-iPrO-5-Pym | O |
| 10-134 | Me | CH(Me)CH₂ | H | CH₂ | OEt | 2-MeS-5-Pym | O |
| 10-135 | Me | CH(Me)CH₂ | H | CH₂ | OEt | 2-EtS-5-Pym | O |
| 10-136 | Me | CH(Me)CH₂ | H | CH₂ | OEt | 2-iPrS-5-Pym | O |
| 10-137 | Me | CH(Me)CH₂ | H | CH₂ | OEt | 2-PhS-5-Pym | O |
| 10-138 | Me | CH(Me)CH₂ | H | CH₂ | OEt | 2-MeSO₂-5-Pym | O |
| 10-139 | Me | CH(Me)CH₂ | H | CH₂ | OEt | 2-EtSO₂-5-Pym | O |
| 10-140 | Me | CH(Me)CH₂ | H | CH₂ | OEt | 2-iPrSO₂-5-Pym | O |
| 10-141 | Me | CH(Me)CH₂ | H | CH₂ | OEt | 2-PhSO₂-5-Pym | O |
| 10-142 | Me | CH(Me)CH₂ | H | CH₂ | OEt | 2-Ind | O |
| 10-143 | Me | CH(Me)CH₂ | H | CH₂ | OEt | 3-Ind | O |
| 10-144 | Me | CH(Me)CH₂ | H | CH₂ | OEt | 1-Me-2-Ind | O |
| 10-145 | Me | CH(Me)CH₂ | H | CH₂ | OEt | 1-Me-3-Ind | O |
| 10-146 | Me | CH(Me)CH₂ | H | CH₂ | OEt | 2-Bimid | O |
| 10-147 | Me | CH(Me)CH₂ | H | CH₂ | OEt | 2-Boxa | O |
| 10-148 | Me | CH(Me)CH₂ | H | CH₂ | OEt | 2-Bthiz | O |
| 10-149 | Me | CH(Me)CH₂ | H | CH₂ | OEt | 2-Quin | O |
| 10-150 | Me | CH(Me)CH₂ | H | CH₂ | OEt | 3-Quin | O |
| 10-151 | Me | CH(Me)CH₂ | H | CH₂ | OEt | 4-Quin | O |
| 10-152 | Me | CH(Me)CH₂ | H | CH₂ | OEt | 1-iQuin | O |
| 10-153 | Me | CH(Me)CH₂ | H | CH₂ | OEt | 3-iQuin | O |
| 10-154 | Me | CH(Me)CH₂ | H | CH₂ | OEt | 4-iQuin | O |
| 10-155 | Me | CH(Me)CH₂ | H | CH₂ | OEt | 3-MeO—Ph | O |
| 10-156 | Me | CH(Me)CH₂ | H | CH₂ | OEt | 4-MeO—Ph | O |
| 10-157 | Me | CH(Me)CH₂ | H | CH₂ | OEt | 3-EtO—Ph | O |
| 10-158 | Me | CH(Me)CH₂ | H | CH₂ | OEt | 4-EtO—Ph | O |
| 10-159 | Me | CH(Me)CH₂ | H | CH₂ | OEt | 3-iPrO—Ph | O |
| 10-160 | Me | CH(Me)CH₂ | H | CH₂ | OEt | 4-iPrO—Ph | O |
| 10-161 | Me | CH(Me)CH₂ | H | CH₂ | OEt | 3-MeS—Ph | O |
| 10-162 | Me | CH(Me)CH₂ | H | CH₂ | OEt | 4-MeS—Ph | O |
| 10-163 | Me | CH(Me)CH₂ | H | CH₂ | OEt | 3-EtS—Ph | O |
| 10-164 | Me | CH(Me)CH₂ | H | CH₂ | OEt | 4-EtS—Ph | O |
| 10-165 | Me | CH(Me)CH₂ | H | CH₂ | OEt | 3-iPrS—Ph | O |
| 10-166 | Me | CH(Me)CH₂ | H | CH₂ | OEt | 4-iPrS—Ph | O |
| 10-167 | Me | CH(Me)CH₂ | H | CH₂ | OEt | 3-MeSO₂—Ph | O |
| 10-168 | Me | CH(Me)CH₂ | H | CH₂ | OEt | 4-MeSO₂—Ph | O |
| 10-169 | Me | CH(Me)CH₂ | H | CH₂ | OEt | 3-EtSO₂—Ph | O |
| 10-170 | Me | CH(Me)CH₂ | H | CH₂ | OEt | 4-EtSO₂—Ph | O |
| 10-171 | Me | CH(Me)CH₂ | H | CH₂ | OEt | 3-iPrSO₂—Ph | O |
| 10-172 | Me | CH(Me)CH₂ | H | CH₂ | OEt | 4-iPrSO₂—Ph | O |
| 10-173 | Me | CH(Me)CH₂ | H | CH₂ | OEt | 3-(1-Me—Imid-4)-Ph | O |
| 10-174 | Me | CH(Me)CH₂ | H | CH₂ | OEt | 4-(1-Me—Imid-4)-Ph | O |
| 10-175 | Me | CH(Me)CH₂ | H | CH₂ | OEt | 1-Me-2-Ph-4-Imid | O |
| 10-176 | Me | CH(Me)CH₂ | H | CH₂ | OEt | 1,4-di-Me-2-Ph-5-Imid | O |
| 10-177 | Me | CH(Me)CH₂ | H | CH₂ | OEt | 1,5-di-Me-2-Ph-4-Imid | O |
| 10-178 | Me | CH(Me)CH₂ | H | CH₂ | OEt | 3,4-MdO—Ph | O |
| 10-179 | Me | CH(Me)CH₂ | H | CH₂ | OEt | 4-(4-MeO—Ph)—Ph | O |
| 10-180 | Me | CH(Me)CH₂ | H | CH₂ | OEt | 4-(3,4-MdO—Ph)—Ph | O |
| 10-181 | Me | CH(Me)CH₂ | H | CH₂ | OEt | 4-[PhSO₂N(Me)]—Ph | O |
| 10-182 | Me | CH(Me)CH₂ | H | CH₂ | OEt | 4-[(Pyr-3)SO₂N(Me)]—Ph | O |
| 10-183 | Me | CH(Me)CH₂ | H | CH₂ | OEt | 4-(PhSO₂NH)—Ph | O |
| 10-184 | Me | CH(Me)CH₂ | H | CH₂ | OEt | 4-[(Pyr-3)SO₂NH]—Ph | O |
| 10-185 | Me | CH(Me)CH₂ | H | CH₂ | OEt | 4-[(Pyr-2)SO₂]—Ph | O |
| 10-186 | Me | CH(Me)CH₂ | H | CH₂ | OEt | 4-[(Pyr-3)SO₂]—Ph | O |
| 10-187 | Me | CH(Me)CH₂ | H | CH₂ | OEt | 4-[(Pyr-2)SO₂N(Me)]—Ph | O |
| 10-188 | Me | CH(Me)CH₂ | H | CH₂ | OEt | 4-[(Pyr-2)SO₂NH]—Ph | O |
| 10-189 | Me | CH(Me)CH₂ | H | CH₂ | OEt | 4-(4-Me—Ph)—Ph | O |
| 10-190 | Me | CH(Me)CH₂ | H | CH₂ | OEt | 4-(4-F—Ph)—Ph | O |
| 10-191 | Me | CH(Me)CH₂ | H | CH₂ | OEt | 4-(4-CF₃—Ph)—Ph | O |
| 10-192 | Me | CH(Me)CH₂ | H | CH₂ | OEt | 2-[4-Me—PhSO₂N(Me)]-5-Pyr | O |
| 10-193 | Me | CH(Me)CH₂ | H | CH₂ | OEt | 2-HO-5-Pyr | O |
| 10-194 | Me | CH(Me)CH₂ | H | CH₂ | OEt | 2-BzO-5-Pyr | O |
| 10-195 | Me | CH(Me)CH₂ | H | CH₂ | OEt | 4-[(Pyr-4)SO₂]—Ph | O |
| 10-196 | Me | CH(Me)CH₂ | H | CH₂ | OEt | 4-(2,4-di-MeO—Ph)—Ph | O |
| 10-197 | Me | CH(Me)CH₂ | H | CH₂ | OEt | 4-(2,5-di-MeO—Ph)—Ph | O |
| 10-198 | Me | CH(Me)CH₂ | H | CH₂ | OEt | 3-HO—Ph | O |
| 10-199 | Me | CH(Me)CH₂ | H | CH₂ | OEt | 4-HO—Ph | O |
| 10-200 | Me | CH(Me)CH₂ | H | CH₂ | OEt | 5-AcO-2-HO-3,4,6-tri-Me—Ph | O |
| 10-201 | Me | CH(Me)CH₂ | H | CH₂ | OEt | 4-HO-3,5-di-Me—Ph | O |
| 10-202 | Me | CH(Me)CH₂ | H | CH₂ | OEt | 3-AcO—Ph | O |
| 10-203 | Me | CH(Me)CH₂ | H | CH₂ | OEt | 4-AcO—Ph | O |

TABLE 11

| Exemplification No. compound. | R¹ | R² | R³ | Z | W | X | Y |
|---|---|---|---|---|---|---|---|
| 11-1 | H | C(Me)$_2$CH$_2$ | H | CH$_2$ | OEt | 4-Et-Ph | O |
| 11-2 | H | C(Me)$_2$CH$_2$ | H | CH$_2$ | OEt | 4-iPr-Ph | O |
| 11-3 | H | C(Me)$_2$CH$_2$ | H | CH$_2$ | OEt | 3-Ph-Ph | O |
| 11-4 | H | C(Me)$_2$CH$_2$ | H | CH$_2$ | OEt | 4-Ph-Ph | O |
| 11-5 | H | C(Me)$_2$CH$_2$ | H | CH$_2$ | OEt | 3-Pyr | O |
| 11-6 | H | C(Me)$_2$CH$_2$ | H | CH$_2$ | OEt | 5-Me-3-Pyr | O |
| 11-7 | H | C(Me)$_2$CH$_2$ | H | CH$_2$ | OEt | 5-Et-3-Pyr | O |
| 11-8 | H | C(Me)$_2$CH$_2$ | H | CH$_2$ | OEt | 5-Ph-3-Pyr | O |
| 11-9 | H | C(Me)$_2$CH$_2$ | H | CH$_2$ | OEt | 6-Me-3-Pyr | O |
| 11-10 | H | C(Me)$_2$CH$_2$ | H | CH$_2$ | OEt | 6-Et-3-Pyr | O |
| 11-11 | H | C(Me)$_2$CH$_2$ | H | CH$_2$ | OEt | 6-Ph-3-Pyr | O |
| 11-12 | H | C(Me)$_2$CH$_2$ | H | CH$_2$ | OEt | 6-MeO-3-Pyr | O |
| 11-13 | H | C(Me)$_2$CH$_2$ | H | CH$_2$ | OEt | 6-EtO-3-Pyr | O |
| 11-14 | H | C(Me)$_2$CH$_2$ | H | CH$_2$ | OEt | 6-iPrO-3-Pyr | O |
| 11-15 | H | C(Me)$_2$CH$_2$ | H | CH$_2$ | OEt | 6-MeS-3-Pyr | O |
| 11-16 | H | C(Me)$_2$CH$_2$ | H | CH$_2$ | OEt | 6-EtS-3-Pyr | O |
| 11-17 | H | C(Me)$_2$CH$_2$ | H | CH$_2$ | OEt | 6-iPrS-3-Pyr | O |
| 11-18 | H | C(Me)$_2$CH$_2$ | H | CH$_2$ | OEt | 6-MeSO$_2$-3-Pyr | O |
| 11-19 | H | C(Me)$_2$CH$_2$ | H | CH$_2$ | OEt | 6-EtSO$_2$-3-Pyr | O |
| 11-20 | H | C(Me)$_2$CH$_2$ | H | CH$_2$ | OEt | 6-iPrSO$_2$-3-Pyr | O |
| 11-21 | H | C(Me)$_2$CH$_2$ | H | CH$_2$ | OEt | 6-Bz-3-Pyr | O |
| 11-22 | H | C(Me)$_2$CH$_2$ | H | CH$_2$ | OEt | 6-PhO-3-Pyr | O |
| 11-23 | H | C(Me)$_2$CH$_2$ | H | CH$_2$ | OEt | 6-PhS-3-Pyr | O |
| 11-24 | H | C(Me)$_2$CH$_2$ | H | CH$_2$ | OEt | 6-PhSO$_2$-3-Pyr | O |
| 11-25 | H | C(Me)$_2$CH$_2$ | H | CH$_2$ | OEt | 2-Quin | O |
| 11-26 | H | C(Me)$_2$CH$_2$ | H | CH$_2$ | OEt | 4-MeO-Ph | O |
| 11-27 | H | C(Me)$_2$CH$_2$ | H | CH$_2$ | OEt | 4-EtO-Ph | O |
| 11-28 | H | C(Me)$_2$CH$_2$ | H | CH$_2$ | OEt | 4-iPrO-Ph | O |
| 11-29 | H | C(Me)$_2$CH$_2$ | H | CH$_2$ | OEt | 4-MeS-Ph | O |
| 11-30 | H | C(Me)$_2$CH$_2$ | H | CH$_2$ | OEt | 4-EtS-Ph | O |
| 11-31 | H | C(Me)$_2$CH$_2$ | H | CH$_2$ | OEt | 4-iPrS-Ph | O |
| 11-32 | H | C(Me)$_2$CH$_2$ | H | CH$_2$ | OEt | 4-MeSO$_2$-Ph | O |
| 11-33 | H | C(Me)$_2$CH$_2$ | H | CH$_2$ | OEt | 4-EtSO$_2$-Ph | O |
| 11-34 | H | C(Me)$_2$CH$_2$ | H | CH$_2$ | OEt | 4-iPrSO$_2$-Ph | O |
| 11-35 | H | C(Me)$_2$CH$_2$ | H | CH$_2$ | OEt | 4-(Pyr-2)Ph | O |
| 11-36 | H | C(Me)$_2$CH$_2$ | H | CH$_2$ | OEt | 4-(Pyr-3)Ph | O |
| 11-37 | H | C(Me)$_2$CH$_2$ | H | CH$_2$ | OEt | 4-(Pyr-3)Ph | O |
| 11-38 | H | C(Me)$_2$CH$_2$ | H | CH$_2$ | OEt | 3-Ph-6-Pyr | O |

TABLE 12

| Exemplification No. compound. | R¹ | R² | R³ | Z | W | X | Y |
|---|---|---|---|---|---|---|---|
| 12-1 | Me | C(Me)$_2$CH$_2$ | H | CH$_2$ | OEt | 4-Et-Ph | O |
| 12-2 | Me | C(Me)$_2$CH$_2$ | H | CH$_2$ | OEt | 4-iPr-Ph | O |
| 12-3 | Me | C(Me)$_2$CH$_2$ | H | CH$_2$ | OEt | 3-Ph-Ph | O |
| 12-4 | Me | C(Me)$_2$CH$_2$ | H | CH$_2$ | OEt | 4-Ph-Ph | O |
| 12-5 | Me | C(Me)$_2$CH$_2$ | H | CH$_2$ | OEt | 3-Pyr | O |
| 12-6 | Me | C(Me)$_2$CH$_2$ | H | CH$_2$ | OEt | 5-Me-3-Pyr | O |
| 12-7 | Me | C(Me)$_2$CH$_2$ | H | CH$_2$ | OEt | 5-Et-3-Pyr | O |
| 12-8 | Me | C(Me)$_2$CH$_2$ | H | CH$_2$ | OEt | 5-Ph-3-Pyr | O |
| 12-9 | Me | C(Me)$_2$CH$_2$ | H | CH$_2$ | OEt | 6-Me-3-Pyr | O |
| 12-10 | Me | C(Me)$_2$CH$_2$ | H | CH$_2$ | OEt | 6-Et-3-Pyr | O |
| 12-11 | Me | C(Me)$_2$CH$_2$ | H | CH$_2$ | OEt | 6-Ph-3-Pyr | O |
| 12-12 | Me | C(Me)$_2$CH$_2$ | H | CH$_2$ | OEt | 6-MeO-3-Pyr | O |
| 12-13 | Me | C(Me)$_2$CH$_2$ | H | CH$_2$ | OEt | 6-EtO-3-Pyr | O |
| 12-14 | Me | C(Me)$_2$CH$_2$ | H | CH$_2$ | OEt | 6-iPrO-3-Pyr | O |
| 12-15 | Me | C(Me)$_2$CH$_2$ | H | CH$_2$ | OEt | 6-MeS-3-Pyr | O |
| 12-16 | Me | C(Me)$_2$CH$_2$ | H | CH$_2$ | OEt | 6-EtS-3-Pyr | O |
| 12-17 | Me | C(Me)$_2$CH$_2$ | H | CH$_2$ | OEt | 6-iPrS-3-Pyr | O |
| 12-18 | Me | C(Me)$_2$CH$_2$ | H | CH$_2$ | OEt | 6-MeSO$_2$-3-Pyr | O |
| 12-19 | Me | C(Me)$_2$CH$_2$ | H | CH$_2$ | OEt | 6-EtSO$_2$-3-Pyr | O |
| 12-20 | Me | C(Me)$_2$CH$_2$ | H | CH$_2$ | OEt | 6-iPrSO$_2$-3-Pyr | O |
| 12-21 | Me | C(Me)$_2$CH$_2$ | H | CH$_2$ | OEt | 6-Bz-3-Pyr | O |
| 12-22 | Me | C(Me)$_2$CH$_2$ | H | CH$_2$ | OEt | 6-PhO-3-Pyr | O |
| 12-23 | Me | C(Me)$_2$CH$_2$ | H | CH$_2$ | OEt | 6-PhS-3-Pyr | O |
| 12-24 | Me | C(Me)$_2$CH$_2$ | H | CH$_2$ | OEt | 6-PhSO$_2$-3-Pyr | O |
| 12-25 | Me | C(Me)$_2$CH$_2$ | H | CH$_2$ | OEt | 2-Quin | O |
| 12-26 | Me | C(Me)$_2$CH$_2$ | H | CH$_2$ | OEt | 4-MeO-Ph | O |
| 12-27 | Me | C(Me)$_2$CH$_2$ | H | CH$_2$ | OEt | 4-EtO-Ph | O |
| 12-28 | Me | C(Me)$_2$CH$_2$ | H | CH$_2$ | OEt | 4-iPrO-Ph | O |
| 12-29 | Me | C(Me)$_2$CH$_2$ | H | CH$_2$ | OEt | 4-MeS-Ph | O |

TABLE 12-continued

| Exemplification No. compound. | R¹ | R² | R³ | Z | W | X | Y |
|---|---|---|---|---|---|---|---|
| 12-30 | Me | C(Me)₂CH₂ | H | CH₂ | OEt | 4-EtS-Ph | O |
| 12-31 | Me | C(Me)₂CH₂ | H | CH₂ | OEt | 4-iPrS-Ph | O |
| 12-32 | Me | C(Me)₂CH₂ | H | CH₂ | OEt | 4-MeSO₂-Ph | O |
| 12-33 | Me | C(Me)₂CH₂ | H | CH₂ | OEt | 4-EtSO₂-Ph | O |
| 12-34 | Me | C(Me)₂CH₂ | H | CH₂ | OEt | 4-iPrSO₂-Ph | O |
| 12-35 | Me | C(Me)₂CH₂ | H | CH₂ | OEt | 4-(Pyr-2)Ph | O |
| 12-36 | Me | C(Me)₂CH₂ | H | CH₂ | OEt | 4-(Pyr-3)Ph | O |
| 12-37 | Me | C(Me)₂CH₂ | H | CH₂ | OEt | 4-(Pyr-3)Ph | O |
| 12-38 | Me | C(Me)₂CH₂ | H | CH₂ | OEt | 3-Ph-6-Pyr | O |

TABLE 13

| Exemplification No. compound. | R¹ | R² | R³ | Z | W | X | Y |
|---|---|---|---|---|---|---|---|
| 13-1 | H | CH₂CH(Me) | H | CH₂ | OEt | 4-Et-Ph | O |
| 13-2 | H | CH₂CH(Me) | H | CH₂ | OEt | 4-iPr-Ph | O |
| 13-3 | H | CH₂CH(Me) | H | CH₂ | OEt | 3-Ph-Ph | O |
| 13-4 | H | CH₂CH(Me) | H | CH₂ | OEt | 4-Ph-Ph | O |
| 13-5 | H | CH₂CH(Me) | H | CH₂ | OEt | 3-Pyr | O |
| 13-6 | H | CH₂CH(Me) | H | CH₂ | OEt | 5-Me-3-Pyr | O |
| 13-7 | H | CH₂CH(Me) | H | CH₂ | OEt | 5-Et-3-Pyr | O |
| 13-8 | H | CH₂CH(Me) | H | CH₂ | OEt | 5-Ph-3-Pyr | O |
| 13-9 | H | CH₂CH(Me) | H | CH₂ | OEt | 6-Me-3-Pyr | O |
| 13-10 | H | CH₂CH(Me) | H | CH₂ | OEt | 6-Et-3-Pyr | O |
| 13-11 | H | CH₂CH(Me) | H | CH₂ | OEt | 6-Ph-3-Pyr | O |
| 13-12 | H | CH₂CH(Me) | H | CH₂ | OEt | 6-MeO-3-Pyr | O |
| 13-13 | H | CH₂CH(Me) | H | CH₂ | OEt | 6-EtO-3-Pyr | O |
| 13-14 | H | CH₂CH(Me) | H | CH₂ | OEt | 6-iPrO-3-Pyr | O |
| 13-15 | H | CH₂CH(Me) | H | CH₂ | OEt | 6-MeS-3-Pyr | O |
| 13-16 | H | CH₂CH(Me) | H | CH₂ | OEt | 6-EtS-3-Pyr | O |
| 13-17 | H | CH₂CH(Me) | H | CH₂ | OEt | 6-iPrS-3-Pyr | O |
| 13-18 | H | CH₂CH(Me) | H | CH₂ | OEt | 6-MeSO₂-3-Pyr | O |
| 13-19 | H | CH₂CH(Me) | H | CH₂ | OEt | 6-EtSO₂-3-Pyr | O |
| 13-20 | H | CH₂CH(Me) | H | CH₂ | OEt | 6-iPrSO₂-3-Pyr | O |
| 13-21 | H | CH₂CH(Me) | H | CH₂ | OEt | 6-Bz-3-Pyr | O |
| 13-22 | H | CH₂CH(Me) | H | CH₂ | OEt | 6-PhO-3-Pyr | O |
| 13-23 | H | CH₂CH(Me) | H | CH₂ | OEt | 6-PhS-3-Pyr | O |
| 13-24 | H | CH₂CH(Me) | H | CH₂ | OEt | 6-PhSO₂-3-Pyr | O |
| 13-25 | H | CH₂CH(Me) | H | CH₂ | OEt | 2-Quin | O |
| 13-26 | H | CH₂CH(Me) | H | CH₂ | OEt | 4-MeO-Ph | O |
| 13-27 | H | CH₂CH(Me) | H | CH₂ | OEt | 4-EtO-Ph | O |
| 13-28 | H | CH₂CH(Me) | H | CH₂ | OEt | 4-iPrO-Ph | O |
| 13-29 | H | CH₂CH(Me) | H | CH₂ | OEt | 4-MeS-Ph | O |
| 13-30 | H | CH₂CH(Me) | H | CH₂ | OEt | 4-EtS-Ph | O |
| 13-31 | H | CH₂CH(Me) | H | CH₂ | OEt | 4-iPrS-Ph | O |
| 13-32 | H | CH₂CH(Me) | H | CH₂ | OEt | 4-MeSO₂-Ph | O |
| 13-33 | H | CH₂CH(Me) | H | CH₂ | OEt | 4-EtSO₂-Ph | O |
| 13-34 | H | CH₂CH(Me) | H | CH₂ | OEt | 4-iPrSO₂-Ph | O |
| 13-35 | H | CH₂CH(Me) | H | CH₂ | OEt | 4-(Pyr-2)Ph | O |
| 13-36 | H | CH₂CH(Me) | H | CH₂ | OEt | 4-(Pyr-3)Ph | O |
| 13-37 | H | CH₂CH(Me) | H | CH₂ | OEt | 4-(Pyr-3)Ph | O |
| 13-38 | H | CH₂CH(Me) | H | CH₂ | OEt | 3-Ph-6-Pyr | O |

TABLE 14

| Exemplification No. compound. | R¹ | R² | R³ | Z | W | X | Y |
|---|---|---|---|---|---|---|---|
| 14-1 | Me | CH₂CH(Me) | H | CH₂ | OEt | 4-Et-Ph | O |
| 14-2 | Me | CH₂CH(Me) | H | CH₂ | OEt | 4-iPr-Ph | O |
| 14-3 | Me | CH₂CH(Me) | H | CH₂ | OEt | 3-Ph-Ph | O |
| 14-4 | Me | CH₂CH(Me) | H | CH₂ | OEt | 4-Ph-Ph | O |
| 14-5 | Me | CH₂CH(Me) | H | CH₂ | OEt | 3-Pyr | O |
| 14-6 | Me | CH₂CH(Me) | H | CH₂ | OEt | 5-Me-3-Pyr | O |
| 14-7 | Me | CH₂CH(Me) | H | CH₂ | OEt | 5-Et-3-Pyr | O |
| 14-8 | Me | CH₂CH(Me) | H | CH₂ | OEt | 5-Ph-3-Pyr | O |
| 14-9 | Me | CH₂CH(Me) | H | CH₂ | OEt | 6-Me-3-Pyr | O |
| 14-10 | Me | CH₂CH(Me) | H | CH₂ | OEt | 6-Et-3-Pyr | O |
| 14-11 | Me | CH₂CH(Me) | H | CH₂ | OEt | 6-Ph-3-Pyr | O |
| 14-12 | Me | CH₂CH(Me) | H | CH₂ | OEt | 6-MeO-3-Pyr | O |

TABLE 14-continued

| Exemplification No. compound. | R¹ | R² | R³ | Z | W | X | Y |
|---|---|---|---|---|---|---|---|
| 14-13 | Me | CH₂CH(Me) | H | CH₂ | OEt | 6-EtO-3-Pyr | O |
| 14-14 | Me | CH₂CH(Me) | H | CH₂ | OEt | 6-iPrO-3-Pyr | O |
| 14-15 | Me | CH₂CH(Me) | H | CH₂ | OEt | 6-MeS-3-Pyr | O |
| 14-16 | Me | CH₂CH(Me) | H | CH₂ | OEt | 6-EtS-3-Pyr | O |
| 14-17 | Me | CH₂CH(Me) | H | CH₂ | OEt | 6-iPrS-3-Pyr | O |
| 14-18 | Me | CH₂CH(Me) | H | CH₂ | OEt | 6-MeSO₂-3-Pyr | O |
| 14-19 | Me | CH₂CH(Me) | H | CH₂ | OEt | 6-EtSO₂-3-Pyr | O |
| 14-20 | Me | CH₂CH(Me) | H | CH₂ | OEt | 6-iPrSO₂-3-Pyr | O |
| 14-21 | Me | CH₂CH(Me) | H | CH₂ | OEt | 6-Bz-3-Pyr | O |
| 14-22 | Me | CH₂CH(Me) | H | CH₂ | OEt | 6-PhO-3-Pyr | O |
| 14-23 | Me | CH₂CH(Me) | H | CH₂ | OEt | 6-PhS-3-Pyr | O |
| 14-24 | Me | CH₂CH(Me) | H | CH₂ | OEt | 6-PhSO₂-3-Pyr | O |
| 14-25 | Me | CH₂CH(Me) | H | CH₂ | OEt | 2-Quin | O |
| 14-26 | Me | CH₂CH(Me) | H | CH₂ | OEt | 4-MeO-Ph | O |
| 14-27 | Me | CH₂CH(Me) | H | CH₂ | OEt | 4-EtO-Ph | O |
| 14-28 | Me | CH₂CH(Me) | H | CH₂ | OEt | 4-iPrO-Ph | O |
| 14-29 | Me | CH₂CH(Me) | H | CH₂ | OEt | 4-MeS-Ph | O |
| 14-30 | Me | CH₂CH(Me) | H | CH₂ | OEt | 4-EtS-Ph | O |
| 14-31 | Me | CH₂CH(Me) | H | CH₂ | OEt | 4-iPrS-Ph | O |
| 14-32 | Me | CH₂CH(Me) | H | CH₂ | OEt | 4-MeSO₂-Ph | O |
| 14-33 | Me | CH₂CH(Me) | H | CH₂ | OEt | 4-EtSO₂-Ph | O |
| 14-34 | Me | CH₂CH(Me) | H | CH₂ | OEt | 4-iPrSO₂-Ph | O |
| 14-35 | Me | CH₂CH(Me) | H | CH₂ | OEt | 4-(Pyr-2)Ph | O |
| 14-36 | Me | CH₂CH(Me) | H | CH₂ | OEt | 4-(Pyr-3)Ph | O |
| 14-37 | Me | CH₂CH(Me) | H | CH₂ | OEt | 4-(Pyr-3)Ph | O |
| 14-38 | Me | CH₂CH(Me) | H | CH₂ | OEt | 3-Ph-6-Pyr | O |

TABLE 15

| Exemplification No. compound. | R¹ | R² | R³ | Z | W | X | Y |
|---|---|---|---|---|---|---|---|
| 15-1 | H | CH(Me)CH(Me) | H | CH₂ | OEt | 4-Et-Ph | O |
| 15-2 | H | CH(Me)CH(Me) | H | CH₂ | OEt | 4-iPr-Ph | O |
| 15-3 | H | CH(Me)CH(Me) | H | CH₂ | OEt | 3-Ph-Ph | O |
| 15-4 | H | CH(Me)CH(Me) | H | CH₂ | OEt | 4-Ph-Ph | O |
| 15-5 | H | CH(Me)CH(Me) | H | CH₂ | OEt | 3-Pyr | O |
| 15-6 | H | CH(Me)CH(Me) | H | CH₂ | OEt | 5-Me-3-Pyr | O |
| 15-7 | H | CH(Me)CH(Me) | H | CH₂ | OEt | 5-Et-3-Pyr | O |
| 15-8 | H | CH(Me)CH(Me) | H | CH₂ | OEt | 5-Ph-3-Pyr | O |
| 15-9 | H | CH(Me)CH(Me) | H | CH₂ | OEt | 6-Me-3-Pyr | O |
| 15-10 | H | CH(Me)CH(Me) | H | CH₂ | OEt | 6-Et-3-Pyr | O |
| 15-11 | H | CH(Me)CH(Me) | H | CH₂ | OEt | 6-Ph-3-Pyr | O |
| 15-12 | H | CH(Me)CH(Me) | H | CH₂ | OEt | 6-MeO-3-Pyr | O |
| 15-13 | H | CH(Me)CH(Me) | H | CH₂ | OEt | 6-EtO-3-Pyr | O |
| 15-14 | H | CH(Me)CH(Me) | H | CH₂ | OEt | 6-iPrO-3-Pyr | O |
| 15-15 | H | CH(Me)CH(Me) | H | CH₂ | OEt | 6-MeS-3-Pyr | O |
| 15-16 | H | CH(Me)CH(Me) | H | CH₂ | OEt | 6-EtS-3-Pyr | O |
| 15-17 | H | CH(Me)CH(Me) | H | CH₂ | OEt | 6-iPrS-3-Pyr | O |
| 15-18 | H | CH(Me)CH(Me) | H | CH₂ | OEt | 6-MeSO₂-3-Pyr | O |
| 15-19 | H | CH(Me)CH(Me) | H | CH₂ | OEt | 6-EtSO₂-3-Pyr | O |
| 15-20 | H | CH(Me)CH(Me) | H | CH₂ | OEt | 6-iPrSO₂-3-Pyr | O |
| 15-21 | H | CH(Me)CH(Me) | H | CH₂ | OEt | 6-Bz-3-Pyr | O |
| 15-22 | H | CH(Me)CH(Me) | H | CH₂ | OEt | 6-PhO-3-Pyr | O |
| 15-23 | H | CH(Me)CH(Me) | H | CH₂ | OEt | 6-PhS-3-Pyr | O |
| 15-24 | H | CH(Me)CH(Me) | H | CH₂ | OEt | 6-PhSO₂-3-Pyr | O |
| 15-25 | H | CH(Me)CH(Me) | H | CH₂ | OEt | 2-Quin | O |
| 15-26 | H | CH(Me)CH(Me) | H | CH₂ | OEt | 4-MeO-Ph | O |
| 15-27 | H | CH(Me)CH(Me) | H | CH₂ | OEt | 4-EtO-Ph | O |
| 15-28 | H | CH(Me)CH(Me) | H | CH₂ | OEt | 4-iPrO-Ph | O |
| 15-29 | H | CH(Me)CH(Me) | H | CH₂ | OEt | 4-MeS-Ph | O |
| 15-30 | H | CH(Me)CH(Me) | H | CH₂ | OEt | 4-EtS-Ph | O |
| 15-31 | H | CH(Me)CH(Me) | H | CH₂ | OEt | 4-iPrS-Ph | O |
| 15-32 | H | CH(Me)CH(Me) | H | CH₂ | OEt | 4-MeSO₂-Ph | O |
| 15-33 | H | CH(Me)CH(Me) | H | CH₂ | OEt | 4-EtSO₂-Ph | O |
| 15-34 | H | CH(Me)CH(Me) | H | CH₂ | OEt | 4-iPrSO₂-Ph | O |
| 15-35 | H | CH(Me)CH(Me) | H | CH₂ | OEt | 4-(Pyr-2)Ph | O |
| 15-36 | H | CH(Me)CH(Me) | H | CH₂ | OEt | 4-(Pyr-3)Ph | O |
| 15-37 | H | CH(Me)CH(Me) | H | CH₂ | OEt | 4-(Pyr-3)Ph | O |
| 15-38 | H | CH(Me)CH(Me) | H | CH₂ | OEt | 3-Ph-6-Pyr | O |

TABLE 16

| Exemplification No. compound. | R¹ | R² | R³ | Z | W | X | Y |
|---|---|---|---|---|---|---|---|
| 16-1 | Me | CH(Me)CH(Me) | H | CH₂ | OEt | 4-Et-Ph | O |
| 16-2 | Me | CH(Me)CH(Me) | H | CH₂ | OEt | 4-iPr-Ph | O |
| 16-3 | Me | CH(Me)CH(Me) | H | CH₂ | OEt | 3-Ph-Ph | O |
| 16-4 | Me | CH(Me)CH(Me) | H | CH₂ | OEt | 4-Ph-Ph | O |
| 16-5 | Me | CH(Me)CH(Me) | H | CH₂ | OEt | 3-Pyr | O |
| 16-6 | Me | CH(Me)CH(Me) | H | CH₂ | OEt | 5-Me-3-Pyr | O |
| 16-7 | Me | CH(Me)CH(Me) | H | CH₂ | OEt | 5-Et-3-Pyr | O |
| 16-8 | Me | CH(Me)CH(Me) | H | CH₂ | OEt | 5-Ph-3-Pyr | O |
| 16-9 | Me | CH(Me)CH(Me) | H | CH₂ | OEt | 6-Me-3-Pyr | O |
| 16-10 | Me | CH(Me)CH(Me) | H | CH₂ | OEt | 6-Et-3-Pyr | O |
| 16-11 | Me | CH(Me)CH(Me) | H | CH₂ | OEt | 6-Ph-3-Pyr | O |
| 16-12 | Me | CH(Me)CH(Me) | H | CH₂ | OEt | 6-MeO-3-Pyr | O |
| 16-13 | Me | CH(Me)CH(Me) | H | CH₂ | OEt | 6-EtO-3-Pyr | O |
| 16-14 | Me | CH(Me)CH(Me) | H | CH₂ | OEt | 6-iPrO-3-Pyr | O |
| 16-15 | Me | CH(Me)CH(Me) | H | CH₂ | OEt | 6-MeS-3-Pyr | O |
| 16-16 | Me | CH(Me)CH(Me) | H | CH₂ | OEt | 6-EtS-3-Pyr | O |
| 16-17 | Me | CH(Me)CH(Me) | H | CH₂ | OEt | 6-iPrS-3-Pyr | O |
| 16-18 | Me | CH(Me)CH(Me) | H | CH₂ | OEt | 6-MeSO₂-3-Pyr | O |
| 16-19 | Me | CH(Me)CH(Me) | H | CH₂ | OEt | 6-EtSO₂-3-Pyr | O |
| 16-20 | Me | CH(Me)CH(Me) | H | CH₂ | OEt | 6-iPrSO₂-3-Pyr | O |
| 16-21 | Me | CH(Me)CH(Me) | H | CH₂ | OEt | 6-Bz-3-Pyr | O |
| 16-22 | Me | CH(Me)CH(Me) | H | CH₂ | OEt | 6-PhO-3-Pyr | O |
| 16-23 | Me | CH(Me)CH(Me) | H | CH₂ | OEt | 6-PhS-3-Pyr | O |
| 16-24 | Me | CH(Me)CH(Me) | H | CH₂ | OEt | 6-PhSO₂-3-Pyr | O |
| 16-25 | Me | CH(Me)CH(Me) | H | CH₂ | OEt | 2-Quin | O |
| 16-26 | Me | CH(Me)CH(Me) | H | CH₂ | OEt | 4-MeO-Ph | O |
| 16-27 | Me | CH(Me)CH(Me) | H | CH₂ | OEt | 4-EtO-Ph | O |
| 16-28 | Me | CH(Me)CH(Me) | H | CH₂ | OEt | 4-iPrO-Ph | O |
| 16-29 | Me | CH(Me)CH(Me) | H | CH₂ | OEt | 4-MeS-Ph | O |
| 16-30 | Me | CH(Me)CH(Me) | H | CH₂ | OEt | 4-EtS-Ph | O |
| 16-31 | Me | CH(Me)CH(Me) | H | CH₂ | OEt | 4-iPrS-Ph | O |
| 16-32 | Me | 9H(Me)CH(Me) | H | CH₂ | OEt | 4-MeSO₂-Ph | O |
| 16-33 | Me | CH(Me)CH(Me) | H | CH₂ | OEt | 4-EtSO₂-Ph | O |
| 16-34 | Me | CH(Me)CH(Me) | H | CH₂ | OEt | 4-iPrSO₂-Ph | O |
| 16-35 | Me | CH(Me)CH(Me) | H | CH₂ | OEt | 4-(Pyr-2)Ph | O |
| 16-36 | Me | CH(Me)CH(Me) | H | CH₂ | OEt | 4-(Pyr-3)Ph | O |
| 16-37 | Me | CH(Me)CH(Me) | H | CH₂ | OEt | 4-(Pyr-3)Ph | O |
| 16-38 | Me | CH(Me)CH(Me) | H | CH₂ | OEt | 3-Ph-6-Pyr | O |

TABLE 17

| Exemplification No. Compound. | R¹ | R² | R³ | Z | W | X | Y |
|---|---|---|---|---|---|---|---|
| 17-1 | Me | (CH₂)₂ | H | CH₂ | OEt | 4-Et-Ph | S |
| 17-2 | Me | (CH₂)₂ | H | CH₂ | OEt | 4-iPr-Ph | S |
| 17-3 | Me | (CH₂)₂ | H | CH₂ | OEt | 3-Ph-Ph | S |
| 17-4 | Me | (CH₂)₂ | H | CH₂ | OEt | 4-Ph-Ph | S |
| 17-5 | Me | (CH₂)₂ | H | CH₂ | OEt | 3-Pyr | S |
| 17-6 | Me | (CH₂)₂ | H | CH₂ | OEt | 5-Me-3-Pyr | S |
| 17-7 | Me | (CH₂)₂ | H | CH₂ | OEt | 5-Et-3-Pyr | S |
| 17-8 | Me | (CH₂)₂ | H | CH₂ | OEt | 5-Ph-3-Pyr | S |
| 17-9 | Me | (CH₂)₂ | H | CH₂ | OEt | 6-Me-3-Pyr | S |
| 17-10 | Me | (CH₂)₂ | H | CH₂ | OEt | 6-Et-3-Pyr | S |
| 17-11 | Me | (CH₂)₂ | H | CH₂ | OEt | 6-Ph-3-Pyr | S |
| 17-12 | Me | (CH₂)₂ | H | CH₂ | OEt | 6-MeO-3-Pyr | S |
| 17-13 | Me | (CH₂)₂ | H | CH₂ | OEt | 6-EtO-3-Pyr | S |
| 17-14 | Me | (CH₂)₂ | H | CH₂ | OEt | 6-iPrO-3-Pyr | S |
| 17-15 | Me | (CH₂)₂ | H | CH₂ | OEt | 6-MeS-3-Pyr | S |
| 17-16 | Me | (CH₂)₂ | H | CH₂ | OEt | 6-EtS-3-Pyr | S |
| 17-17 | Me | (CH₂)₂ | H | CH₂ | OEt | 6-iPrS-3-Pyr | S |
| 17-18 | Me | (CH₂)₂ | H | CH₂ | OEt | 6-MeSO₂-3-Pyr | S |
| 17-19 | Me | (CH₂)₂ | H | CH₂ | OEt | 6-EtSO₂-3-Pyr | S |
| 17-20 | Me | (CH₂)₂ | H | CH₂ | OEt | 6-iPrSO₂-3-Pyr | S |
| 17-21 | Me | (CH₂)₂ | H | CH₂ | OEt | 6-Bz-3-Pyr | S |
| 17-22 | Me | (CH₂)₂ | H | CH₂ | OEt | 6-PhO-3-Pyr | S |
| 17-23 | Me | (CH₂)₂ | H | CH₂ | OEt | 6-PhS-3-Pyr | S |
| 17-24 | Me | (CH₂)₂ | H | CH₂ | OEt | 6-PhSO₂-3-Pyr | S |
| 17-25 | Me | (CH₂)₂ | H | CH₂ | OEt | 2-Quin | S |
| 17-26 | Me | (CH₂)₂ | H | CH₂ | OEt | 4-MeO-Ph | S |
| 17-27 | Me | (CH₂)₂ | H | CH₂ | OEt | 4-EtO-Ph | S |
| 17-28 | Me | (CH₂)₂ | H | CH₂ | OEt | 4-iPrO-Ph | S |
| 17-29 | Me | (CH₂)₂ | H | CH₂ | OEt | 4-MeS-Ph | S |
| 17-30 | Me | (CH₂)₂ | H | CH₂ | OEt | 4-EtS-Ph | S |
| 17-31 | Me | (CH₂)₂ | H | CH₂ | OEt | 4-iPrS-Ph | S |
| 17-32 | Me | (CH₂)₂ | H | CH₂ | OEt | 4-MeSO₂-Ph | S |
| 17-33 | Me | (CH₂)₂ | H | CH₂ | OEt | 4-EtSO₂-Ph | S |
| 17-34 | Me | (CH₂)₂ | H | CH₂ | OEt | 4-iPrSO₂-Ph | S |
| 17-35 | Me | (CH₂)₂ | H | CH₂ | OEt | 4-(Pyr-2)Ph | S |
| 17-36 | Me | (CH₂)₂ | H | CH₂ | OEt | 4-(Pyr-3)Ph | S |
| 17-37 | Me | (CH₂)₂ | H | CH₂ | OEt | 4-(Pyr-3)Ph | S |
| 17-38 | Me | (CH₂)₂ | H | CH₂ | OEt | 3-Ph-6-Pyr | S |

TABLE 18

| Exemplification No. compound. | R¹ | R² | R³ | Z | W | X | Y |
|---|---|---|---|---|---|---|---|
| 18-1 | Me | (CH₂)₂ | H | CH₂ | OEt | 4-Et-Ph | NMe |
| 18-2 | Me | (CH₂)₂ | H | CH₂ | OEt | 4-iPr-Ph | NMe |
| 18-3 | Me | (CH₂)₂ | H | CH₂ | OEt | 3-Ph-Ph | NMe |
| 18-4 | Me | (CH₂)₂ | H | CH₂ | OEt | 4-Ph-Ph | NMe |
| 18-5 | Me | (CH₂)₂ | H | CH₂ | OEt | 3-Pyr | NMe |
| 18-6 | Me | (CH₂)₂ | H | CH₂ | OEt | 5-Me-3-Pyr | NMe |
| 18-7 | Me | (CH₂)₂ | H | CH₂ | OEt | 5-Et-3-Pyr | NMe |
| 18-8 | Me | (CH₂)₂ | H | CH₂ | OEt | 5-Ph-3-Pyr | NMe |
| 18-9 | Me | (CH₂)₂ | H | CH₂ | OEt | 6-Me-3-Pyr | NMe |

TABLE 18-continued

| Exemplification No. compound. | R¹ | R² | R³ | Z | W | X | Y |
|---|---|---|---|---|---|---|---|
| 18-10 | Me | $(CH_2)_2$ | H | $CH_2$ | OEt | 6-Et-3-Pyr | NMe |
| 18-11 | Me | $(CH_2)_2$ | H | $CH_2$ | OEt | 6-Ph-3-Pyr | NMe |
| 18-12 | Me | $(CH_2)_2$ | H | $CH_2$ | OEt | 6-MeO-3-Pyr | NMe |
| 18-13 | Me | $(CH_2)_2$ | H | $CH_2$ | OEt | 6-EtO-3-Pyr | NMe |
| 18-14 | Me | $(CH_2)_2$ | H | $CH_2$ | OEt | 6-iPrO-3-Pyr | NMe |
| 18-15 | Me | $(CH_2)_2$ | H | $CH_2$ | OEt | 6-MeS-3-Pyr | NMe |
| 18-16 | Me | $(CH_2)_2$ | H | $CH_2$ | OEt | 6-EtS-3-Pyr | NMe |
| 18-17 | Me | $(CH_2)_2$ | H | $CH_2$ | OEt | 6-iPrS-3-Pyr | NMe |
| 18-18 | Me | $(CH_2)_2$ | H | $CH_2$ | OEt | 6-MeSO$_2$-3-Pyr | NMe |
| 18-19 | Me | $(CH_2)_2$ | H | $CH_2$ | OEt | 6-EtSO$_2$-3-Pyr | NMe |
| 18-20 | Me | $(CH_2)_2$ | H | $CH_2$ | OEt | 6-iPrSO$_2$-3-Pyr | NMe |
| 18-21 | Me | $(CH_2)_2$ | H | $CH_2$ | OEt | 6-Bz-3-Pyr | NMe |
| 18-22 | Me | $(CH_2)_2$ | H | $CH_2$ | OEt | 6-PhO-3-Pyr | NMe |
| 18-23 | Me | $(CH_2)_2$ | H | $CH_2$ | OEt | 6-PhS-3-Pyr | NMe |
| 18-24 | Me | $(CH_2)_2$ | H | $CH_2$ | OEt | 6-PhSO$_2$-3-Pyr | NMe |
| 18-25 | Me | $(CH_2)_2$ | H | $CH_2$ | OEt | 2-Quin | NMe |
| 18-26 | Me | $(CH_2)_2$ | H | $CH_2$ | OEt | 4-MeO-Ph | NMe |
| 18-27 | Me | $(CH_2)_2$ | H | $CH_2$ | OEt | 4-EtO-Ph | NMe |
| 18-28 | Me | $(CH_2)_2$ | H | $CH_2$ | OEt | 4-iPrO-Ph | NMe |
| 18-29 | Me | $(CH_2)_2$ | H | $CH_2$ | OEt | 4-MeS-Ph | NMe |
| 18-30 | Me | $(CH_2)_2$ | H | $CH_2$ | OEt | 4-EtS-Ph | NMe |
| 18-31 | Me | $(CH_2)_2$ | H | $CH_2$ | OEt | 4-iPrS-Ph | NMe |
| 18-32 | Me | $(CH_2)_2$ | H | $CH_2$ | OEt | 4-MeSO$_2$-Ph | NMe |
| 18-33 | Me | $(CH_2)_2$ | H | $CH_2$ | OEt | 4-EtSO$_2$-Ph | NMe |
| 18-34 | Me | $(CH_2)_2$ | H | $CH_2$ | OEt | 4-iPrSO$_2$-Ph | NMe |
| 18-35 | Me | $(CH_2)_2$ | H | $CH_2$ | OEt | 4-(Pyr-2)Ph | NMe |
| 18-36 | Me | $(CH_2)_2$ | H | $CH_2$ | OEt | 4-(Pyr-3)Ph | NMe |
| 18-37 | Me | $(CH_2)_2$ | H | $CH_2$ | OEt | 4-(Pyr-3)Ph | NMe |
| 18-38 | Me | $(CH_2)_2$ | H | $CH_2$ | OEt | 3-Ph-6-Pyr | NMe |

TABLE 19

| Exemplification No. compound. | R¹ | R² | R³ | Z | W | X | Y |
|---|---|---|---|---|---|---|---|
| 19-1 | Me | $(CH_2)_2$ | H | $CH_2$ | OEt | 4-Et-Ph | NAc |
| 19-2 | Me | $(CH_2)_2$ | H | $CH_2$ | OEt | 4-iPr-Ph | NAc |
| 19-3 | Me | $(CH_2)_2$ | H | $CH_2$ | OEt | 3-Ph-Ph | NAc |
| 19-4 | Me | $(CH_2)_2$ | H | $CH_2$ | OEt | 4-Ph-Ph | NAc |
| 19-5 | Me | $(CH_2)_2$ | H | $CH_2$ | OEt | 3-Pyr | NAc |
| 19-6 | Me | $(CH_2)_2$ | H | $CH_2$ | OEt | 5-Me-3-Pyr | NAc |
| 19-7 | Me | $(CH_2)_2$ | H | $CH_2$ | OEt | 5-Et-3-Pyr | NAc |
| 19-8 | Me | $(CH_2)_2$ | H | $CH_2$ | OEt | 5-Ph-3-Pyr | NAc |
| 19-9 | Me | $(CH_2)_2$ | H | $CH_2$ | OEt | 6-Me-3-Pyr | NAc |
| 19-10 | Me | $(CH_2)_2$ | H | $CH_2$ | OEt | 6-Et-3-Pyr | NAc |
| 19-11 | Me | $(CH_2)_2$ | H | $CH_2$ | OEt | 6-Ph-3-Pyr | NAc |
| 19-12 | Me | $(CH_2)_2$ | H | $CH_2$ | OEt | 6-MeO-3-Pyr | NAc |
| 19-13 | Me | $(CH_2)_2$ | H | $CH_2$ | OEt | 6-EtO-3-Pyr | NAc |
| 19-14 | Me | $(CH_2)_2$ | H | $CH_2$ | OEt | 6-iPrO-3-Pyr | NAc |
| 19-15 | Me | $(CH_2)_2$ | H | $CH_2$ | OEt | 6-MeS-3-Pyr | NAc |
| 19-16 | Me | $(CH_2)_2$ | H | $CH_2$ | OEt | 6-EtS-3-Pyr | NAc |
| 19-17 | Me | $(CH_2)_2$ | H | $CH_2$ | OEt | 6-iPrS-3-Pyr | NAc |
| 19-18 | Me | $(CH_2)_2$ | H | $CH_2$ | OEt | 6-MeSO$_2$-3-Pyr | NAc |
| 19-19 | Me | $(CH_2)_2$ | H | $CH_2$ | OEt | 6-EtSO$_2$-3-Pyr | NAc |
| 19-20 | Me | $(CH_2)_2$ | H | $CH_2$ | OEt | 6-iPrSO$_2$-3-Pyr | NAc |
| 19-21 | Me | $(CH_2)_2$ | H | $CH_2$ | OEt | 6-Bz-3-Pyr | NAc |
| 19-22 | Me | $(CH_2)_2$ | H | $CH_2$ | OEt | 6-PhO-3-Pyr | NAc |
| 19-23 | Me | $(CH_2)_2$ | H | $CH_2$ | OEt | 6-PhS-3-Pyr | NAc |
| 19-24 | Me | $(CH_2)_2$ | H | $CH_2$ | OEt | 6-PhSO$_2$-3-Pyr | NAc |
| 19-25 | Me | $(CH_2)_2$ | H | $CH_2$ | OEt | 2-Quin | NAc |
| 19-26 | Me | $(CH_2)_2$ | H | $CH_2$ | OEt | 4-MeO-Ph | NAc |
| 19-27 | Me | $(CH_2)_2$ | H | $CH_2$ | OEt | 4-EtO-Ph | NAc |
| 19-28 | Me | $(CH_2)_2$ | H | $CH_2$ | OEt | 4-iPrO-Ph | NAc |
| 19-29 | Me | $(CH_2)_2$ | H | $CH_2$ | OEt | 4-MeS-Ph | NAc |
| 19-30 | Me | $(CH_2)_2$ | H | $CH_2$ | OEt | 4-EtS-Ph | NAc |
| 19-31 | Me | $(CH_2)_2$ | H | $CH_2$ | OEt | 4-iPrS-Ph | NAc |
| 19-32 | Me | $(CH_2)_2$ | H | $CH_2$ | OEt | 4-MeSO$_2$-Ph | NAc |
| 19-33 | Me | $(CH_2)_2$ | H | $CH_2$ | OEt | 4-EtSO$_2$-Ph | NAc |
| 19-34 | Me | $(CH_2)_2$ | H | $CH_2$ | OEt | 4-iPrSO$_2$-Ph | NAc |
| 19-35 | Me | $(CH_2)_2$ | H | $CH_2$ | OEt | 4-(Pyr-2)Ph | NAc |
| 19-36 | Me | $(CH_2)_2$ | H | $CH_2$ | OEt | 4-(Pyr-3)Ph | NAc |

TABLE 19-continued

| Exemplification No. compound. | R¹ | R² | R³ | Z | W | X | Y |
|---|---|---|---|---|---|---|---|
| 19-37 | Me | $(CH_2)_2$ | H | $CH_2$ | OEt | 4-(Pyr-3)Ph | NAc |
| 19-38 | Me | $(CH_2)_2$ | H | $CH_2$ | OEt | 3-Ph-6-Pyr | NAc |

TABLE 20

| Exemplification No. compound. | R¹ | R² | R³ | Z | W | X | Y |
|---|---|---|---|---|---|---|---|
| 20-1 | Me | $(CH_2)_2$ | 2-Cl | $CH_2$ | OEt | 4-Et-Ph | O |
| 20-2 | Me | $(CH_2)_2$ | 2-Cl | $CH_2$ | OEt | 4-iPr-Ph | O |
| 20-3 | Me | $(CH_2)_2$ | 2-Cl | $CH_2$ | OEt | 3-Ph-Ph | O |
| 20-4 | Me | $(CH_2)_2$ | 2-Cl | $CH_2$ | OEt | 4-Ph-Ph | O |
| 20-5 | Me | $(CH_2)_2$ | 2-Cl | $CH_2$ | OEt | 3-Pyr | O |
| 20-6 | Me | $(CH_2)_2$ | 2-Cl | $CH_2$ | OEt | 5-Me-3-Pyr | O |
| 20-7 | Me | $(CH_2)_2$ | 2-Cl | $CH_2$ | OEt | 5-Et-3-Pyr | O |
| 20-8 | Me | $(CH_2)_2$ | 2-Cl | $CH_2$ | OEt | 5-Ph-3-Pyr | O |
| 20-9 | Me | $(CH_2)_2$ | 2-Cl | $CH_2$ | OEt | 6-Me-3-Pyr | O |
| 20-10 | Me | $(CH_2)_2$ | 2-Cl | $CH_2$ | OEt | 6-Et-3-Pyr | O |
| 20-11 | Me | $(CH_2)_2$ | 2-Cl | $CH_2$ | OEt | 6-Ph-3-Pyr | O |
| 20-12 | Me | $(CH_2)_2$ | 2-Cl | $CH_2$ | OEt | 6-MeO-3-Pyr | O |
| 20-13 | Me | $(CH_2)_2$ | 2-Cl | $CH_2$ | OEt | 6-EtO-3-Pyr | O |
| 20-14 | Me | $(CH_2)_2$ | 2-Cl | $CH_2$ | OEt | 6-iPrO-3-Pyr | O |
| 20-15 | Me | $(CH_2)_2$ | 2-Cl | $CH_2$ | OEt | 6-MeS-3-Pyr | O |
| 20-16 | Me | $(CH_2)_2$ | 2-Cl | $CH_2$ | OEt | 6-EtS-3-Pyr | O |
| 20-17 | Me | $(CH_2)_2$ | 2-Cl | $CH_2$ | OEt | 6-iPrS-3-Pyr | O |
| 20-18 | Me | $(CH_2)_2$ | 2-Cl | $CH_2$ | OEt | 6-MeSO$_2$-3-Pyr | O |
| 20-19 | Me | $(CH_2)_2$ | 2-Cl | $CH_2$ | OEt | 6-EtSO$_2$-3-Pyr | O |
| 20-20 | Me | $(CH_2)_2$ | 2-Cl | $CH_2$ | OEt | 6-iPrSO$_2$-3-Pyr | O |
| 20-21 | Me | $(CH_2)_2$ | 2-Cl | $CH_2$ | OEt | 6-Bz-3-Pyr | O |
| 20-22 | Me | $(CH_2)_2$ | 2-Cl | $CH_2$ | OEt | 6-PhO-3-Pyr | O |
| 20-23 | Me | $(CH_2)_2$ | 2-Cl | $CH_2$ | OEt | 6-PhS-3-Pyr | O |
| 20-24 | Me | $(CH_2)_2$ | 2-Cl | $CH_2$ | OEt | 6-PhSO$_2$-3-Pyr | O |
| 20-25 | Me | $(CH_2)_2$ | 2-Cl | $CH_2$ | OEt | 2-Quin | O |
| 20-26 | Me | $(CH_2)_2$ | 2-Cl | $CH_2$ | OEt | 4-MeO-Ph | O |
| 20-27 | Me | $(CH_2)_2$ | 2-Cl | $CH_2$ | OEt | 4-EtO-Ph | O |
| 20-28 | Me | $(CH_2)_2$ | 2-Cl | $CH_2$ | OEt | 4-iPrO-Ph | O |
| 20-29 | Me | $(CH_2)_2$ | 2-Cl | $CH_2$ | OEt | 4-MeS-Ph | O |
| 20-30 | Me | $(CH_2)_2$ | 2-Cl | $CH_2$ | OEt | 4-EtS-Ph | O |
| 20-31 | Me | $(CH_2)_2$ | 2-Cl | $CH_2$ | OEt | 4-iPrS-Ph | O |
| 20-32 | Me | $(CH_2)_2$ | 2-Cl | $CH_2$ | OEt | 4-MeSO$_2$-Ph | O |
| 20-33 | Me | $(CH_2)_2$ | 2-Cl | $CH_2$ | OEt | 4-EtSO$_2$-Ph | O |
| 20-34 | Me | $(CH_2)_2$ | 2-Cl | $CH_2$ | OEt | 4-iPrSO$_2$-Ph | O |
| 20-35 | Me | $(CH_2)_2$ | 2-Cl | $CH_2$ | OEt | 4-(Pyr-2)Ph | O |
| 20-36 | Me | $(CH_2)_2$ | 2-Cl | $CH_2$ | OEt | 4-(Pyr-3)Ph | O |
| 20-37 | Me | $(CH_2)_2$ | 2-Cl | $CH_2$ | OEt | 4-(Pyr-3)Ph | O |
| 20-38 | Me | $(CH_2)_2$ | 2-Cl | $CH_2$ | OEt | 3-Ph-6-Pyr | O |

TABLE 21

| Exemplification No. compound. | R¹ | R² | R³ | Z | W | X | Y |
|---|---|---|---|---|---|---|---|
| 21-1 | Me | $(CH_2)_2$ | 3-Cl | $CH_2$ | OEt | 4-Et-Ph | O |
| 21-2 | Me | $(CH_2)_2$ | 3-Cl | $CH_2$ | OEt | 4-iPr-Ph | O |
| 21-3 | Me | $(CH_2)_2$ | 3-Cl | $CH_2$ | OEt | 3-Ph-Ph | O |
| 21-4 | Me | $(CH_2)_2$ | 3-Cl | $CH_2$ | OEt | 4-Ph-Ph | O |
| 21-5 | Me | $(CH_2)_2$ | 3-Cl | $CH_2$ | OEt | 3-Pyr | O |
| 21-6 | Me | $(CH_2)_2$ | 3-Cl | $CH_2$ | OEt | 5-Me-3-Pyr | O |
| 21-7 | Me | $(CH_2)_2$ | 3-Cl | $CH_2$ | OEt | 5-Et-3-Pyr | O |
| 21-8 | Me | $(CH_2)_2$ | 3-Cl | $CH_2$ | OEt | 5-Ph-3-Pyr | O |
| 21-9 | Me | $(CH_2)_2$ | 3-Cl | $CH_2$ | OEt | 6-Me-3-Pyr | O |
| 21-10 | Me | $(CH_2)_2$ | 3-Cl | $CH_2$ | OEt | 6-Et-3-Pyr | O |
| 21-11 | Me | $(CH_2)_2$ | 3-Cl | $CH_2$ | OEt | 6-Ph-3-Pyr | O |
| 21-12 | Me | $(CH_2)_2$ | 3-Cl | $CH_2$ | OEt | 6-MeO-3-Pyr | O |
| 21-13 | Me | $(CH_2)_2$ | 3-Cl | $CH_2$ | OEt | 6-EtO-3-Pyr | O |
| 21-14 | Me | $(CH_2)_2$ | 3-Cl | $CH_2$ | OEt | 6-iPrO-3-Pyr | O |
| 21-15 | Me | $(CH_2)_2$ | 3-Cl | $CH_2$ | OEt | 6-MeS-3-Pyr | O |
| 21-16 | Me | $(CH_2)_2$ | 3-Cl | $CH_2$ | OEt | 6-EtS-3-Pyr | O |

TABLE 21-continued

| Exemplification No. compound. | R¹ | R² | R³ | Z | W | X | Y |
|---|---|---|---|---|---|---|---|
| 21-17 | Me | $(CH_2)_2$ | 3-Cl | $CH_2$ | OEt | 6-iPrS-3-Pyr | O |
| 21-18 | Me | $(CH_2)_2$ | 3-Cl | $CH_2$ | OEt | 6-MeSO$_2$-3-Pyr | O |
| 21-19 | Me | $(CH_2)_2$ | 3-Cl | $CH_2$ | OEt | 6-EtSO$_2$-3-Pyr | O |
| 21-20 | Me | $(CH_2)_2$ | 3-Cl | $CH_2$ | OEt | 6-iPrSO$_2$-3-Pyr | O |
| 21-21 | Me | $(CH_2)_2$ | 3-Cl | $CH_2$ | OEt | 6-Bz-3-Pyr | O |
| 21-22 | Me | $(CH_2)_2$ | 3-Cl | $CH_2$ | OEt | 6-PhO-3-Pyr | O |
| 21-23 | Me | $(CH_2)_2$ | 3-Cl | $CH_2$ | OEt | 6-PhS-3-Pyr | O |
| 21-24 | Me | $(CH_2)_2$ | 3-Cl | $CH_2$ | OEt | 6-PhSO$_2$-3-Pyr | O |
| 21-25 | Me | $(CH_2)_2$ | 3-Cl | $CH_2$ | OEt | 2-Quin | O |
| 21-26 | Me | $(CH_2)_2$ | 3-Cl | $CH_2$ | OEt | 4-MeO-Ph | O |
| 21-27 | Me | $(CH_2)_2$ | 3-Cl | $CH_2$ | OEt | 4-EtO-Ph | O |
| 21-28 | Me | $(CH_2)_2$ | 3-Cl | $CH_2$ | OEt | 4-iPrO-Ph | O |
| 21-29 | Me | $(CH_2)_2$ | 3-Cl | $CH_2$ | OEt | 4-MeS-Ph | O |
| 21-30 | Me | $(CH_2)_2$ | 3-Cl | $CH_2$ | OEt | 4-EtS-Ph | O |
| 21-31 | Me | $(CH_2)_2$ | 3-Cl | $CH_2$ | OEt | 4-iPrS-Ph | O |
| 21-32 | Me | $(CH_2)_2$ | 3-Cl | $CH_2$ | OEt | 4-MeSO$_2$-Ph | O |
| 21-33 | Me | $(CH_2)_2$ | 3-Cl | $CH_2$ | OEt | 4-EtSO$_2$-Ph | O |
| 21-34 | Me | $(CH_2)_2$ | 3-Cl | $CH_2$ | OEt | 4-iPrSO$_2$-Ph | O |
| 21-35 | Me | $(CH_2)_2$ | 3-Cl | $CH_2$ | OEt | 4-(Pyr-2)Ph | O |
| 21-36 | Me | $(CH_2)_2$ | 3-Cl | $CH_2$ | OEt | 4-(Pyr-3)Ph | O |
| 21-37 | Me | $(CH_2)_2$ | 3-Cl | $CH_2$ | OEt | 4-(Pyr-3)Ph | O |
| 21-38 | Me | $(CH_2)_2$ | 3-Cl | $CH_2$ | OEt | 3-Ph-6-Pyr | O |

TABLE 22

| Exemplification No. compound. | R¹ | R² | R³ | Z | W | X | Y |
|---|---|---|---|---|---|---|---|
| 22-1 | Me | $(CH_2)_2$ | 2-MeO | $CH_2$ | OEt | 4-Et-Ph | O |
| 22-2 | Me | $(CH_2)_2$ | 2-MeO | $CH_2$ | OEt | 4-iPr-Ph | O |
| 22-3 | Me | $(CH_2)_2$ | 2-MeO | $CH_2$ | OEt | 3-Ph-Ph | O |
| 22-4 | Me | $(CH_2)_2$ | 2-MeO | $CH_2$ | OEt | 4-Ph-Ph | O |
| 22-5 | Me | $(CH_2)_2$ | 2-MeO | $CH_2$ | OEt | 3-Pyr | O |
| 22-6 | Me | $(CH_2)_2$ | 2-MeO | $CH_2$ | OEt | 5-Me-3-Pyr | O |
| 22-7 | Me | $(CH_2)_2$ | 2-MeO | $CH_2$ | OEt | 5-Et-3-Pyr | O |
| 22-8 | Me | $(CH_2)_2$ | 2-MeO | $CH_2$ | OEt | 5-Ph-3-Pyr | O |
| 22-9 | Me | $(CH_2)_2$ | 2-MeO | $CH_2$ | OEt | 6-Me-3-Pyr | O |
| 22-10 | Me | $(CH_2)_2$ | 2-MeO | $CH_2$ | OEt | 6-Et-3-Pyr | O |
| 22-11 | Me | $(CH_2)_2$ | 2-MeO | $CH_2$ | OEt | 6-Ph-3-Pyr | O |
| 22-12 | Me | $(CH_2)_2$ | 2-MeO | $CH_2$ | OEt | 6-MeO-3-Pyr | O |
| 22-13 | Me | $(CH_2)_2$ | 2-MeO | $CH_2$ | OEt | 6-EtO-3-Pyr | O |
| 22-14 | Me | $(CH_2)_2$ | 2-MeO | $CH_2$ | OEt | 6-iPrO-3-Pyr | O |
| 22-15 | Me | $(CH_2)_2$ | 2-MeO | $CH_2$ | OEt | 6-MeS-3-Pyr | O |
| 22-16 | Me | $(CH_2)_2$ | 2-MeO | $CH_2$ | OEt | 6-EtS-3-Pyr | O |
| 22-17 | Me | $(CH_2)_2$ | 2-MeO | $CH_2$ | OEt | 6-iPrS-3-Pyr | O |
| 22-18 | Me | $(CH_2)_2$ | 2-MeO | $CH_2$ | OEt | 6-MeSO$_2$-3-Pyr | O |
| 22-19 | Me | $(CH_2)_2$ | 2-MeO | $CH_2$ | OEt | 6-EtSO$_2$-3-Pyr | O |
| 22-20 | Me | $(CH_2)_2$ | 2-MeO | $CH_2$ | OEt | 6-iPrSO$_2$-3-Pyr | O |
| 22-21 | Me | $(CH_2)_2$ | 2-MeO | $CH_2$ | OEt | 6-Bz-3-Pyr | O |
| 22-22 | Me | $(CH_2)_2$ | 2-MeO | $CH_2$ | OEt | 6-PhO-3-Pyr | O |
| 22-23 | Me | $(CH_2)_2$ | 2-MeO | $CH_2$ | OEt | 6-PhS-3-Pyr | O |
| 22-24 | Me | $(CH_2)_2$ | 2-MeO | $CH_2$ | OEt | 6-PhSO$_2$-3-Pyr | O |
| 22-25 | Me | $(CH_2)_2$ | 2-MeO | $CH_2$ | OEt | 2-Quin | O |
| 22-26 | Me | $(CH_2)_2$ | 2-MeO | $CH_2$ | OEt | 4-MeO-Ph | O |
| 22-27 | Me | $(CH_2)_2$ | 2-MeO | $CH_2$ | OEt | 4-EtO-Ph | O |
| 22-28 | Me | $(CH_2)_2$ | 2-MeO | $CH_2$ | OEt | 4-iPrO-Ph | O |
| 22-29 | Me | $(CH_2)_2$ | 2-MeO | $CH_2$ | OEt | 4-MeS-Ph | O |
| 22-30 | Me | $(CH_2)_2$ | 2-MeO | $CH_2$ | OEt | 4-EtS-Ph | O |
| 22-31 | Me | $(CH_2)_2$ | 2-MeO | $CH_2$ | OEt | 4-iPrS-Ph | O |
| 22-32 | Me | $(CH_2)_2$ | 2-MeO | $CH_2$ | OEt | 4-MeSO$_2$-Ph | O |
| 22-33 | Me | $(CH_2)_2$ | 2-MeO | $CH_2$ | OEt | 4-EtSO$_2$-Ph | O |
| 22-34 | Me | $(CH_2)_2$ | 2-MeO | $CH_2$ | OEt | 4-iPrSO$_2$-Ph | O |
| 22-35 | Me | $(CH_2)_2$ | 2-MeO | $CH_2$ | OEt | 4-(Pyr-2)Ph | O |
| 22-36 | Me | $(CH_2)_2$ | 2-MeO | $CH_2$ | OEt | 4-(Pyr-3)Ph | O |
| 22-37 | Me | $(CH_2)_2$ | 2-MeO | $CH_2$ | OEt | 4-(Pyr-4)Ph | O |
| 22-38 | Me | $(CH_2)_2$ | 2-MeO | $CH_2$ | OEt | 3-Ph-6-Pyr | O |

TABLE 23

| Exemplification No. compound. | R¹ | R² | R³ | Z | W | X | Y |
|---|---|---|---|---|---|---|---|
| 23-1 | Me | $(CH_2)_2$ | 3-MeO | $CH_2$ | OEt | 4-Et-Ph | O |
| 23-2 | Me | $(CH_2)_2$ | 3-MeO | $CH_2$ | OEt | 4-iPr-Ph | O |
| 23-3 | Me | $(CH_2)_2$ | 3-MeO | $CH_2$ | OEt | 3-Ph-Ph | O |
| 23-4 | Me | $(CH_2)_2$ | 3-MeO | $CH_2$ | OEt | 4-Ph-Ph | O |
| 23-5 | Me | $(CH_2)_2$ | 3-MeO | $CH_2$ | OEt | 3-Pyr | O |

TABLE 23-continued

| Exemplification No. compound. | R¹ | R² | R³ | Z | W | X | Y |
|---|---|---|---|---|---|---|---|
| 23-6 | Me | (CH₂)₂ | 3-MeO | CH₂ | OEt | 5-Me-3-Pyr | O |
| 23-7 | Me | (CH₂)₂ | 3-MeO | CH₂ | OEt | 5-Et-3-Pyr | O |
| 23-8 | Me | (CH₂)₂ | 3-MeO | CH₂ | OEt | 5-Ph-3-Pyr | O |
| 23-9 | Me | (CH₂)₂ | 3-MeO | CH₂ | OEt | 6-Me-3-Pyr | O |
| 23-10 | Me | (CH₂)₂ | 3-MeO | CH₂ | OEt | 6-Et-3-Pyr | O |
| 23-11 | Me | (CH₂)₂ | 3-MeO | CH₂ | OEt | 6-Ph-3-Pyr | O |
| 23-12 | Me | (CH₂)₂ | 3-MeO | CH₂ | OEt | 6-MeO-3-Pyr | O |
| 23-13 | Me | (CH₂)₂ | 3-MeO | CH₂ | OEt | 6-EtO-3-Pyr | O |
| 23-14 | Me | (CH₂)₂ | 3-MeO | CH₂ | OEt | 6-iPrO-3-Pyr | O |
| 23-15 | Me | (CH₂)₂ | 3-MeO | CH₂ | OEt | 6-MeS-3-Pyr | O |
| 23-16 | Me | (CH₂)₂ | 3-MeO | CH₂ | OEt | 6-EtS-3-Pyr | O |
| 23-17 | Me | (CH₂)₂ | 3-MeO | CH₂ | OEt | 6-iPrS-3-Pyr | O |
| 23-18 | Me | (CH₂)₂ | 3-MeO | CH₂ | OEt | 6-MeSO₂-3-Pyr | O |
| 23-19 | Me | (CH₂)₂ | 3-MeO | CH₂ | OEt | 6-EtSO₂-3-Pyr | O |
| 23-20 | Me | (CH₂)₂ | 3-MeO | CH₂ | OEt | 6-iPrSO₂-3-Pyr | O |
| 23-21 | Me | (CH₂)₂ | 3-MeO | CH₂ | OEt | 6-Bz-3-Pyr | O |
| 23-22 | Me | (CH₂)₂ | 3-MeO | CH₂ | OEt | 6-PhO-3-Pyr | O |
| 23-23 | Me | (CH₂)₂ | 3-MeO | CH₂ | OEt | 6-PhS-3-Pyr | O |
| 23-24 | Me | (CH₂)₂ | 3-MeO | CH₂ | OEt | 6-PhSO₂-3-Pyr | O |
| 23-25 | Me | (CH₂)₂ | 3-MeO | CH₂ | OEt | 2-Quin | O |
| 23-26 | Me | (CH₂)₂ | 3-MeO | CH₂ | OEt | 4-MeO-Ph | O |
| 23-27 | Me | (CH₂)₂ | 3-MeO | CH₂ | OEt | 4-EtO-Ph | O |
| 23-28 | Me | (CH₂)₂ | 3-MeO | CH₂ | OEt | 4-iPrO-Ph | O |
| 23-29 | Me | (CH₂)₂ | 3-MeO | CH₂ | OEt | 4-MeS-Ph | O |
| 23-30 | Me | (CH₂)₂ | 3-MeO | CH₂ | OEt | 4-EtS-Ph | O |
| 23-31 | Me | (CH₂)₂ | 3-MeO | CH₂ | OEt | 4-iPrS-Ph | O |
| 23-32 | Me | (CH₂)₂ | 3-MeO | CH₂ | OEt | 4-MeSO₂-Ph | O |
| 23-33 | Me | (CH₂)₂ | 3-MeO | CH₂ | OEt | 4-EtSO₂-Ph | O |
| 23-34 | Me | (CH₂)₂ | 3-MeO | CH₂ | OEt | 4-iPrSO₂-Ph | O |
| 23-35 | Me | (CH₂)₂ | 3-MeO | CH₂ | OEt | 4-(Pyr-2)Ph | O |
| 23-36 | Me | (CH₂)₂ | 3-MeO | CH₂ | OEt | 4-(Pyr-3)Ph | O |
| 23-37 | Me | (CH₂)₂ | 3-MeO | CH₂ | OEt | 4-(Pyr-4)Ph | O |
| 23-38 | Me | (CH₂)₂ | 3-MeO | CH₂ | OEt | 3-Ph-6-Pyr | O |

TABLE 24

| Exemplification No. compound. | R¹ | R² | R³ | Z | W | X | Y |
|---|---|---|---|---|---|---|---|
| 24-1 | Me | (CH₂)₂ | H | CH₂ | OPr | 4-Et-Ph | O |
| 24-2 | Me | (CH₂)₂ | H | CH₂ | OPr | 4-iPr-Ph | O |
| 24-3 | Me | (CH₂)₂ | H | CH₂ | OPr | 3-Ph-Ph | O |
| 24-4 | Me | (CH₂)₂ | H | CH₂ | OPr | 4-Ph-Ph | O |
| 24-5 | Me | (CH₂)₂ | H | CH₂ | OPr | 3-Pyr | O |
| 24-6 | Me | (CH₂)₂ | H | CH₂ | OPr | 5-Me-3-Pyr | O |
| 24-7 | Me | (CH₂)₂ | H | CH₂ | OPr | 5-Et-3-Pyr | O |
| 24-8 | Me | (CH₂)₂ | H | CH₂ | OPr | 5-Ph-3-Pyr | O |
| 24-9 | Me | (CH₂)₂ | H | CH₂ | OPr | 6-Me-3-Pyr | O |
| 24-10 | Me | (CH₂)₂ | H | CH₂ | OPr | 6-Et-3-Pyr | O |
| 24-11 | Me | (CH₂)₂ | H | CH₂ | OPr | 6-Ph-3-Pyr | O |
| 24-12 | Me | (CH₂)₂ | H | CH₂ | OPr | 6-MeO-3-Pyr | O |
| 24-13 | Me | (CH₂)₂ | H | CH₂ | OPr | 6-EtO-3-Pyr | O |
| 24-14 | Me | (CH₂)₂ | H | CH₂ | OPr | 6-iPrO-3-Pyr | O |
| 24-15 | Me | (CH₂)₂ | H | CH₂ | OPr | 6-MeS-3-Pyr | O |
| 24-16 | Me | (CH₂)₂ | H | CH₂ | OPr | 6-EtS-3-Pyr | O |
| 24-17 | Me | (CH₂)₂ | H | CH₂ | OPr | 6-iPrS-3-Pyr | O |
| 24-18 | Me | (CH₂)₂ | H | CH₂ | OPr | 6-MeSO₂-3-Pyr | O |
| 24-19 | Me | (CH₂)₂ | H | CH₂ | OPr | 6-EtSO₂-3-Pyr | O |
| 24-20 | Me | (CH₂)₂ | H | CH₂ | OPr | 6-iPrSO₂-3-Pyr | O |
| 24-21 | Me | (CH₂)₂ | H | CH₂ | OPr | 6-Bz-3-Pyr | O |
| 24-22 | Me | (CH₂)₂ | H | CH₂ | OPr | 6-PhO-3-Pyr | O |
| 24-23 | Me | (CH₂)₂ | H | CH₂ | OPr | 6-PhS-3-Pyr | O |
| 24-24 | Me | (CH₂)₂ | H | CH₂ | OPr | 6-PhSO₂-3-Pyr | O |
| 24-25 | Me | (CH₂)₂ | H | CH₂ | OPr | 2-Quin | O |
| 24-26 | Me | (CH₂)₂ | H | CH₂ | OPr | 4-MeO-Ph | O |
| 24-27 | Me | (CH₂)₂ | H | CH₂ | OPr | 4-EtO-Ph | O |
| 24-28 | Me | (CH₂)₂ | H | CH₂ | OPr | 4-iPrO-Ph | O |
| 24-29 | Me | (CH₂)₂ | H | CH₂ | OPr | 4-MeS-Ph | O |
| 24-30 | Me | (CH₂)₂ | H | CH₂ | OPr | 4-EtS-Ph | O |
| 24-31 | Me | (CH₂)₂ | H | CH₂ | OPr | 4-iPrS-Ph | O |
| 24-32 | Me | (CH₂)₂ | H | CH₂ | OPr | 4-MeSO₂-Ph | O |
| 24-33 | Me | (CH₂)₂ | H | CH₂ | OPr | 4-EtSO₂-Ph | O |
| 24-34 | Me | (CH₂)₂ | H | CH₂ | OPr | 4-iPrSO₂-Ph | O |
| 24-35 | Me | (CH₂)₂ | H | CH₂ | OPr | 4-(Pyr-2)Ph | O |
| 24-36 | Me | (CH₂)₂ | H | CH₂ | OPr | 4-(Pyr-3)Ph | O |
| 24-37 | Me | (CH₂)₂ | H | CH₂ | OPr | 4-(Pyr-4)Ph | O |
| 24-38 | Me | (CH₂)₂ | H | CH₂ | OPr | 3-Ph-6-Pyr | O |

TABLE 25

| Exemplification No. compound. | R¹ | R² | R³ | Z | W | X | Y |
|---|---|---|---|---|---|---|---|
| 25-1 | Me | (CH₂)₂ | H | CH₂ | OiPr | 4-Et-Ph | O |
| 25-2 | Me | (CH₂)₂ | H | CH₂ | OiPr | 4-iPr-Ph | O |
| 25-3 | Me | (CH₂)₂ | H | CH₂ | OiPr | 3-Ph-Ph | O |
| 25-4 | Me | (CH₂)₂ | H | CH₂ | OiPr | 4-Ph-Ph | O |
| 25-5 | Me | (CH₂)₂ | H | CH₂ | OiPr | 3-Pyr | O |
| 25-6 | Me | (CH₂)₂ | H | CH₂ | OiPr | 5-Me-3-Pyr | O |
| 25-7 | Me | (CH₂)₂ | H | CH₂ | OiPr | 5-Et-3-Pyr | O |
| 25-8 | Me | (CH₂)₂ | H | CH₂ | OiPr | 5-Ph-3-Pyr | O |
| 25-9 | Me | (CH₂)₂ | H | CH₂ | OiPr | 6-Me-3-Pyr | O |
| 25-10 | Me | (CH₂)₂ | H | CH₂ | OiPr | 6-Et-3-Pyr | O |
| 25-11 | Me | (CH₂)₂ | H | CH₂ | OiPr | 6-Ph-3-Pyr | O |
| 25-12 | Me | (CH₂)₂ | H | CH₂ | OiPr | 6-MeO-3-Pyr | O |
| 25-13 | Me | (CH₂)₂ | H | CH₂ | OiPr | 6-EtO-3-Pyr | O |
| 25-14 | Me | (CH₂)₂ | H | CH₂ | OiPr | 6-iPrO-3-Pyr | O |
| 25-15 | Me | (CH₂)₂ | H | CH₂ | OiPr | 6-MeS-3-Pyr | O |
| 25-16 | Me | (CH₂)₂ | H | CH₂ | OiPr | 6-EtS-3-Pyr | O |
| 25-17 | Me | (CH₂)₂ | H | CH₂ | OiPr | 6-iPrS-3-Pyr | O |
| 25-18 | Me | (CH₂)₂ | H | CH₂ | OiPr | 6-MeSO₂-3-Pyr | O |
| 25-19 | Me | (CH₂)₂ | H | CH₂ | OiPr | 6-EtSO₂-3-Pyr | O |
| 25-20 | Me | (CH₂)₂ | H | CH₂ | OiPr | 6-iPrSO₂-3-Pyr | O |

TABLE 25-continued

| Exemplification No. compound. | R¹ | R² | R³ | Z | W | X | Y |
|---|---|---|---|---|---|---|---|
| 25-21 | Me | (CH₂)₂ | H | CH₂ | OiPr | 6-Bz-3-Pyr | O |
| 25-22 | Me | (CH₂)₂ | H | CH₂ | OiPr | 6-PhO-3-Pyr | O |
| 25-23 | Me | (CH₂)₂ | H | CH₂ | OiPr | 6-PhS-3-Pyr | O |
| 25-24 | Me | (CH₂)₂ | H | CH₂ | OiPr | 6-PhSO₂-3-Pyr | O |
| 25-25 | Me | (CH₂)₂ | H | CH₂ | OiPr | 2-Quin | O |
| 25-26 | Me | (CH₂)₂ | H | CH₂ | OiPr | 4-MeO-Ph | O |
| 25-27 | Me | (CH₂)₂ | H | CH₂ | OiPr | 4-EtO-Ph | O |
| 25-28 | Me | (CH₂)₂ | H | CH₂ | OiPr | 4-iPrO-Ph | O |
| 25-29 | Me | (CH₂)₂ | H | CH₂ | OiPr | 4-MeS-Ph | O |
| 25-30 | Me | (CH₂)₂ | H | CH₂ | OiPr | 4-EtS-Ph | O |
| 25-31 | Me | (CH₂)₂ | H | CH₂ | OiPr | 4-iPrS-Ph | O |
| 25-32 | Me | (CH₂)₂ | H | CH₂ | OiPr | 4-MeSO₂-Ph | O |
| 25-33 | Me | (CH₂)₂ | H | CH₂ | OiPr | 4-EtSO₂-Ph | O |
| 25-34 | Me | (CH₂)₂ | H | CH₂ | OiPr | 4-iPrSO₂-Ph | O |
| 25-35 | Me | (CH₂)₂ | H | CH₂ | OiPr | 4-(Pyr-2)Ph | O |
| 25-36 | Me | (CH₂)₂ | H | CH₂ | OiPr | 4-(Pyr-3)Ph | O |
| 25-37 | Me | (CH₂)₂ | H | CH₂ | OiPr | 4-(Pyr-4)Ph | O |
| 25-38 | Me | (CH₂)₂ | H | CH₂ | OiPr | 3-Ph-6-Pyr | O |

TABLE 26

| Exemplification No. compound. | R¹ | R² | R³ | Z | W | X | Y |
|---|---|---|---|---|---|---|---|
| 26-1 | Me | (CH₂)₂ | H | CH₂ | SMe | 4-Et-Ph | O |
| 26-2 | Me | (CH₂)₂ | H | CH₂ | SMe | 4-iPr-Ph | O |
| 26-3 | Me | (CH₂)₂ | H | CH₂ | SMe | 3-Ph-Ph | O |
| 26-4 | Me | (CH₂)₂ | H | CH₂ | SMe | 4-Ph-Ph | O |
| 26-5 | Me | (CH₂)₂ | H | CH₂ | SMe | 3-Pyr | O |
| 26-6 | Me | (CH₂)₂ | H | CH₂ | SMe | 5-Me-3-Pyr | O |
| 26-7 | Me | (CH₂)₂ | H | CH₂ | SMe | 5-Et-3-Pyr | O |
| 26-8 | Me | (CH₂)₂ | H | CH₂ | SMe | 5-Ph-3-Pyr | O |
| 26-9 | Me | (CH₂)₂ | H | CH₂ | SMe | 6-Me-3-Pyr | O |
| 26-10 | Me | (CH₂)₂ | H | CH₂ | SMe | 6-Et-3-Pyr | O |
| 26-11 | Me | (CH₂)₂ | H | CH₂ | SMe | 6-Ph-3-Pyr | O |
| 26-12 | Me | (CH₂)₂ | H | CH₂ | SMe | 6-MeO-3-Pyr | O |
| 26-13 | Me | (CH₂)₂ | H | CH₂ | SMe | 6-EtO-3-Pyr | O |
| 26-14 | Me | (CH₂)₂ | H | CH₂ | SMe | 6-iPrO-3-Pyr | O |
| 26-15 | Me | (CH₂)₂ | H | CH₂ | SMe | 6-MeS-3-Pyr | O |
| 26-16 | Me | (CH₂)₂ | H | CH₂ | SMe | 6-EtS-3-Pyr | O |
| 26-17 | Me | (CH₂)₂ | H | CH₂ | SMe | 6-iPrS-3-Pyr | O |
| 26-18 | Me | (CH₂)₂ | H | CH₂ | SMe | 6-MeSO₂-3-Pyr | O |
| 26-19 | Me | (CH₂)₂ | H | CH₂ | SMe | 6-EtSO₂-3-Pyr | O |
| 26-20 | Me | (CH₂)₂ | H | CH₂ | SMe | 6-iPrSO₂-3-Pyr | O |
| 26-21 | Me | (CH₂)₂ | H | CH₂ | SMe | 6-Bz-3-Pyr | O |
| 26-22 | Me | (CH₂)₂ | H | CH₂ | SMe | 6-PhO-3-Pyr | O |
| 26-23 | Me | (CH₂)₂ | H | CH₂ | SMe | 6-PhS-3-Pyr | O |
| 26-24 | Me | (CH₂)₂ | H | CH₂ | SMe | 6-PhSO₂-3-Pyr | O |
| 26-25 | Me | (CH₂)₂ | H | CH₂ | SMe | 2-Quin | O |
| 26-26 | Me | (CH₂)₂ | H | CH₂ | SMe | 4-MeO-Ph | O |
| 26-27 | Me | (CH₂)₂ | H | CH₂ | SMe | 4-EtO-Ph | O |
| 26-28 | Me | (CH₂)₂ | H | CH₂ | SMe | 4-iPrO-Ph | O |
| 26-29 | Me | (CH₂)₂ | H | CH₂ | SMe | 4-MeS-Ph | O |
| 26-30 | Me | (CH₂)₂ | H | CH₂ | SMe | 4-EtS-Ph | O |
| 26-31 | Me | (CH₂)₂ | H | CH₂ | SMe | 4-iPrS-Ph | O |
| 26-32 | Me | (CH₂)₂ | H | CH₂ | SMe | 4-MeSO₂-Ph | O |
| 26-33 | Me | (CH₂)₂ | H | CH₂ | SMe | 4-EtSO₂-Ph | O |
| 26-34 | Me | (CH₂)₂ | H | CH₂ | SMe | 4-iPrSO₂-Ph | O |
| 26-35 | Me | (CH₂)₂ | H | CH₂ | SMe | 4-(Pyr-2)Ph | O |
| 26-36 | Me | (CH₂)₂ | H | CH₂ | SMe | 4-(Pyr-3)Ph | O |
| 26-37 | Me | (CH₂)₂ | H | CH₂ | SMe | 4-(Pyr-4)Ph | O |
| 26-38 | Me | (CH₂)₂ | H | CH₂ | SMe | 3-Ph-6-Pyr | O |

TABLE 27

| Exemplification No. compound. | R¹ | R² | R³ | Z | W | X | Y |
|---|---|---|---|---|---|---|---|
| 27-1 | Me | (CH₂)₂ | H | CH₂ | SEt | 4-Et-Ph | O |
| 27-2 | Me | (CH₂)₂ | H | CH₂ | SEt | 4-iPr-Ph | O |
| 27-3 | Me | (CH₂)₂ | H | CH₂ | SEt | 3-Ph-Ph | O |
| 27-4 | Me | (CH₂)₂ | H | CH₂ | SEt | 4-Ph-Ph | O |
| 27-5 | Me | (CH₂)₂ | H | CH₂ | SEt | 3-Pyr | O |
| 27-6 | Me | (CH₂)₂ | H | CH₂ | SEt | 5-Me-3-Pyr | O |
| 27-7 | Me | (CH₂)₂ | H | CH₂ | SEt | 5-Et-3-Pyr | O |
| 27-8 | Me | (CH₂)₂ | H | CH₂ | SEt | 5-Ph-3-Pyr | O |
| 27-9 | Me | (CH₂)₂ | H | CH₂ | SEt | 6-Me-3-Pyr | O |
| 27-10 | Me | (CH₂)₂ | H | CH₂ | SEt | 6-Et-3-Pyr | O |
| 27-11 | Me | (CH₂)₂ | H | CH₂ | SEt | 6-Ph-3-Pyr | O |
| 27-12 | Me | (CH₂)₂ | H | CH₂ | SEt | 6-MeO-3-Pyr | O |
| 27-13 | Me | (CH₂)₂ | H | CH₂ | SEt | 6-EtO-3-Pyr | O |
| 27-14 | Me | (CH₂)₂ | H | CH₂ | SEt | 6-iPrO-3-Pyr | O |
| 27-15 | Me | (CH₂)₂ | H | CH₂ | SEt | 6-MeS-3-Pyr | O |
| 27-16 | Me | (CH₂)₂ | H | CH₂ | SEt | 6-EtS-3-Pyr | O |
| 27-17 | Me | (CH₂)₂ | H | CH₂ | SEt | 6-iPrS-3-Pyr | O |
| 27-18 | Me | (CH₂)₂ | H | CH₂ | SEt | 6-MeSO₂-3-Pyr | O |
| 27-19 | Me | (CH₂)₂ | H | CH₂ | SEt | 6-EtSO₂-3-Pyr | O |
| 27-20 | Me | (CH₂)₂ | H | CH₂ | SEt | 6-iPrSO₂-3-Pyr | O |
| 27-21 | Me | (CH₂)₂ | H | CH₂ | SEt | 6-Bz-3-Pyr | O |
| 27-22 | Me | (CH₂)₂ | H | CH₂ | SEt | 6-PhO-3-Pyr | O |
| 27-23 | Me | (CH₂)₂ | H | CH₂ | SEt | 6-PhS-3-Pyr | O |
| 27-24 | Me | (CH₂)₂ | H | CH₂ | SEt | 6-PhSO₂-3-Pyr | O |
| 27-25 | Me | (CH₂)₂ | H | CH₂ | SEt | 2-Quin | O |
| 27-26 | Me | (CH₂)₂ | H | CH₂ | SEt | 4-MeO-Ph | O |
| 27-27 | Me | (CH₂)₂ | H | CH₂ | SEt | 4-EtO-Ph | O |
| 27-28 | Me | (CH₂)₂ | H | CH₂ | SEt | 4-iPrO-Ph | O |
| 27-29 | Me | (CH₂)₂ | H | CH₂ | SEt | 4-MeS-Ph | O |
| 27-30 | Me | (CH₂)₂ | H | CH₂ | SEt | 4-EtS-Ph | O |
| 27-31 | Me | (CH₂)₂ | H | CH₂ | SEt | 4-iPrS-Ph | O |
| 27-32 | Me | (CH₂)₂ | H | CH₂ | SEt | 4-MeSO₂-Ph | O |
| 27-33 | Me | (CH₂)₂ | H | CH₂ | SEt | 4-EtSO₂-Ph | O |
| 27-34 | Me | (CH₂)₂ | H | CH₂ | SEt | 4-iPrSO₂-Ph | O |
| 27-35 | Me | (CH₂)₂ | H | CH₂ | SEt | 4-(Pyr-2)Ph | O |
| 27-36 | Me | (CH₂)₂ | H | CH₂ | SEt | 4-(Pyr-3)Ph | O |
| 27-37 | Me | (CH₂)₂ | H | CH₂ | SEt | 4-(Pyr-4)Ph | O |
| 27-38 | Me | (CH₂)₂ | H | CH₂ | SEt | 3-Ph-6-Pyr | O |

TABLE 28

| Exemplification No. compound. | R¹ | R² | R³ | Z | W | X | Y |
|---|---|---|---|---|---|---|---|
| 28-1 | Me | (CH₂)₂ | H | CH₂ | SPr | 4-Et-Ph | O |
| 28-2 | Me | (CH₂)₂ | H | CH₂ | SPr | 4-iPr-Ph | O |
| 28-3 | Me | (CH₂)₂ | H | CH₂ | SPr | 3-Ph-Ph | O |
| 28-4 | Me | (CH₂)₂ | H | CH₂ | SPr | 4-Ph-Ph | O |
| 28-5 | Me | (CH₂)₂ | H | CH₂ | SPr | 3-Pyr | O |
| 28-6 | Me | (CH₂)₂ | H | CH₂ | SPr | 5-Me-3-Pyr | O |
| 28-7 | Me | (CH₂)₂ | H | CH₂ | SPr | 5-Et-3-Pyr | O |
| 28-8 | Me | (CH₂)₂ | H | CH₂ | SPr | 5-Ph-3-Pyr | O |
| 28-9 | Me | (CH₂)₂ | H | CH₂ | SPr | 6-Me-3-Pyr | O |
| 28-10 | Me | (CH₂)₂ | H | CH₂ | SPr | 6-Et-3-Pyr | O |
| 28-11 | Me | (CH₂)₂ | H | CH₂ | SPr | 6-Ph-3-Pyr | O |
| 28-12 | Me | (CH₂)₂ | H | CH₂ | SPr | 6-MeO-3-Pyr | O |
| 28-13 | Me | (CH₂)₂ | H | CH₂ | SPr | 6-EtO-3-Pyr | O |
| 28-14 | Me | (CH₂)₂ | H | CH₂ | SPr | 6-iPrO-3-Pyr | O |
| 28-15 | Me | (CH₂)₂ | H | CH₂ | SPr | 6-MeS-3-Pyr | O |
| 28-16 | Me | (CH₂)₂ | H | CH₂ | SPr | 6-EtS-3-Pyr | O |
| 28-17 | Me | (CH₂)₂ | H | CH₂ | SPr | 6-iPrS-3-Pyr | O |
| 28-18 | Me | (CH₂)₂ | H | CH₂ | SPr | 6-MeSO₂-3-Pyr | O |
| 28-19 | Me | (CH₂)₂ | H | CH₂ | SPr | 6-EtSO₂-3-Pyr | O |
| 28-20 | Me | (CH₂)₂ | H | CH₂ | SPr | 6-iPrSO₂-3-Pyr | O |
| 28-21 | Me | (CH₂)₂ | H | CH₂ | SPr | 6-Bz-3-Pyr | O |
| 28-22 | Me | (CH₂)₂ | H | CH₂ | SPr | 6-PhO-3-Pyr | O |
| 28-23 | Me | (CH₂)₂ | H | CH₂ | SPr | 6-PhS-3-Pyr | O |
| 28-24 | Me | (CH₂)₂ | H | CH₂ | SPr | 6-PhSO₂-3-Pyr | O |
| 28-25 | Me | (CH₂)₂ | H | CH₂ | SPr | 2-Quin | O |
| 28-26 | Me | (CH₂)₂ | H | CH₂ | SPr | 4-MeO-Ph | O |
| 28-27 | Me | (CH₂)₂ | H | CH₂ | SPr | 4-EtO-Ph | O |
| 28-28 | Me | (CH₂)₂ | H | CH₂ | SPr | 4-iPrO-Ph | O |
| 28-29 | Me | (CH₂)₂ | H | CH₂ | SPr | 4-MeS-Ph | O |
| 28-30 | Me | (CH₂)₂ | H | CH₂ | SPr | 4-EtS-Ph | O |
| 28-31 | Me | (CH₂)₂ | H | CH₂ | SPr | 4-iPrS-Ph | O |
| 28-32 | Me | (CH₂)₂ | H | CH₂ | SPr | 4-MeSO₂-Ph | O |

TABLE 28-continued

| Exemplification No. compound. | R¹ | R² | R³ | Z | W | X | Y |
|---|---|---|---|---|---|---|---|
| 28-33 | Me | (CH$_2$)$_2$ | H | CH$_2$ | SPr | 4-EtSO$_2$-Ph | O |
| 28-34 | Me | (CH$_2$)$_2$ | H | CH$_2$ | SPr | 4-iPrSO$_2$-Ph | O |
| 28-35 | Me | (CH$_2$)$_2$ | H | CH$_2$ | SPr | 4-(Pyr-2)Ph | O |
| 28-36 | Me | (CH$_2$)$_2$ | H | CH$_2$ | SPr | 4-(Pyr-3)Ph | O |
| 28-37 | Me | (CH$_2$)$_2$ | H | CH$_2$ | SPr | 4-(Pyr-4)Ph | O |
| 28-38 | Me | (CH$_2$)$_2$ | H | CH$_2$ | SPr | 3-Ph-6-Pyr | O |

TABLE 29

| Exemplification No. compound. | R¹ | R² | R³ | Z | W | X | Y |
|---|---|---|---|---|---|---|---|
| 29-1 | Me | (CH$_2$)$_2$ | H | CH$_2$ | SiPr | 4-Et-Ph | O |
| 29-2 | Me | (CH$_2$)$_2$ | H | CH$_2$ | SiPr | 4-iPr-Ph | O |
| 29-3 | Me | (CH$_2$)$_2$ | H | CH$_2$ | SiPr | 3-Ph-Ph | O |
| 29-4 | Me | (CH$_2$)$_2$ | H | CH$_2$ | SiPr | 4-Ph-Ph | O |
| 29-5 | Me | (CH$_2$)$_2$ | H | CH$_2$ | SiPr | 3-Pyr | O |
| 29-6 | Me | (CH$_2$)$_2$ | H | CH$_2$ | SiPr | 5-Me-3-Pyr | O |
| 29-7 | Me | (CH$_2$)$_2$ | H | CH$_2$ | SiPr | 5-Et-3-Pyr | O |
| 29-8 | Me | (CH$_2$)$_2$ | H | CH$_2$ | SiPr | 5-Ph-3-Pyr | O |
| 29-9 | Me | (CH$_2$)$_2$ | H | CH$_2$ | SiPr | 6-Me-3-Pyr | O |
| 29-10 | Me | (CH$_2$)$_2$ | H | CH$_2$ | SiPr | 6-Et-3-Pyr | O |
| 29-11 | Me | (CH$_2$)$_2$ | H | CH$_2$ | SiPr | 6-Ph-3-Pyr | O |
| 29-12 | Me | (CH$_2$)$_2$ | H | CH$_2$ | SiPr | 6-MeO-3-Pyr | O |
| 29-13 | Me | (CH$_2$)$_2$ | H | CH$_2$ | SiPr | 6-EtO-3-Pyr | O |
| 29-14 | Me | (CH$_2$)$_2$ | H | CH$_2$ | SiPr | 6-iPrO-3-Pyr | O |
| 29-15 | Me | (CH$_2$)$_2$ | H | CH$_2$ | SiPr | 6-MeS-3-Pyr | O |
| 29-16 | Me | (CH$_2$)$_2$ | H | CH$_2$ | SiPr | 6-EtS-3-Pyr | O |
| 29-17 | Me | (CH$_2$)$_2$ | H | CH$_2$ | SiPr | 6-iPrS-3-Pyr | O |
| 29-18 | Me | (CH$_2$)$_2$ | H | CH$_2$ | SiPr | 6-MeSO$_2$-3-Pyr | O |
| 29-19 | Me | (CH$_2$)$_2$ | H | CH$_2$ | SiPr | 6-EtSO$_2$-3-Pyr | O |
| 29-20 | Me | (CH$_2$)$_2$ | H | CH$_2$ | SiPr | 6-iPrSO$_2$-3-Pyr | O |
| 29-21 | Me | (CH$_2$)$_2$ | H | CH$_2$ | SiPr | 6-Bz-3-Pyr | O |
| 29-22 | Me | (CH$_2$)$_2$ | H | CH$_2$ | SiPr | 6-PhO-3-Pyr | O |
| 29-23 | Me | (CH$_2$)$_2$ | H | CH$_2$ | SiPr | 6-PhS-3-Pyr | O |
| 29-24 | Me | (CH$_2$)$_2$ | H | CH$_2$ | SiPr | 6-PhSO$_2$-3-Pyr | O |
| 29-25 | Me | (CH$_2$)$_2$ | H | CH$_2$ | SiPr | 2-Quin | O |
| 29-26 | Me | (CH$_2$)$_2$ | H | CH$_2$ | SiPr | 4-MeO-Ph | O |
| 29-27 | Me | (CH$_2$)$_2$ | H | CH$_2$ | SiPr | 4-EtO-Ph | O |
| 29-28 | Me | (CH$_2$)$_2$ | H | CH$_2$ | SiPr | 4-iPrO-Ph | O |
| 29-29 | Me | (CH$_2$)$_2$ | H | CH$_2$ | SiPr | 4-MeS-Ph | O |
| 29-30 | Me | (CH$_2$)$_2$ | H | CH$_2$ | SiPr | 4-EtS-Ph | O |
| 29-31 | Me | (CH$_2$)$_2$ | H | CH$_2$ | SiPr | 4-iPrS-Ph | O |
| 29-32 | Me | (CH$_2$)$_2$ | H | CH$_2$ | SiPr | 4-MeSO$_2$-Ph | O |
| 29-33 | Me | (CH$_2$)$_2$ | H | CH$_2$ | SiPr | 4-EtSO$_2$-Ph | O |
| 29-34 | Me | (CH$_2$)$_2$ | H | CH$_2$ | SiPr | 4-iPrSO$_2$-Ph | O |
| 29-35 | Me | (CH$_2$)$_2$ | H | CH$_2$ | SiPr | 4-(Pyr-2)Ph | O |
| 29-36 | Me | (CH$_2$)$_2$ | H | CH$_2$ | SiPr | 4-(Pyr-3)Ph | O |
| 29-37 | Me | (CH$_2$)$_2$ | H | CH$_2$ | SiPr | 4-(Pyr-4)Ph | O |
| 29-38 | Me | (CH$_2$)$_2$ | H | CH$_2$ | SiPr | 3-Ph-6-Pyr | O |

TABLE 30

| Exemplification No. compound. | R¹ | R² | R³ | Z | W | X | Y |
|---|---|---|---|---|---|---|---|
| 30-1 | Me | (CH$_2$)$_2$ | H | CH$_2$ | OPh | 4-Et-Ph | O |
| 30-2 | Me | (CH$_2$)$_2$ | H | CH$_2$ | OPh | 4-iPr-Ph | O |
| 30-3 | Me | (CH$_2$)$_2$ | H | CH$_2$ | OPh | 3-Ph-Ph | O |
| 30-4 | Me | (CH$_2$)$_2$ | H | CH$_2$ | OPh | 4-Ph-Ph | O |
| 30-5 | Me | (CH$_2$)$_2$ | H | CH$_2$ | OPh | 3-Pyr | O |
| 30-6 | Me | (CH$_2$)$_2$ | H | CH$_2$ | OPh | 5-Me-3-Pyr | O |
| 30-7 | Me | (CH$_2$)$_2$ | H | CH$_2$ | OPh | 5-Et-3-Pyr | O |
| 30-8 | Me | (CH$_2$)$_2$ | H | CH$_2$ | OPh | 5-Ph-3-Pyr | O |
| 30-9 | Me | (CH$_2$)$_2$ | H | CH$_2$ | OPh | 6-Me-3-Pyr | O |
| 30-10 | Me | (CH$_2$)$_2$ | H | CH$_2$ | OPh | 6-Et-3-Pyr | O |
| 30-11 | Me | (CH$_2$)$_2$ | H | CH$_2$ | OPh | 6-Ph-3-Pyr | O |
| 30-12 | Me | (CH$_2$)$_2$ | H | CH$_2$ | OPh | 6-MeO-3-Pyr | O |
| 30-13 | Me | (CH$_2$)$_2$ | H | CH$_2$ | OPh | 6-EtO-3-Pyr | O |
| 30-14 | Me | (CH$_2$)$_2$ | H | CH$_2$ | OPh | 6-iPrO-3-Pyr | O |
| 30-15 | Me | (CH$_2$)$_2$ | H | CH$_2$ | OPh | 6-MeS-3-Pyr | O |
| 30-16 | Me | (CH$_2$)$_2$ | H | CH$_2$ | OPh | 6-EtS-3-Pyr | O |
| 30-17 | Me | (CH$_2$)$_2$ | H | CH$_2$ | OPh | 6-iPrS-3-Pyr | O |
| 30-18 | Me | (CH$_2$)$_2$ | H | CH$_2$ | OPh | 6-MeSO$_2$-3-Pyr | O |
| 30-19 | Me | (CH$_2$)$_2$ | H | CH$_2$ | OPh | 6-EtSO$_2$-3-Pyr | O |
| 30-20 | Me | (CH$_2$)$_2$ | H | CH$_2$ | OPh | 6-iPrSO$_2$-3-Pyr | O |
| 30-21 | Me | (CH$_2$)$_2$ | H | CH$_2$ | OPh | 6-Bz-3-Pyr | O |
| 30-22 | Me | (CH$_2$)$_2$ | H | CH$_2$ | OPh | 6-PhO-3-Pyr | O |
| 30-23 | Me | (CH$_2$)$_2$ | H | CH$_2$ | OPh | 6-PhS-3-Pyr | O |
| 30-24 | Me | (CH$_2$)$_2$ | H | CH$_2$ | OPh | 6-PhSO$_2$-3-Pyr | O |
| 30-25 | Me | (CH$_2$)$_2$ | H | CH$_2$ | OPh | 2-Quin | O |
| 30-26 | Me | (CH$_2$)$_2$ | H | CH$_2$ | OPh | 4-MeO-Ph | O |
| 30-27 | Me | (CH$_2$)$_2$ | H | CH$_2$ | OPh | 4-EtO-Ph | O |
| 30-28 | Me | (CH$_2$)$_2$ | H | CH$_2$ | OPh | 4-iPrO-Ph | O |
| 30-29 | Me | (CH$_2$)$_2$ | H | CH$_2$ | OPh | 4-MeS-Ph | O |
| 30-30 | Me | (CH$_2$)$_2$ | H | CH$_2$ | OPh | 4-EtS-Ph | O |
| 30-31 | Me | (CH$_2$)$_2$ | H | CH$_2$ | OPh | 4-iPrS-Ph | O |
| 30-32 | Me | (CH$_2$)$_2$ | H | CH$_2$ | OPh | 4-MeSO$_2$-Ph | O |
| 30-33 | Me | (CH$_2$)$_2$ | H | CH$_2$ | OPh | 4-EtSO$_2$-Ph | O |
| 30-34 | Me | (CH$_2$)$_2$ | H | CH$_2$ | OPh | 4-iPrSO$_2$-Ph | O |
| 30-35 | Me | (CH$_2$)$_2$ | H | CH$_2$ | OPh | 4-(Pyr-2)Ph | O |
| 30-36 | Me | (CH$_2$)$_2$ | H | CH$_2$ | OPh | 4-(Pyr-3)Ph | O |
| 30-37 | Me | (CH$_2$)$_2$ | H | CH$_2$ | OPh | 4-(Pyr-4)Ph | O |
| 30-38 | Me | (CH$_2$)$_2$ | H | CH$_2$ | OPh | 3-Ph-6-Pyr | O |

TABLE 31

| Exemplification No. compound. | R¹ | R² | R³ | Z | W | X | Y |
|---|---|---|---|---|---|---|---|
| 31-1 | Me | (CH$_2$)$_2$ | H | CH$_2$ | SPh | 4-Et-Ph | O |
| 31-2 | Me | (CH$_2$)$_2$ | H | CH$_2$ | SPh | 4-iPr-Ph | O |
| 31-3 | Me | (CH$_2$)$_2$ | H | CH$_2$ | SPh | 3-Ph-Ph | O |
| 31-4 | Me | (CH$_2$)$_2$ | H | CH$_2$ | SPh | 4-Ph-Ph | O |
| 31-5 | Me | (CH$_2$)$_2$ | H | CH$_2$ | SPh | 3-Pyr | O |
| 31-6 | Me | (CH$_2$)$_2$ | H | CH$_2$ | SPh | 5-Me-3-Pyr | O |
| 31-7 | Me | (CH$_2$)$_2$ | H | CH$_2$ | SPh | 5-Et-3-Pyr | O |
| 31-8 | Me | (CH$_2$)$_2$ | H | CH$_2$ | SPh | 5-Ph-3-Pyr | O |
| 31-9 | Me | (CH$_2$)$_2$ | H | CH$_2$ | SPh | 6-Me-3-Pyr | O |
| 31-10 | Me | (CH$_2$)$_2$ | H | CH$_2$ | SPh | 6-Et-3-Pyr | O |
| 31-11 | Me | (CH$_2$)$_2$ | H | CH$_2$ | SPh | 6-Ph-3-Pyr | O |
| 31-12 | Me | (CH$_2$)$_2$ | H | CH$_2$ | SPh | 6-MeO-3-Pyr | O |
| 31-13 | Me | (CH$_2$)$_2$ | H | CH$_2$ | SPh | 6-EtO-3-Pyr | O |
| 31-14 | Me | (CH$_2$)$_2$ | H | CH$_2$ | SPh | 6-iPrO-3-Pyr | O |
| 31-15 | Me | (CH$_2$)$_2$ | H | CH$_2$ | SPh | 6-MeS-3-Pyr | O |
| 31-16 | Me | (CH$_2$)$_2$ | H | CH$_2$ | SPh | 6-EtS-3-Pyr | O |
| 31-17 | Me | (CH$_2$)$_2$ | H | CH$_2$ | SPh | 6-iPrS-3-Pyr | O |
| 31-18 | Me | (CH$_2$)$_2$ | H | CH$_2$ | SPh | 6-MeSO$_2$-3-Pyr | O |
| 31-19 | Me | (CH$_2$)$_2$ | H | CH$_2$ | SPh | 6-EtSO$_2$-3-Pyr | O |
| 31-20 | Me | (CH$_2$)$_2$ | H | CH$_2$ | SPh | 6-iPrSO$_2$-3-Pyr | O |
| 31-21 | Me | (CH$_2$)$_2$ | H | CH$_2$ | SPh | 6-Bz-3-Pyr | O |
| 31-22 | Me | (CH$_2$)$_2$ | H | CH$_2$ | SPh | 6-PhO-3-Pyr | O |
| 31-23 | Me | (CH$_2$)$_2$ | H | CH$_2$ | SPh | 6-PhS-3-Pyr | O |
| 31-24 | Me | (CH$_2$)$_2$ | H | CH$_2$ | SPh | 6-PhSO$_2$-3-Pyr | O |
| 31-25 | Me | (CH$_2$)$_2$ | H | CH$_2$ | SPh | 2-Quin | O |
| 31-26 | Me | (CH$_2$)$_2$ | H | CH$_2$ | SPh | 4-MeO-Ph | O |
| 31-27 | Me | (CH$_2$)$_2$ | H | CH$_2$ | SPh | 4-EtO-Ph | O |
| 31-28 | Me | (CH$_2$)$_2$ | H | CH$_2$ | SPh | 4-iPrO-Ph | O |
| 31-29 | Me | (CH$_2$)$_2$ | H | CH$_2$ | SPh | 4-MeS-Ph | O |
| 31-30 | Me | (CH$_2$)$_2$ | H | CH$_2$ | SPh | 4-EtS-Ph | O |
| 31-31 | Me | (CH$_2$)$_2$ | H | CH$_2$ | SPh | 4-iPrS-Ph | O |
| 31-32 | Me | (CH$_2$)$_2$ | H | CH$_2$ | SPh | 4-MeSO$_2$-Ph | O |
| 31-33 | Me | (CH$_2$)$_2$ | H | CH$_2$ | SPh | 4-EtSO$_2$-Ph | O |
| 31-34 | Me | (CH$_2$)$_2$ | H | CH$_2$ | SPh | 4-iPrSO$_2$-Ph | O |
| 31-35 | Me | (CH$_2$)$_2$ | H | CH$_2$ | SPh | 4-(Pyr-2)Ph | O |
| 31-36 | Me | (CH$_2$)$_2$ | H | CH$_2$ | SPh | 4-(Pyr-3)Ph | O |
| 31-37 | Me | (CH$_2$)$_2$ | H | CH$_2$ | SPh | 4-(Pyr-4)Ph | O |
| 31-38 | Me | (CH$_2$)$_2$ | H | CH$_2$ | SPh | 3-Ph-6-Pyr | O |

TABLE 32

| Exemplification No. compound. | R¹ | R² | R³ | Z | W | X | Y |
|---|---|---|---|---|---|---|---|
| 32-1 | Me | (CH$_2$)$_2$ | H | CH$_2$ | NHPh | 4-Et-Ph | O |
| 32-2 | Me | (CH$_2$)$_2$ | H | CH$_2$ | NHPh | 4-iPr-Ph | O |
| 32-3 | Me | (CH$_2$)$_2$ | H | CH$_2$ | NHPh | 3-Ph-Ph | O |
| 32-4 | Me | (CH$_2$)$_2$ | H | CH$_2$ | NHPh | 4-Ph-Ph | O |
| 32-5 | Me | (CH$_2$)$_2$ | H | CH$_2$ | NHPh | 3-Pyr | O |
| 32-6 | Me | (CH$_2$)$_2$ | H | CH$_2$ | NHPh | 5-Me-3-Pyr | O |
| 32-7 | Me | (CH$_2$)$_2$ | H | CH$_2$ | NHPh | 5-Et-3-Pyr | O |
| 32-8 | Me | (CH$_2$)$_2$ | H | CH$_2$ | NHPh | 5-Ph-3-Pyr | O |
| 32-9 | Me | (CH$_2$)$_2$ | H | CH$_2$ | NHPh | 6-Me-3-Pyr | O |
| 32-10 | Me | (CH$_2$)$_2$ | H | CH$_2$ | NHPh | 6-Et-3-Pyr | O |
| 32-11 | Me | (CH$_2$)$_2$ | H | CH$_2$ | NHPh | 6-Ph-3-Pyr | O |
| 32-12 | Me | (CH$_2$)$_2$ | H | CH$_2$ | NHPh | 6-MeO-3-Pyr | O |
| 32-13 | Me | (CH$_2$)$_2$ | H | CH$_2$ | NHPh | 6-EtO-3-Pyr | O |
| 32-14 | Me | (CH$_2$)$_2$ | H | CH$_2$ | NHPh | 6-iPrO-3-Pyr | O |
| 32-15 | Me | (CH$_2$)$_2$ | H | CH$_2$ | NHPh | 6-MeS-3-Pyr | O |
| 32-16 | Me | (CH$_2$)$_2$ | H | CH$_2$ | NHPh | 6-EtS-3-Pyr | O |
| 32-17 | Me | (CH$_2$)$_2$ | H | CH$_2$ | NHPh | 6-iPrS-3-Pyr | O |
| 32-18 | Me | (CH$_2$)$_2$ | H | CH$_2$ | NHPh | 6-MeSO$_2$-3-Pyr | O |
| 32-19 | Me | (CH$_2$)$_2$ | H | CH$_2$ | NHPh | 6-EtSO$_2$-3-Pyr | O |
| 32-20 | Me | (CH$_2$)$_2$ | H | CH$_2$ | NHPh | 6-iPrSO$_2$-3-Pyr | O |
| 32-21 | Me | (CH$_2$)$_2$ | H | CH$_2$ | NHPh | 6-Bz-3-Pyr | O |
| 32-22 | Me | (CH$_2$)$_2$ | H | CH$_2$ | NHPh | 6-PhO-3-Pyr | O |
| 32-23 | Me | (CH$_2$)$_2$ | H | CH$_2$ | NHPh | 6-PhS-3-Pyr | O |
| 32-24 | Me | (CH$_2$)$_2$ | H | CH$_2$ | NHPh | 6-PhSO$_2$-3-Pyr | O |
| 32-25 | Me | (CH$_2$)$_2$ | H | CH$_2$ | NHPh | 2-Quin | O |
| 32-26 | Me | (CH$_2$)$_2$ | H | CH$_2$ | NHPh | 4-MeO-Ph | O |
| 32-27 | Me | (CH$_2$)$_2$ | H | CH$_2$ | NHPh | 4-EtO-Ph | O |
| 32-28 | Me | (CH$_2$)$_2$ | H | CH$_2$ | NHPh | 4-iPrO-Ph | O |
| 32-29 | Me | (CH$_2$)$_2$ | H | CH$_2$ | NHPh | 4-MeS-Ph | O |
| 32-30 | Me | (CH$_2$)$_2$ | H | CH$_2$ | NHPh | 4-EtS-Ph | O |
| 32-31 | Me | (CH$_2$)$_2$ | H | CH$_2$ | NHPh | 4-iPrS-Ph | O |
| 32-32 | Me | (CH$_2$)$_2$ | H | CH$_2$ | NHPh | 4-MeSO$_2$-Ph | O |
| 32-33 | Me | (CH$_2$)$_2$ | H | CH$_2$ | NHPh | 4-EtSO$_2$-Ph | O |
| 32-34 | Me | (CH$_2$)$_2$ | H | CH$_2$ | NHPh | 4-iPrSO$_2$-Ph | O |
| 32-35 | Me | (CH$_2$)$_2$ | H | CH$_2$ | NHPh | 4-(Pyr-2)Ph | O |
| 32-36 | Me | (CH$_2$)$_2$ | H | CH$_2$ | NHPh | 4-(Pyr-3)Ph | O |
| 32-37 | Me | (CH$_2$)$_2$ | H | CH$_2$ | NHPh | 4-(Pyr-4)Ph | O |
| 32-38 | Me | (CH$_2$)$_2$ | H | CH$_2$ | NHPh | 3-Ph-6-Pyr | O |

TABLE 33

| Exemplification No. compound. | R¹ | R² | R³ | Z | W | X | Y |
|---|---|---|---|---|---|---|---|
| 33-1 | Me | (CH$_2$)$_2$ | H | — | OMe | 4-Et-Ph | O |
| 33-2 | Me | (CH$_2$)$_2$ | H | — | OMe | 4-iPr-Ph | O |
| 33-3 | Me | (CH$_2$)$_2$ | H | — | OMe | 3-Ph-Ph | O |
| 33-4 | Me | (CH$_2$)$_2$ | H | — | OMe | 4-Ph-Ph | O |
| 33-5 | Me | (CH$_2$)$_2$ | H | — | OMe | 3-Pyr | O |
| 33-6 | Me | (CH$_2$)$_2$ | H | — | OMe | 5-Me-3-Pyr | O |
| 33-7 | Me | (CH$_2$)$_2$ | H | — | OMe | 5-Et-3-Pyr | O |
| 33-8 | Me | (CH$_2$)$_2$ | H | — | OMe | 5-Ph-3-Pyr | O |
| 33-9 | Me | (CH$_2$)$_2$ | H | — | OMe | 6-Me-3-Pyr | O |
| 33-10 | Me | (CH$_2$)$_2$ | H | — | OMe | 6-Et-3-Pyr | O |
| 33-11 | Me | (CH$_2$)$_2$ | H | — | OMe | 6-Ph-3-Pyr | O |
| 33-12 | Me | (CH$_2$)$_2$ | H | — | OMe | 6-MeO-3-Pyr | O |
| 33-13 | Me | (CH$_2$)$_2$ | H | — | OMe | 6-EtO-3-Pyr | O |
| 33-14 | Me | (CH$_2$)$_2$ | H | — | OMe | 6-iPrO-3-Pyr | O |
| 33-15 | Me | (CH$_2$)$_2$ | H | — | OMe | 6-MeS-3-Pyr | O |
| 33-16 | Me | (CH$_2$)$_2$ | H | — | OMe | 6-EtS-3-Pyr | O |
| 33-17 | Me | (CH$_2$)$_2$ | H | — | OMe | 6-iPrS-3-Pyr | O |
| 33-18 | Me | (CH$_2$)$_2$ | H | — | OMe | 6-MeSO$_2$-3-Pyr | O |
| 33-19 | Me | (CH$_2$)$_2$ | H | — | OMe | 6-EtSO$_2$-3-Pyr | O |
| 33-20 | Me | (CH$_2$)$_2$ | H | — | OMe | 6-iPrSO$_2$-3-Pyr | O |
| 33-21 | Me | (CH$_2$)$_2$ | H | — | OMe | 6-Bz-3-Pyr | O |
| 33-22 | Me | (CH$_2$)$_2$ | H | — | OMe | 6-PhO-3-Pyr | O |
| 33-23 | Me | (CH$_2$)$_2$ | H | — | OMe | 6-PhS-3-Pyr | O |
| 33-24 | Me | (CH$_2$)$_2$ | H | — | OMe | 6-PhSO$_2$-3-Pyr | O |
| 33-25 | Me | (CH$_2$)$_2$ | H | — | OMe | 2-Quin | O |
| 33-26 | Me | (CH$_2$)$_2$ | H | — | OMe | 4-MeO-Ph | O |
| 33-27 | Me | (CH$_2$)$_2$ | H | — | OMe | 4-EtO-Ph | O |
| 33-28 | Me | (CH$_2$)$_2$ | H | — | OMe | 4-iPrO-Ph | O |
| 33-29 | Me | (CH$_2$)$_2$ | H | — | OMe | 4-MeS-Ph | O |
| 33-30 | Me | (CH$_2$)$_2$ | H | — | OMe | 4-EtS-Ph | O |
| 33-31 | Me | (CH$_2$)$_2$ | H | — | OMe | 4-iPrS-Ph | O |
| 33-32 | Me | (CH$_2$)$_2$ | H | — | OMe | 4-MeSO$_2$-Ph | O |
| 33-33 | Me | (CH$_2$)$_2$ | H | — | OMe | 4-EtSO$_2$-Ph | O |
| 33-34 | Me | (CH$_2$)$_2$ | H | — | OMe | 4-iPrSO$_2$-Ph | O |
| 33-35 | Me | (CH$_2$)$_2$ | H | — | OMe | 4-(Pyr-2)Ph | O |
| 33-36 | Me | (CH$_2$)$_2$ | H | — | OMe | 4-(Pyr-3)Ph | O |
| 33-37 | Me | (CH$_2$)$_2$ | H | — | OMe | 4-(Pyr-4)Ph | O |
| 33-38 | Me | (CH$_2$)$_2$ | H | — | OMe | 3-Ph-6-Pyr | O |

TABLE 34

| Exemplification No. compound. | R¹ | R² | R³ | Z | W | X | Y |
|---|---|---|---|---|---|---|---|
| 34-1 | Me | (CH$_2$)$_2$ | H | — | OEt | 4-Et-Ph | O |
| 34-2 | Me | (CH$_2$)$_2$ | H | — | OEt | 4-iPr-Ph | O |
| 34-3 | Me | (CH$_2$)$_2$ | H | — | OEt | 3-Ph-Ph | O |
| 34-4 | Me | (CH$_2$)$_2$ | H | — | OEt | 4-Ph-Ph | O |
| 34-5 | Me | (CH$_2$)$_2$ | H | — | OEt | 3-Pyr | O |
| 34-6 | Me | (CH$_2$)$_2$ | H | — | OEt | 5-Me-3-Pyr | O |
| 34-7 | Me | (CH$_2$)$_2$ | H | — | OEt | 5-Et-3-Pyr | O |
| 34-8 | Me | (CH$_2$)$_2$ | H | — | OEt | 5-Ph-3-Pyr | O |
| 34-9 | Me | (CH$_2$)$_2$ | H | — | OEt | 6-Me-3-Pyr | O |
| 34-10 | Me | (CH$_2$)$_2$ | H | — | OEt | 6-Et-3-Pyr | O |
| 34-11 | Me | (CH$_2$)$_2$ | H | — | OEt | 6-Ph-3-Pyr | O |
| 34-12 | Me | (CH$_2$)$_2$ | H | — | OEt | 6-MeO-3-Pyr | O |
| 34-13 | Me | (CH$_2$)$_2$ | H | — | OEt | 6-EtO-3-Pyr | O |
| 34-14 | Me | (CH$_2$)$_2$ | H | — | OEt | 6-iPrO-3-Pyr | O |
| 34-15 | Me | (CH$_2$)$_2$ | H | — | OEt | 6-MeS-3-Pyr | O |
| 34-16 | Me | (CH$_2$)$_2$ | H | — | OEt | 6-EtS-3-Pyr | O |
| 34-17 | Me | (CH$_2$)$_2$ | H | — | OEt | 6-iPrS-3-Pyr | O |
| 34-18 | Me | (CH$_2$)$_2$ | H | — | OEt | 6-MeSO$_2$-3-Pyr | O |
| 34-19 | Me | (CH$_2$)$_2$ | H | — | OEt | 6-EtSO$_2$-3-Pyr | O |
| 34-20 | Me | (CH$_2$)$_2$ | H | — | OEt | 6-iPrSO$_2$-3-Pyr | O |
| 34-21 | Me | (CH$_2$)$_2$ | H | — | OEt | 6-Bz-3-Pyr | O |
| 34-22 | Me | (CH$_2$)$_2$ | H | — | OEt | 6-PhO-3-Pyr | O |
| 34-23 | Me | (CH$_2$)$_2$ | H | — | OEt | 6-PhS-3-Pyr | O |
| 34-24 | Me | (CH$_2$)$_2$ | H | — | OEt | 6-PhSO$_2$-3-Pyr | O |
| 34-25 | Me | (CH$_2$)$_2$ | H | — | OEt | 2-Quin | O |
| 34-26 | Me | (CH$_2$)$_2$ | H | — | OEt | 4-MeO-Ph | O |
| 34-27 | Me | (CH$_2$)$_2$ | H | — | OEt | 4-EtO-Ph | O |
| 34-28 | Me | (CH$_2$)$_2$ | H | — | OEt | 4-iPrO-Ph | O |
| 34-29 | Me | (CH$_2$)$_2$ | H | — | OEt | 4-MeS-Ph | O |
| 34-30 | Me | (CH$_2$)$_2$ | H | — | OEt | 4-EtS-Ph | O |
| 34-31 | Me | (CH$_2$)$_2$ | H | — | OEt | 4-iPrS-Ph | O |
| 34-32 | Me | (CH$_2$)$_2$ | H | — | OEt | 4-MeSO$_2$-Ph | O |
| 34-33 | Me | (CH$_2$)$_2$ | H | — | OEt | 4-EtSO$_2$-Ph | O |
| 34-34 | Me | (CH$_2$)$_2$ | H | — | OEt | 4-iPrSO$_2$-Ph | O |
| 34-35 | Me | (CH$_2$)$_2$ | H | — | OEt | 4-(Pyr-2)Ph | O |
| 34-36 | Me | (CH$_2$)$_2$ | H | — | OEt | 4-(Pyr-3)Ph | O |
| 34-37 | Me | (CH$_2$)$_2$ | H | — | OEt | 4-(Pyr-4)Ph | O |
| 34-38 | Me | (CH$_2$)$_2$ | H | — | OEt | 3-Ph-6-Pyr | O |

TABLE 35

| Exemplification No. compound. | R¹ | R² | R³ | Z | W | X | Y |
|---|---|---|---|---|---|---|---|
| 35-1 | Me | (CH$_2$)$_2$ | H | — | OPr | 4-Et-Ph | O |
| 35-2 | Me | (CH$_2$)$_2$ | H | — | OPr | 4-iPr-Ph | O |
| 35-3 | Me | (CH$_2$)$_2$ | H | — | OPr | 3-Ph-Ph | O |
| 35-4 | Me | (CH$_2$)$_2$ | H | — | OPr | 4-Ph-Ph | O |
| 35-5 | Me | (CH$_2$)$_2$ | H | — | OPr | 3-Pyr | O |
| 35-6 | Me | (CH$_2$)$_2$ | H | — | OPr | 5-Me-3-Pyr | O |
| 35-7 | Me | (CH$_2$)$_2$ | H | — | OPr | 5-Et-3-Pyr | O |
| 35-8 | Me | (CH$_2$)$_2$ | H | — | OPr | 5-Ph-3-Pyr | O |
| 35-9 | Me | (CH$_2$)$_2$ | H | — | OPr | 6-Me-3-Pyr | O |
| 35-10 | Me | (CH$_2$)$_2$ | H | — | OPr | 6-Et-3-Pyr | O |
| 35-11 | Me | (CH$_2$)$_2$ | H | — | OPr | 6-Ph-3-Pyr | O |

TABLE 35-continued

| Exemplification No. compound. | R¹ | R² | R³ | Z | W | X | Y |
|---|---|---|---|---|---|---|---|
| 35-12 | Me | (CH₂)₂ | H | — | OPr | 6-MeO-3-Pyr | O |
| 35-13 | Me | (CH₂)₂ | H | — | OPr | 6-EtO-3-Pyr | O |
| 35-14 | Me | (CH₂)₂ | H | — | OPr | 6-iPrO-3-Pyr | O |
| 35-15 | Me | (CH₂)₂ | H | — | OPr | 6-MeS-3-Pyr | O |
| 35-16 | Me | (CH₂)₂ | H | — | OPr | 6-EtS-3-Pyr | O |
| 35-17 | Me | (CH₂)₂ | H | — | OPr | 6-iPrS-3-Pyr | O |
| 35-18 | Me | (CH₂)₂ | H | — | OPr | 6-MeSO₂-3-Pyr | O |
| 35-19 | Me | (CH₂)₂ | H | — | OPr | 6-EtSO₂-3-Pyr | O |
| 35-20 | Me | (CH₂)₂ | H | — | OPr | 6-iPrSO₂-3-Pyr | O |
| 35-21 | Me | (CH₂)₂ | H | — | OPr | 6-Bz-3-Pyr | O |
| 35-22 | Me | (CH₂)₂ | H | — | OPr | 6-PhO-3-Pyr | O |
| 35-23 | Me | (CH₂)₂ | H | — | OPr | 6-PhS-3-Pyr | O |
| 35-24 | Me | (CH₂)₂ | H | — | OPr | 6-PhSO₂-3-Pyr | O |
| 35-25 | Me | (CH₂)₂ | H | — | OPr | 2-Quin | O |
| 35-26 | Me | (CH₂)₂ | H | — | OPr | 4-MeO-Ph | O |
| 35-27 | Me | (CH₂)₂ | H | — | OPr | 4-EtO-Ph | O |
| 35-28 | Me | (CH₂)₂ | H | — | OPr | 4-iPrO-Ph | O |
| 35-29 | Me | (CH₂)₂ | H | — | OPr | 4-MeS-Ph | O |
| 35-30 | Me | (CH₂)₂ | H | — | OPr | 4-EtS-Ph | O |
| 35-31 | Me | (CH₂)₂ | H | — | OPr | 4-iPrS-Ph | O |
| 35-32 | Me | (CH₂)₂ | H | — | OPr | 4-MeSO₂-Ph | O |
| 35-33 | Me | (CH₂)₂ | H | — | OPr | 4-EtSO₂-Ph | O |
| 35-34 | Me | (CH₂)₂ | H | — | OPr | 4-iPrSO₂-Ph | O |
| 35-35 | Me | (CH₂)₂ | H | — | OPr | 4-(Pyr-2)Ph | O |
| 35-36 | Me | (CH₂)₂ | H | — | OPr | 4-(Pyr-3)Ph | O |
| 35-37 | Me | (CH₂)₂ | H | — | OPr | 4-(Pyr-4)Ph | O |
| 35-38 | Me | (CH₂)₂ | H | — | OPr | 3-Ph-6-Pyr | O |

TABLE 36

| Exemplification No. compound. | R¹ | R² | R³ | Z | W | X | Y |
|---|---|---|---|---|---|---|---|
| 36-1 | Me | (CH₂)₂ | H | (CH₂)₂ | OiPr | 4-Et-Ph | O |
| 36-2 | Me | (CH₂)₂ | H | (CH₂)₂ | OiPr | 4-iPr-Ph | O |
| 36-3 | Me | (CH₂)₂ | H | (CH₂)₂ | OiPr | 3-Ph-Ph | O |
| 36-4 | Me | (CH₂)₂ | H | (CH₂)₂ | OiPr | 4-Ph-Ph | O |
| 36-5 | Me | (CH₂)₂ | H | (CH₂)₂ | OiPr | 3-Pyr | O |
| 36-6 | Me | (CH₂)₂ | H | (CH₂)₂ | OiPr | 5-Me-3-Pyr | O |
| 36-7 | Me | (CH₂)₂ | H | (CH₂)₂ | OiPr | 5-Et-3-Pyr | O |
| 36-8 | Me | (CH₂)₂ | H | (CH₂)₂ | OiPr | 5-Ph-3-Pyr | O |
| 36-9 | Me | (CH₂)₂ | H | (CH₂)₂ | OiPr | 6-Me-3-Pyr | O |
| 36-10 | Me | (CH₂)₂ | H | (CH₂)₂ | OiPr | 6-Et-3-Pyr | O |
| 36-11 | Me | (CH₂)₂ | H | (CH₂)₂ | OiPr | 6-Ph-3-Pyr | O |
| 36-12 | Me | (CH₂)₂ | H | (CH₂)₂ | OiPr | 6-MeO-3-Pyr | O |
| 36-13 | Me | (CH₂)₂ | H | (CH₂)₂ | OiPr | 6-EtO-3-Pyr | O |
| 36-14 | Me | (CH₂)₂ | H | (CH₂)₂ | OiPr | 6-iPrO-3-Pyr | O |
| 36-15 | Me | (CH₂)₂ | H | (CH₂)₂ | OiPr | 6-MeS-3-Pyr | O |
| 36-16 | Me | (CH₂)₂ | H | (CH₂)₂ | OiPr | 6-EtS-3-Pyr | O |
| 36-17 | Me | (CH₂)₂ | H | (CH₂)₂ | OiPr | 6-iPrS-3-Pyr | O |
| 36-18 | Me | (CH₂)₂ | H | (CH₂)₂ | OiPr | 6-MeSO₂-3-Pyr | O |
| 36-19 | Me | (CH₂)₂ | H | (CH₂)₂ | OiPr | 6-EtSO₂-3-Pyr | O |
| 36-20 | Me | (CH₂)₂ | H | (CH₂)₂ | OiPr | 6-iPrSO₂-3-Pyr | O |
| 36-21 | Me | (CH₂)₂ | H | (CH₂)₂ | OiPr | 6-Bz-3-Pyr | O |
| 36-22 | Me | (CH₂)₂ | H | (CH₂)₂ | OiPr | 6-PhO-3-Pyr | O |
| 36-23 | Me | (CH₂)₂ | H | (CH₂)₂ | OiPr | 6-PhS-3-Pyr | O |
| 36-24 | Me | (CH₂)₂ | H | (CH₂)₂ | OiPr | 6-PhSO₂-3-Pyr | O |
| 36-25 | Me | (CH₂)₂ | H | (CH₂)₂ | OiPr | 2-Quin | O |
| 36-26 | Me | (CH₂)₂ | H | (CH₂)₂ | OiPr | 4-MeO-Ph | O |
| 36-27 | Me | (CH₂)₂ | H | (CH₂)₂ | OiPr | 4-EtO-Ph | O |
| 36-28 | Me | (CH₂)₂ | H | (CH₂)₂ | OiPr | 4-iPrO-Ph | O |
| 36-29 | Me | (CH₂)₂ | H | (CH₂)₂ | OiPr | 4-MeS-Ph | O |
| 36-30 | Me | (CH₂)₂ | H | (CH₂)₂ | OiPr | 4-EtS-Ph | O |
| 36-31 | Me | (CH₂)₂ | H | (CH₂)₂ | OiPr | 4-iPrS-Ph | O |
| 36-32 | Me | (CH₂)₂ | H | (CH₂)₂ | OiPr | 4-MeSO₂-Ph | O |
| 36-33 | Me | (CH₂)₂ | H | (CH₂)₂ | OiPr | 4-EtSO₂-Ph | O |
| 36-34 | Me | (CH₂)₂ | H | (CH₂)₂ | OiPr | 4-iPrSO₂-Ph | O |
| 36-35 | Me | (CH₂)₂ | H | (CH₂)₂ | OiPr | 4-(Pyr-2)Ph | O |
| 36-36 | Me | (CH₂)₂ | H | (CH₂)₂ | OiPr | 4-(Pyr-3)Ph | O |
| 36-37 | Me | (CH₂)₂ | H | (CH₂)₂ | OiPr | 4-(Pyr-4)Ph | O |
| 36-38 | Me | (CH₂)₂ | H | (CH₂)₂ | OiPr | 3-Ph-6-Pyr | O |

TABLE 37

| Exemplification No. compound. | R¹ | R² | R³ | Z | W | X | Y |
|---|---|---|---|---|---|---|---|
| 37-1 | Me | (CH₂)₂ | H | (CH₂)₂ | OMe | 4-Et-Ph | O |
| 37-2 | Me | (CH₂)₂ | H | (CH₂)₂ | OMe | 4-iPr-Ph | O |
| 37-3 | Me | (CH₂)₂ | H | (CH₂)₂ | OMe | 3-Ph-Ph | O |
| 37-4 | Me | (CH₂)₂ | H | (CH₂)₂ | OMe | 4-Ph-Ph | O |
| 37-5 | Me | (CH₂)₂ | H | (CH₂)₂ | OMe | 3-Pyr | O |
| 37-6 | Me | (CH₂)₂ | H | (CH₂)₂ | OMe | 5-Me-3-Pyr | O |
| 37-7 | Me | (CH₂)₂ | H | (CH₂)₂ | OMe | 5-Et-3-Pyr | O |
| 37-8 | Me | (CH₂)₂ | H | (CH₂)₂ | OMe | 5-Ph-3-Pyr | O |
| 37-9 | Me | (CH₂)₂ | H | (CH₂)₂ | OMe | 6-Me-3-Pyr | O |
| 37-10 | Me | (CH₂)₂ | H | (CH₂)₂ | OMe | 6-Et-3-Pyr | O |
| 37-11 | Me | (CH₂)₂ | H | (CH₂)₂ | OMe | 6-Ph-3-Pyr | O |
| 37-12 | Me | (CH₂)₂ | H | (CH₂)₂ | OMe | 6-MeO-3-Pyr | O |
| 37-13 | Me | (CH₂)₂ | H | (CH₂)₂ | OMe | 6-EtO-3-Pyr | O |
| 37-14 | Me | (CH₂)₂ | H | (CH₂)₂ | OMe | 6-iPrO-3-Pyr | O |
| 37-15 | Me | (CH₂)₂ | H | (CH₂)₂ | OMe | 6-MeS-3-Pyr | O |
| 37-16 | Me | (CH₂)₂ | H | (CH₂)₂ | OMe | 6-EtS-3-Pyr | O |
| 37-17 | Me | (CH₂)₂ | H | (CH₂)₂ | OMe | 6-iPrS-3-Pyr | O |
| 37-18 | Me | (CH₂)₂ | H | (CH₂)₂ | OMe | 6-MeSO₂-3-Pyr | O |
| 37-19 | Me | (CH₂)₂ | H | (CH₂)₂ | OMe | 6-EtSO₂-3-Pyr | O |
| 37-20 | Me | (CH₂)₂ | H | (CH₂)₂ | OMe | 6-iPrSO₂-3-Pyr | O |
| 37-21 | Me | (CH₂)₂ | H | (CH₂)₂ | OMe | 6-Bz-3-Pyr | O |
| 37-22 | Me | (CH₂)₂ | H | (CH₂)₂ | OMe | 6-PhO-3-Pyr | O |
| 37-23 | Me | (CH₂)₂ | H | (CH₂)₂ | OMe | 6-PhS-3-Pyr | O |
| 37-24 | Me | (CH₂)₂ | H | (CH₂)₂ | OMe | 6-PhSO₂-3-Pyr | O |
| 37-25 | Me | (CH₂)₂ | H | (CH₂)₂ | OMe | 2-Quin | O |
| 37-26 | Me | (CH₂)₂ | H | (CH₂)₂ | OMe | 4-MeO-Ph | O |
| 37-27 | Me | (CH₂)₂ | H | (CH₂)₂ | OMe | 4-EtO-Ph | O |
| 37-28 | Me | (CH₂)₂ | H | (CH₂)₂ | OMe | 4-iPrO-Ph | O |
| 37-29 | Me | (CH₂)₂ | H | (CH₂)₂ | OMe | 4-MeS-Ph | O |
| 37-30 | Me | (CH₂)₂ | H | (CH₂)₂ | OMe | 4-EtS-Ph | O |
| 37-31 | Me | (CH₂)₂ | H | (CH₂)₂ | OMe | 4-iPrS-Ph | O |
| 37-32 | Me | (CH₂)₂ | H | (CH₂)₂ | OMe | 4-MeSO₂-Ph | O |
| 37-33 | Me | (CH₂)₂ | H | (CH₂)₂ | OMe | 4-EtSO₂-Ph | O |
| 37-34 | Me | (CH₂)₂ | H | (CH₂)₂ | OMe | 4-iPrSO₂-Ph | O |
| 37-35 | Me | (CH₂)₂ | H | (CH₂)₂ | OMe | 4-(Pyr-2)Ph | O |
| 37-36 | Me | (CH₂)₂ | H | (CH₂)₂ | OMe | 4-(Pyr-3)Ph | O |
| 37-37 | Me | (CH₂)₂ | H | (CH₂)₂ | OMe | 4-(Pyr-4)Ph | O |
| 37-38 | Me | (CH₂)₂ | H | (CH₂)₂ | OMe | 3-Ph-6-Pyr | O |

TABLE 38

| Exemplification No. compound. | R¹ | R² | R³ | Z | W | X | Y |
|---|---|---|---|---|---|---|---|
| 38-1 | Me | (CH₂)₂ | H | (CH₂)₂ | OEt | 4-Et-Ph | O |
| 38-2 | Me | (CH₂)₂ | H | (CH₂)₂ | OEt | 4-iPr-Ph | O |
| 38-3 | Me | (CH₂)₂ | H | (CH₂)₂ | OEt | 3-Ph-Ph | O |
| 38-4 | Me | (CH₂)₂ | H | (CH₂)₂ | OEt | 4-Ph-Ph | O |
| 38-5 | Me | (CH₂)₂ | H | (CH₂)₂ | OEt | 3-Pyr | O |
| 38-6 | Me | (CH₂)₂ | H | (CH₂)₂ | OEt | 5-Me-3-Pyr | O |
| 38-7 | Me | (CH₂)₂ | H | (CH₂)₂ | OEt | 5-Et-3-Pyr | O |
| 38-8 | Me | (CH₂)₂ | H | (CH₂)₂ | OEt | 5-Ph-3-Pyr | O |
| 38-9 | Me | (CH₂)₂ | H | (CH₂)₂ | OEt | 6-Me-3-Pyr | O |
| 38-10 | Me | (CH₂)₂ | H | (CH₂)₂ | OEt | 6-Et-3-Pyr | O |
| 38-11 | Me | (CH₂)₂ | H | (CH₂)₂ | OEt | 6-Ph-3-Pyr | O |
| 38-12 | Me | (CH₂)₂ | H | (CH₂)₂ | OEt | 6-MeO-3-Pyr | O |
| 38-13 | Me | (CH₂)₂ | H | (CH₂)₂ | OEt | 6-EtO-3-Pyr | O |
| 38-14 | Me | (CH₂)₂ | H | (CH₂)₂ | OEt | 6-iPrO-3-Pyr | O |
| 38-15 | Me | (CH₂)₂ | H | (CH₂)₂ | OEt | 6-MeS-3-Pyr | O |
| 38-16 | Me | (CH₂)₂ | H | (CH₂)₂ | OEt | 6-EtS-3-Pyr | O |
| 38-17 | Me | (CH₂)₂ | H | (CH₂)₂ | OEt | 6-iPrS-3-Pyr | O |
| 38-18 | Me | (CH₂)₂ | H | (CH₂)₂ | OEt | 6-MeSO₂-3-Pyr | O |
| 38-19 | Me | (CH₂)₂ | H | (CH₂)₂ | OEt | 6-EtSO₂-3-Pyr | O |
| 38-20 | Me | (CH₂)₂ | H | (CH₂)₂ | OEt | 6-iPrSO₂-3-Pyr | O |
| 38-21 | Me | (CH₂)₂ | H | (CH₂)₂ | OEt | 6-Bz-3-Pyr | O |
| 38-22 | Me | (CH₂)₂ | H | (CH₂)₂ | OEt | 6-PhO-3-Pyr | O |
| 38-23 | Me | (CH₂)₂ | H | (CH₂)₂ | OEt | 6-PhS-3-Pyr | O |
| 38-24 | Me | (CH₂)₂ | H | (CH₂)₂ | OEt | 6-PhSO₂-3-Pyr | O |
| 38-25 | Me | (CH₂)₂ | H | (CH₂)₂ | OEt | 2-Quin | O |
| 38-26 | Me | (CH₂)₂ | H | (CH₂)₂ | OEt | 4-MeO-Ph | O |
| 38-27 | Me | (CH₂)₂ | H | (CH₂)₂ | OEt | 4-EtO-Ph | O |

TABLE 38-continued

| Exemplification No. compound. | R¹ | R² | R³ | Z | W | X | Y |
|---|---|---|---|---|---|---|---|
| 38-28 | Me | (CH₂)₂ | H | (CH₂)₂ | OEt | 4-iPrO-Ph | O |
| 38-29 | Me | (CH₂)₂ | H | (CH₂)₂ | OEt | 4-MeS-Ph | O |
| 38-30 | Me | (CH₂)₂ | H | (CH₂)₂ | OEt | 4-EtS-Ph | O |
| 38-31 | Me | (CH₂)₂ | H | (CH₂)₂ | OEt | 4-iPrS-Ph | O |
| 38-32 | Me | (CH₂)₂ | H | (CH₂)₂ | OEt | 4-MeSO₂-Ph | O |
| 38-33 | Me | (CH₂)₂ | H | (CH₂)₂ | OEt | 4-EtSO₂-Ph | O |
| 38-34 | Me | (CH₂)₂ | H | (CH₂)₂ | OEt | 4-iPrSO₂-Ph | O |
| 38-35 | Me | (CH₂)₂ | H | (CH₂)₂ | OEt | 4-(Pyr-2)Ph | O |
| 38-36 | Me | (CH₂)₂ | H | (CH₂)₂ | OEt | 4-(Pyr-3)Ph | O |
| 38-37 | Me | (CH₂)₂ | H | (CH₂)₂ | OEt | 4-(Pyr-4)Ph | O |
| 38-38 | Me | (CH₂)₂ | H | (CH₂)₂ | OEt | 3-Ph-6-Pyr | O |

TABLE 39

| Exemplification No. compound. | R¹ | R² | R³ | Z | W | X | Y |
|---|---|---|---|---|---|---|---|
| 39-1 | Me | (CH₂)₂ | H | (CH₂)₂ | OPr | 4-Et-Ph | O |
| 39-2 | Me | (CH₂)₂ | H | (CH₂)₂ | OPr | 4-iPr-Ph | O |
| 39-3 | Me | (CH₂)₂ | H | (CH₂)₂ | OPr | 3-Ph-Ph | O |
| 39-4 | Me | (CH₂)₂ | H | (CH₂)₂ | OPr | 4-Ph-Ph | O |
| 39-5 | Me | (CH₂)₂ | H | (CH₂)₂ | OPr | 3-Pyr | O |
| 39-6 | Me | (CH₂)₂ | H | (CH₂)₂ | OPr | 5-Me-3-Pyr | O |
| 39-7 | Me | (CH₂)₂ | H | (CH₂)₂ | OPr | 5-Et-3-Pyr | O |
| 39-8 | Me | (CH₂)₂ | H | (CH₂)₂ | OPr | 5-Ph-3-Pyr | O |
| 39-9 | Me | (CH₂)₂ | H | (CH₂)₂ | OPr | 6-Me-3-Pyr | O |
| 39-10 | Me | (CH₂)₂ | H | (CH₂)₂ | OPr | 6-Et-3-Pyr | O |
| 39-11 | Me | (CH₂)₂ | H | (CH₂)₂ | OPr | 6-Ph-3-Pyr | O |
| 39-12 | Me | (CH₂)₂ | H | (CH₂)₂ | OPr | 6-MeO-3-Pyr | O |
| 39-13 | Me | (CH₂)₂ | H | (CH₂)₂ | OPr | 6-EtO-3-Pyr | O |
| 39-14 | Me | (CH₂)₂ | H | (CH₂)₂ | OPr | 6-iPrO-3-Pyr | O |
| 39-15 | Me | (CH₂)₂ | H | (CH₂)₂ | OPr | 6-MeS-3-Pyr | O |
| 39-16 | Me | (CH₂)₂ | H | (CH₂)₂ | OPr | 6-EtS-3-Pyr | O |
| 39-17 | Me | (CH₂)₂ | H | (CH₂)₂ | OPr | 6-iPrS-3-Pyr | O |
| 39-18 | Me | (CH₂)₂ | H | (CH₂)₂ | OPr | 6-MeSO₂-3-Pyr | O |
| 39-19 | Me | (CH₂)₂ | H | (CH₂)₂ | OPr | 6-EtSO₂-3-Pyr | O |
| 39-20 | Me | (CH₂)₂ | H | (CH₂)₂ | OPr | 6-iPrSO₂-3-Pyr | O |
| 39-21 | Me | (CH₂)₂ | H | (CH₂)₂ | OPr | 6-Bz-3-Pyr | O |
| 39-22 | Me | (CH₂)₂ | H | (CH₂)₂ | OPr | 6-PhO-3-Pyr | O |
| 39-23 | Me | (CH₂)₂ | H | (CH₂)₂ | OPr | 6-PhS-3-Pyr | O |
| 39-24 | Me | (CH₂)₂ | H | (CH₂)₂ | OPr | 6-PhSO₂-3-Pyr | O |
| 39-25 | Me | (CH₂)₂ | H | (CH₂)₂ | OPr | 2-Quin | O |
| 39-26 | Me | (CH₂)₂ | H | (CH₂)₂ | OPr | 4-MeO-Ph | O |
| 39-27 | Me | (CH₂)₂ | H | (CH₂)₂ | OPr | 4-EtO-Ph | O |
| 39-28 | Me | (CH₂)₂ | H | (CH₂)₂ | OPr | 4-iPrO-Ph | O |
| 39-29 | Me | (CH₂)₂ | H | (CH₂)₂ | OPr | 4-MeS-Ph | O |
| 39-30 | Me | (CH₂)₂ | H | (CH₂)₂ | OPr | 4-EtS-Ph | O |
| 39-31 | Me | (CH₂)₂ | H | (CH₂)₂ | OPr | 4-iPrS-Ph | O |
| 39-32 | Me | (CH₂)₂ | H | (CH₂)₂ | OPr | 4-MeSO₂-Ph | O |
| 39-33 | Me | (CH₂)₂ | H | (CH₂)₂ | OPr | 4-EtSO₂-Ph | O |
| 39-34 | Me | (CH₂)₂ | H | (CH₂)₂ | OPr | 4-iPrSO₂-Ph | O |
| 39-35 | Me | (CH₂)₂ | H | (CH₂)₂ | OPr | 4-(Pyr-2)Ph | O |
| 39-36 | Me | (CH₂)₂ | H | (CH₂)₂ | OPr | 4-(Pyr-3)Ph | O |
| 39-37 | Me | (CH₂)₂ | H | (CH₂)₂ | OPr | 4-(Pyr-4)Ph | O |
| 39-38 | Me | (CH₂)₂ | H | (CH₂)₂ | OPr | 3-Ph-6-Pyr | O |

TABLE 40

| Exemplification No. compound. | R¹ | R² | R³ | Z | W | X | Y |
|---|---|---|---|---|---|---|---|
| 40-1 | Me | (CH₂)₂ | H | (CH₂)₂ | OiPr | 4-Et-Ph | O |
| 40-2 | Me | (CH₂)₂ | H | (CH₂)₂ | OiPr | 4-iPr-Ph | O |
| 40-3 | Me | (CH₂)₂ | H | (CH₂)₂ | OiPr | 3-Ph-Ph | O |
| 40-4 | Me | (CH₂)₂ | H | (CH₂)₂ | OiPr | 4-Ph-Ph | O |
| 40-5 | Me | (CH₂)₂ | H | (CH₂)₂ | OiPr | 3-Pyr | O |
| 40-6 | Me | (CH₂)₂ | H | (CH₂)₂ | OiPr | 5-Me-3-Pyr | O |
| 40-7 | Me | (CH₂)₂ | H | (CH₂)₂ | OiPr | 5-Et-3-Pyr | O |
| 40-8 | Me | (CH₂)₂ | H | (CH₂)₂ | OiPr | 5-Ph-3-Pyr | O |
| 40-9 | Me | (CH₂)₂ | H | (CH₂)₂ | OiPr | 6-Me-3-Pyr | O |
| 40-10 | Me | (CH₂)₂ | H | (CH₂)₂ | OiPr | 6-Et-3-Pyr | O |
| 40-11 | Me | (CH₂)₂ | H | (CH₂)₂ | OiPr | 6-Ph-3-Pyr | O |
| 40-12 | Me | (CH₂)₂ | H | (CH₂)₂ | OiPr | 6-MeO-3-Pyr | O |
| 40-13 | Me | (CH₂)₂ | H | (CH₂)₂ | OiPr | 6-EtO-3-Pyr | O |
| 40-14 | Me | (CH₂)₂ | H | (CH₂)₂ | OiPr | 6-iPrO-3-Pyr | O |
| 40-15 | Me | (CH₂)₂ | H | (CH₂)₂ | OiPr | 6-MeS-3-Pyr | O |
| 40-16 | Me | (CH₂)₂ | H | (CH₂)₂ | OiPr | 6-EtS-3-Pyr | O |
| 40-17 | Me | (CH₂)₂ | H | (CH₂)₂ | OiPr | 6-iPrS-3-Pyr | O |
| 40-18 | Me | (CH₂)₂ | H | (CH₂)₂ | OiPr | 6-MeSO₂-3-Pyr | O |
| 40-19 | Me | (CH₂)₂ | H | (CH₂)₂ | OiPr | 6-EtSO₂-3-Pyr | O |
| 40-20 | Me | (CH₂)₂ | H | (CH₂)₂ | OiPr | 6-iPrSO₂-3-Pyr | O |
| 40-21 | Me | (CH₂)₂ | H | (CH₂)₂ | OiPr | 6-Bz-3-Pyr | O |
| 40-22 | Me | (CH₂)₂ | H | (CH₂)₂ | OiPr | 6-PhO-3-Pyr | O |
| 40-23 | Me | (CH₂)₂ | H | (CH₂)₂ | OiPr | 6-PhS-3-Pyr | O |
| 40-24 | Me | (CH₂)₂ | H | (CH₂)₂ | OiPr | 6-PhSO₂-3-Pyr | O |
| 40-25 | Me | (CH₂)₂ | H | (CH₂)₂ | OiPr | 2-Quin | O |
| 40-26 | Me | (CH₂)₂ | H | (CH₂)₂ | OiPr | 4-MeO-Ph | O |
| 40-27 | Me | (CH₂)₂ | H | (CH₂)₂ | OiPr | 4-EtO-Ph | O |
| 40-28 | Me | (CH₂)₂ | H | (CH₂)₂ | OiPr | 4-iPrO-Ph | O |
| 40-29 | Me | (CH₂)₂ | H | (CH₂)₂ | OiPr | 4-MeS-Ph | O |
| 40-30 | Me | (CH₂)₂ | H | (CH₂)₂ | OiPr | 4-EtS-Ph | O |
| 40-31 | Me | (CH₂)₂ | H | (CH₂)₂ | OiPr | 4-iPrS-Ph | O |
| 40-32 | Me | (CH₂)₂ | H | (CH₂)₂ | OiPr | 4-MeSO₂-Ph | O |
| 40-33 | Me | (CH₂)₂ | H | (CH₂)₂ | OiPr | 4-EtSO₂-Ph | O |
| 40-34 | Me | (CH₂)₂ | H | (CH₂)₂ | OiPr | 4-iPrSO₂-Ph | O |
| 40-35 | Me | (CH₂)₂ | H | (CH₂)₂ | OiPr | 4-(Pyr-2)Ph | O |
| 40-36 | Me | (CH₂)₂ | H | (CH₂)₂ | OiPr | 4-(Pyr-3)Ph | O |
| 40-37 | Me | (CH₂)₂ | H | (CH₂)₂ | OiPr | 4-(Pyr-4)Ph | O |
| 40-38 | Me | (CH₂)₂ | H | (CH₂)₂ | OiPr | 3-Ph-6-Pyr | O |

TABLE 41

| Exemplification No. compound. | R¹ | R² | R³ | Z | W | X | Y |
|---|---|---|---|---|---|---|---|
| 41-1 | Me | (CH₂)₂ | H | CH₂ | NH₂ | 4-Et-Ph | O |
| 41-2 | Me | (CH₂)₂ | H | CH₂ | NH₂ | 4-iPr-Ph | O |
| 41-3 | Me | (CH₂)₂ | H | CH₂ | NH₂ | 3-Ph-Ph | O |
| 41-4 | Me | (CH₂)₂ | H | CH₂ | NH₂ | 4-Ph-Ph | O |
| 41-5 | Me | (CH₂)₂ | H | CH₂ | NH₂ | 3-Pyr | O |
| 41-6 | Me | (CH₂)₂ | H | CH₂ | NH₂ | 5-Me-3-Pyr | O |
| 41-7 | Me | (CH₂)₂ | H | CH₂ | NH₂ | 5-Et-3-Pyr | O |
| 41-8 | Me | (CH₂)₂ | H | CH₂ | NH₂ | 5-Ph-3-Pyr | O |
| 41-9 | Me | (CH₂)₂ | H | CH₂ | NH₂ | 6-Me-3-Pyr | O |
| 41-10 | Me | (CH₂)₂ | H | CH₂ | NH₂ | 6-Et-3-Pyr | O |
| 41-11 | Me | (CH₂)₂ | H | CH₂ | NH₂ | 6-Ph-3-Pyr | O |
| 41-12 | Me | (CH₂)₂ | H | CH₂ | NH₂ | 6-MeO-3-Pyr | O |
| 41-13 | Me | (CH₂)₂ | H | CH₂ | NH₂ | 6-EtO-3-Pyr | O |
| 41-14 | Me | (CH₂)₂ | H | CH₂ | NH₂ | 6-iPrO-3-Pyr | O |
| 41-15 | Me | (CH₂)₂ | H | CH₂ | NH₂ | 6-MeS-3-Pyr | O |
| 41-16 | Me | (CH₂)₂ | H | CH₂ | NH₂ | 6-EtS-3-Pyr | O |
| 41-17 | Me | (CH₂)₂ | H | CH₂ | NH₂ | 6-iPrS-3-Pyr | O |
| 41-18 | Me | (CH₂)₂ | H | CH₂ | NH₂ | 6-MeSO₂-3-Pyr | O |
| 41-19 | Me | (CH₂)₂ | H | CH₂ | NH₂ | 6-EtSO₂-3-Pyr | O |
| 41-20 | Me | (CH₂)₂ | H | CH₂ | NH₂ | 6-iPrSO₂-3-Pyr | O |
| 41-21 | Me | (CH₂)₂ | H | CH₂ | NH₂ | 6-Bz-3-Pyr | O |
| 41-22 | Me | (CH₂)₂ | H | CH₂ | NH₂ | 6-PhO-3-Pyr | O |
| 41-23 | Me | (CH₂)₂ | H | CH₂ | NH₂ | 6-PhS-3-Pyr | O |
| 41-24 | Me | (CH₂)₂ | H | CH₂ | NH₂ | 6-PhSO₂-3-Pyr | O |
| 41-25 | Me | (CH₂)₂ | H | CH₂ | NH₂ | 2-Quin | O |
| 41-26 | Me | (CH₂)₂ | H | CH₂ | NH₂ | 4-MeO-Ph | O |
| 41-27 | Me | (CH₂)₂ | H | CH₂ | NH₂ | 4-EtO-Ph | O |
| 41-28 | Me | (CH₂)₂ | H | CH₂ | NH₂ | 4-iPrO-Ph | O |
| 41-29 | Me | (CH₂)₂ | H | CH₂ | NH₂ | 4-MeS-Ph | O |
| 41-30 | Me | (CH₂)₂ | H | CH₂ | NH₂ | 4-EtS-Ph | O |
| 41-31 | Me | (CH₂)₂ | H | CH₂ | NH₂ | 4-iPrS-Ph | O |
| 41-32 | Me | (CH₂)₂ | H | CH₂ | NH₂ | 4-MeSO₂-Ph | O |
| 41-33 | Me | (CH₂)₂ | H | CH₂ | NH₂ | 4-EtSO₂-Ph | O |
| 41-34 | Me | (CH₂)₂ | H | CH₂ | NH₂ | 4-iPrSO₂-Ph | O |
| 41-35 | Me | (CH₂)₂ | H | CH₂ | NH₂ | 4-(Pyr-2)Ph | O |

TABLE 41-continued

| Exemplification No. compound. | R$^1$ | R$^2$ | R$^3$ | Z | W | X | Y |
|---|---|---|---|---|---|---|---|
| 41-36 | Me | (CH$_2$)$_2$ | H | CH$_2$ | NH$_2$ | 4-(Pyr-3)Ph | O |
| 41-37 | Me | (CH$_2$)$_2$ | H | CH$_2$ | NH$_2$ | 4-(Pyr-4)Ph | O |
| 41-38 | Me | (CH$_2$)$_2$ | H | CH$_2$ | NH$_2$ | 3-Ph-6-Pyr | O |

TABLE 42

| Exemplification No. compound. | R$^1$ | R$^2$ | R$^3$ | Z | W | X | Y |
|---|---|---|---|---|---|---|---|
| 42-1 | Me | (CH$_2$)$_2$ | H | CH$_2$ | NHMe | 4-Et-Ph | O |
| 42-2 | Me | (CH$_2$)$_2$ | H | CH$_2$ | NHMe | 4-iPr-Ph | O |
| 42-3 | Me | (CH$_2$)$_2$ | H | CH$_2$ | NHMe | 3-Ph-Ph | O |
| 42-4 | Me | (CH$_2$)$_2$ | H | CH$_2$ | NHMe | 4-Ph-Ph | O |
| 42-5 | Me | (CH$_2$)$_2$ | H | CH$_2$ | NHMe | 3-Pyr | O |
| 42-6 | Me | (CH$_2$)$_2$ | H | CH$_2$ | NHMe | 5-Me-3-Pyr | O |
| 42-7 | Me | (CH$_2$)$_2$ | H | CH$_2$ | NHMe | 5-Et-3-Pyr | O |
| 42-8 | Me | (CH$_2$)$_2$ | H | CH$_2$ | NHMe | 5-Ph-3-Pyr | O |
| 42-9 | Me | (CH$_2$)$_2$ | H | CH$_2$ | NHMe | 6-Me-3-Pyr | O |
| 42-10 | Me | (CH$_2$)$_2$ | H | CH$_2$ | NHMe | 6-Et-3-Pyr | O |
| 42-11 | Me | (CH$_2$)$_2$ | H | CH$_2$ | NHMe | 6-Ph-3-Pyr | O |
| 42-12 | Me | (CH$_2$)$_2$ | H | CH$_2$ | NHMe | 6-MeO-3-Pyr | O |
| 42-13 | Me | (CH$_2$)$_2$ | H | CH$_2$ | NHMe | 6-EtO-3-Pyr | O |
| 42-14 | Me | (CH$_2$)$_2$ | H | CH$_2$ | NHMe | 6-iPrO-3-Pyr | O |
| 42-15 | Me | (CH$_2$)$_2$ | H | CH$_2$ | NHMe | 6-MeS-3-Pyr | O |
| 42-16 | Me | (CH$_2$)$_2$ | H | CH$_2$ | NHMe | 6-EtS-3-Pyr | O |
| 42-17 | Me | (CH$_2$)$_2$ | H | CH$_2$ | NHMe | 6-iPrS-3-Pyr | O |
| 42-18 | Me | (CH$_2$)$_2$ | H | CH$_2$ | NHMe | 6-MeSO$_2$-3-Pyr | O |
| 42-19 | Me | (CH$_2$)$_2$ | H | CH$_2$ | NHMe | 6-EtSO$_2$-3-Pyr | O |
| 42-20 | Me | (CH$_2$)$_2$ | H | CH$_2$ | NHMe | 6-iPrSO$_2$-3-Pyr | O |
| 42-21 | Me | (CH$_2$)$_2$ | H | CH$_2$ | NHMe | 6-Bz-3-Pyr | O |
| 42-22 | Me | (CH$_2$)$_2$ | H | CH$_2$ | NHMe | 6-PhO-3-Pyr | O |
| 42-23 | Me | (CH$_2$)$_2$ | H | CH$_2$ | NHMe | 6-PhS-3-Pyr | O |
| 42-24 | Me | (CH$_2$)$_2$ | H | CH$_2$ | NHMe | 6-PhSO$_2$-3-Pyr | O |
| 42-25 | Me | (CH$_2$)$_2$ | H | CH$_2$ | NHMe | 2-Quin | O |
| 42-26 | Me | (CH$_2$)$_2$ | H | CH$_2$ | NHMe | 4-MeO-Ph | O |
| 42-27 | Me | (CH$_2$)$_2$ | H | CH$_2$ | NHMe | 4-EtO-Ph | O |
| 42-28 | Me | (CH$_2$)$_2$ | H | CH$_2$ | NHMe | 4-iPrO-Ph | O |
| 42-29 | Me | (CH$_2$)$_2$ | H | CH$_2$ | NHMe | 4-MeS-Ph | O |
| 42-30 | Me | (CH$_2$)$_2$ | H | CH$_2$ | NHMe | 4-EtS-Ph | O |
| 42-31 | Me | (CH$_2$)$_2$ | H | CH$_2$ | NHMe | 4-iPrS-Ph | O |
| 42-32 | Me | (CH$_2$)$_2$ | H | CH$_2$ | NHMe | 4-MeSO$_2$-Ph | O |
| 42-33 | Me | (CH$_2$)$_2$ | H | CH$_2$ | NHMe | 4-EtSO$_2$-Ph | O |
| 42-34 | Me | (CH$_2$)$_2$ | H | CH$_2$ | NHMe | 4-iPrSO$_2$-Ph | O |
| 42-35 | Me | (CH$_2$)$_2$ | H | CH$_2$ | NHMe | 4-(Pyr-2)Ph | O |
| 42-36 | Me | (CH$_2$)$_2$ | H | CH$_2$ | NHMe | 4-(Pyr-3)Ph | O |
| 42-37 | Me | (CH$_2$)$_2$ | H | CH$_2$ | NHMe | 4-(Pyr-4)Ph | O |
| 42-38 | Me | (CH$_2$)$_2$ | H | CH$_2$ | NHMe | 3-Ph-6-Pyr | O |

TABLE 43

| Exemplification No. compound. | R$^1$ | R$^2$ | R$^3$ | Z | W | X | Y |
|---|---|---|---|---|---|---|---|
| 43-1 | Me | (CH$_2$)$_2$ | H | CH$_2$ | NHEt | 4-Et-Ph | O |
| 43-2 | Me | (CH$_2$)$_2$ | H | CH$_2$ | NHEt | 4-iPr-Ph | O |
| 43-3 | Me | (CH$_2$)$_2$ | H | CH$_2$ | NHEt | 3-Ph-Ph | O |
| 43-4 | Me | (CH$_2$)$_2$ | H | CH$_2$ | NHEt | 4-Ph-Ph | O |
| 43-5 | Me | (CH$_2$)$_2$ | H | CH$_2$ | NHEt | 3-Pyr | O |
| 43-6 | Me | (CH$_2$)$_2$ | H | CH$_2$ | NHEt | 5-Me-3-Pyr | O |
| 43-7 | Me | (CH$_2$)$_2$ | H | CH$_2$ | NHEt | 5-Et-3-Pyr | O |
| 43-8 | Me | (CH$_2$)$_2$ | H | CH$_2$ | NHEt | 5-Ph-3-Pyr | O |
| 43-9 | Me | (CH$_2$)$_2$ | H | CH$_2$ | NHEt | 6-Me-3-Pyr | O |
| 43-10 | Me | (CH$_2$)$_2$ | H | CH$_2$ | NHEt | 6-Et-3-Pyr | O |
| 43-11 | Me | (CH$_2$)$_2$ | H | CH$_2$ | NHEt | 6-Ph-3-Pyr | O |
| 43-12 | Me | (CH$_2$)$_2$ | H | CH$_2$ | NHEt | 6-MeO-3-Pyr | O |
| 43-13 | Me | (CH$_2$)$_2$ | H | CH$_2$ | NHEt | 6-EtO-3-Pyr | O |
| 43-14 | Me | (CH$_2$)$_2$ | H | CH$_2$ | NHEt | 6-iPrO-3-Pyr | O |
| 43-15 | Me | (CH$_2$)$_2$ | H | CH$_2$ | NHEt | 6-MeS-3-Pyr | O |
| 43-16 | Me | (CH$_2$)$_2$ | H | CH$_2$ | NHEt | 6-EtS-3-Pyr | O |
| 43-17 | Me | (CH$_2$)$_2$ | H | CH$_2$ | NHEt | 6-iPrS-3-Pyr | O |
| 43-18 | Me | (CH$_2$)$_2$ | H | CH$_2$ | NHEt | 6-MeSO$_2$-3-Pyr | O |
| 43-19 | Me | (CH$_2$)$_2$ | H | CH$_2$ | NHEt | 6-EtSO$_2$-3-Pyr | O |
| 43-20 | Me | (CH$_2$)$_2$ | H | CH$_2$ | NHEt | 6-iPrSO$_2$-3-Pyr | O |
| 43-21 | Me | (CH$_2$)$_2$ | H | CH$_2$ | NHEt | 6-Bz-3-Pyr | O |
| 43-22 | Me | (CH$_2$)$_2$ | H | CH$_2$ | NHEt | 6-PhO-3-Pyr | O |
| 43-23 | Me | (CH$_2$)$_2$ | H | CH$_2$ | NHEt | 6-PhS-3-Pyr | O |
| 43-24 | Me | (CH$_2$)$_2$ | H | CH$_2$ | NHEt | 6-PhSO$_2$-3-Pyr | O |
| 43-25 | Me | (CH$_2$)$_2$ | H | CH$_2$ | NHEt | 2-Quin | O |
| 43-26 | Me | (CH$_2$)$_2$ | H | CH$_2$ | NHEt | 4-MeO-Ph | O |
| 43-27 | Me | (CH$_2$)$_2$ | H | CH$_2$ | NHEt | 4-EtO-Ph | O |
| 43-28 | Me | (CH$_2$)$_2$ | H | CH$_2$ | NHEt | 4-iPrO-Ph | O |
| 43-29 | Me | (CH$_2$)$_2$ | H | CH$_2$ | NHEt | 4-MeS-Ph | O |
| 43-30 | Me | (CH$_2$)$_2$ | H | CH$_2$ | NHEt | 4-EtS-Ph | O |
| 43-31 | Me | (CH$_2$)$_2$ | H | CH$_2$ | NHEt | 4-iPrS-Ph | O |
| 43-32 | Me | (CH$_2$)$_2$ | H | CH$_2$ | NHEt | 4-MeSO$_2$-Ph | O |
| 43-33 | Me | (CH$_2$)$_2$ | H | CH$_2$ | NHEt | 4-EtSO$_2$-Ph | O |
| 43-34 | Me | (CH$_2$)$_2$ | H | CH$_2$ | NHEt | 4-iPrSO$_2$-Ph | O |
| 43-35 | Me | (CH$_2$)$_2$ | H | CH$_2$ | NHEt | 4-(Pyr-2)Ph | O |
| 43-36 | Me | (CH$_2$)$_2$ | H | CH$_2$ | NHEt | 4-(Pyr-3)Ph | O |
| 43-37 | Me | (CH$_2$)$_2$ | H | CH$_2$ | NHEt | 4-(Pyr-4)Ph | O |
| 43-38 | Me | (CH$_2$)$_2$ | H | CH$_2$ | NHEt | 3-Ph-6-Pyr | O |

TABLE 44

| Exemplification No. compound. | R$^1$ | R$^2$ | R$^3$ | Z | W | X | Y |
|---|---|---|---|---|---|---|---|
| 44-1 | Me | (CH$_2$)$_2$ | H | CH$_2$ | NHPr | 4-Et-Ph | O |
| 44-2 | Me | (CH$_2$)$_2$ | H | CH$_2$ | NHPr | 4-iPr-Ph | O |
| 44-3 | Me | (CH$_2$)$_2$ | H | CH$_2$ | NHPr | 3-Ph-Ph | O |
| 44-4 | Me | (CH$_2$)$_2$ | H | CH$_2$ | NHPr | 4-Ph-Ph | O |
| 44-5 | Me | (CH$_2$)$_2$ | H | CH$_2$ | NHPr | 3-Pyr | O |
| 44-6 | Me | (CH$_2$)$_2$ | H | CH$_2$ | NHPr | 5-Me-3-Pyr | O |
| 44-7 | Me | (CH$_2$)$_2$ | H | CH$_2$ | NHPr | 5-Et-3-Pyr | O |
| 44-8 | Me | (CH$_2$)$_2$ | H | CH$_2$ | NHPr | 5-Ph-3-Pyr | O |
| 44-9 | Me | (CH$_2$)$_2$ | H | CH$_2$ | NHPr | 6-Me-3-Pyr | O |
| 44-10 | Me | (CH$_2$)$_2$ | H | CH$_2$ | NHPr | 6-Et-3-Pyr | O |
| 44-11 | Me | (CH$_2$)$_2$ | H | CH$_2$ | NHPr | 6-Ph-3-Pyr | O |
| 44-12 | Me | (CH$_2$)$_2$ | H | CH$_2$ | NHPr | 6-MeO-3-Pyr | O |
| 44-13 | Me | (CH$_2$)$_2$ | H | CH$_2$ | NHPr | 6-EtO-3-Pyr | O |
| 44-14 | Me | (CH$_2$)$_2$ | H | CH$_2$ | NHPr | 6-iPrO-3-Pyr | O |
| 44-15 | Me | (CH$_2$)$_2$ | H | CH$_2$ | NHPr | 6-MeS-3-Pyr | O |
| 44-16 | Me | (CH$_2$)$_2$ | H | CH$_2$ | NHPr | 6-EtS-3-Pyr | O |
| 44-17 | Me | (CH$_2$)$_2$ | H | CH$_2$ | NHPr | 6-iPrS-3-Pyr | O |
| 44-18 | Me | (CH$_2$)$_2$ | H | CH$_2$ | NHPr | 6-MeSO$_2$-3-Pyr | O |
| 44-19 | Me | (CH$_2$)$_2$ | H | CH$_2$ | NHPr | 6-EtS$_2$-3-Pyr | O |
| 44-20 | Me | (CH$_2$)$_2$ | H | CH$_2$ | NHPr | 6-iPrSO$_2$-3-Pyr | O |
| 44-21 | Me | (CH$_2$)$_2$ | H | CH$_2$ | NHPr | 6-Bz-3-Pyr | O |
| 44-22 | Me | (CH$_2$)$_2$ | H | CH$_2$ | NHPr | 6-PhO-3-Pyr | O |
| 44-23 | Me | (CH$_2$)$_2$ | H | CH$_2$ | NHPr | 6-PhS-3-Pyr | O |
| 44-24 | Me | (CH$_2$)$_2$ | H | CH$_2$ | NHPr | 6-PhSO$_2$-3-Pyr | O |
| 44-25 | Me | (CH$_2$)$_2$ | H | CH$_2$ | NHPr | 2-Quin | O |
| 44-26 | Me | (CH$_2$)$_2$ | H | CH$_2$ | NHPr | 4-MeO-Ph | O |
| 44-27 | Me | (CH$_2$)$_2$ | H | CH$_2$ | NHPr | 4-EtO-Ph | O |
| 44-28 | Me | (CH$_2$)$_2$ | H | CH$_2$ | NHPr | 4-iPrO-Ph | O |
| 44-29 | Me | (CH$_2$)$_2$ | H | CH$_2$ | NHPr | 4-MeS-Ph | O |
| 44-30 | Me | (CH$_2$)$_2$ | H | CH$_2$ | NHPr | 4-EtS-Ph | O |
| 44-31 | Me | (CH$_2$)$_2$ | H | CH$_2$ | NHPr | 4-iPrS-Ph | O |
| 44-32 | Me | (CH$_2$)$_2$ | H | CH$_2$ | NHPr | 4-MeSO$_2$-Ph | O |
| 44-33 | Me | (CH$_2$)$_2$ | H | CH$_2$ | NHPr | 4-EtSO$_2$-Ph | O |
| 44-34 | Me | (CH$_2$)$_2$ | H | CH$_2$ | NHPr | 4-iPrSO$_2$-Ph | O |
| 44-35 | Me | (CH$_2$)$_2$ | H | CH$_2$ | NHPr | 4-(Pyr-2)Ph | O |
| 44-36 | Me | (CH$_2$)$_2$ | H | CH$_2$ | NHPr | 4-(Pyr-3)Ph | O |
| 44-37 | Me | (CH$_2$)$_2$ | H | CH$_2$ | NHPr | 4-(Pyr-4)Ph | O |
| 44-38 | Me | (CH$_2$)$_2$ | H | CH$_2$ | NHPr | 3-Ph-6-Pyr | O |

TABLE 45

| Exemplification No. compound. | R¹ | R² | R³ | Z | W | X | Y |
|---|---|---|---|---|---|---|---|
| 45-1 | Me | (CH₂)₂ | H | CH₂ | NHiPr | 4-Et-Ph | O |
| 45-2 | Me | (CH₂)₂ | H | CH₂ | NHiPr | 4-iPr-Ph | O |
| 45-3 | Me | (CH₂)₂ | H | CH₂ | NHiPr | 3-Ph-Ph | O |
| 45-4 | Me | (CH₂)₂ | H | CH₂ | NHiPr | 4-Ph-Ph | O |
| 45-5 | Me | (CH₂)₂ | H | CH₂ | NHiPr | 3-Pyr | O |
| 45-6 | Me | (CH₂)₂ | H | CH₂ | NHiPr | 5-Me-3-Pyr | O |
| 45-7 | Me | (CH₂)₂ | H | CH₂ | NHiPr | 5-Et-3-Pyr | O |
| 45-8 | Me | (CH₂)₂ | H | CH₂ | NHiPr | 5-Ph-3-Pyr | O |
| 45-9 | Me | (CH₂)₂ | H | CH₂ | NHiPr | 6-Me-3-Pyr | O |
| 45-10 | Me | (CH₂)₂ | H | CH₂ | NHiPr | 6-Et-3-Pyr | O |
| 45-11 | Me | (CH₂)₂ | H | CH₂ | NHiPr | 6-Ph-3-Pyr | O |
| 45-12 | Me | (CH₂)₂ | H | CH₂ | NHiPr | 6-MeO-3-Pyr | O |
| 45-13 | Me | (CH₂)₂ | H | CH₂ | NHiPr | 6-EtO-3-Pyr | O |
| 45-14 | Me | (CH₂)₂ | H | CH₂ | NHiPr | 6-iPrO-3-Pyr | O |
| 45-15 | Me | (CH₂)₂ | H | CH₂ | NHiPr | 6-MeS-3-Pyr | O |
| 45-16 | Me | (CH₂)₂ | H | CH₂ | NHiPr | 6-EtS-3-Pyr | O |
| 45-17 | Me | (CH₂)₂ | H | CH₂ | NHiPr | 6-iPrS-3-Pyr | O |
| 45-18 | Me | (CH₂)₂ | H | CH₂ | NHiPr | 6-MeSO₂-3-Pyr | O |
| 45-19 | Me | (CH₂)₂ | H | CH₂ | NHiPr | 6-EtSO₂-3-Pyr | O |
| 45-20 | Me | (CH₂)₂ | H | CH₂ | NHiPr | 6-iPrSO₂-3-Pyr | O |
| 45-21 | Me | (CH₂)₂ | H | CH₂ | NHiPr | 6-Bz-3-Pyr | O |
| 45-22 | Me | (CH₂)₂ | H | CH₂ | NHiPr | 6-PhO-3-Pyr | O |
| 45-23 | Me | (CH₂)₂ | H | CH₂ | NHiPr | 6-PhS-3-Pyr | O |
| 45-24 | Me | (CH₂)₂ | H | CH₂ | NHiPr | 6-PhSO₂-3-Pyr | O |
| 45-25 | Me | (CH₂)₂ | H | CH₂ | NHiPr | 2-Quin | O |
| 45-26 | Me | (CH₂)₂ | H | CH₂ | NHiPr | 4-MeO-Ph | O |
| 45-27 | Me | (CH₂)₂ | H | CH₂ | NHiPr | 4-EtO-Ph | O |
| 45-28 | Me | (CH₂)₂ | H | CH₂ | NHiPr | 4-iPrO-Ph | O |
| 45-29 | Me | (CH₂)₂ | H | CH₂ | NHiPr | 4-MeS-Ph | O |
| 45-30 | Me | (CH₂)₂ | H | CH₂ | NHiPr | 4-EtS-Ph | O |
| 45-31 | Me | (CH₂)₂ | H | CH₂ | NHiPr | 4-iPrS-Ph | O |
| 45-32 | Me | (CH₂)₂ | H | CH₂ | NHiPr | 4-MeSO₂-Ph | O |
| 45-33 | Me | (CH₂)₂ | H | CH₂ | NHiPr | 4-EtSO₂-Ph | O |
| 45-34 | Me | (CH₂)₂ | H | CH₂ | NHiPr | 4-iPrSO₂-Ph | O |
| 45-35 | Me | (CH₂)₂ | H | CH₂ | NHiPr | 4-(Pyr-2)Ph | O |
| 45-36 | Me | (CH₂)₂ | H | CH₂ | NHiPr | 4-(Pyr-3)Ph | O |
| 45-37 | Me | (CH₂)₂ | H | CH₂ | NHiPr | 4-(Pyr-4)Ph | O |
| 45-38 | Me | (CH₂)₂ | H | CH₂ | NHiPr | 3-Ph-6-Pyr | O |

TABLE 46

| Exemplification No. compound. | R¹ | R² | R³ | Z | W | X | Y |
|---|---|---|---|---|---|---|---|
| 46-1 | Me | (CH₂)₂ | H | CH₂ | N(Me)₂ | 4-Et-Ph | O |
| 46-2 | Me | (CH₂)₂ | H | CH₂ | N(Me)₂ | 4-iPr-Ph | O |
| 46-3 | Me | (CH₂)₂ | H | CH₂ | N(Me)₂ | 3-Ph-Ph | O |
| 46-4 | Me | (CH₂)₂ | H | CH₂ | N(Me)₂ | 4-Ph-Ph | O |
| 46-5 | Me | (CH₂)₂ | H | CH₂ | N(Me)₂ | 3-Pyr | O |
| 46-6 | Me | (CH₂)₂ | H | CH₂ | N(Me)₂ | 5-Me-3-Pyr | O |
| 46-7 | Me | (CH₂)₂ | H | CH₂ | N(Me)₂ | 5-Et-3-Pyr | O |
| 46-8 | Me | (CH₂)₂ | H | CH₂ | N(Me)₂ | 5-Ph-3-Pyr | O |
| 46-9 | Me | (CH₂)₂ | H | CH₂ | N(Me)₂ | 6-Me-3-Pyr | O |
| 46-10 | Me | (CH₂)₂ | H | CH₂ | N(Me)₂ | 6-Et-3-Pyr | O |
| 46-11 | Me | (CH₂)₂ | H | CH₂ | N(Me)₂ | 6-Ph-3-Pyr | O |
| 46-12 | Me | (CH₂)₂ | H | CH₂ | N(Me)₂ | 6-MeO-3-Pyr | O |
| 46-13 | Me | (CH₂)₂ | H | CH₂ | N(Me)₂ | 6-EtO-3-Pyr | O |
| 46-14 | Me | (CH₂)₂ | H | CH₂ | N(Me)₂ | 6-iPrO-3-Pyr | O |
| 46-15 | Me | (CH₂)₂ | H | CH₂ | N(Me)₂ | 6-MeS-3-Pyr | O |
| 46-16 | Me | (CH₂)₂ | H | CH₂ | N(Me)₂ | 6-EtS-3-Pyr | O |
| 46-17 | Me | (CH₂)₂ | H | CH₂ | N(Me)₂ | 6-iPrS-3-Pyr | O |
| 46-18 | Me | (CH₂)₂ | H | CH₂ | N(Me)₂ | 6-MeSO₂-3-Pyr | O |
| 46-19 | Me | (CH₂)₂ | H | CH₂ | N(Me)₂ | 6-EtSO₂-3-Pyr | O |
| 46-20 | Me | (CH₂)₂ | H | CH₂ | N(Me)₂ | 6-iPrSO₂-3-Pyr | O |
| 46-21 | Me | (CH₂)₂ | H | CH₂ | N(Me)₂ | 6-Bz-3-Pyr | O |
| 46-22 | Me | (CH₂)₂ | H | CH₂ | N(Me)₂ | 6-PhO-3-Pyr | O |
| 46-23 | Me | (CH₂)₂ | H | CH₂ | N(Me)₂ | 6-PhS-3-Pyr | O |
| 46-24 | Me | (CH₂)₂ | H | CH₂ | N(Me)₂ | 6-PhSO₂-3-Pyr | O |
| 46-25 | Me | (CH₂)₂ | H | CH₂ | N(Me)₂ | 2-Quin | O |
| 46-26 | Me | (CH₂)₂ | H | CH₂ | N(Me)₂ | 4-MeO-Ph | O |
| 46-27 | Me | (CH₂)₂ | H | CH₂ | N(Me)₂ | 4-EtO-Ph | O |
| 46-28 | Me | (CH₂)₂ | H | CH₂ | N(Me)₂ | 4-iPrO-Ph | O |
| 46-29 | Me | (CH₂)₂ | H | CH₂ | N(Me)₂ | 4-MeS-Ph | O |
| 46-30 | Me | (CH₂)₂ | H | CH₂ | N(Me)₂ | 4-EtS-Ph | O |
| 46-31 | Me | (CH₂)₂ | H | CH₂ | N(Me)₂ | 4-iPrS-Ph | O |
| 46-32 | Me | (CH₂)₂ | H | CH₂ | N(Me)₂ | 4-MeSO₂-Ph | O |
| 46-33 | Me | (CH₂)₂ | H | CH₂ | N(Me)₂ | 4-EtSO₂-Ph | O |
| 46-34 | Me | (CH₂)₂ | H | CH₂ | N(Me)₂ | 4-iPrSO₂-Ph | O |
| 46-35 | Me | (CH₂)₂ | H | CH₂ | N(Me)₂ | 4-(Pyr-2)Ph | O |
| 46-36 | Me | (CH₂)₂ | H | CH₂ | N(Me)₂ | 4-(Pyr-3)Ph | O |
| 46-37 | Me | (CH₂)₂ | H | CH₂ | N(Me)₂ | 4-(Pyr-4)Ph | O |
| 46-38 | Me | (CH₂)₂ | H | CH₂ | N(Me)₂ | 3-Ph-6-Pyr | O |

TABLE 47

| Exemplification No. compound. | R¹ | R² | R³ | Z | W | X | Y |
|---|---|---|---|---|---|---|---|
| 47-1 | Me | (CH₂)₂ | H | CH₂ | N(Et)₂ | 4-Et-Ph | O |
| 47-2 | Me | (CH₂)₂ | H | CH₂ | N(Et)₂ | 4-iPr-Ph | O |
| 47-3 | Me | (CH₂)₂ | H | CH₂ | N(Et)₂ | 3-Ph-Ph | O |
| 47-4 | Me | (CH₂)₂ | H | CH₂ | N(Et)₂ | 4-Ph-Ph | O |
| 47-5 | Me | (CH₂)₂ | H | CH₂ | N(Et)₂ | 3-Pyr | O |
| 47-6 | Me | (CH₂)₂ | H | CH₂ | N(Et)₂ | 5-Me-3-Pyr | O |
| 47-7 | Me | (CH₂)₂ | H | CH₂ | N(Et)₂ | 5-Et-3-Pyr | O |
| 47-8 | Me | (CH₂)₂ | H | CH₂ | N(Et)₂ | 5-Ph-3-Pyr | O |
| 47-9 | Me | (CH₂)₂ | H | CH₂ | N(Et)₂ | 6-Me-3-Pyr | O |
| 47-10 | Me | (CH₂)₂ | H | CH₂ | N(Et)₂ | 6-Et-3-Pyr | O |
| 47-11 | Me | (CH₂)₂ | H | CH₂ | N(Et)₂ | 6-Ph-3-Pyr | O |
| 47-12 | Me | (CH₂)₂ | H | CH₂ | N(Et)₂ | 6-MeO-3-Pyr | O |
| 47-13 | Me | (CH₂)₂ | H | CH₂ | N(Et)₂ | 6-EtO-3-Pyr | O |
| 47-14 | Me | (CH₂)₂ | H | CH₂ | N(Et)₂ | 6-iPrO-3-Pyr | O |
| 47-15 | Me | (CH₂)₂ | H | CH₂ | N(Et)₂ | 6-MeS-3-Pyr | O |
| 47-16 | Me | (CH₂)₂ | H | CH₂ | N(Et)₂ | 6-EtS-3-Pyr | O |
| 47-17 | Me | (CH₂)₂ | H | CH₂ | N(Et)₂ | 6-iPrS-3-Pyr | O |
| 47-18 | Me | (CH₂)₂ | H | CH₂ | N(Et)₂ | 6-MeSO₂-3-Pyr | O |
| 47-19 | Me | (CH₂)₂ | H | CH₂ | N(Et)₂ | 6-EtSO₂-3-Pyr | O |
| 47-20 | Me | (CH₂)₂ | H | CH₂ | N(Et)₂ | 6-iPrSO₂-3-Pyr | O |
| 47-21 | Me | (CH₂)₂ | H | CH₂ | N(Et)₂ | 6-Bz-3-Pyr | O |
| 47-22 | Me | (CH₂)₂ | H | CH₂ | N(Et)₂ | 6-PhO-3-Pyr | O |
| 47-23 | Me | (CH₂)₂ | H | CH₂ | N(Et)₂ | 6-PhS-3-Pyr | O |
| 47-24 | Me | (CH₂)₂ | H | CH₂ | N(Et)₂ | 6-PhSO₂-3-Pyr | O |
| 47-25 | Me | (CH₂)₂ | H | CH₂ | N(Et)₂ | 2-Quin | O |
| 47-26 | Me | (CH₂)₂ | H | CH₂ | N(Et)₂ | 4-MeO-Ph | O |
| 47-27 | Me | (CH₂)₂ | H | CH₂ | N(Et)₂ | 4-EtO-Ph | O |
| 47-28 | Me | (CH₂)₂ | H | CH₂ | N(Et)₂ | 4-iPrO-Ph | O |
| 47-29 | Me | (CH₂)₂ | H | CH₂ | N(Et)₂ | 4-MeS-Ph | O |
| 47-30 | Me | (CH₂)₂ | H | CH₂ | N(Et)₂ | 4-EtS-Ph | O |
| 47-31 | Me | (CH₂)₂ | H | CH₂ | N(Et)₂ | 4-iPrS-Ph | O |
| 47-32 | Me | (CH₂)₂ | H | CH₂ | N(Et)₂ | 4-MeSO₂-Ph | O |
| 47-33 | Me | (CH₂)₂ | H | CH₂ | N(Et)₂ | 4-EtSO₂-Ph | O |
| 47-34 | Me | (CH₂)₂ | H | CH₂ | N(Et)₂ | 4-iPrSO₂-Ph | O |
| 47-35 | Me | (CH₂)₂ | H | CH₂ | N(Et)₂ | 4-(Pyr-2)Ph | O |
| 47-36 | Me | (CH₂)₂ | H | CH₂ | N(Et)₂ | 4-(Pyr-3)Ph | O |
| 47-37 | Me | (CH₂)₂ | H | CH₂ | N(Et)₂ | 4-(Pyr-4)Ph | O |
| 47-38 | Me | (CH₂)₂ | H | CH₂ | N(Et)₂ | 3-Ph-6-Pyr | O |

TABLE 48

| Exemplification No. compound. | R¹ | R² | R³ | Z | W | X | Y |
|---|---|---|---|---|---|---|---|
| 48-1 | Me | (CH₂)₂ | H | CH₂ | N(Me)(Ph) | 4-Et-Ph | O |
| 48-2 | Me | (CH₂)₂ | H | CH₂ | N(Me)(Ph) | 4-iPr-Ph | O |
| 48-3 | Me | (CH₂)₂ | H | CH₂ | N(Me)(Ph) | 3-Ph-Ph | O |
| 48-4 | Me | (CH₂)₂ | H | CH₂ | N(Me)(Ph) | 4-Ph-Ph | O |
| 48-5 | Me | (CH₂)₂ | H | CH₂ | N(Me)(Ph) | 3-Pyr | O |
| 48-6 | Me | (CH₂)₂ | H | CH₂ | N(Me)(Ph) | 5-Me-3-Pyr | O |
| 48-7 | Me | (CH₂)₂ | H | CH₂ | N(Me)(Ph) | 5-Et-3-Pyr | O |
| 48-8 | Me | (CH₂)₂ | H | CH₂ | N(Me)(Ph) | 5-Ph-3-Pyr | O |
| 48-9 | Me | (CH₂)₂ | H | CH₂ | N(Me)(Ph) | 6-Me-3-Pyr | O |
| 48-10 | Me | (CH₂)₂ | H | CH₂ | N(Me)(Ph) | 6-Et-3-Pyr | O |
| 48-11 | Me | (CH₂)₂ | H | CH₂ | N(Me)(Ph) | 6-Ph-3-Pyr | O |
| 48-12 | Me | (CH₂)₂ | H | CH₂ | N(Me)(Ph) | 6-MeO-3-Pyr | O |
| 48-13 | Me | (CH₂)₂ | H | CH₂ | N(Me)(Ph) | 6-EtO-3-Pyr | O |
| 48-14 | Me | (CH₂)₂ | H | CH₂ | N(Me)(Ph) | 6-iPrO-3-Pyr | O |
| 48-15 | Me | (CH₂)₂ | H | CH₂ | N(Me)(Ph) | 6-MeS-3-Pyr | O |
| 48-16 | Me | (CH₂)₂ | H | CH₂ | N(Me)(Ph) | 6-EtS-3-Pyr | O |
| 48-17 | Me | (CH₂)₂ | H | CH₂ | N(Me)(Ph) | 6-iPrS-3-Pyr | O |
| 48-18 | Me | (CH₂)₂ | H | CH₂ | N(Me)(Ph) | 6-MeSO₂-3-Pyr | O |
| 48-19 | Me | (CH₂)₂ | H | CH₂ | N(Me)(Ph) | 6-EtSO₂-3-Pyr | O |
| 48-20 | Me | (CH₂)₂ | H | CH₂ | N(Me)(Ph) | 6-iPrSO₂-3-Pyr | O |
| 48-21 | Me | (CH₂)₂ | H | CH₂ | N(Me)(Ph) | 6-Bz-3-Pyr | O |
| 48-22 | Me | (CH₂)₂ | H | CH₂ | N(Me)(Ph) | 6-PhO-3-Pyr | O |
| 48-23 | Me | (CH₂)₂ | H | CH₂ | N(Me)(Ph) | 6-PhS-3-Pyr | O |
| 48-24 | Me | (CH₂)₂ | H | CH₂ | N(Me)(Ph) | 6-PhSO₂-3-Pyr | O |
| 48-25 | Me | (CH₂)₂ | H | CH₂ | N(Me)(Ph) | 2-Quin | O |
| 48-26 | Me | (CH₂)₂ | H | CH₂ | N(Me)(Ph) | 4-MeO-Ph | O |
| 48-27 | Me | (CH₂)₂ | H | CH₂ | N(Me)(Ph) | 4-EtO-Ph | O |
| 48-28 | Me | (CH₂)₂ | H | CH₂ | N(Me)(Ph) | 4-iPrO-Ph | O |
| 48-29 | Me | (CH₂)₂ | H | CH₂ | N(Me)(Ph) | 4-MeS-Ph | O |
| 48-30 | Me | (CH₂)₂ | H | CH₂ | N(Me)(Ph) | 4-EtS-Ph | O |
| 48-31 | Me | (CH₂)₂ | H | CH₂ | N(Me)(Ph) | 4-iPrS-Ph | O |
| 48-32 | Me | (CH₂)₂ | H | CH₂ | N(Me)(Ph) | 4-MeSO₂-Ph | O |
| 48-33 | Me | (CH₂)₂ | H | CH₂ | N(Me)(Ph) | 4-EtSO₂-Ph | O |
| 48-34 | Me | (CH₂)₂ | H | CH₂ | N(Me)(Ph) | 4-iPrSO₂-Ph | O |
| 48-35 | Me | (CH₂)₂ | H | CH₂ | N(Me)(Ph) | 4-(Pyr-2)Ph | O |
| 48-36 | Me | (CH₂)₂ | H | CH₂ | N(Me)(Ph) | 4-(Pyr-3)Ph | O |
| 48-37 | Me | (CH₂)₂ | H | CH₂ | N(Me)(Ph) | 4-(Pyr-4)Ph | O |
| 48-38 | Me | (CH₂)₂ | H | CH₂ | N(Me)(Ph) | 3-Ph-6-Pyr | O |

TABLE 49

| Exemplification No. compound. | R¹ | R² | R³ | Z | W | X | Y |
|---|---|---|---|---|---|---|---|
| 49-1 | Me | (CH₂)₂ | H | CH₂ | N(Et)(Ph) | 4-Et-Ph | O |
| 49-2 | Me | (CH₂)₂ | H | CH₂ | N(Et)(Ph) | 4-iPr-Ph | O |
| 49-3 | Me | (CH₂)₂ | H | CH₂ | N(Et)(Ph) | 3-Ph-Ph | O |
| 49-4 | Me | (CH₂)₂ | H | CH₂ | N(Et)(Ph) | 4-Ph-Ph | O |
| 49-5 | Me | (CH₂)₂ | H | CH₂ | N(Et)(Ph) | 3-Pyr | O |
| 49-6 | Me | (CH₂)₂ | H | CH₂ | N(Et)(Ph) | 5-Me-3-Pyr | O |
| 49-7 | Me | (CH₂)₂ | H | CH₂ | N(Et)(Ph) | 5-Et-3-Pyr | O |
| 49-8 | Me | (CH₂)₂ | H | CH₂ | N(Et)(Ph) | 5-Ph-3-Pyr | O |
| 49-9 | Me | (CH₂)₂ | H | CH₂ | N(Et)(Ph) | 6-Me-3-Pyr | O |
| 49-10 | Me | (CH₂)₂ | H | CH₂ | N(Et)(Ph) | 6-Et-3-Pyr | O |
| 49-11 | Me | (CH₂)₂ | H | CH₂ | N(Et)(Ph) | 6-Ph-3-Pyr | O |
| 49-12 | Me | (CH₂)₂ | H | CH₂ | N(Et)(Ph) | 6-MeO-3-Pyr | O |
| 49-13 | Me | (CH₂)₂ | H | CH₂ | N(Et)(Ph) | 6-EtO-3-Pyr | O |
| 49-14 | Me | (CH₂)₂ | H | CH₂ | N(Et)(Ph) | 6-iPrO-3-Pyr | O |
| 49-15 | Me | (CH₂)₂ | H | CH₂ | N(Et)(Ph) | 6-MeS-3-Pyr | O |
| 49-16 | Me | (CH₂)₂ | H | CH₂ | N(Et)(Ph) | 6-EtS-3-Pyr | O |
| 49-17 | Me | (CH₂)₂ | H | CH₂ | N(Et)(Ph) | 6-iPrS-3-Pyr | O |
| 49-18 | Me | (CH₂)₂ | H | CH₂ | N(Et)(Ph) | 6-MeSO₂-3-Pyr | O |
| 49-19 | Me | (CH₂)₂ | H | CH₂ | N(Et)(Ph) | 6-EtSO₂-3-Pyr | O |
| 49-20 | Me | (CH₂)₂ | H | CH₂ | N(Et)(Ph) | 6-iPrSO₂-3-Pyr | O |
| 49-21 | Me | (CH₂)₂ | H | CH₂ | N(Et)(Ph) | 6-Bz-3-Pyr | O |
| 49-22 | Me | (CH₂)₂ | H | CH₂ | N(Et)(Ph) | 6-PhO-3-Pyr | O |
| 49-23 | Me | (CH₂)₂ | H | CH₂ | N(Et)(Ph) | 6-PhS-3-Pyr | O |
| 49-24 | Me | (CH₂)₂ | H | CH₂ | N(Et)(Ph) | 6-PhSO₂-3-Pyr | O |
| 49-25 | Me | (CH₂)₂ | H | CH₂ | N(Et)(Ph) | 2-Quin | O |
| 49-26 | Me | (CH₂)₂ | H | CH₂ | N(Et)(Ph) | 4-MeO-Ph | O |
| 49-27 | Me | (CH₂)₂ | H | CH₂ | N(Et)(Ph) | 4-EtO-Ph | O |
| 49-28 | Me | (CH₂)₂ | H | CH₂ | N(Et)(Ph) | 4-iPrO-Ph | O |
| 49-29 | Me | (CH₂)₂ | H | CH₂ | N(Et)(Ph) | 4-MeS-Ph | O |

TABLE 49-continued

| Exemplification No. compound. | R¹ | R² | R³ | Z | W | X | Y |
|---|---|---|---|---|---|---|---|
| 49-30 | Me | (CH₂)₂ | H | CH₂ | N(Et)(Ph) | 4-EtS-Ph | O |
| 49-31 | Me | (CH₂)₂ | H | CH₂ | N(Et)(Ph) | 4-iPrS-Ph | O |
| 49-32 | Me | (CH₂)₂ | H | CH₂ | N(Et)(Ph) | 4-MeSO₂-Ph | O |
| 49-33 | Me | (CH₂)₂ | H | CH₂ | N(Et)(Ph) | 4-EtSO₂-Ph | O |
| 49-34 | Me | (CH₂)₂ | H | CH₂ | N(Et)(Ph) | 4-iPrSO₂-Ph | O |
| 49-35 | Me | (CH₂)₂ | H | CH₂ | N(Et)(Ph) | 4-(Pyr-2)Ph | O |
| 49-36 | Me | (CH₂)₂ | H | CH₂ | N(Et)(Ph) | 4-(Pyr-3)Ph | O |
| 49-37 | Me | (CH₂)₂ | H | CH₂ | N(Et)(Ph) | 4-(Pyr-4)Ph | O |
| 49-38 | Me | (CH₂)₂ | H | CH₂ | N(Et)(Ph) | 3-Ph-6-Pyr | O |

TABLE 50

| Exemplification No. compound. | R¹ | R² | R³ | Z | W | X | Y |
|---|---|---|---|---|---|---|---|
| 50-1 | Me | (CH₂)₂ | H | CH₂ | 1-Pyrr | 4-Et-Ph | O |
| 50-2 | Me | (CH₂)₂ | H | CH₂ | 1-Pyrr | 4-iPr-Ph | O |
| 50-3 | Me | (CH₂)₂ | H | CH₂ | 1-Pyrr | 3-Ph-Ph | O |
| 50-4 | Me | (CH₂)₂ | H | CH₂ | 1-Pyrr | 4-Ph-Ph | O |
| 50-5 | Me | (CH₂)₂ | H | CH₂ | 1-Pyrr | 3-Pyr | O |
| 50-6 | Me | (CH₂)₂ | H | CH₂ | 1-Pyrr | 5-Me-3-Pyr | O |
| 50-7 | Me | (CH₂)₂ | H | CH₂ | 1-Pyrr | 5-Et-3-Pyr | O |
| 50-8 | Me | (CH₂)₂ | H | CH₂ | 1-Pyrr | 5-Ph-3-Pyr | O |
| 50-9 | Me | (CH₂)₂ | H | CH₂ | 1-Pyrr | 6-Me-3-Pyr | O |
| 50-10 | Me | (CH₂)₂ | H | CH₂ | 1-Pyrr | 6-Et-3-Pyr | O |
| 50-11 | Me | (CH₂)₂ | H | CH₂ | 1-Pyrr | 6-Ph-3-Pyr | O |
| 50-12 | Me | (CH₂)₂ | H | CH₂ | 1-Pyrr | 6-MeO-3-Pyr | O |
| 50-13 | Me | (CH₂)₂ | H | CH₂ | 1-Pyrr | 6-EtO-3-Pyr | O |
| 50-14 | Me | (CH₂)₂ | H | CH₂ | 1-Pyrr | 6-iPrO-3-Pyr | O |
| 50-15 | Me | (CH₂)₂ | H | CH₂ | 1-Pyrr | 6-MeS-3-Pyr | O |
| 50-16 | Me | (CH₂)₂ | H | CH₂ | 1-Pyrr | 6-EtS-3-Pyr | O |
| 50-17 | Me | (CH₂)₂ | H | CH₂ | 1-Pyrr | 6-iPrS-3-Pyr | O |
| 50-18 | Me | (CH₂)₂ | H | CH₂ | 1-Pyrr | 6-MeSO₂-3-Pyr | O |
| 50-19 | Me | (CH₂)₂ | H | CH₂ | 1-Pyrr | 6-EtSO₂-3-Pyr | O |
| 50-20 | Me | (CH₂)₂ | H | CH₂ | 1-Pyrr | 6-iPrSO₂-3-Pyr | O |
| 50-21 | Me | (CH₂)₂ | H | CH₂ | 1-Pyrr | 6-Bz-3-Pyr | O |
| 50-22 | Me | (CH₂)₂ | H | CH₂ | 1-Pyrr | 6-PhO-3-Pyr | O |
| 50-23 | Me | (CH₂)₂ | H | CH₂ | 1-Pyrr | 6-PhS-3-Pyr | O |
| 50-24 | Me | (CH₂)₂ | H | CH₂ | 1-Pyrr | 6-PhSO₂-3-Pyr | O |
| 50-25 | Me | (CH₂)₂ | H | CH₂ | 1-Pyrr | 2-Quin | O |
| 50-26 | Me | (CH₂)₂ | H | CH₂ | 1-Pyrr | 4-MeO-Ph | O |
| 50-27 | Me | (CH₂)₂ | H | CH₂ | 1-Pyrr | 4-EtO-Ph | O |
| 50-28 | Me | (CH₂)₂ | H | CH₂ | 1-Pyrr | 4-iPrO-Ph | O |
| 50-29 | Me | (CH₂)₂ | H | CH₂ | 1-Pyrr | 4-MeS-Ph | O |
| 50-30 | Me | (CH₂)₂ | H | CH₂ | 1-Pyrr | 4-EtS-Ph | O |
| 50-31 | Me | (CH₂)₂ | H | CH₂ | 1-Pyrr | 4-iPrS-Ph | O |
| 50-32 | Me | (CH₂)₂ | H | CH₂ | 1-Pyrr | 4-MeSO₂-Ph | O |
| 50-33 | Me | (CH₂)₂ | H | CH₂ | 1-Pyrr | 4-EtSO₂-Ph | O |
| 50-34 | Me | (CH₂)₂ | H | CH₂ | 1-Pyrr | 4-iPrSO₂-Ph | O |
| 50-35 | Me | (CH₂)₂ | H | CH₂ | 1-Pyrr | 4-(Pyr-2)Ph | O |
| 50-36 | Me | (CH₂)₂ | H | CH₂ | 1-Pyrr | 4-(Pyr-3)Ph | O |
| 50-37 | Me | (CH₂)₂ | H | CH₂ | 1-Pyrr | 4-(Pyr-4)Ph | O |
| 50-38 | Me | (CH₂)₂ | H | CH₂ | 1-Pyrr | 3-Ph-6-Pyr | O |

TABLE 51

| Exemplification No. compound. | R¹ | R² | R³ | Z | W | X | Y |
|---|---|---|---|---|---|---|---|
| 51-1 | Me | (CH₂)₂ | H | CH₂ | 1-Pyrd | 4-Et-Ph | O |
| 51-2 | Me | (CH₂)₂ | H | CH₂ | 1-Pyrd | 4-iPr-Ph | O |
| 51-3 | Me | (CH₂)₂ | H | CH₂ | 1-Pyrd | 3-Ph-Ph | O |
| 51-4 | Me | (CH₂)₂ | H | CH₂ | 1-Pyrd | 4-Ph-Ph | O |
| 51-5 | Me | (CH₂)₂ | H | CH₂ | 1-Pyrd | 3-Pyr | O |
| 51-6 | Me | (CH₂)₂ | H | CH₂ | 1-Pyrd | 5-Me-3-Pyr | O |
| 51-7 | Me | (CH₂)₂ | H | CH₂ | 1-Pyrd | 5-Et-3-Pyr | O |
| 51-8 | Me | (CH₂)₂ | H | CH₂ | 1-Pyrd | 5-Ph-3-Pyr | O |
| 51-9 | Me | (CH₂)₂ | H | CH₂ | 1-Pyrd | 6-Me-3-Pyr | O |
| 51-10 | Me | (CH₂)₂ | H | CH₂ | 1-Pyrd | 6-Et-3-Pyr | O |
| 51-11 | Me | (CH₂)₂ | H | CH₂ | 1-Pyrd | 6-Ph-3-Pyr | O |
| 51-12 | Me | (CH₂)₂ | H | CH₂ | 1-Pyrd | 6-MeO-3-Pyr | O |
| 51-13 | Me | (CH₂)₂ | H | CH₂ | 1-Pyrd | 6-EtO-3-Pyr | O |
| 51-14 | Me | (CH₂)₂ | H | CH₂ | 1-Pyrd | 6-iPrO-3-Pyr | O |
| 51-15 | Me | (CH₂)₂ | H | CH₂ | 1-Pyrd | 6-MeS-3-Pyr | O |
| 51-16 | Me | (CH₂)₂ | H | CH₂ | 1-Pyrd | 6-EtS-3-Pyr | O |
| 51-17 | Me | (CH₂)₂ | H | CH₂ | 1-Pyrd | 6-iPrS-3-Pyr | O |
| 51-18 | Me | (CH₂)₂ | H | CH₂ | 1-Pyrd | 6-MeSO₂-3-Pyr | O |
| 51-19 | Me | (CH₂)₂ | H | CH₂ | 1-Pyrd | 6-EtSO₂-3-Pyr | O |
| 51-20 | Me | (CH₂)₂ | H | CH₂ | 1-Pyrd | 6-iPrSO₂-3-Pyr | O |
| 51-21 | Me | (CH₂)₂ | H | CH₂ | 1-Pyrd | 6-Bz-3-Pyr | O |
| 51-22 | Me | (CH₂)₂ | H | CH₂ | 1-Pyrd | 6-PhO-3-Pyr | O |
| 51-23 | Me | (CH₂)₂ | H | CH₂ | 1-Pyrd | 6-PhS-3-Pyr | O |
| 51-24 | Me | (CH₂)₂ | H | CH₂ | 1-Pyrd | 6-PhSO₂-3-Pyr | O |
| 51-25 | Me | (CH₂)₂ | H | CH₂ | 1-Pyrd | 2-Quin | O |
| 51-26 | Me | (CH₂)₂ | H | CH₂ | 1-Pyrd | 4-MeO-Ph | O |
| 51-27 | Me | (CH₂)₂ | H | CH₂ | 1-Pyrd | 4-EtO-Ph | O |
| 51-28 | Me | (CH₂)₂ | H | CH₂ | 1-Pyrd | 4-iPrO-Ph | O |
| 51-29 | Me | (CH₂)₂ | H | CH₂ | 1-Pyrd | 4-MeS-Ph | O |
| 51-30 | Me | (CH₂)₂ | H | CH₂ | 1-Pyrd | 4-EtS-Ph | O |
| 51-31 | Me | (CH₂)₂ | H | CH₂ | 1-Pyrd | 4-iPrS-Ph | O |
| 51-32 | Me | (CH₂)₂ | H | CH₂ | 1-Pyrd | 4-MeSO₂-Ph | O |
| 51-33 | Me | (CH₂)₂ | H | CH₂ | 1-Pyrd | 4-EtSO₂-Ph | O |
| 51-34 | Me | (CH₂)₂ | H | CH₂ | 1-Pyrd | 4-iPrSO₂-Ph | O |
| 51-35 | Me | (CH₂)₂ | H | CH₂ | 1-Pyrd | 4-(Pyr-2)Ph | O |
| 51-36 | Me | (CH₂)₂ | H | CH₂ | 1-Pyrd | 4-(Pyr-3)Ph | O |
| 51-37 | Me | (CH₂)₂ | H | CH₂ | 1-Pyrd | 4-(Pyr-4)Ph | O |
| 51-38 | Me | (CH₂)₂ | H | CH₂ | 1-Pyrd | 3-Ph-6-Pyr | O |

TABLE 52

| Exemplification No. compound. | R¹ | R² | R³ | Z | W | X | Y |
|---|---|---|---|---|---|---|---|
| 52-1 | Me | (CH₂)₂ | H | CH₂ | 1-Imid | 4-Et-Ph | O |
| 52-2 | Me | (CH₂)₂ | H | CH₂ | 1-Imid | 4-iPr-Ph | O |
| 52-3 | Me | (CH₂)₂ | H | CH₂ | 1-Imid | 3-Ph-Ph | O |
| 52-4 | Me | (CH₂)₂ | H | CH₂ | 1-Imid | 4-Ph-Ph | O |
| 52-5 | Me | (CH₂)₂ | H | CH₂ | 1-Imid | 3-Pyr | O |
| 52-6 | Me | (CH₂)₂ | H | CH₂ | 1-Imid | 5-Me-3-Pyr | O |
| 52-7 | Me | (CH₂)₂ | H | CH₂ | 1-Imid | 5-Et-3-Pyr | O |
| 52-8 | Me | (CH₂)₂ | H | CH₂ | 1-Imid | 5-Ph-3-Pyr | O |
| 52-9 | Me | (CH₂)₂ | H | CH₂ | 1-Imid | 6-Me-3-Pyr | O |
| 52-10 | Me | (CH₂)₂ | H | CH₂ | 1-Imid | 6-Et-3-Pyr | O |
| 52-11 | Me | (CH₂)₂ | H | CH₂ | 1-Imid | 6-Ph-3-Pyr | O |
| 52-12 | Me | (CH₂)₂ | H | CH₂ | 1-Imid | 6-MeO-3-Pyr | O |
| 52-13 | Me | (CH₂)₂ | H | CH₂ | 1-Imid | 6-EtO-3-Pyr | O |
| 52-14 | Me | (CH₂)₂ | H | CH₂ | 1-Imid | 6-iPrO-3-Pyr | O |
| 52-15 | Me | (CH₂)₂ | H | CH₂ | 1-Imid | 6-MeS-3-Pyr | O |
| 52-16 | Me | (CH₂)₂ | H | CH₂ | 1-Imid | 6-EtS-3-Pyr | O |
| 52-17 | Me | (CH₂)₂ | H | CH₂ | 1-Imid | 6-iPrS-3-Pyr | O |
| 52-18 | Me | (CH₂)₂ | H | CH₂ | 1-Imid | 6-MeSO₂-3-Pyr | O |

TABLE 52-continued

| Exemplification No. compound. | R$^1$ | R$^2$ | R$^3$ | Z | W | X | Y |
|---|---|---|---|---|---|---|---|
| 52-19 | Me | (CH$_2$)$_2$ | H | CH$_2$ | 1-Imid | 6-EtSO$_2$-3-Pyr | O |
| 52-20 | Me | (CH$_2$)$_2$ | H | CH$_2$ | 1-Imid | 6-iPrSO$_2$-3-Pyr | O |
| 52-21 | Me | (CH$_2$)$_2$ | H | CH$_2$ | 1-Imid | 6-Bz-3-Pyr | O |
| 52-22 | Me | (CH$_2$)$_2$ | H | CH$_2$ | 1-Imid | 6-PhO-3-Pyr | O |
| 52-23 | Me | (CH$_2$)$_2$ | H | CH$_2$ | 1-Imid | 6-PhS-3-Pyr | O |
| 52-24 | Me | (CH$_2$)$_2$ | H | CH$_2$ | 1-Imid | 6-PhSO$_2$-3-Pyr | O |
| 52-25 | Me | (CH$_2$)$_2$ | H | CH$_2$ | 1-Imid | 2-Quin | O |
| 52-26 | Me | (CH$_2$)$_2$ | H | CH$_2$ | 1-Imid | 4-MeO-Ph | O |
| 52-27 | Me | (CH$_2$)$_2$ | H | CH$_2$ | 1-Imid | 4-EtO-Ph | O |
| 52-28 | Me | (CH$_2$)$_2$ | H | CH$_2$ | 1-Imid | 4-iPrO-Ph | O |
| 52-29 | Me | (CH$_2$)$_2$ | H | CH$_2$ | 1-Imid | 4-MeS-Ph | O |
| 52-30 | Me | (CH$_2$)$_2$ | H | CH$_2$ | 1-Imid | 4-EtS-Ph | O |
| 52-31 | Me | (CH$_2$)$_2$ | H | CH$_2$ | 1-Imid | 4-iPrS-Ph | O |
| 52-32 | Me | (CH$_2$)$_2$ | H | CH$_2$ | 1-Imid | 4-MeSO$_2$-Ph | O |
| 52-33 | Me | (CH$_2$)$_2$ | H | CH$_2$ | 1-Imid | 4-EtSO$_2$-Ph | O |
| 52-34 | Me | (CH$_2$)$_2$ | H | CH$_2$ | 1-Imid | 4-iPrSO$_2$-Ph | O |
| 52-35 | Me | (CH$_2$)$_2$ | H | CH$_2$ | 1-Imid | 4-(Pyr-2)Ph | O |
| 52-36 | Me | (CH$_2$)$_2$ | H | CH$_2$ | 1-Imid | 4-(Pyr-3)Ph | O |
| 52-37 | Me | (CH$_2$)$_2$ | H | CH$_2$ | 1-Imid | 4-(Pyr-4)Ph | O |
| 52-38 | Me | (CH$_2$)$_2$ | H | CH$_2$ | 1-Imid | 3-Ph-6-Pyr | O |

TABLE 53

| Exemplification No. compound. | R$^1$ | R$^2$ | R$^3$ | Z | W | X | Y |
|---|---|---|---|---|---|---|---|
| 53-1 | Me | (CH$_2$)$_2$ | H | CH$_2$ | 1-Pip | 4-Et-Ph | O |
| 53-2 | Me | (CH$_2$)$_2$ | H | CH$_2$ | 1-Pip | 4-iPr-Ph | O |
| 53-3 | Me | (CH$_2$)$_2$ | H | CH$_2$ | 1-Pip | 3-Ph-Ph | O |
| 53-4 | Me | (CH$_2$)$_2$ | H | CH$_2$ | 1-Pip | 4-Ph-Ph | O |
| 53-5 | Me | (CH$_2$)$_2$ | H | CH$_2$ | 1-Pip | 3-Pyr | O |
| 53-6 | Me | (CH$_2$)$_2$ | H | CH$_2$ | 1-Pip | 5-Me-3-Pyr | O |
| 53-7 | Me | (CH$_2$)$_2$ | H | CH$_2$ | 1-Pip | 5-Et-3-Pyr | O |
| 53-8 | Me | (CH$_2$)$_2$ | H | CH$_2$ | 1-Pip | 5-Ph-3-Pyr | O |
| 53-9 | Me | (CH$_2$)$_2$ | H | CH$_2$ | 1-Pip | 6-Me-3-Pyr | O |
| 53-10 | Me | (CH$_2$)$_2$ | H | CH$_2$ | 1-Pip | 6-Et-3-Pyr | O |
| 53-11 | Me | (CH$_2$)$_2$ | H | CH$_2$ | 1-Pip | 6-Ph-3-Pyr | O |
| 53-12 | Me | (CH$_2$)$_2$ | H | CH$_2$ | 1-Pip | 6-MeO-3-Pyr | O |
| 53-13 | Me | (CH$_2$)$_2$ | H | CH$_2$ | 1-Pip | 6-EtO-3-Pyr | O |
| 53-14 | Me | (CH$_2$)$_2$ | H | CH$_2$ | 1-Pip | 6-iPrO-3-Pyr | O |
| 53-15 | Me | (CH$_2$)$_2$ | H | CH$_2$ | 1-Pip | 6-MeS-3-Pyr | O |
| 53-16 | Me | (CH$_2$)$_2$ | H | CH$_2$ | 1-Pip | 6-EtS-3-Pyr | O |
| 53-17 | Me | (CH$_2$)$_2$ | H | CH$_2$ | 1-Pip | 6-iPrS-3-Pyr | O |
| 53-18 | Me | (CH$_2$)$_2$ | H | CH$_2$ | 1-Pip | 6-MeSO$_2$-3-Pyr | O |
| 53-19 | Me | (CH$_2$)$_2$ | H | CH$_2$ | 1-Pip | 6-EtSO$_2$-3-Pyr | O |
| 53-20 | Me | (CH$_2$)$_2$ | H | CH$_2$ | 1-Pip | 6-iPrSO$_2$-3-Pyr | O |
| 53-21 | Me | (CH$_2$)$_2$ | H | CH$_2$ | 1-Pip | 6-Bz-3-Pyr | O |
| 53-22 | Me | (CH$_2$)$_2$ | H | CH$_2$ | 1-Pip | 6-PhO-3-Pyr | O |
| 53-23 | Me | (CH$_2$)$_2$ | H | CH$_2$ | 1-Pip | 6-PhS-3-Pyr | O |
| 53-24 | Me | (CH$_2$)$_2$ | H | CH$_2$ | 1-Pip | 6-PhSO$_2$-3-Pyr | O |
| 53-25 | Me | (CH$_2$)$_2$ | H | CH$_2$ | 1-Pip | 2-Quin | O |
| 53-26 | Me | (CH$_2$)$_2$ | H | CH$_2$ | 1-Pip | 4-MeO-Ph | O |
| 53-27 | Me | (CH$_2$)$_2$ | H | CH$_2$ | 1-Pip | 4-EtO-Ph | O |
| 53-28 | Me | (CH$_2$)$_2$ | H | CH$_2$ | 1-Pip | 4-iPrO-Ph | O |
| 53-29 | Me | (CH$_2$)$_2$ | H | CH$_2$ | 1-Pip | 4-MeS-Ph | O |
| 53-30 | Me | (CH$_2$)$_2$ | H | CH$_2$ | 1-Pip | 4-EtS-Ph | O |
| 53-31 | Me | (CH$_2$)$_2$ | H | CH$_2$ | 1-Pip | 4-iPrS-Ph | O |
| 53-32 | Me | (CH$_2$)$_2$ | H | CH$_2$ | 1-Pip | 4-MeSO$_2$-Ph | O |
| 53-33 | Me | (CH$_2$)$_2$ | H | CH$_2$ | 1-Pip | 4-EtSO$_2$-Ph | O |
| 53-34 | Me | (CH$_2$)$_2$ | H | CH$_2$ | 1-Pip | 4-iPrSO$_2$-Ph | O |
| 53-35 | Me | (CH$_2$)$_2$ | H | CH$_2$ | 1-Pip | 4-(Pyr-2)Ph | O |
| 53-36 | Me | (CH$_2$)$_2$ | H | CH$_2$ | 1-Pip | 4-(Pyr-3)Ph | O |
| 53-37 | Me | (CH$_2$)$_2$ | H | CH$_2$ | 1-Pip | 4-(Pyr-4)Ph | O |
| 53-38 | Me | (CH$_2$)$_2$ | H | CH$_2$ | 1-Pip | 3-Ph-6-Pyr | O |

TABLE 54

| Exemplification No. compound. | R$^1$ | R$^2$ | R$^3$ | Z | W | X | Y |
|---|---|---|---|---|---|---|---|
| 54-1 | Me | (CH$_2$)$_2$ | H | CH$_2$ | 1-Mor | 4-Et-Ph | O |
| 54-2 | Me | (CH$_2$)$_2$ | H | CH$_2$ | 1-Mor | 4-iPr-Ph | O |
| 54-3 | Me | (CH$_2$)$_2$ | H | CH$_2$ | 1-Mor | 3-Ph-Ph | O |
| 54-4 | Me | (CH$_2$)$_2$ | H | CH$_2$ | 1-Mor | 4-Ph-Ph | O |
| 54-5 | Me | (CH$_2$)$_2$ | H | CH$_2$ | 1-Mor | 3-Pyr | O |
| 54-6 | Me | (CH$_2$)$_2$ | H | CH$_2$ | 1-Mor | 5-Me-3-Pyr | O |
| 54-7 | Me | (CH$_2$)$_2$ | H | CH$_2$ | 1-Mor | 5-Et-3-Pyr | O |
| 54-8 | Me | (CH$_2$)$_2$ | H | CH$_2$ | 1-Mor | 5-Ph-3-Pyr | O |
| 54-9 | Me | (CH$_2$)$_2$ | H | CH$_2$ | 1-Mor | 6-Me-3-Pyr | O |
| 54-10 | Me | (CH$_2$)$_2$ | H | CH$_2$ | 1-Mor | 6-Et-3-Pyr | O |
| 54-11 | Me | (CH$_2$)$_2$ | H | CH$_2$ | 1-Mor | 6-Ph-3-Pyr | O |
| 54-12 | Me | (CH$_2$)$_2$ | H | CH$_2$ | 1-Mor | 6-MeO-3-Pyr | O |
| 54-13 | Me | (CH$_2$)$_2$ | H | CH$_2$ | 1-Mor | 6-EtO-3-Pyr | O |
| 54-14 | Me | (CH$_2$)$_2$ | H | CH$_2$ | 1-Mor | 6-iPrO-3-Pyr | O |
| 54-15 | Me | (CH$_2$)$_2$ | H | CH$_2$ | 1-Mor | 6-MeS-3-Pyr | O |
| 54-16 | Me | (CH$_2$)$_2$ | H | CH$_2$ | 1-Mor | 6-EtS-3-Pyr | O |
| 54-17 | Me | (CH$_2$)$_2$ | H | CH$_2$ | 1-Mor | 6-iPrS-3-Pyr | O |
| 54-18 | Me | (CH$_2$)$_2$ | H | CH$_2$ | 1-Mor | 6-MeSO$_2$-3-Pyr | O |
| 54-19 | Me | (CH$_2$)$_2$ | H | CH$_2$ | 1-Mor | 6-EtSO$_2$-3-Pyr | O |
| 54-20 | Me | (CH$_2$)$_2$ | H | CH$_2$ | 1-Mor | 6-iPrSO$_2$-3-Pyr | O |
| 54-21 | Me | (CH$_2$)$_2$ | H | CH$_2$ | 1-Mor | 6-Bz-3-Pyr | O |
| 54-22 | Me | (CH$_2$)$_2$ | H | CH$_2$ | 1-Mor | 6-PhO-3-Pyr | O |
| 54-23 | Me | (CH$_2$)$_2$ | H | CH$_2$ | 1-Mor | 6-PhS-3-Pyr | O |
| 54-24 | Me | (CH$_2$)$_2$ | H | CH$_2$ | 1-Mor | 6-PhSO$_2$-3-Pyr | O |
| 54-25 | Me | (CH$_2$)$_2$ | H | CH$_2$ | 1-Mor | 2-Quin | O |
| 54-26 | Me | (CH$_2$)$_2$ | H | CH$_2$ | 1-Mor | 4-MeO-Ph | O |
| 54-27 | Me | (CH$_2$)$_2$ | H | CH$_2$ | 1-Mor | 4-EtO-Ph | O |
| 54-28 | Me | (CH$_2$)$_2$ | H | CH$_2$ | 1-Mor | 4-iPrO-Ph | O |
| 54-29 | Me | (CH$_2$)$_2$ | H | CH$_2$ | 1-Mor | 4-MeS-Ph | O |
| 54-30 | Me | (CH$_2$)$_2$ | H | CH$_2$ | 1-Mor | 4-EtS-Ph | O |
| 54-31 | Me | (CH$_2$)$_2$ | H | CH$_2$ | 1-Mor | 4-iPrS-Ph | O |
| 54-32 | Me | (CH$_2$)$_2$ | H | CH$_2$ | 1-Mor | 4-MeSO$_2$-Ph | O |
| 54-33 | Me | (CH$_2$)$_2$ | H | CH$_2$ | 1-Mor | 4-EtSO$_2$-Ph | O |
| 54-34 | Me | (CH$_2$)$_2$ | H | CH$_2$ | 1-Mor | 4-iPrSO$_2$-Ph | O |
| 54-35 | Me | (CH$_2$)$_2$ | H | CH$_2$ | 1-Mor | 4-(Pyr-2)Ph | O |
| 54-36 | Me | (CH$_2$)$_2$ | H | CH$_2$ | 1-Mor | 4-(Pyr-3)Ph | O |
| 54-37 | Me | (CH$_2$)$_2$ | H | CH$_2$ | 1-Mor | 4-(Pyr-4)Ph | O |
| 54-38 | Me | (CH$_2$)$_2$ | H | CH$_2$ | 1-Mor | 3-Ph-6-Pyr | O |

TABLE 55

| Exemplification No. compound. | R$^1$ | R$^2$ | R$^3$ | Z | W | X | Y |
|---|---|---|---|---|---|---|---|
| 55-1 | Me | (CH$_2$)$_2$ | H | CH$_2$ | OH | 4-Et-Ph | O |
| 55-2 | Me | (CH$_2$)$_2$ | H | CH$_2$ | OH | 4-iPr-Ph | O |
| 55-3 | Me | (CH$_2$)$_2$ | H | CH$_2$ | OH | 3-Ph-Ph | O |
| 55-4 | Me | (CH$_2$)$_2$ | H | CH$_2$ | OH | 4-Ph-Ph | O |
| 55-5 | Me | (CH$_2$)$_2$ | H | CH$_2$ | OH | 3-Pyr | O |
| 55-6 | Me | (CH$_2$)$_2$ | H | CH$_2$ | OH | 5-Me-3-Pyr | O |
| 55-7 | Me | (CH$_2$)$_2$ | H | CH$_2$ | OH | 5-Et-3-Pyr | O |
| 55-8 | Me | (CH$_2$)$_2$ | H | CH$_2$ | OH | 5-Ph-3-Pyr | O |
| 55-9 | Me | (CH$_2$)$_2$ | H | CH$_2$ | OH | 6-Me-3-Pyr | O |
| 55-10 | Me | (CH$_2$)$_2$ | H | CH$_2$ | OH | 6-Et-3-Pyr | O |
| 55-11 | Me | (CH$_2$)$_2$ | H | CH$_2$ | OH | 6-Ph-3-Pyr | O |
| 55-12 | Me | (CH$_2$)$_2$ | H | CH$_2$ | OH | 6-MeO-3-Pyr | O |
| 55-13 | Me | (CH$_2$)$_2$ | H | CH$_2$ | OH | 6-EtO-3-Pyr | O |
| 55-14 | Me | (CH$_2$)$_2$ | H | CH$_2$ | OH | 6-iPrO-3-Pyr | O |
| 55-15 | Me | (CH$_2$)$_2$ | H | CH$_2$ | OH | 6-MeS-3-Pyr | O |
| 55-16 | Me | (CH$_2$)$_2$ | H | CH$_2$ | OH | 6-EtS-3-Pyr | O |
| 55-17 | Me | (CH$_2$)$_2$ | H | CH$_2$ | OH | 6-iPrS-3-Pyr | O |
| 55-18 | Me | (CH$_2$)$_2$ | H | CH$_2$ | OH | 6-MeSO$_2$-3-Pyr | O |
| 55-19 | Me | (CH$_2$)$_2$ | H | CH$_2$ | OH | 6-EtSO$_2$-3-Pyr | O |
| 55-20 | Me | (CH$_2$)$_2$ | H | CH$_2$ | OH | 6-iPrSO$_2$-3-Pyr | O |
| 55-21 | Me | (CH$_2$)$_2$ | H | CH$_2$ | OH | 6-Bz-3-Pyr | O |
| 55-22 | Me | (CH$_2$)$_2$ | H | CH$_2$ | OH | 6-PhO-3-Pyr | O |
| 55-23 | Me | (CH$_2$)$_2$ | H | CH$_2$ | OH | 6-PhS-3-Pyr | O |
| 55-24 | Me | (CH$_2$)$_2$ | H | CH$_2$ | OH | 6-PhSO$_2$-3-Pyr | O |
| 55-25 | Me | (CH$_2$)$_2$ | H | CH$_2$ | OH | 2-Quin | O |
| 55-26 | Me | (CH$_2$)$_2$ | H | CH$_2$ | OH | 4-MeO-Ph | O |
| 55-27 | Me | (CH$_2$)$_2$ | H | CH$_2$ | OH | 4-EtO-Ph | O |
| 55-28 | Me | (CH$_2$)$_2$ | H | CH$_2$ | OH | 4-iPrO-Ph | O |

TABLE 55-continued

| Exemplification No. compound. | R¹ | R² | R³ | Z | W | X | Y |
|---|---|---|---|---|---|---|---|
| 55-29 | Me | (CH$_2$)$_2$ | H | CH$_2$ | OH | 4-MeS-Ph | O |
| 55-30 | Me | (CH$_2$)$_2$ | H | CH$_2$ | OH | 4-EtS-Ph | O |
| 55-31 | Me | (CH$_2$)$_2$ | H | CH$_2$ | OH | 4-iPrS-Ph | O |
| 55-32 | Me | (CH$_2$)$_2$ | H | CH$_2$ | OH | 4-MeSO$_2$-Ph | O |
| 55-33 | Me | (CH$_2$)$_2$ | H | CH$_2$ | OH | 4-EtSO$_2$-Ph | O |
| 55-34 | Me | (CH$_2$)$_2$ | H | CH$_2$ | OH | 4-iPrSO$_2$-Ph | O |
| 55-35 | Me | (CH$_2$)$_2$ | H | CH$_2$ | OH | 4-(Pyr-2)Ph | O |
| 55-36 | Me | (CH$_2$)$_2$ | H | CH$_2$ | OH | 4-(Pyr-3)Ph | O |
| 55-37 | Me | (CH$_2$)$_2$ | H | CH$_2$ | OH | 4-(Pyr-4)Ph | O |
| 55-38 | Me | (CH$_2$)$_2$ | H | CH$_2$ | OH | 3-Ph-6-Pyr | O |

TABLE 56

| Exemplification No. compound. | R¹ | R² | R³ | Z | W | X | Y |
|---|---|---|---|---|---|---|---|
| 56-1 | Me | (CH$_2$)$_2$ | H | CH$_2$ | OMe | 4-Et-Ph | O |
| 56-2 | Me | (CH$_2$)$_2$ | H | CH$_2$ | OMe | 4-iPr-Ph | O |
| 56-3 | Me | (CH$_2$)$_2$ | H | CH$_2$ | OMe | 3-Ph-Ph | O |
| 56-4 | Me | (CH$_2$)$_2$ | H | CH$_2$ | OMe | 4-Ph-Ph | O |
| 56-5 | Me | (CH$_2$)$_2$ | H | CH$_2$ | OMe | 3-Pyr | O |
| 56-6 | Me | (CH$_2$)$_2$ | H | CH$_2$ | OMe | 5-Me-3-Pyr | O |
| 56-7 | Me | (CH$_2$)$_2$ | H | CH$_2$ | OMe | 5-Et-3-Pyr | O |
| 56-8 | Me | (CH$_2$)$_2$ | H | CH$_2$ | OMe | 5-Ph-3-Pyr | O |
| 56-9 | Me | (CH$_2$)$_2$ | H | CH$_2$ | OMe | 6-Me-3-Pyr | O |
| 56-10 | Me | (CH$_2$)$_2$ | H | CH$_2$ | OMe | 6-Et-3-Pyr | O |
| 56-11 | Me | (CH$_2$)$_2$ | H | CH$_2$ | OMe | 6-Ph-3-Pyr | O |
| 56-12 | Me | (CH$_2$)$_2$ | H | CH$_2$ | OMe | 6-MeO-3-Pyr | O |
| 56-13 | Me | (CH$_2$)$_2$ | H | CH$_2$ | OMe | 6-EtO-3-Pyr | O |
| 56-14 | Me | (CH$_2$)$_2$ | H | CH$_2$ | OMe | 6-iPrO-3-Pyr | O |
| 56-15 | Me | (CH$_2$)$_2$ | H | CH$_2$ | OMe | 6-MeS-3-Pyr | O |
| 56-16 | Me | (CH$_2$)$_2$ | H | CH$_2$ | OMe | 6-EtS-3-Pyr | O |
| 56-17 | Me | (CH$_2$)$_2$ | H | CH$_2$ | OMe | 6-iPrS-3-Pyr | O |
| 56-18 | Me | (CH$_2$)$_2$ | H | CH$_2$ | OMe | 6-MeSO$_2$-3-Pyr | O |
| 56-19 | Me | (CH$_2$)$_2$ | H | CH$_2$ | OMe | 6-EtSO$_2$-3-Pyr | O |
| 56-20 | Me | (CH$_2$)$_2$ | H | CH$_2$ | OMe | 6-iPrSO$_2$-3-Pyr | O |
| 56-21 | Me | (CH$_2$)$_2$ | H | CH$_2$ | OMe | 6-Bz-3-Pyr | O |
| 56-22 | Me | (CH$_2$)$_2$ | H | CH$_2$ | OMe | 6-PhO-3-Pyr | O |
| 56-23 | Me | (CH$_2$)$_2$ | H | CH$_2$ | OMe | 6-PhS-3-Pyr | O |
| 56-24 | Me | (CH$_2$)$_2$ | H | CH$_2$ | OMe | 6-PhSO$_2$-3-Pyr | O |
| 56-25 | Me | (CH$_2$)$_2$ | H | CH$_2$ | OMe | 2-Quin | O |
| 56-26 | Me | (CH$_2$)$_2$ | H | CH$_2$ | OMe | 4-MeO-Ph | O |
| 56-27 | Me | (CH$_2$)$_2$ | H | CH$_2$ | OMe | 4-EtO-Ph | O |
| 56-28 | Me | (CH$_2$)$_2$ | H | CH$_2$ | OMe | 4-iPrO-Ph | O |
| 56-29 | Me | (CH$_2$)$_2$ | H | CH$_2$ | OMe | 4-MeS-Ph | O |
| 56-30 | Me | (CH$_2$)$_2$ | H | CH$_2$ | OMe | 4-EtS-Ph | O |
| 56-31 | Me | (CH$_2$)$_2$ | H | CH$_2$ | OMe | 4-iPrS-Ph | O |
| 56-32 | Me | (CH$_2$)$_2$ | H | CH$_2$ | OMe | 4-MeSO$_2$-Ph | O |
| 56-33 | Me | (CH$_2$)$_2$ | H | CH$_2$ | OMe | 4-EtSO$_2$-Ph | O |
| 56-34 | Me | (CH$_2$)$_2$ | H | CH$_2$ | OMe | 4-iPrSO$_2$-Ph | O |
| 56-35 | Me | (CH$_2$)$_2$ | H | CH$_2$ | OMe | 4-(Pyr-2)Ph | O |
| 56-36 | Me | (CH$_2$)$_2$ | H | CH$_2$ | OMe | 4-(Pyr-3)Ph | O |
| 56-37 | Me | (CH$_2$)$_2$ | H | CH$_2$ | OMe | 4-(Pyr-4)Ph | O |
| 56-38 | Me | (CH$_2$)$_2$ | H | CH$_2$ | OMe | 3-Ph-6-Pyr | O |

TABLE 57

| Exemplification No. compound. | R¹ | R² | R³ | Z | W | X | Y |
|---|---|---|---|---|---|---|---|
| 57-1 | Me | (CH$_2$)$_2$ | H | CH$_2$ | OEt | 4-Et-Ph | O |
| 57-2 | Me | (CH$_2$)$_2$ | H | CH$_2$ | OEt | 4-iPr-Ph | O |
| 57-3 | Me | (CH$_2$)$_2$ | H | CH$_2$ | OEt | 3-Ph-Ph | O |
| 57-4 | Me | (CH$_2$)$_2$ | H | CH$_2$ | OEt | 4-Ph-Ph | O |
| 57-5 | Me | (CH$_2$)$_2$ | H | CH$_2$ | OEt | 3-Pyr | O |
| 57-6 | Me | (CH$_2$)$_2$ | H | CH$_2$ | OEt | 5-Me-3-Pyr | O |
| 57-7 | Me | (CH$_2$)$_2$ | H | CH$_2$ | OEt | 5-Et-3-Pyr | O |
| 57-8 | Me | (CH$_2$)$_2$ | H | CH$_2$ | OEt | 5-Ph-3-Pyr | O |
| 57-9 | Me | (CH$_2$)$_2$ | H | CH$_2$ | OEt | 6-Me-3-Pyr | O |
| 57-10 | Me | (CH$_2$)$_2$ | H | CH$_2$ | OEt | 6-Et-3-Pyr | O |
| 57-11 | Me | (CH$_2$)$_2$ | H | CH$_2$ | OEt | 6-Ph-3-Pyr | O |
| 57-12 | Me | (CH$_2$)$_2$ | H | CH$_2$ | OEt | 6-MeO-3-Pyr | O |
| 57-13 | Me | (CH$_2$)$_2$ | H | CH$_2$ | OEt | 6-EtO-3-Pyr | O |
| 57-14 | Me | (CH$_2$)$_2$ | H | CH$_2$ | OEt | 6-iPrO-3-Pyr | O |
| 57-15 | Me | (CH$_2$)$_2$ | H | CH$_2$ | OEt | 6-MeS-3-Pyr | O |
| 57-16 | Me | (CH$_2$)$_2$ | H | CH$_2$ | OEt | 6-EtS-3-Pyr | O |
| 57-17 | Me | (CH$_2$)$_2$ | H | CH$_2$ | OEt | 6-iPrS-3-Pyr | O |
| 57-18 | Me | (CH$_2$)$_2$ | H | CH$_2$ | OEt | 6-MeSO$_2$-3-Pyr | O |
| 57-19 | Me | (CH$_2$)$_2$ | H | CH$_2$ | OEt | 6-EtSO$_2$-3-Pyr | O |
| 57-20 | Me | (CH$_2$)$_2$ | H | CH$_2$ | OEt | 6-iPrSO$_2$-3-Pyr | O |
| 57-21 | Me | (CH$_2$)$_2$ | H | CH$_2$ | OEt | 6-Bz-3-Pyr | O |
| 57-22 | Me | (CH$_2$)$_2$ | H | CH$_2$ | OEt | 6-PhO-3-Pyr | O |
| 57-23 | Me | (CH$_2$)$_2$ | H | CH$_2$ | OEt | 6-PhS-3-Pyr | O |
| 57-24 | Me | (CH$_2$)$_2$ | H | CH$_2$ | OEt | 6-PhSO$_2$-3-Pyr | O |
| 57-25 | Me | (CH$_2$)$_2$ | H | CH$_2$ | OEt | 2-Quin | O |
| 57-26 | Me | (CH$_2$)$_2$ | H | CH$_2$ | OEt | 4-MeO-Ph | O |
| 57-27 | Me | (CH$_2$)$_2$ | H | CH$_2$ | OEt | 4-EtO-Ph | O |
| 57-28 | Me | (CH$_2$)$_2$ | H | CH$_2$ | OEt | 4-iPrO-Ph | O |
| 57-29 | Me | (CH$_2$)$_2$ | H | CH$_2$ | OEt | 4-MeS-Ph | O |
| 57-30 | Me | (CH$_2$)$_2$ | H | CH$_2$ | OEt | 4-EtS-Ph | O |
| 57-31 | Me | (CH$_2$)$_2$ | H | CH$_2$ | OEt | 4-iPrS-Ph | O |
| 57-32 | Me | (CH$_2$)$_2$ | H | CH$_2$ | OEt | 4-MeSO$_2$-Ph | O |
| 57-33 | Me | (CH$_2$)$_2$ | H | CH$_2$ | OEt | 4-EtSO$_2$-Ph | O |
| 57-34 | Me | (CH$_2$)$_2$ | H | CH$_2$ | OEt | 4-iPrSO$_2$-Ph | O |
| 57-35 | Me | (CH$_2$)$_2$ | H | CH$_2$ | OEt | 4-(Pyr-2)Ph | O |
| 57-36 | Me | (CH$_2$)$_2$ | H | CH$_2$ | OEt | 4-(Pyr-3)Ph | O |
| 57-37 | Me | (CH$_2$)$_2$ | H | CH$_2$ | OEt | 4-(Pyr-4)Ph | O |
| 57-38 | Me | (CH$_2$)$_2$ | H | CH$_2$ | OEt | 3-Ph-6-Pyr | O |

TABLE 58

| Exemplification No. compound. | R¹ | R² | R³ | Z | W | X | Y |
|---|---|---|---|---|---|---|---|
| 58-1 | Me | (CH$_2$)$_2$ | H | CH$_2$ | OPr | 4-Et-Ph | O |
| 58-2 | Me | (CH$_2$)$_2$ | H | CH$_2$ | OPr | 4-iPr-Ph | O |
| 58-3 | Me | (CH$_2$)$_2$ | H | CH$_2$ | OPr | 3-Ph-Ph | O |
| 58-4 | Me | (CH$_2$)$_2$ | H | CH$_2$ | OPr | 4-Ph-Ph | O |
| 58-5 | Me | (CH$_2$)$_2$ | H | CH$_2$ | OPr | 3-Pyr | O |
| 58-6 | Me | (CH$_2$)$_2$ | H | CH$_2$ | OPr | 5-Me-3-Pyr | O |
| 58-7 | Me | (CH$_2$)$_2$ | H | CH$_2$ | OPr | 5-Et-3-Pyr | O |
| 58-8 | Me | (CH$_2$)$_2$ | H | CH$_2$ | OPr | 5-Ph-3-Pyr | O |
| 58-9 | Me | (CH$_2$)$_2$ | H | CH$_2$ | OPr | 6-Me-3-Pyr | O |
| 58-10 | Me | (CH$_2$)$_2$ | H | CH$_2$ | OPr | 6-Et-3-Pyr | O |
| 58-11 | Me | (CH$_2$)$_2$ | H | CH$_2$ | OPr | 6-Ph-3-Pyr | O |
| 58-12 | Me | (CH$_2$)$_2$ | H | CH$_2$ | OPr | 6-MeO-3-Pyr | O |
| 58-13 | Me | (CH$_2$)$_2$ | H | CH$_2$ | OPr | 6-EtO-3-Pyr | O |
| 58-14 | Me | (CH$_2$)$_2$ | H | CH$_2$ | OPr | 6-iPrO-3-Pyr | O |
| 58-15 | Me | (CH$_2$)$_2$ | H | CH$_2$ | OPr | 6-MeS-3-Pyr | O |
| 58-16 | Me | (CH$_2$)$_2$ | H | CH$_2$ | OPr | 6-EtS-3-Pyr | O |
| 58-17 | Me | (CH$_2$)$_2$ | H | CH$_2$ | OPr | 6-iPrS-3-Pyr | O |
| 58-18 | Me | (CH$_2$)$_2$ | H | CH$_2$ | OPr | 6-MeSO$_2$-3-Pyr | O |
| 58-19 | Me | (CH$_2$)$_2$ | H | CH$_2$ | OPr | 6-EtSO$_2$-3-Pyr | O |
| 58-20 | Me | (CH$_2$)$_2$ | H | CH$_2$ | OPr | 6-iPrSO$_2$-3-Pyr | O |
| 58-21 | Me | (CH$_2$)$_2$ | H | CH$_2$ | OPr | 6-Bz-3-Pyr | O |
| 58-22 | Me | (CH$_2$)$_2$ | H | CH$_2$ | OPr | 6-PhO-3-Pyr | O |
| 58-23 | Me | (CH$_2$)$_2$ | H | CH$_2$ | OPr | 6-PhS-3-Pyr | O |
| 58-24 | Me | (CH$_2$)$_2$ | H | CH$_2$ | OPr | 6-PhSO$_2$-3-Pyr | O |
| 58-25 | Me | (CH$_2$)$_2$ | H | CH$_2$ | OPr | 2-Quin | O |
| 58-26 | Me | (CH$_2$)$_2$ | H | CH$_2$ | OPr | 4-MeO-Ph | O |
| 58-27 | Me | (CH$_2$)$_2$ | H | CH$_2$ | OPr | 4-EtO-Ph | O |
| 58-28 | Me | (CH$_2$)$_2$ | H | CH$_2$ | OPr | 4-iPrO-Ph | O |
| 58-29 | Me | (CH$_2$)$_2$ | H | CH$_2$ | OPr | 4-MeS-Ph | O |
| 58-30 | Me | (CH$_2$)$_2$ | H | CH$_2$ | OPr | 4-EtS-Ph | O |
| 58-31 | Me | (CH$_2$)$_2$ | H | CH$_2$ | OPr | 4-iPrS-Ph | O |
| 58-32 | Me | (CH$_2$)$_2$ | H | CH$_2$ | OPr | 4-MeSO$_2$-Ph | O |
| 58-33 | Me | (CH$_2$)$_2$ | H | CH$_2$ | OPr | 4-EtSO$_2$-Ph | O |
| 58-34 | Me | (CH$_2$)$_2$ | H | CH$_2$ | OPr | 4-iPrSO$_2$-Ph | O |
| 58-35 | Me | (CH$_2$)$_2$ | H | CH$_2$ | OPr | 4-(Pyr-2)Ph | O |
| 58-36 | Me | (CH$_2$)$_2$ | H | CH$_2$ | OPr | 4-(Pyr-3)Ph | O |
| 58-37 | Me | (CH$_2$)$_2$ | H | CH$_2$ | OPr | 4-(Pyr-4)Ph | O |
| 58-38 | Me | (CH$_2$)$_2$ | H | CH$_2$ | OPr | 3-Ph-6-Pyr | O |

TABLE 59

| Exemplification No. compound. | R¹ | R² | R³ | Z | W | X | Y |
|---|---|---|---|---|---|---|---|
| 59-1 | Me | (CH₂)₂ | H | CH₂ | OiPr | 4-Et—Ph | O |
| 59-2 | Me | (CH₂)₂ | H | CH₂ | OiPr | 4-iPr—Ph | O |
| 59-3 | Me | (CH₂)₂ | H | CH₂ | OiPr | 3-Ph—Ph | O |
| 59-4 | Me | (CH₂)₂ | H | CH₂ | OiPr | 4-Ph—Ph | O |
| 59-5 | Me | (CH₂)₂ | H | CH₂ | OiPr | 3-Pyr | O |
| 59-6 | Me | (CH₂)₂ | H | CH₂ | OiPr | 5-Me-3-Pyr | O |
| 59-7 | Me | (CH₂)₂ | H | CH₂ | OiPr | 5-Et-3-Pyr | O |
| 59-8 | Me | (CH₂)₂ | H | CH₂ | OiPr | 5-Ph-3-Pyr | O |
| 59-9 | Me | (CH₂)₂ | H | CH₂ | OiPr | 6-Me-3-Pyr | O |
| 59-10 | Me | (CH₂)₂ | H | CH₂ | OiPr | 6-Et-3-Pyr | O |
| 59-11 | Me | (CH₂)₂ | H | CH₂ | OiPr | 6-Ph-3-Pyr | O |
| 59-12 | Me | (CH₂)₂ | H | CH₂ | OiPr | 6-MeO-3-Pyr | O |
| 59-13 | Me | (CH₂)₂ | H | CH₂ | OiPr | 6-EtO-3-Pyr | O |
| 59-14 | Me | (CH₂)₂ | H | CH₂ | OiPr | 6-iPrO-3-Pyr | O |
| 59-15 | Me | (CH₂)₂ | H | CH₂ | OiPr | 6-MeS-3-Pyr | O |
| 59-16 | Me | (CH₂)₂ | H | CH₂ | OiPr | 6-EtS-3-Pyr | O |
| 59-17 | Me | (CH₂)₂ | H | CH₂ | OiPr | 6-iPrS-3-Pyr | O |
| 59-18 | Me | (CH₂)₂ | H | CH₂ | OiPr | 6-MeSO₂-3-Pyr | O |
| 59-19 | Me | (CH₂)₂ | H | CH₂ | OiPr | 6-EtSO₂-3-Pyr | O |
| 59-20 | Me | (CH₂)₂ | H | CH₂ | OiPr | 6-iPrSO₂-3-Pyr | O |
| 59-21 | Me | (CH₂)₂ | H | CH₂ | OiPr | 6-Bz-3-Pyr | O |
| 59-22 | Me | (CH₂)₂ | H | CH₂ | OiPr | 6-PhO-3-Pyr | O |
| 59-23 | Me | (CH₂)₂ | H | CH₂ | OiPr | 6-PhS-3-Pyr | O |
| 59-24 | Me | (CH₂)₂ | H | CH₂ | OiPr | 6-PhSO₂-3-Pyr | O |
| 59-25 | Me | (CH₂)₂ | H | CH₂ | OiPr | 2-Quin | O |
| 59-26 | Me | (CH₂)₂ | H | CH₂ | OiPr | 4-MeO—Ph | O |
| 59-27 | Me | (CH₂)₂ | H | CH₂ | OiPr | 4-EtO—Ph | O |
| 59-28 | Me | (CH₂)₂ | H | CH₂ | OiPr | 4-iPrO—Ph | O |
| 59-29 | Me | (CH₂)₂ | H | CH₂ | OiPr | 4-MeS—Ph | O |
| 59-30 | Me | (CH₂)₂ | H | CH₂ | OiPr | 4-EtS—Ph | O |
| 59-31 | Me | (CH₂)₂ | H | CH₂ | OiPr | 4-iPrS—Ph | O |
| 59-32 | Me | (CH₂)₂ | H | CH₂ | OiPr | 4-MeSO₂—Ph | O |
| 59-33 | Me | (CH₂)₂ | H | CH₂ | OiPr | 4-EtSO₂—Ph | O |
| 59-34 | Me | (CH₂)₂ | H | CH₂ | OiPr | 4-iPrSO₂—Ph | O |
| 59-35 | Me | (CH₂)₂ | H | CH₂ | OiPr | 4-(Pyr-2)Ph | O |
| 59-36 | Me | (CH₂)₂ | H | CH₂ | OiPr | 4-(Pyr-3)Ph | O |
| 59-37 | Me | (CH₂)₂ | H | CH₂ | OiPr | 4-(Pyr-4)Ph | O |
| 59-38 | Me | (CH₂)₂ | H | CH₂ | OiPr | 3-Ph-6-Pyr | O |

TABLE 60

| Exemplification No. compound. | R¹ | R² | R³ | Z | W | X | Y |
|---|---|---|---|---|---|---|---|
| 60-1 | Me | (CH₂)₃ | H | CH₂ | OMe | 4-Et-Ph | O |
| 60-2 | Me | (CH₂)₃ | H | CH₂ | OMe | 4-iPr-Ph | O |
| 60-3 | Me | (CH₂)₃ | H | CH₂ | OMe | 3-Ph-Ph | O |
| 60-4 | Me | (CH₂)₃ | H | CH₂ | OMe | 4-Ph-Ph | O |
| 60-5 | Me | (CH₂)₃ | H | CH₂ | OMe | 3-Pyr | O |
| 60-6 | Me | (CH₂)₃ | H | CH₂ | OMe | 5-Me-3-Pyr | O |
| 60-7 | Me | (CH₂)₃ | H | CH₂ | OMe | 5-Et-3-Pyr | O |
| 60-8 | Me | (CH₂)₃ | H | CH₂ | OMe | 5-Ph-3-Pyr | O |
| 60-9 | Me | (CH₂)₃ | H | CH₂ | OMe | 6-Me-3-Pyr | O |
| 60-10 | Me | (CH₂)₃ | H | CH₂ | OMe | 6-Et-3-Pyr | O |
| 60-11 | Me | (CH₂)₃ | H | CH₂ | OMe | 6-Ph-3-Pyr | O |
| 60-12 | Me | (CH₂)₃ | H | CH₂ | OMe | 6-MeO-3-Pyr | O |
| 60-13 | Me | (CH₂)₃ | H | CH₂ | OMe | 6-EtO-3-Pyr | O |
| 60-14 | Me | (CH₂)₃ | H | CH₂ | OMe | 6-iPrO-3-Pyr | O |
| 60-15 | Me | (CH₂)₃ | H | CH₂ | OMe | 6-MeS-3-Pyr | O |
| 60-16 | Me | (CH₂)₃ | H | CH₂ | OMe | 6-EtS-3-Pyr | O |
| 60-17 | Me | (CH₂)₃ | H | CH₂ | OMe | 6-iPrS-3-Pyr | O |
| 60-18 | Me | (CH₂)₃ | H | CH₂ | OMe | 6-MeSO₂-3-Pyr | O |
| 60-19 | Me | (CH₂)₃ | H | CH₂ | OMe | 6-EtSO₂-3-Pyr | O |
| 60-20 | Me | (CH₂)₃ | H | CH₂ | OMe | 6-iPrSO₂-3-Pyr | O |
| 60-21 | Me | (CH₂)₃ | H | CH₂ | OMe | 6-Bz-3-Pyr | O |
| 60-22 | Me | (CH₂)₃ | H | CH₂ | OMe | 6-PhO-3-Pyr | O |
| 60-23 | Me | (CH₂)₃ | H | CH₂ | OMe | 6-PhS-3-Pyr | O |
| 60-24 | Me | (CH₂)₃ | H | CH₂ | OMe | 6-PhSO₂-3-Pyr | O |
| 60-25 | Me | (CH₂)₃ | H | CH₂ | OMe | 2-Quin | O |
| 60-26 | Me | (CH₂)₃ | H | CH₂ | OMe | 4-MeO-Ph | O |
| 60-27 | Me | (CH₂)₃ | H | CH₂ | OMe | 4-EtO-Ph | O |
| 60-28 | Me | (CH₂)₃ | H | CH₂ | OMe | 4-iPrO-Ph | O |
| 60-29 | Me | (CH₂)₃ | H | CH₂ | OMe | 4-MeS-Ph | O |
| 60-30 | Me | (CH₂)₃ | H | CH₂ | OMe | 4-EtS-Ph | O |
| 60-31 | Me | (CH₂)₃ | H | CH₂ | OMe | 4-iPrS-Ph | O |
| 60-32 | Me | (CH₂)₃ | H | CH₂ | OMe | 4-MeSO₂-Ph | O |
| 60-33 | Me | (CH₂)₃ | H | CH₂ | OMe | 4-EtSO₂-Ph | O |
| 60-34 | Me | (CH₂)₃ | H | CH₂ | OMe | 4-iPrSO₂-Ph | O |
| 60-35 | Me | (CH₂)₃ | H | CH₂ | OMe | 4-(Pyr-2)Ph | O |
| 60-36 | Me | (CH₂)₃ | H | CH₂ | OMe | 4-(Pyr-3)Ph | O |
| 60-37 | Me | (CH₂)₃ | H | CH₂ | OMe | 4-(Pyr-4)Ph | O |
| 60-38 | Me | (CH₂)₃ | H | CH₂ | OMe | 3-Ph-6-Pyr | O |

TABLE 61

| Exemplification No. compound. | R¹ | R² | R³ | Z | W | X | Y |
|---|---|---|---|---|---|---|---|
| 61-1 | Me | (CH₂)₃ | H | CH₂ | OEt | 4-Et—Ph | O |
| 61-2 | Me | (CH₂)₃ | H | CH₂ | OEt | 4-iPr—Ph | O |
| 61-3 | Me | (CH₂)₃ | H | CH₂ | OEt | 3-Ph—Ph | O |
| 61-4 | Me | (CH₂)₃ | H | CH₂ | OEt | 4-Ph—Ph | O |
| 61-5 | Me | (CH₂)₃ | H | CH₂ | OEt | 3-Pyr | O |
| 61-6 | Me | (CH₂)₃ | H | CH₂ | OEt | 5-Me-3-Pyr | O |
| 61-7 | Me | (CH₂)₃ | H | CH₂ | OEt | 5-Et-3-Pyr | O |
| 61-8 | Me | (CH₂)₃ | H | CH₂ | OEt | 5-Ph-3-Pyr | O |
| 61-9 | Me | (CH₂)₃ | H | CH₂ | OEt | 6-Me-3-Pyr | O |
| 61-10 | Me | (CH₂)₃ | H | CH₂ | OEt | 6-Et-3-Pyr | O |
| 61-11 | Me | (CH₂)₃ | H | CH₂ | OEt | 6-Ph-3-Pyr | O |
| 61-12 | Me | (CH₂)₃ | H | CH₂ | OEt | 6-MeO-3-Pyr | O |
| 61-13 | Me | (CH₂)₃ | H | CH₂ | OEt | 6-EtO-3-Pyr | O |
| 61-14 | Me | (CH₂)₃ | H | CH₂ | OEt | 6-iPrO-3-Pyr | O |
| 61-15 | Me | (CH₂)₃ | H | CH₂ | OEt | 6-MeS-3-Pyr | O |
| 61-16 | Me | (CH₂)₃ | H | CH₂ | OEt | 6-EtS-3-Pyr | O |
| 61-17 | Me | (CH₂)₃ | H | CH₂ | OEt | 6-iPrS-3-Pyr | O |
| 61-18 | Me | (CH₂)₃ | H | CH₂ | OEt | 6-MeSO₂-3-Pyr | O |
| 61-19 | Me | (CH₂)₃ | H | CH₂ | OEt | 6-EtSO₂-3-Pyr | O |
| 61-20 | Me | (CH₂)₃ | H | CH₂ | OEt | 6-iPrSO₂-3-Pyr | O |
| 61-21 | Me | (CH₂)₃ | H | CH₂ | OEt | 6-Bz-3-Pyr | O |
| 61-22 | Me | (CH₂)₃ | H | CH₂ | OEt | 6-PhO-3-Pyr | O |
| 61-23 | Me | (CH₂)₃ | H | CH₂ | OEt | 6-PhS-3-Pyr | O |
| 61-24 | Me | (CH₂)₃ | H | CH₂ | OEt | 6-PhSO₂-3-Pyr | O |
| 61-25 | Me | (CH₂)₃ | H | CH₂ | OEt | 2-Quin | O |
| 61-26 | Me | (CH₂)₃ | H | CH₂ | OEt | 4-MeO—Ph | O |
| 61-27 | Me | (CH₂)₃ | H | CH₂ | OEt | 4-EtO—Ph | O |
| 61-28 | Me | (CH₂)₃ | H | CH₂ | OEt | 4-iPrO—Ph | O |
| 61-29 | Me | (CH₂)₃ | H | CH₂ | OEt | 4-MeS—Ph | O |
| 61-30 | Me | (CH₂)₃ | H | CH₂ | OEt | 4-EtS—Ph | O |
| 61-31 | Me | (CH₂)₃ | H | CH₂ | OEt | 4-iPrS—Ph | O |
| 61-32 | Me | (CH₂)₃ | H | CH₂ | OEt | 4-MeSO₂—Ph | O |
| 61-33 | Me | (CH₂)₃ | H | CH₂ | OEt | 4-EtSO₂—Ph | O |
| 61-34 | Me | (CH₂)₃ | H | CH₂ | OEt | 4-iPrSO₂—Ph | O |
| 61-35 | Me | (CH₂)₃ | H | CH₂ | OEt | 4-(Pyr-2)Ph | O |
| 61-36 | Me | (CH₂)₃ | H | CH₂ | OEt | 4-(Pyr-3)Ph | O |
| 61-37 | Me | (CH₂)₃ | H | CH₂ | OEt | 4-(Pyr-4)Ph | O |
| 61-38 | Me | (CH₂)₃ | H | CH₂ | OEt | 3-Ph-6-Pyr | O |

TABLE 62

| Exemplification No. compound. | R¹ | R² | R³ | Z | W | X | Y |
|---|---|---|---|---|---|---|---|
| 62-1 | Me | (CH₂)₃ | H | CH₂ | OPr | 4-Et—Ph | O |
| 62-2 | Me | (CH₂)₃ | H | CH₂ | OPr | 4-iPr—Ph | O |
| 62-3 | Me | (CH₂)₃ | H | CH₂ | OPr | 3-Ph—Ph | O |
| 62-4 | Me | (CH₂)₃ | H | CH₂ | OPr | 4-Ph—Ph | O |
| 62-5 | Me | (CH₂)₃ | H | CH₂ | OPr | 3-Pyr | O |
| 62-6 | Me | (CH₂)₃ | H | CH₂ | OPr | 5-Me-3-Pyr | O |
| 62-7 | Me | (CH₂)₃ | H | CH₂ | OPr | 5-Et-3-Pyr | O |
| 62-8 | Me | (CH₂)₃ | H | CH₂ | OPr | 5-Ph-3-Pyr | O |
| 62-9 | Me | (CH₂)₃ | H | CH₂ | OPr | 6-Me-3-Pyr | O |
| 62-10 | Me | (CH₂)₃ | H | CH₂ | OPr | 6-Et-3-Pyr | O |
| 62-11 | Me | (CH₂)₃ | H | CH₂ | OPr | 6-Ph-3-Pyr | O |
| 62-12 | Me | (CH₂)₃ | H | CH₂ | OPr | 6-MeO-3-Pyr | O |

TABLE 62-continued

| Exemplification No. compound. | R¹ | R² | R³ | Z | W | X | Y |
|---|---|---|---|---|---|---|---|
| 62-13 | Me | (CH₂)₃ | H | CH₂ | OPr | 6-EtO-3-Pyr | O |
| 62-14 | Me | (CH₂)₃ | H | CH₂ | OPr | 6-iPrO-3-Pyr | O |
| 62-15 | Me | (CH₂)₃ | H | CH₂ | OPr | 6-MeS-3-Pyr | O |
| 62-16 | Me | (CH₂)₃ | H | CH₂ | OPr | 6-EtS-3-Pyr | O |
| 62-17 | Me | (CH₂)₃ | H | CH₂ | OPr | 6-iPrS-3-Pyr | O |
| 62-18 | Me | (CH₂)₃ | H | CH₂ | OPr | 6-MeSO₂-3-Pyr | O |
| 62-19 | Me | (CH₂)₃ | H | CH₂ | OPr | 6-EtSO₂-3-Pyr | O |
| 62-20 | Me | (CH₂)₃ | H | CH₂ | OPr | 6-iPrSO₂-3-Pyr | O |
| 62-21 | Me | (CH₂)₃ | H | CH₂ | OPr | 6-Bz-3-Pyr | O |
| 62-22 | Me | (CH₂)₃ | H | CH₂ | OPr | 6-PhO-3-Pyr | O |
| 62-23 | Me | (CH₂)₃ | H | CH₂ | OPr | 6-PhS-3-Pyr | O |
| 62-24 | Me | (CH₂)₃ | H | CH₂ | OPr | 6-PhSO₂-3-Pyr | O |
| 62-25 | Me | (CH₂)₃ | H | CH₂ | OPr | 2-Quin | O |
| 62-26 | Me | (CH₂)₃ | H | CH₂ | OPr | 4-MeO—Ph | O |
| 62-27 | Me | (CH₂)₃ | H | CH₂ | OPr | 4-EtO—Ph | O |
| 62-28 | Me | (CH₂)₃ | H | CH₂ | OPr | 4-iPrO—Ph | O |
| 62-29 | Me | (CH₂)₃ | H | CH₂ | OPr | 4-MeS—Ph | O |
| 62-30 | Me | (CH₂)₃ | H | CH₂ | OPr | 4-EtS—Ph | O |
| 62-31 | Me | (CH₂)₃ | H | CH₂ | OPr | 4-iPrS—Ph | O |
| 62-32 | Me | (CH₂)₃ | H | CH₂ | OPr | 4-MeSO₂—Ph | O |
| 62-33 | Me | (CH₂)₃ | H | CH₂ | OPr | 4-EtSO₂—Ph | O |
| 62-34 | Me | (CH₂)₃ | H | CH₂ | OPr | 4-iPrSO₂—Ph | O |
| 62-35 | Me | (CH₂)₃ | H | CH₂ | OPr | 4-(Pyr-2)Ph | O |
| 62-36 | Me | (CH₂)₃ | H | CH₂ | OPr | 4-(Pyr-3)Ph | O |
| 62-37 | Me | (CH₂)₃ | H | CH₂ | OPr | 4-(Pyr-4)Ph | O |
| 62-38 | Me | (CH₂)₃ | H | CH₂ | OPr | 3-Ph-6-Pyr | O |

TABLE 63

| Exemplification No. compound. | R¹ | R² | R³ | Z | W | X | Y |
|---|---|---|---|---|---|---|---|
| 63-1 | Me | CH(Me)CH₂ | H | CH₂ | OEt | 4-Et—Ph | O |
| 63-2 | Me | CH(Me)CH₂ | H | CH₂ | OEt | 4-iPr—Ph | O |
| 63-3 | Me | CH(Me)CH₂ | H | CH₂ | OEt | 3-Ph—Ph | O |
| 63-4 | Me | CH(Me)CH₂ | H | CH₂ | OEt | 4-Ph—Ph | O |
| 63-5 | Me | CH(Me)CH₂ | H | CH₂ | OEt | 3-Pyr | O |
| 63-6 | Me | CH(Me)CH₂ | H | CH₂ | OEt | 5-Me-3-Pyr | O |
| 63-7 | Me | CH(Me)CH₂ | H | CH₂ | OEt | 5-Et-3-Pyr | O |
| 63-8 | Me | CH(Me)CH₂ | H | CH₂ | OEt | 5-Ph-3-Pyr | O |
| 63-9 | Me | CH(Me)CH₂ | H | CH₂ | OEt | 6-Me-3-Pyr | O |
| 63-10 | Me | CH(Me)CH₂ | H | CH₂ | OEt | 6-Et-3-Pyr | O |
| 63-11 | Me | CH(Me)CH₂ | H | CH₂ | OEt | 6-Ph-3-Pyr | O |
| 63-12 | Me | CH(Me)CH₂ | H | CH₂ | OEt | 6-MeO-3-Pyr | O |
| 63-13 | Me | CH(Me)CH₂ | H | CH₂ | OEt | 6-EtO-3-Pyr | O |
| 63-14 | Me | CH(Me)CH₂ | H | CH₂ | OEt | 6-iPrO-3-Pyr | O |
| 63-15 | Me | CH(Me)CH₂ | H | CH₂ | OEt | 6-MeS-3-Pyr | O |
| 63-16 | Me | CH(Me)CH₂ | H | CH₂ | OEt | 6-EtS-3-Pyr | O |
| 63-17 | Me | CH(Me)CH₂ | H | CH₂ | OEt | 6-iPrS-3-Pyr | O |
| 63-18 | Me | CH(Me)CH₂ | H | CH₂ | OEt | 6-MeSO₂-3-Pyr | O |
| 63-19 | Me | CH(Me)CH₂ | H | CH₂ | OEt | 6-EtSO₂-3-Pyr | O |
| 63-20 | Me | CH(Me)CH₂ | H | CH₂ | OEt | 6-iPrSO₂-3-Pyr | O |
| 63-21 | Me | CH(Me)CH₂ | H | CH₂ | OEt | 6-Bz-3-Pyr | O |
| 63-22 | Me | CH(Me)CH₂ | H | CH₂ | OEt | 6-PhO-3-Pyr | O |
| 63-23 | Me | CH(Me)CH₂ | H | CH₂ | OEt | 6-PhS-3-Pyr | O |
| 63-24 | Me | CH(Me)CH₂ | H | CH₂ | OEt | 6-PhSO₂-3-Pyr | O |
| 63-25 | Me | CH(Me)CH₂ | H | CH₂ | OEt | 2-Quin | O |
| 63-26 | Me | CH(Me)CH₂ | H | CH₂ | OEt | 4-MeO—Ph | O |
| 63-27 | Me | CH(Me)CH₂ | H | CH₂ | OEt | 4-EtO—Ph | O |
| 63-28 | Me | CH(Me)CH₂ | H | CH₂ | OEt | 4-iPrO—Ph | O |
| 63-29 | Me | CH(Me)CH₂ | H | CH₂ | OEt | 4-MeS—Ph | O |
| 63-30 | Me | CH(Me)CH₂ | H | CH₂ | OEt | 4-EtS—Ph | O |
| 63-31 | Me | CH(Me)CH₂ | H | CH₂ | OEt | 4-iPrS—Ph | O |
| 63-32 | Me | CH(Me)CH₂ | H | CH₂ | OEt | 4-MeSO₂—Ph | O |
| 63-33 | Me | CH(Me)CH₂ | H | CH₂ | OEt | 4-EtSO₂—Ph | O |
| 63-34 | Me | CH(Me)CH₂ | H | CH₂ | OEt | 4-iPrSO₂—Ph | O |
| 63-35 | Me | CH(Me)CH₂ | H | CH₂ | OEt | 4-(Pyr-2)Ph | O |
| 63-36 | Me | CH(Me)CH₂ | H | CH₂ | OEt | 4-(Pyr-3)Ph | O |
| 63-37 | Me | CH(Me)CH₂ | H | CH₂ | OEt | 4-(Pyr-4)Ph | O |
| 63-38 | Me | CH(Me)CH₂ | H | CH₂ | OEt | 3-Ph-6-Pyr | O |

TABLE 64

| Exemplification No. compound. | R¹ | R² | R³ | Z | W | X | Y |
|---|---|---|---|---|---|---|---|
| 64-1 | Me | CH(Me)₂CH₂ | H | CH₂ | OEt | 4-Et—Ph | O |
| 64-2 | Me | CH(Me)₂CH₂ | H | CH₂ | OEt | 4-iPr—Ph | O |
| 64-3 | Me | CH(Me)₂CH₂ | H | CH₂ | OEt | 3-Ph—Ph | O |
| 64-4 | Me | CH(Me)₂CH₂ | H | CH₂ | OEt | 4-Ph—Ph | O |
| 64-5 | Me | CH(Me)₂CH₂ | H | CH₂ | OEt | 3-Pyr | O |
| 64-6 | Me | CH(Me)₂CH₂ | H | CH₂ | OEt | 5-Me-3-Pyr | O |
| 64-7 | Me | CH(Me)₂CH₂ | H | CH₂ | OEt | 5-Et-3-Pyr | O |
| 64-8 | Me | CH(Me)₂CH₂ | H | CH₂ | OEt | 5-Ph-3-Pyr | O |
| 64-9 | Me | CH(Me)₂CH₂ | H | CH₂ | OEt | 6-Me-3-Pyr | O |
| 64-10 | Me | CH(Me)₂CH₂ | H | CH₂ | OEt | 6-Et-3-Pyr | O |
| 64-11 | Me | CH(Me)₂CH₂ | H | CH₂ | OEt | 6-Ph-3-Pyr | O |
| 64-12 | Me | CH(Me)₂CH₂ | H | CH₂ | OEt | 6-MeO-3-Pyr | O |
| 64-13 | Me | CH(Me)₂CH₂ | H | CH₂ | OEt | 6-EtO-3-Pyr | O |
| 64-14 | Me | CH(Me)₂CH₂ | H | CH₂ | OEt | 6-iPrO-3-Pyr | O |
| 64-15 | Me | CH(Me)₂CH₂ | H | CH₂ | OEt | 6-MeS-3-Pyr | O |
| 64-16 | Me | CH(Me)₂CH₂ | H | CH₂ | OEt | 6-EtS-3-Pyr | O |
| 64-17 | Me | CH(Me)₂CH₂ | H | CH₂ | OEt | 6-iPrS-3-Pyr | O |
| 64-18 | Me | CH(Me)₂CH₂ | H | CH₂ | OEt | 6-MeSO₂-3-Pyr | O |
| 64-19 | Me | CH(Me)₂CH₂ | H | CH₂ | OEt | 6-EtSO₂-3-Pyr | O |
| 64-20 | Me | CH(Me)₂CH₂ | H | CH₂ | OEt | 6-iPrSO₂-3-Pyr | O |
| 64-21 | Me | CH(Me)₂CH₂ | H | CH₂ | OEt | 6-Bz-3-Pyr | O |
| 64-22 | Me | CH(Me)₂CH₂ | H | CH₂ | OEt | 6-PhO-3-Pyr | O |
| 64-23 | Me | CH(Me)₂CH₂ | H | CH₂ | OEt | 6-PhS-3-Pyr | O |
| 64-24 | Me | CH(Me)₂CH₂ | H | CH₂ | OEt | 6-PhSO₂-3-Pyr | O |
| 64-25 | Me | CH(Me)₂CH₂ | H | CH₂ | OEt | 2-Quin | O |
| 64-26 | Me | CH(Me)₂CH₂ | H | CH₂ | OEt | 4-MeO—Ph | O |
| 64-27 | Me | CH(Me)₂CH₂ | H | CH₂ | OEt | 4-EtO—Ph | O |
| 64-28 | Me | CH(Me)₂CH₂ | H | CH₂ | OEt | 4-iPrO—Ph | O |
| 64-29 | Me | CH(Me)₂CH₂ | H | CH₂ | OEt | 4-MeS—Ph | O |
| 64-30 | Me | CH(Me)₂CH₂ | H | CH₂ | OEt | 4-EtS—Ph | O |
| 64-31 | Me | CH(Me)₂CH₂ | H | CH₂ | OEt | 4-iPrS—Ph | O |
| 64-32 | Me | CH(Me)₂CH₂ | H | CH₂ | OEt | 4-MeSO₂—Ph | O |
| 64-33 | Me | CH(Me)₂CH₂ | H | CH₂ | OEt | 4-EtSO₂—Ph | O |
| 64-34 | Me | CH(Me)₂CH₂ | H | CH₂ | OEt | 4-iPrSO₂—Ph | O |
| 64-35 | Me | CH(Me)₂CH₂ | H | CH₂ | OEt | 4-(Pyr-2)Ph | O |
| 64-36 | Me | CH(Me)₂CH₂ | H | CH₂ | OEt | 4-(Pyr-3)Ph | O |
| 64-37 | Me | CH(Me)₂CH₂ | H | CH₂ | OEt | 4-(Pyr-4)Ph | O |
| 64-38 | Me | CH(Me)₂CH₂ | H | CH₂ | OEt | 3-Ph-6-Pyr | O |

TABLE 65

| Exemplification No. compound. | R¹ | R² | R³ | Z | W | X | Y |
|---|---|---|---|---|---|---|---|
| 65-1 | Me | CH₂CH(Me) | H | CH₂ | OEt | 4-Et—Ph | O |
| 65-2 | Me | CH₂CH(Me) | H | CH₂ | OEt | 4-iPr—Ph | O |
| 65-3 | Me | CH₂CH(Me) | H | CH₂ | OEt | 3-Ph—Ph | O |
| 65-4 | Me | CH₂CH(Me) | H | CH₂ | OEt | 4-Ph—Ph | O |
| 65-5 | Me | CH₂CH(Me) | H | CH₂ | OEt | 3-Pyr | O |
| 65-6 | Me | CH₂CH(Me) | H | CH₂ | OEt | 5-Me-3-Pyr | O |
| 65-7 | Me | CH₂CH(Me) | H | CH₂ | OEt | 5-Et-3-Pyr | O |
| 65-8 | Me | CH₂CH(Me) | H | CH₂ | OEt | 5-Ph-3-Pyr | O |
| 65-9 | Me | CH₂CH(Me) | H | CH₂ | OEt | 6-Me-3-Pyr | O |
| 65-10 | Me | CH₂CH(Me) | H | CH₂ | OEt | 6-Et-3-Pyr | O |
| 65-11 | Me | CH₂CH(Me) | H | CH₂ | OEt | 6-Ph-3-Pyr | O |
| 65-12 | Me | CH₂CH(Me) | H | CH₂ | OEt | 6-MeO-3-Pyr | O |
| 65-13 | Me | CH₂CH(Me) | H | CH₂ | OEt | 6-EtO-3-Pyr | O |
| 65-14 | Me | CH₂CH(Me) | H | CH₂ | OEt | 6-iPrO-3-Pyr | O |
| 65-15 | Me | CH₂CH(Me) | H | CH₂ | OEt | 6-MeS-3-Pyr | O |
| 65-16 | Me | CH₂CH(Me) | H | CH₂ | OEt | 6-EtS-3-Pyr | O |
| 65-17 | Me | CH₂CH(Me) | H | CH₂ | OEt | 6-iPrS-3-Pyr | O |
| 65-18 | Me | CH₂CH(Me) | H | CH₂ | OEt | 6-MeSO₂-3-Pyr | O |
| 65-19 | Me | CH₂CH(Me) | H | CH₂ | OEt | 6-EtSO₂-3-Pyr | O |
| 65-20 | Me | CH₂CH(Me) | H | CH₂ | OEt | 6-iPrSO₂-3-Pyr | O |
| 65-21 | Me | CH₂CH(Me) | H | CH₂ | OEt | 6-Bz-3-Pyr | O |
| 65-22 | Me | CH₂CH(Me) | H | CH₂ | OEt | 6-PhO-3-Pyr | O |
| 65-23 | Me | CH₂CH(Me) | H | CH₂ | OEt | 6-PhS-3-Pyr | O |
| 65-24 | Me | CH₂CH(Me) | H | CH₂ | OEt | 6-PhSO₂-3-Pyr | O |
| 65-25 | Me | CH₂CH(Me) | H | CH₂ | OEt | 2-Quin | O |
| 65-26 | Me | CH₂CH(Me) | H | CH₂ | OEt | 4-MeO—Ph | O |

TABLE 65-continued

| Exemplification No. compound. | R¹ | R² | R³ | Z | W | X | Y |
|---|---|---|---|---|---|---|---|
| 65-27 | Me | CH₂CH(Me) | H | CH₂ | OEt | 4-EtO—Ph | O |
| 65-28 | Me | CH₂CH(Me) | H | CH₂ | OEt | 4-iPrO—Ph | O |
| 65-29 | Me | CH₂CH(Me) | H | CH₂ | OEt | 4-MeS—Ph | O |
| 65-30 | Me | CH₂CH(Me) | H | CH₂ | OEt | 4-EtS—Ph | O |
| 65-31 | Me | CH₂CH(Me) | H | CH₂ | OEt | 4-iPrS—Ph | O |
| 65-32 | Me | CH₂CH(Me) | H | CH₂ | OEt | 4-MeSO₂—Ph | O |
| 65-33 | Me | CH₂CH(Me) | H | CH₂ | OEt | 4-EtSO₂—Ph | O |
| 65-34 | Me | CH₂CH(Me) | H | CH₂ | OEt | 4-iPrSO₂—Ph | O |
| 65-35 | Me | CH₂CH(Me) | H | CH₂ | OEt | 4-(Pyr-2)Ph | O |
| 65-36 | Me | CH₂CH(Me) | H | CH₂ | OEt | 4-(Pyr-3)Ph | O |
| 65-37 | Me | CH₂CH(Me) | H | CH₂ | OEt | 4-(Pyr-4)Ph | O |
| 65-38 | Me | CH₂CH(Me) | H | CH₂ | OEt | 3-Ph-6-Pyr | O |

TABLE 66

| Exemplification No. compound. | R¹ | R² | R³ | Z | W | X | Y |
|---|---|---|---|---|---|---|---|
| 66-1 | Me | (CH₂)₂ | H | CH₂ | Ph | 4-Ph—Ph | O |
| 66-2 | Me | (CH₂)₂ | H | CH₂ | Ph | 4-(Pyr-2)Ph | O |
| 66-3 | Me | (CH₂)₂ | H | CH₂ | CH₂Ph | 4-Ph—Ph | O |
| 66-4 | Me | (CH₂)₂ | H | CH₂ | CH₂Ph | 4-(Pyr-2)Ph | O |
| 66-5 | Me | (CH₂)₂ | H | CH₂ | (CH₂)₂Ph | 4-Ph—Ph | O |
| 66-6 | Me | (CH₂)₂ | H | CH₂ | (CH₂)₂Ph | 4-(Pyr-2)Ph | O |
| 66-7 | Me | (CH₂)₂ | H | CH₂ | (CH₂)₃Ph | 4-Ph—Ph | O |
| 66-8 | Me | (CH₂)₂ | H | CH₂ | (CH₂)₃Ph | 4-(Pyr-2)Ph | O |
| 66-9 | Me | (CH₂)₂ | H | CH₂ | (CH₂)₄Ph | 4-Ph—Ph | O |
| 66-10 | Me | (CH₂)₂ | H | CH₂ | (CH₂)₄Ph | 4-(Pyr-2)Ph | O |
| 66-11 | Me | (CH₂)₂ | H | CH₂ | (CH₂)₅Ph | 4-Ph—Ph | O |
| 66-12 | Me | (CH₂)₂ | H | CH₂ | (CH₂)₅Ph | 4-(Pyr-2)Ph | O |
| 66-13 | Me | (CH₂)₂ | H | CH₂ | (CH₂)₆Ph | 4-Ph—Ph | O |
| 66-14 | Me | (CH₂)₂ | H | CH₂ | (CH₂)₆Ph | 4-(Pyr-2)Ph | O |

TABLE 67

| Exemplification No. compound. | R¹ | R² | R³ | Z | W | X | Y |
|---|---|---|---|---|---|---|---|
| 67-1 | Me | (CH₂)₂ | H | CH₂ | Me | 4-Ph—Ph | O |
| 67-2 | Me | (CH₂)₂ | H | CH₂ | Me | 4-(Pyr-2)Ph | O |
| 67-3 | Me | (CH₂)₂ | H | CH₂ | Et | 4-Ph—Ph | O |
| 67-4 | Me | (CH₂)₂ | H | CH₂ | Et | 4-(Pyr-2)Ph | O |
| 67-5 | Me | (CH₂)₂ | H | CH₂ | Pr | 4-Ph—Ph | O |
| 67-6 | Me | (CH₂)₂ | H | CH₂ | Pr | 4-(Pyr-2)Ph | O |
| 67-7 | Me | (CH₂)₂ | H | CH₂ | Bu | 4-Ph—Ph | O |
| 67-8 | Me | (CH₂)₂ | H | CH₂ | Bu | 4-(Pyr-2)Ph | O |
| 67-9 | Me | (CH₂)₂ | H | CH₂ | Pen | 4-Ph—Ph | O |
| 67-10 | Me | (CH₂)₂ | H | CH₂ | Pen | 4-(Pyr-2)Ph | O |
| 67-11 | Me | (CH₂)₂ | H | CH₂ | Hex | 4-Ph—Ph | O |
| 67-12 | Me | (CH₂)₂ | H | CH₂ | Hex | 4-(Pyr-2)Ph | O |

TABLE 68

| Exemplification No. compound. | R¹ | R² | R³ | Z | W | X | Y |
|---|---|---|---|---|---|---|---|
| 68-1 | Me | (CH₂)₂ | H | CH₂ | OPh | 4-Ph—Ph | O |
| 68-2 | Me | (CH₂)₂ | H | CH₂ | OPh | 4-(Pyr-2)Ph | O |
| 68-3 | Me | (CH₂)₂ | H | CH₂ | OCH₂Ph | 4-Ph—Ph | O |
| 68-4 | Me | (CH₂)₂ | H | CH₂ | OCH₂Ph | 4-(Pyr-2)Ph | O |
| 68-5 | Me | (CH₂)₂ | H | CH₂ | O(CH₂)₂Ph | 4-Ph—Ph | O |
| 68-6 | Me | (CH₂)₂ | H | CH₂ | O(CH₂)₂Ph | 4-(Pyr-2)Ph | O |
| 68-7 | Me | (CH₂)₂ | H | CH₂ | O(CH₂)₃Ph | 4-Ph—Ph | O |
| 68-8 | Me | (CH₂)₂ | H | CH₂ | O(CH₂)₃Ph | 4-(Pyr-2)Ph | O |
| 68-9 | Me | (CH₂)₂ | H | CH₂ | O(CH₂)₄Ph | 4-Ph—Ph | O |
| 68-10 | Me | (CH₂)₂ | H | CH₂ | O(CH₂)₄Ph | 4-(Pyr-2)Ph | O |

TABLE 68-continued

| Exemplification No. compound. | R¹ | R² | R³ | Z | W | X | Y |
|---|---|---|---|---|---|---|---|
| 68-11 | Me | (CH₂)₂ | H | CH₂ | O(CH₂)₅Ph | 4-Ph—Ph | O |
| 68-12 | Me | (CH₂)₂ | H | CH₂ | O(CH₂)₅Ph | 4-(Pyr-2)Ph | O |
| 68-13 | Me | (CH₂)₂ | H | CH₂ | O(CH₂)₆Ph | 4-Ph—Ph | O |
| 68-14 | Me | (CH₂)₂ | H | CH₂ | O(CH₂)₆Ph | 4-(Pyr-2)Ph | O |

In the above Tables, (1) Preferred compounds are those of Exemplification No. compounds. 1-1, 1-2, 1-3, 1-4, 1-5, 1-7, 1-10, 1-11, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-53, 1-56, 1-58, 1-60, 1-66, 1-70, 1-72, 1-78, 1-80, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-144, 1-145, 1-146, 1-147, 1-148, 1-149, 1-150, 1-155, 1-156, 1-157, 1-158, 1-161, 1-162, 1-163, 1-164, 1-165, 1-166, 1-167, 1-168, 1-169, 1-170, 1-171, 1-172, 1-175, 1-176, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 2-1, 2-2, 2-3, 2-4, 2-5, 2-7, 2-10, 2-11, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-53, 2-56, 2-58, 2-60, 2-66, 2-70, 2-72, 2-78, 2-80, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-144, 2-145, 2-146, 2-147, 2-148, 2-149, 2-150, 2-155, 2-156, 2-157, 2-158, 2-161, 2-162, 2-163, 2-164, 2-165, 2-166, 2-167, 2-168, 2-169, 2-170, 2-171, 2-172, 2-175, 2-176, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 3-1, 3-2, 3-3, 3-4, 3-5, 3-7, 3-10, 3-11, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-53, 3-56, 3-58, 3-60, 3-66, 3-70, 3-72, 3-78, 3-80, 3-87, 3-88, 3-89, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-144, 3-145, 3-146, 3-147, 3-148, 3-149, 3-150, 3-155, 3-156, 3-157, 3-158, 3-161, 3-162, 3-163, 3-164, 3-165, 3-166, 3-167, 3-168, 3-169, 3-170, 3-171, 3-172, 3-175, 3-176, 3-180, 3-181, 3-182, 3-183, 3-184, 3-185, 3-186, 3-187, 3-188, 3-189, 3-190, 3-191, 3-192, 3-193, 3-194, 3-195, 3-196, 3-197, 3-198, 3-199, 3-200, 3-201, 3-202, 3-203, 4-1, 4-2, 4-3, 4-4, 4-5, 4-7, 4-10, 4-11, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-53, 4-56, 4-58, 4-60, 4-66, 4-70, 4-72, 4-78, 4-80, 4-87, 4-88, 4-89, 4-90, 4-91, 4-92, 4-93, 4-94, 4-95, 4-96, 4-97, 4-98, 4-99, 4-100, 4-101, 4-102, 4-103, 4-104, 4-105, 4-106, 4-107, 4-108, 4-109, 4-110, 4-111, 4-112, 4-144, 4-145, 4-146, 4-147, 4-148, 4-149, 4-150, 4-155, 4-156, 4-157, 4-158, 4-161, 4-162, 4-163, 4-164, 4-165, 4-166, 4-167, 4-168, 4-169, 4-170, 4-171, 4-172, 4-175, 4-176, 4-180, 4-181, 4-182, 4-183, 4-184, 4-185, 4-186, 4-187, 4-188, 4-189, 4-190, 4-191, 4-192, 4-193, 4-194, 4-195, 4-196, 4-197, 4-198, 4-199, 4-200, 4-201, 4-202, 4-203, 5-1, 5-2, 5-3, 5-4, 5-5, 5-7, 5-10, 5-11, 5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-37, 5-38, 5-39, 5-40, 5-41, 5-42, 5-43, 5-44, 5-45, 5-53, 5-56, 5-58, 5-60, 5-66, 5-70, 5-72, 5-78, 5-80, 5-87, 5-88, 5-89, 5-90, 5-91, 5-92, 5-93, 5-94, 5-95, 5-96, 5-97, 5-98, 5-99, 5-100, 5-101, 5-102, 5-103, 5-104, 5-105, 5-106, 5-107, 5-108, 5-109, 5-110, 5-111, 5-112, 5-144, 5-145, 5-146, 5-147, 5-148, 5-149, 5-150, 5-155, 5-156, 5-157, 5-158, 5-161, 5-162, 5-163, 5-164, 5-165, 5-166, 5-167, 5-168, 5-169, 5-170, 5-171, 5-172, 5-175, 5-176, 5-180, 5-181, 5-182, 5-183, 5-184, 5-185, 5-186, 5-187, 5-188, 5-189, 5-190, 5-191, 5-192, 5-193, 5-194, 5-195, 5-196, 5-197, 5-198, 5-199, 5-200, 5-201, 5-202, 5-203, 6-1, 6-2, 6-3, 6-4, 6-5, 6-7, 6-10, 6-11, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-53, 6-56, 6-58, 6-60, 6-66, 6-70, 6-72, 6-78, 6-80, 6-87, 6-88, 6-89, 6-90, 6-91, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-144, 6-145, 6-146, 6-147, 6-148, 6-149, 6-150, 6-155, 6-156, 6-157, 6-158, 6-161, 6-162, 6-163, 6-164, 6-165, 6-166, 6-167, 6-168, 6-169, 6-170, 6-171, 6-172, 6-175, 6-176, 6-180, 6-181, 6-182, 6-183, 6-184, 6-185, 6-186, 6-187, 6-188, 6-189, 6-190, 6-191, 6-192, 6-193, 6-194, 6-195, 6-196, 6-197, 6-198, 6-199, 6-200, 6-201, 6-202, 6-203, 7-1, 7-2, 7-3, 7-4, 7-5, 7-7, 7-10, 7-11, 7-14, 7-15, 7-16, 7-17, 7-18, 7-19, 7-20, 7-21, 7-22, 7-23, 7-24, 7-25, 7-26, 7-27, 7-28, 7-29, 7-30, 7-31, 7-32, 7-33, 7-34, 7-35, 7-36, 7-37, 7-38, 7-39, 7-40, 7-41, 7-42, 7-43, 7-44, 7-45, 7-53, 7-56, 7-58, 7-60, 7-66, 7-70, 7-72, 7-78, 7-80, 7-87, 7-88, 7-89, 7-90, 7-91, 7-92, 7-93, 7-94, 7-95, 7-96, 7-97, 7-98, 7-99, 7-100, 7-101, 7-102, 7-103, 7-104, 7-105, 7-106, 7-107, 7-108, 7-109, 7-110, 7-111, 7-112, 7-144, 7-145, 7-146, 7-147, 7-148, 7-149, 7-150, 7-155, 7-156, 7-157, 7-158, 7-161, 7-162, 7-163, 7-164, 7-165, 7-166, 7-167, 7-168, 7-169, 7-170, 7-171, 7-172, 7-175, 7-176, 7-180, 7-181, 7-182, 7-183, 7-184, 7-185, 7-186, 7-187, 7-188, 7-189, 7-190, 7-191, 7-192, 7-193, 7-194, 7-195, 7-196, 7-197, 7-198, 7-199, 7-200, 7-201, 7-202, 7-203, 8-1, 8-2, 8-3, 8-4, 8-5, 8-7, 8-10, 8-11, 8-14, 8-15, 8-16, 8-17, 8-18, 8-19, 8-20, 8-21, 8-22, 8-23, 8-24, 8-25, 8-26, 8-27, 8-28, 8-29, 8-30, 8-31, 8-32, 8-33, 8-34, 8-35, 8-36, 8-37, 8-38, 8-39, 8-40, 8-41, 8-42, 8-43, 8-44, 8-45, 8-53, 8-56, 8-58, 8-60, 8-66, 8-70, 8-72, 8-78, 8-80, 8-87, 8-88, 8-89, 8-90, 8-91, 8-92, 8-93, 8-94, 8-95, 8-96, 8-97, 8-98, 8-99, 8-100, 8-101, 8-102, 8-103, 8-104, 8-105, 8-106, 8-107, 8-108, 8-109, 8-110, 8-111, 8-112, 8-144, 8-145, 8-146, 8-147, 8-148, 8-149, 8-150, 8-155, 8-156, 8-157, 8-158, 8-161, 8-162, 8-163, 8-164, 8-165, 8-166, 8-167, 8-168, 8-169, 8-170, 8-171, 8-172, 8-175, 8-176, 8-180, 8-181, 8-182, 8-183, 8-184, 8-185, 8-186, 8-187, 8-188, 8-189, 8-190, 8-191, 8-192, 8-193, 8-194, 8-195, 8-196, 8-197, 8-198, 8-199, 8-200, 8-201, 8-202, 8-203, 9-1, 9-2, 9-3, 9-4, 9-5, 9-7, 9-10, 9-11, 9-14, 9-15, 9-16, 9-17, 9-18, 9-19, 9-20, 9-21, 9-22, 9-23, 9-24, 9-25, 9-26, 9-27, 9-28, 9-29, 9-30, 9-31, 9-32, 9-33, 9-34, 9-35, 9-36, 9-37, 9-38, 9-39, 9-40, 9-41, 9-42, 9-43, 9-44, 9-45, 9-53, 9-56, 9-58, 9-60, 9-66, 9-70, 9-72, 9-78, 9-80, 9-87, 9-88, 9-89, 9-90, 9-91, 9-92, 9-93, 9-94, 9-95, 9-96, 9-97, 9-98, 9-99, 9-100, 9-101, 9-102, 9-103, 9-104, 9-105, 9-106, 9-107, 9-108, 9-109, 9-110, 9-111, 9-112, 9-144, 9-145, 9-146, 9-147, 9-148, 9-149, 9-150, 9-155, 9-156, 9-157, 9-158, 9-161, 9-162, 9-163, 9-164, 9-165, 9-166, 9-167, 9-168, 9-169, 9-170, 9-171, 9-172, 9-175, 9-176, 9-180, 9-181, 9-182, 9-183, 9-184, 9-185, 9-186, 9-187, 9-188, 9-189, 9-190, 9-191, 9-192, 9-193, 9-194, 9-195, 9-196, 9-197, 9-198, 9-199, 9-200, 9-201, 9-202, 9-203, 10-1, 10-2, 10-3, 10-4, 10-5, 10-7, 10-10, 10-11, 10-14, 10-15, 10-16, 10-17, 10-18, 10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 10-41, 10-42, 10-43, 10-44, 10-45, 10-53, 10-56, 10-58, 10-60, 10-66, 10-70, 10-72, 10-78, 10-80, 10-87, 10-88, 10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-144, 10-145, 10-146, 10-147, 10-148, 10-149, 10-150, 10-155, 10-156, 10-157, 10-158, 10-161, 10-162, 10-163, 10-164, 10-165, 10-166, 10-167, 10-168, 10-169, 10-170, 10-171, 10-172, 10-175, 10-176, 10-180, 10-181, 10-182, 10-183, 10-184, 10-185, 10-186, 10-187, 10-188, 10-189, 10-190, 10-191, 10-192, 10-193, 10-194, 10-195, 10-196, 10-197, 10-198, 10-199, 10-200, 10-201, 10-202, 10-203, 11-4, 11-11, 11-12, 11-13, 11-14, 11-35, 11-36, 11-37, 11-38, 12-4, 12-11, 12-12, 12-13, 12-14, 12-35, 12-36, 12-37, 12-38, 13-4, 13-11, 13-12, 13-13, 13-14, 13-35, 13-36, 13-37, 13-38, 14-4, 14-11, 14-12, 14-13, 14-14, 14-35, 14-36, 14-37, 14-38, 15-4, 15-11, 15-12, 15-13, 15-14, 15-35, 15-36, 15-37, 15-38, 16-4, 16-11, 16-12, 16-13, 16-14, 16-35, 16-36, 16-37, 16-38, 17-4, 17-11, 17-12, 17-13, 17-14, 17-35, 17-36, 17-37, 17-38, 18-4, 18-11, 18-12, 18-13, 18-14, 18-35, 18-36, 18-37, 18-38, 19-4, 19-11, 19-12, 19-13, 19-14, 19-35, 19-36, 19-37, 19-38, 20-4, 20-11, 20-12, 20-13, 20-14, 20-35, 20-36, 20-37, 20-38, 21-4, 21-11, 21-12, 21-13, 21-14, 21-35, 21-36, 21-37, 21-38, 22-4, 22-11, 22-12, 22-13, 22-14, 22-35, 22-36, 22-37, 22-38, 23-4, 23-11, 23-12, 23-13, 23-14, 23-35, 23-36, 23-37, 23-38, 24-4, 24-11, 24-12, 24-13, 24-14, 24-35, 24-36, 24-37, 24-38, 25-4, 25-11, 25-12, 25-13, 25-14, 25-35, 25-36, 25-37, 25-38, 26-4, 26-11, 26-12, 26-13, 26-14, 26-35, 26-36, 26-37, 26-38, 27-4, 27-11, 27-12, 27-13, 27-14, 27-35, 27-36, 27-37, 27-38, 28-4, 28-11, 28-12, 28-13, 28-14, 28-35, 28-36, 28-37, 28-38, 29-4, 29-11, 29-12, 29-13, 29-14, 29-35, 29-36, 29-37, 29-38, 30-4, 30-11, 30-12, 30-13, 30-14, 30-35, 30-36, 30-37, 30-38, 31-4, 31-11, 31-12, 31-13, 31-14, 31-35, 31-36, 31-37, 31-38, 32-4, 32-11, 32-12, 32-13, 32-14, 32-35, 32-36, 32-37, 32-38, 33-4, 33-11, 33-12, 33-13, 33-14, 33-35, 33-36, 33-37, 33-38, 34-4, 34-11, 34-12, 34-13, 34-14, 34-35, 34-36, 34-37, 34-38, 35-4, 35-11, 35-12, 35-13, 35-14, 35-35, 35-36, 35-37, 35-38, 36-4, 36-11, 36-12, 36-13, 36-14, 36-35, 36-36, 36-37, 36-38, 37-4, 37-11, 37-12, 37-13, 37-14, 37-35, 37-36, 37-37, 37-38, 38-4, 38-11, 38-12, 38-13, 38-14, 38-35, 38-36, 38-37, 38-38, 39-4, 39-11, 39-12, 39-13, 39-14, 39-35, 39-36, 39-37, 39-38, 40-4, 40-11, 40-12, 40-13, 40-14, 40-35, 40-36, 40-37, 40-38, 41-4, 41-11, 41-12, 41-13, 41-14, 41-35, 41-36, 41-37, 41-38, 42-4, 42-11, 42-12, 42-13, 42-14, 42-35, 42-36, 42-37, 42-38, 43-4, 43-11, 43-12, 43-13, 43-14, 43-35, 43-36, 43-37, 43-38, 44-4, 44-11, 44-12, 44-13, 44-14, 44-35, 44-36, 44-37, 44-38, 45-4, 45-11, 45-12, 45-13, 45-14, 45-35, 45-36, 45-37, 45-38, 46-4, 46-11, 46-12, 46-13, 46-14, 46-35, 46-36, 46-37, 46-38, 47-4, 47-11, 47-12, 47-13, 47-14, 47-35, 47-36, 47-37, 47-38, 48-4, 48-11, 48-12, 48-13, 48-14, 48-35, 48-36, 48-37, 48-38, 49-4, 49-11, 49-12, 49-13, 49-14, 49-35, 49-36, 49-37, 49-38, 50-4, 50-11, 50-12, 50-13, 50-14, 50-35, 50-36, 50-37, 50-38, 51-4, 51-11, 51-12, 51-13, 51-14, 51-35, 51-36, 51-37, 51-38, 52-4, 52-11, 52-12, 52-13, 52-14, 52-35, 52-36, 52-37, 52-38, 53-4, 53-11, 53-12, 53-13, 53-14, 53-35, 53-36, 53-37, 53-38, 54-4, 54-11, 54-12, 54-13, 54-14, 54-35, 54-36, 54-37, 54-38, 55-4, 55-11, 55-12, 55-13, 55-14, 55-35, 55-36, 55-37, 55-38, 66-3, 66-4, 66-5, 66-6, 66-7, 66-8, 66-9, 66-10, 66-11, 66-12, 66-13, 66-14, 67-1, 67-2, 67-3, 67-4, 67-5, 67-6, 67-7, 67-8, 67-9, 67-10, 67-11, 67-12, 68-1, 68-2, 68-3, 68-4, 68-5, 68-6, 68-7, 68-8, 68-9, 68-10, 68-11, 68-12, 68-13 and 68-14, (2) More preferred compounds are those of Exemplification No. compounds. 1-1, 1-2, 1-3, 1-10, 1-11, 1-14, 1-15, 1-16, 1-17, 1-18, 1-19, 1-20, 1-21, 1-22, 1-23, 1-25, 1-29, 1-31, 1-33, 1-34, 1-35, 1-36, 1-37, 1-38, 1-39, 1-41, 1-43, 1-45, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-149, 1-150, 1-156, 1-158, 1-162, 1-164, 1-166, 1-168, 1-170, 1-172, 1-175, 1-176, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 2-1, 2-2, 2-3, 2-10, 2-11, 2-14, 2-15, 2-16, 2-17, 2-18, 2-19, 2-20, 2-21, 2-22, 2-23, 2-25, 2-29, 2-31, 2-33, 2-34, 2-35, 2-36, 2-37, 2-38, 2-39, 2-41, 2-43, 2-45, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-111, 2-112, 2-149, 2-150, 2-156, 2-158, 2-162, 2-164, 2-166, 2-168, 2-170, 2-172, 2-175, 2-176, 2-180, 2-181, 2-182, 2-183, 2-184, 2-185, 2-186, 2-187, 2-188, 2-189, 2-190, 2-191, 2-192, 2-193, 2-194, 2-195, 2-196, 2-197, 2-198, 2-199, 2-200, 2-201, 2-202, 2-203, 3-1, 3-2, 3-3, 3-10, 3-11, 3-14, 3-15, 3-16, 3-17, 3-18, 3-19, 3-20, 3-21, 3-22, 3-23, 3-25, 3-29, 3-31, 3-33, 3-34, 3-35, 3-36, 3-37, 3-38, 3-39, 3-41, 3-43, 3-45, 3-87, 3-88, 3-89, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-111, 3-112, 3-149, 3-150, 3-156, 3-158, 3-162, 3-164, 3-166, 3-168, 3-170, 3-172, 3-175, 3-176, 3-180, 3-181, 3-182 ,3-183, 3-184, 3-185, 3-186, 3-187, 3-188, 3-189, 3-190, 3-191, 3-192, 3-193, 3-194, 3-195, 3-196, 3-197, 3-198, 3-199, 3-200, 3-201, 3-202, 3-203, 4-15, 4-35, 4-37, 4-39, 4-95, 4-96, 4-97, 4-98, 4-110, 5-15, 5-35, 5-37, 5-39, 5-95, 5-96, 5-97, 5-98, 5-110, 6-1, 6-2, 6-3, 6-10, 6-11, 6-14, 6-15, 6-16, 6-17, 6-18, 6-19, 6-20, 6-21, 6-22, 6-23, 6-25, 6-29, 6-31, 6-33, 6-34, 6-35, 6-36, 6-37, 6-38, 6-39, 6-41, 6-43, 6-45, 6-87, 6-88, 6-89, 6-90, 6-91, 6-92, 6-93, 6-94, 6-95, 6-96, 6-97, 6-98, 6-99, 6-100, 6-101, 6-102, 6-103, 6-104, 6-105, 6-106, 6-107, 6-108, 6-109, 6-110, 6-111, 6-112, 6-149, 6-150, 6-156, 6-158, 6-162, 6-164, 6-166, 6-168, 6-170, 6-172, 6-175, 6-176, 6-180, 6-181, 6-182, 6-183, 6-184, 6-185, 6-186, 6-187, 6-188, 6-189, 6-190, 6-191, 6-192, 6-193, 6-194, 6-195, 6-196, 6-197, 6-198, 6-199, 6-200, 6-201, 6-202, 6-203, 7-15, 7-35, 7-37, 7-39, 7-95, 7-96, 7-97, 7-98, 7-110, 8-1, 8-2, 8-3, 8-10, 8-11, 8-14, 8-15, 8-16, 8-17, 8-18, 8-19, 8-20, 8-21, 8-22, 8-23, 8-25, 8-29, 8-31, 8-33, 8-34, 8-35, 8-36, 8-37, 8-38, 8-39, 8-41, 8-43, 8-45, 8-87, 8-88, 8-89, 8-90, 8-91, 8-92, 8-93, 8-94, 8-95, 8-96, 8-97, 8-98, 8-99, 8-100, 8-101, 8-102, 8-103, 8-104, 8-105, 8-106, 8-107, 8-108, 8-109, 8-110, 8-111, 8-112, 8-149, 8-150, 8-156, 8-158, 8-162, 8-164, 8-166, 8-168, 8-170, 8-172, 8-175, 8-176, 8-180, 8-181, 8-182, 8-183, 8-184, 8-185, 8-186, 8-187, 8-188, 8-189, 8-190, 8-191, 8-192, 8-193, 8-194, 8-195, 8-196, 8-197, 8-198, 8-199, 8-200, 8-201, 8-202, 8-203, 9-15, 9-35, 9-37, 9-39, 9-95, 9-96, 9-97, 9-98, 9-110, 10-1, 10-2, 10-3, 10-10, 10-11, 10-14, 10-15, 10-16, 10-17, 10-18, 10-19, 10-20, 10-21, 10-22, 10-23, 10-25, 10-29, 10-31, 10-33, 10-34, 10-35, 10-36, 10-37, 10-38, 10-39, 10-41, 10-43, 10-45, 10-87, 10-88, 10-89, 10-90, 10-91, 10-92, 10-93, 10-94, 10-95, 10-96, 10-97, 10-98, 10-99, 10-100, 10-101, 10-102, 10-103, 10-104, 10-105, 10-106, 10-107, 10-108, 10-109, 10-110, 10-111, 10-112, 10-149, 10-150, 10-156, 10-158, 10-162, 10-164, 10-166, 10-168, 10-170, 10-172, 10-175, 10-176, 10-180, 10-181, 10-182, 10-183, 10-184, 10-185, 10-186, 10-187, 10-188, 10-189, 10-190, 10-191, 10-192, 10-193, 10-194, 10-195, 10-196, 10-197, 10-198, 10-199, 10-200, 10-201, 10-202, 10-203, 24-4, 24-11, 24-12, 24-13, 24-14, 24-35, 24-36, 24-37, 24-38, 25-4, 25-11, 25-12, 25-13, 25-14, 25-35, 25-36, 25-37, 25-38, 26-4, 26-11, 26-12, 26-13, 26-14, 26-35, 26-36, 26-37, 26-38, 27-4, 27-11, 27-12, 27-13, 27-14, 27-35, 27-36, 27-37, 27-38, 28-4, 28-11, 28-12, 28-13, 28-14, 28-35, 28-36, 28-37, 28-38, 29-4, 29-11, 29-12, 29-13, 29-14, 29-35, 29-36, 29-37, 29-38, 30-4, 30-11, 30-12, 30-13, 30-14, 30-35, 30-36, 30-37, 30-38, 31-4, 31-11, 31-12, 31-13, 31-14, 31-35, 31-36, 31-37, 31-38,
32-4, 32-11, 32-12, 32-13, 32-14, 32-35, 32-36, 32-37, 32-38,
33-4, 33-11, 33-12, 33-13, 33-14, 33-35, 33-36, 33-37, 33-38,
34-4, 34-11, 34-12, 34-13, 34-14, 34-35, 34-36, 34-37, 34-38,
35-4, 35-11, 35-12, 35-13, 35-14, 35-35, 35-36, 35-37, 35-38,
36-4, 36-11, 36-12, 36-13, 36-14, 36-35, 36-36, 36-37, 36-38,
37-4, 37-11, 37-12, 37-13, 37-14, 37-35, 37-36, 37-37, 37-38,
38-4, 38-11, 38-12, 38-13, 38-14, 38-35, 38-36, 38-37, 38-38,
39-4, 39-11, 39-12, 39-13, 39-14, 39-35, 39-36, 39-37, 39-38,
40-4, 40-11, 40-12, 40-13, 40-14, 40-35, 40-36, 40-37, 40-38,
41-4, 41-11, 41-12, 41-13, 41-14, 41-35, 41-36, 41-37, 41-38,
42-4, 42-11, 42-12, 42-13, 42-14, 42-35, 42-36, 42-37, 42-38,
43-4, 43-11, 43-12, 43-13, 43-14, 43-35, 43-36, 43-37, 43-38,
44-4, 44-11, 44-12, 44-13, 44-14, 44-35, 44-36, 44-37, 44-38,
45-4, 45-11, 45-12, 45-13, 45-14, 45-35, 45-36, 45-37, 45-38,
47-4, 47-11, 47-12, 47-13, 47-14, 47-35, 47-36, 47-37, 47-38,
49-4, 49-11, 49-12, 49-13, 49-14, 49-35, 49-36, 49-37, 49-38,
50-4, 50-11, 50-12, 50-13, 50-14, 50-35, 50-36, 50-37, 50-38,
51-4, 51-11, 51-12, 51-13, 51-14, 51-35, 51-36, 51-37, 51-38,
52-4, 52-11, 52-12, 52-13, 52-14, 52-35, 52-36, 52-37, 52-38,
53-4, 53-11, 53-12, 53-13, 53-14, 53-35, 53-36, 53-37, 53-38,
54-4, 54-11, 54-12, 54-13, 54-14, 54-35, 54-36, 54-37, 54-38,
66-3, 66-4, 66-5, 66-6, 66-7, 66-8, 66-9, 66-10, 66-11, 66-12, 66-13, 66-14,
67-1, 67-2, 67-3, 67-4, 67-5, 67-6, 67-7, 67-8, 67-9, 67-10, 67-11, 67-12,
68-1, 68-2, 68-3, 68-4, 68-5, 68-6, 68-7, 68-8, 68-9 and 68-10, (3) More preferred compounds are those of Exemplification No. compounds. 1-14, 1-15 15, 1-16, 1-17, 1-18, 1-19, 1-20, 1-21, 1-22, 1-23, 1-29, 1-31, 1-33, 1-34, 1-35, 1-36, 1-37, 1-38, 1-39, 1-41, 1-43, 1-45, 1-88, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-181, 1-182, 1-183, 1-184, 1-185, 1-186, 1-187, 1-188, 1-189, 1-192, 1-193, 1-195,
2-14, 2-15, 2-16, 2-17, 2-18, 2-19, 2-20, 2-21, 2-22, 2-23, 2-29, 2-31, 2-33, 2-34, 2-35, 2-36, 2-37, 2-38, 2-39, 2-41, 2-43, 2-45, 2-88, 2-90, 2-91, 2-92, 2-93, 2-94, 2-95, 2-96, 2-97, 2-98, 2-99, 2-100, 2-101, 2-102, 2-103, 2-104, 2-105, 2-106, 2-107, 2-108, 2-109, 2-110, 2-181, 2-182, 2-183, 2-184, 2-185, 2-186, 2-187, 2-188, 2-189, 2-192, 2-193, 2-195,
3-14, 3-15, 3-16, 3-17, 3-18, 3-19, 3-20, 3-21, 3-22, 3-23, 3-29, 3-31, 3-33, 3-34, 3-35, 3-36, 3-37, 3-38, 3-39, 3-41, 3-43, 3-45, 3-88, 3-90, 3-91, 3-92, 3-93, 3-94, 3-95, 3-96, 3-97, 3-98, 3-99, 3-100, 3-101, 3-102, 3-103, 3-104, 3-105, 3-106, 3-107, 3-108, 3-109, 3-110, 3-181, 3-182, 3-183, 3-184, 3-185, 3-186, 3-187, 3-188, 3-189, 3-192, 3-193, 3-195,
5-15, 5-35, 5-37, 5-39, 5-95, 5-96, 5-97, 5-98, 5-110,
6-15, 6-35, 6-37, 6-39, 6-95, 6-96, 6-97, 6-98, 6-110,
24-4, 24-11, 24-12, 24-13, 24-14, 24-35, 24-36, 24-37, 24-38,
25-4, 25-11, 25-12, 25-13, 25-14, 25-35, 25-36, 25-37, 25-38,
26-4, 26-11, 26-12, 26-13, 26-14, 26-35, 26-36, 26-37, 26-38,
27-4, 27-11, 27-12, 27-13, 27-14, 27-35, 27-36, 27-37, 27-38,
28-4, 28-11, 28-12, 28-13, 28-14, 28-35, 28-36, 28-37, 28-38,
29-4, 29-11, 29-12, 29-13, 29-14, 29-35, 29-36, 29-37, 29-38,
30-4, 30-11, 30-12, 30-13, 30-14, 30-35, 30-36, 30-37, 30-38,
31-4, 31-11, 31-12, 31-13, 31-14, 31-35, 31-36, 31-37, 31-38,
32-4, 32-11, 32-12, 32-13, 32-14, 32-35, 32-36, 32-37, 32-38,
33-4, 33-11, 33-12, 33-13, 33-14, 33-35, 33-36, 33-37, 33-38,
34-4, 34-11, 34-12, 34-13, 34-14, 34-35, 34-36, 34-37, 34-38,
35-4, 35-11, 35-12, 35-13, 35-14, 35-35, 35-36, 35-37, 35-38,
36-4, 36-11, 36-12, 36-13, 36-14, 36-35, 36-36, 36-37, 36-38,
37-4, 37-11, 37-12, 37-13, 37-14, 37-35, 37-36, 37-37, 37-38,
38-4, 38-11, 38-12, 38-13, 38-14, 38-35, 38-36, 38-37, 38-38,
39-4, 39-11, 39-12, 39-13, 39-14, 39-35, 39-36, 39-37, 39-38,
40-4, 40-11, 40-12, 40-13, 40-14, 40-35, 40-36, 40-37, 40-38,
41-4, 41-11, 41-12, 41-13, 41-14, 41-35, 41-36, 41-37, 41-38,
42-4, 42-11, 42-12, 42-13, 42-14, 42-35, 42-36, 42-37, 42-38,
43-4, 43-11, 43-12, 43-13, 43-14, 43-35, 43-36, 43-37, 43-38,
44-4, 44-11, 44-12, 44-13, 44-14, 44-35, 44-36, 44-37, 44-38,
45-4, 45-11, 45-12, 45-13, 45-14, 45-35, 45-36, 45-37, 45-38,
47-4, 47-11, 47-12, 47-13, 47-14, 47-35, 47-36, 47-37, 47-38,
49-4, 49-11, 49-12, 49-13, 49-14, 49-35, 49-36, 49-37, 49-38,
50-4, 50-11, 50-12, 50-13, 50-14, 50-35, 50-36, 50-37, 50-38,
51-4, 51-11, 51-12, 51-13, 51-14, 51-35, 51-36, 51-37, 51-38,
52-4, 52-11, 52-12, 52-13, 52-14, 52-35, 52-36, 52-37, 52-38,
53-4, 53-11, 53-12, 53-13, 53-14, 53-35, 53-36, 53-37, 53-38,
54-4, 54-11, 54-12, 54-13, 54-14, 54-35, 54-36, 54-37, 54-38,
66-5, 66-6, 66-7, 66-8, 66-9, 66-10,
67-5, 67-6, 67-7, 67-8, 68-2 and 68-3, (4) More preferred compounds are those of Exemplification No. compounds. 1-15, 1-17, 1-19, 1-21, 1-23, 1-35, 1-37, 1-39, 1-95, 1-96, 1-97, 1-98, 1-99, 1-100, 1-101, 1-102, 1-103, 1-104, 1-105, 1-108, 1-183, 1-185, 1-187, 1-189, 1-195, 2-15, 2-17, 2-19, 2-21, 2-23, 2-35, 2-37, 2-39, 2-95, 2-96, 2-97, 2-98, 2-99, 2-100, 2-101, 2-102, 2-103, 2-104, 2-105, 2-108, 2-183, 2-185, 2-187, 2-189, 2-195, 3-15, 3-17, 3-19, 3-21, 3-23, 3-35, 3-37, 3-39, 3-95, 3-96, 3-97, 3-98, 3-99, 3-100, 3-101, 3-102, 3-103, 3-104, 3-105, 3-108, 3-183, 3-185, 3-187, 3-189, 3-195, 5-15, 5-35, 5-37, 5-39,
24-4, 24-11, 24-35, 24-36, 24-37,
25-4, 25-11, 25-35, 25-36, 25-37,
26-4, 26-11, 26-35, 26-36, 26-37,
27-4, 27-11, 27-35, 27-36, 27-37,
28-4, 28-11, 28-35, 28-36, 28-37,
29-4, 29-11, 29-35, 29-36, 29-37,
30-4, 30-11, 30-35, 30-36, 30-37,
31-4, 31-11, 31-35, 31-36, 31-37,
32-4, 32-11, 32-35, 32-36, 32-37,
33-4, 33-11, 33-35, 33-36, 33-37,
34-4, 34-11, 34-35, 34-36, 34-37,
35-4, 35-11, 35-35, 35-36, 35-37,
36-4, 36-11, 36-35, 36-36, 36-37,
37-4, 37-11, 37-35, 37-36, 37-37,
38-4, 38-11, 38-35, 38-36, 38-37,
39-4, 39-11, 39-35, 39-36, 39-37,
40-4, 40-11, 40-35, 40-36, 40-37,
41-4, 41-11, 41-35, 41-36, 41-37,
42-4, 42-11, 42-35, 42-36, 42-37,
43-4, 43-11, 43-35, 43-36, 43-37,
44-4, 44-11, 44-35, 44-36, 44-37,
45-4, 45-11, 45-35, 45-36, 45-37,
47-4, 47-11, 47-35, 47-36, 47-37,
49-4, 49-11, 49-35, 49-36, 49-37,
50-4, 50-11, 50-35, 50-36, 50-37,
51-4, 51-11, 51-35, 51-36, 51-37,
52-4, 52-11, 52-35, 52-36, 52-37,
53-4, 53-11, 53-35, 53-36, 53-37,
54-4, 54-11, 54-35, 54-36, 54-37,
66-6, 66-8, 66-10, 67-6, 67-8 and 68-2, (5) More preferred compounds are those of Exemplification No. compounds. 2-15, 2-17, 2-19, 2-21, 2-23, 2-35, 2-37, 2-39, 2-95, 2-96, 2-97, 2-98, 2-99, 2-100, 2-101, 2-102, 2-103, 2-104, 2-105, 2-108, 2-183, 2-185, 2-187, 2-189, 2-195, 3-15, 3-17, 3-19, 3-21, 3-23, 3-35, 3-37, 3-39, 3-95, 3-96, 3-97, 3-98, 3-99, 3-100, -101, 3-102, 3-103, 3-104, 3-105, 3-108, 3-183, 3-185, 3-187, 3-189, 3-195, 6-15, 6-35, 6-37, 6-39, 24-4, 24-11, 24-35, 24-36, 24-37, 25-4, 25-11, 25-35, 25-36, 25-37, 26-4, 26-11, 26-35, 26-36, 26-37, 27-4, 27-11, 27-35, 27-36, 27-37, 28-4, 28-11, 28-35, 28-36, 28-37, 31-4, 31-11, 31-35, 31-36, 31-37, 32-4, 32-11, 32-35, 32-36, 32-37, 42-4, 42-11, 42-35, 42-36, 42-37, 43-4, 43-11, 43-35, 43-36, 43-37, 44-4, 44-11, 44-35, 44-36, 44-37, 45-4, 45-11, 45-35, 45-36, 45-37, 47-4, 47-11, 47-35, 47-36, 47-37, 49-4, 49-11, 49-35, 49-36, 49-37, 50-4, 50-11, 50-35, 50-36, 50-37, 51-4, 51-11, 51-35, 51-36, 51-37, 52-4, 52-11, 52-35, 52-36, 52-37, 53-4, 53-11, 53-35, 53-36, 53-37, 54-4, 54-11, 54-35, 54-36, 54-37, 66-6, 66-8, 66-10, 67-6, 67-8 and 68-2, (6) More preferred compounds are those of Exemplification No. compounds. 2-15, 2-23, 2-35, 2-37, 2-39, 2-95, 2-96, 2-97, 2-98, 2-105, 3-15, 3-23, 3-35, 3-37, 3-39, 3-95, 3-96, 3-97, 3-98, 3-105, 6-15, 6-35, 6-37, 24-4, 24-11, 24-35, 24-36, 25-4, 25-11, 25-35, 25-36, 26-4, 26-11, 26-35, 26-36, 27-4, 27-11, 27-35, 27-36, 28-4, 28-11, 28-35, 28-36, 31-4, 31-11, 31-35, 31-36, 32-4, 32-11, 32-35, 32-36, 42-4, 42-11, 42-35, 42-36, 43-4, 43-11, 43-35, 43-36, 44-4, 44-11, 44-35, 44-36, 45-4, 45-11, 45-35, 45-36, 47-4, 47-11, 47-35, 47-36, 49-4, 49-11, 49-35, 49-36, 50-4, 50-11, 50-35, 50-36, 66-8, 66-10, 67-6, 67-8 and 68-2, (7) More preferred compounds are those of Exemplification No. compounds.

2-15) 2-ethoxy-3-[4-[2-[[1-(4-biphenylyl)ethylidene]aminoxy]ethoxy]phenyl]propionic acid, 2-23) 2-ethoxy-3-[4-[2-[[1-(4-phenylsulfonylphenyl)ethylidene]aminoxy]ethoxy]phenyl]propionic acid, 2-35) 2-ethoxy-3-[4-[2-[[1-[4-(2-pyridyl)phenyl]ethylidene]aminoxy]ethoxy]phenyl]propionic acid, 2-37) 2-ethoxy-3-[4-[2-[[1-[4-(3-pyridyl)phenyl]ethylidene]aminoxy]ethoxy]phenyl]propionic acid, 2-39) 2-ethoxy-3-[4-[2-[[1-[4-(4-pyridyl)phenyl]ethylidene]aminoxy]ethoxy]phenyl]propionic acid, 2-95) 2-ethoxy-3-[4-[2-[[1-(2-phenyl-5-pyridyl)ethylidene]aminoxy]ethoxy]phenyl]propionic acid, 2-96) 2-ethoxy-3-[4-[2-[[1-(2-methoxy-5-pyridyl)ethylidene]aminoxy]ethoxy]phenyl]propionic acid, 2-97) 2-ethoxy-3-[4-[2-[[1-(2-ethoxy-5-pyridyl)ethylidene]aminoxy]ethoxy]phenyl]propionic acid, 2-98) 2-ethoxy-3-[4-[2-[[1-(2-isopropoxy-5-pyridyl)ethylidene]aminoxy]ethoxy]phenyl]propionic acid, 2-105) 3-[4-[2-[[1-(2-benzyl-5-pyridyl)ethylidene]aminoxy]ethoxy]phenyl]-2-ethoxypropionic acid, 6-35) 2-methoxy-3-[4-[2-[[1-[4-(2-pyridyl)phenyl]ethylidene]aminoxy]ethoxy]phenyl]propionic acid, 24-35) 2-propoxy-3-[4-[2-[[1-[4-(2-pyridyl)phenyl]ethylidene]aminoxy]ethoxy]phenyl]propionic acid, 25-35) 2-isopropoxy-3-[4-[2-[[1-[4-(2-pyridyl)phenyl]ethylidene]aminoxy]ethoxy]phenyl]propionic acid, 26-35) 2-methylthio-3-[4-[2-[[1-[4-(2-pyridyl)phenyl]ethylidene]aminoxy]ethoxy]phenyl]propionic acid, 27-35) 2-ethylthio-3-[4-[2-[[1-[4-(2-pyridyl)phenyl]ethylidene]aminoxy]ethoxy]phenyl]propionic acid, 28-35) 2-propylthio-3-[4-[2-[[1-[4-(2-pyridyl)phenyl]ethylidene]aminoxy]ethoxy]phenyl]propionic acid, 31-35) 2-phenylthio-3-[4-[2-[[1-[4-(2-pyridyl)phenyl]ethylidene]aminoxy]ethoxy]phenyl]propionic acid, 32-4) 3-[4-[2-[[1-(4-biphenylyl)ethylidene]aminoxy]ethoxy]phenyl]-2-(phenylamino)propionic acid, 32-35) 2-phenylamino-3-[4-[2-[[1-[4-(2-pyridyl)phenyl]ethylidene]aminoxy]ethoxy]phenyl]propionic acid, 42-35) 2-methylamino-3-[4-[2-[[1-[4-(2-pyridyl)phenyl]ethylidene]aminoxy]ethoxy]phenyl]propionic acid, 43-35) 2-ethylamino-3-[4-[2-[[1-[4-(2-pyridyl)phenyl]ethylidene]aminoxy]ethoxy]phenyl]propionic acid, 44-35) 2-propylamino-3-[4-[2-[[1-[4-(2-pyridyl)phenyl]ethylidene]aminoxy]ethoxy]phenyl]propionic acid, 45-35) 2-isopropylamino-3-[4-[2-[[1-[4-(2-pyridyl)phenyl]ethylidene]aminoxy]ethoxy]phenyl]propionic acid, 47-35) 2-(N,N-diethylamino)-3-[4-[2-[[1-[4-(2-pyridyl)phenyl]ethylidene]aminoxy]ethoxy]phenyl]propionic acid, 49-4) 3-[4-[2-[[1-(4-biphenylyl)ethylidene]aminoxy]ethoxy]phenyl]-2-[N-phenyl-N-ethylamino]propionic acid, 50-4) 3-[4-[2-[[1-(4-biphenylyl)ethylidene]aminoxy]ethoxy]phenyl]-2-pyrrolyl-propionic acid, 66-8) 2-(3-phenylpropyl)-3-[4-[2-[[1-[4-(2-pyridyl)phenyl]ethylidene]aminoxy]ethoxy]phenyl]propionic acid, 66-10) 2-(4-phenylbutyl)-3-[4-[2-[[1 -[4-(2-pyridyl)phenyl]ethylidene]aminoxy]ethoxy]phenyl]propionic acid, 67-6) 2-propyl-3-[4-[2-[[1-[4-(2-pyridyl)phenyl]ethylidene]aminoxy]ethoxy]phenyl]propionic acid, 67-8) 2-butyl-3-[4-[2-[[1-[4-(2-pyridyl)phenyl]ethylidene]aminoxy]ethoxy]phenyl]propionic acid, or
68-2) 2-phenoxy-3-[4-[2-[[1-[4-(2-pyridyl)phenyl]ethylidene]aminoxy]ethoxy]phenyl]propionic acid, 8) The most preferred compounds are those of Exemplification No. compound.
2-15) 2-ethoxy-3-[4-[2-[[1-(4-biphenylyl)ethylidene]aminoxy]ethoxy]phenyl]propionic acid,
2-35) 2-ethoxy-3-[4-[2-[[1-[4-(2-pyridyl)phenyl]ethylidene]aminoxy]ethoxy]phenyl]propionic acid,
26-35) 2-methylthio-3-[4-[2-[[1-[4-(2-pyridyl)phenyl]ethylidene]aminoxy]ethoxy]phenyl]propionic acid,
31-35) 2-phenylthio-3-[4-[2-[[1-[4-(2-pyridyl)phenyl]ethylidene]aminoxy]ethoxy]phenyl]propionic acid,
32-4) 3-[4-[2-[[1-(4-(biphenylyl)ethylidene]aminoxy]ethoxy]phenyl]-2-(phenylamino)propionic acid,
43-35) 2-ethylamino-3-[4-[2-[[1-[4-(2-pyridyl)phenyl]ethylidene]aminoxy]ethoxy]phenyl]propionic acid,
66-8) 2-(3-phenylpropyl)-3-[4-[2-[[1-[4-(2-pyridyl)phenyl]ethylidene]aminoxy]ethoxy]phenyl]propionic acid,
67-8) 2-butyl-3-[4-[2-[[1-[4-(2-pyridyl)phenyl]ethylidene]aminoxy]ethoxy]phenyl]propionic acid and
68-2) 2-phenoxy-3-[4-[2-[[1-[4-(2-pyridyl)phenyl]ethylidene]aminoxy]ethoxy]phenyl]propionic acid.

The phenylalkylcarboxylic acid derivative of formula (I) of the present invention, the pharmacologically acceptable salt thereof or the pharmacologically acceptable ester thereof is easily prepared according to the following Method A.

Method A

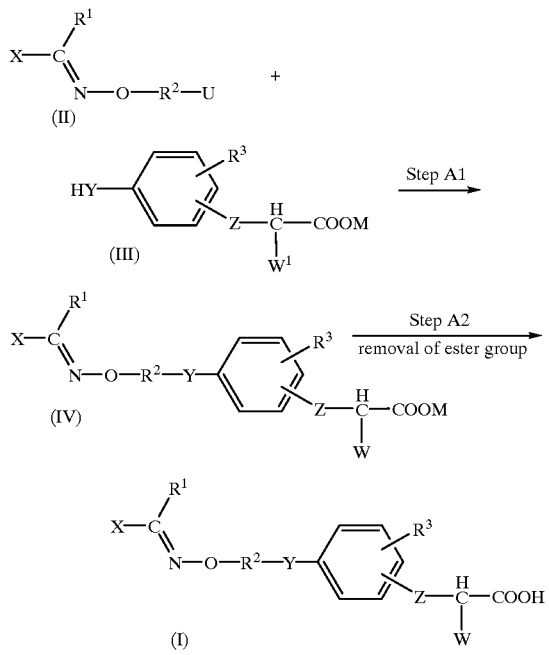

Wherein $R^1$, $R^2$, $R^3$, X, Y and Z have the same meanings as defined above. In the case where W represents a primary or secondary amino group, $W^1$ represents an amino group in which the amino group of W is protected by a usual protecting group such as t-butoxycarbonyl. In the case where $W^1$ represents other groups, $W^1$ has the same meaning as defined above for W.

M represents the ester residual group in the case where the phenylalkylcarboxylic acid of formula (I) forms an ester.

U represents a hydroxyl group, a halogen atom (preferably the chlorine, bromine and iodine atoms) or a group of formula —O—$SO_2$—$R^5$ (wherein $R^5$ represents an alkyl group having from 1 to 6 carbon atoms such as methyl and ethyl; a halogenated alkyl group having from 1 to 4 carbon atoms such as trifluoromethyl; or an aryl group having from 6 to 10 carbon atoms which may have alkyl having from 1 to 4 carbon atoms, nitro or halogen as the substituent such as phenyl, p-tolyl, p-nitrophenyl and p-bromophenyl).

Step A1

Step A1 is to prepare a compound of formula (IV), and the compound is prepared by reacting a compound of formula (II) with a compound of formula (III).

In the case where U is a hydroxyl group, the reaction is carried out according to the reaction of the conventional Mitsunobu reaction [O. Mitsunobu, Synthesis. 1 (1981)].

The reaction is usually carried out by contacting the starting compounds with azo compounds and phosphines in a solvent. The azo compounds used in the reaction are $C_1$–$C_4$ alkyl azodicarboxylates such as diethyl azodicarboxylate and azodicarboxamides such as 1,1'-(azodicarbonyl) dipiperidine. As the phosphines, a triarylphosphine such as triphenylphosphine and a tri($C_1$–$C_4$ alkyl)phosphine such as tributylphosphine are used.

The reaction is usually carried out in a solvent preferably. The solvent is not particularly limited so long as it has no adverse effect on the present reaction. Examples of suitable solvents include hydrocarbons such as benzene, toluene, xylene, hexane and heptane; halogenated hydrocarbons such as chloroform, methylene chloride, carbon tetrachloride and 1,2-dichloroethane; ethers such as diethyl ether, tetrahydrofuran and dioxane; amides such as dimethylformamide, dimethylacetamide and hexamethylphosphoric triamide; and a mixture thereof, preferably the hydrocarbons, halogenated hydrocarbons and ethers. The reaction temperature is 10 to 100° C., preferably 20 to 80° C.

While the reaction time varies depending on the reaction reagent, reaction temperature and solvent, it is usually one hour to 3 days, preferably 5 hours to 2 days.

In the case where U is the halogen atom or a group of formula: —O—$SO_2$—$R^5$ (wherein $R^5$ has the same meaning as defined above), the reaction is carried out in the presence of a base in an inert solvent.

The base employed includes, for example, alkali metal carbonates such as sodium carbonate and potassium carbonate; alkali metal hydrides such as sodium hydride, potassium hydride and lithium hydride; alkali metal alkoxides such as sodium methoxide, sodium ethoxide, potassium t-butoxide and lithium methoxide; alkyllithiums such as butyllithium and methyllithium; lithium amides such as lithium diethylamides, lithium diisopropylamide and lithium bis(trimethylsilyl)amide; alkali metal hydrogencarbonates such as sodium hydrogencarbonate and potassium hydrogencarbonate; and tertiary organic amines such as 1,5-diazabicyclo[4.3.0]non-5-ene, 1,8-diazabicyclo[5.4.0]undec-7-ene and N,N-diisopropylethylamine, preferably alkali metal carbonates, alkali metal hydrides and alkali metal alkoxides.

The inert solvent used in the reaction is not particularly limited so long as it has no adverse effect on the reaction. Examples of suitable solvents include hydrocarbons such as benzene and toluene; ethers such as tetrahydrofuran and dioxane; alcohols such as methanol, ethanol and t-butanol; amides such as dimethylformamide, dimethylacetamide and N-methylpyrrolidinone; ketones such as acetone and 2-butanone; nitrites such as acetonitrile; sulfoxides such as dimethyl sulfoxide and a mixture thereof, preferably the ethers, amides, ketones and sulfoxides.

In the case where the present reaction is carried out in the presence of a phase transfer catalyst such as benzyltriethylammonium iodide and tetrabutylammonium iodide, alkali metal hydroxides such as sodium hydroxide and potassium hydroxide are used as a base. The reaction is carried out in a solvent of a two-layer system of water and halogenated hydrocarbons such as methylene chloride and chloroform.

The reaction temperature is −10 to 120° C., preferably 10 to 100° C.

While the reaction time varies depending on the reagent used, the reaction temperature, etc., it is 30 minutes to 48 hours, preferably 1 to 16 hours.

Further, in the case where $W^1$ represents a primary or secondary amino group which is protected by a conventional protecting group such as t-butoxycarbonyl, after the reaction, deprotection can be carried out according to a known method, for example, by reaction of a compound of formula (IV) with an acid such as hydrochloric acid at room temperature for 30 minutes to 2 hours.

Step A2

Step A2 is to prepare a phenylalkylcarboxylic acid derivative of formula (I) and the compound is prepared by removing the ester residue of a compound of formula (IV).

The present step is carried out by hydrolysis of a compound of formula (IV) with a base in a solvent.

In the present reaction, the solvent is not particularly limited so long as it has no adverse effect on the reaction, and preferably includes, for example, ethers such as diethyl ether, tetrahydrofuran and dioxane; alcohols such as methanol and ethanol; water; and a mixture thereof.

The base used in the reaction includes, for example, alkali metal hydroxides such as lithium hydroxide, sodium hydroxide and potassium hydroxide and alkali metal carbonates such as lithium carbonate, sodium carbonate anti potassium carbonate, preferably alkali metal hydroxides.

While the reaction temperature varies depending on the solvent and base used, it is 0 to 100° C., preferably 10 to 80° C.

While the reaction time varies depending on the solvent, the base used and the reaction temperature, it is usually 10 minutes to 24 hours, preferably 30 minutes to 16 hours.

Further, in the case where the ester residue is the t-butyl, diphenylmethyl or p-methoxybenzyl group, the present step is also carried out by reacting the compound of formula (IV) with organic acids such as formic acid, acetic acid, trifluoroacetic acid, methanesulfonic acid, benzenesulfonic acid, p-toluenesulfonic acid and trifluoromethanesulfonic acid and mineral acids such as hydrochloric acid and sulfuric acid in the presence or absence of a solvent. The present step is carried out preferably by the reaction with trifluoroacetic acid or hydrochloric acid.

In the present reaction, in the case where the solvent is used, the solvent employed is not particularly limited so long as it has no adverse effect on the reaction. Examples of suitable solvents include hydrocarbons such as benzene, toluene, xylene, hexane and heptane; halogenated hydrocarbons such as chloroform, methylene chloride and carbon tetrachloride; ethers such as diethyl ether, tetrahydrofuran and dioxane; alcohols such as methanol and ethanol; amides such as dimethylformamide, dimethylacetamide and hexamethylphosphoric triamide; esters such as methyl acetate and ethyl acetate; water; a mixture thereof, preferably the ethers.

While the reaction temperature varies depending on the acid used, it is −10 to 120° C., preferably 0 to 100° C.

While the reaction time varies depending on the acid and the reaction temperature, it is usually 10 minutes to 24 hours, preferably 30 minutes to 16 hours.

Further, in the case where the ester residue is the aralkyl group such as the benzyl and diphenylmethyl groups, the present step is also carried out by catalytic hydrogenation of the compound of formula (IV). The catalyst employed includes, for example, palladium-carbon, palladium black, platinum oxide and platinum black, preferably palladium-carbon.

The reaction is usually carried out in the presence of a solvent preferably. The solvent employed is not particularly limited so long as it has no adverse effect on the reaction. Examples of suitable solvents include hydrocarbons such as benzene, toluene, xylene, hexane and heptane; halogenated hydrocarbons such as chloroform, methylene chloride and carbon tetrachloride; ethers such as diethyl ether, tetrahydrofuran and dioxane; alcohols such as methanol, ethanol and isopropanol; amides such as dimethylformamide, dimethylacetamide and hexamethylphosphoric triamide; carboxylic acids such as formic acid and acetic acid; and a mixture of them, preferably the alcohols.

The reaction temperature is 10 to 140° C., preferably 20 to 120° C.

While the reaction time varies depending on the reaction reagents reaction temperature and the solvent, it is usually 30 minutes to 3 days, preferably one hour to one day.

The compound of formula (IV) used in Method A can also be prepared according to Method B.

(Method B)

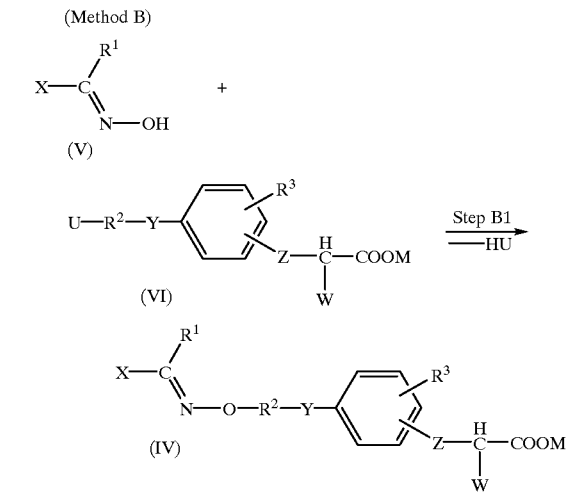

Wherein $R^1$, $R^2$, $R^3$, U, X, Y, Z, W and M have the same meanings as defined above.

Step B1 in Method B is to prepare the compound of formula (IV). The compound is prepared by reaction of a compound of formula (V) with a compound of formula (VI).

The reaction is carried out in a similar manner to that described in Step A1 of Method A which has been already described in detail.

The phenylalkylcarboxylic acid derivative of formula (I) and the compound of formula (IV) can be also prepared according to the following Method C.

(Method C)

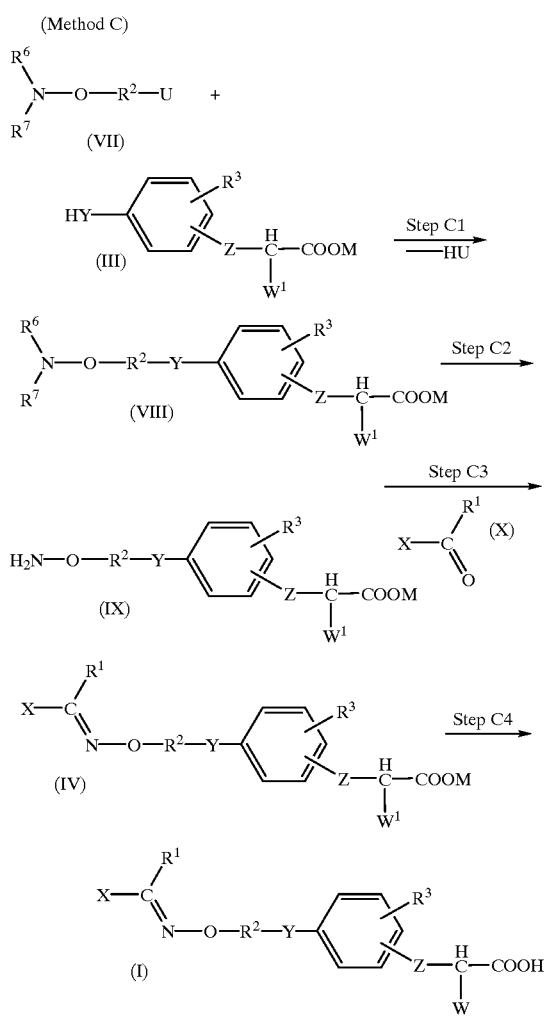

Wherein $R^1$, $R^2$, $R^3$, U, X, Y, W, $W^1$ and M have the same meanings as defined above.

$R^6$ represents a hydrogen atom, $R^7$ represents a protecting group of the amino group, or $R^6$ and $R^7$ together represent a protecting group of amino group.

The protecting group of the amino group is a protecting group known in organic synthetic chemistry. Examples of such protecting groups include a $C_7$–$C_{14}$ aralkyl group such as benzyl, diphenylmethyl and trityl. a $C_1$–$C_4$ aliphatic acyl group which may be substituted by fluorine such as formyl and trifluoroacetyl; a ($C_1$–$C_4$ alkoxy)carbonyl group such as t-butoxycarbonyl; and a benzyloxycarbonyl group which may be substituted by methoxy or nitro such as benzyloxycarbonyl, p-methoxybenzyloxycarbonyl and p-nitrobenzyloxycarbonyl. In the case where $R^6$ and $R^7$ taken together represent the protecting group of the amino group, the protecting groups include, for example, phthaloyl groups. The benzyl, trityl, t-butoxycarbonyl, benzyloxycarbonyl and phthaloyl groups are preferred.

Step C1

Step C1 is to prepare the compound of formula (VII) and is carried out by reaction of a compound of formula (VII) with a compound of formula (III).

The present step is carried out in a similar manner to that described in Step A1 of Method A.

Step C2

Step C2 is to prepare a compound of formula (IX) and is carried out by removing the protecting group $R^7$ of the compound of formula (VIII).

Where the protecting group $R^7$ is a group which can be removed by catalytic reduction such as the aralkyl and aralkyloxycarbonyl groups or a group which can be removed by an acid such as the trityl and t-butoxycarbonyl groups, the deprotection reaction is carried out in a similar manner to that described in Step A2 of Method A.

In the case where the protecting group $R^7$ is an aliphatic acyl group such as formyl and trifluoroacetyl, it is removed under basic conditions.

The base employed here includes alkali metal hydroxides such as sodium hydroxide, potassium hydroxide and lithium hydroxide; and alkali metal carbonates such as sodium carbonate and potassium carbonate, preferably the alkali metal hydroxides.

The present reaction is preferably carried out in an inert solvent, for example, alcohols such as methanol and ethanol; water; ethers such as tetrahydrofuran and dioxane; or a mixture thereof, more preferably the alcohols.

The reaction temperature is 0 to 100° C., preferably 10 to 80° C.

While the reaction time varies depending on the reagent, reaction temperature and solvent, it is usually 30 minutes to 24 hours, preferably 1 to 16 hours.

In the case where $R^6$ and $R^7$ taken together represent a protecting group of the amino group, the protecting group includes a phthaloyl group, and it can be removed by treatment with hydrazines or primary amines.

The hydrazines employed here include, for example hydrazine, methylhydrazine and phenylhydrazine, preferably hydrazine. Further, the primary amines employable here include, for example, methylamine, ethylamine, propylamine, butylamine, isobutylamine, pentylamine and hexylamine, preferably propylamine and butylamine.

The present reaction is carried out in an inert solvent, for example, alcohols such as methanol and ethanol; ethers such as tetrahydrofuran and dioxane; halogenated hydrocarbons such as methylene chloride and chloroform; or a mixture of them, preferably the alcohols.

The reaction temperature is 0 to 100° C., preferably 10 to 80° C.

While the reaction time varies depending on the reaction reagent, reaction temperature and solvent, it is usually 30 minutes to 24 hours, preferably one hour to 16 hours.

Step C3

Step C3 is to prepare a compound of formula (IV) and is carried out by dehydration-condensation reaction of an amino compound of formula (IX) with a carbonyl compound of formula (X).

The present step is carried out in an inert solvent. The inert solvent employed here is not particularly limited so long as it has no adverse effect on the reaction. Examples of suitable solvents include hydrocarbons such as hexane, benzene and xylene; halogenated hydrocarbons such as methylene chloride, chloroform and 1,2-dichloroethane; ethers such as tetrahydrofuran and dioxane; alcohols such as methanol and ethanol; esters such as ethyl acetate and butyl acetate; and amides such as dimethylformamide and dimethylacetamide, preferably the hydrocarbons, halogenated hydrocarbons, ethers and alcohols.

The reaction temperature is 0 to 120° C. preferably 10 to 100° C.

While the reaction time varies depending on the reaction reagent, reaction temperature and solvent, it is usually 30 minutes to 24 hours, preferably 1 hour to 16 hours.

Step C4

Step C4 is to prepare a compound of formula (I). In the case where $W^1$ is an amino group which is protected by the usual protecting group such as t-butoxycarbonyl, if desired, after the amino protecting group is removed, a compound of formula (IV) is converted to a compound of formula (I) by removing the ester residual group. In the reaction, removal of the amino protecting group is carried out in a similar manner to that described in Step A1 of Method A and removal of the ester residue is carried out in a similar manner to that described in Step A2 of Method A.

A compound of formula (II) which is a starting material in Method A, can be prepared, for example, according to Method D.

(Method D)

$$X-\underset{\underset{N-OH}{\parallel}}{\overset{R^1}{C}} + Br-R^2-O-\text{(THP)} \xrightarrow{\text{Step D1}}$$

(V)    (XI)

$$X-\underset{\underset{N-O-R^2-O-\text{(THP)}}{\parallel}}{\overset{R^1}{C}} \xrightarrow{\text{Step D2}}$$

(XII)

$$X-\underset{\underset{N-O-R^2-OH}{\parallel}}{\overset{R^1}{C}} \xrightarrow{\text{Step D3}} X-\underset{\underset{N-O-R^2-U^1}{\parallel}}{\overset{R^1}{C}}$$

(IIa)    (IIb)

Wherein $R^1$, $R^2$ and X have the same meanings as defined above, $U^1$ represents a halogen atom or a group of the formula: $-O-SO_2-R^5$ (wherein $R^5$ has the same meaning as defined above) in U.

The compound of formula (IIa) prepared according to the present process is a compound of formula (II) in which U is a hydroxyl group. The compound of formula (IIb) is a compound of formula (II) in which U is a halogen atom or a group of formula $-O-SO_2-R^5$ (wherein $R^5$ has the same meaning as defined above).

Step D1

Step D1 is to prepare a compound of formula (XII) and the compound is prepared by reaction of a compound of formula (V) with a compound of formula (XI).

The present reaction is carried out in a similar manner to that already described in Step A1 of Method A, where U is a halogen atom or a group of formula: $-O-SO_2-R^5$ (wherein $R^5$ has the same meaning as defined above).

Step D2

Step D2 is to prepare a compound of formula (IIa) and the compound is prepared by removal of the tetrahydropyranyl group of the compound of formula (XII).

The present reaction is carried out in a similar manner to that described on deprotection by the acid already described in Step A2 of Method A.

Step D3

Step D3 is to prepare a compound of formula (IIb) and the compound is prepared by converting the hydroxyl group in the compound of formula (IIa) to a halogen atom or a group of formula $-O-SO_2-R^5$ (wherein $R^5$ has the same meaning as defined above).

In the case where $U^1$ in the compound of formula (IIb) is a halogen atom, a compound of formula (II) is prepared by reaction of compound (IIa) with a halogenating agent in a solvent.

The halogenating agent employed includes a thionyl halide such as thionyl chloride and thionyl bromide; a phosphorus pentahalide such as phosphorus pentachloride and phosphorus pentabromide; a phosphorus oxyhalide such as phosphorus oxychloride and phosphorus oxybromide; oxalyl chloride and the like, preferably a thionyl halide and oxalyl chloride.

The inert solvent employed here is not particularly limited so long as it has no adverse effect on the reaction. Examples of suitable solvents include hydrocarbons such as hexane, benzene, toluene and xylene; halogenated hydrocarbons such as methylene chloride, chloroform and 1,2-dichloroethane; ethers such as tetrahydrofuran and dioxane; and esters such as ethyl acetate and butyl acetate, preferably the halogenated hydrocarbons and ethers.

The reaction temperature is −10 to 100° C., preferably 10 to 80° C.

While the reaction time varies depending on the reagent, temperature and solvent, it is usually 30 minutes to 24 hours, preferably 1 hour to 16 hours.

Alternatively, a compound of formula (IIb) is also prepared by reacting a compound of formula (IIa) with a halogenating agent such as tetrahalogenated carbon, e.g. carbon tetrachloride and carbon tetrabromide and N-halogenosuccinimide, e.g. N-bromosuccinimide and N-chlorosuccinimide in the presence of tri-$C_6$–$C_{10}$ aryl or tri-$C_1$–$C_4$ alkylphosphines such as triphenylphosphine and tributylphosphine. The reaction conditions of the present reaction are similar to those in the Mitsunobu reaction described in Step A1 of Process A.

In the case where $U^1$ in the compound of formula (IIa) is a group of formula $-O-SO_2-R^5$ (wherein $R^5$ has the same meaning as defined above), a compound of formula (IIb) is prepared by reacting a compound of formula (IIa) with a compound of formula $R^5-SO_2-Cl$ (wherein $R^5$ has the same meaning as defined above) or a compound of formula $(R^5-SO_2)_2O$ (wherein $R^5$ has the same meaning as defined above) in an inert solvent in the presence of a base.

The base employed includes preferably tertiary amines such as triethylamine, N-methylmorpholine and N,N-diisopropylethylamine.

The inert solvent employed is not particularly limited so long as it has no adverse effect on the reaction. Examples of suitable solvents include hydrocarbons such as hexane, benzene, toluene and xylene; halogenated hydrocarbons such as methylene chloride, chloroform and 1,2-dichloroethane; ethers such as tetrahydrofuran and dioxane; and esters such as ethyl acetate and butyl acetate, preferably the halogenated hydrocarbons and ethers.

The reaction temperature is −10 to 100° C., preferably 0 to 60° C.

While the reaction time varies depending on the reagent, temperature and solvent, it is usually 30 minutes to 24 hours, preferably 1 to 16 hours.

Further, compounds of formula (V) which are the starting compounds are known compounds or are easily prepared according to a known method. The compounds are easily prepared by a dehydration-condensation reaction of the corresponding carbonyl compounds with hydroxylamine, (for example, Shin-jikken kagaku koza, 14(III), P. 1325, compiled by The Chemical Society of Japan, published by Maruzen K.K.; "Comprehensive Organic Functional Group Transformations", 3, P. 425, authors: A. R. Katritzby et al., published by Pergamon (United Kingdom), 1995, etc.).

Desired compounds obtained in Method A to D can be purified, if necessary, by a conventional method, for example, by column chromatography, recrystallization, reprecipitation and the like, after each reaction. The purified product can be obtained, for example, by appropriately neutralizing the reaction mixture, adding a solvent to the reaction mixture to extract it, evaporating the solvent from the extract, and purifying the residue by column chromatography using silica gel.

The phenylalkylcarboxylic acid derivatives of formula (I) of the present invention, the pharmacological acceptable salts thereof or the pharmacological acceptable esters thereof are used as therapeutic or preventive agents, especially as therapeutic agents, for a lot of disease. Examples of such diseases are those caused by insulin resistance such as hyperlipemia, hyperglycemia, obesity, the state of impaired glucose tolerance (IGT), the state of insulin resistant non-IGT (NGT), hypertension, osteoporosis, pancreatitis, cachexia, fatty liver, diabetic complication (e.g., retinopathy, nephropathy, cataract, coronary artery diseases and the like), arteriosclerosis, cataract, gestational diabetes mellitus (GDM) and polycystic ovary syndrome (PCOS), inflammatory diseases (e.g., arthrosteitis, pain, pyrexia, inflammatory enteritis, etc.), acne, sunburn, psoriasis, eczema, allergic diseases, asthma, GI ulcer, cardiovascular diseases (e.g., ischemic heart diseases, etc.), cell injury induced by atherosclerosis and ischemic diseases (e.g., brain injury caused by apoplexy), autoimmune diseases (e.g., systemic lupus erythematosas, rheumatoid arthritis, juvenile rheumatoid arthritis, Sjogren's syndrome, diffuse scleroderma, mixed connective-tissue disease, dermatomyositis, Hashimoto's disease, primary myxedema, thyrotoxicosis, pernicious anemia, ulcerative colitis, autoimmune atrophic gastritis, idiopathic Addison disease, male sterility, Goodpasture's syndrome, acute progressive glomerular nephritis, myasthenia gravis, polymyositis, pemphigus vulgaris, bullous pemphigoid, sympathetic ophthalmitis, multiple sclerosis, autoimmune hemolytic anemia, idiopathic thrombocytopenic purpura, postmyocardial infarction syndrome, rheumatic fever, lupoid hepatitis, primary biliary cirrhosis, Behcet's disease, CREST syndrome, etc), preferably, therapeutic or preventive agents (particularly therapeutic agents) for hyperglycemia, osteogenesis, pancreatitis or rheumatism, particularly hyperglycemia, pancreatitis or rheumatism.

The phenylalkylcarboxylic acid derivatives of formula (I), the pharmacologically acceptable salts or the esters thereof are administered in various forms. The administration form is not particularly limited and is determined depending on the various kinds of preparation forms, age, sex, other conditions of the patient and the like. For example, the compound is orally administered in the form of tablets, pills, powders, granules, syrups, solutions, suspensions, emulsions, granules and capsules. Further, in the case of injections, they are intravenously administered alone or in a mixture with a conventional adjuvant such as glucose and an amino acid, and further, if necessary, it is singly administered intramuscularly, intracutaneously, subcutaneously or intraperitoneally. In the case of suppositories, it is intrarectally administered. Oral administration is preferable.

Various kinds of these preparations can be prepared by mixing a known adjuvant commonly used in known pharmaceutical preparation field such as excipients, binders, disintegrating agents, lubricants, solubilizers, flavors and coating agents with a component of formula (I) according to a conventional method.

When the present compound is molded into the form of tablets, substances conventionally known in this field as carriers can be widely used. Examples of such substances include excipients such as lactose, sucrose, sodium chloride, glucose, urea, starch, calcium carbonate, kaolin, crystalline cellulose and silicic acid; binders such as water, ethanol, propanol, single syrup, glucose solution, starch solution, gelatin solution, carboxymethyl cellulose, shellac, methyl cellulose, potassium phosphate, and polyvinylpyrrolidone; disintegrants such as dry search, sodium alginate, agar powder, laminaran powder, sodium hydrogencarbonate, calcium carbonate, polyoxyethylenesorbitan fatty acid ester, sodium lauryl sulfate, stearic acid monoglyceride, starch and lactose; disintegration inhibiting agents such as sucrose, stearic acid, cacao butter and hydrogenated oil; absorption accelerating agents such as quaternary ammonium base and sodium lauryl sulfate; humectants such as glycerine and starch; adsorbing agents such as starch, lactose, kaolin, bentonite and colloidal silicic acid; and lubricants such as purified talc, stearate, boric acid powder and polyethylene glycol. Further, the tablets can be formed, if necessary, into such tablets as to be applied with a coating film, for example, a sugar coating tablet, a gelatin coating tablet, an enteric coated tablet, a film coating tablet, a double layer tablet or a multilayer tablet.

When the present compound is molded into the form of pills, those conventionally known in this field as a carrier can be widely used, and include, for example, excipients such as glucose, lactose, starch, cacao butter, hydrogenated vegetable oil, kaolin and talc; binders such as gum arabic powder, tragacanth powder, gelatin and ethanol; and disintegrating agents such as laminaran and agar. When the present compound is molded into the form of suppositories, those conventionally known in this field as a carrier can be widely used, and include, for example, polyethylene glycol, cacao butter, higher alcohols, esters of higher alcohol, gelatin and semi-synthetic glyceride.

In the case where the present compound is prepared as an injection, it is preferable that the solution and suspension are sterilized and are isotonic to blood. When the present compound is formulated into such solutions, emulsions and suspensions, all substances conventionally used in this field as diluents can be used, and include, for example, water, ethyl alcohol, propylene glycol, ethoxylated isostearyl alcohol, polyoxylated isostearyl alcohol and polyoxyethylenesorbitan fatty acid ester. Incidentally, in this case, a sufficient amount of NaCl, glucose or glycerine to prepare the isotonic solution may be contained in pharmaceutical preparations. Further, common solubility improvers, buffers and soothing agents may be also added thereto.

Further, coloring agents, preservatives, perfumes, flavors, sweeteners and other pharmaceuticals may be contained therein, if necessary.

The amount of the active ingredients contained in the above-mentioned pharmaceutical formulations is not particularly limited and appropriately selected in a wide range, and it is appropriate that the content is usually from 1 to 70% by weight in all compositions, preferably from 1 to 30% by weight.

The dose will vary depending on the condition of the patient, age, body weight, the administration method and the form of the formulation. The dosage is usually 0.001 mg (preferably 0.01 mg, more preferably 0.1 mg) as a lower limit and 2,000 mg (preferably 200 mg, more preferably 20 mg) as an upper limit once to several times per day for an adult.

BEST MODE FOR CARRYING OUT THE INVENTION

In the following, the present invention will be described in more detail by way of Examples, Reference examples, Test example and Formulation examples, but the present invention is not limited thereto.

Example 1

Ethyl 2-ethoxy-3-[4-[2-[[1-[4-(2-pyridyl)phenyl] ethylidene]aminoxy]ethoxy]phenyl]propionate (ethyl ester of Exemplification No.2-35 compound)

49 mg of sodium hydride (55% oil suspension) was added to a mixture of 242 mg of ethyl 2-ethoxy-3-(4-hydroxyphenyl)propionate in 4 ml of N,N-dimethylformamide and 2 ml of toluene, and the mixture was stirred at room temperature for 30 minutes.

A solution of 340 mg of 4'-(2-pyridyl)acetophenoneoxime O-2-(methanesulfonyloxy)ethyl ether obtained in Reference example 2 in 3 ml of N,N-dimethylformamide was added dropwise to the reaction mixture, and the resulting mixture was stirred at 80° C. for 3 hours. After the reaction, ethyl acetate and water were added to the reaction mixture, the ethyl acetate layer was separated, dried over anhydrous magnesium sulfate and concentrated under reduced pressure. The residue was subjected to silica gel column chromatography (ethyl acetate:hexane=3:7) to obtain 373 mg of the desired compound as a syrup, which soon crystallized.

1) m.p. 59–61° C.

2) $^1$H-NMR spectrum: δ ppm;

$^1$H-NMR spectrum (270 MHz) determined using TMS (tetramethylsilane) as the internal standard in deuterated chloroform was as follows:

1.16 (3H, t, J=7 Hz), 1.23 (3H, t, J=7 Hz), 2.28 (3H, s), 2.95 (2H, d, J=6.5 Hz), 3.29–3.40 (1H, m), 3.54–3.65 (1H, m), 3.97 (1H, t, J=6.5 Hz), 4.17 (2H, q, J=7 Hz), 4.28 (2H, t, J=5 Hz), 4.55 (2H, t, J=5 Hz), 6.88 (2H, d, J=8.5 Hz), 7.16 (2H, d, J=8. Hz), 7.22–7.27 (1H, m), 7.75–7.80 (2H, m), 7.76 (2H, d, J=8.5 Hz), 8.01 (2H, d, J=8.5 Hz), 8.70 (1H, d, J=5 Hz).

Example 2

2-Ethoxy-3-[4-[2-[[1-[4-(2-pyridyl)phenyl] ethylidene]aminoxy]ethoxy]phenyl]propionic acid (Exemplification No. 2-35 compound.)

1.30 ml of a 1N aqueous sodium hydroxide solution was added to a solution of 310 mg of ethyl 2-ethoxy-3-[4-[2-[[1-[4-(2-pyridyl)phenyl]ethylidene]aminoxy]ethoxy] phenyl]propionate obtained in Example 1 in 5 ml of ethanol, and the mixture was stirred at room temperature for 1.5 hours. After the reaction, the ethanol was evaporated under reduced pressure, and the pH of the mixture was adjusted to a value of 3 with 1N hydrochloric acid. The reaction mixture thus obtained was extracted with ethyl acetate, and the extract was dried over anhydrous magnesium sulfate and concentrated under reduced pressure. The crystalline crude product thus obtained was washed with isopropyl ether and hexane to obtain 232 mg of the desired compound.

1) m.p. 133–135° C.

2) $^1$H-NMR spectrum: δ ppm:

$^1$H-NMR spectrum (270 MHz) determined using TMS (tetramethylsilane) as the internal standard in deuterated chloroform was as follows:

1.18 (3H, t, J=7 Hz), 2.28 (3H, s), 2.95 (1H, d, d, J=7.5, 14 Hz), 3.08 (1H, d, d, J=4.5, 14 Hz), 3.39–3.50 (1H, m), 3.55–3.66 (1H, m), 4.04 (1H, d, d, J=4.5, 7.5 Hz), 4.29 (2H, t, J=5 Hz), 4.56 (2H, t, J=5 Hz), 6.89 (2H, d, J=8.5 Hz), 7.17 (2H, d, J=8.5 Hz), 7.25–7.30 (1H, m), 7.74 (2H, d, J=8.5 Hz), 7.76–7.80 (2H, m), 7.96 (2H, d, J=8.5 Hz), 8.72 (1H, d, J=4.5 Hz).

Example 3

Methyl 2-phenylthio-3-[4-[2-[[1-[4-(2-pyridyl) phenyl]ethylidene]aminoxy]ethoxy]phenyl] propionate (methyl ester of Exemplification No. 31-35 compound)

3.3 ml of a solution of 222 mg of diethyl azodicarboxylate in toluene was added dropwise to a solution of 256 mg of 2-[[1-[4-(2-pyridyl)phenyl]ethylidene]aminoxy]ethanol obtained in Reference example 1, 288 mg of methyl 3-(4-hydroxyphenyl)-2-(phenylthio)propionate obtained in Reference example 7 and 289 mg of triphenylphosphine in 5 ml of tetrahydrofuran. The mixture was stirred at room temperature for 18 hours and the reaction mixture was concentrated. The residue was subjected twice to silica gel column chromatography (ethyl acetate:hexane=1:2 and ethyl acetate:benzene=1:4) to obtain 366 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

2.27 (3H, s), 3.00 (1H, d, d, J=6, 14 Hz), 3.14 (1H, d, d, J=9, 14 Hz), 3.58 (3H, s), 3.86 (1H, d, d, J=6, 9 Hz), 4.27 (2H, t, J=5 Hz), 4.55 (2H, t, J=5 Hz), 6.87 (2H, d, J=8.5 Hz), 7.10 (2H, d, J=8.5 Hz), 7.22–7.34 (4H, m), 7.41–7.45 (2H, m), 7.72–7.80 (2H, m), 7.76 (2H, d, J=8.5 Hz), 8.01 (2H, d, J=8.5 Hz), 8.71 (1H, d, J=4.5 Hz).

Example 4

2-Phenylthio-3-[4-[2-[[1-[4-(2-pyridyl)phenyl] ethylidene]aminoxy]ethoxy]phenyl]propionic acid (Exemplification No. 31-35 compound)

2.00 ml of a 1N aqueous sodium hydroxide solution was added to a mixture of 350 mg of methyl 2-phenylthio-3-[4-[2-[[1-[4(2-pyridyl)phenyl]ethylidene]aminoxy]ethoxy] phenyl]propionate obtained in Example 3, 3 ml of methanol and 2 ml of dioxane, and the mixture was stirred at 50° C. for 4 hours. After the reaction, the reaction mixture was concentrated and diluted with water. Then, the pH of the reaction mixture was adjusted to a value of 3 with 1N hydrochloric acid and extracted with ethyl acetate. The extract was dried over anhydrous magnesium sulfate and concentrated to obtain 324 mg of the desired compound as a foamy solid.

1) $^1$H-NMR spectrum: δ ppm:

$^1$H-NMR spectrum (270 MHz) determined using TMS (tetramethylsilane) as the internal standard in deuterated chloroform was as follows:

2.24 (3H, s), 3.01 (1H, d, d, J=6, 14 Hz), 3.15 (1H, d, d, J=9.5, 14 Hz), 3.87 (1H, d, d, J=6, 9.5 Hz), 4.30 (2H, t, J=5

Hz), 4.54 (2H, t, J=5 Hz), 6.87 (2H, d, J=8.5 Hz), 7.13 (2H, d, J=8.5 Hz), 7.23–7.32 (4H, m), 7.43–7.49 (2H, m), 7.64 (2H, d, J=8.5 Hz), 7.68–7.80 (2H, m), 7.85 (2H, d, J=8.5 Hz), 8.66 (1H, d, J=5.5 Hz).

Example 5

Ethyl 2-phenylamino-3-[4-[2-[[1-[4-(2-pyridyl) phenyl]ethylidene]aminoxy]ethoxy]phenyl] propionate (ethyl ester of Exemplification No. 32- 35 compound)

Reaction and post-treatment were carried out according to Example 3 using 256 mg of 2-[[1-[4-(2-pyridyl)phenyl] ethylidene]aminoxy]ethanol obtained in Reference example 1, 285 mg of ethyl 3-(4-hydroxyphenyl)-2-(phenylamino) propionate obtained in Reference example 5, 289 mg of triphenylphosphine and 222 mg of diethyl azodicarboxylate to obtain 375 mg of the desired compound as crystals.

1) m.p. 140° C.

2) $^1$H-NMR spectrum: δ ppm:

$^1$H-NMR spectrum (270 MHz) determined using TMS (tetramethylsilane) as the internal standard in deuterated chloroform was as follows:

1.19 (3H, t, J=7 Hz), 2.28 (3H, s), 3.00–3.14 (2H, m), 4.13 (,2H, q, J=7 Hz), 4.15 (1H, brs), 4.26–4.34 (3H, m), 4.55 (2H, t, J=5 Hz), 6.60 (2H, d, J=8.5 Hz), 6.73 (1H, t, J=7.5 Hz), 6.88 (2H, d, J=8.5 Hz), 7.09 (2H, d, J=8.5 Hz), 7.13–7.27 (3H, m), 7.75–7.78 (2H, m), 7.76 (2H, d, J=8.5 Hz), 8.01 (2H, d, J=8.5 Hz), 8.71 (1H, d, J=4.5 Hz).

Example 6

2-Phenylamino-3-[4-[2-[[1-[4-(2-pyridyl)phenyl] ethylidene]aminoxy]ethoxy]phenyl]propionic acid (Exemplification No. 32-35 compound)

The reaction was carried out according to Example 4 using 260 mg of ethyl 2-phenylamino-3-[4-[2-[[1-[4-(2-pyridyl)phenyl]ethylidene]aminoxy]ethoxy]phenyl] propionate obtained in Example 5 and 1.00 ml of a 1N aqueous sodium hydroxide solution. After the reaction, the reaction mixture was concentrated and diluted with water. The pH of the reaction mixture was adjusted to a value of 4 with 1N hydrochloric acid, and precipitate was obtained by filtration. The precipitate was washed with water and isopropyl ether to obtain 224 mg of the desired compound.

1) m.p. 149–152° C.

2) $^1$H-NMR spectrum: δ ppm:

$^1$H-NMR spectrum (270 MHz) determined using TMS (tetramethylsilane) as the internal standard in deuterated chloroform was as follows:

2.27 (3H, s), 3.04 (1H, d, d, J=6.5, 14 Hz), 3.17 (1H, d, d, J=5.5, 14 Hz), 4.25–4.30 (3H, m), 4.54 (2H, t, J=5 Hz), 6.60 (2H, d, J=8 Hz), 6.69 (1H, d, J=7.5 Hz), 6.87 (2H, d, J=8.5 Hz), 7.12–7.17 (4H, m), 7.25–7.30 (1H, m), 7.76 (2H, d, J=8.5 Hz), 7.77–7.83 (2H, m), 8.01 (2H, d, J=8.5 Hz), 8.71 (1H, d, J=4.5 Hz).

Example 7

Ethyl 2-(N,N-diethylamino)-3-[4-[2-[[1-[4-(2-pyridyl)phenyl]ethylidene]aminoxy]ethoxy]phenyl] propionate (ethyl ester of Exemplification No. 47- 35 compound)

Reaction and post-treatment were carried out according to Example 1 using 337 mg of 4'-(2-pyridyl) acetophenoneoxime O-2-(methanesulfonyloxy)ethyl ether obtained in Reference example 2, 243 mg of ethyl 2-(N,N-diethylamino)-3-(4-hydroxyphenyl)propionate obtained in Reference example 9 and 44 mg of sodium hydride (55% oil suspension) to obtain 481 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.02 (6H, t, J=7 Hz), 1.16 (3H, t, J=7 Hz), 2.28 (3H, s), 2.52 (2H, sextet, J=7 Hz), 2.78 (2H, sextet, J=7 Hz), 2.80 (1H, d, d, J=6, 13.5 Hz), 3.01 (1H, d, d, J=9, 13.5 Hz), 3.56 (1H, d, d, J=6, 9 Hz), 4.00–4.14 (2H, m), 4.27 (2H, t, J=5 Hz), 4.55 (2H, t, J=5 Hz), 6.86 (2H, d, J=8.5 Hz), 7.12 (2H, d, J=8.5 Hz), 7.22–7.27 (1H, m), 7.75–7.78 (4H, m), 8.01 (2H, d, J=8.5 Hz), 8.70 (1H, d, J=4.5 Hz).

Example 8

2-(N,N-Diethylamino)-3-[4-[2-[[1-[4-(2-pyridyl) phenyl]ethylidene]aminoxy]ethoxy]phenyl]propionic acid (Exemplification No. 47-35 compound)

2.75 ml of a 1N aqueous sodium hydroxide solution was added to a mixture of 474 mg of ethyl 2-(N,N-diethylamino)-3-[4-[2-[[1-[4-(2-pyridyl)phenyl]ethylidene] aminoxy]ethoxy]phenyl]propionate obtained in Example 7, 5 ml of methanol and 3 ml of dioxane. The resulting mixture was stirred at 50° C. for 18 hours. After the reaction, methanol and dioxane were evaporated under reduced pressure, and then the residue was diluted with water. The pH of the mixture was adjusted to a value of 4 by addition of 2.75 ml of 1N hydrochloric acid, and precipitate was collected by filtration. The precipitate was washed with water and isopropyl ether to obtain 440 mg of the desired compound.

1) m.p. 157–159° C.

2) $^1$H-NMR spectrum: δ ppm:

$^1$H-NMR spectrum (270 MHz) determined using TMS (tetramethylsilane) as the internal standard in deuterated dimethyl sulfoxide was as follows:

0.96 (6H, t, J=7 Hz), 2.23 (3H, s), 2.54–2.78 (5H, m), 2.96 (1H, d, d, J=7.5, 14 Hz), 3.48 (1H, t, J=7 Hz), 4.25 (2H, t, J=5 Hz), 4.46 (2H, t, J=5 Hz), 6.88 (2H, d, J=8.5 Hz), 7.16 (2H, d, J=8.5 Hz), 7.35–7.40 (1H, m), 7.80 (2H, d, J=8.5 Hz), 7.90 (1H, d, t, J=1.5, 7.5 Hz), 8.01 (1H, d, J=8 Hz), 8.13 (2H, d, J=8.5 Hz), 8.68 (1H d, J=4 Hz).

Example 9

Ethyl 3-[4-[2-[[1-(4-biphenylyl)ethylidene]aminoxy] ethoxy]phenyl]-2-(phenylamino)propionate (ethyl ester of Exemplification No. 32-4 compound)

Reaction and post-treatment were carried out according to Example 3 using 179 mg of 2-[[1-(4-biphenylyl)ethylidene] aminoxy]ethanol obtained in Reference example 3, 200 mg of ethyl 3-(4-hydroxyphenyl)-2-(phenylamino)propionate obtained in Reference example 5, 183 mg of triphenylphosphine and 122 mg of diethyl azodicarboxylate to obtain 282 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.19 (3H, t, J=7 Hz), 2.27 (3H, s), 3.00–3.14 (2H, m), 4.12 (2H, d, q, J=1, 7 Hz), 4.25–4.33 (3H, m), 4.54 (2H, t, J=5

Hz), 6.60 (2H, d, J=8.5 Hz), 6.73 (1H, t, J=7.5 Hz), 6.88 (2H, d, J=8.5 Hz), 7.08 (2H, d, J=8.5 Hz), 7.16 (2H, t, J=7.5 Hz), 7.33–7.48 (3H, m), 7.58–7.61 (4H, m), 7.70–7.74 (2H, m).

Example 10

3-[4-[2-[[1-(4-Biphenylyl)ethylidene]aminoxy]ethoxy]phenyl]-2-(phenylamino)propionic acid (Exemplification No. 32-4 compound)

A solution of 72 mg of lithium hydroxide monohydrate and 3 ml of water was added to a solution of 282 mg of ethyl 3-[4-[2-[[1-(4-biphenylyl)ethylidene]aminoxy]ethoxy]phenyl]-2-(phenylamino)propionate obtained in Example 9 in 3 ml of dioxane. The mixture was stirred at 60° C. for one hour. After the reaction, the reaction mixture was concentrated and diluted with water. Then, 1.71 ml of 1N hydrochloric acid was added to the resulting mixture, and the product thus obtained was extracted with a large amount of hot ethyl acetate. The extract was concentrated to about 5 ml, and 229 mg of the desired compound was obtained by filtration.

1) m.p. 184–187° C.

2) $^1$H-NMR spectrum: δ ppm:

$^1$H-NMR spectrum (270 MHz) determined using TMS (tetramethylsilane) as the internal standard in deuterated dimethyl sulfoxide was as follows:

2.20 (3H, s), 2.90 (1H, d, d, J=8, 14 Hz), 3.00 (1H, d, d, J=6, 14 Hz), 4.05 (2H, d, d, J=6, 8 Hz), 4.25 (2H, t, J=5 Hz), 4.46 (2H, t, J=5 Hz), 6.51–6.58 (3H, m), 6.89 (2H, d, J=8.5 Hz), 7.05 (2H, t, J=8 Hz), 7.21 (2H, t, J=8.5 Hz), 7.36–7.51 (3H, m), 7.68–7.77 (6H, m).

Example 11

Ethyl 3-[4-[2-[[1-(4-biphenylyl)ethylidene]aminoxy]ethoxy]phenyl]-2-(N-phenyl-N-ethylamino) propionate (ethyl ester of Exemplification No. 49-4 compound)

Reaction and post-treatment were carried out according to Example 3 using 230 mg of 2-[[1-(4-biphenylyl)ethylidene]aminoxy]ethanol obtained in Reference example 3, 300 mg of ethyl 3-(4-hydroxyphenyl)-2-(N-phenyl-N-ethylamino)propionate obtained in Reference example 6, 236 mg of triphenylphosphine and 157 mg of diethyl azodicarboxylate to obtain 353 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.08 (3H, t, J=7 Hz), 1.15 (3H, t, J=7 Hz), 2.27 (3H, s), 3.05 (1H, d, d, J=7.5, 14 Hz), 3.24–3.46 (3H, m), 4.09 (2H, q, J=7 Hz), 4.26 (2H, t, J=5 Hz), 4.39 (1H, t, J=7.5 Hz), 4.53 (2H, t, J=5 Hz), 6.66–6.76 (3H, m), 6.86 (2H, d, J=8.5 Hz), 7.10 (2H, d, J=8.5 Hz), 7.18–7.25 (2H, m), 7.33–7.38 (1H, m), 7.45 (2H, d, J=7.5 Hz), 7.58–7.61 (4H, m), 7.72 (2H, d, J=8.5 Hz).

Example 12

3-[4-[2-[[1-(4-Biphenylyl)ethylidene]aminoxy]ethoxy]phenyl]-2-(N-phenyl-N-ethylamino)propionic acid hydrochloride (hydrochloride of Exemplification No. 49-4 compound)

Reaction and post-treatment were carried out according to Example 4 using 353 mg of ethyl 3-[4-[2-[[1-(4-biphenylyl)ethylidene]aminoxy]ethoxy]phenyl]-2-(N-phenyl-N-ethylamino)propionate obtained in Example 11 and 2 ml of a 1N aqueous sodium hydroxide solution. The product thus obtained was further treated with a 4N hydrogen chloride-dioxane solution to obtain 280 mg of hydrochloride of the desired compound as an amorphous powder.

1) $^1$H-NMR spectrum: δ ppm:

$^1$H-NMR spectrum (270 MHz) determined using TMS (tetramethylsilane) as the internal standard in deuterated dimethyl sulfoxide was as follows:

0.94 (3H, t, J=7 Hz), 2.21 (3H, s), 3.02 (1H, d, d, J=9, 14 H,), 3.17 (1H, d, d, J=6, 14 Hz), 3.20–3.40 (2H, m), 4.23 (2H, t, J=5 Hz), 4.45 (2H, t, J=5 Hz), 4.53 (1H, d, d, J=6, 9 Hz), 6.61–6.72 (3H, m), 6.86 (2H, d, J=8.5 Hz), 7.12–7.17 (4H, m), 7.36–7.51 (3H, m), 7.69–7.78 (6H, m).

Example 13

Ethyl 3-[4-[2-[[1-[4-biphenylyl)ethylidene]aminoxy]ethoxy]phenyl]-2-pyrrolylpropionate (ethyl ester of Exemplification No. compound. 50-4)

Reaction and post-treatment were carried out according to Example 1 using 333 mg of 2-[[1-(4-biphenylyl)ethylidene]aminoxy]ethyl methanesulfonate obtained in Reference example 4, 260 mg of ethyl 3-(4-hydroxyphenyl)-2-pyrrolylpropionate obtained in Reference example 8 and 50 mg of sodium hydride (55% oil suspension) to obtain 440 mg of the desired compound as a gum.

1) $^1$H-NMR spectrum: δ ppm:

$^1$H-NMR spectrum (270 MHz) determined using TMS (tetramethylsilane) as the internal standard in deuterated chloroform was as follows:

1.20 (3H, t, J=7 Hz), 2.27 (3H, s), 3.19 (1H, d, d, J=8.5, 14 Hz), 3.34 (1H, d d, J=6.5, 14 Hz), 4.17 (2H, q, J=7 Hz), 4.25 (2H, t, J=5 Hz), 4.52 (1H, t, J=5 Hz), 4.68 (1H, d, d, J=6.5, 8.5 Hz), 6.13–6.15 (2H, m), 6.71–6.73 (2H, m), 6.82 (2H, d, J=8.5 Hz), 6.93 (2H, d, J=8.5 Hz), 7.33–7.48 (3H, m), 7.58–7.61 (4H, m), 7.72 (2H, d, J=8.5 Hz).

Example 14

3-[4-[2-[[1-(4-Biphenylyl)ethylidene]aminoxy]ethoxy]phenyl]-2-pyrrolylpropionic acid (Exemplification No. 50-4 compound)

Reaction and post-treatment were carried out according to Example 10 using 167 mg of ethyl 3-[4-[2-[[1-(4-biphenylyl)ethylidene]aminoxy]ethoxy]phenyl]-2-pyrrolylpropionate obtained in Example 13 and 42 mg of lithium hydroxide monohydrate to obtain 135 mg of the desired compound as crystals.

1) m.p. 163–165° C.

2) $^1$H-NMR spectrum: δ ppm:

$^1$H-NMR spectrum (270 MHz) determined using TMS (tetramethylsilane) as the internal standard in deuterated chloroform and a small amount of deuterated dimethyl sulfoxide was as follows:

2.26 (3H, s), 3.17 (1H, d, d, J=9.5, 14 Hz), 3.38 (1H, d, d, J=5.5, 14 Hz), 4.24 (2H, t, J=5 Hz), 4.51 (2H, t, J=5 Hz), 4.67 (1H, d, d, J=5.5, 9.5 Hz), 6.09–6.11 (2H, m), 6.70–6.72 (2H, m), 6.80 (2H, d, J=8.5 Hz), 6.92 (2H, d, J=8.5 Hz), 7.33–7.48 (3H, m), 7.56–7.62 (4H, m), 7.72 (2H, d, J=8.5 Hz).

Example 15

Ethyl 2-ethylamino-3-[4-[2-[[1-[4-(2-pyridyl)phenyl]ethylidene]aminoxy]ethoxy]phenyl]propionate hydrochloride (ethyl ester hydrochloride of Exemplification No. 43-35 compound)

(a) Ethyl 2-N-(t-butoxycarbonyl)ethylamino-3-[4-[2-[[1-[4-(2-pyridyl)phenyl]ethylidene]aminoxy]ethoxy]phenyl]propionate Reaction and post-treatment were carried out according to Example 3 using 256 mg of 2-[[1-[4-(2-pyridyl)phenyl]ethylidene]aminoxy]ethanol obtained in Reference example 1, 337 mg of ethyl 2-N-(t-butoxycarbonyl)ethylamino-3-(4-hydroxyphenyl)propionate obtained in Reference example 10, 289 mg of triphenylphosphine and 556 mg of diisopropyl azodicarboxylate to obtain 320 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

0.92 (3H, t, J=7 Hz), 1.18–1.32 (3H, m), 1.45 (9H, s), 2.29 (3H, s), 2.55–2.85 (1H, m), 3.00–3.40 (3H, m), 3.85–4.25 (3H, m), 4.28 (2H, t, J=5 Hz), 4.55 (2H, t, J=5 Hz), 6.88 (2H, d, J=8.5 Hz), 7.05–7.14 (2H, brd, J=8.5 Hz), 7.22–7.26 (1H, m), 7.75–7.82 (4H, m), 8.01 (2H, d, J=8.5 Hz), 8.71 (1H, d, J=5 Hz).

(b) Ethyl 2-ethylamino-3-[4-[2-[[1-[4-(2-pyridyl)phenyl]ethylidene]aminoxy]ethoxy]phenyl]propionate hydrochloride 312 mg of ethyl 2-N-(t-butoxycarbonyl)ethylamino-3-[4-[2-[[1-[4-(2-pyridyl)phenyl]ethylidene]aminoxy]ethoxy]phenyl]-propionate obtained in Example 15(a) was dissolved in 5 ml of a 4N hydrogen chloride-dioxane solution, and the mixture was stirred at room temperature for 2 hours. After the reaction, the reaction mixture was concentrated. The residue was powdered in ethyl ether and the powder was collected by filtration to obtain 273 mg of hygroscopic hydrochloride of the desired compound.

1) $^1$H-NMR spectrum: δ ppm:

$^1$H-NMR spectrum (270 MHz) determined using TMS (tetramethylsilane) as the internal standard in deuterated dimethyl sulfoxide was as follows:

1.10 (3H, t, J=7 Hz), 1.24 (3H, t, J=7 Hz), 2.25 (3H, s), 2.95–3.06 (2H, m), 3.39 (1H, q, J=7 Hz), 4.08 (2H, q, J=7 Hz), 4.18–4.22 (1H, m), 4.29 (2H, t, J=5 Hz), 4.50 (2H, t, J=5 Hz), 6.95 (2H, d, J=8.5 Hz), 7.16 (2H, d, J=8.5 Hz), 7.59–7.64 (1H, m), 7.85 (2H, d, J=8.5 Hz), 8.15 (2H, d, J=8.5 Hz), 8.17–8.21 (2H, m), 8.77 (1H, d, J=5 Hz).

Example 16

2-Ethylamino-3-[4-[2-[[1-[4-(2-pyridyl)phenyl]ethylidene]aminoxy]ethoxy]phenyl]propionic acid
(Exemplification No. 43-35 compound)

Reaction was carried out according to Example 2 using 273 mg of ethyl 2-ethylamino-3-[4-[2-[[1-[4-(2-pyridyl)phenyl]ethylidene]aminoxy]ethoxy]phenyl]propionate obtained in Example 15 and 2.4 ml of a 1N aqueous sodium hydroxide solution. When the pH of the reaction mixture thus obtained was adjusted to a value of 4 with 1N hydrochloric acid, the desired compound was obtained as a precipitate. The precipitate was collected by filtration and washed with water to obtain 186 mg of the desired compound.

m.p. 220–222° C. (decomp.).

Example 17

Ethyl 2-methylthio-3-[4-[2-[[1-[4-(2-pyridyl)phenyl]ethylidene]aminoxy]ethoxy]phenyl]propionate
(ethyl ester of Exemplification No. 26-35 compound)

Reaction and post-treatment were carried out according to Example 1 using 1.26 g of 4'-(2-pyridyl)acetophenoneoxime O-2-(methanesulfonyloxy)ethyl ether obtained in Reference example 2, 0.83 g of ethyl 3-(4-hydroxyphenyl)-2-(methylthio)propionate obtained in Reference example 11(b) and 0.17 g of sodium hydride (55% oil suspension) to obtain 1.50 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.22 (3H, t, J=7 Hz), 2.16 (3H, s), 2.28 (3H, s), 2.90 (1H, d, d, J=6.5, 14 Hz), 3.15 (1H, d, d, J=9,14 Hz), 3.40 (1H, d, d, J=6.5, 9 Hz), 4.13 (2H, d, q, J=3, 7 Hz), 4.28 (2H, t, J=5 Hz), 4.55 (2H, t, J=5 Hz), 6.89 (2H, d, J=8.5 Hz), 7.13 (2H, d, J=8.5 Hz), 7.22–7.27 (1H, m), 7.75–7.78 (4H, m), 8.01 (2H, d, J=8.5 Hz), 8.71 (1H, d, J=4.5 Hz).

Example 18

2-Methylthio-3-[4-[2-[[1-[4-(2-pyridyl)phenyl]ethylidene]aminoxy]ethoxy]phenyl]propionic acid
(Exemplification No. 26-35 compound)

5.05 ml of a 1N aqueous sodium hydroxide solution was added to a solution of 1.20 g of ethyl 2-methylthio-3-[4-[2-[[2-[[1-[4-(2-pyridyl)phenyl]ethylidene]aminoxy]ethoxy]phenyl]propionate obtained in Example 17 in 20 ml of ethanol, and the mixture was stirred at 50° C. for 30 minutes. After the reaction, the ethanol was evaporated under reduced pressure, and 5.05 ml of 1N hydrochloric acid was added to the residue thus obtained, followed by extraction of the precipitated product with ethyl acetate. The extract thus obtained was dried over anhydrous magnesium sulfate and evaporated under reduced pressure. The residual powder thus obtained was washed with isopropyl ether to obtain 0.95 g of the desired compound.

1) m.p. 114–118° C.

2) $^1$H-NMR spectrum: δ ppm:

$^1$H-NMR spectrum (270 MHz) determined using TMS (tetramethylsilane) as the internal standard in deuterated chloroform was as follows:

2.22 (3H, s), 2.25 (3H, s), 2.91 (1H, d, d, J=5.5, 14 Hz), 3.18 (1H, d, d, J=10,14 Hz), 3.44 (1H, d, d, J=5.5, 10 Hz), 4.33 (2H, t, J=5.5 Hz), 4.55 (2H, t, J=5.5 Hz), 6.89 (2H, d, J=8.5 Hz), 7.15 (2H, d, J=8.5 Hz), 7.26–7.32 (1H, m), 7.63 (2H, d, J=8.5 Hz), 7.71–7.84 (2H, m), 7.87 (2H, d, J=8.5 Hz), 8.70 (1H, d, J=4.5 Hz).

Example 19

Ethyl 2-(3-phenylpropyl)-3-[4-[2-[[1-[4-(2-pyridyl)phenyl]ethylidene]aminoxy]ethoxy]phenyl]propionate (ethyl ester of Exemplification No. 66-8 compound)

Reaction and post-treatment were carried out according to Example 1 using 1.09 g of 4'-(2-pyridyl)acetophenoneoxime O-2-(methanesulfonyloxy)ethyl ether obtained in Reference example 2, 1.00 g of ethyl 2-(4-hydroxybenzyl)-5-phenylvalerate obtained in Reference example 12(c) and 160 mg of sodium hydride (55% oil suspension)to obtain 1.54 g of the desired compound as crystals.

1) m.p. 53–55° C.

2) $^1$H-NMR spectrum: δ ppm:

$^1$H-NMR spectrum (270 MHz) determined using TMS (tetramethylsilane) as the internal standard in deuterated chloroform was as follows:

1.14 (3H, t, J=7 Hz), 1.49–1.75 (4H, m), 2.28 (3H, s), 2.56–2.71 (4H, m), 2.84 (1H, d, d, J=7.5, 12.5 Hz), 4.05 (2H, q, J=7 Hz), 4.27 (2H, t, J=5 Hz), 4.55 (2H, t, J=5 Hz), 6.86 (2H, d, J=8.5 Hz), 7.05 (2H, d, J=8.5 Hz), 7.12–7.29 (6H, m), 7.75–7.78 (4H, m), 8.01 (2H, d, J=8.5 Hz), 8.70 (1H, d, J=5 Hz).

Example 20

2-(3-Phenylpropyl)-3-[4-[2-[[1-[4-(2-pyridyl)phenyl] ethylidene]aminoxy]ethoxy]phenyl]propionic acid (Exemplification No. 66-8 compound)

0.67 g of potassium hydroxide was added to a solution of 1.20 g of ethyl 2-(3-phenylpropyl)-3-[4-[2-[[1-[4(2-pyridyl) phenyl]ethylidene]aminoxy]ethoxy]phenyl]propionate obtained in Example 19 in 20 ml of ethanol, and the mixture was stirred at 80° C. for 2 hours. After the reaction, the reaction mixture was concentrated. To the residue were added water, ice and ethyl acetate and the pH of the reaction mixture was adjusted to a value of 4 with 3N hydrochloric acid. Then, the ethyl acetate layer was separated. The extract thus obtained was dried over anhydrous magnesium sulfate and then evaporated under reduced pressure to obtain 1.10 g of the desired compound as a gum.

415 mg of the desired compound thus obtained was dissolved in 10 ml of ethanol, and 0.80 ml of a 1N aqueous sodium hydroxide solution was added thereto, followed by concentration of the resulting mixture. The solid thus obtained was washed with ethyl ether to obtain 0.42 g of sodium salt of the desired compound as an amorphous solid.

1) $^1$H-NMR spectrum: δ ppm:

$^1$H-NMR spectrum (270 MHz) measured using TMS (tetramethylsilane) as an internal standard in deuterated dimethyl sulfoxide was as follows:

1.40–1.67 (5H, m), 2.24 (3H, s), 2.36–2.51 (4H, m), 2.83 (2H, d, d, J=7, 13.5 Hz), 4.23 (2H, t, J=4 Hz), 4.48 (2H, t, J=4 Hz), 6.81 (2H, d, J=8.5 Hz), 7.06–7.12 (5H, m), 7.17–7.23 (2H, m), 7.35 (1H, d, d, J=5, 6 Hz), 7.79 (2H, d, J=8.5 Hz), 7.87 (1H, d, t, J=1.5, 8 Hz), 7.97 (1H, d, J=8 Hz), 8.12 (2H, d, J=8.5 Hz), 8.67 (1H, d, J=5 Hz).

Example 21

Ethyl 2-phenoxy-3-[4-[2-[[1-[4-(2-pyridyl)phenyl] ethylidene]aminoxy]ethoxy]phenyl]propionate (ethyl ester of Exemplification No. 68-2 compound)

Reaction and post-treatment were carried out according to Example 1 using 1.18 g of 4'-(2-pyridyl)acetophenoneoxime O-2-(methanesulfonyloxy)ethyl ether obtained in Reference example 2, 1.28 g of ethyl 3-(4-hydroxyphenyl)-2-phenoxypropionate obtained in Reference example 13(c) and 154 mg of sodium hydride (55% oil suspension) to obtain 1.28 g of the desired compound as a syrup.

1) $^1$H-NMR spectrum: δ ppm:

$^1$H-NMR spectrum (270 MHz) measured using TMS (tetramethylsilane) as an internal standard in deuterated chloroform was as follows:

1.19 (3H, t, J=7 Hz), 2.26 (3H, s), 3.17–3.20 (2H,m), 4.17 (2H, q, J=7 Hz), 4.27 (2H, t, J=5 Hz), 4.54 (2H, t, J=5 Hz), 4.74 (1H, d, d, J=5.5, 6.5 Hz), 6.82–6.96 (5H, m), 7.21–7.26 (5H, m), 7.74–7.77 (4H, m), 8.01 (2H, d, J=8.5 Hz), 8.70 (1H, d, J=5 Hz).

Example 22

2-Phenoxy-3-[4-[2-[[1-[4-(2-pyridyl)phenyl] ethylidene]aminoxy]ethoxy]phenyl]propionic acid (Exemplification No. 68-2 compound)

Reaction and post-treatment were carried out according to Example 18 using 1.28 g of ethyl 2-phenoxy-3-[4-[2-[[1-[4-(2-pyridyl)phenyl]ethylidene]aminoxy]ethoxy]phenyl] propionate obtained in Example 20 and 7.00 ml of a 1N aqueous sodium hydroxide solution to obtain 1.13 g of the desired compound as a crystalline powder.

1)m.p. 145–148° C.

2) $^1$H-NMR spectrum: δ ppm:

$^1$H-NMR spectrum (270 MHz) determined using TMS (tetramethylsilane) as the internal standard in deuterated chloroform was as follows:

2.25 (3H, s), 3.22 (2H, d, J=6 Hz), 4.29 (2H, t, J=4.5 Hz), 4.54 (2H, t, J=4.5 Hz), 4.81 (1H, t, J=6 Hz), 6.86–6.97 (5H, m), 7.21–7.31 (5H, m), 7.67–7.89 (6H, m), 8.72 (1H, d, J=5 Hz).

Example 23

Ethyl 2-butyl-3-[4-[2-[[1-[4-(2-pyridyl)phenyl] ethylidene]aminoxy]ethoxy]phenyl]propionate (ethyl ester of Exemplification No. 67-8 compound)

Reaction and post-treatment were carried out according to Example 1 using 1.35 g of 4'-(2-pyridyl)acetophenoneoxime O-2-(methanesulfonyloxy)ethyl ether obtained in Reference example 2, 1.00 g of ethyl 2-(4-hydroxybenzyl)caproate obtained in Reference example 14(c) and 200 mg of sodium hydride (55% oil suspension) to obtain 0.94 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

0.87 (3H, t, J=7 Hz), 1.16 (3H, t, J=7 Hz), 1.20–1.40 (4H, m), 1.40–1.70 (2H, m), 2.28 (3H, s), 2.51–2.72 (2H, m), 2.86 (1H, d, d, J=8.5, 13.5 Hz), 4.06 (2H, q, J=7 Hz), 4.27 (2H, t, J=5 Hz), 4.54 (2H, t, J=5 Hz), 6.87 (2H, d, 8.5 Hz), 7.07 (2H, d, J=8.5 Hz), 7.21–7.27 (1H, m), 7.71–7.80 (4H, m), 8.01 (2H, d, J=8.5 Hz), 8.71 (1H, d, J=5 Hz).

Example 24

2-Butyl-3-[4-[2-[[1-[4-(2-pyridyl)phenyl]ethylidene] aminoxy]ethoxy]phenyl]propionic acid (Exemplification No. 67-8 compound)

Reaction and post-treatment were carried out according to Example 18 using 0.94 g of ethyl 2-butyl-3-[4-[2-[[1-[4(2-pyridyl)phenyl]ethylidene]aminoxy]ethoxy]benzyl] propionate obtained in Reference example 23 and 3.86 ml of a 1N aqueous sodium hydroxide solution to obtain 0.69 g of the desired compound as a gum.

1) $^1$H-NMR spectrum: δ ppm:

$^1$H-NMR spectrum (270 MHz) determined using TMS (tetramethylsilane) as the internal standard in deuterated chloroform was as follows:

0.88 (3H, t, J=8.5 Hz), 1.23–1.37 (4H, m), 1.43–1.73 (2H, m), 2.60–2.74 (2H, m), 2.90 (1H, d, d, J=8.5, 13.5 Hz), 4.30 (2H, t, J=5 Hz), 4.55 (2H, t, J=5 Hz), 6.87 (2H, d, J=8.5 Hz), 7.10 (2H, d, J=8.5 Hz), 7.24–7.28 (1H, m), 7.68–7.81 (4H, m), 7.95 (2H, d, J=8.5 Hz), 8.70 (1H, d, J=5 Hz).

Example25

2-Butyl-3-[4-[2-[[1-[4-(2-pyridyl)phenyl]ethylidene] aminoxy]ethoxy]phenyl]propionic acid sodium salt (sodium salt of Exemplification No. 67-8 compound)

0.69 g of 2-butyl-3-[4-[2-[[1-[4-(2-pyridyl)phenyl] ethylidene]aminoxy]ethoxy]phenyl]propionic acid obtained in Example 24 was treated with 1.50 ml of 1N sodium hydroxide according to Example 20 to obtain 0.65 g of the desired compound as a powder.

1) $^1$H-NMR spectrum: δ ppm:

$^1$H-NMR spectrum (270 MHz) determined using TMS (tetramethylsilane) as the internal standard in deuterated dimethyl sulfoxide was as follows:

0.79 (3H, t, J=6.5 Hz), 1.04–1.30 (5H, m), 1.30–1.49 (1H, m), 2.09–2.25 (1H, m), 2.23 (3H, s), 2.39 (1H, d, d, J=7.5, 13.5 Hz), 2.78 (1H, d, d, J=7.5, 13.5 Hz), 4.23 (2H, t, J=4.5 Hz), 4.47 (2H, t, J=4.5 Hz), 6.83 (2H, d, J=8.5 Hz), 7.07 (2H, d, J=8.5 Hz), 7.37 (1H, d, d, J=6, 7.5 Hz), 7.80 (2H, d, J=8.5 Hz), 7.90 (1H, d, t, J=2, 8.5 Hz), 8.00 (1H, d, J=8 Hz), 8.13 (2H, d, J=8.5 Hz), 8.69 (1H, d, J=4.5 Hz).

Reference Example 1

2-[[1-[4-(2-Pyridyl)phenyl]ethylidene]aminoxy] ethanol (a) 4'-(2-Pyridyl)acetophenone After 21 ml of a 3M methyl magnesium bromide-diethyl ether solution was added dropwise to a solution of 3.10 g of 4-(2-pyridyl)benzonitrile in 120 ml of dichloromethane under ice-cooling in a nitrogen atmosphere, the mixture was stirred at room temperature for 20 hours. After the reaction, an aqueous ammonium chloride solution and ethyl acetate were added to the reaction mixture, followed by stirring of the resulting mixture. The ethyl acetate layer was separated from the reaction mixture, dried over anhydrous magnesium sulfate and concentrated under reduced pressure. The residue was subjected to silica gel column chromatography (ethyl acetate:hexane=1:2) to obtain the crude desired compound as crystals. Further, the crude compound was washed with diisopropyl ether-hexane to obtain 1.56 g of the desired compound.

1) m.p. 116–118° C.

2) $^1$H-NMR spectrum: δ ppm:

$^1$H-NMR spectrum (270 MHz) determined using TMS (tetramethylsilane) as the internal standard in deuterated chloroform was as follows:

2.66 (3H, s), 7.30 (1H, d, d, J=4.5, 9 Hz), 7.79–7.81 (2H, m), 8.05–8.13 (4H, m), 8.74 (1H, d, J=4.5 Hz).

(b) 4'-(2-Pyridyl)acetophenone oxime 46.0 g of hydroxylamine-hydrochloride was added to a sodium methoxide-methanol solution prepared from 14.1 g of sodium and 300 ml of methanol, and the mixture was stirred at 50° C. for 30 minutes. 23.0 g of 4'-(2-pyridyl) acetophenone obtained in Reference example 1(a) was added to the resulting slurry, and the mixture was stirred at 50° C. for 3 hours. After the reaction, the reaction mixture was concentrated. 0.3 liter of ethyl acetate and 0.3 liter of water were added to the residue, and the mixture was stirred, followed by collecting of 10.98 g of the precipitated desired compound by filtration. The ethyl acetate layer in the filtrate was separated and dried over anhydrous magnesium sulfate, followed by concentration under reduced pressure. The crystalline residue thus obtained was washed with diisopropyl ether to obtain 12.56 g of the desired compound.

1) m.p. 177–178° C.

2) $^1$H-NMR spectrum: δ ppm:

$^1$H-NMR spectrum (270 MHz) determined using TMS (tetramethylsilane) as the internal standard in deuterated chloroform was as follows:

2.20 (3H, s), 7.35 (1H, d, d, J=4, 7.5 Hz), 7.78 (2H, d, J=8.5 Hz), 7.89 (1H, d, d, J=7.5, 8 Hz), 8.00 (1H, d, J=8 Hz), 8.12 (2H, d, J=8.5 Hz), 8.68 (1H, d, J=4 Hz).

(c) 4'-(2-Pyridyl)acetophenone oxime O-2-[(tetrahydropyran-2-yl)oxy]ethyl ether 6.00 g of potassium carbonate was added to a solution of 3.20 g of 2-(2-bromoethoxy)tetrahydropyran, 1.30 g of 4'-(2-pyridyl)acetophenone oxime obtained in Reference example 1(b) in 27 ml of N,N-dimethylacetamide, and the mixture was stirred at 80° C. for 16 hours. After the reaction, the reaction mixture was dissolved in ethyl acetate and water. The ethyl acetate layer was separated and the extract was dried over anhydrous magnesium sulfate. The ethyl acetate was evaporated under reduced pressure and the residue was purified by silica gel column chromatography (hexane:ethyl acetate=3:1) to obtain 2.01 g of the desired compound as a syrup.

(d) 2-[[1-[4-(2-Pyridyl)phenyl]ethylidene]aminoxy]ethanol 1.30 g of p-toluenesulfonic acid monohydrate was added to a solution of 2.01 g of 4'-(2-pyridyl)acetophenone oxime O-2-[(tetrahydropyran-2-yl)oxy]ethyl ether obtained in Reference example 1(c) in 30 ml of methanol, and the mixture was stirred at room temperature for 2 hours, followed by concentration of the reaction mixture under reduced pressure. The residue was dissolved in ethyl acetate and aqueous sodium bicarbonate and neutralized with sodium bicarbonate powder. The ethyl acetate layer was separated and dried over anhydrous magnesium sulfate. The extract was concentrated under reduced pressure to obtain the crude desired compound as crystals. This crude compound was washed with diisopropyl ether-hexane to obtain 1.35 g of the desired compound.

1) m.p. 74–76° C.

2) $^1$H-NMR spectrum: δ ppm:

$^1$H-NMR spectrum (270 MHz) determined using TMS (tetramethylsilane) as the internal standard in deuterated chloroform was as follows:

2.31 (3H, s), 2.57 (1H, t, J=6 Hz), 3.95–3.99 (2H, m), 4.34–4.36 (2H, m), 7.24–7.27 (1H, m), 7.74–7.77 (4H, m), 8.02 (2H, d, J=8.5 Hz), 8.71 (1H, d, d, J=1.5, 5 Hz).

Reference Example 2

4'-2-(2-Pyridyl)acetophenoneoxime O-2-(methanesulfonyloxy)ethyl ether 0.82 ml of triethylamine was added dropwise to a solution of 10 ml of dichloromethane containing 1.00 g of 2-[[1-[4-[(2-pyridyl)phenyl]ethylidene]aminoxy]ethanol obtained in Reference example 1 and 493 mg of methanesulfonyl chloride, and the mixture was stirred at room temperature for 5 hours. After the reaction, the reaction mixture was concentrated, and the residue was dissolved in ethyl acetate and water. Then, the ethyl acetate layer was separated and dried over anhydrous magnesium sulfate. The ethyl acetate layer was concentrated to obtain the crystalline residue. The residue was washed with isopropyl ether and hexane to obtain 1.26 g of the desired compound.

1) m.p. 99–101° C.

2) $^1$H-NMR spectrum: δ ppm:

$^1$H-NMR spectrum (270 MHz) determined using TMS (tetramethylsilane) as the internal standard in deuterated chloroform was as follows:

2.30 (3H, s), 3.04 (3H, s), 4.46–4.49 (2H, m), 4.55–4.58 (2H, m), 7.23–7.28 (1H, m), 7.74–7.78 (4H, m), 8.02 (2H, d, J=8.5 Hz), 8.71 (1H, d, J=5 Hz).

Reference Example 3

2-[[1-(4-Biphenylyl)ethylidene]aminoxy]ethanol (a) 4-Acetylbiphenyl oxime O-2-[(tetrahydropyran-2-yl) oxy]ethyl ether Reaction and post-treatment were carried out according to Reference example 1(c) using 15.8 g of 2-(2-bromoethoxy) tetrahydropyran, 6.40 g of 4-acetylbiphenyl oxime and 20.9 g of potassium carbonate to obtain 10.2 g of the desired compound as a syrup.

(b) 2-[]-(4-Biphenylyl)ethylideneaminoxy]ethanol

Reaction and post-treatment were carried out according to Reference example 1(d) using 10.2 g of 4-acetylbiphenyl oxime O-2-[(tetrahydropyran-2-yl)oxy]ethyl ether obtained in Reference example 3(a) to obtain 6.53 g of the desired compound.

1) m.p. 128–130° C.

2) $^1$H-NMR spectrum: δ ppm:

$^1$H-NMR spectrum (270 MHz) determined using TMS (tetramethylsilane) as the internal standard in deuterated chloroform was as follows:

2.30 (3H, s), 2.58 (1H, br.s), 3.95–3.99 (2H, m), 4.32–4.36 (2H, m), 7.36–7.48 (3H, m), 7.59–7.62 (4H, m), 7.71 (2H, d, J=8.5 Hz).

Reference Example 4

2-[[1-(4-Biphenylyl)ethylidene]aminoxy]ethyl methanesulfonate

Reaction and post-treatment were carried out according to Reference example 2 using 3.20 g of 2-[[1-(4-biphenylyl) ethylideneaminoxy]ethanol obtained in Reference example 3, 1.49 g of methanesulfonyl chloride and 1.80 g of triethylamine to obtain 3.80 g of the desired compound.

1) m.p. 103–104° C.

2) $^1$H-NMR spectrum: δ ppm:

$^1$H-NMR spectrum (270 MHz) determined using TMS (tetramethylsilane) as the internal standard in deuterated chloroform was as follows:

2.30 (3H, s), 3.04 (3H, s), 4.45–4.48 (2H, m), 4.54–4.58 (2H, m), 7.34–7.48 (3H, m), 7.61 (4H, d, J=8.5 Hz), 7.73 (2H, d, J=8.5 Hz).

Reference Example 5

Ethyl 3-(4-hydroxyphenyl)-2-(phenylamino) propionate (a) Ethyl 3-(4-benzyloxyphenyl)-2-(phenylamino) propionate A mixture of 4.00 g of ethyl 3-(4-benzyloxyphenyl)-2-methanesulfonyloxypropionate and 5 ml of aniline was stirred at 110° C. for 24 hours. The reaction mixture was purified by silica gel column chromatography (ethyl acetate:hexane=1:4) to obtain 3.94 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows: 1.17 (3H, t, J=7 Hz), 3.00–3.14 (2H, m), 4.12 (2H, d, q, J=1.5, 7 Hz), 4.30 (1H, t, J=6 Hz), 5.04 (2H, s), 6.60 (2H, d, J=8.5 Hz), 6.73 (1H, t, J=7.5 Hz), 6.89 (2H, d, J=8.5 Hz), 7.09 (2H, d, J=8.5 Hz), 7.16 (2H, d, J=8.5 Hz), 7.31–7.44 (5H, m)

(b) Ethyl 3-(4-hydroxyphenyl)-2-(phenylamino)propionate 0.80 g of 5% palladium-carbon was added to a mixture of 3.94 g of ethyl 3-(4-benzyloxyphenyl)-2-(phenylamino) propionate obtained in Reference example 5(a), 40 ml of ethanol and 20 ml of tetrahydrofuran, and the mixture was stirred at 50° C. under hydrogen at normal pressure for 6 hours. The catalyst was removed by filtration from the reaction mixture, and the solvent was evaporated. The residue was subjected to silica gel column chromatography (ethyl acetate:hexane=1:2) to obtain 2.95 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.19 (3H, t, J=7 Hz), 3.00–3.13 (2H, m), 4.13 (2H, d, q, J=1, 7 Hz), 4.30 (1H, brt, J=6 Hz), 4.88 (1H, brs), 6.60 (2H, d, J=8 Hz), 6.71–6.76 (3H, m), 7.03 (2H, d, J=8 Hz), 7.14–7.20 (2H, m).

Reference Example 6

Ethyl 3-(4-hydroxyphenyl)-2-(N-phenyl-N-ethylamino)propionate (a) Ethyl 3-(4-benzyloxyphenyl)-2-(N-phenyl-N-ethylamino)propionate Reaction and post-treatment were carried out according to Reference example 5(a) using 4.50 g of ethyl 3-(4-benzyloxyphenyl)-2-methanesulfonyloxypropionate and 5.6 ml of N-ethylaniline to obtain 6.30 g of a mixture of the desired compound and N-ethylaniline as a syrup.

1) $^1$H-NMR spectrum: δ ppm:

$^1$H-NMR spectrum (270 MHz) determined using TMS (tetramethylsilane) as the internal standard in deuterated chloroform was as follows:

1.07 (3H, t, 3H, J=7 Hz), 1.14 (3H, t, J=7 Hz), 3.01–3.45 (4H, m), 4.09 (2H, q, J=7 Hz), 4.39 (1H, t, J=7.5 Hz), 5.02 (2H, s), 6.66–6.75 (3H, m), 6.87 (2H, d, J=8 Hz), 7.10 (2H, d, J=8.5 Hz), 7.15–7.25 (2H, m), 7.31–7.44 (5H, m).

(b) Ethyl 3-(4-hydroxyphenyl)-2-(-phenyl-N-ethylamino) propionate

Reaction and post-treatment were carried out according to Reference example 5(b) using 6.30 g of a mixture of ethyl 3-(4-benzyloxyphenyl)-2-( phenyl-N-ethylamino) propionate and N-ethylaniline obtained in Reference example 6(a) to obtain 2.37 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.07 (3H, t, J=7 Hz), 1.15 (3H, t, J=7 Hz), 3.05 (1H, d, d, J=8, 14 Hz), 3.26 (1H, d, d, J=7.5, 14 Hz), 3.30–3.46 (2H, m), 4.10 (2H, q, J=7 Hz), 4.38 (1H, t, J=8 Hz), 4.75 (1H, br.s), 6.67–6.79 (5H, m), 7.05 (2H, d, J=8.5 Hz), 7.18–7.26 (2H, m).

Reference Example 7

Methyl 3-(4-hydroxyphenyl)-2-(phenylthio) propionate (a) Methyl 3-(4-methoxymethoxyphenyl)-2-(phenylthio) propionate A solution of 15 ml of N,N-dimethylformamide containing 745 mg of methyl 3-(4-methoxymethoxyphenyl)-2-methanesulfonyloxypropionate, 310 mg of thiophenol and 390 mg of potassium carbonate was stirred at 50° C. for 0.5 hours, and ethyl acetate and water were added to the reaction mixture. Then, the ethyl acetate layer was separated and dried over anhydrous magnesium sulfate. The ethyl acetate layer was concentrated under reduced pressure, and the residue was subjected to silica gel column chromatography (ethyl acetate:hexane=1:4) to obtain 698 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

3.00 (1H, d, d, J=6.5, 14 Hz), 3.15 (1H, d, d, J=9, 14 Hz), 3.47 (3H, s), 3.59 (3H, s), 3.86 (1H, d, d, J=6.5, 9 Hz), 5.15 (2H, s), 6.94 (2H, d, J=8.5 Hz), 7.10 (2H, d, J=8.5 Hz), 7.29–7.33 (3H, m), 7.40–7.45 (2H, m).

(b) Methyl 3-(4-hydroxphenyl)-2-(phenylthio)propionate

A solution of 689 mg of methyl 3-(4-methoxymethoxyphenyl)-2-(phenylthio)propionate obtained in Reference example 7(a) in 3 ml of 4N hydrogen chloride-dioxane was stirred at room temperature for 0.5 hours and concentrated under reduced pressure. The residue was dissolved in ethyl acetate and water, and then the ethyl acetate layer was separated and dried over anhydrous magnesium sulfate. The solvent was evaporated to obtain 595 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

2.99 (1H, d, d, J=6.5, 14 Hz), 3.12 (1H, d, d, J=9, 14 Hz), 3.58 (3H, s), 3.86 (1H, d, d, J=6.5, 9 Hz), 4.97 (1H, br s), 6.72 (2H, d, J=8.5 Hz), 7.05 (2H, d, J=8.5 Hz), 7.23–7.34 (3H, m), 7.40–7.45 (2H, m).

Reference Example 8

Ethyl 3-(4-hydroxyphenyl)-2-pyrrolylpropionate (a) Ethyl 3-(4-benzyloxyphenyl)-2-pyrrolylpropionate 3.30 g of 1,4-dichloro-1,4-dimethoxybutane was added to a solution of 3.30 g of ethyl 3-(4-benzyloxyphenyl)-2-aminopropionate in 80 ml of dichloromethane, and 20 g of Amberlist A-21 was further added to the resulting mixture, followed by stirring of the mixture at room temperature for 18 hours. After the reaction, the reaction mixture was filtered. The filtrate was concentrated, and the residue was purified by silica gel column chromatography (ethyl acetate-:hexane 1:5) to obtain 1.00 g of the desired compound as a syrup.

1) $^1$H-NMR spectrum: δ ppm:

$^1$H-NMR spectrum (27 MHz) determined using TMS (tetramethylsilane) as the internal standard in deuterated chloroform was as follows:

1.19 (3H, t, J=7 Hz), 3.19 (1H, d, d, J=8.5, 14 Hz), 3.34(1H, d, d, J=7, 14 Hz), 4.14 (2H, q, J=7 Hz), 4.68 (1H, d, d, J=7, 8.5 Hz), 5.01 (2H, s), 6.15 (2H, t, J=2 Hz), 6.73 (2H, t, J=2 Hz), 6.84 (2H, d, J=8.5 Hz), 6.94 (2H, d, J=8.5 Hz), 7.28–7.43 (5H, m).

(b) Ethyl 3-(4-hydroxyphenyl)-2-[N-(phenyl)ethylamino]propionate

Reaction and post-treatment were carried out according to Reference example 5(b) using 1.00 g of ethyl 3-(4-benzyloxyphenyl)-2-pyrrolylpropionate obtained in Reference Example 8(a) and 0.12 g of 5% palladium-carbon to obtain 0.71 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.20 (3H, t, J=7 Hz), 3.18 (1H, d, d, J=8.5, 14 Hz), 3.33 (1H, d, d, J=7, 14 Hz), 4.15 (2H, q, J=7 Hz), 4.67 (1H, d, d, J=7, 8.5 Hz), 4.80 (1H, s), 6.14 (2H, t, J=2 Hz), 6.71 (2H, d, J=8.5 Hz), 6.72 (2H, d, J=2 Hz), 6.88 (2H, d, J=8.5 Hz).

Reference Example 9

Ethyl 2-(N,N-diethylamino)-3-(4-hydroxyphenyl)propionate 0.3 ml of acetic acid and 0.5 ml of acetaldehyde were added to a solution of 491 mg of DL-tyrosine ethyl ester hydrochloride in 5 ml of methanol. Sodium cyanoborohydride (126 mg) was added thereto under ice-cooling, followed by stirring of the mixture at room temperature for 2 hours. After the reaction, the reaction mixture was concentrated. The residue was dissolved in ethyl acetate and water, and then the ethyl acetate layer was separated. The extract was washed with an aqueous sodium bicarbonate solution, dried over anhydrous magnesium sulfate and concentrated under reduced pressure. The residue was purified by silica gel column chromatography (methanol:dichloromethane= 1:20) to obtain 420 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.02 (6H, t, J=7 Hz), 1.16 (3H, t, J=7 Hz), 2.53 (2H, sextet, J=7 Hz), 2.79 (2H, sextet, J=7 Hz), 2.81 (1H, d, d, J=6, 13.5 Hz), 2.99 (1H, d, d, J=9, 13.5 Hz), 3.55 (1H, d, d, J=6, 9 Hz), 4.02–4.11 (2H, m), 6.72 (2H, d, J=8.5 Hz), 7.02 (2H, d, J=8.5 Hz).

Reference Example 10

Ethyl 2-N-(t-butoxycarbonyl)ethylamino-3-(4-hydroxyphenyl)propionate (a) Ethyl 2-ethylamino-3-(4-hydroxyphenyl)propionate Reaction and post-treatment were carried out according to Reference example 9 using 983 mg of DL-tyrosine ethyl ester hydrochloride, 0.26 ml of acetaldehyde and 100 mg of sodium cyanoborohydride to obtain 515 mg of the desired compound as a syrup which soon crystallized.

1) m.p. 87–89° C.

2) $^1$H-NMR spectrum: δ ppm:

$^1$H-NMR spectrum (270 MHz) determined using TMS (tetramethylsilane) as the internal standard in deuterated chloroform was as follows:

1.08 (3H, t, J=7 Hz), 1.18 (3H, t, J=7 Hz), 2.48–2.72 (2H, m), 2.82–2.96 (2H, m), 3.50 (1H, t, J=7 Hz), 4.11 (2H, q, J=7 Hz), 6.68 (2H, d, J=8.5 Hz), 7.01 (2H, d, J=8.5 Hz).

(b) Ethyl 2-N-(t-butoxycarbonyl)ethylamino-3-(4-hydroxyphenyl)propionate 1 ml of triethylamine was added dropwise under ice-cooling to a solution of 569 mg of ethyl 2-ethylamino-3-(4-hydroxyphenyl)propionate obtained in Reference example 10(a), 785 mg of di-t-butyl dicarbonate in 10 ml of dichloromethane, and the mixture was stirred at room temperature for 4 hours. After the reaction, the reaction mixture was concentrated. The residue was dissolved in ethyl acetate and water, and then the ethyl acetate layer was separated. The extract was dried over anhydrous magnesium sulfate and concentrated under reduced pressure. The residue was subjected to silica gel column chromatography (ethyl acetate:hexane=1:2) to obtain 663 mg of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

0.90 (3H, br t, J=7 Hz), 1.21–1.31 (3H, m), 1.45 (9H, s), 3.15–3.37 (1H, m), 3.08 (1H, d, d, J=10, 14 Hz), 3.15–3.37 (1H, m), 3.24 (1H, d, d, J=5, 14 Hz), 3.85–4.30 (3H, m), 6.76 (2H, br d, J=8.5 Hz), 7.00–7.11 (2H, m).

Reference Example 11

Ethyl 3-(4-hydroxyphenyl)-2-(methylthio))propionate (a) Ethyl 3-(4-methoxymethoxyphenyl)-2-methylthiopropionate A solution of 17.2 g of ethyl 3-(4-methoxymethoxyphenyl)-2-methanesulfonyloxypropionate, 4.20 g of sodium thiomethoxide in 300 ml of N,N-dimethylformamide was stirred at 50° C. for 1.5 hours. After the reaction, ethyl acetate and water were added to the reaction mixture. Then, the ethyl acetate layer was separated and dried over anhydrous magnesium sulfate. The extract thus obtained was concentrated, and the residue was subjected to silica gel column chromatography (ethyl acetate:hexane=1:4) to obtain 11.37 g of the desired compound as a syrup.

1) $^1$H-NMR spectrum: δ ppm:
$^1$H-NMR spectrum (270 MHz) determined using TMS (tetramethylsilane) as the internal standard in deuterated chloroform was as follows:
1.22 (3H, t, J=7 Hz), 2.17 (3H, s), 2.91 (1H, d, d, J=6.5, 14 Hz), 3.15 (1H, d, d, J=9, 14 Hz), 3.41 (1H, d, d, J=6.5, 9 Hz), 3.47 (2H, s), 4.09–4.23 (2H, m), 5.15 (3H, s), 6.96 (2H, d, J=8.5 Hz), 7.13 (2H, d, J=8.5 Hz).

(b) Ethyl 3-(4-hydroxyphenyl)-2-(methylthio)propionate

Reaction and post-treatment were carried out according to Reference example 7(b) using 2.01 g of ethyl 3-(4-methoxymethoxyphenyl)-2-(methylthio)propionate obtained in Reference example 11(a) and 11 ml of a 4N hydrogen chloride-dioxane to obtain 1.70 g of the desired compound.

1) $^1$H-NMR spectrum: δ ppm:
$^1$H-NMR spectrum (270 MHz) determined using TMS (tetramethylsilane) as the internal standard in deuterated chloroform was as follows:
1.22 (3H, t, J=7.5 Hz), 2.17 (3H, s), 2.89 (1H, d, d, J=6.5, 14 Hz), 3.13 (1H, d, d, J=9, 14 Hz), 3.41 (1H, d, d, J=6.5, 14 Hz), 4.09–4.20 (2H, m), 5.05 (1H, s), 6.74 (2H, d, J=8.5 Hz), 7.07 (2H, d, J=8.5 Hz).

Reference Example 12

Ethyl 2-(4-hydroxybenzyl)-5-phenylvalerate (a) Diethyl 2-(4-benzyloxybenzyl)-2-(3-phenylpropyl)malonate 0.48 g of sodium hydride (55% oil suspension) was added to a mixture of 2.78 g of diethyl 2-(3-phenylpropyl)malonate, 20 ml of toluene and 10 ml of N,N-dimethylacetamide, and the resulting mixture was stirred at room temperature for 30 minutes. Then, 2.45 g of 4-benzyloxybenzyl chloride was added to the reaction mixture, and the mixture was stirred at room temperature for 30 minutes and then at 60° C. for 30 minutes. After the reaction, ethyl acetate and water were added to the reaction mixture, and then the ethyl acetate layer was separated. The extract thus obtained was dried over anhydrous magnesium sulfate and concentrated. The residue thus obtained was subjected to silica gel column chromatography (ethyl acetate:hexane=1:9) to obtain 3.91 g of the desired compound as a syrup.

1) $^1$H-NMR spectrum: δ ppm:
$^1$H-NMR spectrum (270 MHz) determined using TMS (tetramethylsilane) as the internal standard in deuterated chloroform was as follows:
1.21 (6H, s), 1.57–1.66 (2H, m), 1.76–1.85 (2H, m), 2.61 (2), t, J=6.5 Hz), 3.14 (2H, s), 4.15 (4H, d, q, J=1.5, 7 Hz), 5.01 (2H, s), 6.79 (2H, d, J=8.5 Hz), 6.89 (2H, d, J=8.5 Hz), 7.15–7.44 (10H, m).

(b) Ethyl 2-(4-benzyloxybenzyl)-5-phenylvalerate 2.00 g of potassium hydroxide was added to a mixture of 3.91 g of diethyl 2-(4-benzyloxybenzyl)-2-(3-phenylpropyl)malonate obtained in Reference example 12(a), 30 ml of 2-methoxyethanol and 3 ml of water, and the resulting mixture was stirred on an oil bath of 130° C. for 1.5 hours. After the reaction, the reaction mixture was concentrated, water and ethyl acetate were added to the concentrated mixture, and then 6N hydrochloric acid was added thereto to make it acidic. Then, the ethyl acetate layer was separated, washed with an aqueous NaCl solution and dried over anhydrous magnesium sulfate, followed by concentration. The residual syrup was dissolved in 20 ml of xylene, and the mixture was stirred for one hour and concentrated. The syrup-like 2-(4-benzyloxybenzyl)-5-phenylvaleric acid thus obtained was dissolved in 40 ml of ethanol, and 1 ml of conc. sulfuric acid was added thereto. The resulting mixture was stirred at 80° C. for 3 hours and allowed to stand at room temperature for 16 hours. The reaction mixture was concentrated, and the residue was dissolved in ethyl acetate and water, followed by separation of the ethyl acetate layer. The extract thus obtained was dried over anhydrous magnesium sulfate and concentrated to obtain 3.32 g of the desired compound as a syrup.

1) $^1$H-NMR spectrum: δ ppm:
$^1$H-NMR spectrum (270 MHz) determined using TMS (tetramethylsilane) as the internal standard in deuterated chloroform was as follows:
1.13 (3H, t, J=7 Hz), 1.50–1.80 (4H, m), 2.53–2.71 (4H, m), 2.82–2.90 (1H, m), 4.04 (2H, q, J=7 Hz), 5.04 (2H, s), 6.87 (2H, d, J=8.5 Hz), 7.05 (2H, d, J=8.5 Hz), 7.10–7.44 (10H, m).

(c) Ethyl 2-(4-hydroxybenzyl-5-phenylvalerate

Reaction and post-treatment were carried out according to Reference example 5(b) using 3.32 g of ethyl 2-(4-benzyloxybenzyl)-5-phenylvalerate obtained in Reference Example 12(b) and 0.4 g of 5% palladium-carbon to obtain 2.56 g of the desired compound as a syrup.

1) $^1$H-NMR spectrum: δ ppm:
$^1$H-NMR spectrum (270 MHz) determined using TMS (tetramethylsilane) as the internal standard in deuterated chloroform was as follows:
1.14 (3H, t, J=7 Hz), 1.50–1.75 (4H, m), 2.53–2.71 (4H, m), 2.78–2.87 (1H, m), 4.05 (2H, q, J=7 Hz), 6.70 (2H, d, J=8.5 Hz), 6.98 (2H, d, J=8.5 Hz), 7.12–7.29 (5H, m).

Reference Example 13

Ethyl 3-(4-hydroxyphenyl)-2-phenoxypropionate (a) Diethyl 2-(4-benzyloxybenzyl)-2-phenoxymalonate Reaction and post-treatment were carried out according to Reference example 12(a) using 2.81 g of diethyl phenoxymalonate, 2.59 g of 4-benzyloxybenzyl chloride and 530 mg of sodium hydride (55% oil suspension) to obtain 3.10 g of the desired compound as a syrup.

1) $^1$H-NMR spectrum: δ ppm:
$^1$H-NMR spectrum (270 MHz) determined using TMS (tetramethylsilane) as the internal standard in deuterated chloroform was as follows:
1.12 (6H, t, J=7 Hz), 3.57 (2H, s), 4.15 (4H, q, J=7 Hz), 5.02 (2H, s), 6.84–7.14 (6H, m), 7.22–7.41 (8H, m).

(b) Ethyl 3-(4-benzyloxyphenyl)-2-phenoxypropionate

Reaction and post-treatment were carried out according to Reference example 12(b) using 3.10 g of diethyl 2-(4-benzyloxybenzyl)-2-phenoxymalonate obtained in Reference example 13(a) and 2.10 g of potassium hydroxide to obtain 2.10 g of the desired compound as a syrup through the syrup-like 3-(4-benzyloxyphenyl)-2-phenoxypropionic acid.

1) $^1$H-NMR spectrum: δ ppm:

$^1$H-NMR spectrum (270 MHz) determined using TMS (tetramethylsilane) as the internal standard in deuterated chloroform was as follows:

1.18 (3H, t, J=7 Hz), 3.11–3.20 (2H, m), 4.16 (2H, q, J=7 Hz), 4.74 (1H, d, d, J=5.5, 6.5 Hz), 5.04 (2H, s), 6.84 (2H, d, J=8 Hz), 6.91 (2H, d, J=8.5 Hz), 6.92–6.97 (1H, m), 7.05–7.09 (1H, m), 7.22 (2H, d, J=8.5 Hz), 7.20–7.43 (6H, m).

(c) Ethyl 3-(4-hydroxyphenyl)-2-phenoxypropionate

Reaction and post-treatment were carried out according to Reference example 5(b) using 2.10 g of ethyl 3-(4-benzyloxyphenyl)-2-phenoxypropionate obtained in Reference Example 13(b) and 0.32 g of 5% palladium-carbon to obtain 1.01 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

1.19 (3H, t, J=7 Hz), 3.10–3.24 (2H, m), 4.17 (2H, q, J=7 Hz), 4.74 (1H, d, d, J=6, 7 Hz), 5.00 (1H, s), 6.74 (2H, d, J=8.5 Hz), 6.84 (2H, d, J=8 Hz), 6.95 (1H, t, J=7.5 Hz), 7.16 (2H, d, J=8.5 Hz), 7.21–7.26 (2H, m).

Reference Example 14

Ethyl 2-(4-hydroxybenzyl)caproate (a) Diethyl 2-(4-benzyloxybenzyl)-2-butylmalonate Reaction and post-treatment were carried out according to Reference example 12(a) using 2.16 g of diethyl butylmalonate, 2.44 g of 4-benzyloxybenzyl chloride and 480 mg of sodium hydride (55% oil suspension) to obtain 3.67 g of the desired compound as crystals.

1) m.p. 73° C.

2) $^1$H-NMR spectrum: δ ppm:

$^1$H-NMR spectrum (270 MHz) determined using TMS (tetramethylsilane) as the internal standard in deuterated chloroform was as follows:

0.91 (3H, t, J=7 Hz), 1.24 (6H, t, J=7 Hz), 1.20–1.38 (4H, m), 1.74–1.80 (2H, m), 3.18 (2H, s), 4.11–4.23 (4H, m), 5.02 (2H, s), 6.86 (2H, d, J=8.5 Hz), 6.99 (2H, d, J=8.5 Hz), 7.31–7.44 (5H, m).

(b) Ethyl 2-(4-benzyloxybenzyl)caproate

Reaction and post-treatment were carried out according to Reference example 12(b) using 3.60 g of diethyl 2-(4-benzyloxybenzyl)-2-butylmalonate obtained in Reference Example 14(a) and 2.00 g of potassium hydroxide to obtain 2.71 g of the desired compound as a syrup through the crystalline 2-(4-benzyloxybenzyl)caproic acid.

1) $^1$H-NMR spectrum: δ ppm:

$^1$H-NMR spectrum (270 MHz) determined using TMS (tetramethylsilane) as the internal standard in deuterated chloroform was as follows:

0.87 (3H, t, J=7 Hz), 1.14 (3H, t, J=7 Hz), 1.20–1.70 (6H, m), 2.51–2.72 (2H, m), 2.85 (1H, d, d, J=8.5, 13.5 Hz), 4.05 (2H, q, J=7 Hz), 5.03 (2H, s), 6.88 (2H, d, J=8.5 Hz), 7.07 (2H, d, J=8.5 Hz),7.31–7.45 (5H, m).

(c) Ethyl 2-(4-hydroxybenzyl)caproate

Reaction and post-treatment were carried out according to Reference example 5(b) using 2.71 g of ethyl 2-(4-benzyloxybenzyl)caproate obtained in Reference example 14(a) and 0.40 g of 5% palladium-carbon to obtain 1.90 g of the desired compound as a syrup.

1) $^1$H-NMR spectrum: δ ppm:

$^1$H-NMR spectrum (270 MHz) determined using TMS (tetramethylsilane) as the internal standard in deuterated chloroform was as follows:

0.87 (3H, t, J=7 Hz), 1.16 (3H, t, J=7 Hz), 1.20–1.35 (4H, m), 1.40–1.70 (2H, m), 2.53–2.72 (2H, m), 2.84 (1H, d, d, J=8.5, 13.5 Hz), 4.06 (2H, q, J=7 Hz), 4.93 (1H, s), 6.72 (2H, d, J=8.5 Hz ), 7.02 (2H, d, J=8 .5 Hz).

Test Example

Blood Glucose Lowering Effect (Method 1)

1 mg/kg of each compound was mixed into a solvent consisting of a 1:1 ratio of polyethylene glycol 400 and 0.5% w/v carboxymethyl cellulose in physiological saline, and orally administered to hyperglycemic male KK mice having a body weight of 40 g or more. The animals were allowed to be under a condition of well-feeding for 18 hours. Next, blood samples were collected from the caudal vein in the absence of anesthesia followed by measurement of blood glucose level using a glucose analyzer (GL-101: Mitsubishi Chemical Corp.).

The lowering rate of blood glucose level was calculated according to the following equation:

Glucose lowering rate (%)=[(glucose level of group of animals to which the solvent was administered−glucose level of group of animals to which a compound of formula (I) was administered)/glucose level of group of animals to which the solvent was administered]×100

The results obtained are shown in Table 69.

TABLE 69

| Test Compound | Blood Glucose Lowering Rate (%) |
| --- | --- |
| Compound of Example 2 | 21.9 |
| Compound of Example 4 | *20.2 |
| Compound of Example 10 | 24.1 |
| Compound of Example 16 | 26.9 |

*Indicates blood glucose lowering rate three hours after the administration of test compound.

It can be seen from Table 69 that the compounds of the present invention have excellent glucose lowering effect.

Blood Glucose Lowering Effect (Method 2)

Each of the test compounds was mixed with powdered feed F-2 (Funabashi Farms) at the ratio of 0.01% (about 10 mg/kg/day). The mixture was administered orally to hyperglycemic male KK mice having a body weight of 40 g or more for three days. A different group of mice were given a powdered feed only and used as the control group. Next, blood samples were collected from the caudal vein in the absence of anesthesia, and the blood glucose level in the plasma obtained by centrifugal separation was measured using Glucorotor F (A & T Corp.).

The blood glucose lowering rate was calculated according to the following equation:

Blood glucose lowering rate (%)=[(glucose level of control group−glucose level of group to which test compound was administered/glucose level of control group]×100

The results obtained are shown in Table 70.

TABLE 70

| Test Compound | Blood Glucose Lowering Rate (%) |
|---|---|
| Compound of Example 18 | 20.4 |
| Compound of Example 20 | 47.0 |

It can be seen from Table 70 that the compounds of the present invention have the excellent glucose lowering effect.

Preparation Example (1) Capsule

| | |
|---|---|
| Compound of Example 2 | 10 mg |
| Lactose | 110 mg |
| Corn starch | 58 mg |
| Magnesium stearate | 2 mg |
| | 180 mg |

Powder of each component mentioned above was mixed well and passed through a sieve of 60 mesh (the standard of mesh was based on Tyler). 180 mg of the powder thus obtained was weighed and filled in a gelatin capsule (No. 3) to prepare a capsule.

(2) Tablet

| | |
|---|---|
| Compound of Example 2 | 10 mg |
| Lactose | 85 mg |
| Corn starch | 34 mg |
| Finely crystallized cellulose | 20 mg |
| Magnesium stearate | 1 mg |
| | 150 mg |

Powder of each component shown above was mixed well and compression-molded to a tablet of 150 mg weight. If necessary, these tablets may be coated with sugar or a film.

(3) Granule

| | |
|---|---|
| Compound of Example 2 | 10 mg |
| Lactose | 839 mg |
| Corn starch | 150 mg |
| Hydroxypropyl cellulose | 1 mg |
| | 1000 mg |

Powder of each component shown above was mixed well and wetted with pure water, followed by granulation by means of a basket type granulator and drying to obtain a granule.

Industrial Applicability

The phenylalkylcarboxylic acid derivatives, the pharmacologically acceptable salts thereof or the pharmacologically acceptable esters thereof are useful as therapeutic or preventive agents for a lot of diseases. Examples of such diseases are hyperlipemia, hyperglycemia, the state of impaired glucose tolerance, the state of insulin resistant non-IGT, hypertension, osteoporosis, pancreatitis, diabetic complication, arteriosclerosis, cataract, gestational diabetes, polycystic ovary syndrome, inflammatory diseases, psoriasis, asthma, arteriosclerosis, autoimmune diseases and the like.

We claim:
1. Phenylalkylcarboxylic acid compounds of formula (I):

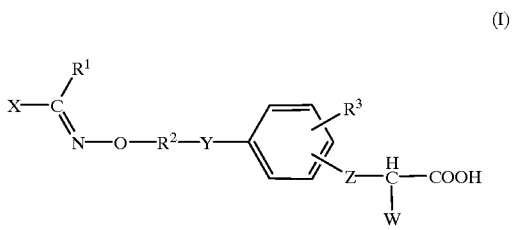

wherein, $R^1$ represents a hydrogen atom or a straight- or branched-chain alkyl group having from 1 to 6 carbon atoms, $R^2$ represents a straight- or branched-chain alkylene group having from 2 to 6 carbon atoms, $R^3$ represents (i) a hydrogen atom, (ii) a straight- or branched-chain alkyl group having from 1 to 6 carbon atoms, (iii) a straight- or branched-chain alkoxy group having from 1 to 4 carbon atoms, (iv) a straight- or branched-chain alkylthio group having from 1 to 4 carbon atoms, (v) a halogen atom, (vi) a nitro group, (vii) a straight- or branched-chain dialkylamino group in which alkyl groups are the same as or different from each other and each has from 1 to 4 carbon atoms, (viii) an aryl group having from 6 to 10 carbon atoms which is unsubstituted or substituted by 1 to 3 substituents α mentioned below, or (ix) an aralkyl group having from 7 to 12 carbon atoms which is unsubstituted or substituted by 1 to 3 substituents α mentioned below in the aryl moiety, Z represents a single bond or a straight- or branched-chain alkylene group having from 1 to 6 carbon atoms, W represents (i) a straight- or branched-chain alkyl group having from 1 to 6 carbon atoms, (ii) a hydroxyl group, (iii) a straight- or branched-chain alkoxy group having from 1 to 4 carbon atoms, (iv) a straight- or branched-chain alkylthio group having from 1 to 4 carbon atoms, (v) an amino group, (vi) a straight- or branched-chain monoalkylamino group having from 1 to 4 carbon atoms, (vii) a straight- or branched-chain dialkylamino group in which alkyl groups are the same as or different from each other and each has from 1 to 4 carbon atoms, (viii) an N-alkyl-N-arylamino group having a straight- or branched-chain alkyl having from 1 to 4 carbon atoms and an aryl having from 6 to 10 carbon atoms which is unsubstituted or substituted by 1 to 3 substituents α mentioned below, (ix) an aryl group having from 6 to 10 carbon atoms which is unsubstituted or substituted by 1 to 3 substituents α mentioned below, (x) an aryloxy group having from 6 to 10 carbon atoms which is unsubstituted or substituted by 1 to 3 substituents α mentioned below in the aryl moiety, (xi) an arylthio group having from 6 to 10 carbon atoms which is unsubstituted or substituted by 1 to 3 substituents α mentioned below in the aryl moiety, (xii) an arylamino group having from 6 to 10 carbon atoms which is unsubstituted or substituted by 1 to 3 substituents α mentioned below in the aryl moiety, (xiii) an aralkyl group having from 7 to 12 carbon atoms which is unsubstituted or substituted by 1 to 3 substituents α mentioned below in the aryl moiety, (xiv) an aralkyloxy group having from 7 to 12 carbon atoms which is unsubstituted or substituted by 1 to 3 substituents α mentioned below in the aryl moiety, (xv) an aralkylthio group having from 7 to 12 carbon atoms which is unsubstituted or substituted by 1 to 3 substituents α mentioned below in the aryl moiety, (xvi) an aralkylamino group having from 7 to 12 carbon atoms which is unsubstituted or substituted by 1 to 3 substituents α mentioned below in the aryl moiety, (xvii) a 1-pyrrolyl group, (xviii) a 1-pyrrolidinyl group, (xix) a 1-imidazolyl group, (xx) a piperidino group or (xxi) a morpholino group, X represents an aryl group having from 6 to 10 carbon atoms which is unsubstituted or substituted by 1 to 3 substituents α mentioned below, or a 5- to 10-membered monocyclic or bicyclic hetero aromatic group which is unsubstituted or substituted by 1 to 3 substituents α mentioned below containing from 1 to 4 hetero atoms selected from the group consisting of oxygen, nitrogen and sulfur atoms, the substituent α being (i) a straight- or branched-chain alkyl group having from 1 to 6 carbon atoms, (ii) a straight- or branched-chain halogenated alkyl group having from 1 to 4 carbon atoms, (iii) a hydroxyl group, (iv) a straight- or branched-chain aliphatic acyloxy group having from 1 to 4 carbon atoms, (v) a straight- or branched-chain alkoxy group having from 1 to 4 carbon atoms, (vi) a straight- or branched-chain alkylenedioxy group having from 1 to 4 carbon atoms, (vii) an aralkyloxy group having from 7 to 12 carbon atoms, (viii) a straight- or branched-chain alkylthio group having from 1 to 4 carbon atoms, (ix) a straight- or branched-chain alkylsulfonyl group having from 1 to 4 carbon atoms, (x) a halogen atom, (xi) a nitro group, (xii) a straight- or branched-chain dialkylamino group in which alkyl groups are the same as or different from each other and each has from 1 to 4 carbon atoms, (xiii) an aralkyl group having from 7 to 12 carbon atoms, (xiv) an aryl group having from 6 to 10 carbon atoms (the aryl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) an aryloxy group having from 6 to 10 carbon atoms (the aryl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) an arylthio group having from 6 to 10 carbon atoms (the aryl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) an arylsulfonyl group having from 6 to 10 carbon atoms (the aryl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) an arylsulfonylamino group having from 6 to 10 carbon atoms (the aryl moiety is unsubstituted or substituted by straight- or branched-chain alkyl having from 1 to 6 carbon atoms, straight- or branched-chair halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms, and the nitrogen atom of the amino moiety is unsubstituted or substituted by straight- or branched-chain alkyl having from 1 to 6 carbon atoms), (xix) a 5- to 10-membered monocyclic or bicyclic hetero aromatic group containing from 1 to 4 hetero atoms selected from the group consisting of oxygen, nitrogen and sulfur atoms, (xx) a 5- to 10-membered monocyclic or bicyclic hetero aromatic oxy group containing from 1 to 4 hetero atoms selected from the group consisting of oxygen, nitrogen and sulfur atoms, (xxi) a 5- to 10-membered monocyclic or bicyclic hetero aromatic thio group containing from 1 to 4 hetero atoms selected from the group consisting of oxygen, nitrogen and sulfur atoms, (xxii) a 5- to 10-membered monocyclic or bicyclic hetero aromatic sulfonyl group containing from 1 to 4 hetero atoms selected from the group consisting of oxygen, nitrogen and sulfur atoms, or (xxiii) a 5- to 10-membered monocyclic or bicyclic hetero aromatic sulfonylamino group containing from 1 to 4 hetero atoms selected from the group consisting of oxygen, nitrogen and sulfur atoms (the nitrogen atom of the amino moiety is unsubstituted or substituted by straight- or branched-chain alkyl having from 1 to 6 carbon atoms), and Y represents an oxygen atom, a sulfur atom or a group of the formula: >N—$R^4$ (wherein $R^4$ represents a hydrogen atom, a straight- or branched-chain alkyl group having from 1 to 6 carbon atoms or a straight- or branched-chain aliphatic acyl group or aromatic acyl group having from 1 to 8 carbon), the pharmacologically acceptable salts thereof or the pharmacologically acceptable esters thereof.

2. A phenylalkylcarboxylic acid compound, the pharmacologically acceptable salts thereof or the pharmacologically acceptable esters thereof according to claim 1, wherein $R^1$ is a hydrogen atom or a straight- or branched-chain alkyl group having from 1 to 4 carbon atoms.

3. A phenylalkylcarboxylic acid compound, the pharmacologically acceptable salts thereof or the pharmacologically acceptable esters thereof according to claim 1, wherein $R^1$ is a hydrogen atom or a straight- or branched-chain alkyl group having from 1 to 3 carbon atoms.

4. A phenylalkylcarboxylic acid compound, the pharmacologically acceptable salts thereof or the pharmacologically acceptable esters thereof according to claim 1, wherein $R^1$ is a hydrogen atom or the alkyl group having one or two carbon atoms.

5. A phenylalkylcarboxylic acid compound, the pharmacologically acceptable salts thereof or the pharmacologically acceptable esters thereof according to claim 1, wherein $R^1$ is an alkyl group having one or two carbon atoms.

6. A phenylalkylcarboxylic acid compound, the pharmacologically acceptable salts thereof or the pharmacologically acceptable esters thereof according to claim 1, wherein $R^2$ is a straight- or branched-chain alkylene group having from 2 to 5 carbon atoms.

7. A phenylalkylcarboxylic acid compound, the pharmacologically acceptable salts thereof or the pharmacologically acceptable esters thereof according to claim 1, wherein $R^2$ is 8. A phenylalkylcarboxylic acid compound, the pharmacologically acceptable salts thereof or the pharmacologically acceptable esters thereof according to claim 1, wherein $R^2$ is an ethylene, trimethylene or methylethylene group.

9. A phenylalkylcarboxylic acid compound, the pharmacologically acceptable salts thereof or the pharmacologically acceptable esters thereof according to claim 1, wherein $R^2$ is an ethylene group.

10. A phenylalkylcarboxylic acid compound, the pharmacologically acceptable salts thereof or the pharmacologically acceptable esters thereof according to claim 1, wherein $R^3$ is a hydrogen atom, a straight- or branched-chain alkyl group having from 1 to 4 carbon atoms, an alkoxy group having one or two carbon atoms, an alkylthio group having one or two carbon atoms or a halogen atom.

11. A phenylalkylcarboxylic acid compound, the pharmacologically acceptable salts thereof or the pharmacologically acceptable esters thereof according to claim 1, wherein $R^3$ is a hydrogen atom.

12. A phenylalkylcarboxylic acid compound, the pharmacologically acceptable salts thereof or the pharmacologically acceptable esters thereof according to claim 1, wherein X is an aryl group having from 6 to 10 carbon atoms which is unsubstituted or substituted by 1 to 3 substituents α mentioned below or a 5- to 10-membered hetero aromatic group (comprising monocyclic or bicyclic) containing from 1 to 4 hetero atoms selected from the group consisting of oxygen, nitrogen and sulfur atoms which is unsubstituted or substituted by 1 to 3 substituents α mentioned below, the substituent α being selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl heaving from 7 to 12 carbon atoms, (xiv) phenyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) phenoxy (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) phenylthio (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) phenylsulfonylamino (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms, and the nitrogen atom of the amino moiety is unsubstituted or substituted by straight- or branched-chain alkyl having from 1 to 6 carbon atoms), (xix) furyl, (xx) thienyl, (xxi) oxazolyl, (xxii) isoxazolyl, (xxiii) thiazolyl (xxiv) pyridyl, (xxv) pyridyloxy, (xxvi) pyridylthio, (xxvii) pyridylsulfonyl, (xxviii) imidazolyl (the nitrogen atom of the ring is unsubstituted or substituted by straight- or branched-chain alkyl having from 1 to 6 carbon atoms) and (xxix) pyridylsulfonylamino (the nitrogen atom of the amino moiety is unsubstituted or substituted by straight- or branched-chain alkyl having from 1 to 6 carbon atoms).

13. A phenylalkylcarboxylic acid compound, the pharmacologically acceptable salts thereof or the pharmacologically acceptable esters thereof according to claim 1, wherein X is a phenyl group, a naphthyl group, an imidazolyl group, an oxazolyl group, a pyridyl group, an indolyl group, a quinolyl group or an isoquinolyl group, and these groups is unsubstituted or substituted b1 to 3 substituents α mentioned below the substituent α being selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) methylenedioxy, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl having from 7 to 12 carbon atoms, (xiv) phenyl (the phenyl moiety is unsubstituted or substituted by methyl, trifluoromethyl, methoxy, fluoro or methylenedioxy), (xv) phenoxy (the phenyl moiety is unsubstituted or substituted by methyl, trifluoromethyl, methoxy, fluoro or methylenedioxy), (xvi) phenylthio (the phenyl moiety is unsubstituted or substituted by methyl, trifluoromethyl, methoxy, fluoro or methylenedioxy), (xvii) phenylsulfonyl (the phenyl moiety is unsubstituted or substituted by methyl, trifluoromethyl, methoxy, fluoro or methylenedioxy), (xviii) phenylsulfonylamino (the phenyl moiety is unsubstituted or substituted by methyl, trifluoromethyl, methoxy, fluoro or methylenedioxy, and the nitrogen atom of the amino moiety is unsubstituted or substituted by straight- or branched-chain alkyl having from 1 to 6 carbon atoms), (xix) furyl, (xx) thienyl, (xxi) oxazolyl, (xxii) isoxazolyl, (xxiii) thiazolyl, (xxiv) pyridyl, (xxv) pyridyloxy, (xxvi) pyridylthio, (xxvii) pyridylsulfonyl, (xxviii) imidazolyl (the nitrogen atom of the ring is unsubstituted or substituted by straight- or branched-chain alkyl having from 1 to 6 carbon atoms) and (xxix) pyridylsulfonylamino (the nitrogen atom of the amino moiety is unsubstituted or substituted by straight- or branched-chain alkyl having from 1 to 6 carbon atoms).

14. A phenylalkylcarboxylic acid compound, the pharmacologically acceptable salts thereof or the pharmacologically acceptable esters thereof according to claim 1, wherein X is a phenyl group, a naphthyl group, an imidazolyl group, an oxazolyl group, a pyridyl group, an indolyl group, a quinolyl group or an isoquinolyl group, and these group is unsubstituted or substituted by 1 to 3 substituents α mentioned below the substituent α being selected frog the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) methylenedioxy, (vii) benzyloxy, (viii) phenethyloxy, (ix) naphthylmethoxy, (x) straight- or branched-chain alkylthio having from 1 to 4 carbon atoms, (xi) straight- or branched-chain alkylsulfonyl having from 1 to 4 carbon atoms, (xii) fluorine atom, (xiii) chlorine atom, (xiv) bromine atom, (xv) benzyl, (xvi) phenyl (the phenyl moiety is unsubstituted or substituted by methyl, trifluoromethyl, methoxy, fluoro or methylenedioxy), (xvii) phenoxy (the phenyl moiety is unsubstituted or substituted by methyl, trifluoromethyl, methoxy, fluoro or methylenedioxy), (xviii) phenylthio, (xix) phenylsulfonyl, (xx) phenylsulfonylamino, (xxi) N-methylphenylsulfonylamino, (xxii) furyl, (xxiii) thienyl, (xxiv) oxazolyl, (xxv) isoxazolyl, (xxvi) thiazolyl, (xxvii) pyridyl, (xxviii) pyridyloxy, (xxix) pyridylthio, (xxx) pyridylsulfonyl, (xxxi) pyridylsulfonylamino, (xxxii) N-methylpyridylsulfonylamino and (xxxiii) imidazolyl (the nitrogen atom of the ring is unsubstituted or substituted by straight- or branched-chain alkyl having from 1 to 6 carbon atoms).

15. A phenylalkylcarboxylic acid compound, the pharmacologically acceptable salts thereof or the pharmacologically acceptable esters thereof according to claim 1, wherein X is a phenyl group, a naphthyl group, a pyridyl group, an indolyl group, a quinolyl group or an isoquinolyl group, and these groups is unsubstituted or substituted by one or two substituents α mentioned below the substituent a being selected from the group consisting of straight- or branched-chain alkyl having from 1 to 3 carbon atoms, methyl having from 1 to 3 fluorine atoms, hydroxy, alkanoyloxy having one or two carbon atoms, straight- or branched-chain alkoxy having from 1 to 3 carbon atoms, methylenedioxy, benzyloxy, alkylthio having one or two carbon atoms, alkylsulfonyl having one or two carbon atoms, fluorine atom, chlorine atom, bromine atom, benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and N-methylpyridylsulfonylamino groups.

16. A phenylalkylcarboxylic acid compound, the pharmacologically acceptable salts thereof or the pharmacologically acceptable esters thereof according to claim 1, wherein X is a phenyl group, naphthyl, pyridyl, quinolyl or isoquinolyl group, and these groups is unsubstituted or substituted by one substituent a mentioned below the substituent α being selected from methyl, ethyl, isopropyl, trifluoromethyl, hydroxy, acetoxy, methoxy, ethoxy, isopropoxy, methylenedioxy, benzyloxy, alkylthio having one or two carbon atoms, alkylsulfonyl having one or two carbon atoms, chlorine atom, benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and N-methylpyridylsulfonylamino groups.

17. A phenylalkylcarboxylic acid compound, the pharmacologically acceptable salts thereof or the pharmacologically acceptable esters thereof according to claim 1, wherein X is a phenyl group which is unsubstituted or substituted by one substituent α mentioned below, the substituent α being selected from the group consisting of methyl, hydroxy and acetoxy, chlorine atom, the benzyl, phenyl, phenoxy, phenylthio, phenylsulfonyl, phenylsulfonylamino, N-methylphenylsulfonylamino, pyridyl, pyridyloxy, pyridylthio and pyridylsulfonyl, or X is a pyridyl group which is unsubstituted or substituted by one substituent α mentioned below, the substituent α being selected from the group consisting of methoxy, ethoxy, isopropoxy and benzyloxy, alkylthio having one or two carbon atoms, alkylsulfonyl having one or two carbon atoms, benzyl, phenyl, phenoxy, phenylthio, phenylsulfonyl, phenylsulfonylamino and N-methylphenylsulfonylamino.

18. A phenylalkylcarboxylic acid compound, the pharmacologically acceptable salts thereof or the pharmacologically acceptable esters thereof according to claim 1, wherein X is a phenyl group which is unsubstituted or substituted by one substituent α mentioned below, the substituent α being selected from the group consisting of hydroxy, chlorine atom, benzyl, phenyl, phenoxy, phenylthio, pyridyl, pyridyloxy and pyridylthio.

19. A phenylalkylcarboxylic acid compound, the pharmacologically acceptable salts thereof or the pharmacologically acceptable esters thereof according to claim 1, wherein Y is an oxygen atom, a sulfur atom or a group of formula >N—$R^4$ (wherein $R^4$ represents a hydrogen atom, a straight- or branched-chain alkyl group having from 1 to 3 carbon atoms or a straight- or branched-chain alkanoyl group having from 2 to 5 carbon atoms).

20. A phenylalkylcarboxylic acid compound, the pharmacologically acceptable salts thereof or the pharmacologically acceptable esters thereof according to claim 1, wherein Y is an oxygen atom.

21. A phenylalkylcarboxylic acid compound, the pharmacologically acceptable salts thereof or the pharmacologically acceptable esters thereof according to claim 1, wherein Z is a single bond or a straight- or branched-chain alkylene group having from 1 to 4 carbon atoms.

22. A phenylalkylcarboxylic acid compound, the pharmacologically acceptable salts thereof or the pharmacologically acceptable esters thereof according to claim 1, wherein Z is a straight- or branched-chain alkylene group having from 1 to 4 carbon atoms.

23. A phenylalkylcarboxylic acid compound, the pharmacologically acceptable salts thereof or the pharmacologically acceptable esters thereof according to claim 1, wherein Z is a straight- or branched-chain alkylene group having one or two carbon atoms.

24. A phenylalkylcarboxylic acid compound, the pharmacologically acceptable salts thereof or the pharmacologically acceptable esters thereof according to claim 1, wherein Z is a methylene group.

25. A phenylalkylcarboxylic acid compound, the pharmacologically acceptable salts thereof or the pharmacologically acceptable esters thereof according to claim 1, wherein W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which alkyl groups are the same as or different from each other and each has from 1 to 4 carbon atoms, (vi) an N-alkyl-N-arylamino group having a straight- or branched-chain alkyl having from 1 to 4 carbon atoms and aryl having from 6 to 10 carbon atoms which is unsubstituted or substituted by 1 to 3 substituents α mentioned below in the aryl moiety, (vii) an aryloxy group having from 6 to 10 carbon atoms which is unsubstituted or substituted by 1 to 3 substituents α mentioned below in the aryl moiety, (viii) an arylthio group having from 6 to 10 carbon atoms which is unsubstituted or substituted by 1 to 3 substituents α mentioned below in the aryl moiety, (ix) an arylamino group having from 6 to 10 carbon atoms which is unsubstituted or substituted by 1 to 3 substituents α mentioned below in the aryl moiety, (x) an aralkyl group having from 7 to 12 carbon atoms which is unsubstituted or substituted by 1 to 3 substituents α mentioned below in the aryl moiety, (xi) a 1-pyrrolyl group, (xii) a 1-pyrrolidinyl group, (xiii) a 1-imidazolyl group, (xiv) a piperidino group or (xv) a morpholino group, the substituent α being selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl having from 7 to 12 carbon atoms, (xiv) phenyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) phenoxy (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvi) phenylthio (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) phenylsulfonylamino (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms, and the nitrogen atom of the amino moiety is unsubstituted or substituted by straight- or branched-chain alkyl having from 1 to 6 carbon atoms), (xix) furyl, (xx) thienyl, (xxi) oxazolyl, (xxii) isoxazolyl, (xxiii) thiazolyl (xxiv) pyridyl, (xxv) pyridyloxy, (xxvi) pyridylthio, (xxvii) pyridylsulfonyl, (xxviii) imidazolyl (the nitrogen atom of the ring is unsubstituted or substituted by straight- or branched-chain alkyl having from 1 to 6 carbon atoms) and (xxix) pyridylsulfonylamino (the nitrogen atom of the amino moiety is unsubstituted or substituted by straight- or branched-chain alkyl having from 1 to 6 carbon atoms).

26. A phenylalkylcarboxylic acid compound, the pharmacologically acceptable salts thereof or the pharmacologically acceptable esters thereof according to claim 1, wherein W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chair monoalkylamino group having from 1 to 4 carbon atoms, (v) a straight- or branched-chain dialkylamino group in which alkyl groups are the same as or different from each other and each has from 1 to 4 carbon atoms, (vi) an N-alkyl-N-arylamino group having straight- or branched-chain alkyl having from 1 to 4 carbon atoms and aryl having from 6 to 10 carbon atoms which is unsubstituted or substituted by 1 to 3 substituents α mentioned below in the aryl moiety, (vii) an aryloxy group having from 6 to 10 carbon atoms which is unsubstituted or substituted by 1 to 3 substituents α mentioned below in the aryl moiety, (viii) an arylthio group having from 6 to 10 carbon atoms which is unsubstituted or substituted by 1 to 3 substituents α mentioned below in the aryl moiety, (ix) an arylamino group having from 6 to 10 carbon atoms which is unsubstituted or substituted by 1 to 3 substituents α mentioned below in the aryl moiety, (x) an aralkyl croup having from 7 to 12 carbon atoms which is unsubstituted or substituted by 1 to 3 substituents α mentioned below in the aryl moiety, or (xi) a 1-pyrrolyl group, the substituent α being selected from hydroxy, chlorine atom, benzyl, phenyl, phenoxy, phenylthio, pyridyl, pyridyloxy and pyridylthio.

27. A phenylalkylcarboxylic acid compound, the pharmacologically acceptable salts thereof or the pharmacologically acceptable esters thereof according to claim 1, wherein W is (i) a straight- or branched-chain alkyl group having from 1 to 4 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which the alkyl groups are the same as or different from each other and each has from 1 to 4 carbon atoms, (vi) an N-alkyl-N-arylamino group having straight- or branched-chain alkyl having from 1 to 4 carbon atoms and aryl having from 6 to 10 carbon atoms, (vii) a phenoxy group, (viii) a phenylthio group, (ix) a phenylamino group, (x) an aralkyl group having from 7 to 10 carbon atoms, (xi) a 1-pyrrolyl group, (xii) a 1-pyrrolidinyl group or (xiii) a 1-imidazolyl group.

28. A phenylalkylcarboxylic acid compound, the pharmacologically acceptable salts thereof or the pharmacologically acceptable esters thereof according to claim 1, wherein W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group.

29. A phenylalkylcarboxylic acid compound, the pharmacologically acceptable salts thereof or the pharmacologically acceptable esters thereof according to claim 1, wherein W is a butyl, ethoxy, methylthio, ethylamino, diethylamino, N-phenyl-N-ethylamino, phenoxy, phenylthio, phenylamino, 3-phenylpropyl or 1-pyrrolyl group.

30. A phenylalkylcarboxylic acid compound, the pharmacologically acceptable salts thereof or the pharmacologically acceptable esters thereof according to claim 1, wherein W is a butyl, ethoxy, methylthio, ethylamino, phenoxy, phenylthio, phenylamino or 3-phenylpropyl group.

31. A phenylalkylcarboxylic acid compound, the pharmacologically acceptable salts thereof or the pharmacologically acceptable esters thereof according to claim 1, wherein $R^1$ is a hydrogen atom or a straight- or branched-chain alkyl group having from 1 to 4 carbon atoms;

$R^2$ is a straight- or branched-chain alkylene group having from 2 to 5 carbon atoms;

$R^3$ is a hydrogen atom, a straight- or branched-chain alkyl group having from 1 to 4 carbon atoms, an alkoxy group having one or two carbon atoms, an alkylthio group having one or two carbon atoms or a halogen atom;

Z is a single bond or a straight- or branched-chain alkylene group having from 1 to 4 carbon atoms;

W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which alkyl groups are the same as or different from each other and each has from 1 to 4 carbon atoms, (vi) an N-alkyl-N-arylamino group having straight- or branched-chain alkyl having from 1 to 4 carbon atoms and aryl having from 6 to 10 carbon atoms which is unsubstituted or substituted by 1 to 3 substituents α mentioned below in the aryl moiety, (vii) an aryloxy group having from 6 to 10 carbon atoms which is unsubstituted or substituted by 1 to 3 substituents α mentioned below in the aryl moiety, (viii) an arylthio group having from 6 to 10 carbon atoms which is unsubstituted or substituted by 1 to 3 substituents α mentioned below in the aryl moiety, (ix) an arylamino group having from 6 to 10 carbon atoms which is unsubstituted or substituted by 1 to 3 substituents α mentioned below in the aryl moiety, (x) an aralkyl group having from 7 to 12 carbon atoms which is unsubstituted or substituted by 1 to 3 substituents α mentioned below in the aryl moiety, (xi) a 1-pyrrolyl group, (xii) a 1-pyrrolidinyl group, (xiii) a 1-imidazolyl group, (xiv) a piperidino group or (xv) a morpholino group;

X is an aryl group having from 6 to 10 carbon atoms which is unsubstituted or substituted by 1 to 3 substituents α mentioned below or a 5- to 10-membered hetero aromatic group (comprising monocyclic or bicyclic) having from 1 to 4 hetero atoms selected from the group consisting of oxygen, nitrogen and sulfur atoms which is unsubstituted or substituted by 1 to 3 substituents α mentioned below;

the substituent α mentioned below being selected from the group consisting of (i) straight- or branched-chain alkyl having from 1 to 6 carbon atoms, (ii) straight- or branched-chain halogenated alkyl having from 1 to 4 carbon atoms, (iii) hydroxy, (iv) straight- or branched-chain alkanoyloxy having from 1 to 4 carbon atoms, (v) straight- or branched-chain alkoxy having from 1 to 4 carbon atoms, (vi) straight- or branched-chain alkylenedioxy having from 1 to 4 carbon atoms, (vii) aralkyloxy having from 7 to 12 carbon atoms, (viii) straight- or branched-chain alkylthio having from 1 to 4 carbon atoms, (ix) straight- or branched-chain alkylsulfonyl having from 1 to 4 carbon atoms, (x) fluorine atom, (xi) chlorine atom, (xii) bromine atom, (xiii) aralkyl having from 7 to 12 carbon atoms, (xiv) phenyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xv) phenoxy (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen or straight- or branched-chain alkylenedioxy having from 1 to 4 carbon atoms), (xvi) phenylthio (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xvii) phenylsulfonyl (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms), (xviii) phenylsulfonylamino (the phenyl moiety is unsubstituted or substituted by straight- or branched-chain alkyl having from 1 to 6 carbon atoms, straight- or branched-chain halogenated alkyl having from 1 to 4 carbon atoms, straight- or branched-chain alkoxy having from 1 to 4 carbon atoms, halogen, or straight- or branched-chain alkylenedioxy having from 1 to 4 carbon atoms, and the nitrogen atom of the amino moiety is unsubstituted or substituted by straight- or branched-chain alkyl having from 1 to 6 carbon atoms), (xix) furyl, (xx) thienyl, (xxi) oxazolyl, (xxii) isoxazolyl, (xxiii) thiazolyl, (xxiv) pyridyl, (xxv) pyridyloxy, (xxvi) pyridylthio, (xxvii) pyridylsulfonyl, (xxviii) imidazolyl (the nitrogen atom of the ring is unsubstituted or substituted by straight- or branched-chain alkyl having from 1 to 6 carbon atoms) and (xxix) pyridylsulfonylamino (the nitrogen atom of the amino moiety is unsubstituted or substituted by straight- or branched-chain alkyl having from 1 to 6 carbon atoms); and Y is an oxygen or sulfur atom or a group of formula >N—$R^4$ (wherein $R^4$ represents a hydrogen atom, a straight- or branched-chain alkyl group having from 1 to 3 carbon atoms or a straight- or branched-chain alkanoyl group having from 2 to 5 carbon atoms).

32. A phenylalkylcarboxylic, acid compound, the pharmacologically acceptable salts thereof or the pharmacologically acceptable esters thereof according to claim 1, wherein $R^1$ is a straight- or branched-chain alkyl group having from 1 to 4 carbon atoms;

$R^2$ is a straight- or branched-chain alkylene group having from 2 to 5 carbon atoms;

$R^3$ is a hydrogen atom;

Z is a straight- or branched-chain alkylene group having from 1 to 4 carbon atoms;

W is (i) a straight- or branched-chain alkyl group having from 1 to 6 carbon atoms, (ii) a straight- or branched-chain alkoxy group having from 1 to 4 carbon atoms, (iii) a straight- or branched-chain alkylthio group having from 1 to 4 carbon atoms, (iv) a straight- or branched-chain monoalkylamino group having from 1 to 4 carbon atoms, (v) a straight- or branched-chain dialkylamino group in which alkyl groups are the same as or different from each other and each has from 1 to 4 carbon atoms, (vi) an N-alkyl-N-arylamino group having straight- or branched-chain alkyl having from 1 to 4 carbon atoms and aryl having from 6 to 10 carbon atoms which is unsubstituted or substituted by 1 to 3 substituents α mentioned below in the aryl moiety, (vii) an aryloxy group having from 6 to 10 carbon atoms which is unsubstituted or substituted by 1 to 3 substituents α mentioned below in the aryl moiety, (viii) an arylthio group having from 6 to 10 carbon atoms which is unsubstituted or substituted by 1 to 3 substituents α mentioned below in the aryl moiety, (ix) an arylamino group having from 6 to 10 carbon atoms which is unsubstituted or substituted by 1 to 3 substituents α mentioned below in the aryl moiety, (x) an aralkyl group having from 7 to 12 carbon atoms which is unsubstituted or substituted by 1 to 3 substituents α mentioned below in the aryl moiety or (xi) a 1-pyrrolyl group;

X is a phenyl group which is unsubstituted or substituted by one substituent α mentioned below;

the substituent α being selected from the group consisting of hydroxy, chlorine atom, benzyl, phenyl, phenoxy, phenylthio, pyridyl, pyridyloxy and pyridylthio; and Y is an oxygen atom.

33. A phenylalkylcarboxylic acid compound, the pharmacologically acceptable salts thereof or the pharmacologically acceptable esters thereof according to claim 1, wherein $R^1$ is an alkyl group having one or two carbon atoms;

$R^2$ is an ethylene group;

$R^3$ is a hydrogen atom;

Z is a methylene group;

W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group;

X is a phenyl group which is unsubstituted or substituted by one substituent α mentioned below;

the substituent α being selected from the group consisting of methyl, hydroxy, acetoxy, chlorine atom, benzyl, phenyl, phenoxy, phenylthio, phenylsulfonyl, phenylsulfonylamino, N-methylphenylsulfonylamino, pyridyl, pyridyloxy, pyridylthio and pyridylsulfonyl; or X is a pyridyl group which is unsubstituted or substituted by one substituent α mentioned below;

the substituent α being selected from the group consisting of methoxy, ethoxy, isopropoxy, benzyloxy, alkylthio having one or two carbon atoms, alkylsulfonyl having one or two carbon atoms, benzyl, phenyl, phenoxy, phenylthio, phenylsulfonyl, phenylsulfonylamino and N-methylphenylsulfonylamino groups; and Y is an oxygen atom.

34. A phenylalkylcarboxylic acid compound, the pharmacologically acceptable salts thereof or the pharmacologically acceptable esters thereof according to claim 1, wherein $R^1$ is an alkyl group having one or two carbon atoms;

$R^2$ is an ethylene group;

$R^3$ is a hydrogen atom;

Z is a methylene group;

W is (i) a propyl or butyl group, (ii) a straight- or branched-chain alkoxy group having from 1 to 3 carbon atoms, (iii) a straight- or branched-chain alkylthio group having from 1 to 3 carbon atoms, (iv) a straight- or branched-chain monoalkylamino group having from 1 to 3 carbon atoms, (v) a diethylamino group, (vi) an N-phenyl-N-ethylamino group, (vii) a phenoxy group, (viii) a phenylthio group, (ix) a phenylamino group, (x) a 3-phenylpropyl group, (xi) a 4-phenylbutyl group or (xii) a 1-pyrrolyl group;

X is a phenyl group which is unsubstituted or substituted by one substituent α mentioned below;

the substituent α being selected from the group consisting of hydroxy, chlorine atom, benzyl, phenyl, phenoxy, phenylthio, pyridyl, pyridyloxy and pyridylthio groups; and Y is an oxygen atom.

35. A phenylalkylcarboxylic acid compound, the pharmacologically acceptable salts thereof or the pharmacologically acceptable esters thereof according to claim 1, wherein $R^1$ is an alkyl group having one or two carbon atoms;

$R^2$ is an ethylene group;

$R^3$ is a hydrogen atom;

Z is a methylene group;

W is a butyl, ethoxy, methylthio, ethylamino, diethylamino, N-phenyl-N-ethylamino, phenoxy, phenylthio, phenylamino, 3-phenylpropyl or 1-pyrrolyl group;

X is a phenyl group which is unsubstituted or substituted by one substituent α mentioned below;

the substituent α being selected from the group consisting of hydroxy, chlorine atom, benzyl, phenyl, phenoxy, phenylthio, pyridyl, pyridyloxy and pyridylthio; and Y is an oxygen atom.

36. A phenylalkylcarboxylic acid compound, the pharmacologically acceptable salts thereof or the pharmacologically acceptable esters thereof according to claim 1, wherein $R^1$ is an alkyl group having one or two carbon atoms;

$R^2$ is an ethylene group;

$R^3$ is a hydrogen atom;

Z is a methylene group;

W is a butyl, ethoxy, methylthio, ethylamino, phenoxy, phenylthio, phenylamino or 3-phenylpropyl group;

X is a phenyl group which is unsubstituted or substituted by one substituent α mentioned below;

the substituent α being selected from the group consisting of hydroxy, chlorine atom, benzyl, phenyl, phenoxy, phenylthio, pyridyl, pyridyloxy and pyridylthio groups; and Y is an oxygen atom.

37. A phenylalkylcarboxylic acid compound or the pharmacologically acceptable esters thereof according to claim 1 selected from the group of compounds consisting of:

1) 2-ethoxy-3-[4-[2-[[1-(4-biphenylyl)ethylidene]aminoxy]ethoxy]phenyl]propionic acid,
2) 2-ethoxy-3-[4-[2-[[1-(4-phenylsulfonylphenyl)ethylidene]aminoxy]ethoxy]phenyl]propionic acid,
3) 2-ethoxy-3-[4-[2-[[1-[4-(2-pyridyl)phenyl]ethylidene]aminoxy]ethoxy]phenyl]propionic acid,
4) 2-ethoxy-3-[4-[2-[[1-[4-(3-pyridyl)phenyl]ethylidene]aminoxy]ethoxy]phenyl]propionic acid,
5) 2-ethoxy-3-[4-[2-[[1-[4-(4-pyridyl)phenyl]ethylidene]aminoxy]ethoxy]phenyl]propionic acid,
6) 2-ethoxy-3-[4-[2-[[1-(2-phenyl-5-pyridyl)ethylidene]aminoxy]ethoxy]phenyl]propionic acid,
7) 2-ethoxy-3-[4-[2-[[1-(2-methoxy-5-pyridyl)ethylidene]aminoxy]ethoxy]phenyl]propionic acid,
8) 2-ethoxy-3-[4-[2-[[1-(2-ethoxy-5-pyridyl)ethylidene]aminoxy]ethoxy]phenyl]propionic acid,
9) 2-ethoxy-3-[4-[2-[[1-(2-isopropoxy-5-pyridyl)ethylidene]aminoxy]ethoxy]phenyl]propionic acid,
10) 3-[4-[2-[[1-(2-benzyl-5-pyridyl)ethylidene]aminoxy]ethoxy]phenyl]-2-ethoxypropionic acid,
11) 2-methoxy-3-[4-[2-[[1-[4-(2-pyridyl)phenyl]ethylidene]aminoxy]ethoxy]phenyl]propionic acid,
12) 2-propoxy-3-[4-[2-[[1-[4-(2-pyridyl)phenyl]ethylidene]aminoxy]ethoxy]phenyl]propionic acid,
13) 2-isopropoxy-3-[4-[2-[[1-[4-(2-pyridyl)phenyl]ethylidene]aminoxy]ethoxy]phenyl]propionic acid,
14) 2-methylthio-3-[4-[2-[[1-[4-(2-pyridyl)phenyl]ethylidene]aminoxy]ethoxy]phenyl]propionic acid,
15) 2-ethylthio-3-[4-[2-[[1-[4-(2-pyridyl)phenyl]ethylidene]aminoxy]ethoxy]phenyl]propionic acid,
16) 2-propylthio-3-[4-[2-[[1-[4-(2-pyridyl)phenyl]ethylidene]aminoxy]ethoxy]phenyl]propionic acid,
17) 2-phenylthio-3-[4-[2-[[1-[4-(2-pyridyl)phenyl]ethylidene]aminoxy]ethoxy]phenyl]propionic acid,
18) 3-[4-[2-[[1-(4-biphenylyl)ethylidene]aminoxy]ethoxy]phenyl]-2-(phenylamino)propionic acid,
19) 2-phenylamino-3-[4-[2-[[1-[4-(2-pyridyl)phenyl]ethylidene]aminoxy]ethoxy]phenyl]propionic acid,
20) 2-methylamino-3-[4-[2-[[1-[4-(2-pyridyl)phenyl]ethylidene]aminoxy]ethoxy]phenyl]propionic acid,
21) 2-ethylamino-3-[4-[2-[[1-[4-(2-pyridyl)phenyl]ethylidene]aminoxy]ethoxy]phenyl]propionic acid,
22) 2-propylamino-3-[4-[2-[[1-[4-(2-pyridyl)phenyl]ethylidene]aminoxy]ethoxy]phenyl]propionic acid,
23) 2-isopropylamino-3-[4-[2-[[1-[4-(2-pyridyl)phenyl]ethylidene]aminoxy]ethoxy]phenyl]propionic acid,
24) 2-(N,N-diethylamino)-3-[4-[2-[[1-[4-(2-pyridyl)phenyl]ethylidene]aminoxy]ethoxy]-phenyl]propionic acid,
25) 3-[4-[2-[[1-(4-biphenylyl)ethylidene]aminoxy]ethoxy]phenyl]-2-[N-phenyl-N-ethylamino]propionic acid,
26) 3-[4-[2-[[1-(4-biphenylyl)ethylidene]aminoxy]ethoxy]phenyl]-2-pyrrolylpropionic acid,
27) 2-(3-phenylpropyl)-3-[4-[2-[[1-[4-(2-pyridyl)phenyl]ethylidene]aminoxy]ethoxy]phenyl]propionic acid,
28) 2-(4-phenylbutyl)-3-[4-[2-[[1-[4-(2-pyridyl)phenyl]ethylidene]aminoxy]ethoxy]phenyl]propionic acid,
29) 2-propyl-3-[4-[2-[[1-[4-(2-pyridyl)phenyl]ethylidene]aminoxy]ethoxy]phenyl]propionic acid,
30) 2-butyl-3-[4-[2-[[1-[4-(2-pyridyl)phenyl]ethylidene]aminoxy]ethoxy]phenyl]propionic acid, and
31) 2-phenoxy-3-[4-[2-[[1-[4-(2-pyridyl)phenyl]ethylidene]aminoxy]ethoxy]phenyl]propionic acid, the pharmacologically acceptable salts thereof or the pharmacologically acceptable esters thereof.

38. The phenylalkylcarboxylic acid compound or the pharmacologically acceptable esters thereof as set forth in claim 1 selected from the group consisting of:

1) 2-ethoxy-3-[4-[2-[[1-(4-biphenylyl)ethylidene]aminoxy]ethoxy]phenyl]propionic acid,
2) 2-ethoxy-3-[4-[2-[[1-[4-(2-pyridyl)phenyl]ethylidene]aminoxy]ethoxy]phenyl]propionic acid,
3) 2-methylthio-3-[4-[2-[[1-[4-(2-pyridyl)phenyl]ethylidene]aminoxy]ethoxy]phenyl]propionic acid,
4) 2-phenylthio-3-[4-[2-[[1-[4-(2-pyridyl)phenyl]ethylidene]aminoxy]ethoxy]phenyl]propionic acid,
5) 3-[4-[2-[[1-(4-biphenylyl)ethylidene]aminoxy]ethoxy]phenyl]-2-(phenylamino)propionic acid,
6) 2-ethylamino-3-[4-[2-[[1-[4-(2-pyridyl)phenyl]ethylidene]aminoxy]ethoxy]phenyl]propionic acid,
7) 2-(3-phenylpropyl)-3-[4-[2-[[1-[4-(2-pyridyl)phenyl]ethylidene]aminoxy]ethoxy]phenyl]propionic acid,
8) 2-butyl-3-[4-[2-[[1-[4-(2-pyridyl)phenyl]ethylidene]aminoxy]ethoxy]phenyl]propionic acid, and
9) 2-phenoxy-3-[4-[2-[[1-[4-(2-pyridyl)phenyl]ethylidene]aminoxy]ethoxy]phenyl]propionic acid;

the pharmacologically acceptable salts thereof or the pharmacologically acceptable esters thereof.

39. A composition for therapeutic or preventive agents for hyperglycemia containing as an active ingredient the phenylalkylcarboxylic acid compound, the pharmacologically acceptable salts thereof or the pharmacologically acceptable esters thereof as set forth in any of claim 1 to claim 38 together with a pharmaceutical adjuvant.

40. A method for the treatment or prophylaxis of diseases caused by hyperglycemia comprising administering to a patient suffering from insulin resistance, a therapeutically effective amount of a phenylalkylcarboxylic acid compound, a pharmaceutically acceptable salt thereof or a pharmaceutically acceptable ester thereof, as set forth in claim 1.

* * * * *